United States Patent
Quibell et al.

(10) Patent No.: US 12,023,333 B2
(45) Date of Patent: Jul. 2, 2024

(54) PHENYL-SULFAMOYL.BENZOYC ACIDS AS ERAP1 MODULATORS

(71) Applicant: GREY WOLF THERAPEUTICS LIMITED, Abingdon (GB)

(72) Inventors: Martin Quibell, Oxford (GB); Jason John Shiers, Oxford (GB); Michael Sparenberg, Oxford (GB)

(73) Assignee: GREY WOLF THERAPEUTICS LIMITED, Abingdon (GB)

(*) Notice: Subject to any disclaimer, the term of this patent is extended or adjusted under 35 U.S.C. 154(b) by 68 days.

(21) Appl. No.: 17/609,177

(22) PCT Filed: May 7, 2020

(86) PCT No.: PCT/GB2020/051128
§ 371 (c)(1),
(2) Date: Feb. 23, 2022

(87) PCT Pub. No.: WO2020/225569
PCT Pub. Date: Nov. 12, 2020

(65) Prior Publication Data
US 2022/0347176 A1    Nov. 3, 2022

(30) Foreign Application Priority Data

May 9, 2019 (GB) ..................................... 1906572
Nov. 14, 2019 (GB) ..................................... 1916595

(51) Int. Cl.
*A61K 31/505* (2006.01)
*A61K 31/192* (2006.01)
(Continued)

(52) U.S. Cl.
CPC .......... *A61K 31/505* (2013.01); *A61K 31/192* (2013.01); *A61K 31/277* (2013.01); *A61K 31/341* (2013.01); *A61K 31/381* (2013.01); *A61K 31/40* (2013.01); *A61K 31/402* (2013.01); *A61K 31/41* (2013.01); *A61K 31/415* (2013.01); *A61K 31/4155* (2013.01); *A61K 31/4164* (2013.01); *A61K 31/4196* (2013.01); *A61K 31/421* (2013.01); *A61K 31/422* (2013.01); *A61K 31/425* (2013.01); *A61K 31/426* (2013.01); *A61K 31/427* (2013.01);
(Continued)

(58) Field of Classification Search
None
See application file for complete search history.

(56) References Cited

FOREIGN PATENT DOCUMENTS

| WO | WO 2008/008374 A2 | 1/2008 |
| WO | WO 2008/010934 A1 | 1/2008 |

(Continued)

OTHER PUBLICATIONS

Database Registry Chemical Abstracts Service, Columbus, Ohio, Accession No. RN 949213-69-8, Entered STN: Oct. 5, 2007.*
Database Registry Chemical Abstracts Service, Columbus, Ohio, Accession No. RN 1054082-93-7, Entered STN: Sep. 28, 2008.*
Advanced Organic Chemistry, 3rd Edition, ed. March, J., John Wiley and Sons, New York, 1985).
Akos Out of Stock Catalog, publication date May 4, 2015, CAS Registry No. 938382-63-9. Chemcats Accession No. 1908473310.
Ambinter Stock Collection, publication date Oct. 8, 2018, CAS Registry No. 1208407-96-8. Chemcats Accession No. 1987159712.
Aurora Building Blocks 3, publication date Feb. 21, 2019, CAS Registry No. 1387359-18-3. Chemcats Accession No. 1892295046.
(Continued)

*Primary Examiner* — Samantha L Shterengarts
(74) *Attorney, Agent, or Firm* — Lathrop GPM LLP; Brian C. Trinque

(57) ABSTRACT

The present invention relates to a compound of formula (I), or a pharmaceutically acceptable salt or hydrate thereof, wherein: the group X—Y is —NHSO$_2$— or —SO$_2$NH—; Z is a monocyclic aryl or heteroaryl group, each of which is optionally substituted by one or more substituents selected from alkyl, cycloalkyl, halo, alkoxy, CN, haloalkyl and OH; $R_1$ is H or alkyl; $R_2$ is selected from COOH and a tetrazolyl group; $R_3$ is selected from H, C land alkyl; $R_4$ is selected from H and halo; $R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy; $R_6$ is H; $R_7$ is selected from H, CN, haloalkyl, halo, SO$_2$-alkyl, SO$_2$NR$_{12}$R$_{13}$, heteroaryl, CONR$_{10}$R$_{11}$ and alkyl, wherein said heteroaryl group is optionally substituted by one or more substituents selected from alkyl, halo, alkoxy, CN, haloalkyl and OH; $R_8$ is selected from H, alkyl, haloalkyl and halo; and $R_9$ is H, alkyl or halo; $R_{10}$ and $R_{11}$ are each independently H or alkyl; and $R_{12}$ and $R_{13}$ are each independently H or alkyl. Further aspects of the invention relate to such compounds for use in the field of immuno-oncology and related applications. Another aspect of the invention relates to compounds of formulae (1a) and (1b).

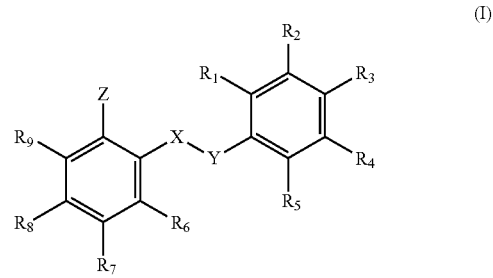

(I)

11 Claims, No Drawings

(51) Int. Cl.

| | | |
|---|---|---|
| A61K 31/277 | (2006.01) | |
| A61K 31/341 | (2006.01) | |
| A61K 31/381 | (2006.01) | |
| A61K 31/40 | (2006.01) | |
| A61K 31/402 | (2006.01) | |
| A61K 31/41 | (2006.01) | |
| A61K 31/415 | (2006.01) | |
| A61K 31/4155 | (2006.01) | |
| A61K 31/4164 | (2006.01) | |
| A61K 31/4196 | (2006.01) | |
| A61K 31/421 | (2006.01) | |
| A61K 31/422 | (2006.01) | |
| A61K 31/425 | (2006.01) | |
| A61K 31/426 | (2006.01) | |
| A61K 31/427 | (2006.01) | |
| A61K 31/4418 | (2006.01) | |
| A61K 31/4439 | (2006.01) | |
| A61K 31/50 | (2006.01) | |
| A61K 45/06 | (2006.01) | |
| A61P 37/02 | (2006.01) | |
| C07C 311/29 | (2006.01) | |
| C07D 207/325 | (2006.01) | |
| C07D 207/327 | (2006.01) | |
| C07D 207/335 | (2006.01) | |
| C07D 213/42 | (2006.01) | |
| C07D 213/56 | (2006.01) | |
| C07D 213/57 | (2006.01) | |
| C07D 231/12 | (2006.01) | |
| C07D 233/64 | (2006.01) | |
| C07D 237/08 | (2006.01) | |
| C07D 239/26 | (2006.01) | |
| C07D 249/08 | (2006.01) | |
| C07D 257/04 | (2006.01) | |
| C07D 263/32 | (2006.01) | |
| C07D 275/02 | (2006.01) | |
| C07D 277/28 | (2006.01) | |
| C07D 277/30 | (2006.01) | |
| C07D 307/52 | (2006.01) | |
| C07D 333/20 | (2006.01) | |
| C07D 333/22 | (2006.01) | |
| C07D 333/24 | (2006.01) | |
| C07D 333/38 | (2006.01) | |
| C07D 401/10 | (2006.01) | |
| C07D 403/10 | (2006.01) | |
| C07D 409/10 | (2006.01) | |
| C07D 413/10 | (2006.01) | |
| C07D 417/10 | (2006.01) | |

(52) U.S. Cl.
CPC ...... *A61K 31/4418* (2013.01); *A61K 31/4439* (2013.01); *A61K 31/50* (2013.01); *A61K 45/06* (2013.01); *A61P 37/02* (2018.01); *C07C 311/29* (2013.01); *C07D 207/325* (2013.01); *C07D 207/327* (2013.01); *C07D 207/335* (2013.01); *C07D 213/42* (2013.01); *C07D 213/56* (2013.01); *C07D 213/57* (2013.01); *C07D 231/12* (2013.01); *C07D 233/64* (2013.01); *C07D 237/08* (2013.01); *C07D 239/26* (2013.01); *C07D 249/08* (2013.01); *C07D 257/04* (2013.01); *C07D 263/32* (2013.01); *C07D 275/02* (2013.01); *C07D 277/28* (2013.01); *C07D 277/30* (2013.01); *C07D 307/52* (2013.01); *C07D 333/20* (2013.01); *C07D 333/22* (2013.01); *C07D 333/24* (2013.01); *C07D 333/38* (2013.01); *C07D 401/10* (2013.01); *C07D 403/10* (2013.01); *C07D 409/10* (2013.01); *C07D 413/10* (2013.01); *C07D 417/10* (2013.01)

(56) References Cited

FOREIGN PATENT DOCUMENTS

| WO | 2009/064388 A2 | 5/2009 |
|---|---|---|
| WO | 2020/104822 A1 | 5/2020 |

OTHER PUBLICATIONS

Aurora Building Blocks 4, publication date Feb. 21, 2019, CAS Registry No. 1253400-29-1. Chemcats Accession No. 1949438129.
Aurora Screening Compounds 1, publication date Feb. 21, 2019, CAS Registry No. 1197600-86-4. Chemcats Accession No. 2023358758.
Aurora Screening Compounds 1, publication date Feb. 21, 2019, CAS Registry No. 1389286-41-2. Chemcats Accession No. 1972503672.
Aurora Screening Compounds 2, publication 2, publication date Feb. 21, 2019, CAS Registry No. 1317436-84-2. Chemcats Accession No. 2072113262.
Berge et al., "Pharmaceutical salts", Journal of Pharmaceutical Sciences, 66:1-19 (1977).
Chemical Abstracts, Database Accession No. 1445085-97-1.
Chen et al., "Silencing or inhibition of endoplasmic reticulum aminopeptidase 1 (ERAP1) suppresses free heavy chain expression and Th17 responses in ankylosing spondylitis", *Annals of the Rheumatic Diseases* 75:916 (2014).
Cifaldi et al., "ERAP1 Regulates Natural Killer Cell Function by Controlling the Engagement of Inhibitory Receptors", *Cancer Research* 75:824 (2015).
Conde-Jaldon et al., "Epistatic interaction of ERAP1 and HLA-B in Behçet disease: a replication study in the Spanish population", *PLoS One* 14;9(7) (2014).
Evans et al., "Interaction between ERAP1 and HLA-B27 in ankylosing spondylitis implicates peptide handling in the mechanism for HLA-B27 in disease susceptibility", *Nature Genetics* 10:43(8):761-767 (2011).
Fingl et al., "The Pharmacological Basis of Therapeutics", Chapter 1—General Principles, p. 1-46 (1975).
Handbook of Pharmaceutical Excipients, 2nd Edition, (1994), Edited by A Wade and PJ Weller.
James et al., "Induction of Protective Antitumor Immunity through Attenuation of ERAAP Function", *Journal of Immunology* 190:5839 (2013).
Kim et al., "Human cytomegalovirus microRNA miR-US4-1 inhibits CD8+T cell responses by targeting the aminopeptidase ERAP1", *Nature Immunology* 12:984 (2011).
Kuiper et al., "Intraocular interleukin-17 and proinflammatory cytokines in HLA-A29-associated birdshot chorioretinopathy", *American Journal of Ophthalmology* 152(2):177-182 (2011).
Kuiper et al., "Interleukin-17 production and T helper 17 cells in peripheral blood mononuclear cells in response to ocular lysate in patients with birdshot chorioretinopathy", *Molecular Vision* 19:2606-2614 (2013).
Kuiper et al., "A genome-wide association study identifies a functional ERAP2 haplotype associated with birdshot chorioretinopathy", *Human Molecular Genetics* 23(22):6081-6087 (2014).
Kuiper et al., "Functionally distinct ERAP1 and ERAP2 are a hallmark of HLA-A29-(Birdshot) Uveitis", *Human Molecular Genetics* doi: 10.1093/hmg/ddy319 (2018).
Nagarajan et al., "ERAAP Shapes the Peptidome Associated with Classical and Nonclassical MHC Class I Molecules"; *Journal of Immunology* 197:1035 (2016).
Nicolaou et al., "Calicheamicin θ: A Rationally Designed Molecule with Extremely Potent and Selective DNA Cleaving Properties and Apoptosis Inducing Activity", Angewandte Chemie Intl. Ed. Engl., 33:183-186 (1994).

(56) References Cited

OTHER PUBLICATIONS

Pepelyayeva et al., "ERAP1 deficient mice have reduced Type 1 regulatory T cells and develop skeletal and intestinal features of Ankylosing Spondylitis", *Science Reports* 8:12464 (2018).
Reeves et al., "The role of polymorphic ERAP1 in autoinflammatory disease", *Bioscience Reports* 29, p38 (2018).
Remington's Pharmaceutical Sciences, Mack Publishing Co. (A. R. Gennaro edit. 1985).
Serwold et al., "ERAAP customizes peptides for MHC class I molecules in the endoplasmic reticulum" *Nature* 419:480 (2002).
Sheehan, "The ramifications of HLA-B27", *Journal of the Royal Society of Medicine* 97(1):10-14 (Jan. 2004).
Smith, "Update on ankylosing spondylitis: current concepts in pathogenesis", *Current Allergy and Asthma Reports* 15(1):489 (Jan. 2015).
Snyder et al., "Genetic Basis for Clinical Response to CTLA-4 Blockade in Melanoma", *The New England Journal of Medicine* 371:2189 (2014).
Steinbach et al., "ERAP1 overexpression in HPV-induced malignancies: A possible novel immune evasion mechanism", *Oncoimmunology* 6:e1336594 (2017).
Strange et al., "Genome-wide association study identifies new psoriasis susceptibility loci and an interaction between HLA-C and ERAP1", *Nature Genetics* 42(11):985-990 (2010).
Tenzer et al., "Antigen processing influences HIV-specific cytotoxic T lymphocyte immunodominance", *Nature Immunology* 10:636 (2009).
Van Allen et al., "Genomic correlates of response to CTLA-4 blockade in metastatic melanoma", *Science* 348:124 (2015).
ZA6707186A (Ciba Ltd). CAS Abstract Accession No. 1969:67908.
International Preliminary Report on Patentability for PCT International Patent Application No. PCT/GB2020/051128, dated Jul. 13, 2020.
Pubchem Compounds: "4-Methoxy-3-{[2-(piperidin-1-yl)-5-(trifluoromethyl)phenyl}sulfamoyl}benzioc acid", N.C.B.I., Jul. 19, 2005 (Jul. 19, 2005), XP055659781, Retrieved from the Internet: URL: https://pubchem.ncbi.nlm.nih.gov/compound/4798291— [retrieved on Jan. 21, 2020].
Pubchem Bioassay N.C.B.I: "AID 1117287—MLPCN ERAP1 Measured in Biochemical System Using Plate Reader—7016-01_", PubChem AID: 1117287, Nov. 24, 2015 (Nov. 24, 2015), XP55659786, Retrieved from the Internet: URL:https://pubchem.ncbi.nlm.nih.gov/bioassay/1117287 [retrieved on Jan. 21, 2020].
E. Zervoudi et al: "Rationally designed inhibitor targeting antigen-trimming aminopeptidases enhances antigen presentation and cytotoxic T-cell responses", Proceedings of the National Academy of Sciences, vol. 110, No. 49, Nov. 18, 2013 (Nov. 18, 2013), pp. 19890-19895, XP055118358, ISSN: 0027-8424, DOI: 10.1073/pnas. 1309781110.
Registry Database Online, CAS database accession No. 2262410-05-7, retrieved Jan. 30, 2019.
Registry Database Online, CAS database accession No. 1387521-52-9, retrieved Aug. 7, 2012.
Registry Database Online, CAS database accession No. 1386410-88-3, retrieved Aug. 3, 2012.
Registry Database Online, CAS database accession No. RN 1385527-18-3, retrieved Aug. 2, 2012.
Registry Database Online, CAS database accession No. RN 1376313-85-7, retrieved Jun. 7, 2012.
Registry Database Online, CAS database accession No. RN 1090950-51-8, retrieved Dec. 28, 2008.
Registry Database Online, CAS database accession No. RN 1030157-49-3, retrieved Jun. 24, 2008.
Registry Database Online, CAS database accession No. RN 1010539-89-5, retrieved Mar. 28, 2008.
Registry Database Online, CAS database accession No. RN 949213-69-8, retrieved Oct. 5, 2007.
Registry Database Online, CAS database accession No. RN 942767-14-8, retrieved Jul. 19, 2007.
Registry Database Online, CAS database accession No. RN 794585-44-7, retrieved Dec. 8, 2004.
Registry Database Online, CAS database accession No. RN 744204-12-4, retrieved Sep. 14, 2004.
Zachary Maben et al: "Discovery of Selective Inhibitors of Endoplasmic Reticulum Aminopeptidase 1", Journal of Medicinal Chemistry, vol. 63, No. 1, Jan. 9, 2020 (Jan. 9, 2020), pp. 103-121, XP055710217, US ISSN: 0022-2623, DOI: 10.1021/acs.jmedchem. 9b00293.

* cited by examiner

PHENYL-SULFAMOYL.BENZOYC ACIDS AS ERAP1 MODULATORS

CROSS REFERENCE TO RELATED APPLICATIONS

This application is a 35 U.S.C. § 371 filing of International Patent Application No. PCT/GB2020/051128, filed May 7, 2020, which application claims the priority and benefit of United Kingdom Patent Application No. 1916595.0 filed on Nov. 14, 2019, and United Kingdom Patent Application No. 1906572.1, filed May 9, 2019, the entire contents of each of which are incorporated herein by reference in their entirety.

The present invention relates to compounds that are capable of modulating ERAP1. The compounds have potential therapeutic applications in the treatment of a variety of disorders, including proliferative, viral, immune and inflammatory disorders.

BACKGROUND TO THE INVENTION

ERAP1 (Endoplasmic Reticulum Aminopeptidase 1; also referred to as APPILS or ARTS1) is an aminopeptidase important in the generation of a proportion of antigens and neoantigens as part of the antigen presentation pathway[1]. The antigen presentation pathway starts with the breakdown of proteins by the proteasome into peptides. These peptides are transported into the endoplasmic reticulum where a proportion are processed by ERAP1 before binding to the Major Histocompatibility Complex Class I (MHC Class I)[1]. Antigens bound to MHC Class I are then transported to the surface of a cell and presented to CD8+ T-cells and recognised as either self or non-self. Neoantigens are antigens that are specific to cancer and can be recognised as foreign by the immune system leading to destruction of cancer cells. Neoantigens are created either as a direct result of somatic mutations in the DNA of cancer cells, leading to the generation of mutated proteins, or through the indirect consequences of somatic mutations on protein processing and expression. Those cancers with higher rates of mutation and correspondingly higher levels of neoantigens have much greater response rates to the checkpoint inhibitor immunotherapies anti-PD-1 (e.g. pembrolizumab, nivolumab), anti-PD-L1 (e.g. atezolizumab, avelumab, durvalumab) and anti-CTLA4 antibodies (e.g. ipilimumab, tremelimuab) compared with cancers harbouring lower numbers of neoantigens[2,3].

The role of ERAP1 in the antigen presentation pathway is to trim a proportion of peptides, via its aminopeptidase activity, to create antigens and neoantigens of the optimal length for binding to MHC Class I. ERAP1 also over-trims some neoantigens, preventing their binding to MHC Class I and presentation at the cell surface[4]. Ablation of ERAP1 activity has been shown to change the antigen and neoantigen repertoire, leading to an increase in presentation of certain antigens/neoantigens and the presentation of entirely novel antigens/neoantigens[5]. In addition, ERAP1 ablation causes CD8+ T cell dependent tumour rejection in mouse cancer models[4].

Accordingly, modulators of ERAP1 activity may be useful for cancer treatment, either used alone or in combination with current cancer immunotherapy agents, including checkpoint inhibitors, because they change the antigens and neoantigens presented on the surface of cancer cells and make them more visible to the immune system, leading to tumour attack and destruction.

Knockdown of ERAP1 is also shown to reduce the levels of regulatory-like T cells and enhance the killing of cancer cells by natural killer cells[6,7]. This suggests that modulators of ERAP1 activity might be effective cancer treatments by both modulating cancer cell visibility and creating a more anti-tumourogenic immune response. ERAP1's peptide processing role in antigen presentation is also applicable in infectious viral disease.

The present invention seeks to provide compounds that are capable of modulating ERAP1. Such compounds have potential therapeutic applications in the treatment of a variety of disorders, including proliferative disorders, immune disorders and inflammatory disorders.

STATEMENT OF INVENTION

A first aspect of the invention relates to a compound of formula (I), or a pharmaceutically acceptable salt or hydrate thereof,

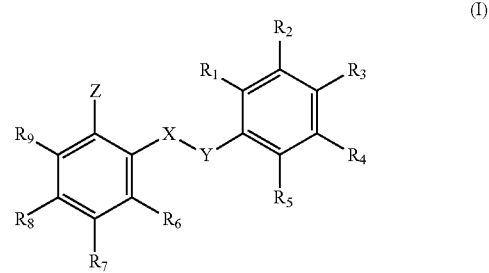

wherein:
the group X—Y is —NHSO$_2$— or —SO$_2$NH—;
Z is a monocyclic aryl or heteroaryl group, each of which is optionally substituted by one or more substituents selected from alkyl, cycloalkyl, halo, alkoxy, CN, haloalkyl and OH;
R$_1$ is H, CN or alkyl;
R$_2$ is selected from COOH and a tetrazolyl group;
R$_3$ is selected from H, Cl and alkyl;
R$_4$ is selected from H and halo;
R$_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy; R$_6$ is H;
R$_7$ is selected from H, CN, haloalkyl, halo, SO$_2$-alkyl, SO$_2$NR$_{12}$R$_{13}$, heteroaryl, CONR$_{10}$R$_{11}$ and alkyl, wherein said heteroaryl group is optionally substituted by one or more substituents selected from alkyl, halo, alkoxy, CN, haloalkyl and OH;
R$_8$ is selected from H, alkyl, haloalkyl and halo;
R$_9$ is H, alkyl or halo, more preferably H or halo;
R$_{10}$ and R$_{11}$ are each independently H or alkyl; and
R$_{12}$ and R$_{13}$ are each independently H or alkyl;
for use in treating or preventing a disorder selected from a proliferative disorder, an immune disorder, a viral disorder and an inflammatory disorder.

Advantageously, the presently claimed compounds are capable of modulating ERAP 1, thereby rendering the compounds of therapeutic interest in the treatment of various disorders, for example, in the field of oncology and immuno-oncology.

A second aspect of the invention relates to a compound of formula (Ia), or a pharmaceutically acceptable salt or hydrate thereof,

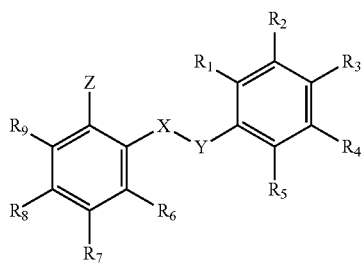

(Ia)

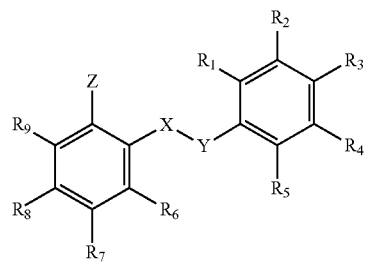

(Ib)

wherein:
the group X—Y is —NHSO$_2$— or —SO$_2$NH—;
Z is:
a monocyclic aryl group, or
a monocyclic heteroaryl group selected from pyridinyl, thienyl, thiazolyl, pyradizinyl, isothiazolyl, tetrazolyl, imidazolyl, pyrimidinyl, 1H-pyrazol-5-yl, 1H-pyrazol-3-yl, 1H-pyrazol-4-yl, triazinyl, 1H-pyrrol-2-yl, 1H-pyrrol-3-yl, 1H-pyrrol-4-yl, furanyl, oxazolyl, 1H-1,2,4-triazol-3-yl, 1H-1,2,4-triazol-5-yl, 1H-1,2,3-triazol-4-yl, 1H-1,2,3-triazol-5-yl and 1H-1,2,3-triazol-1-yl;
each of which is optionally substituted by one or more substituents selected from alkyl, cycloalkyl, halo, alkoxy, CN, haloalkyl and OH;
$R_1$ is H, CN or alkyl;
$R_2$ is selected from COOH and a tetrazolyl group;
$R_3$ is selected from H, Cl and alkyl;
$R_4$ is selected from H and halo;
$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
$R_6$ is H;
$R_7$ is selected from H, CN, haloalkyl, halo, SO$_2$-alkyl, SO$_2$NR$_{12}$R$_{13}$, heteroaryl, CONR$_{10}$R$_{11}$ and alkyl, wherein said heteroaryl group is optionally substituted by one or more substituents selected from alkyl, halo, alkoxy, CN, haloalkyl and OH;
$R_8$ is selected from H, alkyl, haloalkyl and halo;
$R_9$ is H, alkyl or halo;
$R_{10}$ and $R_{11}$ are each independently H or alkyl; and
$R_{12}$ and $R_{13}$ are each independently H or alkyl;
with the proviso that:
when Z is unsubstituted phenyl, X is NH, Y is SO$_2$, $R_1$, $R_3$, $R_4$, and $R_6$-$R_9$ are all H, and $R_5$ is OMe, $R_2$ is other than CO$_2$H;
when Z is unsubstituted phenyl, X is NH, Y is SO$_2$, $R_1$, $R_4$ and $R_6$-$R_9$ are all H, and $R_3$ and $R_5$ are both Cl, $R_2$ is other than CO$_2$H; and
when Z is unsubstituted thien-2-yl, X is NH, Y is SO$_2$, $R_1$, $R_4$, $R_5$, and $R_6$-$R_9$ are all H, and $R_3$ is Me, $R_2$ is other than CO$_2$H.

A third aspect of the invention relates to a compound of formula (Ib), or a pharmaceutically acceptable salt or hydrate thereof, wherein:
the group X—Y is —NHSO$_2$— or —SO$_2$NH—;
Z is a monocyclic aryl or heteroaryl group, each of which is optionally substituted by one or more substituents selected from alkyl, cycloalkyl, halo, alkoxy, CN, haloalkyl and OH;
$R_1$ is H, CN or alkyl;
$R_2$ is selected from COOH and a tetrazolyl group;
$R_3$ is selected from H, Cl and alkyl;
$R_4$ is selected from H and halo;
$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
$R_6$ is H;
$R_7$ is a heteroaryl group which is optionally substituted by one or more substituents selected from alkyl, halo, alkoxy, CN, haloalkyl and OH;
$R_8$ is selected from H, alkyl, haloalkyl and halo; and
$R_9$ is H, alkyl or halo.

Another aspect of the invention relates to a pharmaceutical composition comprising at least one compound as described above and a pharmaceutically acceptable carrier, diluent or excipient.

Another aspect of the invention relates to a compound as described above for use in medicine.

Another aspect of the invention relates to the use of a compound as described above in the preparation of a medicament for treating or preventing a disorder selected from a proliferative disorder, an immune disorder, a viral disorder and an inflammatory disorder.

Another aspect of the invention relates to a compound as described above for use in the prevention or treatment of a disorder caused by, associated with or accompanied by any abnormal ERAP1 activity.

Another aspect of the invention relates to the use of a compound as described above in the preparation of a medicament for the prevention or treatment of a disorder caused by, associated with or accompanied by abnormal ERAP1 activity.

Another aspect of the invention relates to a method of treating a mammal having a disease state alleviated by modulation of ERAP1, wherein the method comprises administering to a mammal a therapeutically effective amount of a compound as described above.

Another aspect of the invention relates to a compound as described above for use in treating or preventing a disease state alleviated by modulation of ERAP1.

Another aspect of the invention relates to the use of a compound as described above in the preparation of a medicament for treating or preventing a disease state alleviated by modulation of ERAP1.

Another aspect of the invention relates to a method of treating or preventing a disorder selected from a proliferative disorder, an immune disorder, a viral disorder and an inflammatory disorder in a subject, wherein the method comprises administering to the subject a therapeutically effective amount of a compound as described above.

DETAILED DESCRIPTION

The present invention relates to bis-aryl sulfonamide compounds that are capable of modulating ERAP1.

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{1-6}$ alkyl, for example, methyl, ethyl, propyl, isopropyl, butyl, isobutyl, tert-butyl, pentyl, hexyl. More preferably, the alkyl is a $C_{1-3}$ alkyl. The term "alkyl"/"alk" in "haloalky"l or "alkoxy" is construed accordingly.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, tetrazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc. Particularly preferred heteroaryl groups include 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-2-yl, thiazol-4-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl.

"Heterocycloalkyl" refers to a cyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is monocyclic or bicyclic. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

Compounds of Formula (I)

One aspect of the invention relates to compounds of formula (I) as described above for use in treating or preventing a disorder selected from a proliferative disorder, an immune disorder, a viral disorder and an inflammatory disorder.

Another aspect of the invention relates to a compound of formula (I), or a pharmaceutically acceptable salt or hydrate thereof, as depicted by the structure shown above, wherein:
the group X—Y is —NHSO$_2$— or —SO$_2$NH—;
Z is a monocyclic aryl or heteroaryl group, each of which is optionally substituted by one or more substituents selected from alkyl, halo, alkoxy, CN haloalkyl and OH;
$R_1$ is H, CN or alkyl;
$R_2$ is selected from COOH and a tetrazolyl group;
$R_3$ is selected from H, Cl and alkyl;
$R_4$ is selected from H and halo;
$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
$R_6$ is H;
$R_7$ is selected from H, CN, haloalkyl, halo, SO$_2$-alkyl, heteroaryl and alkyl;
$R_8$ is selected from H, alkyl, haloalkyl and halo; and
$R_9$ is H or halo.

In the compounds of formula (I), Z is a monocyclic aryl or heteroaryl group, each of which is optionally substituted by one or more substituents selected from alkyl, halo, CN, alkoxy, haloalkyl and OH.

In one preferred embodiment, Z is selected from phenyl, pyridinyl, thienyl, imidazolyl, pyrimidinyl, pyrazolyl, triazinyl, pyrrolyl, thiazolyl, pyradizinyl, isothiazolyl, furanyl, oxazolyl, tetrazozyl and triazolyl, each of which is optionally substituted by one or more substituents selected from alkyl, cycloalkyl, halo, alkoxy, CN, haloalkyl and OH.

In one preferred embodiment, Z is selected from phenyl, pyrimidinyl, pyridinyl, thienyl, imidazolyl, pyrazolyl, pyrrolyl, furanyl, thiazolyl, isothiazolyl, pyradizinyl, oxazolyl, triazinyl, tetrazolyl, and triazolyl, each of which is optionally substituted by one or more substituents selected from alkyl, cycloalkyl, halo, alkoxy, CN, haloalkyl and OH.

In one preferred embodiment, Z is selected from phenyl, pyridinyl, thienyl, imidazolyl, pyrazolyl, pyrrolyl, furanyl, oxazolyl and triazolyl, each of which is optionally substituted by one or more substituents selected from alkyl, halo, alkoxy, CN, haloalkyl and OH.

In one preferred embodiment, Z is selected from pyridinyl, pyrimidinyl, pyrrolyl, thiazolyl and isothiazolyl, each of which is optionally substituted by one or more substituents selected from alkyl, cycloalkyl, halo, alkoxy, CN, haloalkyl and OH.

In one preferred embodiment, Z is selected from phenyl, pyridinyl, thienyl, pyrrolyl, thiazolyl, pyradizinyl, isothiazolyl, pyrazolyl, furanyl, oxazolyl and triazolyl, each of which is optionally substituted by one or more substituents selected from alkyl, cycloalkyl, halo, alkoxy, CN, haloalkyl and OH.

In one preferred embodiment, Z is selected from phenyl, pyridin-2-yl, pyridin-3-yl, pyrimidin-2-yl, pyrimidin-4-yl, pyrimidin-5-yl, pyridin-4-yl, thien-2-yl, thien-3-yl, 1H-imidazol-1-yl, 1H-imidazol-2-yl, 1H-imidazol-4-yl, 1H-imidazol-5-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, 1,3,5-triazin-1-yl, 1,2,3-triazin-4-yl, 1,2,3-triazinyl-5-yl, 1,2,4-triazin-3-yl, 1,2,4-triazin-5-yl, 1,2,4-triazin-6-yl, thiazol-2-yl, thiazol-5-yl, thiazol-4-yl, pyradizin-3-yl, pyradizin-4-yl, isothiazol-5-yl, isothiazol-4-yl, isothiazol-3-yl, 1H-1,2,3,4-tetrazol-4-yl, 2H-1,2,3,4-tetrazol-5-yl, furan-2-yl and furan-3-yl, each of which is optionally substituted by one or more substituents selected from alkyl, halo, cycloalkyl, CN, alkoxy, haloalkyl and OH.

In one preferred embodiment, Z is selected from phenyl, pyridin-2-yl, pyridin-3-yl, pyridin-4-yl, pyrimidin-2-yl, pyrimidin-4-yl, pyrimidin-5-yl, thien-2-yl, thien-3-yl, 1H-imidazol-1-yl, 1H-imidazol-2-yl, 1H-imidazol-4-yl, 1H-imidazol-5-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, 1H-1,2,3,4-tetrazol-4-yl, 2H-1,2,3,4-tetrazol-5-yl, 1,3,5-triazin-1-yl, 1,2,3-triazin-4-yl, 1,2,3-triazinyl-5-yl, 1,2,4-triazin-3-yl, 1,2,4-triazin-5-yl, 1,2,4-triazin-6-yl, thiazol-2-yl, thiazol-5-yl, thiazol-4-yl, pyradizin-3-yl, pyradizin-4-yl, isothiazol-5-yl, isothiazol-4-yl, isothiazol-3-yl, furan-2-yl and furan-3-yl, each of which is optionally substituted by one or more substituents selected from alkyl, cycloalkyl, CN, halo, alkoxy, haloalkyl and OH.

In one preferred embodiment, Z is selected from phenyl, pyridin-2-yl, pyridin-3-yl, pyridin-4-yl, thien-2-yl, thien-3-yl, 1H-imidazol-1-yl, 1H-imidazol-2-yl, 1H-imidazol-4-yl, 1H-imidazol-5-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, furan-2-yl and furan-3-yl, each of which is optionally substituted by one or more substituents selected from alkyl, CN, halo, alkoxy, haloalkyl and OH.

In one particularly preferred embodiment, Z is selected from phenyl, pyridin-2-yl, pyridin-3-yl, pyrimidin-2-yl, pyrimidin-4-yl, pyrimidin-5-yl, pyridin-4-yl, thien-2-yl, thien-3-yl, 1H-imidazol-1-yl, 1H-pyrrol-1-yl, 1H-pyrrol-2-yl, 1H-pyrazol-1-yl, 1H-pyrazol-5-yl, thiazol-2-yl, thiazol-5-yl, thiazol-4-yl, pyradizin-3-yl, isothiazol-5-yl, oxazol-5-yl, 1H-1,2,4-triazol-1-yl, furan-2-yl and furan-3-yl, each of which is optionally substituted by one or more substituents selected from alkyl, cycloalkyl, halo, CN, alkoxy, haloalkyl and OH.

In one highly preferred embodiment, Z is selected from phenyl, pyridin-2-yl, pyridin-3-yl, thien-2-yl, 1H-pyrrol-1-yl, 1H-pyrrol-2-yl, each of which is optionally substituted by one or more substituents selected from Me, F, Cl, CN, cyclopropyl and MeO.

In one preferred embodiment, Z is selected from pyridin-2-yl, pyridin-3-yl, pyrimidin-2-yl, pyrimidin-4-yl, pyrimidin-5-yl, 1H-pyrrol-1-yl, 1H-pyrrol-2-yl, thiazol-2-yl, thiazol-5-yl, thiazol-4-yl, isothiazol-3-yl, isothiazol-4-yl and isothiazol-5-yl, each of which is optionally substituted by one or more substituents selected from alkyl, cycloalkyl, halo, alkoxy, CN, haloalkyl and OH. Preferably, the one or more optional substituents are selected from Me, F, Cl, CN, cyclopropyl and MeO.

In one preferred embodiment, Z is selected from pyridin-2-yl, pyrimidin-2-yl, 1H-pyrrol-1-yl, thiazol-4-yl and isothiazol-3-yl, each of which is optionally substituted by one or more substituents selected from alkyl, cycloalkyl, halo, alkoxy, CN, haloalkyl and OH.

Preferably, the one or more optional substituents are selected from Me, F, Cl, CN, cyclopropyl and MeO.

In another preferred embodiment, Z is selected from the following:

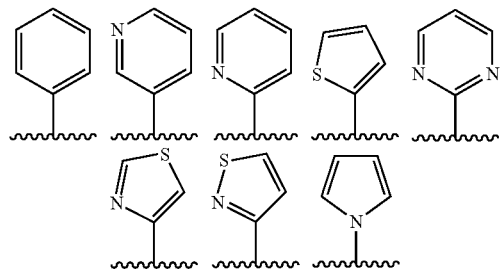

each of which is optionally substituted by by one or more substituents selected from alkyl, cycloalkyl, halo, alkoxy, CN, haloalkyl and OH. Preferably, the one or more optional substituents are selected from Me, F, Cl, CN, cyclopropyl and MeO.

In one preferred embodiment, Z is selected from the following:

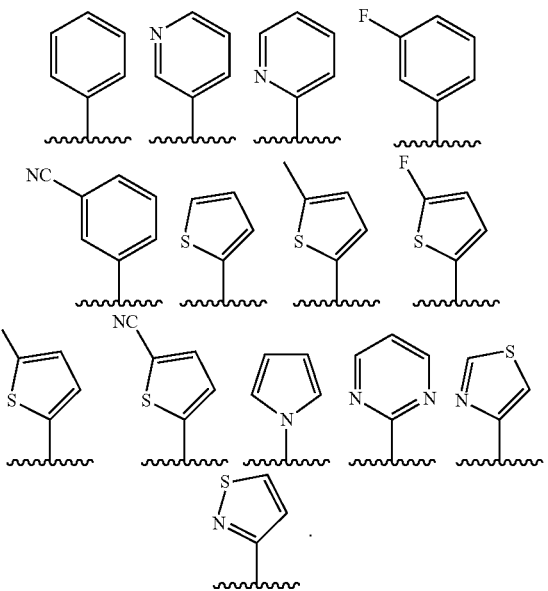

In one preferred embodiment, $R_1$ is H, CN or Me, more preferably H.

In one preferred embodiment, $R_2$ is COOH.

In one particularly preferred embodiment, X—Y is NH—$SO_2$.

In another preferred embodiment, X—Y is $SO_2$—NH.

In one preferred embodiment, $R_4$ is selected from H, Cl and F.

In one preferred embodiment, $R_5$ is selected from alkyl, haloalkyl, $SO_2$-alkyl, Cl, alkoxy, OH, CN, hydroxyalkyl, alkylthio, heteroaryl, cycloalkyl, heterocycloalkyl and haloalkoxy.

In one preferred embodiment, $R_5$ is selected from alkyl, alkoxy and cycloalkyl.

In one particularly preferred embodiment, $R_5$ is selected from OMe, OEt, Me, Et, cyclobutyl and cyclopropyl.

In one particularly preferred embodiment, $R_5$ is selected from OMe, OEt, Me, Et and cyclopropyl.

In another preferred embodiment, $R_5$ is selected from H, Me, $CF_3$, $CHF_2$, $SO_2$-Me, Cl, MeO, OH, $CH_2OH$, SMe, cyclopropyl, triazolyl, oxetanyl and CN. More preferably, $R_5$ is selected from H, CN, Me, $SO_2$-Me, $CF_3$ and $CHF_2$, $CH_2OH$, SMe, cyclopropyl, 3,4-triazol-1-yl, oxetan-3-yl. Even more preferably, $R_5$ is selected from H, CN, Me, $SO_2$-Me, $CF_3$ and $CHF_2$.

In another preferred embodiment, $R_5$ is selected from OMe, Me, Et, Pr and Cl, and is more preferably OMe or Et.

In one particularly preferred embodiment, $R_5$ is selected from OMe, Et, and cyclopropyl.

In one particularly preferred embodiment, $R_5$ is OMe.

In one highly preferred embodiment, $R_5$ is cyclopropyl.

In another particularly preferred embodiment, $R_5$ is Et.

In one preferred embodiment, $R_7$ is selected from H, CN, haloalkyl, Cl, F, $SO_2$-alkyl, $CONR_{10}R_{11}$, heteroaryl and alkyl, wherein said heteroaryl group is optionally substituted by one or more substituents selected from alkyl, halo, alkoxy, CN, haloalkyl and OH.

In one preferred embodiment, $R_7$ is selected from H, CN, haloalkyl, Cl, F, $SO_2$-alkyl, $CONR_{10}R_{11}$, heteroaryl and alkyl, wherein the heteroaryl group is selected from pyrazolyl, isothiazolyl, triazolyl, tetrazolyl and isoxazolyl, each of which is optionally substituted by one or more substituents selected from alkyl, halo, alkoxy, CN, haloalkyl and OH In one preferred embodiment, $R_7$ is selected from H, CN, $CF_3$, $CHF_2$, Cl, F, $SO_2$-Me, $CONH_2$, heteroaryl and Me, wherein said heteroaryl group is optionally substituted by one or more substituents selected from alkyl, halo, alkoxy, CN, haloalkyl and OH.

In one preferred embodiment, $R_7$ is selected from H, CN, $CF_3$, $CHF_2$, Cl, F, $SO_2$-Me, $CONH_2$, heteroaryl and Me, wherein said heteroaryl group is selected from pyrazolyl, isothiazolyl, triazolyl, tetrazolyl and isoxazolyl, each of which is optionally substituted by one or more substituents selected from alkyl, halo, alkoxy, CN, haloalkyl and OH In one preferred embodiment, $R_y$ is selected from H, CN, haloalkyl, Cl, F, $SO_2$-alkyl, $CONR_{10}R_{11}$, heteroaryl and alkyl, wherein the heteroaryl group is selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

In one preferred embodiment, $R_7$ is selected from H, CN, $CF_3$, $CHF_2$, Cl, F, $SO_2$-Me, $CONH_2$, heteroaryl and Me, wherein said heteroaryl group is selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

In one preferred embodiment, $R_7$ is selected from H, CN, Me, $SO_2$-Me, $CONH_2$, tetrazolyl, $CF_3$ and $CHF_2$.

In another preferred embodiment, $R_7$ is selected from CN, haloalkyl, $SO_2$-alkyl, $CONR_{10}R_{11}$ and tetrazolyl. More preferably $R_7$ is selected from CN, haloalkyl, $SO_2$-alkyl, and tetrazolyl. Even more preferably for this embodiment, $R_7$ is selected from $CF_3$, CN, 1H-1,2,3,4-tetrazol-1-yl, $CONH_2$ and $SO_2Me$.

In one preferred embodiment, $R_7$ is haloalkyl or heteroaryl, more preferably tetrazolyl.

In one preferred embodiment, $R_7$ is a heteroaryl group which is optionally substituted by one or more substituents selected from alkyl, halo, alkoxy, CN, haloalkyl and OH. Preferably, the heteroaryl group is selected from pyrazolyl, isothiazolyl, triazolyl, tetrazolyl and isoxazolyl, each of which is optionally substituted by one or more substituents selected from alkyl, halo, alkoxy, CN, haloalkyl and OH.

In one preferred embodiment, $R_7$ is a heteroaryl group selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

In one preferred embodiment, $R_7$ is haloalkyl, more preferably, $CF_3$.

In one preferred embodiment, $R_7$ is CN.

In one preferred embodiment, $R_7$ is $SO_2$-alkyl, more preferably $SO_2Me$.

In one preferred embodiment, $R_7$ is $SO_2NR_{12}R_{13}$, more preferably $SO_2NH_2$.

In one preferred embodiment, $R_8$ is selected from H, alkyl, haloalkyl and Cl.

In another preferred embodiment, $R_5$ is selected from alkyl and halo. More preferably, $R_8$ is selected from Me, Cl and F. Even more preferably, $R_8$ is selected from Cl and F.

In one preferred embodiment, $R_8$ is H or haloalkyl, more preferably H or $CF_3$, even more preferably H.

In one preferred embodiment, $R_8$ is selected from H and halo, more preferably H, Cl and F.

In one preferred embodiment, $R_9$ is H or halo.

In one preferred embodiment, $R_9$ is H or F, more preferably, H.

In another preferred embodiment, $R_9$ is H, F or Me, more preferably H.

In one preferred embodiment, $R_1$, $R_3$, $R_4$, $R_6$, $R_8$ and $R_9$ are all H.

In one preferred embodiment, $R_{10}$, $R_{11}$, $R_{12}$ and $R_{13}$ are each independently H or Me, more preferably H.

In one preferred embodiment:

$R_2$ is COOH;

X—Y is NH—$SO_2$;

$R_5$ is selected from OMe, OEt, Me, Et, and cyclopropyl, and is more preferably OMe or Et; $R_1$, $R_3$, $R_4$, $R_6$, $R_8$ and $R_9$ are all H; and $R_7$ is selected from CN, haloalkyl, $SO_2$-alkyl and tetrazolyl, and is more preferably, $SO_2$ Me or $CF_3$.

In one preferred embodiment:

$R_2$ is COOH;

X—Y is NH—$SO_2$;

$R_5$ is selected from OMe, OEt, Me, Et, and cyclopropyl, and is more preferably cyclopropyl;

$R_1$, $R_3$, $R_4$, $R_6$, $R_5$ and $R_9$ are all H; and $R_7$ is selected from CN, haloalkyl, $SO_2$-alkyl and tetrazolyl, and is more preferably, $SO_2$ Me or $CF_3$.

In one preferred embodiment:

$R_2$ is COOH;

X—Y is NH—$SO_2$;

$R_5$ is selected from OMe, OEt, Me, Et, and cyclopropyl, and is more preferably cyclopropyl; $R_1$, $R_3$, $R_4$, $R_6$, $R_5$ and $R_9$ are all H; and $R_7$ is selected from CN, haloalkyl, $SO_2$-alkyl and tetrazolyl, and is more preferably, CN.

In one preferred embodiment:
R₂ is COOH;
X—Y is NH—SO₂;
R₅ is selected from cyclopropyl, OMe and Et, and is more preferably cyclopropyl;
R₁, R₃, R₄, R₆, R₈ and R₉ are all H; and
R₇ is selected from CN, haloalkyl, heteroaryl and SO₂-alkyl, and is more preferably CN; and
Z is selected from the following:

[structures]

In one preferred embodiment:
R₂ is COOH;
X—Y is NH—SO₂;
R₅ is selected from cyclopropyl, OMe and Et, and is more preferably cyclopropyl;
R₁, R₃, R₄, R₆, and R₉ are all H;
R₇ is selected from CN, haloalkyl, heteroaryl and SO₂-alkyl, and is more preferably CN;
R₈ is H, Cl or F, more preferably Cl or F; and
Z is selected from the following:

[structures]

In one preferred embodiment:
R₂ is COOH;
X—Y is NH—SO₂;
R₅ is selected from cyclopropyl, OMe and Et;
R₁, R₃, R₄, R₆, R₈ and R₉ are all H; and
R₇ is selected from CN, haloalkyl, heteroaryl and SO₂-alkyl; and
Z is selected from the following:

[structures]

In one preferred embodiment:
R₂ is COOH;
X—Y is NH—SO₂;
R₅ is cyclopropyl;
R₁, R₃, R₄, R₆, R₈ and R₉ are all H; and
R₇ is selected from CN, haloalkyl and SO₂-alkyl, and is more preferably, SO₂Me or CF₃; and
Z is selected from the following:

[structures]

In one preferred embodiment:
R$_2$ is COOH;
X—Y is NH—SO$_2$;
R$_5$ is cyclopropyl;
R$_1$, R$_3$, R$_4$, R$_6$, R$_8$ and R$_9$ are all H; and
R$_7$ is selected from CN, haloalkyl and SO$_2$-alkyl, and is more preferably, SO$_2$Me or CF$_3$; and
Z is selected from the following:

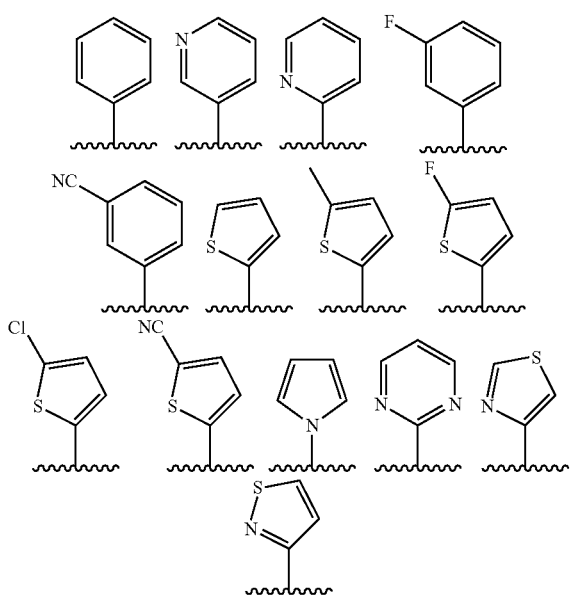

In one preferred embodiment:
R$_2$ is COOH;
X—Y is NH—SO$_2$;
R$_5$ is cyclopropyl;
R$_1$, R$_3$, R$_4$, R$_6$, R$_8$ and R$_9$ are all H;
R$_7$ is CF$_3$; and
Z is phenyl.

In one preferred embodiment:
R$_2$ is COOH;
X—Y is NH—SO$_2$;
R$_5$ is Et;
R$_1$, R$_3$, R$_4$, R$_6$, R$_8$ and R$_9$ are all H; and
R$_7$ is selected from CN, haloalkyl, heteroaryl, SO$_2$-alkyl; and
Z is selected from the following:

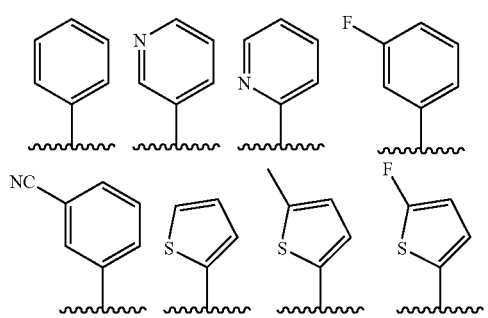

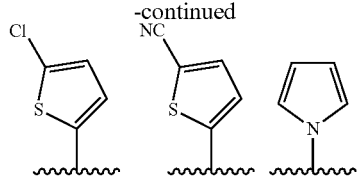

In one preferred embodiment:
R$_2$ is COOH;
X—Y is NH—SO$_2$;
R$_5$ is Et;
R$_1$, R$_3$, R$_4$, R$_6$, R$_8$ and R$_9$ are all H; and
R$_7$ is selected from CN and CF$_3$; and
Z is selected from the following:

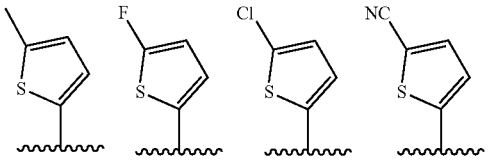

In one preferred embodiment:
R$_2$ is COOH;
X—Y is NH—SO$_2$;
R$_5$ is Et;
R$_1$, R$_3$, R$_4$, R$_6$, R$_8$ and R$_9$ are all H; and
R$_7$ is selected from CN and CF$_3$; and
Z is selected from the following:

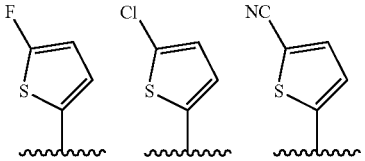

In one preferred embodiment:
R$_2$ is COOH;
X—Y is NH—SO$_2$;
R$_5$ is MeO;
R$_1$, R$_3$, R$_4$, R$_6$, R$_8$ and R$_9$ are all H; and
R$_7$ is selected from CN, haloalkyl and SO$_2$-alkyl; and
Z is selected from the following:

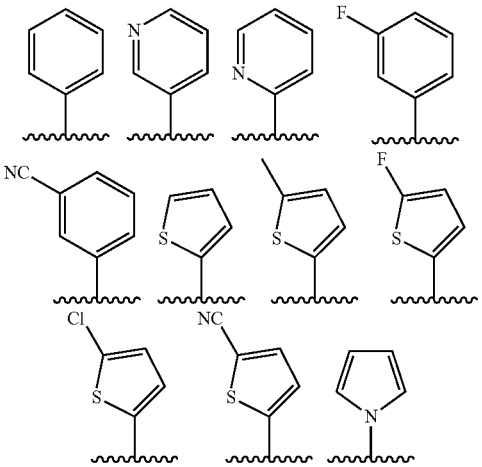

In one preferred embodiment:

$R_2$ is COOH;

X—Y is NH—SO$_2$;

$R_5$ is MeO;

$R_1$, $R_3$, $R_4$, $R_6$, $R_8$ and $R_9$ are all H; and $R_7$ is CF$_3$; and

Z is selected from the following:

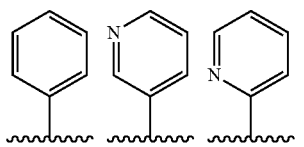

In one preferred embodiment:

$R_2$ is COOH;

X—Y is NH—SO$_2$;

$R_5$ is MeO;

$R_1$, $R_3$, $R_4$, $R_6$, $R_8$ and $R_9$ are all H; and $R_7$ is CF$_3$; and

Z is selected from the following:

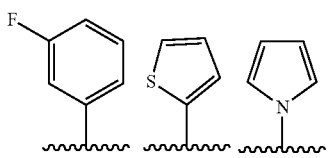

In one preferred embodiment, the compound of formula (I) is selected from the following:

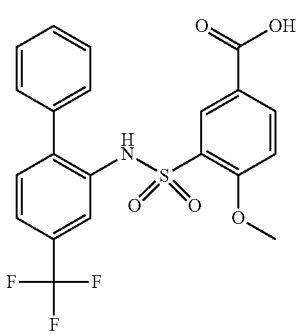

(1)

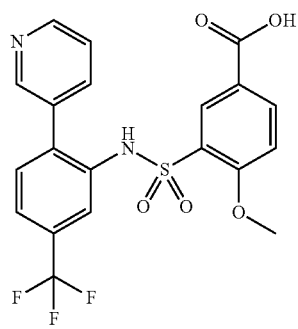

(2)

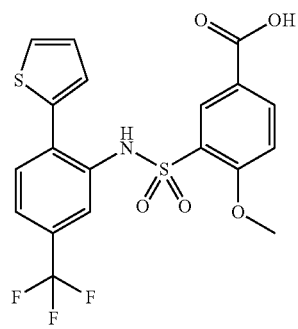

(3)

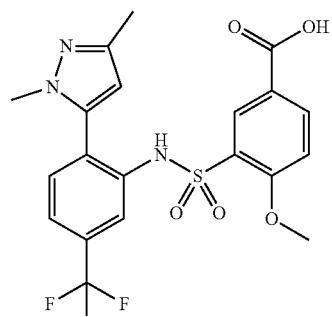

(4)

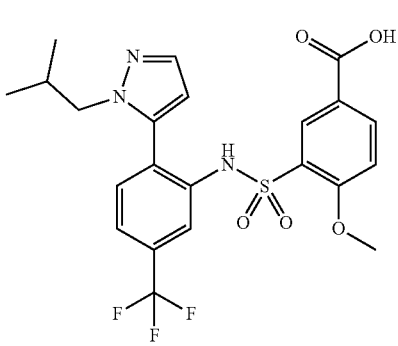

(5)

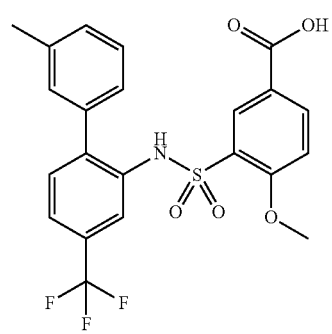

(6)

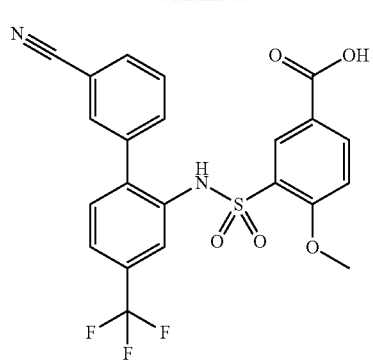
(7)
(8)
(9)
(10)
(11)
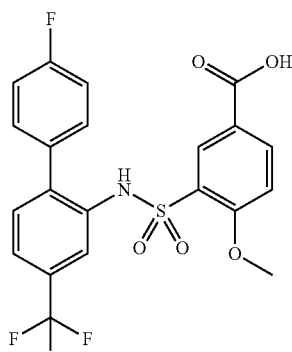
(12)
(13)
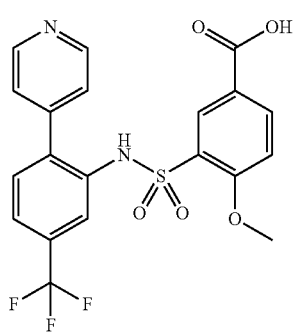
(14)
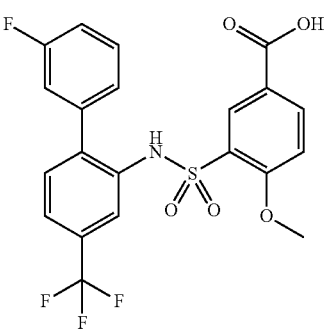
(15)

-continued
(16)
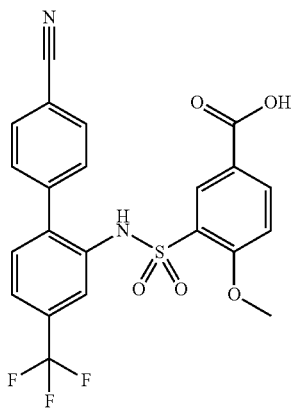
(17)
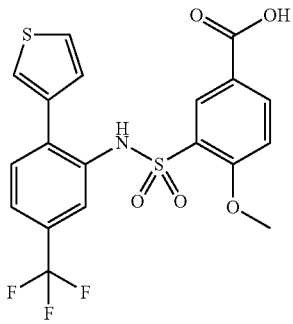
(18)
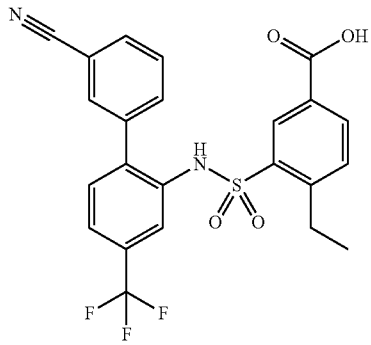
(19)
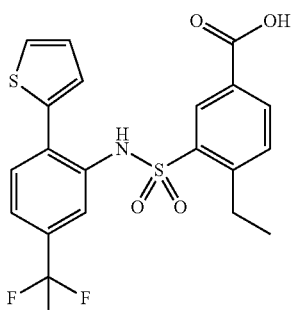
-continued
(20)
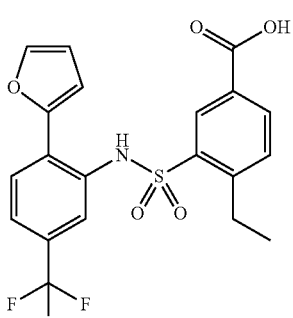
(21)
(22)
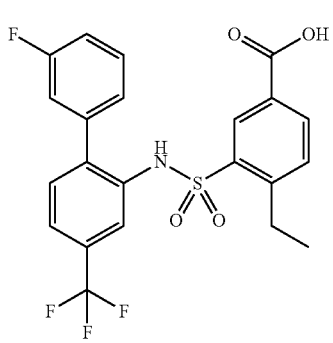
(23)
(24)

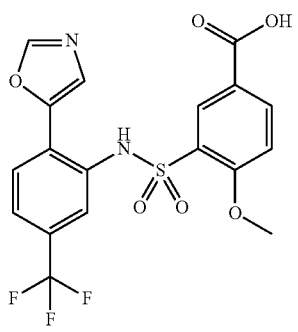
(25)
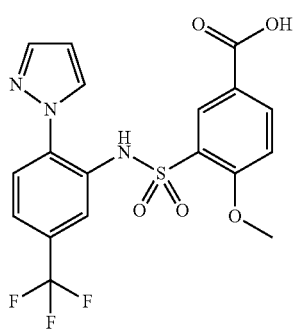
(30)
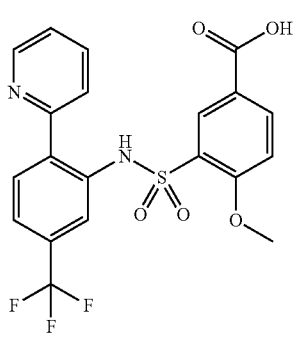
(26)
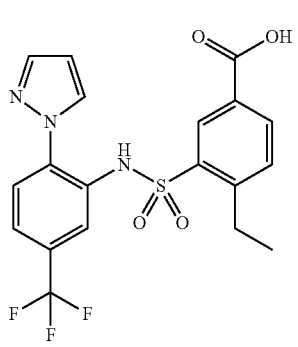
(31)
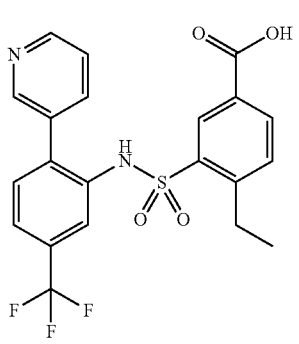
(27)
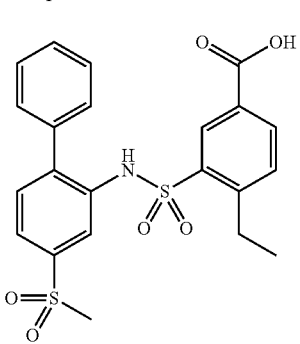
(32)
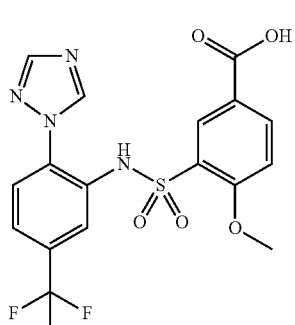
(28)
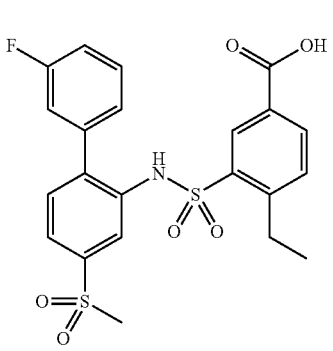
(33)
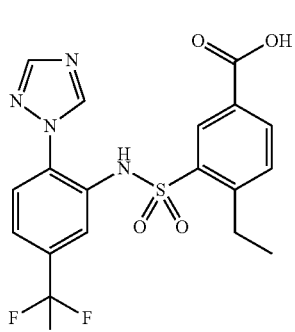
(29)
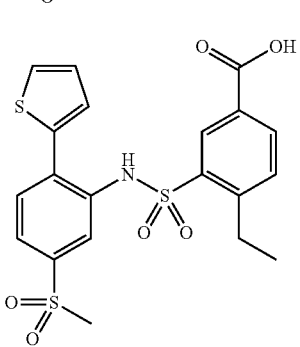
(34)

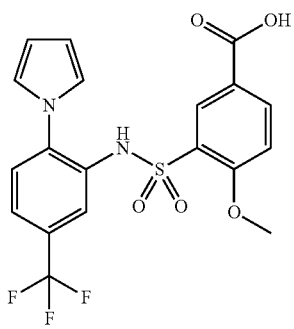
(35)
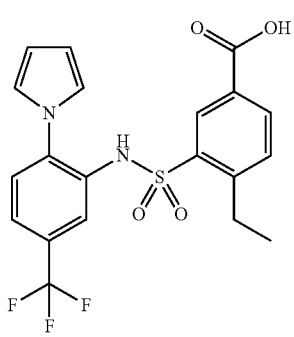
(36)
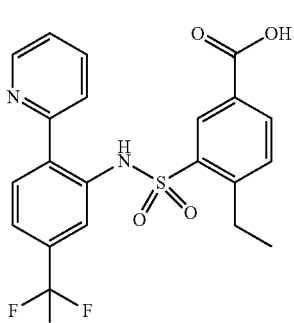
(37)
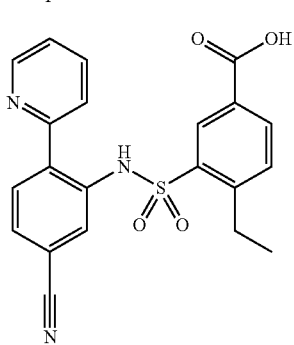
(38)
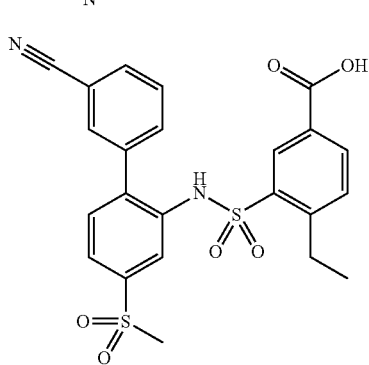
(39)
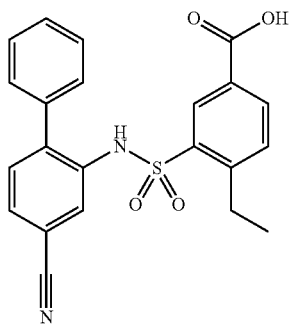
(40)
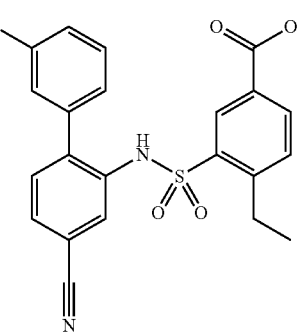
(41)
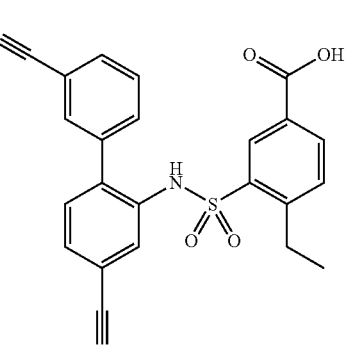
(42)
(43)
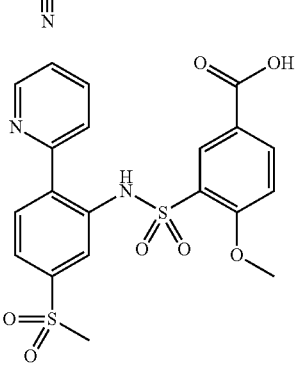
(44)

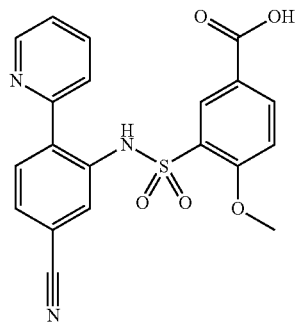
(45)
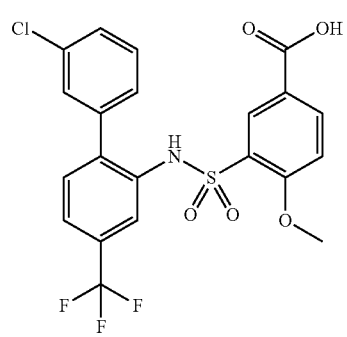
(46)
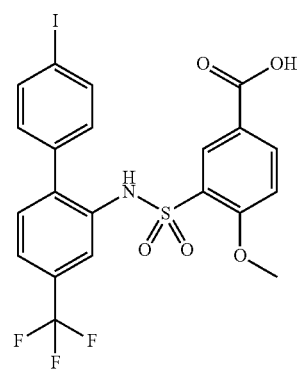
(47)
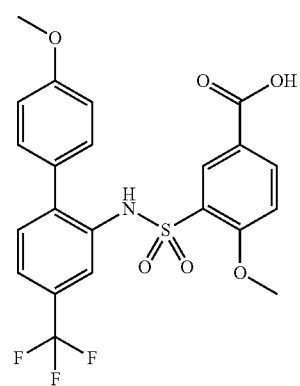
(48)
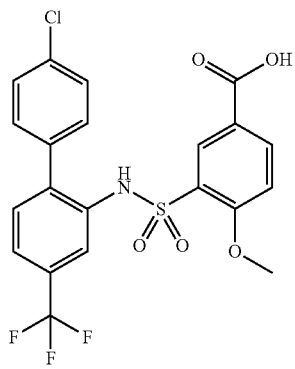
(50)
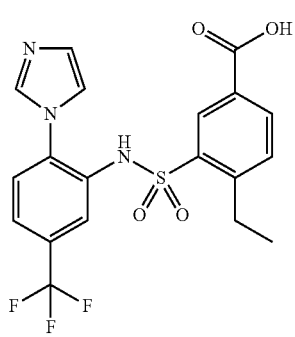
(50)
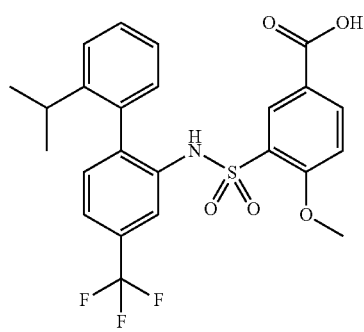
(51)
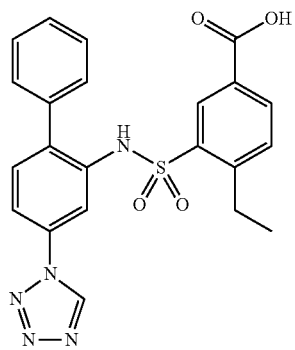
(52)

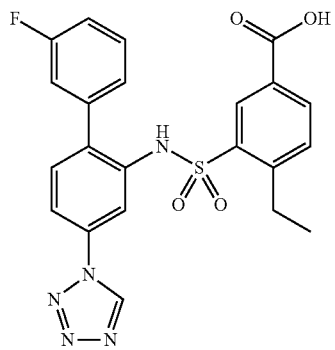
(53)
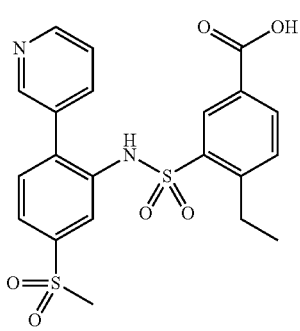
(54)
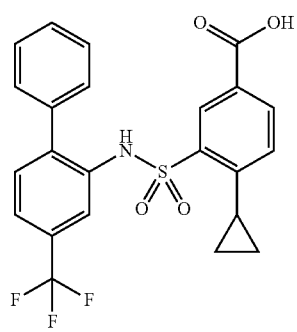
(55)
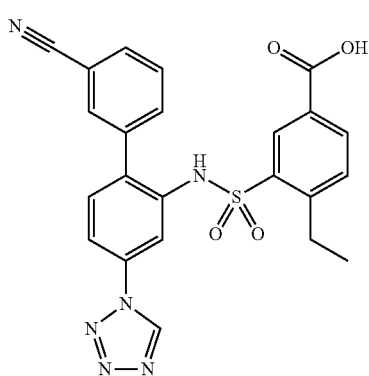
(56)
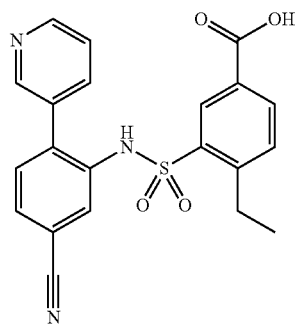
(57)
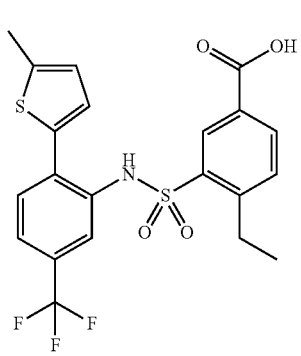
(58)
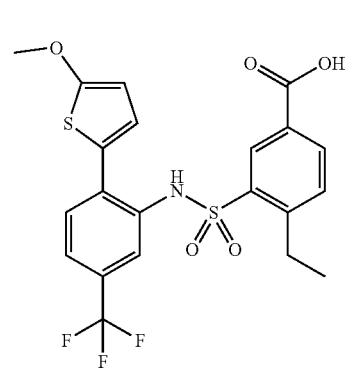
(59)
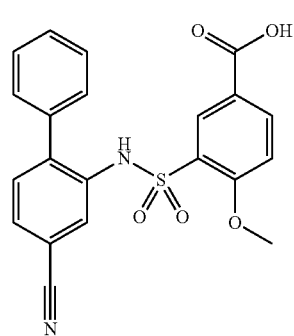
(60)

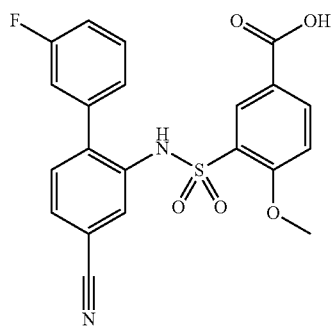
(61)
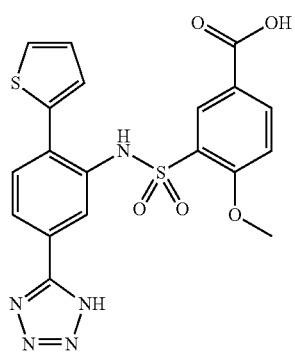
(65)
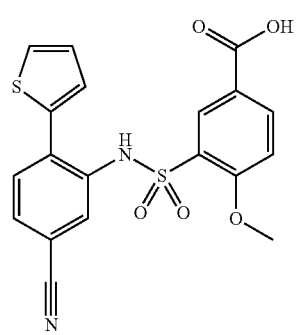
(62)
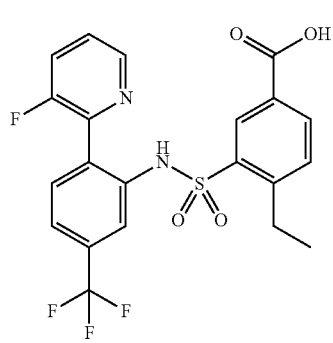
(66)
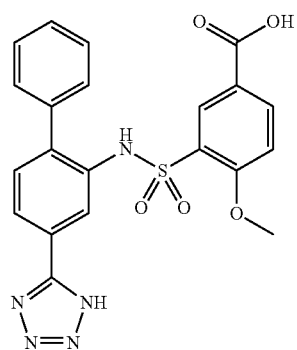
(63)
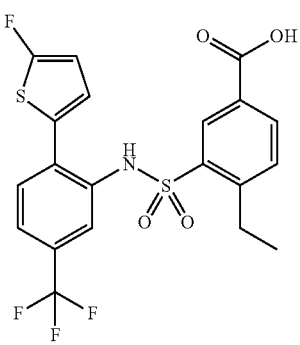
(67)
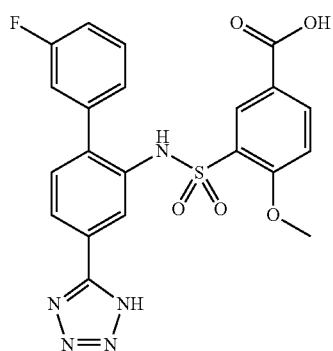
(64)
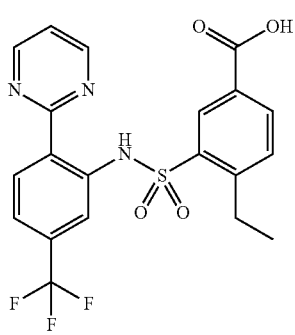
(68)

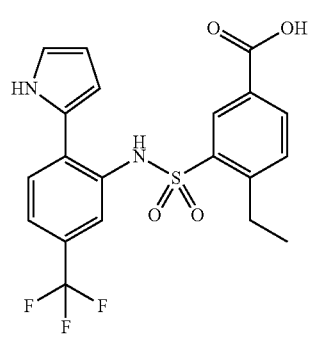
(69)
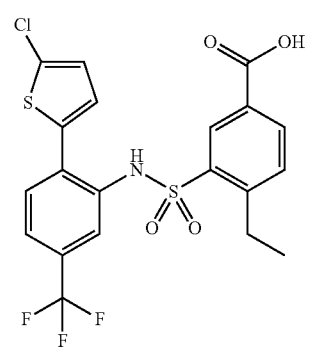
(70)
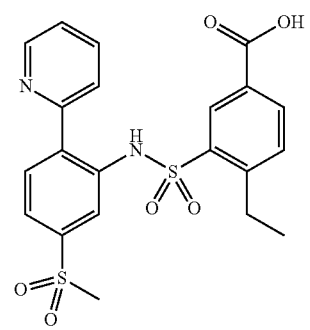
(71)
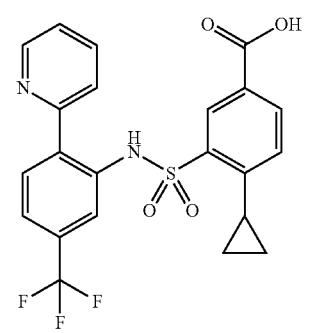
(72)
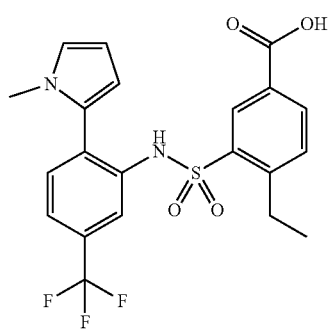
(73)
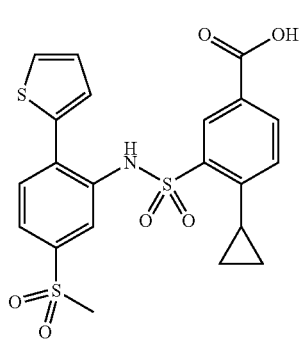
(74)
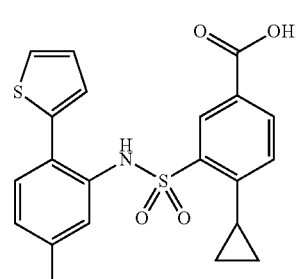
(75)
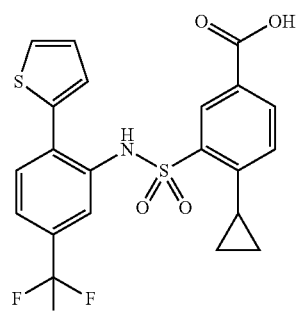
(76)
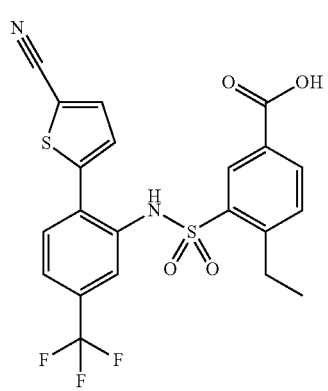
(77)

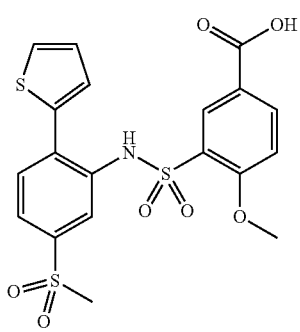 (78)
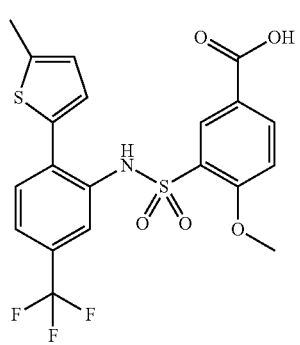 (79)
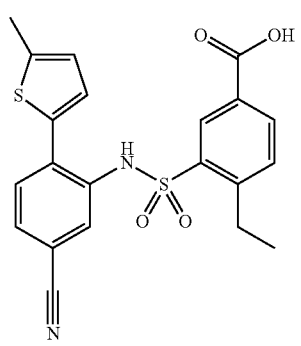 (80)
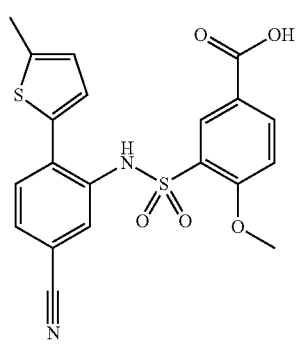 (81)
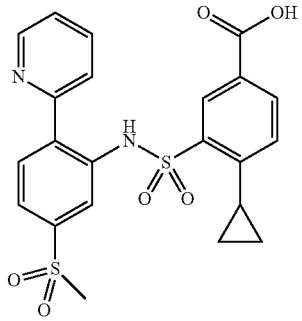 (82)
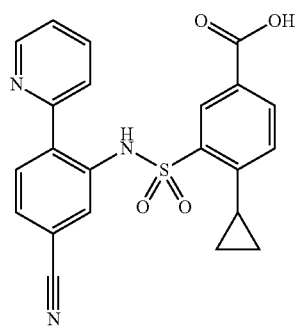 (83)
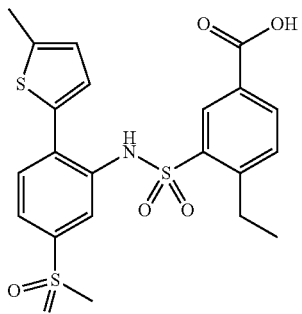 (84)
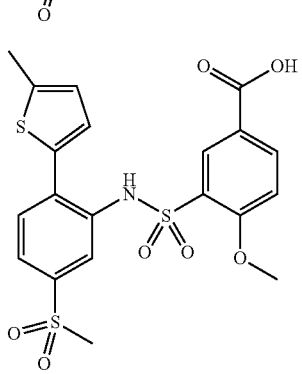 (85)
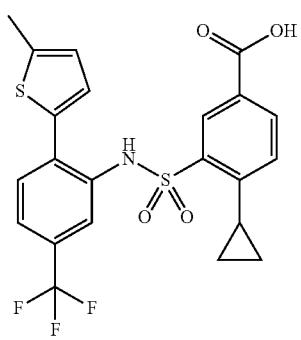 (86)

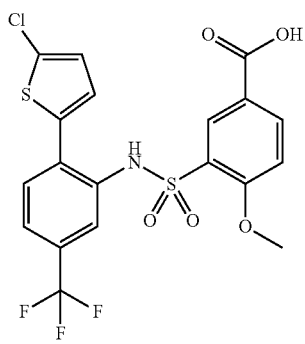
(87)
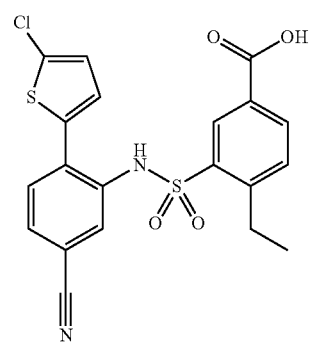
(91)
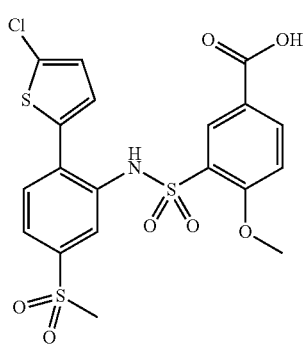
(88)
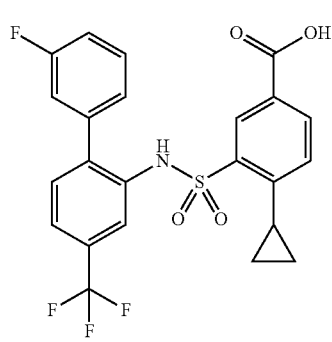
(92)
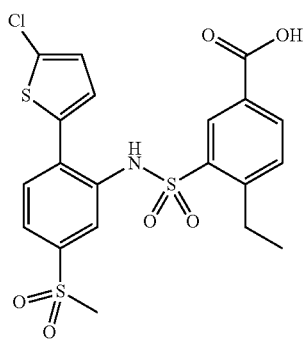
(89)
(93)
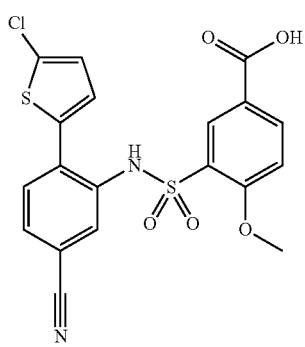
(90)
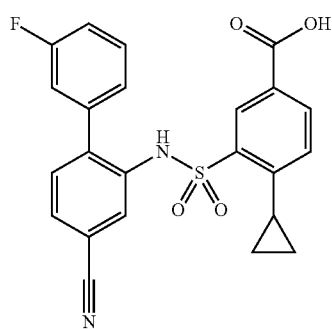
(94)

(95) 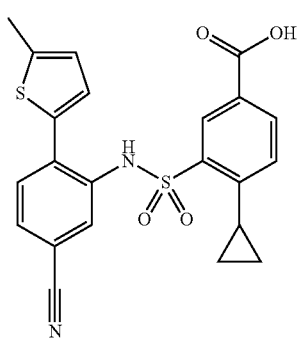
(96) 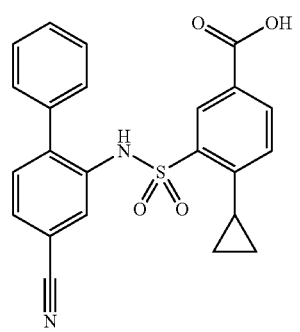
(97) 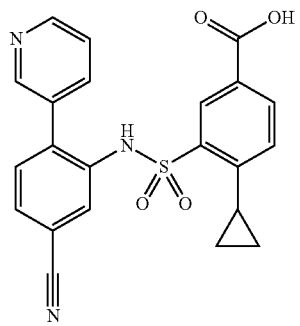
(98) 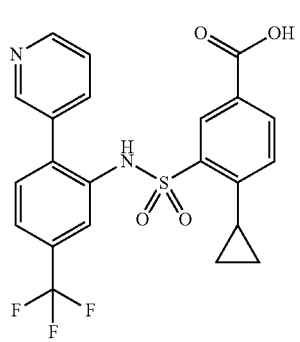
(99) 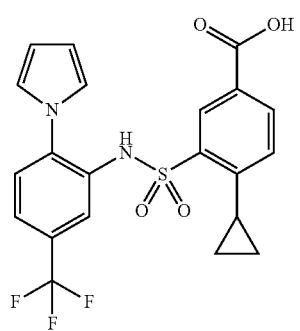
(100) 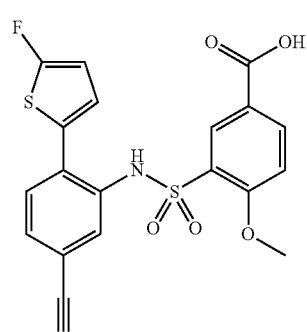
(101) 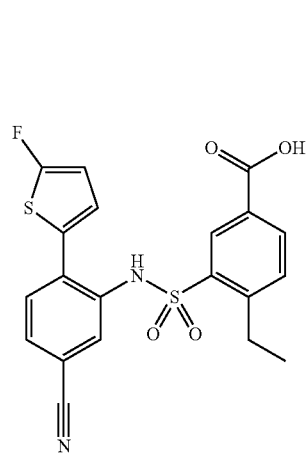
(102) 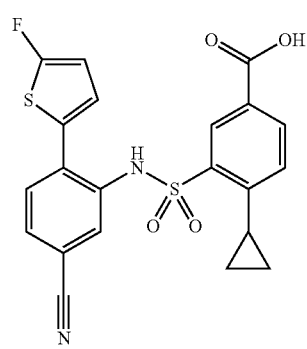
(103) 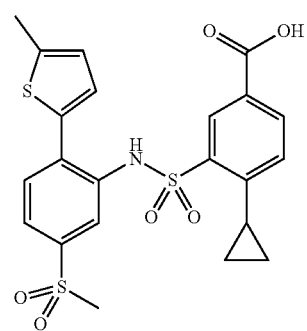

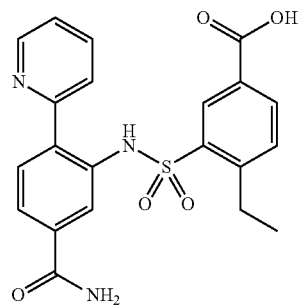
(104)
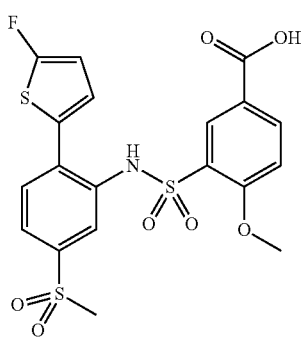
(105)
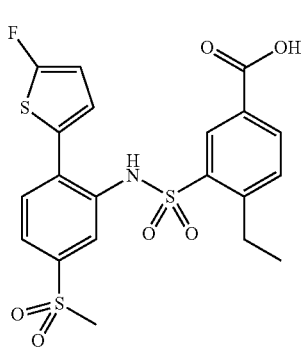
(106)
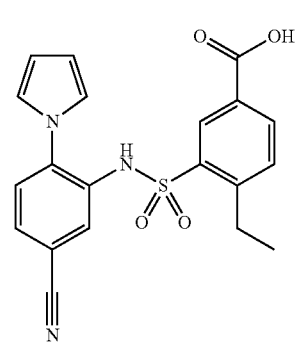
(107)
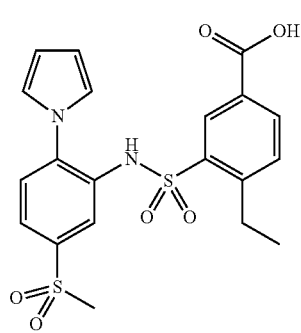
(108)
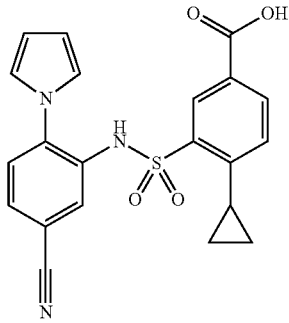
(109)
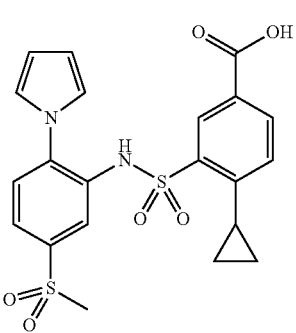
(110)
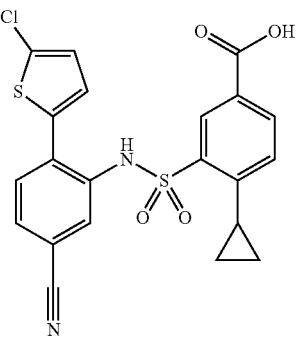
(111)
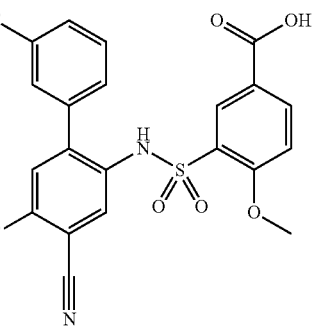
(112)
(113)

(114) 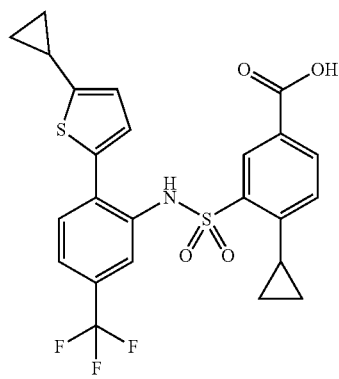
(115) 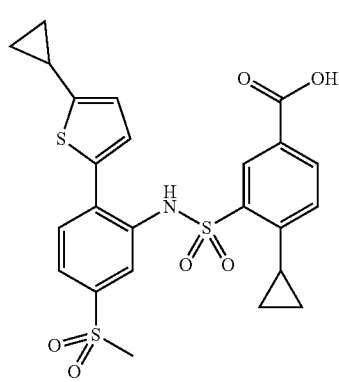
(116) 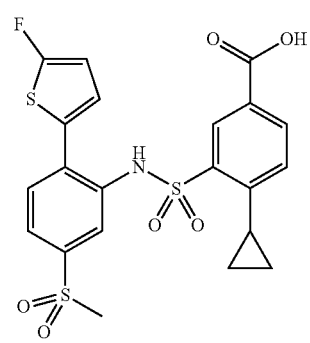
(117)
(118) 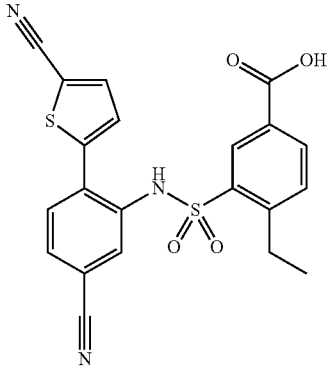
(119) 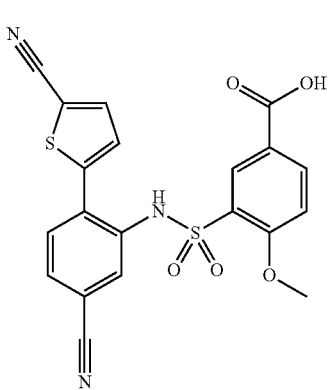
(120) 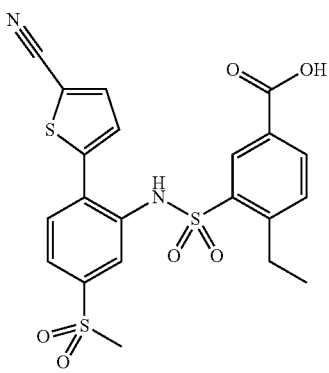
(121) 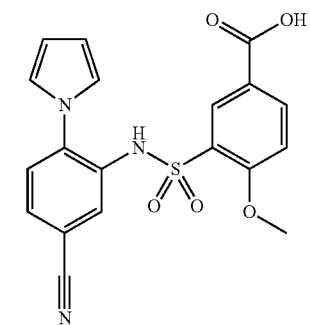

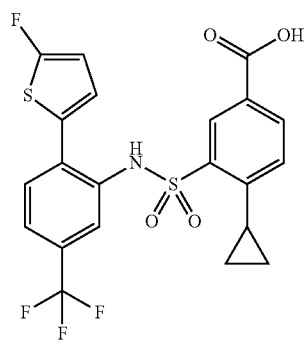
(122)
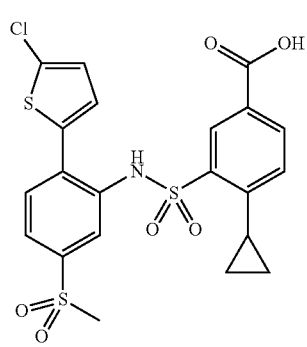
(123)
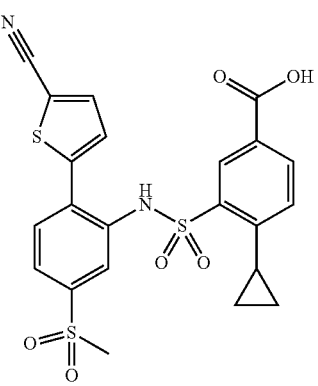
(124)
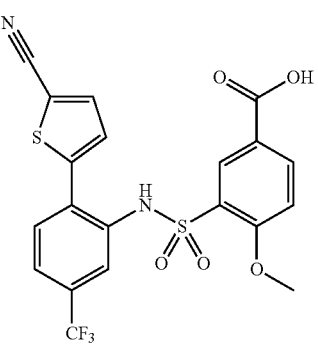
(125)
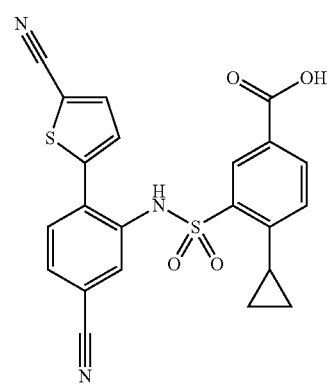
(126)
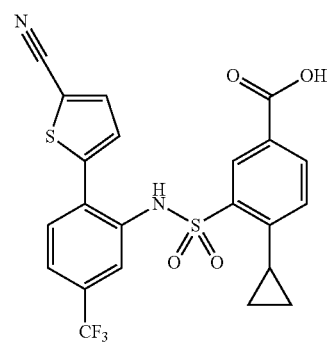
(127)
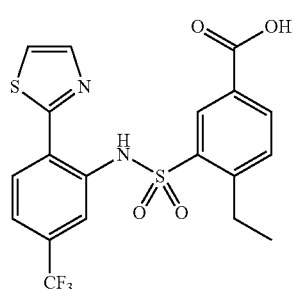
(128)
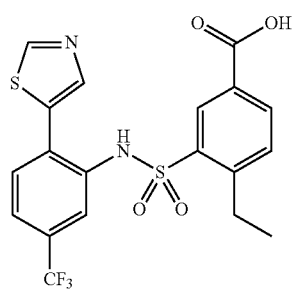
(129)
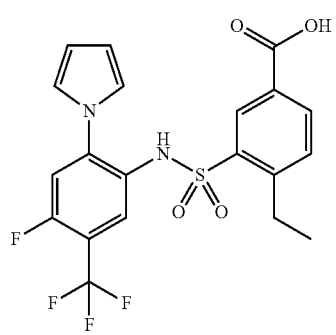
(130)

(131)
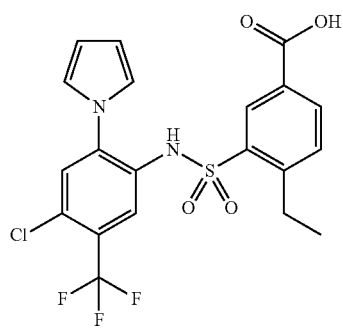
(135)
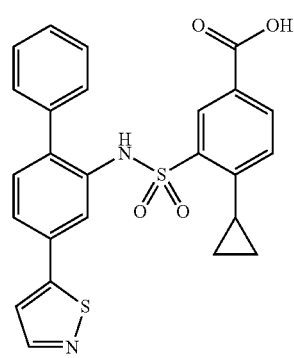
(132)
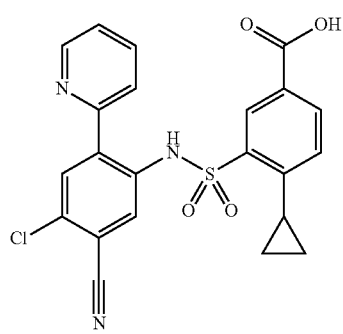
(136)
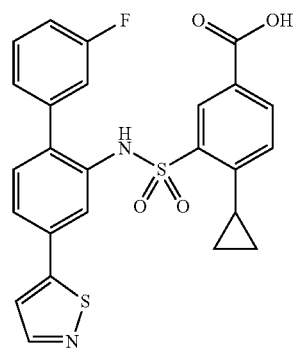
(133)
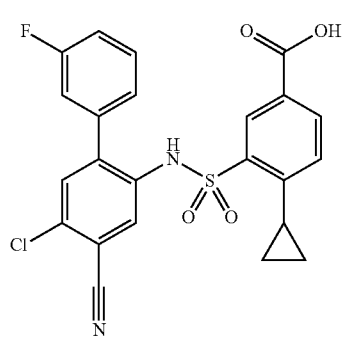
(137)
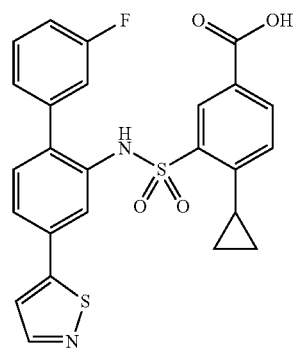
(134)
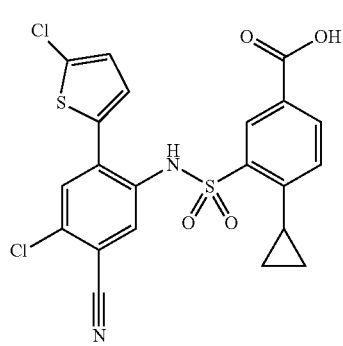
(138)
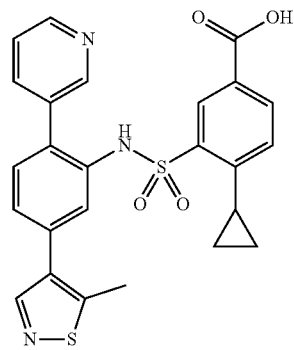

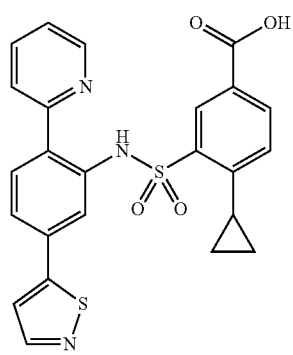 (139)
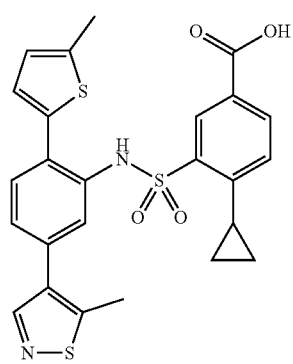 (140)
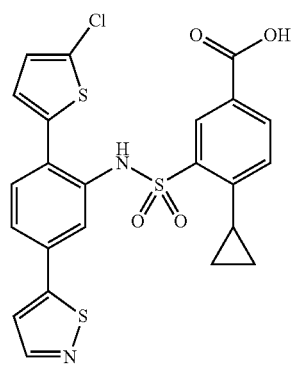 (141)
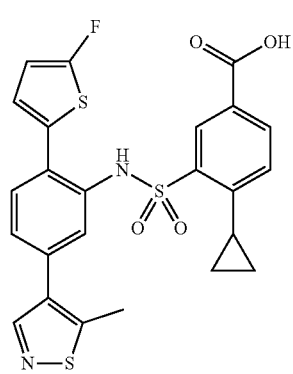 (142)
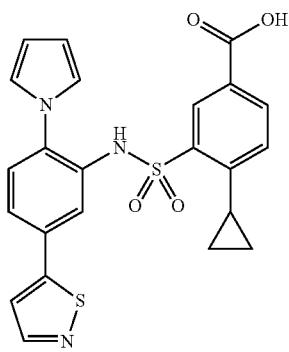 (143)
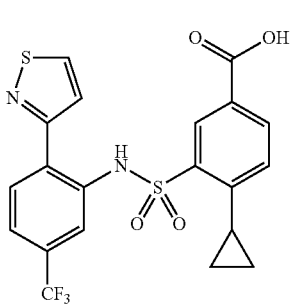 (151)
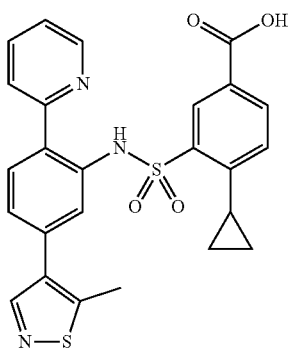 (144)
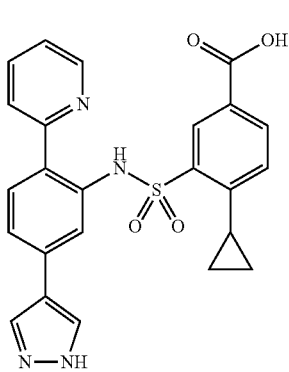 (145)

(146) 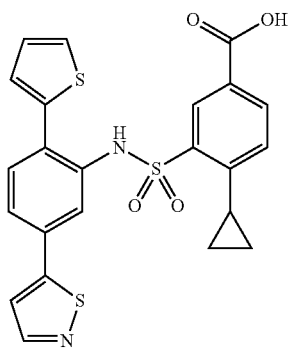
(147) 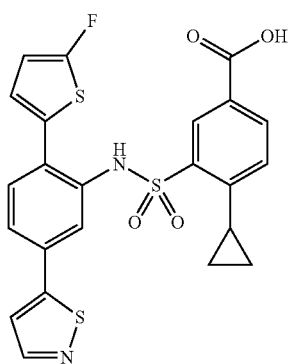
(148) 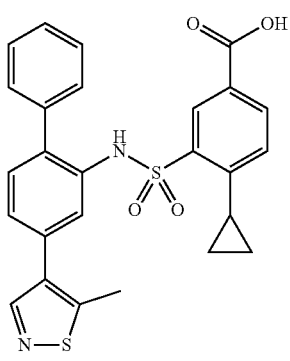
(149) 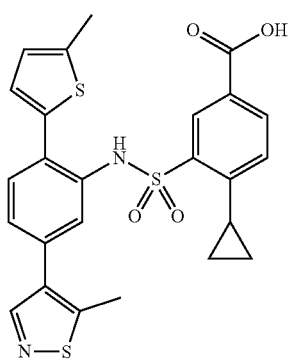
(150) 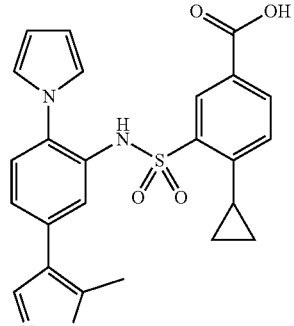
(152) 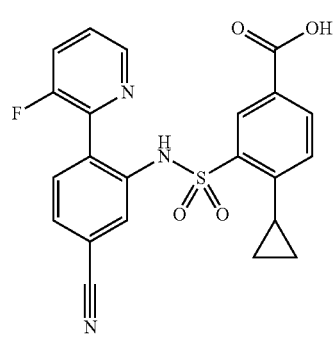
(153) 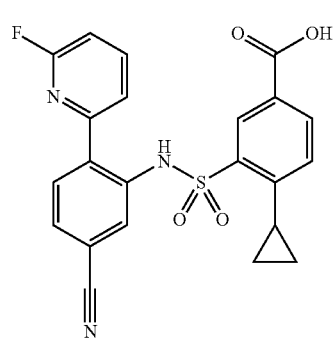
(154) 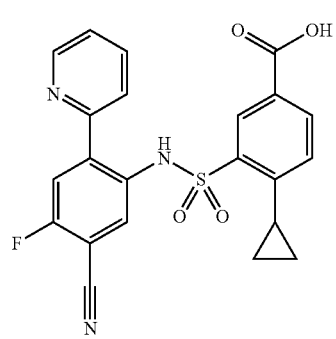
(155) 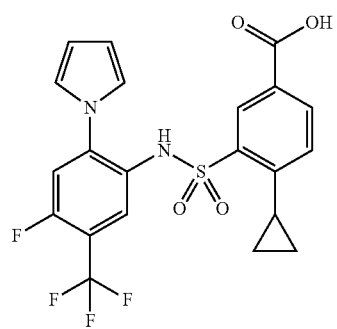

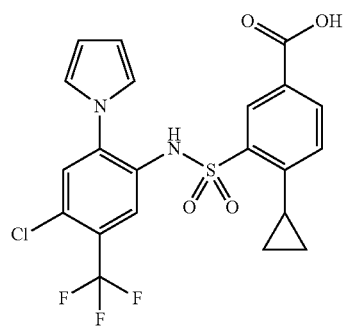
(156)
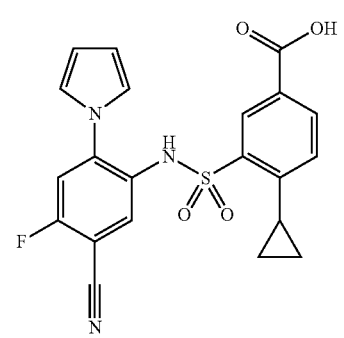
(157)
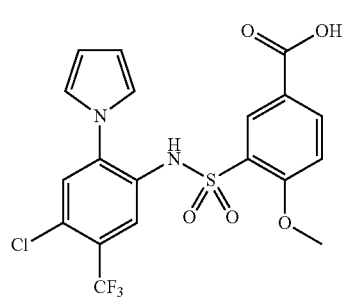
(158)
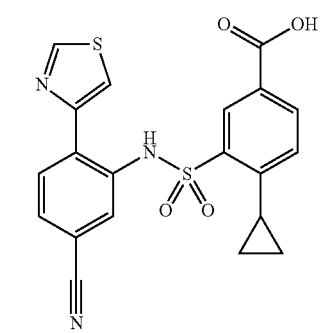
(159)
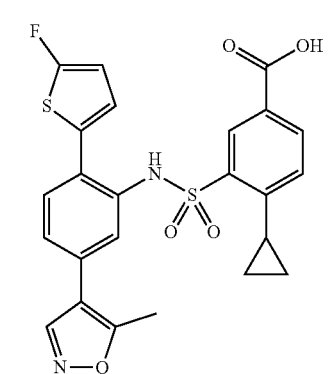
(160)
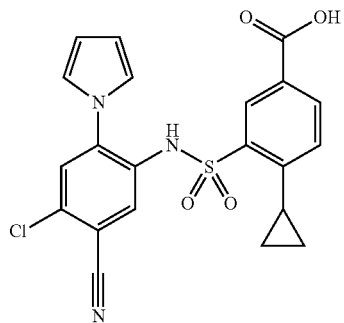
(161)
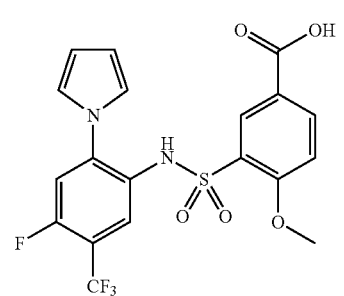
(162)
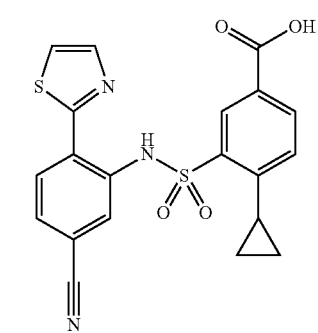
(163)
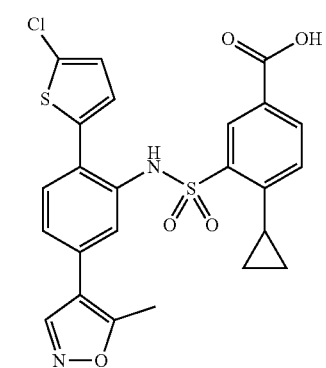
(164)
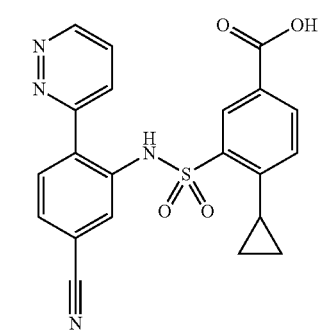
(165)

53
-continued
(166)
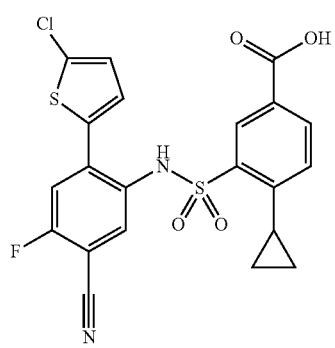
(167)
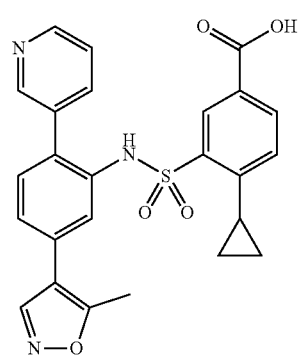
(168)
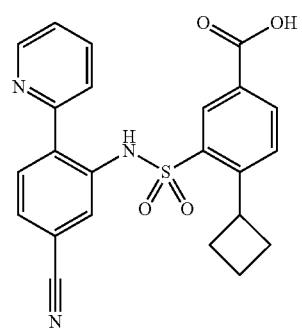
(169)
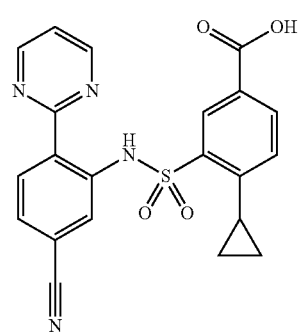
54
-continued
(170)
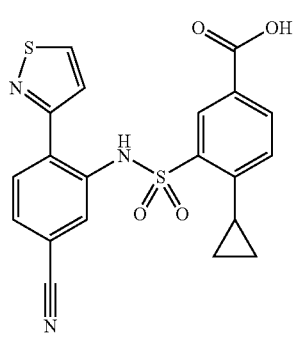
(171)
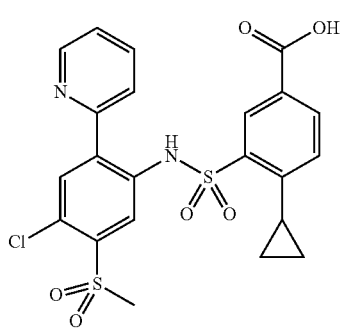
(172)
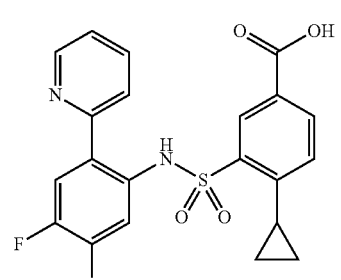
(173)
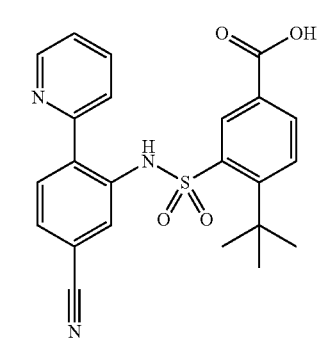
(175)
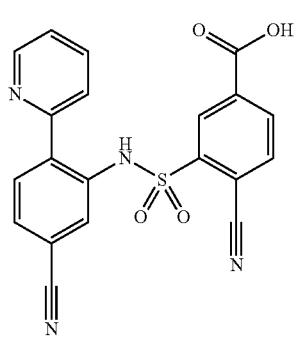

(176) 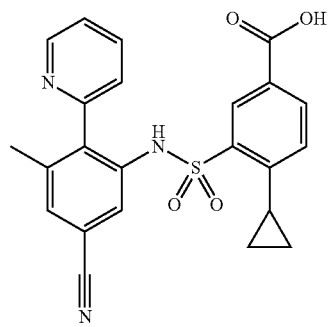
(177) 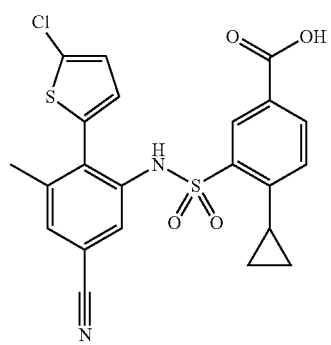
(178) 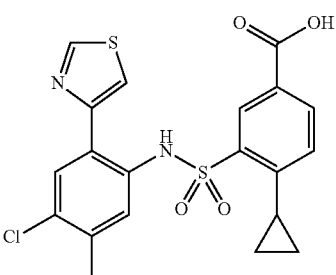
(179) 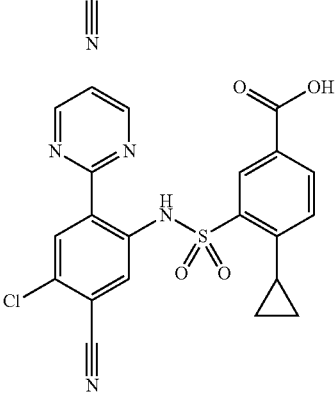
(180) 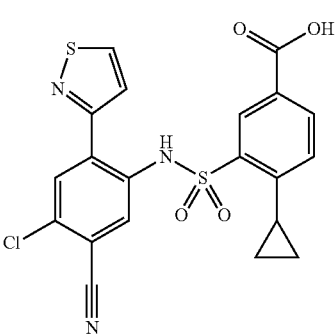
(181) 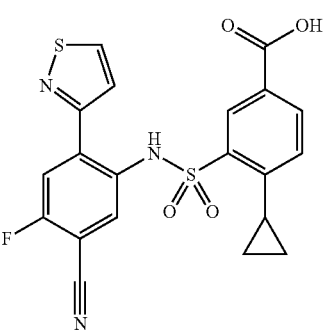
(182) 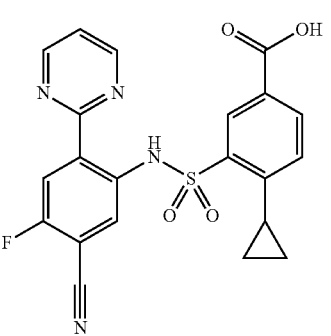
(183) 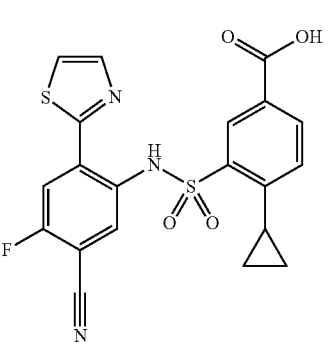
(184) 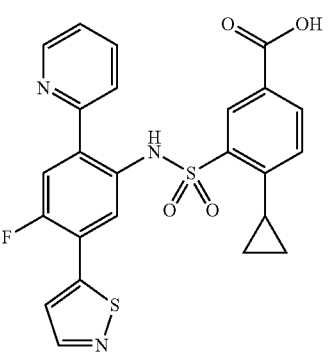

(185) 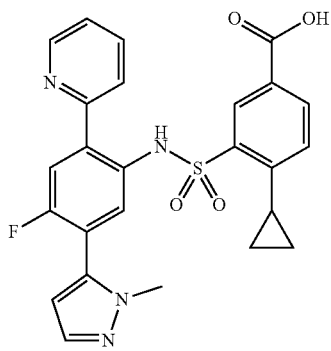
(186)
(187)
(188)
(189) 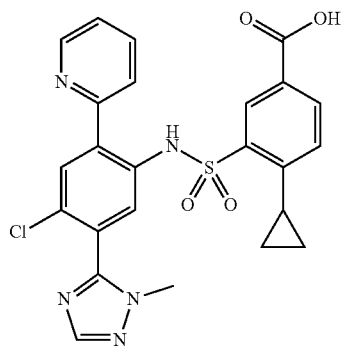
(190) 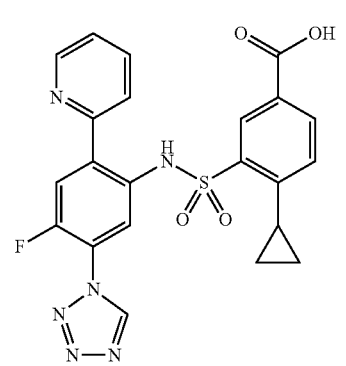
(191) 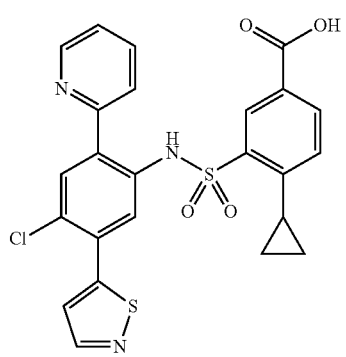
(192) 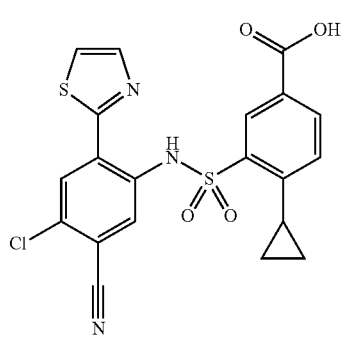

(201) 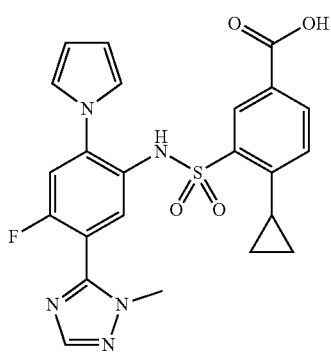

(202) 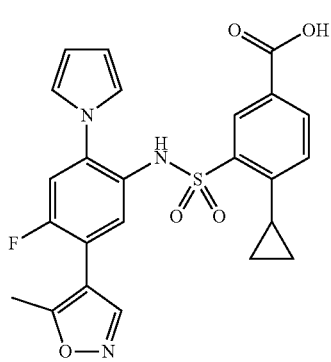

(203) 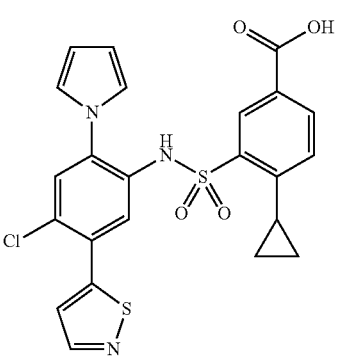

(204) 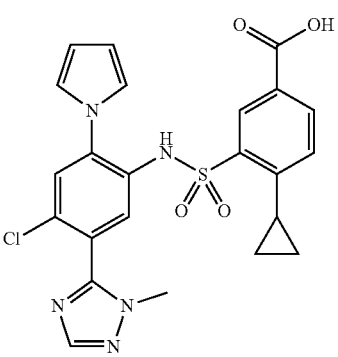

(205) 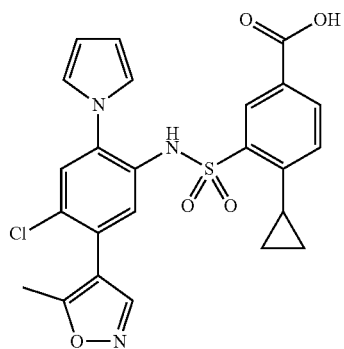

(206) 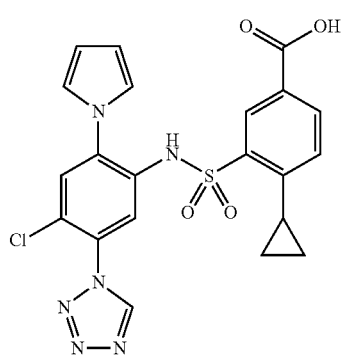

(207) 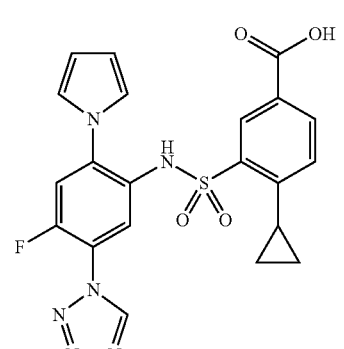

(208) 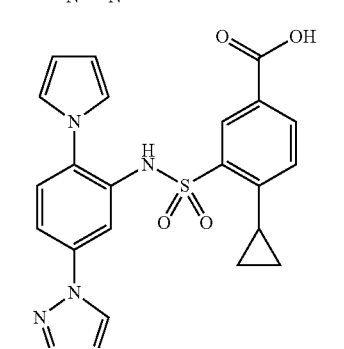

and pharmaceutically acceptable salts and hydrates thereof.

A further aspect of the invention relates to a compound as set out in the table above, other than (28), (30), (31) and (35) and pharmaceutically acceptable salts and hydrates thereof.

Therapeutic Applications

One aspect of the invention relates to compounds as described herein for use in medicine. The compounds have particular use in the field of oncology and immuno-oncology, as described in more detail below.

Yet another aspect of the invention relates to compounds as described herein for use in treating or preventing a disorder selected from a proliferative disorder, an immune disorder, an inflammatory disorder and a viral disorder.

In a preferred embodiment, the compound of the invention modulates ERAP1.

In one embodiment the compound inhibits the activity of ERAP1.

In an alternative embodiment the compound increases the activity of ERAP1.

In one embodiment the compound of the invention may change the repertoire of presented antigens.

One aspect of the invention relates to a compound as described herein for use in treating a proliferative disorder. Preferably, the proliferative disorder is a cancer or leukemia.

A cancer may be selected from: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

Without wishing to be bound by theory, it is understood that ERAP1 modulators are capable of changing at least 10% of the antigen and neoantigen repertoire of cancer cells, as measured using immunopeptidomics and mass spectrometry analysis. Approximately 50% of this change is an upregulation in the presentation of certain antigens and neoantigens, whilst the other 50% is the presentation of entirely novel antigens and neoantigens. Both changes lead to an increase in the visibility of the tumour to the immune system, leading to measurable changes in the CD8$^+$ T cell repertoire and CD8$^+$ T cell activation status. This change in CD8$^+$ T cell response leads to immune-mediated tumour clearance and can be potentially enhanced by combining with cancer therapeutics such as antibody checkpoint inhibitors (e.g. anti-PD-1).

Without wishing to be bound by theory, it is understood that modulators of ERAP1 cause killing of cancer cells by natural killer (NK) cells due to disruption of the interaction between killer cell Ig-like receptors (KIR) or lectin-like receptor CD94-NKG2A on NK cells with classical or non-classical MHC-1-peptide (pMHC-1) complexes on cancer cells.

In one preferred embodiment, the disorder is cancer, and the compound increases the visibility of cancer cells to the immune system by altering the repertoire of antigens and neoantigens presented to the immune system.

A further aspect of the invention relates to a method of increasing the visibility of cancer cells to the immune system in a subject by altering the repertoire of antigens and neoantigens presented to the immune system, said method comprising administering to the subject a compound as described herein.

In one preferred embodiment, the compound increases the CD8+ T cell response to the cancer cell.

In one preferred embodiment, the compound of the invention is for use in the treatment of a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is modulated by the ERAP1 pathway.

In one preferred embodiment, the disease of uncontrolled cell growth, proliferation and/or survival, inappropriate cellular immune response, or inappropriate cellular inflammatory response is selected from a haematological tumour, a solid tumour and/or metastases thereof.

More preferably, the compound is for use in treating a disorder selected from leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The compound may kill cancer cells, reduce the number of proliferating cells in the cancer and/or reduce the volume or size of a tumour comprising the cancer cells. The compound may reduce the number of metastasising cancer cells.

In one embodiment the compound may be used in treating cancer in a subject who has previously had cancer. The compound may be used to reduce the likelihood of the cancer recurring, or the likelihood of further cancer developing. The compound may induce a neoantigen in the recurring or further cancer to which the subject already possesses an existing immune response. As such, the compound may increase or boost an immune response against the cancer.

In one embodiment the compound is for use in preventing cancer. The compound may be used for prophylaxis against the development of cancer. That is to say, the compound may stimulate an immune response, such as a vaccine response, against a future cancer. The compound may stimulate in a subject an immune response directed to a neoantigen. Once a cancer develops in the subject, they may be treated again with the compound (or a different compound) to stimulate development of the same neoantigen, thereby eliciting the subject's pre-exisiting immune response to said neoantigen to treat or prevent the cancer.

The same or a different compound may be used before and after the cancer develops in a subject.

In one embodiment the compound may be used for the prevention of cancer.

In one embodiment the subject may previously have had cancer, may have a familial history of cancer, may have a high risk for developing cancer, may have a genetic predisposition to developing cancer, or may have been exposed to a carcinogenic agent. In one embodiment the subject may be in remission from cancer.

One embodiment provides ex vivo generated antigen-presenting cells, such as dendritic cells (DCs). The antigen-presenting cells may be produced ex vivo to present neo-antigens, such as those generated by a compound according to the present invention. The compound may be used in a method for producing ex vivo an antigen-presenting cell which presents a neo-antigen, and wherein the cell may be used as a vaccine against cancer.

The antigen presenting cell such as a dendritic cell may be pulsed or loaded with the neo-antigen or genetically modified (via DNA or RNA transfer) to express one, two or more neo-antigens. Methods of preparing dendritic cell vaccines are known in the art.

The neo-antigen may be generated from the subject's normal tissue in which ERAP1 is modulated with a compound according to the invention. Sources of normal tissue may be fibroblasts or B cells, for example, that can be readily expanded in vitro. Alternatively, RNA from the cancer, total or mRNA enriched poly A+ RNA may be used. Poly A+ RNA can be also amplified to generate sufficient antigen for DC loading and thereby limit the ex vivo culture step.

In one embodiment a dendritic cell which has been treated with the compound as described above may be used to treat a subject. The dendritic cell may be contacted with the compound ex vivo, and then the dendritic cell may be administered to the subject. The compound may therefore be used in vitro or in vivo, for example either for in situ treatment or for ex vivo treatment followed by the administration of the treated cells to the subject.

Another aspect of the invention relates to a compound as described above for use in treating an immune disorder. In one preferred embodiment, the immune disorder is an autoimmune disorder.

Examples of the autoimmune disorders include, but are not limited to: rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust pneumoconioses, sarcoidosis, autoimmune hemolytic anemia, immunological platelet disorders, cryopathies such as cryofibrinogenemia, psoriasis, Behçet's disease, birdshot chorioretinopathy and autoimmune polyendocrinopathies.

Polymorphisms in the ERAP1 gene that impact ERAP1 enzymatic activity are strongly associated with an increased risk of autoimmunity, including the diseases ankylosing spondylitis, psoriasis, Behçet's disease and birdshot chorioretinopathy[11]. Variants of ERAP1 that reduce ERAP1 enzymatic activity are protective against disease, whilst those that reportedly elevate activity are associated with increased disease risk[12]. This suggests that modulation of ERAP1 activity could be an effective treatment for autoimmune diseases.

Thus, in one preferred embodiment, the immune disorder is selected from ankylosing spondylitis, psoriasis, Behçet's disease and birdshot chorioretinopathy.

In one preferred embodiment, the immune disorder is ankylosing spondylitis. Ankylosing spondylitis (AS) is a type of arthritis in which there is long term inflammation of the joints of the spine. Typically the joints where the spine joins the pelvis are also affected. Occasionally other joints such as the shoulders or hips are involved. Between 0.1% and 1.8% of people are affected and onset is typically in young adults. Although the cause of ankylosing spondylitis is unknown, it involves a combination of genetic and environmental factors. More than 90% of those affected have a specific human leukocyte antigen known as the HLA-B27 antigen.[13] In addition, certain variants of ERAP1, in conjunction with HLA-B27, are clearly associated with either an elevated or reduced risk of disease, providing evidence of a clear role for modulated antigen presentation in disease.[18] There is no cure for ankylosing spondylitis and current treatments serve only to improve symptoms and prevent worsening. Medications used to date include NSAIDs, steroids, DMARDs such as sulfasalazine, and biologic agents such as infliximab.

In one preferred embodiment, the immune disorder is Behçet's disease (BD). Behçet's disease (BD) is a type of inflammatory disorder which affects multiple parts of the body. The most common symptoms include painful mouth sores, genital sores, inflammation of parts of the eye, and arthritis. The cause is not well-defined, and whilst environmental factors play a role, genetic studies have shown an increased risk of disease in patients carrying HLA-B51 in conjunction with specific variants of ERAP1.[19] The disease is primarily characterized by auto-inflammation of the blood vessels, hence it is sometimes characterised as an auto-inflammatory disease. There is currently no cure for Behçet's disease, but the symptoms can be controlled with medicines that reduce inflammation in the affected parts of the body, for example, with corticosteroids, immunosuppressants or biological therapies that target the biological processes involved in the process of inflammation.

In one preferred embodiment, the immune disorder is birdshot chorioretinopathy. Birdshot chorioretinopathy, also known as Birdshot Uveitis or HLA-A29 Uveitis, is a rare form of bilateral posterior uveitis affecting the eye. It causes severe, progressive inflammation of both the choroid and retina. Symptoms include floaters, blurred vision, photopsia (flashing lights in eyes), loss of color vision and nyctalopia. Birdshot chorioretinopathy is thought to be an autoimmune disease. The disease has strong association with the Human leukocyte antigen haplotype (HLA)-A29. This indicates a role for T-lymphocytes in the pathogenesis. Birdshot chorioretinopathy is associated with IL-17, a hallmark cytokine of TH17 cells that play an important role in autoimmunity.[15, 16] A genome-wide association study has ascertained HLA-A29:02 as the primary risk factor and identified that both ERAP1 and ERAP2 are associated with birdshot chorioretinopathy.[17, 20] Genetic variants within the ERAP1 and ERAP2 loci modulate enzyme activity and also mRNA and protein expression. ERAP2 is an aminopeptidase that, together with ERAP1, trims peptides in the endoplasmic reticulum and loads these peptides on HLA molecules for presentation to T cells of the immune system.

In one preferred embodiment, the immune disorder is psoriasis. Psoriasis is a chronic skin disease in which skin cells rapidly build up on the surface of the skin forming scales and red patches that are itchy and sometimes painful. The cause is not well-defined but includes both environmental and genetic factors. HLA-C06 strongly associates with risk of disease and variants in ERAP1, possibly in conjunction with HLA-C06, are also strongly associated with disease.[21] There is no cure for psoriasis and current treatments serve only to improve symptoms and prevent worsening. Medications used in therapy include steroids, methotrexate, sulfasalazine, and biologic agents such as etanercept.

Another aspect of the invention relates to a compound as described above for use in treating or preventing a viral disorder. Modulators of ERAP1 such as the compounds described herein are capable of changing the antigen repertoire of multiple viruses, which leads to the recognition and destruction of viral infected cells. Accordingly, ERAP1 modulators have potential therapeutic applications in the treatment of viral infection and diseases. ERAP1 modulates certain viral antigens, including those from human papilloma virus (HPV), human cytomegalovirus (CMV) hepatitis C (HCV) and human immunodeficiency virus (HIV)[8, 9, 10] In addition, knockdown of ERAP1 in HPV infected cells changes the repertoire of presented HPV antigens leading to greater recognition by CD8+ T cells[8].

In one preferred embodiment, the viral disorder is a viral disease or viral infection selected from HIV, HPV, CMV and HCV.

In one preferred embodiment, the viral disorder is HIV.
In one preferred embodiment, the viral disorder is HPV.
In one preferred embodiment, the viral disorder is CMV.
In one preferred embodiment, the viral disorder is HCV.

Another aspect relates to a compound as described herein for use in the prevention or treatment of a disorder caused by, associated with or accompanied by abnormal activity against ERAP1.

Another aspect relates to a compound as described herein for use in the the prevention or treatment of an ERAP1-associated disease or disorder.

Yet another aspect relates to the use of a compound as described herein in the preparation of a medicament for the prevention or treatment of a disorder caused by, associated with or accompanied by any abnormal activity against ERAP1.

As used herein the phrase "preparation of a medicament" includes the use of the components of the invention directly as the medicament in addition to their use in any stage of the preparation of such a medicament.

Another aspect relates to the use of a compound as described above in the preparation of a medicament for treating or preventing a disorder selected from a proliferative disorder, an immune disorder, a viral disorder and an inflammatory disorder.

Yet another aspect relates to the use of a compound as described herein in the preparation of a medicament for the prevention or treatment of an ERAP1-associated disease or disorder.

Another aspect of the invention relates to a method of treating an ERAP1-associated disease or disorder in a subject. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Another aspect relates to a method of treating a disorder selected from a proliferative disorder, an immune disorder, a viral disorder and an inflammatory disorder in a subject, said method comprising administering to the subject a compound as described herein.

Yet another aspect of the invention relates to a method of treating a subject having a disease state alleviated by modulation of ERAP1 wherein the method comprises administering to the subject a therapeutically effective amount of a compound according to the invention.

Another aspect relates to a method of treating a disease state alleviated by modulation of ERAP1, wherein the method comprises administering to a subject a therapeutically effective amount of a compound according to the invention.

Preferably, the subject is a mammal, more preferably a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "ERAP1-related disease or disorder" refers to a disease or disorder characterized by inappropriate ERAP1 activity. Inappropriate activity refers to either an increase or decrease in ERAP1 activity relative to wildtype ERAP1 (Uniprot ID Q9NZ08), caused by variation in the ERAP1 protein sequence, as measured by enzyme or cellular assays. Inappropriate activity could also be due to overexpression of ERAP1 in diseased tissue compared with healthy adjacent tissue.

Preferred diseases or disorders that the compounds described herein may be useful in preventing include proliferative disorders, viral disorders, immune disorders and inflammatory disorders as described hereinbefore.

Thus, the present invention further provides use of compounds as defined herein for the preparation or manufacture of medicaments for the treatment of diseases where it is desirable to modulate ERAP1. Such diseases include proliferative disorders, viral disorders, immune disorders and inflammatory disorders as described hereinbefore.

In one preferred embodiment, the compound activates ERAP1's conversion of (L)-leucine-7-amido-4-methylcoumarin (L-AMC) to (L)-leucine and the fluorescent molecule 7-amino-4-methylcoumarin. While the same assay can also identify inhibitors of ERAP1's cleavage of the amide bond in L-AMC, for the purposes of this application this assay is referred to as the "L-AMC activator assay". The potency of any activator is calculated and expressed as the concentration of the activator required to increase the enzyme activity of ERAP1 by 50% over its baseline level (i.e. an $EC_{50}$).

In one preferred embodiment, the compound exhibits an $EC_{50}$ value in an L-AMC activator assay of less than about 25 µM. More preferably, the compound exhibits an $EC_{50}$ value in the L-AMC activator assay of less than about 10 µM, more preferably, less than about 5 µM, even more preferably, less than about 1 µM, even more preferably, less than about 0.1 µM, even more preferably, less than about 0.01 µM.

In one preferred embodiment, the compound inhibits ERAP1's ability to hydrolyse the decapeptide substrate WRVYEKCdnpALK. This peptide has minimal fluorescence as the N-terminal tryptophan residue's fluorescence is quenched by the dinitrophenol (DNP) residue within the peptide. However, as ERAP1 hydrolyses the N-terminal amide bond and tryptophan is released this internal quenching is lost and the reaction is monitored by the increase in tryptophan fluorescence over the course of the assay. For the purposes of this application this assay is referred to as the "10mer inhibition assay" and compound potencies are calculated and expressed as $IC_{50}$ as would be familiar to a person skilled in the art.

In one preferred embodiment, the compound exhibits an $IC_{50}$ value in the 10mer assay of less than about 25 µM. More preferably, the compound exhibits an $IC_{50}$ value in the 10mer assay of less than about 10 µM, more preferably, less than about 5 µM, even more preferably, less than about 1 µM, even more preferably, less than about 0.1 µM, even more preferably, less than about 0.01 µM.

Compounds of Formula (Ia)

A further aspect of the invention relates to a compound of formula (Ia), or a pharmaceutically acceptable salt or hydrate thereof,

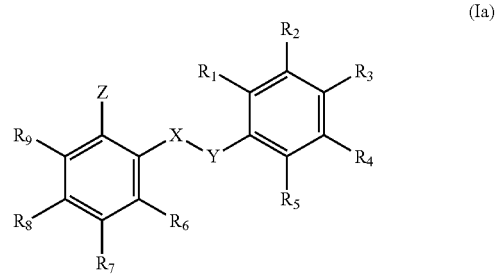

(Ia)

wherein:
the group X—Y is —NHSO$_2$— or —SO$_2$NH—;
Z is:
a monocyclic aryl group, or
a monocyclic heteroaryl group selected from pyridinyl, thienyl, imidazolyl, pyrimidinyl, tetrazolyl, thiazolyl, pyradizinyl, isothiazolyl, 1H-pyrazol-5-yl, 1H-pyrazol-3-yl, 1H-pyrazol-4-yl, triazinyl, 1H-pyrrol-2-yl, 1H-pyrrol-3-yl, 1H-pyrrol-4-yl, furanyl, oxazolyl, 1H-1,2,4-triazol-3-yl, 1H-1,2,4-triazol-5-yl, 1H-1,2,3-triazol-4-yl, 1H-1,2,3-triazol-5-yl and 1H-1,2,3-triazol-1-yl;
each of which is optionally substituted by one or more substituents selected from alkyl, cycloalkyl, halo, alkoxy, CN, haloalkyl and OH;
R$_1$ is H, CN or alkyl;
R$_2$ is selected from COOH and a tetrazolyl group;
R$_3$ is selected from H, Cl and alkyl;
R$_4$ is selected from H and halo;
R$_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
R$_6$ is H;
R$_7$ is selected from H, CN, haloalkyl, halo, SO$_2$-alkyl, SO$_2$NR$_{12}$R$_{13}$, heteroaryl, CONR$_{10}$R$_{11}$ and alkyl, wherein said heteroaryl group is optionally substituted by one or more substituents selected from alkyl, halo, alkoxy, CN, haloalkyl and OH;
R$_8$ is selected from H, alkyl, haloalkyl and halo;
R$_9$ is H, alkyl or halo, more preferably H or halo;
R$_{10}$ and R$_{11}$ are each independently H or alkyl; and
R$_{12}$ and R$_{13}$ are each independently H or alkyl
with the proviso that:
when Z is unsubstituted phenyl, X is NH, Y is SO$_2$, R$_1$, R$_3$, R$_4$, and R$_8$-R$_9$ are all H, and R$_5$ is OMe, R$_2$ is other than CO$_2$H;
when Z is unsubstituted phenyl, X is NH, Y is SO$_2$, R$_1$, R$_4$ and Re—R$_9$ are all H, and R$_3$ and R$_5$ are both Cl, R$_2$ is other than CO$_2$H; and
when Z is unsubstituted thien-2-yl, X is NH, Y is SO$_2$, R$_1$, R$_4$, R$_5$, and R$_6$-R$_9$ are all H, and R$_3$ is Me, R$_2$ is other than CO$_2$H.

Another aspect of the invention relates to a compound of formula (Ia), or a pharmaceutically acceptable salt or hydrate thereof,

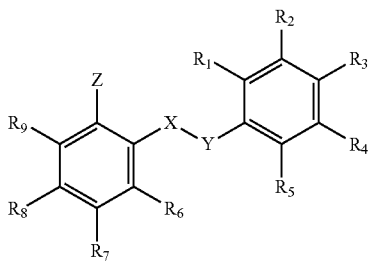

(Ia)

wherein:
the group X—Y is —NHSO$_2$— or —SO$_2$NH—;
Z is:
a monocyclic aryl group, or
a monocyclic heteroaryl group selected from pyridinyl, thienyl, imidazolyl, pyrimidinyl, tetrazolyl, thiazolyl, pyradizinyl, isothiazolyl, 1H-pyrazol-5-yl, 1H-pyrazol-3-yl, 1H-pyrazol-4-yl, triazinyl, 1H-pyrrol-2-yl, 1H-pyrrol-3-yl, 1H-pyrrol-4-yl, furanyl, oxazolyl, 1H-1,2,4-triazol-3-yl, 1H-1,2,4-triazol-5-yl, 1H-1,2,3-triazol-4-yl, 1H-1,2,3-triazol-5-yl and 1H-1,2,3-triazol-1-yl;
each of which is optionally substituted by one or more substituents selected from alkyl, cycloalkyl, halo, alkoxy, CN, haloalkyl and OH;
$R_1$ is H, CN or alkyl;
$R_2$ is selected from COOH and a tetrazolyl group;
$R_3$ is selected from H, Cl and alkyl;
$R_4$ is selected from H and halo;
$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
$R_6$ is H;
$R_7$ is selected from H, CN, haloalkyl, halo, SO$_2$-alkyl, SO$_2$NR$_{12}$R$_{12}$, heteroaryl, CONR$_{10}$R$_{11}$ and alkyl, wherein said heteroaryl group is optionally substituted by one or more substituents selected from alkyl, halo, alkoxy, CN, haloalkyl and OH;
$R_8$ is selected from H, alkyl, haloalkyl and halo;
$R_9$ is H, alkyl or halo, more preferably H or halo;
$R_{10}$ and $R_{11}$ are each independently H or alkyl; and
$R_{12}$ and $R_{13}$ are each independently H or alkyl.
Preferred definitions for X, Y and $R_1$-$R_{13}$ are as set out above for formula (I).

For compounds of formula (Ia), the following particularly preferred embodiments apply.

In one preferred embodiment, Z is selected from an optionally substituted monocyclic heteroaryl group selected from pyridinyl, thienyl, imidazolyl, pyrimidinyl, tetrazolyl, thiazolyl, pyradizinyl, isothiazolyl, 1H-pyrazol-5-yl, 1H-pyrazol-3-yl, 1H-pyrazol-4-yl, triazinyl, 1H-pyrrol-2-yl, 1H-pyrrol-3-yl, 1H-pyrrol-4-yl, furanyl, oxazolyl, 1H-1,2,3-triazol-5-yl and 1H-1,2,3-triazol-1-yl.

In one preferred embodiment, Z is selected from phenyl, pyridinyl, thienyl, imidazolyl, furanyl, tetrazolyl, and oxazolyl, each of which is optionally substituted by one or more substituents selected from alkyl, cycloalkyl, halo, alkoxy, CN, haloalkyl and OH.

In another preferred embodiment, Z is selected from pyridinyl, pyrimidinyl, thiazolyl and isothiazolyl, each of which is optionally substituted by one or more substituents selected from alkyl, cycloalkyl, halo, alkoxy, CN, haloalkyl and OH.

In one preferred embodiment, Z is selected from phenyl, pyridin-2-yl, pyridin-3-yl, pyridin-4-yl, pyrimidin-2-yl, pyrimidin-4-yl, pyrimidin-5-yl, thien-2-yl, thien-3-yl, 1H-imidazol-1-yl, 1H-imidazol-2-yl, 1H-imidazol-4-yl, 1H-imidazol-5-yl, 1H-pyrrol-2-yl, 1H-pyrrol-3-yl, 1H-pyrrol-4-yl, 1H-pyrrol-5-yl, 1H-pyrazol-5-yl, 1H-pyrazol-3-yl, 1H-pyrazol-4-yl, oxazol-2-yl, oxazol-4-yl, oxazol-5-yl, thiazol-2-yl, thiazol-5-yl, thiazol-4-yl, pyradizin-3-yl, pyradizin-4-yl, isothiazol-5-yl, isothiazol-4-yl, isothiazol-3-yl, 1H-1,2,4-triazol-3-yl, 1H-1,2,4-triazol-5-yl, 1H-1,2,3-triazol-4-yl, 1H-1,2,3-triazol-5-yl, 1H-1,2,3-triazol-1-yl, 1H-1,2,3,4-tetrazol-4-yl, 2H-1,2,3,4-tetrazol-5-yl, 1,3,5-triazin-1-yl, 1,2,3-triazin-4-yl, 1,2,3-triazinyl-5-yl, 1,2,4-triazin-3-yl, 1,2,4-triazin-5-yl, 1,2,4-triazin-6-yl, furan-2-yl and furan-3-yl, each of which is optionally substituted by one or more substituents selected from alkyl, cycloalkyl, CN, halo, alkoxy, haloalkyl and OH.

In one preferred embodiment, Z is selected from phenyl, pyridin-2-yl, pyridin-3-yl, thien-2-yl, 1H-pyrrol-2-yl, each of which is optionally substituted by one or more substituents selected from Me, F, Cl, CN, cyclopropyl and MeO.

In one preferred embodiment, Z is selected from pyridin-2-yl, pyridin-3-yl, pyrimidin-2-yl, pyrimidin-4-yl, pyrimidin-5-yl, thiazol-2-yl, thiazol-5-yl, thiazol-4-yl, isothiazol-3-yl, isothiazol-4-yl and isothiazol-5-yl, each of which is optionally substituted by one or more substituents selected from alkyl, cycloalkyl, halo, alkoxy, CN, haloalkyl and OH. Preferably, the one or more optional substituents are selected from Me, F, Cl, CN, cyclopropyl and MeO.

In one preferred embodiment, Z is selected from pyridin-2-yl, pyrimidin-2-yl, thiazol-4-yl and isothiazol-3-yl, each of which is optionally substituted by one or more substituents selected from alkyl, cycloalkyl, halo, alkoxy, CN, haloalkyl and OH. Preferably, the one or more optional substituents are selected from Me, F, Cl, CN, cyclopropyl and MeO.

In one preferred embodiment, $R_1$ is H, CN or Me, more preferably H.

In one preferred embodiment, $R_2$ is COOH.

In one preferred embodiment, X—Y is NH—SO$_2$.

In another preferred embodiment, X—Y is SO$_2$—NH.

In one preferred embodiment, $R_4$ is selected from H, Cl and F.

In one preferred embodiment, $R_5$ is selected from alkyl, haloalkyl, SO$_2$-alkyl, Cl, alkoxy, OH, CN, hydroxyalkyl, alkylthio, heteroaryl, cycloalkyl, heterocycloalkyl and haloalkoxy.

In one preferred embodiment, $R_5$ is selected from alkyl, alkoxy and cycloalkyl.

In another preferred embodiment, $R_5$ is selected from H, Me, CF$_3$, CHF$_2$, SO$_2$-Me, Cl, MeO, OH, CH$_2$OH, SMe, cyclopropyl, triazolyl, oxetanyl and CN. More preferably, $R_5$ is selected from H, CN, Me, SO$_2$-Me, CF$_3$ and CHF$_2$, CH$_2$OH, SMe, cyclopropyl, 3,4-triazol-1-yl, oxetan-3-yl. More preferably, $R_5$ is selected from H, CN, Me, SO$_2$-Me, CF$_3$ and CHF$_2$.

In another preferred embodiment, $R_5$ is selected from OMe, Me, Et, Pr and Cl, and is more preferably OMe or Et.

In one particularly preferred embodiment, $R_5$ is selected from OMe, OEt, Me, Et, cyclobutyl and cyclopropyl.

In one preferred embodiment, $R_5$ is selected from OMe, OEt, Me, Et, and cyclopropyl, more preferably, OMe, Et and cyclopropyl.

In one particularly preferred embodiment, $R_5$ is OMe.

In one particularly preferred embodiment, $R_5$ is Et.

In one particularly preferred embodiment, $R_5$ is cyclopropyl.

In one preferred embodiment, $R_1$, $R_3$, $R_4$, $R_6$, $R_8$ and $R_5$ are all H.

In one preferred embodiment, $R_7$ is selected from H, CN, haloalkyl, Cl, F, $SO_2$-alkyl, $CONR_{10}R_{11}$, heteroaryl and alkyl, wherein said heteroaryl group is optionally substituted by one or more substituents selected from alkyl, halo, alkoxy, CN, haloalkyl and OH.

In one preferred embodiment, $R_7$ is selected from H, CN, $CF_3$, $CHF_2$, Cl, F, $SO_2$-Me, $CONH_2$, heteroaryl and Me, wherein said heteroaryl group is optionally substituted by one or more substituents selected from alkyl, halo, alkoxy, CN, haloalkyl and OH. More preferably, $R_7$ is selected from H, CN, Me, $SO_2$-Me, $CONH_2$, tetrazolyl, $CF_3$ and $CHF_2$.

In another preferred embodiment, $R_7$ is selected from CN, haloalkyl, $SO_2$-alkyl, $CONR_{10}R_{11}$ and tetrazolyl. More preferably for this embodiment, $R_7$ is selected from $CF_3$, CN, 1H-1,2,3,4-tetrazol-1-yl, $CONH_2$ and $SO_2Me$.

In one preferred embodiment, $R_7$ is haloalkyl or heteroaryl, more preferably tetrazolyl.

In one preferred embodiment, $R_7$ is a heteroaryl group which is optionally substituted by one or more substituents selected from alkyl, halo, alkoxy, CN, haloalkyl and OH.

Preferably, the heteroaryl group is selected from pyrazolyl, isothiazolyl, triazolyl, tetrazolyl and isoxazolyl, each of which is optionally substituted by one or more substituents selected from alkyl, halo, alkoxy, CN, haloalkyl and OH.

In one preferred embodiment, $R_7$ is a heteroaryl selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

In one preferred embodiment, $R_7$ is haloalkyl, more preferably, $CF_3$.

In one preferred embodiment, $R_7$ is CN.

In one preferred embodiment, $R_7$ is $SO_2$-alkyl, more preferably $SO_2Me$.

In one preferred embodiment, $R_7$ is $SO_2NR_{12}R_{13}$, more preferably $SO_2NH_2$.

In one preferred embodiment, $R_8$ is selected from H, alkyl, haloalkyl and Cl.

In another preferred embodiment, $R_8$ is selected from alkyl and halo. More preferably, $R_8$ is selected from Me, Cl and F. Even more preferably, $R_8$ is selected from C and F.

In one preferred embodiment, $R_8$ is H or haloalkyl, more preferably H or $CF_3$, even more preferably H.

In one preferred embodiment, $R_8$ is selected from H, Cl and F.

In one preferred embodiment, $R_9$ is H or halo.

In one preferred embodiment, $R_9$ is H or F, more preferably, H.

In another preferred embodiment, $R_9$ is H, Me or F, more preferably, H.

In one preferred embodiment, $R_{10}$, $R_{11}$, $R_{12}$ and $R_{13}$ are each independently H or Me, more preferably H.

In one preferred embodiment:
$R_2$ is COOH;
X—Y is NH—$SO_2$;
$R_5$ is selected from OMe, OEt, Me, Et, and cyclopropyl, and is more preferably cyclopropyl;
$R_1$, $R_3$, $R_4$, $R_6$, $R_8$ and $R_9$ are all H; and
$R_7$ is selected from CN, haloalkyl, $SO_2$-alkyl and tetrazolyl, and is more preferably, $SO_2$ Me or $CF_3$.

In one preferred embodiment:
$R_2$ is COOH;
X—Y is NH—$SO_2$;
$R_5$ is selected from OMe, OEt, Me, Et, and cyclopropyl, and is more preferably cyclopropyl;
$R_1$, $R_3$, $R_4$, $R_6$, $R_8$ and $R_9$ are all H; and
$R_7$ is selected from CN, haloalkyl, $SO_2$-alkyl and isothiazolyl, and is more preferably, isothiazolyl, even more preferably, isothiazol-5-yl.

In one preferred embodiment:
$R_2$ is COOH;
X—Y is NH—$SO_2$;
$R_5$ is selected from cyclopropyl, OMe and Et, and is more preferably cyclopropyl;
$R_1$, $R_3$, $R_4$, $R_6$, and $R_9$ are all H;
$R_7$ is selected from CN, haloalkyl, heteroaryl and $SO_2$-alkyl, and is more preferably CN;
$R_8$ is H, Cl or F, more preferably Cl or F; and
Z is selected from the following:

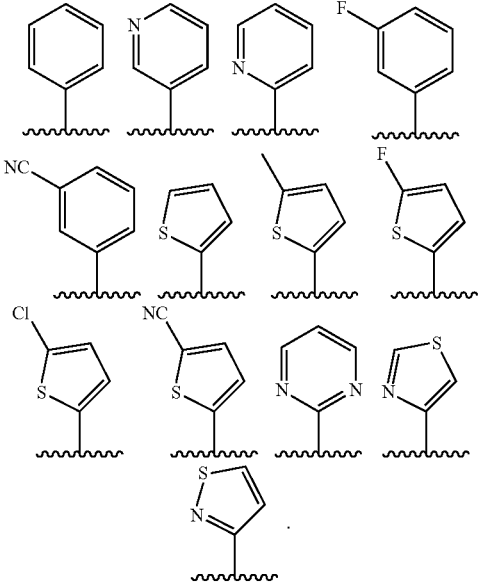

In one preferred embodiment:
$R_2$ is COOH;
X—Y is NH—$SO_2$;
$R_5$ is selected from cyclopropyl, OMe and Et;
$R_1$, $R_3$, $R_4$, $R_6$, $R_8$ and $R_9$ are all H; and
$R_7$ is selected from CN, haloalkyl, heteroaryl and $SO_2$-alkyl; and
Z is selected from the following:

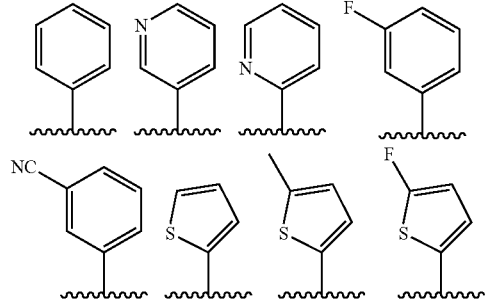

-continued

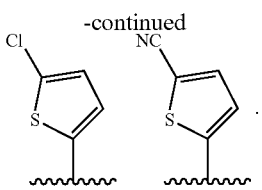

In one preferred embodiment:
R₂ is COOH;
X—Y is NH—SO₂;
R₅ is selected from OMe, OEt, Me, Et, and cyclopropyl, and is more preferably OMe or Et;
R₁, R₃, R₄, R₆, R₈ and R₉ are all H; and
R₇ is selected from CN, haloalkyl, SO₂-alkyl and tetrazolyl, and is more preferably, SO₂Me or CF₃.

In one preferred embodiment:
R₂ is COOH;
X—Y is NH—SO₂;
R₅ is selected from cyclopropyl, OMe and Et;
R₁, R₃, R₄, R₆, R₈ and R₉ are all H; and
R₇ is selected from CN, haloalkyl, heteroaryl and SO₂-alkyl; and
Z is selected from the following:

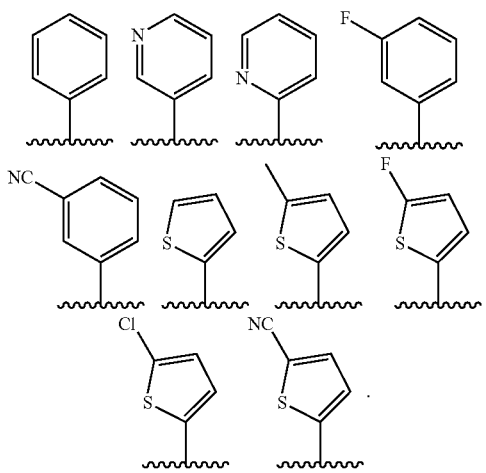

In one preferred embodiment:
R₂ is COOH;
X—Y is NH—SO₂;
R₅ is cyclopropyl;
R₁, R₃, R₄, R₆, R₈ and R₉ are all H; and
R₇ is selected from CN, haloalkyl and SO₂-alkyl, and is more preferably, SO₂Me or CF₃; and
Z is selected from the following:

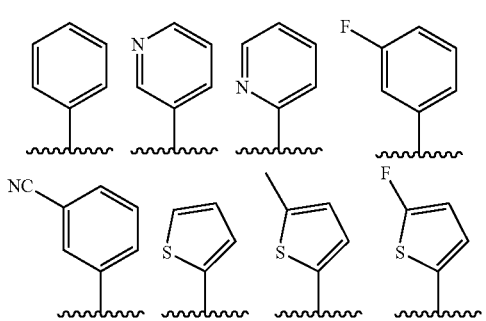

In one preferred embodiment:
R₂ is COOH;
X—Y is NH—SO₂;
R₅ is cyclopropyl;
R₁, R₃, R₄, R₆, R₈ and R₉ are all H;
R₇ is CF₃; and
Z is phenyl.

In one preferred embodiment:
R₂ is COOH;
X—Y is NH—SO₂;
R₅ is Et;
R₁, R₃, R₄, R₆, R₈ and R₉ are all H; and
R₇ is selected from CN, haloalkyl, heteroaryl, SO₂-alkyl; and
Z is selected from the following:

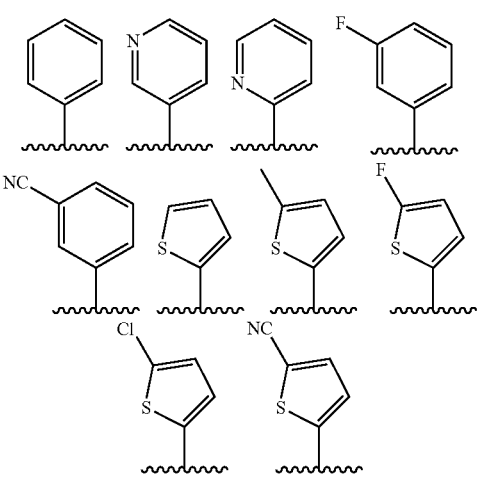

In one preferred embodiment:
R₂ is COOH;
X—Y is NH—SO₂;
R₅ is Et;
R₁, R₃, R₄, R₆, R₅ and R₉ are all H; and
R₇ is selected from CN and CF₃; and
Z is selected from the following:

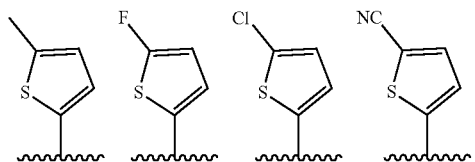

In one preferred embodiment:
R₂ is COOH;
X—Y is NH—SO₂;
R₅ is Et;
R₁, R₃, R₄, R₆, R₈ and R₉ are all H; and
R₇ is selected from CN and CF₃; and Z is selected from the following:

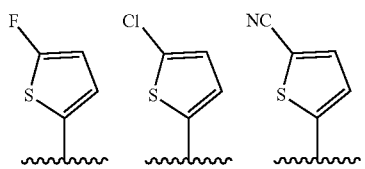

In one preferred embodiment:
R₂ is COOH;
X—Y is NH—SO₂;
R₅ is MeO;
R₁, R₃, R₄, R₆, R₈ and R₉ are all H; and
R₇ is selected from CN, haloalkyl and SO₂-alkyl; and
Z is selected from the following:

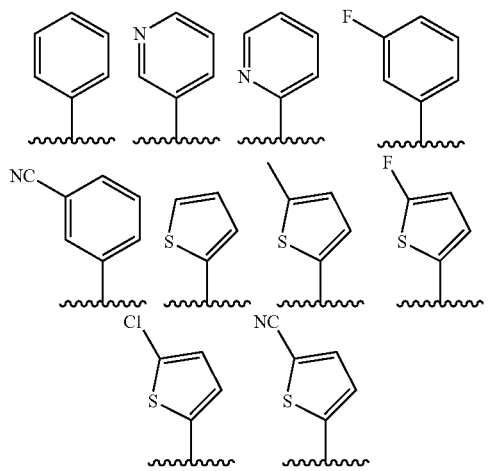

In one preferred embodiment:
R₂ is COOH;
X—Y is NH—SO₂;
R₅ is MeO;
R₁, R₃, R₄, R₆, R₈ and R₉ are all H; and
R₇ is CF₃; and
Z is selected from the following:

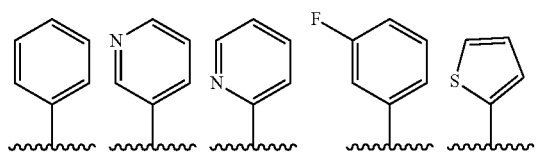

In one preferred embodiment:
R₂ is COOH;
X—Y is NH—SO₂;
R₅ is MeO;
R₁, R₃, R₄, R₆, R₈ and R₉ are all H; and
R₇ is CF₃; and Z is selected from the following:

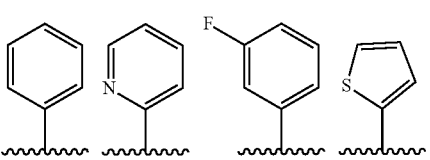

In one preferred embodiment, the compound of formula (Ia) is selected from the following:

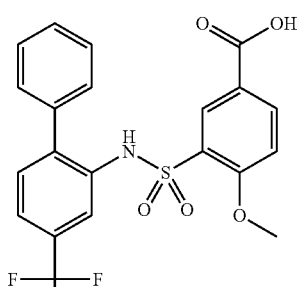
(1)

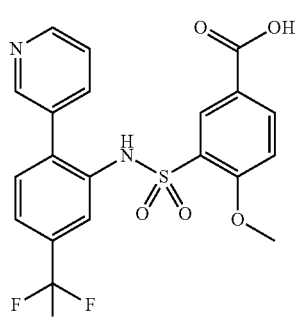
(2)

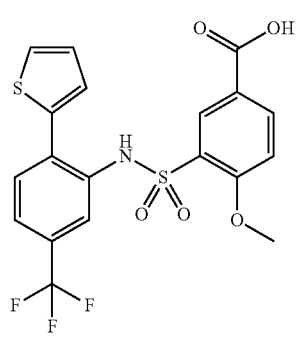 [SMILES: COc1ccc(C(=O)O)cc1S(=O)(=O)Nc1cc(C(F)(F)F)ccc1-c1cccs1]
(3)

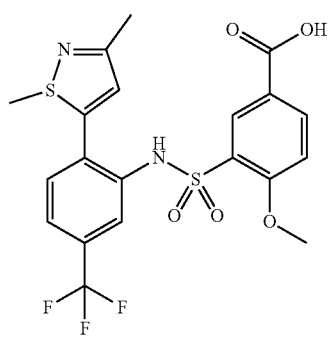
(4)

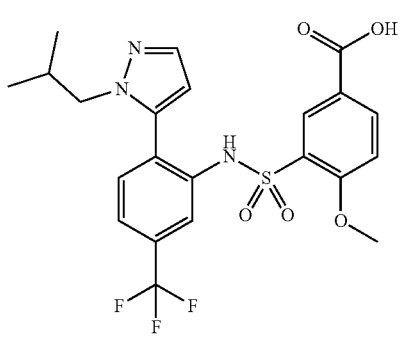 [SMILES: COc1ccc(C(=O)O)cc1S(=O)(=O)Nc1cc(C(F)(F)F)ccc1-c1ccnn1CC(C)C] (5)
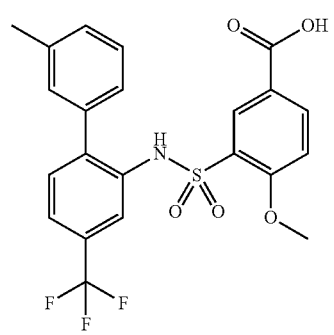 [SMILES: COc1ccc(C(=O)O)cc1S(=O)(=O)Nc1cc(C(F)(F)F)ccc1-c1cccc(C)c1] (6)
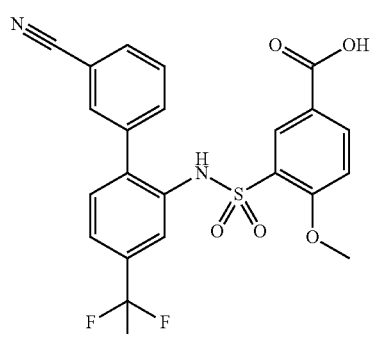 (7)
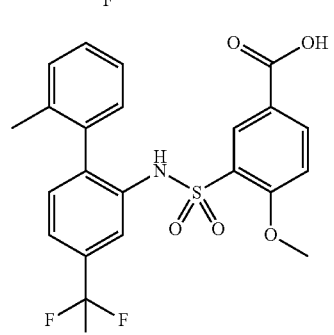 (8)
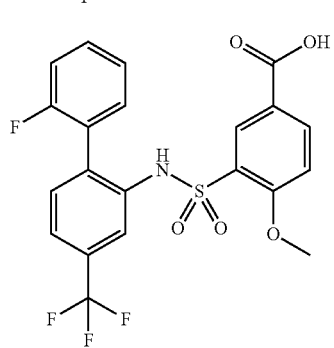 (9)
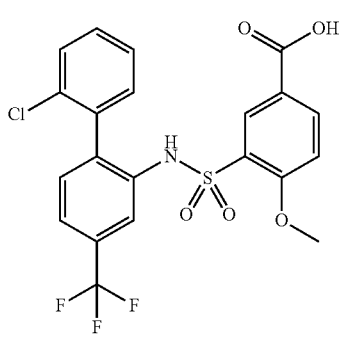 (10)
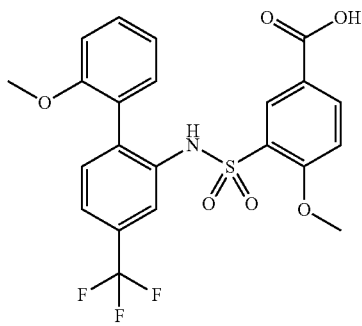 (11)
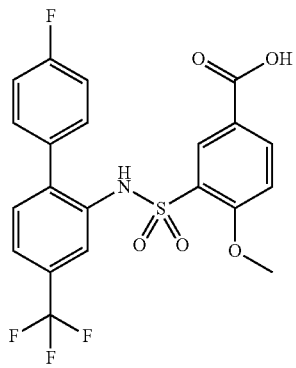 (12)
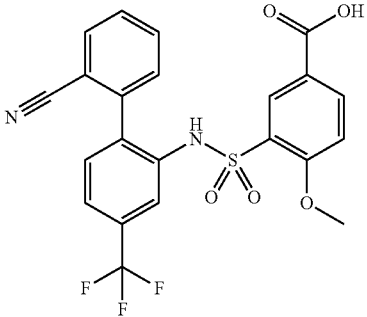 (13)

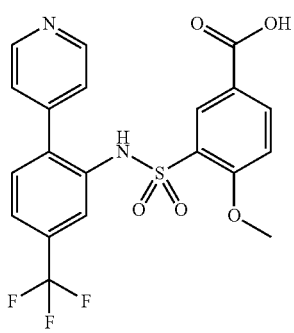
(14)
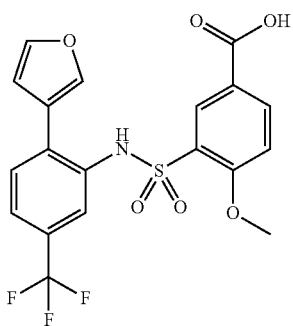
(18)
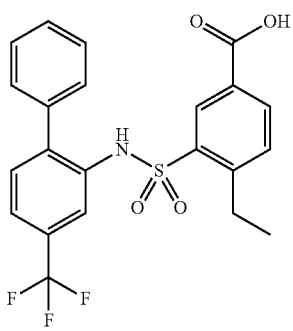
(19)
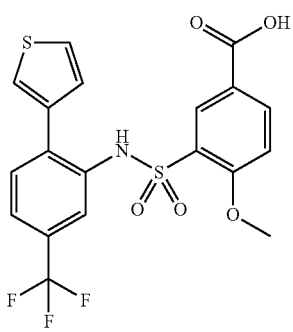
(20)
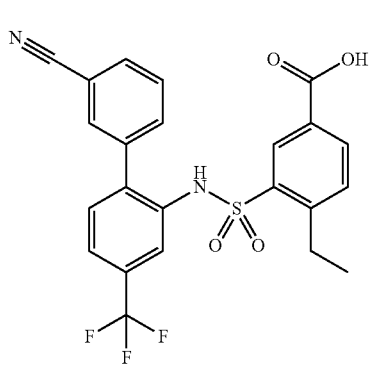
(21)
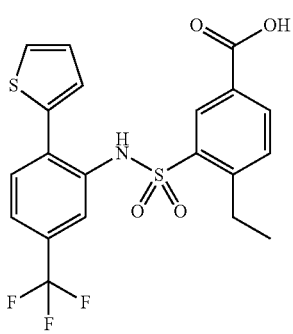
(22)

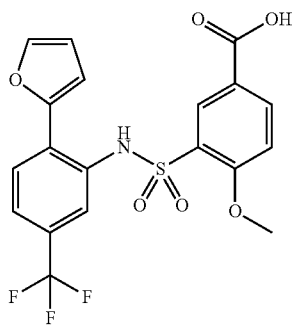
(23)
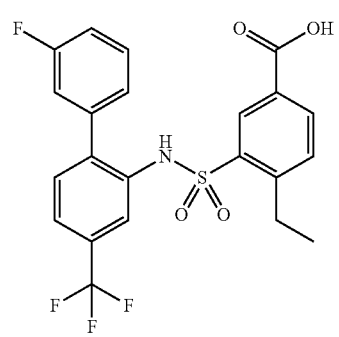
(24)
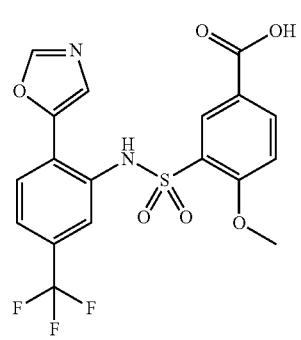
(25)
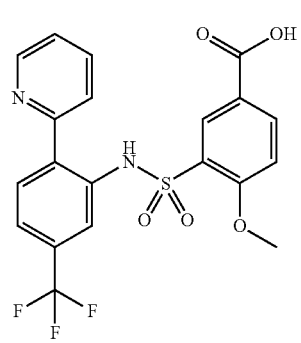
(26)
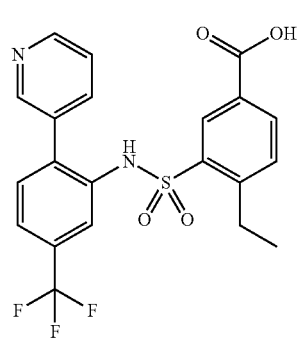
(27)
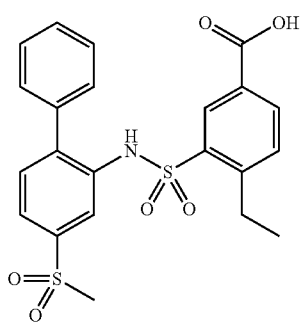
(32)
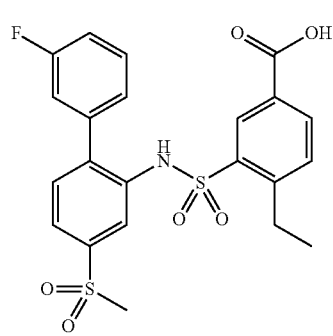
(33)
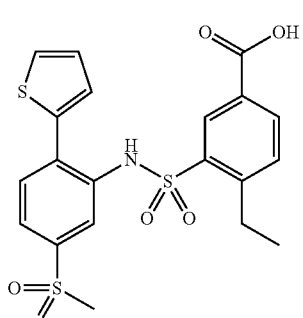
(34)
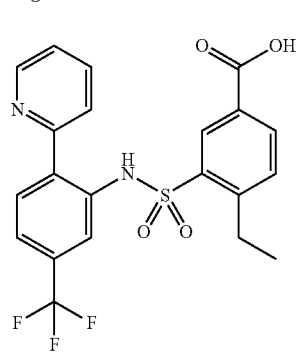
(37)
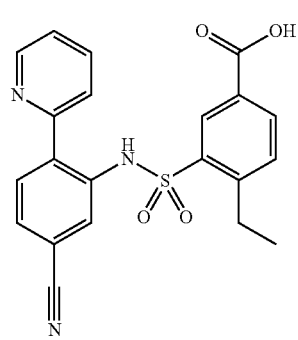
(38)

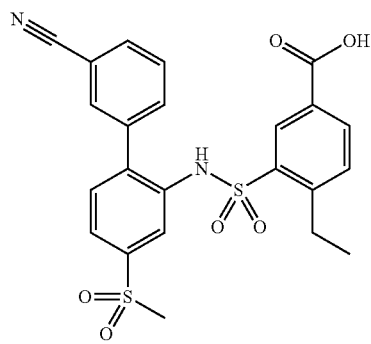
(39)
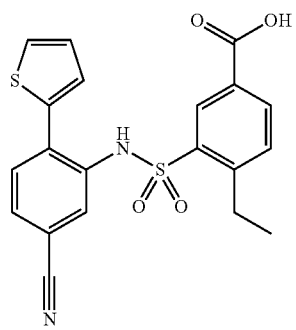
(43)
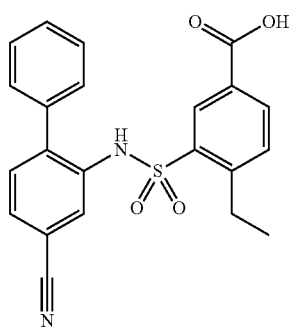
(40)
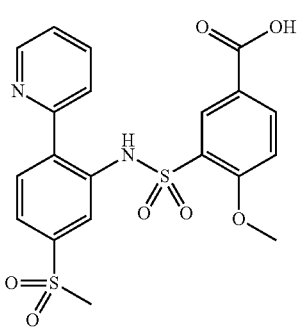
(44)
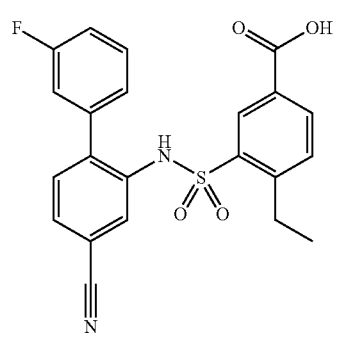
(41)
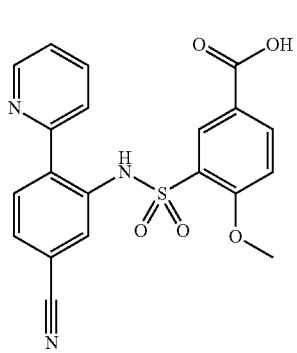
(45)
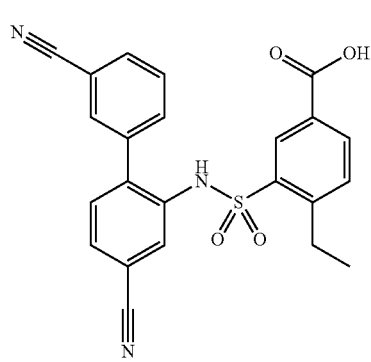
(42)
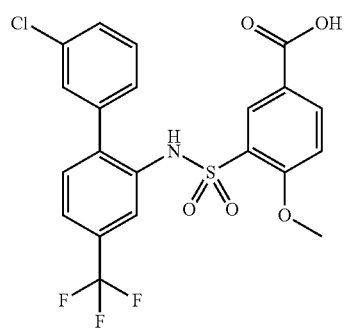
(46)

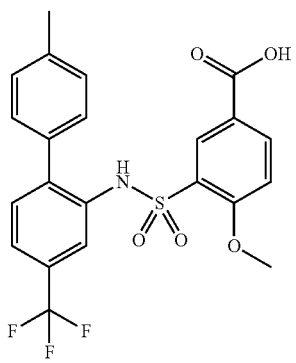
(47)
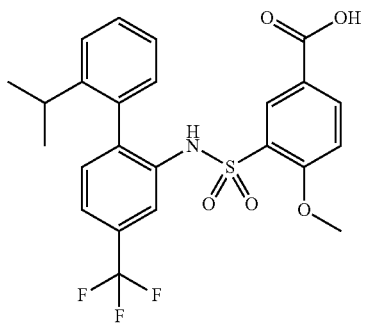
(51)
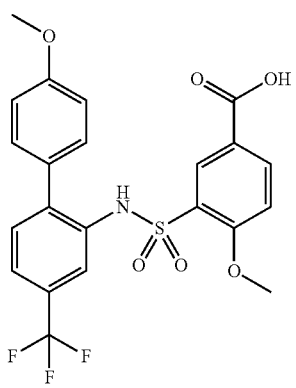
(48)
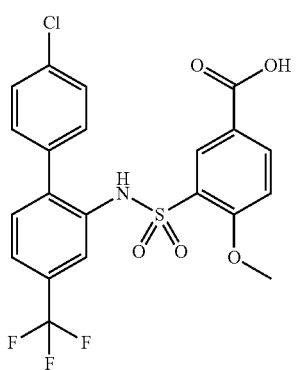
(49)
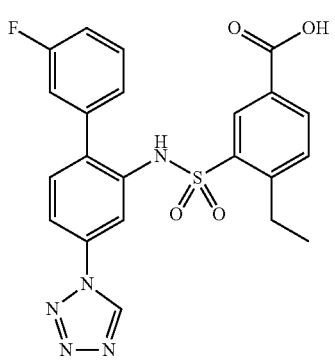
(52)
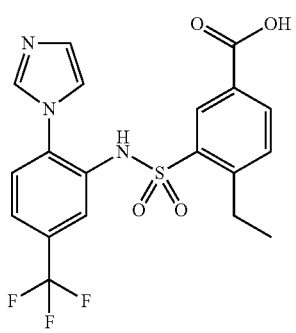
(50)
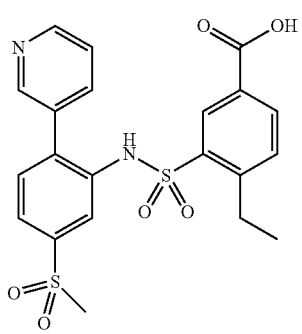
(53)
(54)

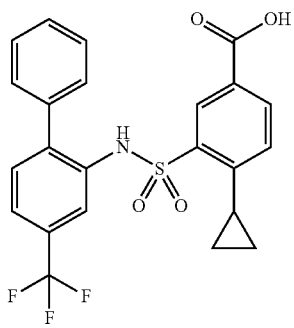
(55)
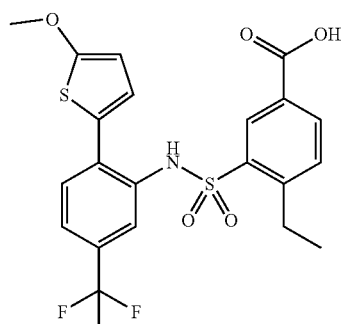
(59)
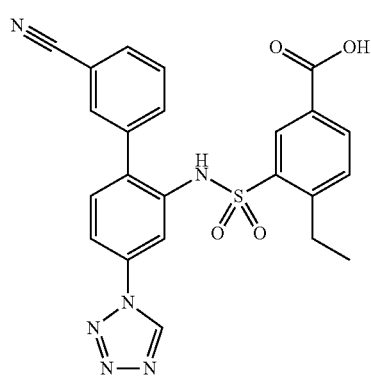
(56)
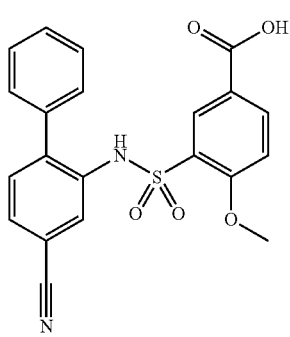
(60)
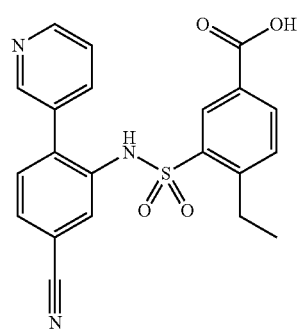
(57)
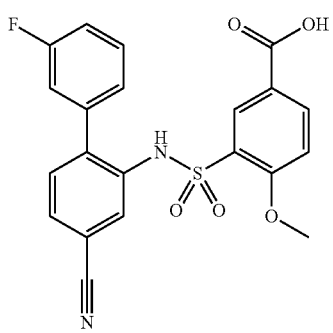
(61)
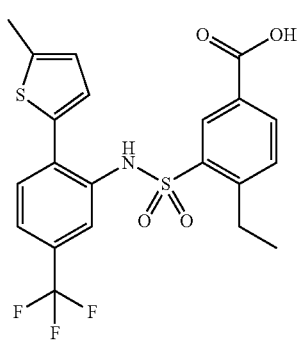
(58)
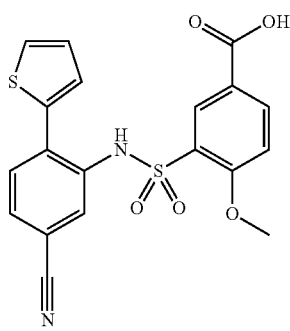
(62)

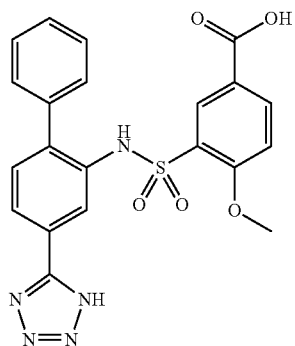
(63)
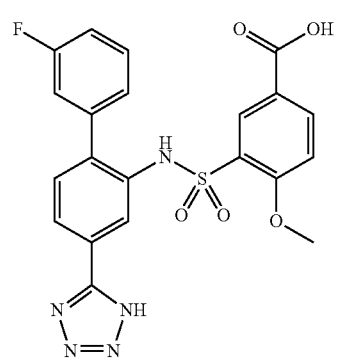
(64)
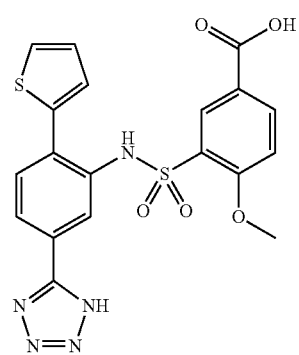
(65)
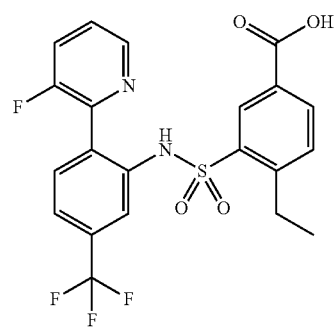
(66)
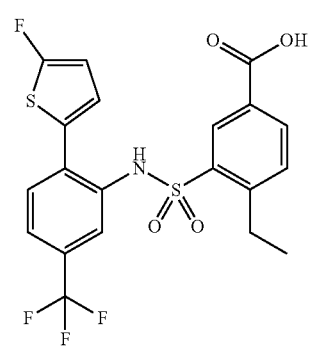
(67)
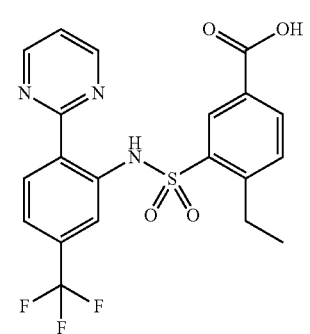
(68)
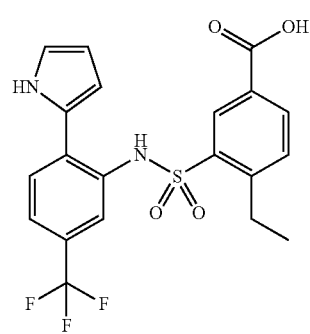
(69)
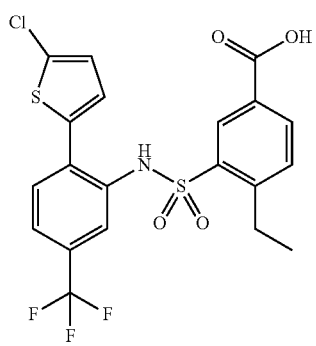
(70)

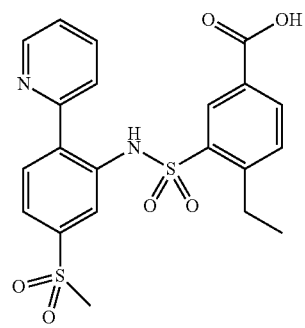 (71)
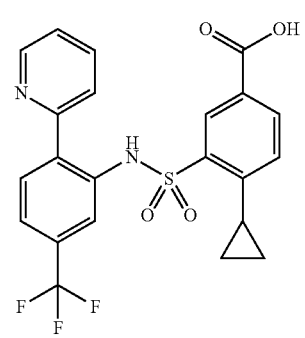 (72)
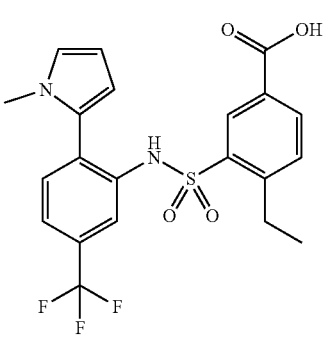 (73)
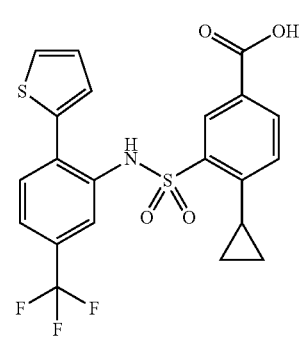 (74)
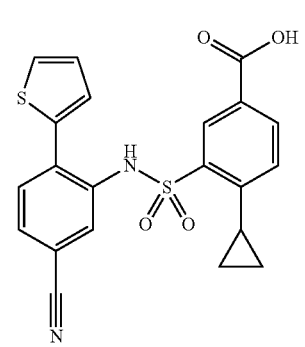 (75)
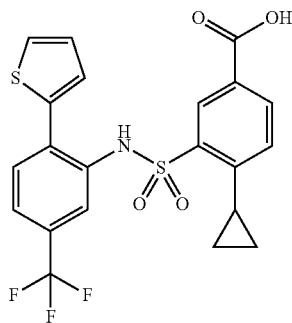 (76)
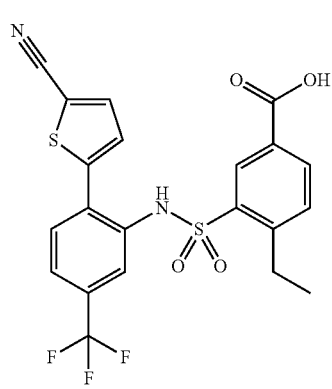 (77)
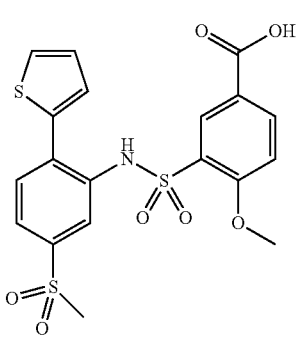 (78)
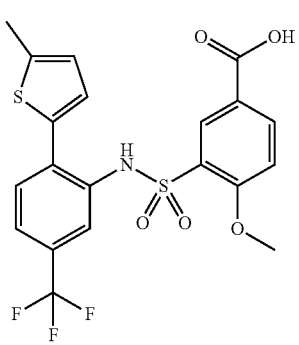 (79)

(80) 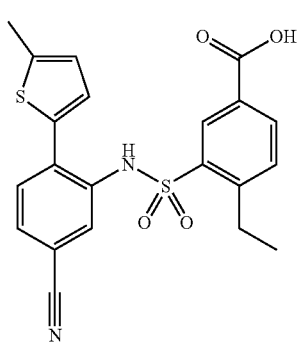
(81) 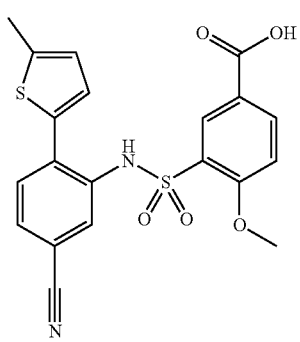
(82) 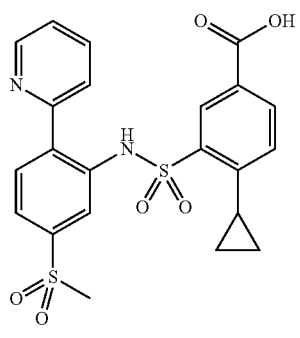
(83) 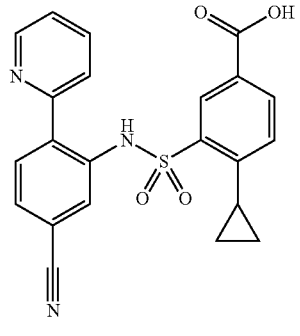
(84) 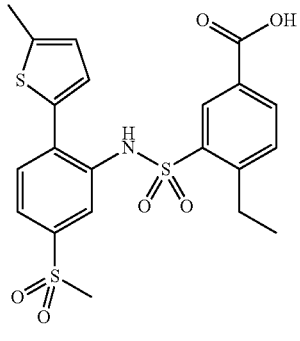
(85) 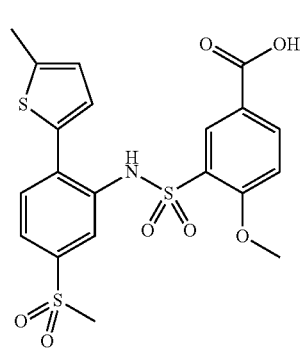
(86) 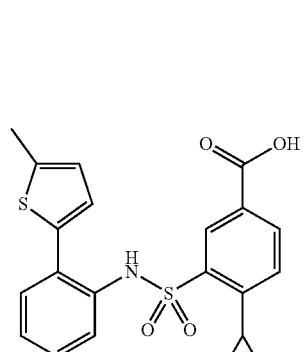
(87) 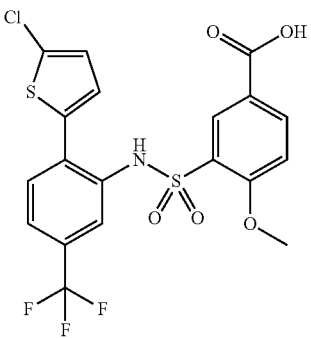
(88) 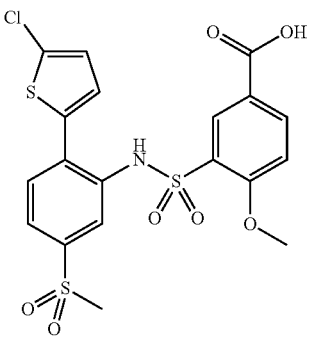

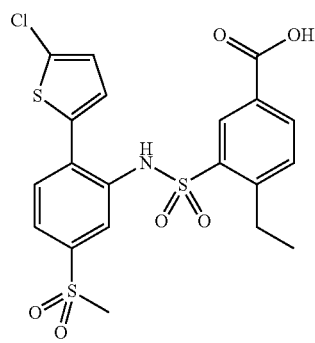
(89)
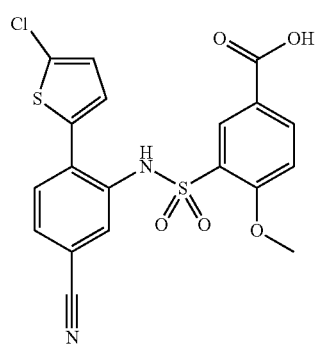
(90)
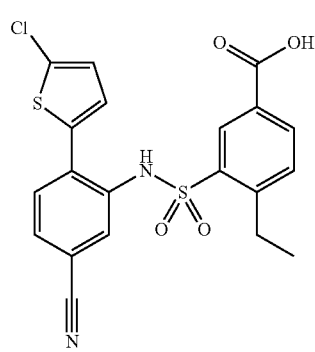
(91)
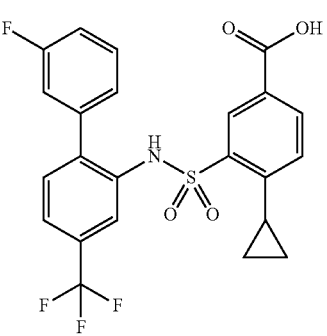
(92)
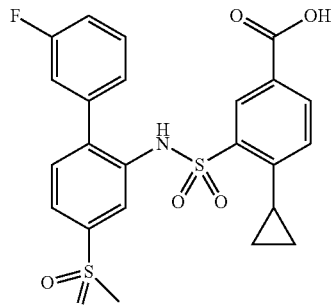
(93)
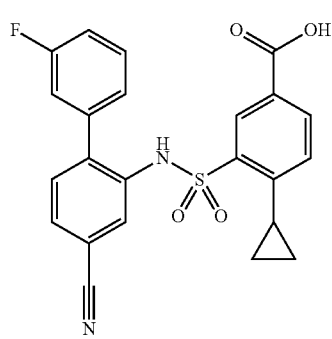
(94)
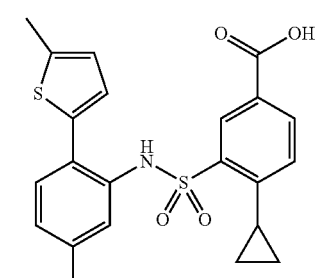
(95)
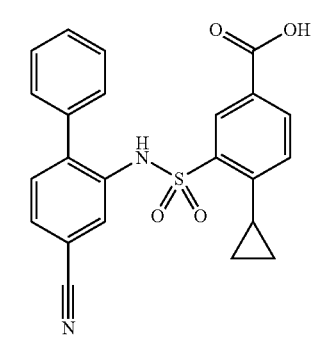
(96)
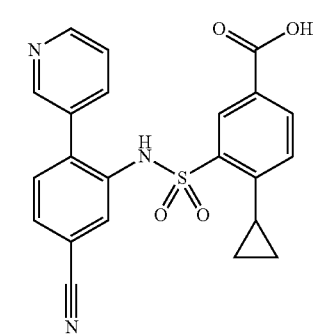
(97)

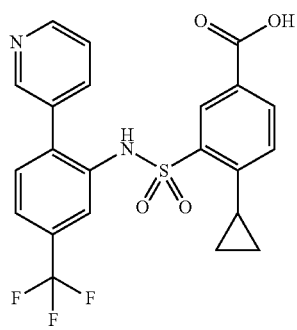
(98)
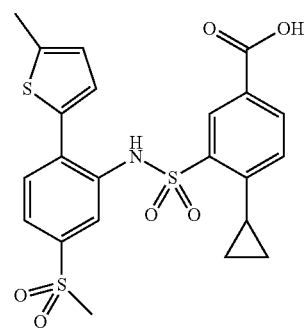
(103)
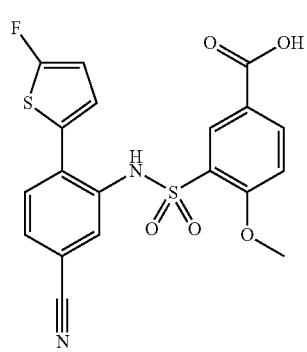
(100)
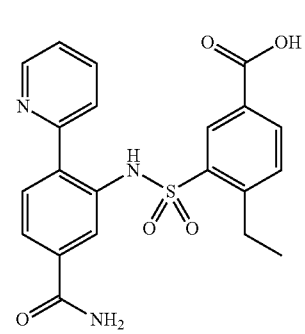
(104)
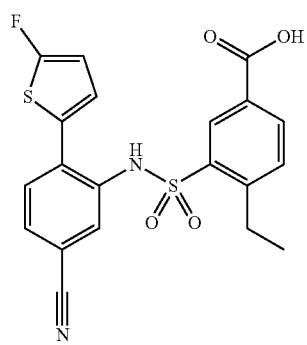
(101)
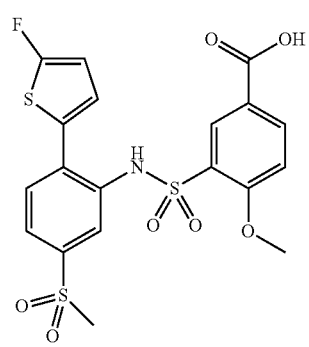
(105)
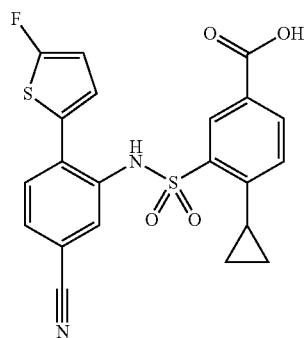
(102)
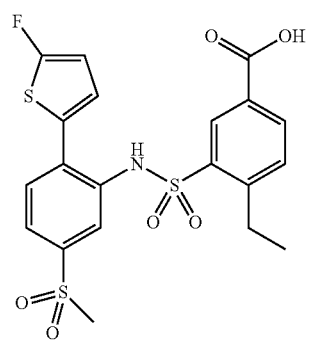
(106)

-continued
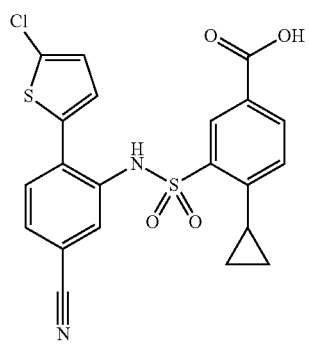
(111)
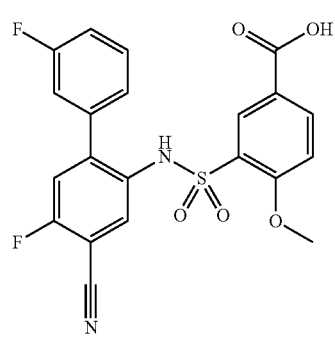
(112)
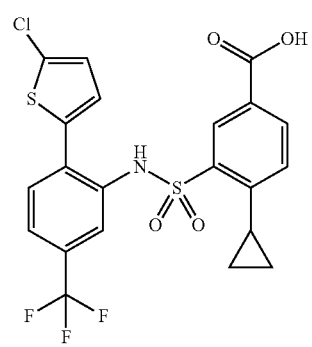
(113)
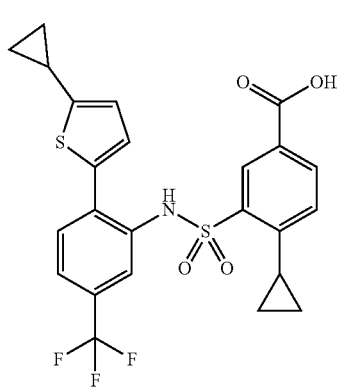
(114)
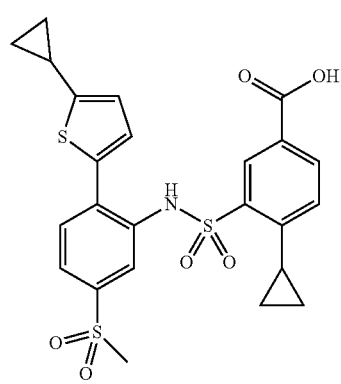
(115)
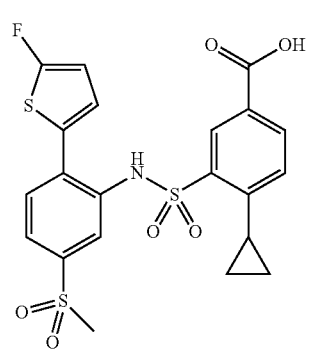
(116)
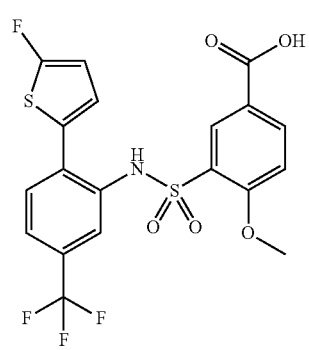
(117)
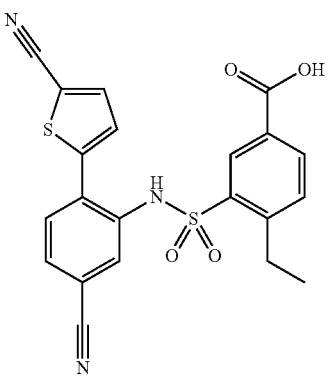
(118)

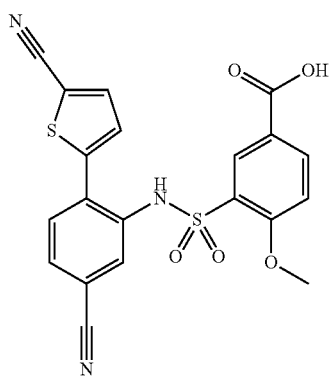
(119)
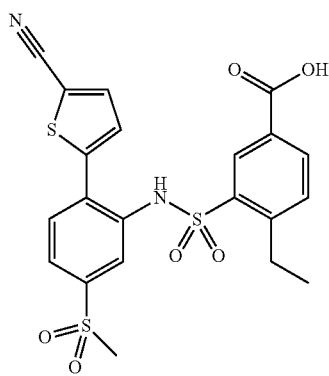
(120)
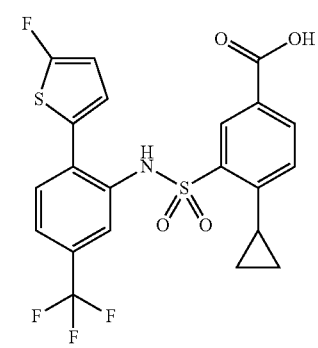
(122)
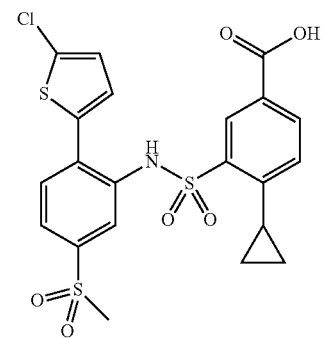
(123)
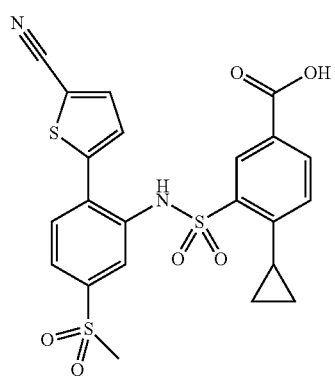
(124)
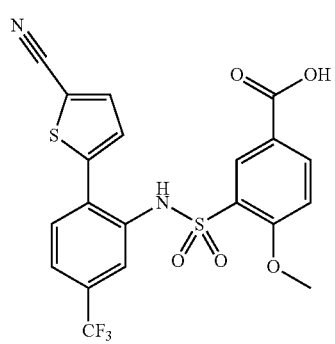
(125)
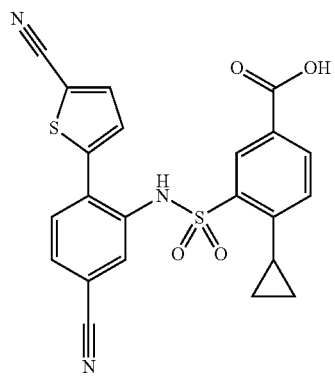
(126)
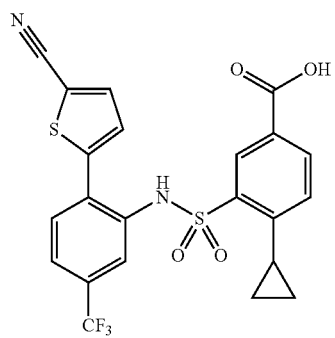
(127)

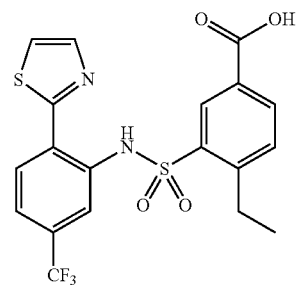
(128)
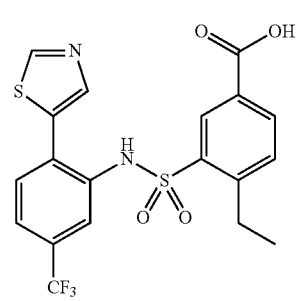
(129)
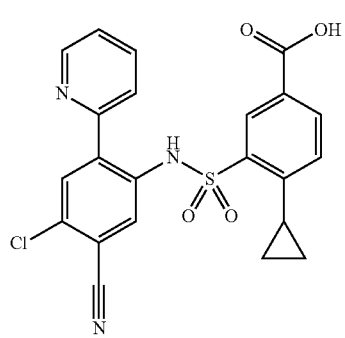
(132)
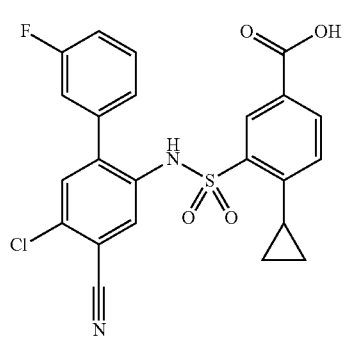
(133)
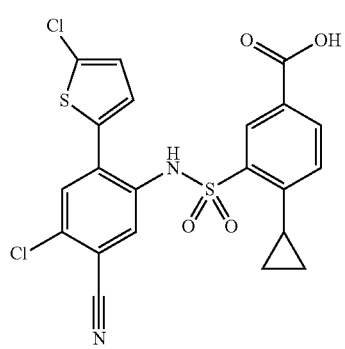
(134)
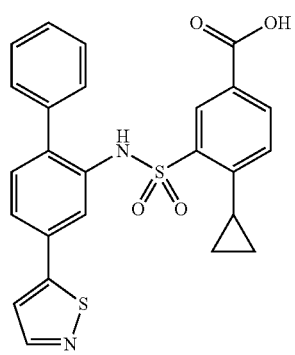
(135)
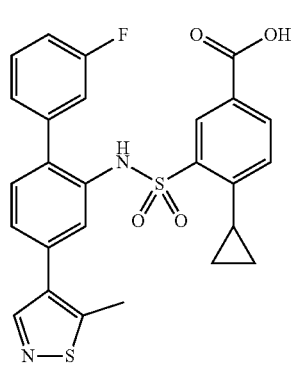
(136)
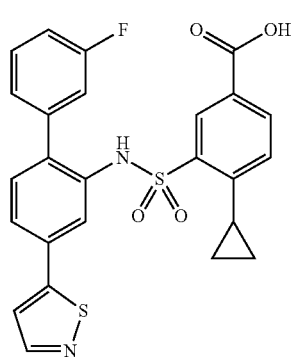
(137)
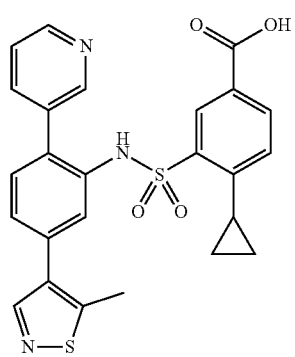
(138)

(139) 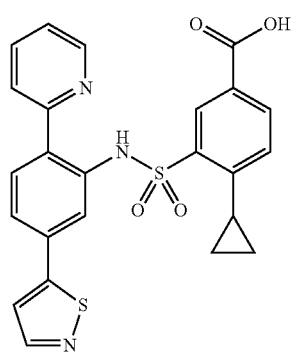
(140) 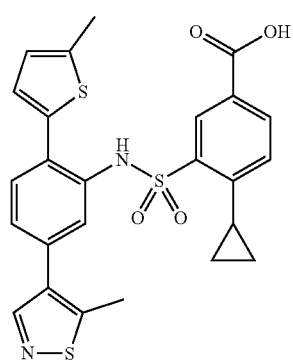
(141) 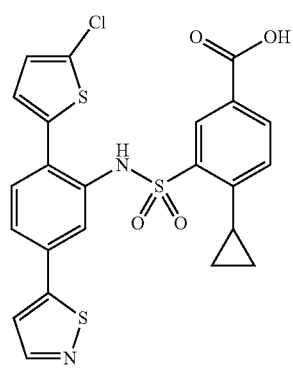
(142) 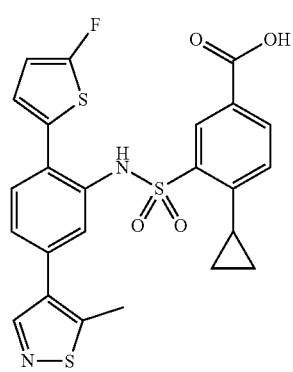
(151) 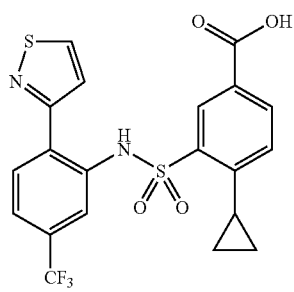
(144) 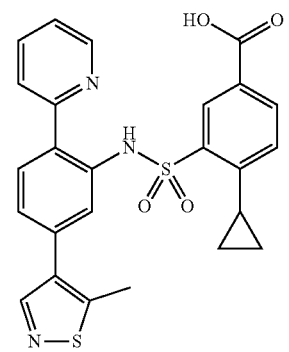
(145) 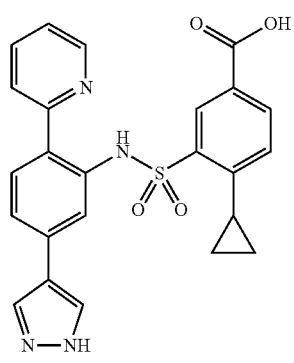
(146) 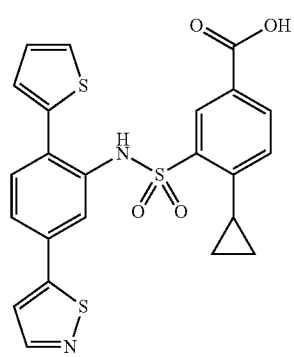

(147) 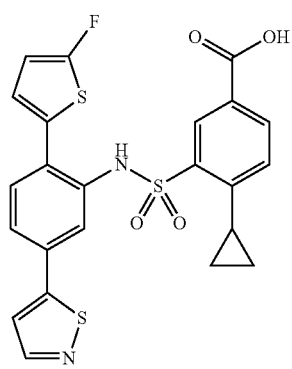
(153) 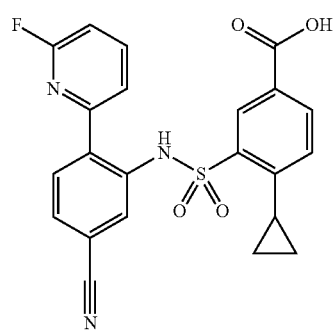
(148) 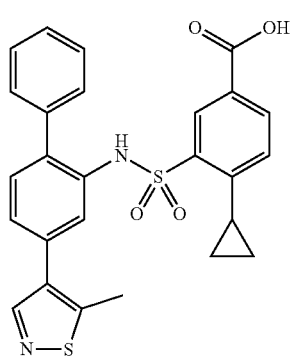
(154) 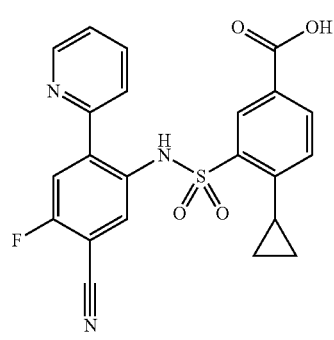
(149) 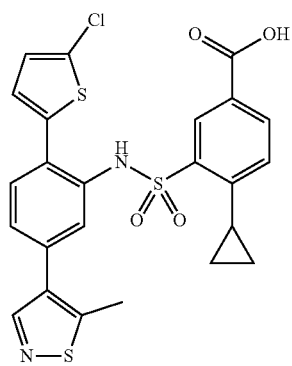
(159) 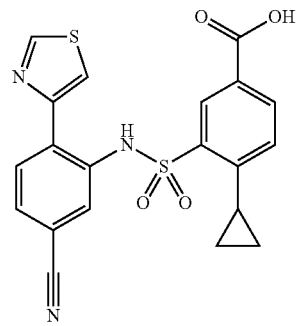
(152) 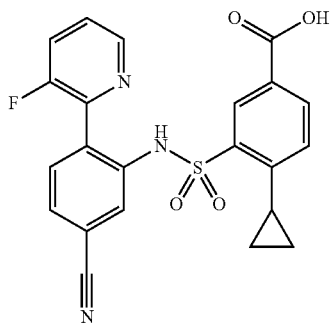
(160) 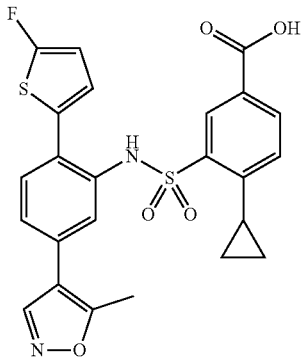

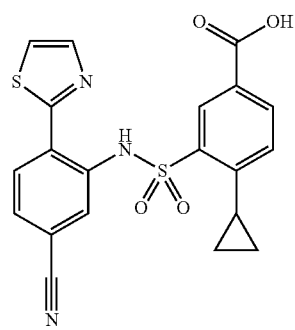
(163)
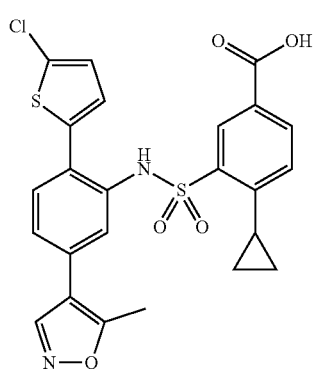
(164)
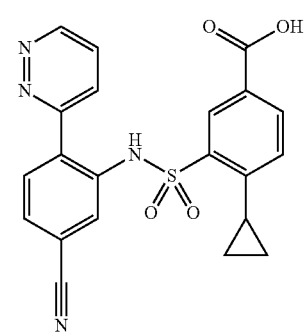
(165)
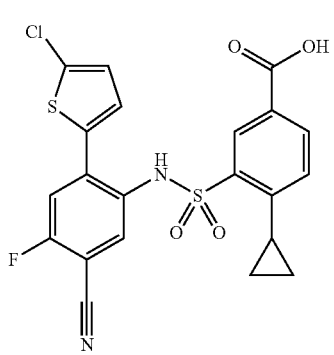
(166)
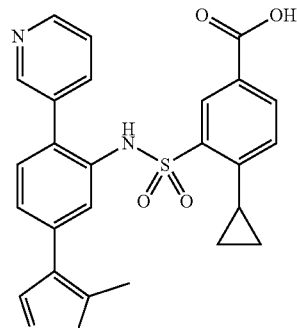
(167)
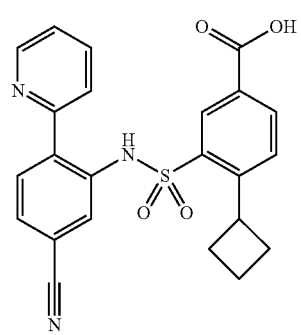
(168)
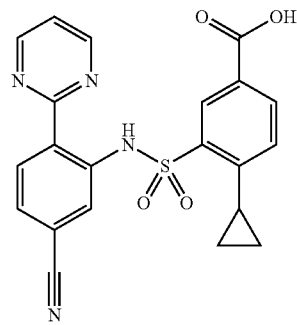
(169)
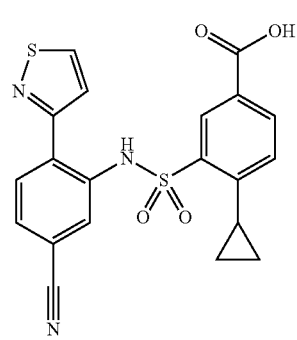
(170)
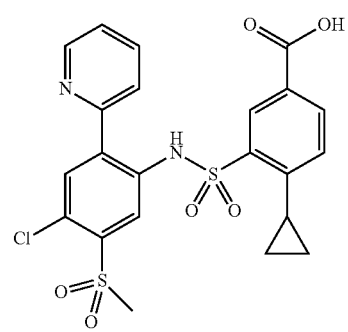
(171)

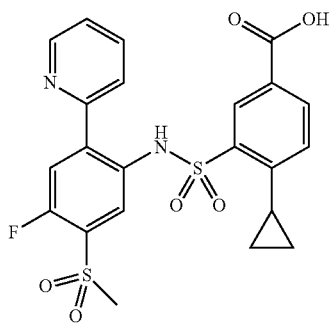 (172)
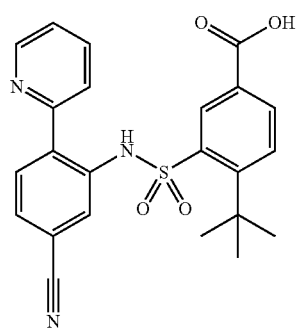 (173)
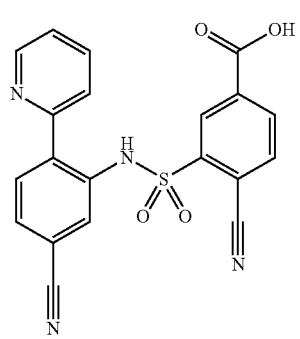 (175)
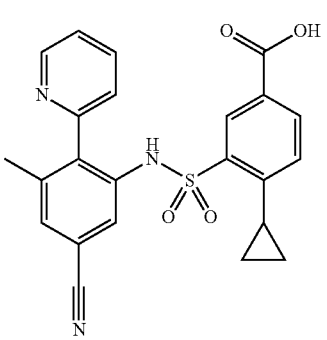 (176)
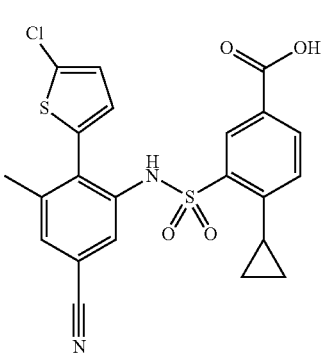 (177)
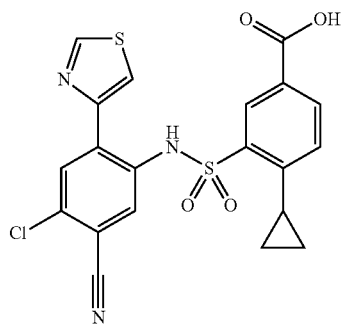 (178)
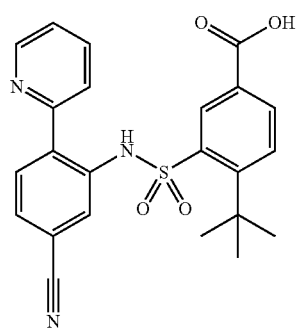 (179)
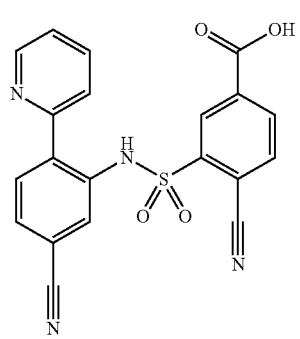 (180)
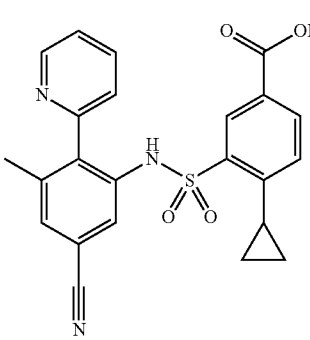 (181)
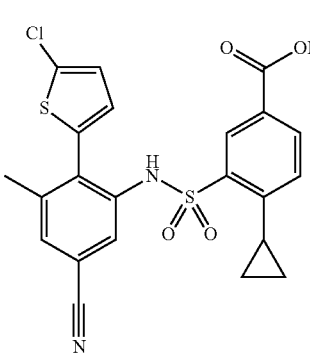 (182)

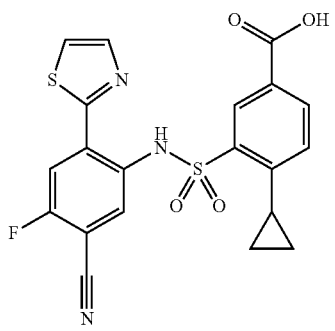
(183)
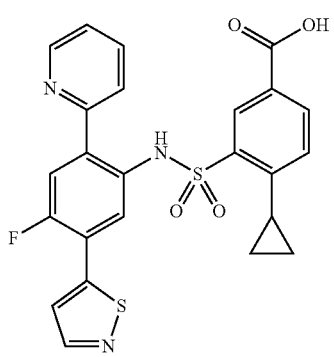
(184)
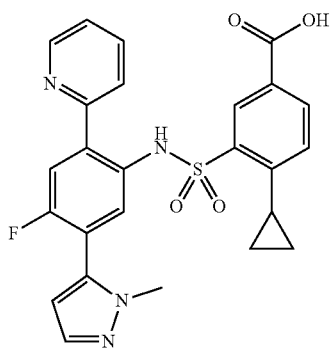
(185)
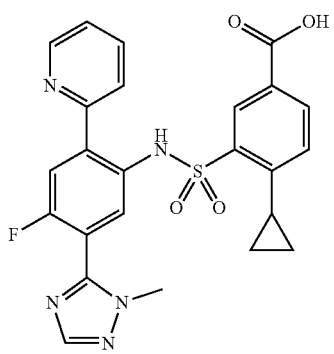
(186)
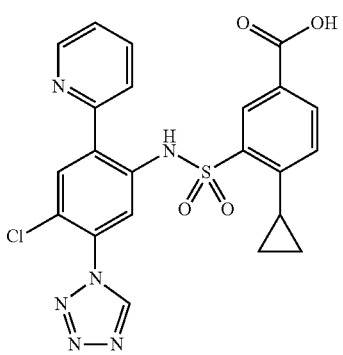
(187)
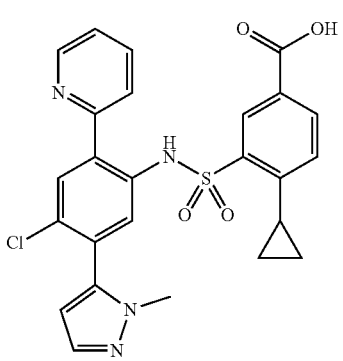
(188)
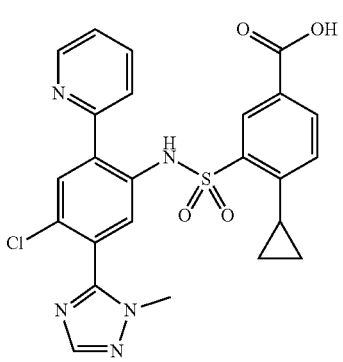
(189)
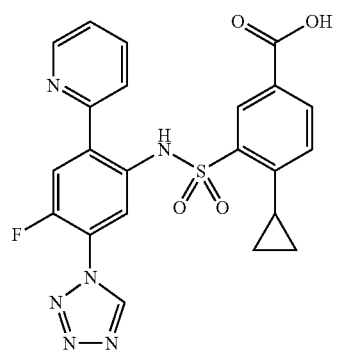
(190)

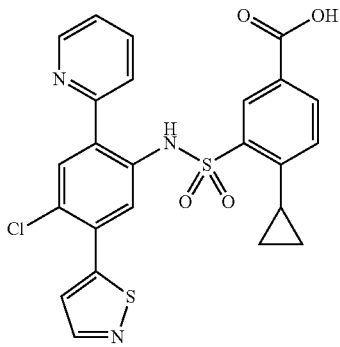

(191)

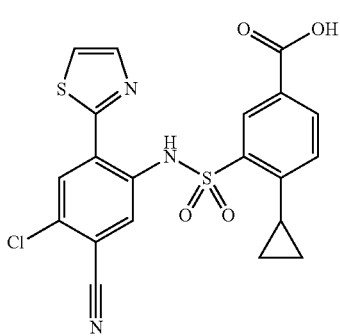

(192)

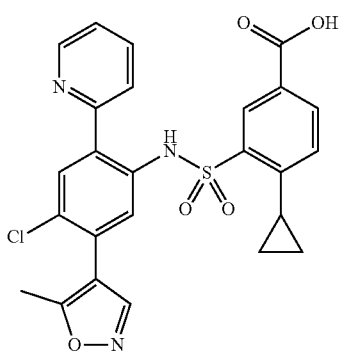

(193)

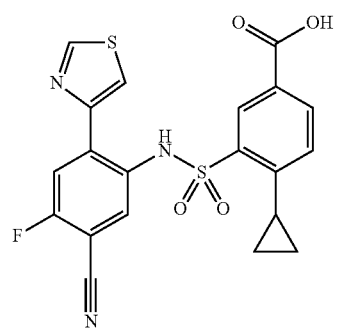

(196)

and pharmaceutically acceptable salts and hydrates thereof.

Compounds of Formula (Ib)

Another aspect of the invention relates to a compound of formula (Ib), or a pharmaceutically acceptable salt or hydrate thereof,

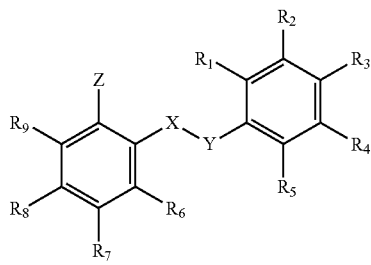

(Ib)

wherein:
the group X—Y is —NHSO$_2$— or —SO$_2$NH—;
Z is a monocyclic aryl or heteroaryl group, each of which is optionally substituted by one or more substituents selected from alkyl, cycloalkyl, halo, alkoxy, CN, haloalkyl and OH;
R$_1$ is H, CN or alkyl;
R$_2$ is selected from COOH and a tetrazolyl group;
R$_3$ is selected from H, Cl and alkyl;
R$_4$ is selected from H and halo;
R$_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
R$_6$ is H;
R$_7$ is a heteroaryl group which is optionally substituted by one or more substituents selected from alkyl, halo, alkoxy, CN, haloalkyl and OH;
R$_8$ is selected from H, alkyl, haloalkyl and halo; and
R$_9$ is H, alkyl or halo.

In one preferred embodiment, R$_7$ is a heteroaryl group which is optionally substituted by one or more substituents selected from alkyl, halo, alkoxy, CN, haloalkyl and OH. Preferably, the heteroaryl group is selected from pyrazolyl, isothiazolyl, triazolyl, tetrazolyl and isoxazolyl, each of which is optionally substituted by one or more substituents selected from alkyl, halo, alkoxy, CN, haloalkyl and OH.

In one preferred embodiment, R$_7$ is a heteroaryl group selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

Preferred definitions for groups X, Y, Z, R$_{1-5}$, R$_6$, R$_5$ and R$_9$ are as set out above for formulae (I) and (Ia).

In one preferred embodiment, Z is selected from pyridin-2-yl, pyridin-3-yl, pyrimidin-2-yl, pyrimidin-4-yl, pyrimidin-5-yl, 1H-pyrrol-1-yl, 1H-pyrrol-2-yl, thiazol-2-yl, thiazol-5-yl, thiazol-4-yl, isothiazol-3-yl, isothiazol-4-yl and isothiazol-5-yl, each of which is optionally substituted by one or more substituents selected from alkyl, cycloalkyl, halo, alkoxy, CN, haloalkyl and OH. Preferably, the one or more optional substituents are selected from Me, F, Cl, CN, cyclopropyl and MeO.

In one preferred embodiment, Z is selected from pyridin-2-yl, pyrimidin-2-yl, 1H-pyrrol-1-yl, thiazol-4-yl and isothiazol-3-yl, each of which is optionally substituted by one or more substituents selected from alkyl, cycloalkyl, halo, alkoxy, CN, haloalkyl and OH. Preferably, the one or more optional substituents are selected from Me, F, Cl, CN, cyclopropyl and MeO.

In one preferred embodiment, Z is selected from pyrrolyl, pyrazolyl and triazolyl, each of which is optionally substituted by one or more substituents selected from alkyl, cycloalkyl, halo, alkoxy, CN, haloalkyl and OH. More preferably, Z is selected from 1H-pyrrol-1-yl, pyrazol-1-yl and 1,2,4-triazol-1-yl, each of which is optionally substituted by one or more substituents selected from alkyl, cycloalkyl, halo, alkoxy, CN, haloalkyl and OH.

Even more preferably, Z is optionally substituted 1H-pyrrol-1-yl. Preferably, the one or more optional substituents are selected from Me, F, Cl, CN, cyclopropyl and MeO.

In another preferred embodiment, Z is selected from the following:

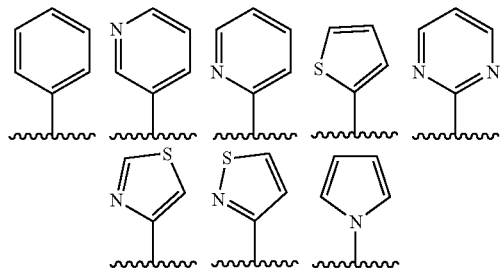

each of which is optionally substituted by by one or more substituents selected from alkyl, cycloalkyl, halo, alkoxy, CN, haloalkyl and OH. Preferably, the one or more optional substituents are selected from Me, F, Cl, CN, cyclopropyl and MeO.

In one preferred embodiment, Z is selected from:

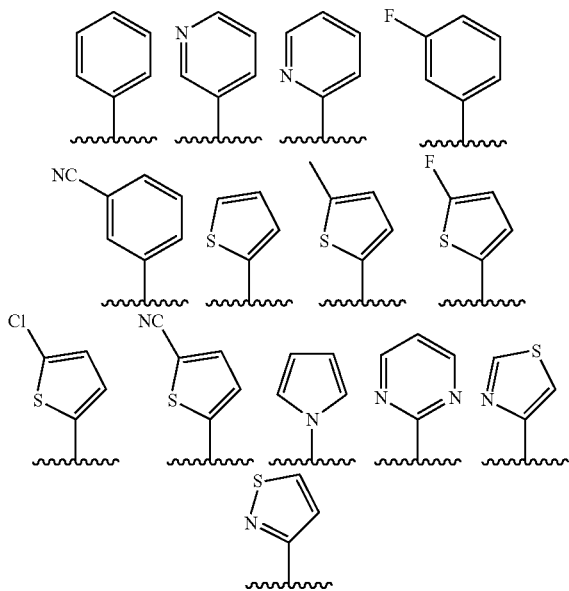

In one preferred embodiment:

$R_2$ is COOH;

X—Y is NH—$SO_2$;

$R_5$ is selected from cyclopropyl, OMe and Et, and is more preferably cyclopropyl;

$R_1$, $R_3$, $R_4$, $R_6$, and $R_9$ are all H;

$R_8$ is H, Cl or F, more preferably Cl or F; and

Z is selected from the following:

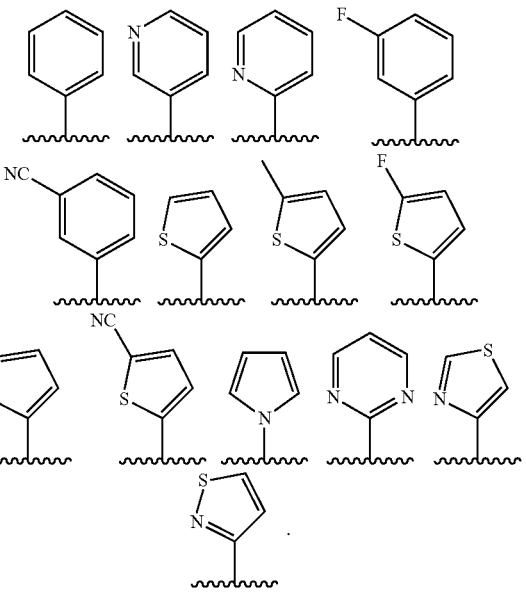

Particularly preferred compounds of formula (Ib) are selected from the following compounds listed in the tables herein: (52), (53), (56), (63), (64), (65), (135)-(143), (144)-(150), (160), (164), (167), (184)-(191), (193)-(195), (197)-(208), and pharmaceutically acceptable salts and hydrates thereof.

The invention also relates to compositions of formulae (I), (Ia) and (Ib) for use in medicine, and for use in the therapeutic applications described herein.

Pharmaceutical Compostions

The invention also relates to pharmaceutical compositions comprising a compound as described herein in admixed with a pharmaceutically acceptable diluent, excipient or carrier. For use according to the present invention, the compounds or physiologically acceptable salts, esters or other physiologically functional derivatives thereof, described herein, may be presented as a pharmaceutical formulation, comprising the compounds or physiologically acceptable salt, ester or other physiologically functional derivative thereof, together with one or more pharmaceutically acceptable carriers therefor and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and PJ Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound as described herein into conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as 3H or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Atropisomers

Some of the compounds of the invention may exist as atropisomers. Atropisomers are stereoisomers arising because of hindered rotation about a single bond, where energy differences due to steric strain or other contributors create a barrier to rotation that is high enough to allow for isolation of individual conformers. The invention encompasses all such atropisomers.

Prodrugs

The invention further includes the compounds of the present invention in prodrug form, i.e. covalently bonded compounds which release the active parent drug in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms. Preferably, the solvate is a hydrate.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The dosage amount will further be modified according to the mode of administration of the compound. For example, to achieve an "effective amount" for acute therapy, parenteral administration of a compound is typically preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to modulate ERAP1. The compounds may be administered one to four times daily at a level to achieve a total daily dose of about 0.4 to about 400 mg/kg/day. The precise amount of a compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

A further aspect of the inventiont relates to a combination comprising a compound as described herein and one or more additional active agents. In a particularly preferred embodiment, the one or more compounds of the invention are administered in combination with one or more additional active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

In one preferred embodiment, the additional active agent is an immunotherapy agent, more preferably a cancer immunotherapy agent. An "immunotherapy agent" refers to a treatment that uses the subject's own immune system to fight diseases such as cancer.

In one preferred embodiment the compound of the invention inhibits the activity of ERAP1, and the compound is administered in combination with an immunotherapy. The compound may increase the sensitivity of cancer cells to an immunotherapy. The immunotherapy may be mediated by T cells. In one embodiment the compound may increase the number of CD8+ T cells in a tumour.

In one embodiment the compound may be used to treat cancers which are weakly responsive or not responsive to immunotherapies.

In one preferred embodiment, the additional active agent is a molecule capable of immune checkpoint intervention, a co-stimulatory antibody, a chemotherapy agent, a radiotherapy agent, a targeted therapy agent or an antibody, particularly a monoclonal antibody.

In one preferred embodiment the additional active agent is a molecule capable of immune checkpoint intervention.

Immune checkpoint molecules include CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4, B7.1, B7.2, ILT-2, ILT-4, TIGIT, HHLA2, IDO, CD39, CD73, A2aR and butyrophilins.

Immune checkpoint molecules include both inhibitory and activatory molecules, and interventions may apply to either or both types of molecule.

Immune checkpoint inhibitors include, but are not limited to, PD-1 inhibitors, PD-L1 inhibitors, LAG-3 inhibitors, TIM-3 inhibitors, TIGIT inhibitors, BTLA inhibitors and CTLA-4 inhibitors, for example. Co-stimulatory antibodies deliver positive signals through immune-regulatory receptors including but not limited to ICOS, CD137, CD27 OX-40 and GITR.

In one highly preferred embodiment, the the additional active agent is an antibody checkpoint inhibitor. Suitable examples of antibody checkpoint inhibitors, include, but are not limited to, anti-PD-1 antibodies, anti-PD-L1 antibodies and anti-CTLA4 antibodies. In one preferred embodiment, the antibody checkpoint inhibitor is an anti-PD-1 antibody, more preferably selected from pembrolizumab, cemiplimab and nivolumab.

In one preferred embodiment, the antibody checkpoint inhibitor is an anti-PD-L1 antibody, more preferably selected from atezolizumab, avelumab and durvalumab.

In one preferred embodiment, the antibody checkpoint inhibitor is an anti-CTLA4 antibody, more preferably selected from ipilimumab and tremelimumab.

In one preferred embodiment the immunotherapy is an anti-cancer vaccine or virus, such as an oncolytic virus.

In one preferred embodiment the immunotherapy is a cell-based therapy. In one embodiment the cell-based therapy may be a T cell therapy, such as adoptive T cell therapy, or therapy with CAR-T cells.

Adoptive cell-based immunotherapy may include the following: Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, for example expressing cytokines such as GM-CSF, and/or to express tumor-associated antigen (TAA) antigens, such as Mage-1, gp-100, patient-specific neoantigen vaccines, and the like.

In a further embodiment, the immunotherapy may comprise non-cell-based immunotherapies. In one embodiment, compositions comprising antigens with or without vaccine-enhancing adjuvants may be used. Such compositions exist in many well-known forms, such as peptide compositions, oncolytic viruses, and recombinant antigen comprising fusion proteins.

In an alternative embodiment, immunomodulatory interleukins, such as IL-2, IL-6, IL-7, IL-12, IL-17, IL-23, as well as modulators thereof (e.g., blocking antibodies or more potent or longer lasting forms) may be used. Immunomodulatory cytokines, such as interferons, G-CSF, imiquimod, T F alpha, and the like, as well as modulators thereof (e.g., blocking antibodies or more potent or longer lasting forms) may also be used. In another embodiment, immunomodulatory chemokines, such as CCL3, CCL26, and CXCL7, and the like, as well as modulators thereof (e.g., blocking antibodies or more potent or longer lasting forms) may be used. In a further embodiment, immunomodulatory molecules targeting immunosuppression, such as STAT3 signaling modulators, FkappaB signaling modulators, and immune checkpoint modulators, may be used.

In another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (Cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an EVIPDH inhibitor, mycophenolic acid, myriocin, fingolimod, an NF-xB inhibitor, raloxifene, drotrecogin alfa, denosumab, an F-xB signaling cascade inhibitor, disulfiram, olmesartan, dithiocarbamate, a proteasome inhibitor, bortezomib, MG132, Prol, PI-0052, curcumin, genistein, resveratrol, parthenolide, thalidomide, lenalidomide, flavopiridol, non-steroidal anti-inflammatory drugs (NSAIDs), arsenic tri oxide, dehydroxymethylepoxyquinomycin (DH-MEQ), I3C(indole-3-carbinol)/DIM(di-indolmethane) (13C/DIM), Bay 1 1-7082, luteolin, cell permeable peptide SN-50, IKBa-super repressor overexpression, FKB decoy oligodeoxynucleotide (ODN), or a derivative or analog of any thereto, may be used.

In yet another embodiment, immunomodulatory antibodies or protein may be used. For example, antibodies that bind to CD40, Toll-like receptor (TLR), OX40, GITR, CD27, or to 4-IBB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CDI I a antibody, efalizumab, an anti-CD 18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab.

In one embodiment, the subject may be undergoing or have previously undergone treatment with a chemotherapeutic agent. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, III.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-a, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

The present invention is further described by way of the following non-limiting examples.

EXAMPLES

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

General Schemes

Abbreviations aq: aqueous; br: broad; ca.: circa; d: doublet; DCM: dichloromethane; dioxane: 1,4-dioxane; DMF: dimethylformamide; dppf: 1,1'-ferrocenediyl-bis(diphenylphosphine); Et$_3$N: triethylamine; EtOAc: ethyl acetate; EtOH: ethanol; h: hours; HPLC: high performance liquid chromatography; IPA, isopropanol; LC: liquid chromatography; m: multiplet; M: molar, molecular ion; MeCN: acetonitrile; MeOH: methanol; min: minutes; MS: mass spectrometry; NMR: nuclear magnetic resonance; PDA: photodiode array; q: quartet; RT: room temperature (ca. 20° C.); R$_T$: retention time; s: singlet, solid; t: triplet; TBME: tert-butyl methyl ether; tBuXPhos Pd G3: [(2-di-tert-butylphosphino-2',4',6'-triisopropyl-1,1'-biphenyl)-2-(2'-amino-1,1'-biphenyl)]palladium(II) methanesulfonate (CAS: 1447963-75-8); TFA: trifluoroacetic acid; THF: tetrahydrofuran; UPLC: ultra performance liquid chromatography; UV: ultraviolet; XPhos: 2-dicyclohexylphosphino-2',4',6'-triisopropylbiphenyl; XPhos Pd G2: XPhos aminobiphenyl palladium chloride pre-catalyst (CAS: 1310584-14-5); XPhos Pd G3: (2-Dicyclohexylphosphino-2',4',6'-triisopropyl-1,1'-biphenyl)[2-(2'-amino-1,1'-biphenyl)]palladium(II) methanesulfonate (CAS: 1445085-55-1); NBS: n-bromosuccinimide; Pd-174: allyl(2-di-tert-butylphosphino-2',4',6'-triisopropyl-1,1'-biphenyl) palladium(II) triflate (CAS: 1798782-25-8); XantPhos-Pd-G3: [(4,5-Bis(diphenylphosphino)-9,9-dimethylxanthene)-2-(2'-amino-1,1'-biphenyl)]palladium(II) methanesulfonate (CAS: 1445085-97-1); Boc$_2$O: Di-tert-butyl dicarbonate. Other abbreviations are intended to convey their generally accepted meaning.

Scheme 1

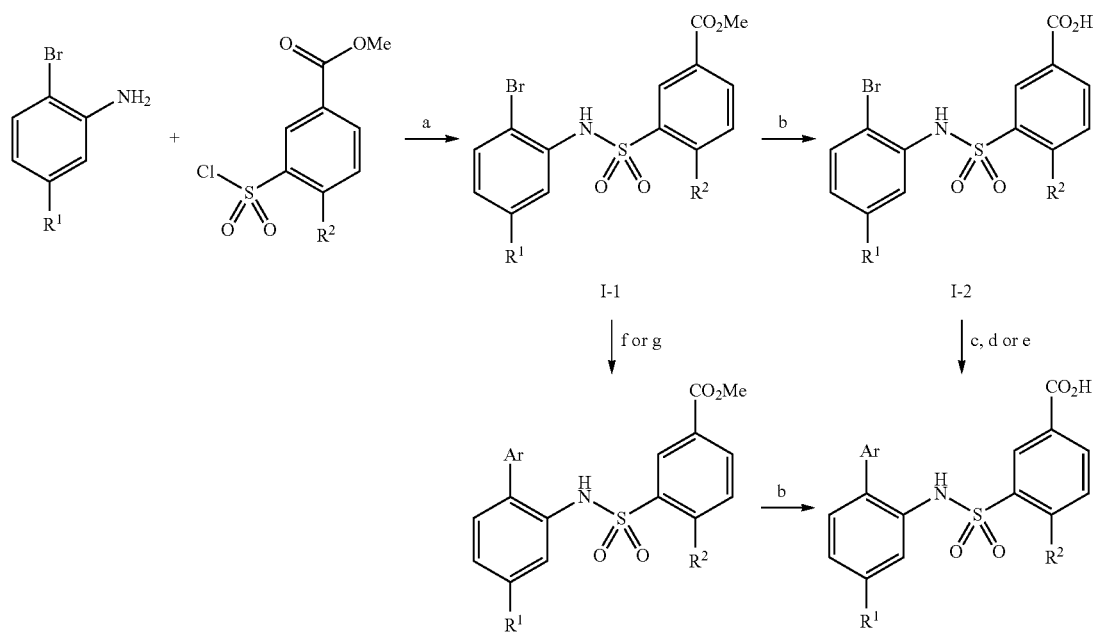

Reagents (a) Pyridine, DCM; (b) LiOH, water, THF or dioxane; (c) Boronic acid, $K_3PO_4$, Pd(OAc)$_2$, XPhos, dioxane; (d) Boronic acid, $Cs_2CO_3$, Pd(PPh$_3$)$_4$, dioxane, water, CuCl; (e) Boronic acid, $Na_2CO_3$, Pd(OAc)$_2$, XPhos, THF, (f) Boronic acid, $K_3PO_4$, XPhos Pd G2/G3, dioxane; (g) Boronic acid, $Na_2CO_3$, Pd(dppf)Cl$_2$·DCM, THF.

The appropriate aniline and sulfonyl chloride were reacted together to afford sulfonamide I-1. The ester group was hydrolysed to the corresponding acid, providine I-2, which was reacted with the appropriate boronic acid or boronic ester to provide I-3. Alternatively, the steps may be carried out in an alternative sequence as indicated.

Scheme 2

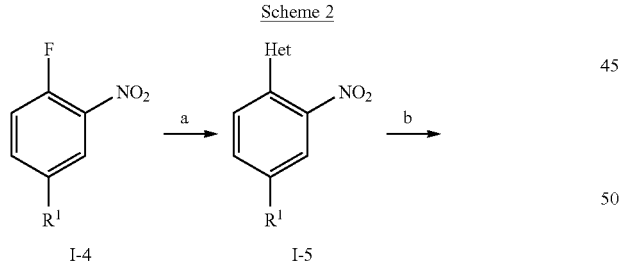

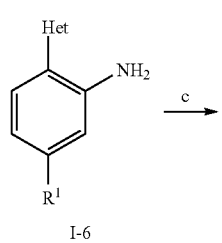

-continued

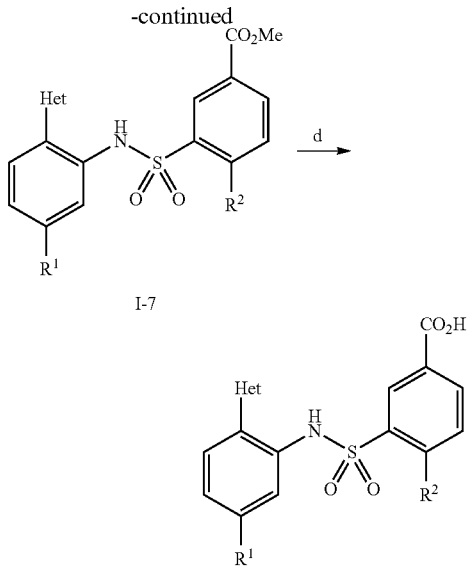

Reagents: (a) Amine, DCM; (b) H$_2$, 10% Pd/C, EtOH; (c) sulfonyl chloride, pyridine, DCM; (d) LiOH(aq), THF, MeOH.

The appropriate aryl fluoride (I-4) was reacted with the appropriate heteroaromatic compound in a nucleophilic substitution reaction, followed by reduction of the resultant nitro-compound I-5 to aniline I-6. This was reacted with the appropriate sulfonyl chloride to afford sulfonamide I-7. Ester hydrolysis provided the corresponding carboxylic acid I-8.

General Experimental Conditions

All starting materials and solvents were obtained either from commercial sources or prepared according to the literature citation. Reaction mixtures were magnetically stirred and reactions performed at room temperature (ca. 20° C.) unless otherwise indicated. Column chromatography was performed on an automated flash chromatography system, such as a CombiFlash Rf system, using pre-packed silica (40 μm) cartridges, unless otherwise indicated.

$^1$H NMR spectra were recorded using a Bruker Avance III HD spectrometer at 500 MHz, equipped with a Bruker 5 mm SmartProbe™. Chemical shifts are expressed in parts per million using either the central peaks of the residual protic solvent or an internal standard of tetramethylsilane as references. The spectra were recorded at 298 K unless otherwise indicated.

Analytical UPLC-MS experiments to determine retention times and associated mass ions were performed using a Waters ACQUITY UPLC® H-Class system, equipped with ACQUITY PDA Detector and ACQUITY QDa Mass Detector, running one of the analytical methods described below.

Analytical LC-MS experiments to determine retention times and associated mass ions were performed using an Agilent 1200 series HPLC system coupled to an Agilent 1956, 6100 or 6120 series single quadrupole mass spectrometer running one of the analytical methods described below.

Preparative HPLC purifications were performed either using a Waters X-Select CSH C18, 5 μm, 19×50 mm column using a gradient of MeCN and water, both modified with 0.1% v/v formic acid, or on a Waters X-Bridge BEH C18, 5 μm, 19×50 mm column using a gradient of MeCN and 10 mM ammonium bicarbonate(aq). Fractions were collected following detection by UV at a single wavelength measured by a variable wavelength detector.

Nomenclature of structures was generated using 'Structure to Name' conversion from ChemDraw® Professional 17 (PerkinElmer).

Analytical Methods
Method 1—Acidic 3 Min Method
  Column: Waters ACQUITY UPLC® CSH C18, 1.7 μm, 2.1×30 mm at 40° C.
  Detection: UV at 254 nm unless otherwise indicated, MS by electrospray ionisation
  Solvents: A: 0.1% v/v Formic acid in water, B: 0.1% v/v Formic acid in MeCN
  Gradient:

| Time | % A | % B | Flow rate (ml/min) |
|---|---|---|---|
| 0.00 | 95 | 5 | 0.77 |
| 0.11 | 95 | 5 | 0.77 |
| 2.15 | 5 | 95 | 0.77 |
| 2.56 | 5 | 95 | 0.77 |
| 2.83 | 95 | 5 | 0.77 |
| 3.00 | 95 | 5 | 0.77 |

Method 2—Basic 3 Min Method
  Column: Waters ACQUITY UPLC® BEH C18, 1.7 μm, 2.1×30 mm at 40° C.
  Solvents: A: 10 mM ammonium bicarbonate(aq), B: MeCN
  (other parameters the same as Method 1)
Method 3—Acidic 4 Min Method
  Column: Waters X-Select CSH C18, 2.5 μm, 4.6×30 mm at 40° C.
  Detection: UV at 254 nm unless otherwise indicated, MS by electrospray ionisation
  Solvents: A: 0.1% v/v Formic acid in water, B: 0.1% v/v Formic acid in MeCN
  Gradient:

| Time | % A | % B | Flow rate (ml/min) |
|---|---|---|---|
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 4—Basic 4 Min Method
  Column: Waters X-Bridge BEH C18, 2.5 μm, 4.6×30 mm at 40° C.
  Solvents: A: 10 mM ammonium bicarbonate(aq), B: MeCN
  (other parameters the same as Method 3)
Method 5—Acidic 4 min Method
  Column: YMC Triart C18, 1.6 μm, 50×2.1 mm at 35° C.
  Detection: UV at 254 nm unless otherwise indicated, MS by electrospray ionisation
  Solvents: A: 0.1% v/v Formic acid in water, B: MeCN
  Gradient:

| Time | % A | % B | Flow rate (ml/min) |
|---|---|---|---|
| 0.00 | 97 | 3 | 0.8 |
| 0.20 | 97 | 3 | 0.8 |
| 2.70 | 2 | 98 | 0.8 |
| 3.00 | 0 | 100 | 1.0 |
| 3.50 | 0 | 100 | 1.0 |
| 3.51 | 97 | 3 | 0.8 |
| 4.00 | 97 | 3 | 0.8 |

Method 6—Acidic 1 Min Method
  Column: Waters ACQUITY UPLC® CSH C18, 1.7 μm, 2.1×30 mm at 40° C.
  Detection: UV at 254 nm unless otherwise indicated, MS by electrospray ionisation
  Solvents: A: 0.1% v/v Formic acid in water, B: 0.1% v/v Formic acid in MeCN
  Gradient:

| Time | % A | % B | Flow rate (ml/min) |
|---|---|---|---|
| 0.00 | 95 | 5 | 1.00 |
| 0.08 | 95 | 5 | 1.00 |
| 0.70 | 5 | 95 | 1.00 |
| 0.80 | 5 | 95 | 1.00 |
| 0.90 | 95 | 5 | 1.00 |
| 1.00 | 95 | 5 | 1.00 |

Method 7—Basic 1 Min Method
  Column: Waters ACQUITY UPLC® BEH C18, 1.7 μm, 2.1×30 mm at 40° C.
  Solvents: A: 10 mM ammonium bicarbonate(aq), B: MeCN
  (other parameters the same as Method 6)
Method 8—Basic 7 Min Method
  Column: C18, 3.5 μm, 4.6×50 mm at 35° C.
  Detection: UV, MS by electrospray ionisation
  Solvents: A: 5 mM Ammonium Bicarbonate in water, B: MeOH Gradient:

| Time | % A | % B | Flow rate (ml/min) |
|------|-----|-----|--------------------|
| 0.00 | 92  | 8   | 1.00 |
| 0.75 | 92  | 8   | 1.00 |
| 3.00 | 30  | 70  | 1.00 |
| 3.70 | 5   | 95  | 1.00 |
| 4.20 | 0   | 100 | 1.00 |
| 5.20 | 0   | 100 | 1.00 |
| 5.21 | 92  | 8   | 1.00 |
| 7.00 | 92  | 8   | 1.00 |

Example 1: 4-methoxy-3-(N-(4-(trifluoromethyl)-[1,1'-biphenyl]-2-yl)sulfamoyl)benzoic acid

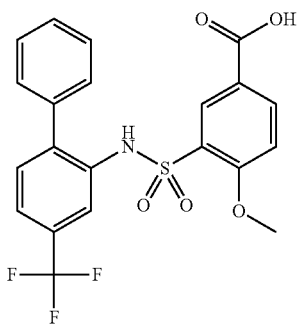

Step 1: methyl 3-(N-(2-bromo-5-(trifluoromethyl)phenyl)sulfamoyl)-4-methoxybenzoate: A solution of 2-bromo-5-(trifluoromethyl)aniline (1.5 g, 6.25 mmol), methyl 3-(chlorosulfonyl)-4-methoxybenzoate (2 g, 7.56 mmol) and pyridine (1.5 ml, 18.6 mmol) in DCM (10 ml) was stirred at RT overnight. The solution was concentrated in vacuo and the residue was loaded onto silica gel. The crude product was purified by chromatography on silica gel (40 g cartridge, 0-100% EtOAc/isohexane) to afford the product (2.76 g). This was further purified by chromatography on silica gel (80 g cartridge, 0-100% EtOAc/isohexane) to afford the title compound (2.19 g, 4.63 mmol, 74% yield, 99% purity) as a white solid. UPLC-MS (Method 2) m/z 466.0 (M−H)− at 1.44 min. $^1$H NMR (500 MHz, DMSO-$d_6$) δ 10.18 (s, 1H), 8.24 (d, J=2.3 Hz, 1H), 8.19 (dd, J=8.8, 2.3 Hz, 1H), 7.85 (d, J=8.5 Hz, 1H), 7.59 (d, J=2.3 Hz, 1H), 7.51 (dd, J=8.5, 2.3 Hz, 1H), 7.35 (d, J=8.8 Hz, 1H), 3.82 (s, 3H), 3.81 (s, 3H).

Step 2: 3-(N-(2-bromo-5-(trifluoromethyl)phenyl)sulfamoyl)-4-methoxybenzoic acid: 1 M LiOH (aq) (100 ml, 100 mmol) was added to a solution of the product from Step 1 above (2.19 g, 4.68 mmol) in dioxane (100 ml) and the solution was stirred at RT overnight. The reaction mixture was concentrated to water and extracted with EtOAc (3×100 ml). The aqueous phase was acidified using 1 M HCl(aq) and the product was extracted into DCM (3×150 ml). The organic phases were combined, dried by passage through a phase separator and the solvent was removed in vacuo to give the title compound (1.98 g, 4.27 mmol, 91% yield, 98% purity) as a white solid. UPLC-MS (Method 1) m/z 452.0 (M−H)− at 1.43 min. $^1$H NMR (500 MHz, DMSO-$d_6$) δ 13.06 (s, 1H), 10.12 (s, 1H), 8.23 (d, J=2.2 Hz, 1H), 8.17 (dd, J=8.7, 2.2 Hz, 1H), 7.86 (d, J=8.4 Hz, 1H), 7.58 (d, J=2.2 Hz, 1H), 7.50 (dd, J=8.4, 2.2 Hz, 1H), 7.32 (d, J=8.7 Hz, 1H), 3.80 (s, 3H).

Step 3: 4-methoxy-3-(N-(4-(trifluoromethyl)-[1,1'-biphenyl]-2-yl)sulfamoyl)benzoic acid: A mixture of the product from step 2 above (91 mg, 0.200 mmol), phenylboronic acid (34 mg, 0.279 mmol), 1 M $K_3PO_4$ (0.24 ml, 0.240 mmol), Pd(OAc)$_2$ (2 mg, 8.91 μmol) and XPhos (8 mg, 0.017 mmol) in dioxane (2 ml) was degassed with $N_2$ and then stirred at 80° C. for 16 h.

The solution was filtered and the solvent removed in vacuo. The residue was dissolved in DMSO (1 ml) and acidified using formic acid. The crude product was purified by preparative HPLC (Waters X-Select Prep-C18, 5 μm, 19×50 mm column, 25-55% MeCN in Water (0.1% Formic acid)) to afford the title compound as a white solid (37 mg, 0.080 mmol, 40% yield, 97% purity). UPLC-MS (Method 1) m/z 452.3 (M+H)+, 450.2 (M−H)− at 1.57 min. $^1$H NMR (500 MHz, DMSO-$d_6$) δ 13.04 (br s, 1H), 9.53 (br s, 1H), 8.10 (dd, J=8.7, 2.2 Hz, 1H), 8.03 (d, J=2.2 Hz, 1H), 7.63 (d, J=8.0 Hz, 1H), 7.46 (d, J=8.0 Hz, 1H), 7.44-7.40 (m, 1H), 7.37-7.31 (m, 3H), 7.31-7.24 (m, 2H), 7.20 (d, J=8.8 Hz, 1H), 3.78 (s, 3H).

Example 2: 4-methoxy-3-(N-(2-(pyridin-3-yl)-5-(trifluoromethyl)phenyl)sulfamoyl)benzoic acid

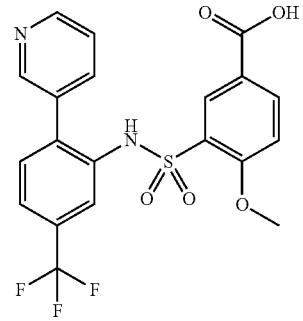

A mixture of the product from Example 1, Step 2 (50 mg, 0.110 mmol), tetrakis-(triphenylphosphine)palladium(0) (12.7 mg, 0.011 mmol), pyridin-3-ylboronic acid (27.1 mg, 0.220 mmol) and cesium carbonate (79 mg, 0.242 mmol) in water (0.4 ml) and dioxane (1.6 ml) was degassed with $N_2$ for 10 min. The resultant mixture was stirred with microwave heating at 100° C. for 90 min. The reaction mixture was filtered through cotton wool and concentrated in vacuo. The crude product was purified by chromatography (12 g reverse phase C18 cartridge, 15-75% MeCN/0.1% formic acid(aq)) to afford the title compound (17 mg, 0.037 mmol, 34% yield, 99% purity) as an off white solid. UPLC-MS (Method 1) m/z 453.3 (M+H)+, 451.3 (M−H)− at 1.03 min. $^1$H NMR (500 MHz, DMSO-$d_6$) δ 13.02 (br s, 1H), 9.92 (br s, 1H), 8.51 (br d, J=3.9 Hz, 1H), 8.48 (br s, 1H), 8.09 (dd, J=8.6, 2.3 Hz, 1H), 8.01 (br s, 1H), 7.73-7.61 (m, 2H), 7.52 (br d, J=8.0 Hz, 1H), 7.45-7.39 (m, 1H), 7.35 (dd, J=7.8, 4.8 Hz, 1H), 7.20 (d, J=8.7 Hz, 1H), 3.83 (s, 3H).

Example 3: 4-methoxy-3-(N-(2-(thiophen-2-yl)-5-(trifluoromethyl)phenyl) sulfamoyl)benzoic acid

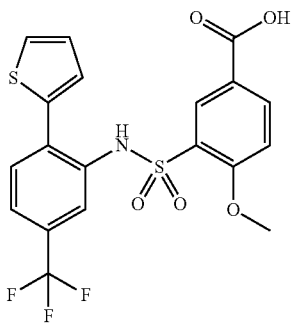

The product from Example 1, Step 2 (53.2 mg, 0.117 mmol), Pd(OAc)$_2$ (1.32 mg, 5.86 μmol), XPhos (5.59 mg, 0.012 mmol) and thiophen-2-ylboronic acid (30 mg, 0.234 mmol) were combined. The reaction vessel was flushed with N$_2$ for 10 min, a mixture of THF and 2 M Na$_2$CO$_3$ (aq) (2:1, 0.9 ml) was added and the reaction mixture was heated to 80° C. for 2 h. The reaction mixture was cooled to RT, filtered through Celite®, washed with MeOH (10 ml), dried by passage through a phase separator and concentrated in vacuo. The crude product was purified by preparative HPLC (Waters X-Select Prep-C18, 5 μm, 19×50 mm column, 25-95% MeCN in Water (0.1% Formic acid)) to afford a white solid. This was suspended in water (3 ml) and 2 M NaOH (aq) was added until pH>12. The aqueous phase was extracted with TBME (2×3 ml) and acidified using 1 M HCl(aq) until pH 4-5. The aqueous phase was re-extracted with TBME (2×5 ml) and the organic phases were combined, dried (MgSO$_4$) and concentrated in vacuo to afford the title compound (21.9 mg, 0.048 mmol, 41% yield) as a white solid. UPLC-MS (Method 1) m/z 456.1 (M−H)$^-$ at 1.54 min. $^1$H NMR (500 MHz, DMSO-d$_6$) δ 13.07 (br s, 1H), 9.84 (br s, 1H), 8.18-8.13 (m, 1H), 8.13-8.09 (m, 1H), 7.81 (d, J=8.2 Hz, 1H), 7.70-7.59 (m, 2H), 7.56-7.51 (m, 1H), 7.30 (d, J=8.7 Hz, 1H), 7.22-7.16 (m, 1H), 7.13 (dd, J=5.1, 3.7 Hz, 1H), 3.83 (s, 3H).

The following examples were prepared by methods analogous to Example 3, substituting appropriate starting materials and intermediates where necessary:

| Example | Structure | Name/Analytical Data |
|---|---|---|
| 4 | 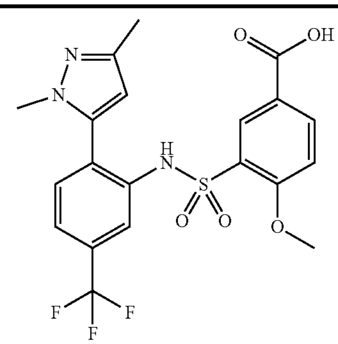 | 3-(N-(2-(1,3-dimethylpyrazol-5-yl)-5-(trifluoromethyl)phenyl)sulfamoyl)-4-methoxybenzoic acid<br>UPLC-MS (Method 1) m/z 470.3 (M + H)$^+$, 468.0 (M − H)$^-$ at 1.33 min. $^1$H NMR (500 MHz, DMSO-d$_6$) δ 13.07 (brs, 1H), 9.68 (brs, 1H), 8.14 (dd, J = 8.8, 2.2 Hz, 1H), 8.10-8.06 (m, 1H), 7.68-7.61 (m, 1H), 7.60-7.57 (m, 1H), 7.52-7.46 (m, 1H), 7.28 (d, J = 8.7 Hz, 1H), 5.80 (s, 1H), 3.81 (s, 3H), 3.38 (s, 3H), 2.09 (s, 3H). |
| 5 | 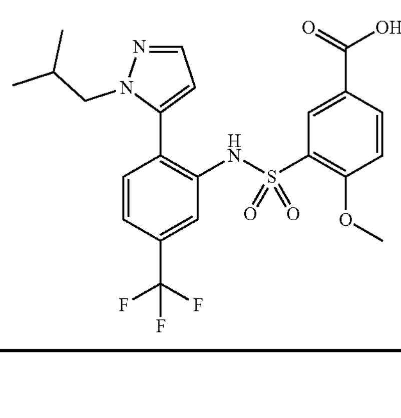 | 3-(N-(2-(1-isobutylpyrazol-5-yl)-5-(trifluoromethyl)phenyl)sulfamoyl)-4-methoxybenzoic acid<br>UPLC-MS (Method 1) m/z 498.3 (M + H)$^+$, 496.1 (M − H)$^-$ at 1.52 min. $^1$H NMR (500 MHz, MeOD-d$_4$) δ 8.35 (d, J = 2.2 Hz, 1H), 8.25 (dd, J = 8.7, 2.2 Hz, 1H), 7.81-7.78 (m, 1H), 7.60-7.55 (m, 1H), 7.55 (d, J = 1.9 Hz, 1H), 7.45 (d, J = 8.0 Hz, 1H), 7.25 (d, J = 8.7 Hz, 1H), 6.23 (d, J = 1.9 Hz, 1H), 3.90 (s, 3H), 3.54 (d, J = 7.5 Hz, 2H), 2.02 (app. septet, J = 6.9 Hz, 1H), 0.72 (d, J = 6.7 Hz, 6H). Two exchangeable protons not observed. |

141

Example 6: 4-methoxy-3-(N-(3'-methyl-4-(trifluoromethyl)-[1,1'-biphenyl]-2-yl)sulfamoyl)benzoic acid

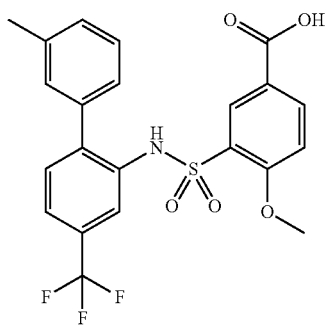

Step 1: methyl 4-methoxy-3-(N-(3'-methyl-4-(trifluoromethyl)-[1,1'-biphenyl]-2-yl)sulfamoyl)benzoate: To a reaction vessel containing the product from Example 1 Step 1 (70.2 mg, 0.15 mmol) and m-tolylboronic acid (41 mg, 0.302 mmol) was added 1 M $K_3PO_4$ (aq) (0.25 ml, 0.250 mmol), dioxane (1.5 ml) and XPhos Pd G2 (6 mg, 7.63 μmol). The reaction mixture was degassed with $N_2$ for 10 min, heated to 80° C. for 18 h then cooled to RT and concentrated in vacuo. The crude product was purified by chromatography on silica gel (10 g cartridge, 0-30% EtOAc/isohexane) to afford the title compound (74.8 mg, 0.150 mmol, 100% yield, 96% purity) as a pale yellow solid. UPLC-MS (Method 1) m/z 480.4 (M+H)$^+$, 478.2 (M–H)$^-$ at 1.80 min.

Step 2: 4-methoxy-3-(N-(3'-methyl-4-(trifluoromethyl)-[1,1'-biphenyl]-2-yl)sulfamoyl)benzoic acid: 1 M LiOH (aq) (0.60 ml, 0.600 mmol) was added to a solution of the product from step 1 above (71.9 mg, 0.15 mmol) in THF (1.20 ml) at RT. The solution was stirred at RT for 88 h and then concentrated in vacuo. The residue was dissolved in water (3 ml) and washed with EtOAc (3 ml). The aqueous phase was acidified using 1 M HCl(aq) until pH 4-5 and the product was extracted into EtOAc (2×4 ml). The combined organic phases were dried (MgSO$_4$) and concentrated in vacuo to afford the title compound (51.1 mg, 0.109 mmol, 73% yield, 99% purity) as an off-white solid. UPLC-MS (Method 1) m/z 466.3 (M+H)$^+$, 464.1 (M–H)$^-$ at 1.65 min. $^1$H NMR (500 MHz, DMSO-d$_6$) δ 13.03 (br s, 1H), 9.49 (br s, 1H), 8.08 (dd, J=8.7, 2.2 Hz, 1H), 7.98 (d, J=2.2 Hz, 1H), 7.64-7.59 (m, 1H), 7.51-7.48 (m, 1H), 7.41 (d, J=8.0 Hz, 1H), 7.20 (t, J=7.6 Hz, 1H), 7.16 (d, J=8.8 Hz, 1H), 7.13-7.09 (m, 1H), 7.06-7.02 (m, 1H), 6.93-6.90 (m, 1H), 3.72 (s, 3H), 2.22 (s, 3H).

142

Example 7: 3-(N-(3'-cyano-4-(trifluoromethyl)-[1,1'-biphenyl]-2-yl)sulfamoyl)-4-methoxybenzoic acid

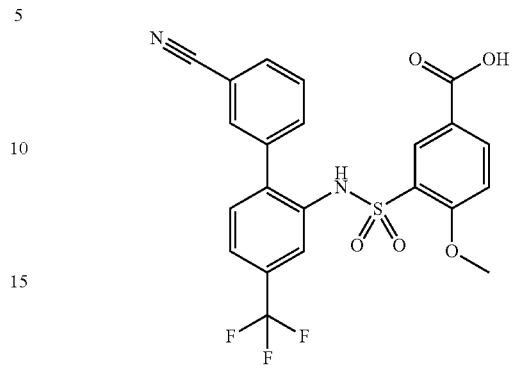

Step 1: methyl 3-(N-(3'-cyano-4-(trifluoromethyl)-[1,1'-biphenyl]-2-yl)sulfamoyl)-4-methoxybenzoate: To the reaction vessel containing the product from Example 1 Step 1 (60.9 mg, 0.13 mmol), (3-cyanophenyl)boronic acid (66 mg, 0.449 mmol), 1 M $K_3PO_4$ (aq) (0.22 ml, 0.220 mmol) and dioxane (1.5 ml) was added XPhos Pd G2 (5.5 mg, 6.99 μmol). The reaction mixture was degassed with $N_2$ for 10 min, heated to 80° C. for 16 h then cooled to RT and concentrated in vacuo. The crude product was purified by chromatography on silica gel (10 g cartridge, 0-50% EtOAc/pentane) to afford the title compound (54.8 mg, 0.108 mmol, 83% yield, 97% purity) as an off-white solid. UPLC-MS (Method 1) m/z 489.1 (M–H)$^-$ at 1.60 min.

Step 2: 3-(N-(3'-cyano-4-(trifluoromethyl)-[1,1'-biphenyl]-2-yl)sulfamoyl)-4-methoxybenzoic acid: 1 M LiOH (aq) (0.427 ml, 0.427 mmol) was added to a solution of the product from Step 1 above (54 mg, 0.107 mmol) in THF (1.20 ml) at RT. The solution was stirred at RT for 72 h. Additional 1 M LiOH (aq) (0.21 ml, 0.210 mmol) was added and the solution was stirred at RT for a further 27 h. The reaction mixture was concentrated in vacuo. The residue was dissolved in water (3 ml) and washed with DCM (3 ml). The aqueous phase was acidified using 1 M HCl(aq) until pH 4-5 and the product was extracted into EtOAc (2×4 ml). The combined organic phase was dried over MgSO$_4$ and concentrated in vacuo. The crude product was purified by chromatography on silica gel (10 g cartridge, 0-5% MeOH/DCM) to afford the title compound (32 mg, 0.066 mmol, 62% yield, 99% purity) as an off-white solid. UPLC-MS (Method 1) m/z 475.1 (M–H)$^-$ at 1.45 min. $^1$H NMR (500 MHz, DMSO-d$_6$) δ 13.02 (br s, 1H), 9.90 (br s, 1H), 8.09 (dd, J=8.7, 2.2 Hz, 1H), 7.98-7.88 (m, 1H), 7.75 (app. dt, J=7.6, 1.5 Hz, 1H), 7.73-7.62 (m, 2H), 7.57 (d, J=7.9 Hz, 1H), 7.54-7.48 (m, 2H), 7.48-7.43 (m, 1H), 7.20 (d, J=8.8 Hz, 1H), 3.82 (s, 3H).

The following examples were prepared by methods analogous to Example 7, substituting appropriate starting materials and intermediates where necessary:

| Example | Structure | Name/Analytical Data |
| --- | --- | --- |
| 8 | 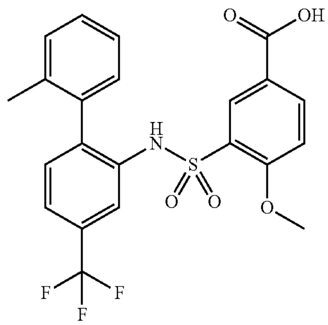 | 4-methoxy-3-(N-(2'-methyl-4-(trifluoromethyl)-[1,1'-biphenyl]-2-yl)sulfamoyl)benzoic acid<br>UPLC-MS (Method 1) m/z 466.3 (M + H)$^+$, 464.2 (M − H)$^−$ at 1.64 min. $^1$H NMR (500 MHz, DMSO-d$_6$) δ 13.04 (brs, 1H), 9.14 (brs, 1H), 8.10 (dd, J = 8.7, 2.2 Hz, 1H), 8.03 (d, J = 2.2 Hz, 1H), 7.60-7.54 (m, 2H), 7.32 (d, J = 7.9 Hz, 1H), 7.23-7.15 (m, 2H), 7.15-7.10 (m, 2H), 6.97-6.92 (m, 1H), 3.74 (s, 3H), 1.83 (s, 3H). |
| 9 | 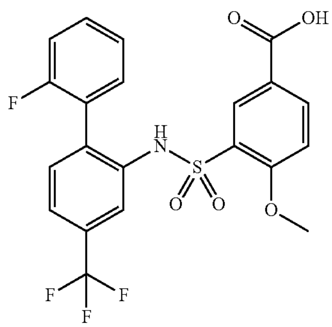 [SMILES: COc1ccc(C(=O)O)cc1S(=O)(=O)Nc1cc(C(F)(F)F)ccc1-c1ccccc1F] | 3-(N-(2'-fluoro-4-(trifluoromethyl)-[1,1'-biphenyl]-2-yl)sulfamoyl)-4-methoxybenzoic acid<br>UPLC-MS (Method 1) m/z 470.2 (M + H)$^+$, 468.2 (M − H)$^−$ at 1.51 min. $^1$H NMR (500 MHz, DMSO-d$_6$) δ 13.04 (brs, 1H), 9.63 (brs, 1H), 8.10 (dd, J = 8.7, 2.3 Hz, 1H), 8.01 (d, J = 2.2 Hz, 1H), 7.67-7.60 (m, 1H), 7.49-7.43 (m, 2H), 7.40-7.34 (m, 1H), 7.23-7.09 (m, 4H), 3.80 (s, 3H). |
| 10 | 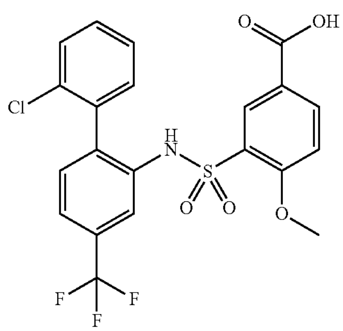 [SMILES: COc1ccc(C(=O)O)cc1S(=O)(=O)Nc1cc(C(F)(F)F)ccc1-c1ccccc1Cl] | 3-(N-(2'-chloro-4-(trifluoromethyl)-[1,1'-biphenyl]-2-yl)sulfamoyl)-4-methoxybenzoic acid<br>UPLC-MS (Method 1) m/z 486.2 (M + H)$^+$, 484.1 (M − H)$^−$ at 1.57 min. $^1$H NMR (500 MHz, DMSO-d$_6$) δ 13.02 (brs, 1H), 9.48 (brs, 1H), 8.10 (dd, J = 8.7, 2.2 Hz, 1H), 8.04 (d, J = 2.2 Hz, 1H), 7.66-7.58 (m, 1H), 7.58-7.55 (m, 1H), 7.41-7.28 (m, 4H), 7.21-7.16 (m, 2H), 3.78 (s, 3H). |
| 11 | 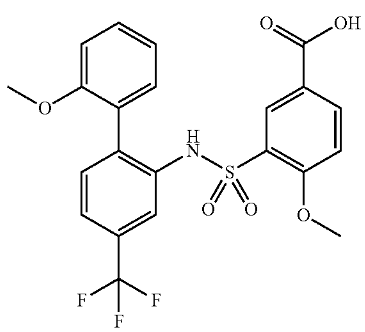 | 4-methoxy-3-(N-(2'-methoxy-4-(trifluoromethyl)-[1,1'-biphenyl]-2-yl)sulfamoyl)benzoic acid<br>UPLC-MS (Method 1) m/z 482.2 (M + H)$^+$, 480.2 (M − H)$^−$ at 1.54 min. $^1$H NMR (500 MHz, DMSO-d$_6$) δ 13.06 (br s, 1H), 8.63 (br s, 1H), 8.06 (dd, J = 8.7, 2.2 Hz, 1H), 7.99 (d, J = 2.2 Hz, 1H), 7.63-7.61 (m, 1H), 7.59-7.53 (m, 1H), 7.36 (app. ddd, J = 8.9, 5.8, 3.3 Hz, 1H), 7.32 (d, J = 8.0 Hz, 1H), 7.07 (d, J = 8.8 Hz, 1H), 7.04 (d, J = 8.4 Hz, 1H), 6.91-6.86 (m, 2H), 3.68 (s, 3H), 3.67 (s, 3H). |

| Example | Structure | Name/Analytical Data |
|---|---|---|
| 12 | 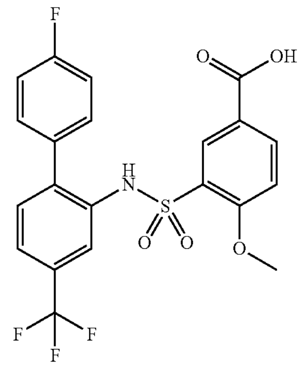 [SMILES: COc1ccc(C(=O)O)cc1S(=O)(=O)Nc1cc(C(F)(F)F)ccc1-c1ccc(F)cc1] | 3-(N-(4'-fluoro-4-(trifluoromethyl)-[1,1'-biphenyl]-2-yl)sulfamoyl)-4-methoxybenzoic acid<br>UPLC-MS (Method 1) m/z 470.3 (M + H)⁺, 468.2 (M − H)⁻ at 1.56 min. ¹H NMR (500 MHz, DMSO-d₆) δ 13.02 (br s, 1H), 9.67 (br s, 1H), 8.10 (dd, J = 8.7, 2.2 Hz, 1H), 7.96 (d, J = 2.2 Hz, 1H), 7.64 (d, J = 8.0 Hz, 1H), 7.46 (d, J = 8.0 Hz, 1H), 7.41-7.37 (m, 1H), 7.32-7.27 (m, 2H), 7.23 (d, J = 8.8 Hz, 1H), 7.15-7.09 (m, 2H), 3.84 (s, 3H). |
| 13 | 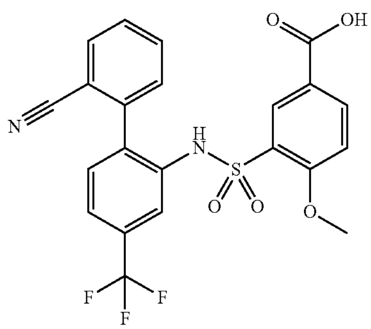 [SMILES: COc1ccc(C(=O)O)cc1S(=O)(=O)Nc1cc(C(F)(F)F)ccc1-c1ccccc1C#N] | 3-(N-(2'-cyano-4-(trifluoromethyl)-[1,1'-biphenyl]-2-yl)sulfamoyl)-4-methoxybenzoic acid<br>UPLC-MS (Method 1) m/z 499.3 (M + Na)⁺, 475.2 (M − H)⁻ at 1.40 min. ¹H NMR (500 MHz, MeOD-d₄) δ 8.17 (dd, J = 8.7, 2.2 Hz, 1H), 8.11 (d, J = 2.2 Hz, 1H), 7.72-7.68 (m, 1H), 7.65-7.58 (m, 3H), 7.48-7.41 (m, 2H), 7.38-7.33 (m, 1H), 7.14 (d, J = 8.7 Hz, 1H), 3.85 (s, 3H). Two exchangeable protons not observed. |

Example 14: 4-methoxy-3-(N-(2-(pyridin-4-yl)-5-(trifluoromethyl)phenyl) sulfamoyl)benzoic acid

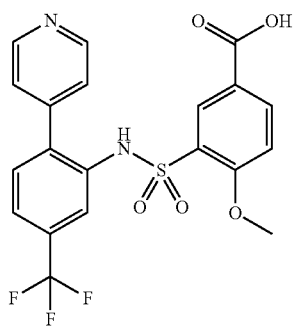 [SMILES: COc1ccc(C(=O)O)cc1S(=O)(=O)Nc1cc(C(F)(F)F)ccc1-c1ccncc1]

Step 1: methyl 4-methoxy-3-(N-(2-(pyridin-4-yl)-5-(trifluoromethyl)phenyl)sulfamoyl)benzoate: To a reaction vessel was added the product from Example 1 Step 1 (50 mg, 0.107 mmol), pyridin-4-ylboronic acid hydrate (30.1 mg, 0.214 mmol) and Pd(dppf)Cl₂·DCM (4.36 mg, 5.34 µmol) in a mixture of THF and 2 M Na₂CO₃ (aq) (2:1, 0.75 ml). The resultant mixture was degassed with N₂ for 5 min and then heated to 80° C. for 18 h. The reaction was cooled to RT and then concentrated in vacuo. The crude product was purified by chromatography on silica gel (10 g cartridge, 0-3.5% MeOH/DCM) to afford the title compound (32.6 mg, 0.069 mmol, 65% yield, 99% purity) as a tan solid. UPLC-MS (Method 1) 467.3 (M+H)⁺, 465.1 (M−H)⁻ at 1.12 min.

Step 2: 4-methoxy-3-(N-(2-(pyridin-4-yl)-5-(trifluoromethyl)phenyl)sulfamoyl)benzoic acid: 1 M LiOH (aq) (0.273 ml, 0.273 mmol) was added to a solution of the product from Step 1 above (32.5 mg, 0.068 mmol) in THF (0.55 ml) at RT. The solution was stirred at RT for 20 h then concentrated in vacuo. The residue was dissolved in water (3 ml) and washed with EtOAc (2×5 ml). The aqueous phase was acidified using 1 M HCl(aq) until pH 4-5 and the product was extracted into EtOAc (3×5 ml). The combined organic phase was dried over MgSO₄ and concentrated in vacuo to afford the title compound (5.9 mg, 0.013 mmol, 19% yield) as a tan solid. The aqueous phase was re-extracted with TBME (2×5 ml) and EtOAc (2×5 ml). The combined organic phases were dried (MgSO₄) and concentrated in vacuo to afford a second batch of the title compound (9.7 mg, 0.020 mmol, 30% yield, 95% purity) as a cream solid. UPLC-MS (Method 1) m/z 453.0 (M+H)⁺, 451.0 (M−H)⁻ at 0.95 min. ¹H NMR (500 MHz, DMSO-d₆) δ 8.54-8.49 (m, 2H), 8.17 (d, J=2.2 Hz, 1H), 8.08 (dd, J=8.7, 2.2 Hz, 1H), 7.55 (s, 1H), 7.50-7.41 (m, 2H), 7.38-7.32 (m, 2H), 7.17 (d, J=8.7 Hz, 1H), 3.79 (s, 3H). Two exchangeable protons not observed.

147

Example 15: 3-(N-(3'-fluoro-4-(trifluoromethyl)-[1,1'-biphenyl]-2-yl)sulfamoyl)-4-methoxybenzoic acid

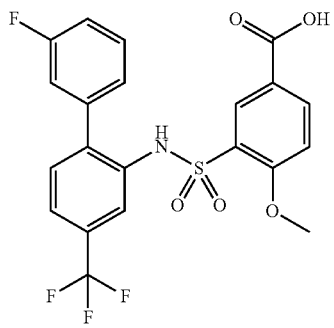 [SMILES: COc1ccc(C(=O)O)cc1S(=O)(=O)Nc1cc(C(F)(F)F)ccc1-c1cccc(F)c1]

Step 1: methyl 3-(N-(3'-fluoro-4-(trifluoromethyl)-[1,1'-biphenyl]-2-yl)sulfamoyl)-4-methoxybenzoate: To the reaction vessel containing the product from Example 1 Step 1 (250 mg, 0.534 mmol), (3-fluorophenyl)boronic acid (98 mg, 0.700 mmol), 1 M $K_3PO_4$(aq) (0.88 ml, 0.88 mmol) and dioxane (5.3 ml) was added XPhos Pd G3 (25 mg, 0.030 mmol). The reaction mixture was degassed with $N_2$ for 15 min and then heated to 80° C. for 3 h. The reaction was cooled to RT and concentrated in vacuo. The crude product was purified by chromatography on silica gel (24 g cartridge, 0-40% EtOAc/isohexane) to afford the title compound (291 mg, 0.536 mmol, 100% yield, 89% purity) as a yellow oil. UPLC-MS (Method 1) m/z 484.3 (M+H)$^+$, 482.2 (M−H)$^−$ at 1.74 min.

Step 2: 3-(N-(3'-fluoro-4-(trifluoromethyl)-[1,1'-biphenyl]-2-yl)sulfamoyl)-4-methoxybenzoic acid: 1 M LiOH (aq) (2.14 ml, 2.14 mmol) was added to a solution of the product from Step 1 above (258 mg, 0.534 mmol) in THF (4.28 ml) at RT. The solution was stirred at RT for 23 h. The reaction mixture was concentrated in vacuo and the residue was dissolved in water (8 ml) and washed with EtOAc (8 ml). The aqueous phase was acidified using 1 M HCl(aq) until pH 4-5 and the product was extracted with EtOAc (3×8 ml). The organic phases were combined, dried over $MgSO_4$, filtered and concentrated in vacuo. The crude product was partially purified by chromatography on silica gel (12 g cartridge, 0-3% MeOH/DCM), then purified by chromatography (12 g reverse phase C18 cartridge, 50-80% MeCN/ 0.1% formic acid(aq)) to afford the title compound (135 mg, 0.285 mmol, 53% yield, 99% purity) as an off-white solid. UPLC-MS (Method 1) m/z 468.2 (M−H)$^−$ at 1.56 min. $^1$H NMR (500 MHz, DMSO-$d_6$) δ 13.02 (br s, 1H), 9.75 (br s, 1H), 8.09 (dd, J=8.7, 2.2 Hz, 1H), 7.99 (d, J=2.2 Hz, 1H), 7.66 (br d, J=8.0 Hz, 1H), 7.49 (d, J=8.0 Hz, 1H), 7.45-7.41 (m, 1H), 7.35 (app. td, J=8.1, 6.1 Hz, 1H), 7.20 (d, J=8.8 Hz, 1H), 7.14 (app. td, J=8.6, 2.6 Hz, 1H), 7.11-7.04 (m, 2H), 3.81 (s, 3H).

148

Example 16: 3-(N-(4'-cyano-4-(trifluoromethyl)-[1,1'-biphenyl]-2-yl)sulfamoyl)-4-methoxybenzoic acid

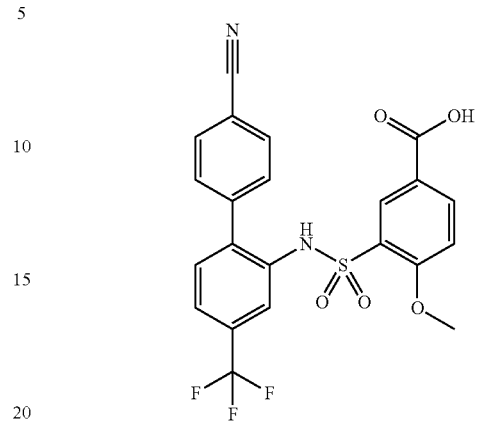

Step 1: methyl 3-(N-(4'-cyano-4-(trifluoromethyl)-[1,1'-biphenyl]-2-yl)sulfamoyl)-4-methoxybenzoate: To the reaction vessel containing the product from Example 1 Step 1 (70 mg, 0.149 mmol), (4-cyanophenyl)boronic acid (34 mg, 0.231 mmol), 1 M $K_3PO_4$(aq) (0.249 ml, 0.249 mmol) and dioxane (1.5 ml) was added XPhos Pd G2 (6 mg, 7.63 μmol). The reaction mixture was degassed with $N_2$ for 10 min and then heated to 80° C. for 21 h. The reaction was cooled to RT and concentrated in vacuo. The crude product was purified by chromatography on silica gel (12 g cartridge, 0-50% EtOAc/isohexane) to afford the title compound (53.3 mg, 0.097 mmol, 65% yield, 89% purity) as an off-white solid. UPLC-MS (Method 1) m/z 489.2 (M−H)$^−$ at 1.61 min. $^1$H NMR (500 MHz, DMSO-$d_6$) δ 9.94 (br s, 1H), 8.13 (dd, J=8.7, 2.3 Hz, 1H), 7.86 (d, J=2.2 Hz, 1H), 7.75-7.67 (m, 3H), 7.52 (d, J=8.0 Hz, 1H), 7.46-7.42 (m, 3H), 7.26 (d, J=8.8 Hz, 1H), 3.88 (s, 3H), 3.83 (s, 3H).

Step 2: 3-(N-(4'-cyano-4-(trifluoromethyl)-[1,1'-biphenyl]-2-yl)sulfamoyl)-4-methoxybenzoic acid: 1 M LiOH (aq) (0.370 ml, 0.370 mmol) was added to a solution of the product from Step 1 above (51 mg, 0.093 mmol) in THF (0.74 ml) at RT. The solution was stirred at RT for 20 h. The reaction mixture was concentrated in vacuo and the residue was dissolved in water (3 ml) and washed with EtOAc (3 ml). The aqueous phase was acidified using 1 M HCl(aq) until pH 4-5 and the product was extracted with EtOAc (3×3 ml). The organic phases were combined, dried over $MgSO_4$, filtered and concentrated in vacuo. The crude product was purified by chromatography on silica gel (12 g cartridge, 0-5% MeOH/DCM) to afford the title compound (30.2 mg, 0.061 mmol, 66% yield, 97% purity) as an off-white solid. UPLC-MS (Method 1) m/z 475.2 (M−H)$^−$ at 1.44 min. $^1$H NMR (500 MHz, DMSO-$d_6$) δ 13.03 (br s, 1H), 9.87 (br s, 1H), 8.11 (dd, J=8.6, 2.2 Hz, 1H), 7.94 (br s, 1H), 7.80-7.74 (m, 2H), 7.72-7.61 (m, 1H), 7.51 (d, J=8.1 Hz, 1H), 7.48 (d, J=8.0 Hz, 2H), 7.41 (d, J=1.6 Hz, 1H), 7.23 (d, J=8.8 Hz, 1H), 3.86 (s, 3H).

Example 17: 4-methoxy-3-(N-(3'-methoxy-4-(trifluoromethyl)-[1,1'-biphenyl]-2-yl)sulfamoyl)benzoic acid

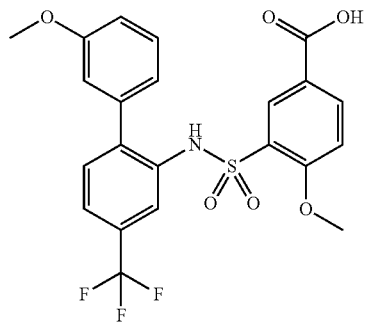

Step 1: methyl 4-methoxy-3-(N-(3'-methoxy-4-(trifluoromethyl)-[1,1'-biphenyl]-2-yl)sulfamoyl)benzoate: To the reaction vessel containing the product from Example 1 Step 1 (94 mg, 0.201 mmol), (3-methoxyphenyl)boronic acid (39.7 mg, 0.261 mmol), 1 M $K_3PO_4$(aq) (0.33 ml, 0.33 mmol) and dioxane (2.0 ml) was added XPhos Pd G2 (7.90 mg, 10.0 µmol). The reaction mixture was degassed with $N_2$ for 10 min and then heated to 80° C. for 17 h. The reaction was cooled to RT and concentrated in vacuo. The crude product was purified by chromatography on silica gel (12 g cartridge, 0-50% EtOAc/isohexane) to afford the title compound (99.2 mg, 0.192 mmol, 96% yield, 96% purity) as an off-white solid. UPLC-MS (Method 1) m/z 496.2 $(M+H)^+$, 494.2 $(M-H)^-$ at 1.73 min. $^1$H NMR (500 MHz, DMSO-$d_6$) δ 9.62 (s, 1H), 8.09 (dd, J=8.7, 2.3 Hz, 1H), 7.96 (d, J=2.2 Hz, 1H), 7.64 (d, J=8.0 Hz, 1H), 7.48 (d, J=1.9 Hz, 1H), 7.44 (d, J=8.0 Hz, 1H), 7.21-7.16 (m, 2H), 6.83 (app. ddd, J=8.3, 2.6, 0.9 Hz, 1H), 6.78-6.72 (m, 2H), 3.82 (s, 3H), 3.79 (s, 3H), 3.70 (s, 3H).

Step 2: 4-methoxy-3-(N-(3'-methoxy-4-(trifluoromethyl)-[1,1'-biphenyl]-2-yl)sulfamoyl)benzoic acid: 1 M LiOH(aq) (0.767 ml, 0.767 mmol) was added to a solution of the product from step 1 above (95 mg, 0.192 mmol) in THF (1.53 ml) at RT. The solution was stirred at RT for 23 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo. The crude product was purified by chromatography on silica gel (12 g cartridge, 0-5% MeOH/DCM) to afford the title compound (70 mg, 0.141 mmol, 74% yield, 97% purity) as a white solid. UPLC-MS (Method 1) m/z 482.4 $(M+H)^+$, 480.2 $(M-H)^-$ at 1.57 min. $^1$H NMR (500 MHz, DMSO-$d_6$) δ 13.02 (br s, 1H), 9.54 (br s, 1H), 8.08 (dd, J=8.7, 2.2 Hz, 1H), 8.00 (d, J=2.2 Hz, 1H), 7.63 (d, J=8.0 Hz, 1H), 7.48 (d, J=1.9 Hz, 1H), 7.45 (d, J=8.0 Hz, 1H), 7.22 (t, J=7.9 Hz, 1H), 7.17 (d, J=8.8 Hz, 1H), 6.87 (app. ddd, J=8.3, 2.6, 1.0 Hz, 1H), 6.81-6.75 (m, 2H), 3.78 (s, 3H), 3.72 (s, 3H).

Example 18: 3-(N-(2-(furan-3-yl)-5-(trifluoromethyl)phenyl)sulfamoyl)-4-methoxybenzoic acid

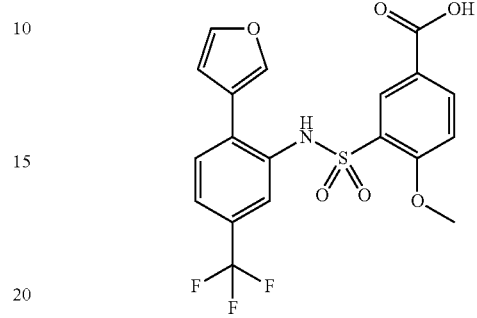

Step 1: methyl 3-(N-(2-(furan-3-yl)-5-(trifluoromethyl)phenyl)sulfamoyl)-4-methoxybenzoate: To the reaction vessel containing the product from Example 1 Step 1 (80 mg, 0.171 mmol), furan-3-ylboronic acid (24.9 mg, 0.222 mmol), 1 M $K_3PO_4$(aq) (0.286 ml, 0.286 mmol) and dioxane (1.7 ml) was added XPhos Pd G2 (6.72 mg, 8.54 µmol). The reaction mixture was degassed with $N_2$ for 10 min and then heated to 80° C. for 17 h. The reaction mixture was concentrated in vacuo, dissolved in DCM (2 ml) and dried by passage through a phase separator. The filtrate was purified directly by chromatography on silica gel (24 g cartridge, 0-50% EtOAc/isohexane) to afford the title compound (77 mg, 0.144 mmol, 84% yield, 85% purity) as a pale yellow solid. UPLC-MS (Method 1) m/z 456.4 $(M+H)^+$, 454.2 $(M-H)^-$ at 1.60 min.

Step 2: 3-(N-(2-(furan-3-yl)-5-(trifluoromethyl)phenyl)sulfamoyl)-4-methoxybenzoic acid: The product from Step 1 above (75 mg, 0.165 mmol) was dissolved in THF (2 ml) and treated with 1.1 M LiOH(aq) (599 µl, 0.659 mmol). MeOH was added dropwise until the mixture was a solution and the reaction was stirred at 30° C. for 3 days. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy solution which was concentrated in vacuo to ~2 ml. The precipitate was collected by filtration, washing with water (2×2 ml). The solid was suspended in MeCN (4 ml), concentrated in vacuo and dried at 45° C. to afford the title compound (50.9 mg, 0.110 mmol, 67% yield, 95% purity) as a light yellow solid. UPLC-MS (Method 1) m/z 442.2 $(M+H)^+$, 440.2 $(M-H)^-$ at 1.44 min. $^1$H NMR (500 MHz, DMSO-$d_6$) δ 13.06 (s, 1H), 9.79 (s, 1H), 8.13 (dd, J=8.7, 2.2 Hz, 1H), 8.09 (d, J=2.2 Hz, 1H), 8.07 (s, 1H), 7.73-7.67 (m, 2H), 7.62 (d, J=8.3 Hz, 1H), 7.28 (d, J=8.8 Hz, 1H), 7.25-7.22 (m, 1H), 6.81-6.79 (m, 1H), 3.84 (s, 3H).

Example 19: 4-ethyl-3-(N-(4-(trifluoromethyl)-[1,1'-biphenyl]-2-yl)sulfamoyl) benzoic acid

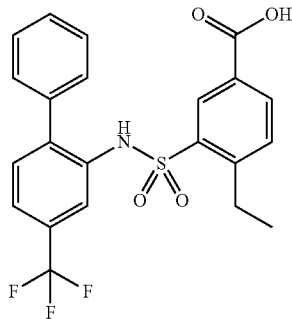 [SMILES: CCc1ccc(C(=O)O)cc1S(=O)(=O)Nc1cc(C(F)(F)F)ccc1-c1ccccc1]

Step 1: 3-(chlorosulfonyl)-4-ethylbenzoic acid: 4-ethylbenzoic acid (7 g, 46.6 mmol) in chlorosulfonic acid (20 ml, 299 mmol) was heated to 100° C. for 5 h. The mixture was cooled and carefully added to stirred ice-water (200 ml). The solid precipitated out was collected by filtration, washed with water (100 ml) and dried in vacuo to give the title compound (10.9 g, 41.5 mmol, 89% yield, 95% purity) as a white solid. $^1$H NMR (500 MHz, DMSO-$d_6$) δ 13.65 (br s, 1H), 8.34 (d, J=1.9 Hz, 1H), 7.82 (dd, J=7.9, 2.0 Hz, 1H), 7.32 (d, J=7.9 Hz, 1H), 3.08 (q, J=7.5 Hz, 2H), 1.18 (t, J=7.5 Hz, 3H).

Step 2: methyl 3-(chlorosulfonyl)-4-ethylbenzoate: Thionyl Chloride (10 ml, 137 mmol) was added portionwise to the product from step 1 above (4 g, 16.1 mmol) at RT. The mixture was heated to 75° C. for 2 h, cooled to RT, concentrated in vacuo and azeotroped with toluene. The solid was dissolved in DCM (10 ml) and treated with MeOH (0.716 ml, 17.7 mmol) followed by Et$_3$N (2.41 ml, 17.7 mmol) and stirred at RT overnight. The mixture was diluted with DCM (50 ml), washed with water (50 ml), dried (MgSO$_4$) and concentrated in vacuo. The crude product was purified by chromatography on silica gel (40 g cartridge, 0-50% EtOAc/isohexane) to afford the title compound (3.60 g, 13.02 mmol, 81% yield, 95% purity) as a white solid. $^1$H NMR (500 MHz, DMSO-$d_6$) δ 8.74 (d, J=1.8 Hz, 1H), 8.32 (dd, J=8.0, 1.8 Hz, 1H), 7.61 (d, J=8.0 Hz, 1H), 3.99 (s, 3H), 3.28 (q, J=7.5 Hz, 2H), 1.41 (t, J=7.5 Hz, 3H).

Step 3: methyl 3-(N-(2-bromo-5-(trifluoromethyl)phenyl)sulfamoyl)-4-ethylbenzoate: A solution of 2-bromo-5-(trifluoromethyl)aniline (0.655 ml, 4.57 mmol), the product from Step 2 above (1 g, 3.81 mmol) and pyridine (0.924 ml, 11.4 mmol) in DCM (6 ml) was stirred at RT for 67 h. The reaction mixture was dry loaded onto Celite® and purified by chromatography on silica gel (80 g cartridge, 0-30% EtOAc/isohexane) to afford the title compound (1.47 g, 3.09 mmol, 81% yield, 98% purity) as a white solid. UPLC-MS (Method 1) m/z 464.1 (M–H)$^−$ at 1.74 min. $^1$H NMR (500 MHz, DMSO-$d_6$) δ 10.64 (br s, 1H), 8.22 (d, J=1.9 Hz, 1H), 8.12 (dd, J=8.0, 1.9 Hz, 1H), 7.84 (d, J=8.4 Hz, 1H), 7.64 (d, J=8.1 Hz, 1H), 7.56-7.46 (m, 1H), 7.43 (d, J=2.2 Hz, 1H), 3.83 (s, 3H), 3.04 (q, J=7.5 Hz, 2H), 1.20 (t, J=7.4 Hz, 3H).

Step 4: methyl 4-ethyl-3-(N-(4-(trifluoromethyl)-[1,1'-biphenyl]-2-yl)sulfamoyl)benzoate: To the reaction vessel containing the product from step 3 above (80 mg, 0.172 mmol), phenylboronic acid (28 mg, 0.230 mmol), 1 M K$_3$PO$_4$(aq) (0.28 ml, 0.28 mmol) and dioxane (1.72 ml) was added XPhos Pd G3 (9.5 mg, 0.011 mmol). The reaction mixture was degassed with N$_2$ for 10 min and then heated to 80° C. for 19 h. The reaction was cooled to RT and concentrated in vacuo. The crude product was purified by chromatography on silica gel (12 g cartridge, 0-40% EtOAc/isohexane) to afford the title compound (93.5 mg, 0.171 mmol, 100% yield, 85% purity) as an orange oil. UPLC-MS (Method 1) m/z 462.2 (M–H)$^−$ at 1.86 min.

Step 5: 4-ethyl-3-(N-(4-(trifluoromethyl)-[1,1'-biphenyl]-2-yl)sulfamoyl)benzoic acid: 1 M LiOH(aq) (0.688 ml, 0.688 mmol) was added to a solution of the product from step 4 above (80 mg, 0.172 mmol) in THF (1.37 ml) at RT. The solution was stirred at RT for 65 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over MgSO$_4$, filtered and concentrated in vacuo afford the title compound (58.5 mg, 0.129 mmol, 75% yield, 99% purity) as a pale yellow solid. UPLC-MS (Method 1) m/z 448.3 (M–H)$^−$ at 1.71 min. $^1$H NMR (500 MHz, DMSO-$d_6$) δ 13.20 (br s, 1H), 10.13 (br s, 1H), 8.07 (d, J=1.8 Hz, 1H), 8.03 (dd, J=8.0, 1.9 Hz, 1H), 7.65 (br d, J=8.0 Hz, 1H), 7.45 (d, J=8.0 Hz, 1H), 7.43 (d, J=8.1 Hz, 1H), 7.33-7.28 (m, 4H), 7.20-7.16 (m, 2H), 2.76 (q, J=7.4 Hz, 2H), 1.10 (t, J=7.4 Hz, 3H).

Example 20: 4-methoxy-3-(N-(2-(thiophen-3-yl)-5-(trifluoromethyl)phenyl)sulfamoyl) benzoic acid

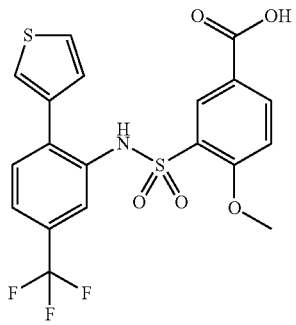 [SMILES: COc1ccc(C(=O)O)cc1S(=O)(=O)Nc1cc(C(F)(F)F)ccc1-c1ccsc1]

Step 1: methyl 4-methoxy-3-(N-(2-(thiophen-3-yl)-5-(trifluoromethyl)phenyl)sulfamoyl)benzoate: To the reaction vessel containing the product from Example 1 Step 1 (80 mg, 0.171 mmol), thiophen-3-ylboronic acid (28 mg, 0.219 mmol), 1 M K$_3$PO$_4$(aq) (0.28 ml, 0.28 mmol) and dioxane (1.7 ml) was added XPhos Pd G3 (8.5 mg, 10.04 μmol). The reaction mixture was degassed with N$_2$ for 10 min and then heated to 80° C. for 19 h. The reaction was cooled to RT and concentrated in vacuo. The crude product was purified by chromatography on silica gel (12 g cartridge, 0-50% EtOAc/isohexane) to afford the title compound (99.5 mg, 0.171 mmol, 100% yield, 81% purity) as a yellow oil. UPLC-MS (Method 1) m/z 472.1 (M+H)$^+$, 470.2 (M–H)$^−$ at 1.69 min.

Step 2: 4-methoxy-3-(N-(2-(thiophen-3-yl)-5-(trifluoromethyl)phenyl)sulfamoyl)benzoic acid: 1 M LiOH(aq) (0.684 ml, 0.684 mmol) was added to a solution of the product from step 1 above (81 mg, 0.171 mmol) in THF (1.37 ml) at RT. The solution was stirred at RT for 65 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over MgSO$_4$, filtered and concentrated in vacuo to afford the title compound (62.1 mg, 0.134 mmol, 79% yield, 99% purity) as an off-white solid. UPLC-MS (Method 1) m/z 458.2 (M+H)+, 456.2 (M−H)− at 1.53 min. ¹H NMR (500 MHz, DMSO-d₆) δ 13.04 (br s, 1H), 9.63 (br s, 1H), 8.11 (dd, J=8.7, 2.2 Hz, 1H), 8.07 (d, J=2.2 Hz, 1H), 7.70 (dd, J=3.0, 1.3 Hz, 1H), 7.63-7.58 (m, 2H), 7.57 (dd, J=5.0, 2.9 Hz, 1H), 7.35-7.33 (m, 1H), 7.27-7.23 (m, 2H), 3.82 (s, 3H).

Example 21: 3-(N-(3'-cyano-4-(trifluoromethyl)-[1,1'-biphenyl]-2-yl)sulfamoyl)-4-ethylbenzoic acid

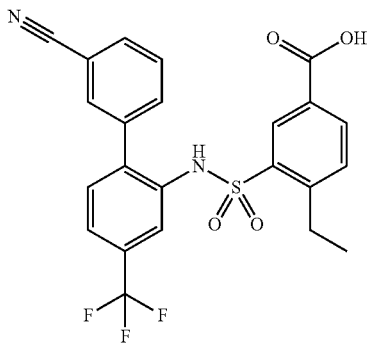 [SMILES: CCc1ccc(C(=O)O)cc1S(=O)(=O)Nc1cc(C(F)(F)F)ccc1-c1cccc(C#N)c1]

Step 1: methyl 3-(N-(3'-cyano-4-(trifluoromethyl)-[1,1'-biphenyl]-2-yl)sulfamoyl)-4-ethylbenzoate: To the reaction vessel containing the product from Example 19 Step 3 (80 mg, 0.172 mmol), (3-cyanophenyl)boronic acid (32.8 mg, 0.223 mmol), 1 M K₃PO₄(aq) (0.286 ml, 0.286 mmol) and dioxane (1.7 ml) was added XPhos Pd G2 (6.75 mg, 8.58 µmol). The reaction mixture was degassed with N₂ for 10 min and then heated to 80° C. for 20 h. The reaction was concentrated in vacuo, dissolved in DCM (2 ml) and dried by passage through a phase separator. The filtrate was purified directly by chromatography on silica gel (12 g cartridge, 0-100% EtOAc/isohexane) to afford the title compound (58 mg, 0.115 mmol, 67% yield, 97% purity) as a pale yellow oil. UPLC-MS (Method 1) m/z 487.2 (M−H)− at 1.73 min.

Step 2: 3-(N-(3'-cyano-4-(trifluoromethyl)-[1,1'-biphenyl]-2-yl)sulfamoyl)-4-ethylbenzoic acid: The product from Step 1 above (58 mg, 0.119 mmol) was dissolved in THF (2 ml) and treated with 1.1 M LiOH(aq) (432 µl, 0.475 mmol). MeOH was added dropwise until the mixture was a solution and the reaction was stirred at 30° C. for 20 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy solution which was concentrated in vacuo to ~2 ml. The precipitate was collected by filtration, washing with water (2×2 ml). The solid was suspended in MeCN (4 ml), concentrated in vacuo and dried at 45° C. to afford the title compound (43 mg, 0.086 mmol, 73% yield, 95% purity) as a white solid. UPLC-MS (Method 1) m/z 473.1 (M−H)− at 1.60 min. ¹H NMR (500 MHz, DMSO-d₆) δ 13.22 (s, 1H), 10.29 (s, 1H), 8.02 (dd, J=8.0, 1.9 Hz, 1H), 7.99-7.96 (m, 1H), 7.78-7.69 (m, 2H), 7.60-7.57 (m, 1H), 7.55-7.39 (m, 5H), 2.73 (q, J=7.4 Hz, 2H), 1.10 (t, J=7.4 Hz, 3H).

Example 22: 4-ethyl-3-(N-(2-(thiophen-2-yl)-5-(trifluoromethyl)phenyl) sulfamoyl)benzoic acid

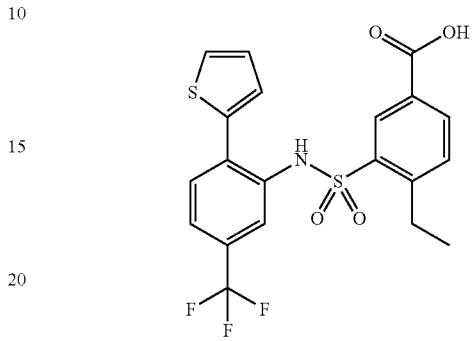

Step 1: methyl 4-ethyl-3-(N-(2-(thiophen-2-yl)-5-(trifluoromethyl)phenyl)sulfamoyl)benzoate: To the reaction vessel containing the product from Example 19 Step 3 (80 mg, 0.172 mmol), thiophen-2-ylboronic acid (28.5 mg, 0.223 mmol), 1 M K₃PO₄(aq) (0.286 ml, 0.286 mmol) and dioxane (1.7 ml) was added XPhos Pd G2 (6.75 mg, 8.58 µmol). The reaction mixture was degassed with N₂ for 10 min and then heated to 80° C. for 20 h. The reaction was concentrated in vacuo, dissolved in DCM (2 ml) and dried by passage through a phase separator. The filtrate was purified directly by chromatography on silica gel (12 g cartridge, 0-100% EtOAc/isohexane) to afford the title compound (80 mg, 0.170 mmol, 99% yield) as a light brown oil. UPLC-MS (Method 1) m/z 468.2 (M−H)− at 1.82 min.

Step 2: 4-ethyl-3-(N-(2-(thiophen-2-yl)-5-(trifluoromethyl)phenyl)sulfamoyl)benzoic acid: The product from step 1 above (50 mg, 0.106 mmol) was dissolved in THF (2 ml) and treated with 1.1 M LiOH(aq) (387 µl, 0.426 mmol). MeOH was added dropwise until the mixture was a solution and the reaction was stirred at 30° C. for 5 days. Additional 1.1 M LiOH(aq) (387 µl, 0.426 mmol) was added, and MeOH added dropwise until the mixture was a solution and the reaction was stirred at 40° C. for 4 h. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy solution which was concentrated in vacuo to ~2 ml. The precipitate was collected by filtration, washing with water (2×2 ml). The solid was suspended in MeCN (4 ml), concentrated in vacuo and dried at 45° C. to afford the title compound (31.3 mg, 0.065 mmol, 61% yield, 95% purity) as a cream solid. UPLC-MS (Method 1) m/z 454.2 (M−H)− at 1.68 min. ¹H NMR (500 MHz, DMSO-d₆) δ 13.23 (s, 1H), 10.27 (s, 1H), 8.18 (s, 1H), 8.08 (d, J=7.8 Hz, 1H), 7.81 (d, J=8.1 Hz, 1H), 7.75-7.59 (m, 2H), 7.58-7.51 (m, 2H), 7.15-7.10 (m, 1H), 6.96 (s, 1H), 2.97-2.85 (m, 2H), 1.15 (t, J=7.4 Hz, 3H).

Example 23: 3-(N-(2-(furan-2-yl)-5-(trifluoromethyl)phenyl)sulfamoyl)-4-methoxybenzoic acid

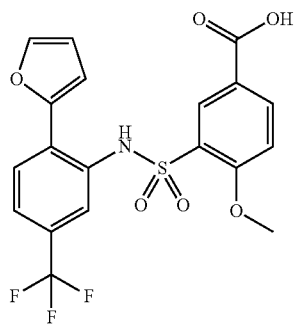

Step 1: methyl 3-(N-(2-(furan-2-yl)-5-(trifluoromethyl)phenyl)sulfamoyl)-4-methoxybenzoate: To the reaction vessel containing the product from Example 1 Step 1 (80 mg, 0.171 mmol), furan-2-ylboronic acid (25 mg, 0.223 mmol), 1 M $K_3PO_4$(aq) (0.28 ml, 0.28 mmol) and dioxane (1.7 ml) was added XPhos Pd G3 (9 mg, 10.6 μmol). The reaction mixture was degassed with $N_2$ for 10 min and then heated to 80° C. for 23 h. The reaction was cooled to RT and concentrated in vacuo. The crude product was purified by chromatography on silica gel (12 g cartridge, 0-40% EtOAc/isohexane) to afford the title compound (65.4 mg, 0.135 mmol, 79% yield, 94% purity) as an orange solid. UPLC-MS (Method 1) m/z 456.2 (M+H)$^+$, 454.2 (M−H)$^−$ at 1.66 min.

Step 2: 3-(N-(2-(furan-2-yl)-5-(trifluoromethyl)phenyl)sulfamoyl)-4-methoxybenzoic acid: 1 M LiOH(aq) (0.540 ml, 0.540 mmol) was added to a solution of the product from Step 1 above (61.5 mg, 0.135 mmol) in THF (1.08 ml) at RT. The solution was stirred at RT for 20 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo. The crude product was purified by preparative HPLC (Waters X-Select Prep-C18, 5 μm, 19×50 mm column, 35-65% MeCN in Water (0.1% Formic acid)) to afford the title compound (30.2 mg, 0.068 mmol, 50% yield, 99% purity) as a white solid. UPLC-MS (Method 1) m/z 442.2 (M+H)$^+$, 440.2 (M−H)$^−$ at 1.50 min. $^1$H NMR (500 MHz, DMSO-$d_6$) δ 13.08 (br s, 1H), 9.85 (br s, 1H), 8.19 (d, J=2.2 Hz, 1H), 8.14 (dd, J=8.7, 2.3 Hz, 1H), 7.91 (d, J=8.3 Hz, 1H), 7.80 (d, J=1.7 Hz, 1H), 7.64 (br d, J=8.4 Hz, 1H), 7.30-7.25 (m, 2H), 7.15 (d, J=3.5 Hz, 1H), 6.63 (dd, J=3.5, 1.8 Hz, 1H), 3.75 (s, 3H).

Example 24: 4-ethyl-3-(N-(3'-fluoro-4-(trifluoromethyl)-[1,1'-biphenyl]-2-yl)sulfamoyl) benzoic acid

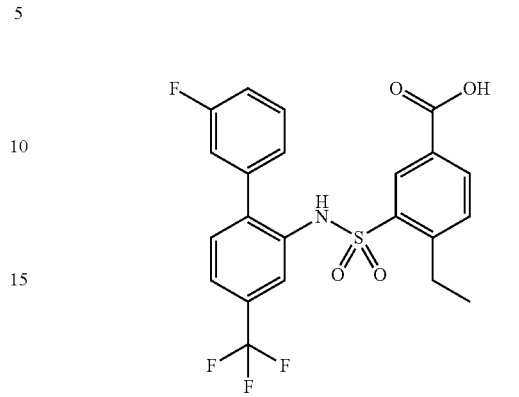

Step 1: methyl 4-ethyl-3-(N-(3'-fluoro-4-(trifluoromethyl)-[1,1'-biphenyl]-2-yl)sulfamoyl)benzoate: To the reaction vessel containing the product from Example 19 Step 3 (80 mg, 0.172 mmol), (3-fluorophenyl)boronic acid (32 mg, 0.229 mmol), 1 M $K_3PO_4$(aq) (0.28 ml, 0.28 mmol) and dioxane (1.7 ml) was added XPhos Pd G3 (9 mg, 10.6 μmol). The reaction mixture was degassed with $N_2$ for 10 min and then heated to 80° C. for 16 h. The reaction was cooled to RT and concentrated in vacuo. The crude product was purified by chromatography on silica gel (12 g cartridge, 0-40% EtOAc/isohexane) to afford the title compound (77.3 mg, 0.157 mmol, 92% yield, 98% purity) as a pale yellow solid. UPLC-MS (Method 1) m/z 480.2 (M−H)$^−$ at 1.85 min.

Step 2: 4-ethyl-3-(N-(3'-fluoro-4-(trifluoromethyl)-[1,1'-biphenyl]-2-yl)sulfamoyl)benzoic acid: 1 M LiOH(aq) (0.631 ml, 0.631 mmol) was added to a solution of the product from Step 1 above (76 mg, 0.158 mmol) in THF (1.26 ml) at RT. The solution was stirred at RT for 20 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo to afford the title compound (55.8 mg, 0.117 mmol, 74% yield, 98% purity) as a cream solid. UPLC-MS (Method 1) m/z 466.2 (M−H)$^−$ at 1.70 min. $^1$H NMR (500 MHz, DMSO-$d_6$) δ 13.21 (br s, 1H), 10.22 (br s, 1H), 8.06-7.99 (m, 2H), 7.69 (br d, J=8.1 Hz, 1H), 7.49 (d, J=8.0 Hz, 1H), 7.43 (d, J=7.9 Hz, 1H), 7.36 (d, J=1.9 Hz, 1H), 7.33 (app. td, J=8.0, 6.0 Hz, 1H), 7.13 (app. td, J=8.8, 2.6 Hz, 1H), 7.01-6.94 (m, 2H), 2.77 (q, J=7.4 Hz, 2H), 1.11 (t, J=7.4 Hz, 3H).

Example 25: 4-methoxy-3-(N-(2-(oxazol-5-yl)-5-(trifluoromethyl)phenyl)sulfamoyl) benzoic acid

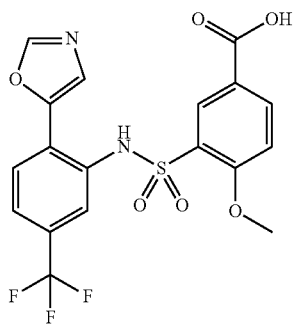 [SMILES: COc1ccc(C(=O)O)cc1S(=O)(=O)Nc1cc(C(F)(F)F)ccc1-c1cnco1]

Step 1: methyl 4-methoxy-3-(N-(2-(oxazol-5-yl)-5-(trifluoromethyl)phenyl)sulfamoyl)benzoate: Two reactions were set up. To the first reaction vessel containing the product from Example 1 step 1 (30 mg, 0.064 mmol), 5-(4,4,5,5-tetramethyl-1,3,2-dioxaborolan-2-yl)oxazole (16.2 mg, 0.083 mmol), 1 M $K_3PO_4$(aq) (0.107 ml, 0.107 mmol) and dioxane (2.2 ml) was added XPhos Pd G2 (2.52 mg, 3.20 µmol). The reaction mixture was degassed with $N_2$ for 10 min and then heated to 80° C. for 17 h. To the second reaction vessel containing the product from Example 1 step 1 (60 mg, 0.128 mmol), 5-(4,4,5,5-tetramethyl-1,3,2-dioxaborolan-2-yl)oxazole (32.5 mg, 0.167 mmol), 1 M $K_3PO_4$(aq) (0.214 ml, 0.214 mmol) and dioxane (1.3 ml) was added XPhos Pd G2 (5.04 mg, 6.41 µmol). The reaction mixture was degassed with $N_2$ for 10 min and then heated to 80° C. for 17 h. The reaction mixtures were combined, concentrated in vacuo, dissolved in DCM (2 ml) and dried by passage through a phase separator. The filtrate was purified directly by chromatography on silica gel (24 g cartridge, 0-50% EtOAc/isohexane) to afford the title compound (9 mg, 0.020 mmol, 10% yield) as a cream solid. UPLC-MS (Method 1) m/z 457.3 $(M+H)^+$, 455.2 $(M-H)^-$ at 1.41 min.

Step 2: 4-methoxy-3-(N-(2-(oxazol-5-yl)-5-(trifluoromethyl)phenyl)sulfamoyl)benzoic acid: The product from step 1 above (9 mg, 0.020 mmol) was dissolved in THF (2 ml) and treated with 1.1 M LiOH(aq) (71.7 µl, 0.079 mmol). MeOH was added dropwise until the mixture was a solution and the reaction was stirred at 30° C. for 4 days. The reaction mixture was diluted with water (3 ml), concentrated in vacuo and the resultant aqueous solution diluted with water (to ~5 ml). The aqueous phase was washed with EtOAc (2×5 ml) and neutralised to ~pH 6 using 1 M HCl(aq). The resultant lumpy suspension was sonicated to afford a cloudy solution which was concentrated in vacuo to ~2 ml. The precipitate was collected by filtration, washing with water (2×2 ml). The solid was suspended in MeCN (4 ml), concentrated in vacuo and dried at 45° C. to afford the title compound (6.5 mg, 0.014 mmol, 71% yield, 95% purity) as a pale yellow solid. UPLC-MS (Method 1) m/z 443.3 $(M+H)^+$, 441.1 $(M-H)^-$ at 1.25 min. $^1$H NMR (500 MHz, DMSO-$d_6$) δ 13.09 (s, 1H), 10.11 (s, 1H), 8.48 (s, 1H), 8.18-8.13 (m, 2H), 7.90 (d, J=8.2 Hz, 1H), 7.74 (dd, J=8.4, 1.9 Hz, 1H), 7.69 (s, 1H), 7.31-7.27 (m, 2H), 3.77 (s, 3H).

Example 26: 4-methoxy-3-(N-(2-(pyridin-2-yl)-5-(trifluoromethyl)phenyl)sulfamoyl) benzoic acid

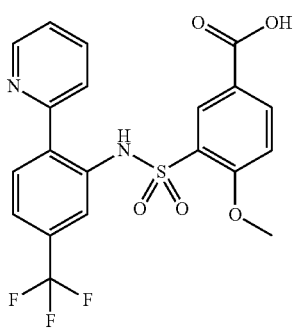 [SMILES: COc1ccc(C(=O)O)cc1S(=O)(=O)Nc1cc(C(F)(F)F)ccc1-c1ccccn1]

Step 1: methyl 4-methoxy-3-(N-(2-(pyridin-2-yl)-5-(trifluoromethyl)phenyl)sulfamoyl)benzoate: 2-(Tributylstannyl)pyridine (0.118 g, 0.320 mmol) was added to a solution of the product from Example 1 Step 1 (0.150 g, 0.320 mmol) in toluene (10 ml) and tetrakis-(triphenylphosphine)palladium(0) (0.037 g, 0.032 mmol) was added. The mixture was degassed with $N_2$ and heated to 90° C. overnight. The solvent was removed in vacuo and the crude product was purified by chromatography on silica gel (24 g cartridge, 0-100% EtOAc/isohexane) to afford the title compound (0.130 g, 0.251 mmol, 78% yield, 90% purity) as a yellow solid. UPLC-MS (Method 1) m/z 467.3 $(M+H)^+$, 465.2 (M-H)– at 1.66 min.

Step 2: 4-methoxy-3-(N-(2-(pyridin-2-yl)-5-(trifluoromethyl)phenyl)sulfamoyl)benzoic acid: 1 M LiOH(aq) (0.836 ml, 0.836 mmol) was added to a solution of the product from Step 1 above (0.130 g, 0.279 mmol) in THF (5 ml) at RT. The solution was stirred at RT overnight.

The reaction mixture was concentrated in vacuo and the resultant aqueous solution was washed with EtOAc (50 ml). The aqueous phase was acidified using 1 M HCl(aq) until pH 6 to form a precipitate which was filtered and washed with water (10 ml) and isohexane (20 ml). The crude product was purified by preparative HPLC (Waters X-Select Prep-C18, 5 µm, 19×50 mm column, 35-65% MeCN in Water (0.1% Formic acid)) to afford the title compound (18.8 mg, 0.039 mmol, 14% yield, 95% purity) as a white solid. UPLC-MS (Method 1) m/z 453.3 $(M+H)^+$, 451.2 $(M-H)^-$ at 1.49 min. $^1$H NMR (500 MHz, DMSO-$d_6$) δ 13.10 (br s, 2H), 8.86 (br d, J=5.0 Hz, 1H), 8.32 (d, J=2.2 Hz, 1H), 8.14-7.99 (m, 4H), 7.83 (d, J=1.9 Hz, 1H), 7.60 (dd, J=8.8, 4.8 Hz, 1H), 7.46 (d, J=8.1 Hz, 1H), 7.11 (d, J=8.8 Hz, 1H), 3.40 (s, 3H).

Example 27: 4-ethyl-3-(N-(2-(pyridin-3-yl)-5-(trifluoromethyl)phenyl)sulfamoyl)benzoic acid

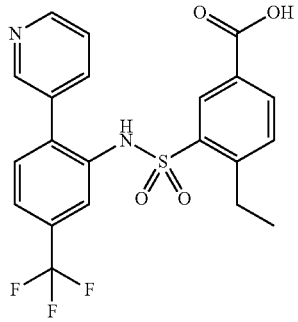 [SMILES: CCc1ccc(C(=O)O)cc1S(=O)(=O)Nc1cc(C(F)(F)F)ccc1-c1cccnc1]

Step 1: methyl 4-ethyl-3-(N-(2-(pyridin-3-yl)-5-(trifluoromethyl)phenyl)sulfamoyl)benzoate: To the reaction vessel containing the product from Example 19 Step 3 (80 mg, 0.172 mmol), was added pyridin-3-ylboronic acid (42 mg, 0.342 mmol), copper(I) chloride (34 mg, 0.343 mmol), cesium carbonate (123 mg, 0.378 mmol) and tetrakis-(triphenylphosphine)palladium(0) (19 mg, 0.016 mmol) in a mixture of dioxane and water (4:1, 2.10 ml). The reaction mixture was degassed with $N_2$ for 10 min and then stirred with microwave heating at 100° C. for 90 min. The reaction mixture was filtered through Celite® and washed with MeOH (15 ml). The filtrate was concentrated in vacuo and the residue was partitioned between EtOAc (5 ml) and water (5 ml). The phases were separated and the aqueous phase was extracted with EtOAc (5 ml). The organic phases were combined, washed with brine (5 ml), dried over $MgSO_4$, filtered and concentrated in vacuo to afford the title compound (107 mg, 0.149 mmol, 87% yield, 65% purity) as a green oil. UPLC-MS (Method 1) m/z 465.3 $(M+H)^+$, 463.2 $(M-H)^-$ at 1.41 min.

Step 2: 4-ethyl-3-(N-(2-(pyridin-3-yl)-5-(trifluoromethyl)phenyl)sulfamoyl)benzoic acid: 1 M LiOH(aq) (0.689 ml, 0.689 mmol) was added to a solution of the product from step 1 above (80 mg, 0.172 mmol) in THF (1.38 ml) at RT. The solution was stirred at RT for 17 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo. The crude product was purified by preparative HPLC (Waters X-Select Prep-C18, 5 µm, 19×50 mm column, 20-50% MeCN in Water (0.1% Formic acid)) to afford the title compound (22.8 mg, 0.050 mmol, 29% yield, 98% purity) as a white solid. UPLC-MS (Method 1) m/z 451.3 $(M+H)^+$, 449.2 $(M-H)^-$ at 1.25 min. $^1$H NMR (500 MHz, DMSO-$d_6$) δ 13.22 (br s, 1H), 10.30 (br s, 1H), 8.53 (br s, 1H), 8.42 (br s, 1H), 8.10-8.05 (m, 1H), 8.03 (dd, J=8.0, 1.9 Hz, 1H), 7.73-7.65 (m, 1H), 7.63-7.59 (m, 1H), 7.54 (d, J=8.1 Hz, 1H), 7.45 (d, J=8.0 Hz, 1H), 7.35 (dd, J=7.9, 4.7 Hz, 1H), 7.32-7.29 (m, 1H), 2.77 (q, J=7.4 Hz, 2H), 1.10 (t, J=7.4 Hz, 3H).

Example 28: 3-(N-(2-(1,2,4-triazol-1-yl)-5-(trifluoromethyl)phenyl)sulfamoyl)-4-methoxybenzoic acid

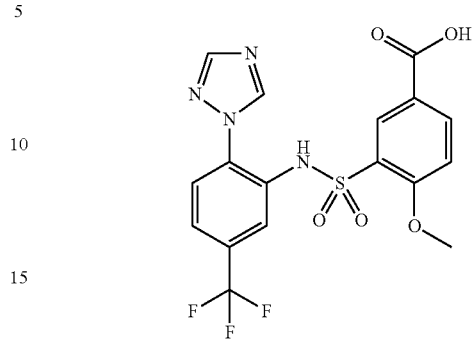

Step 1: 1-(2-nitro-4-(trifluoromethyl)phenyl)-1,2,4-triazole: A mixture of 1-fluoro-2-nitro-4-(trifluoromethyl)benzene (0.2 ml, 1.43 mmol), 1,2,4-triazole (110 mg, 1.59 mmol) and $K_2CO_3$ (237 mg, 1.72 mmol) in DMF (2 ml) was heated at 80° C. and stirred for 4 h. The mixture was diluted with water (10 ml) and extracted with EtOAc (3×20 ml). The combined organic extracts were washed with brine (2×20 ml), dried by passage through a phase separator and the solvent was removed in vacuo. The residue was loaded onto silica and purified by chromatography on silica gel (12 g cartridge, 0-100% EtOAc/isohexane) to afford the title compound (343 mg, 1.32 mmol, 92% yield, 99% purity) as a yellow oil. UPLC-MS (Method 1) m/z 259.1 $(M+H)^+$ at 1.13 min. $^1$H NMR (500 MHz, DMSO-$d_6$) δ 9.26 (s, 1H), 8.60 (d, J=2.1 Hz, 1H), 8.38-8.33 (m, 2H), 8.24-8.18 (m, 1H).

Step 2: 2-(1,2,4-triazol-1-yl)-5-(trifluoromethyl)aniline: A mixture of the product from step 1 above (343 mg, 1.32 mmol) and 10% Pd-C (Type 39) (140 mg, 0.132 mmol) in EtOH (7 ml) was stirred at RT under $H_2$ (3 bar pressure) overnight. The mixture was filtered over Celite® and the solvent was removed in vacuo to give the title compound (297 mg, 1.30 mmol, 99% yield) as a white solid. UPLC-MS (Method 2) m/z 229.1 $(M+H)^+$, 227.0 $(M-H)^-$ at 1.02 min. $^1$H NMR (500 MHz, DMSO-$d_6$) δ 8.96 (s, 1H), 8.30 (s, 1H), 7.49 (d, J=8.2 Hz, 1H), 7.24 (d, J=2.0 Hz, 1H), 6.96 (dd, J=8.2, 2.0 Hz, 1H), 5.93 (s, 2H).

Step 3: methyl 3-(N-(2-(1,2,4-triazol-1-yl)-5-(trifluoromethyl)phenyl)sulfamoyl)-4-methoxybenzoate: A mixture of the product from step 2 above (100 mg, 0.438 mmol), methyl 3-(chlorosulfonyl)-4-methoxybenzoate (128 mg, 0.482 mmol) and pyridine (35.4 µl, 0.438 mmol) in DCM (2 ml) was stirred at 35° C. over the weekend. The mixture was concentrated onto silica and purified by chromatography on silica gel (4 g cartridge, 0-10% MeOH/DCM) to afford the title compound (164 mg, 0.216 mmol, 49% yield, 60% purity) as a white solid. UPLC-MS (Method 1) m/z 457.2 $(M+H)^+$, 455.1 $(M-H)^-$ at 1.40 min.

Step 4: 3-(N-(2-(1,2,4-triazol-1-yl)-5-(trifluoromethyl)phenyl)sulfamoyl)-4-methoxybenzoic acid: A mixture of the product from step 3 above (164 mg, 0.216 mmol) and LiOH (21 mg, 0.877 mmol) in THF/MeOH/water (4:1:1, 3 ml) was stirred at 40° C. overnight. The mixture was diluted with water (5 ml), adjusted to ~pH 4 using 1 M HCl(aq) and extracted with EtOAc (3×15 ml). The combined organic extracts were washed with brine (10 ml), dried by passage through a phase separator and the solvent was removed in vacuo. The residue was loaded onto silica and purified by chromatography on silica gel (4 g cartridge, 0-10% MeOH/

DCM) to afford the title compound (53.7 mg, 0.116 mmol, 54% yield, 95% purity) as a white solid. UPLC-MS (Method 1) m/z 443.1 (M+H)+, 441.1 (M−H)− at 1.21 min. $^1$H NMR (500 MHz, DMSO-$d_6$) δ 13.13 (s, 1H), 10.28 (s, 1H), 9.04 (s, 1H), 8.32 (s, 1H), 8.16 (d, J=2.2 Hz, 1H), 8.12 (dd, J=8.7, 2.2 Hz, 1H), 7.84 (d, J=8.5 Hz, 1H), 7.76-7.71 (m, 2H), 7.23 (d, J=8.7 Hz, 1H), 3.72 (s, 3H).

Example 29: 3-(N-(2-(1,2,4-triazol-1-yl)-5-(trifluoromethyl)phenyl)sulfamoyl)-4-ethylbenzoic acid

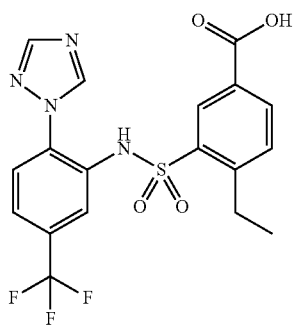 [SMILES: CCc1ccc(C(=O)O)cc1S(=O)(=O)Nc1cc(C(F)(F)F)ccc1-n1cncn1]

Step 1: methyl 3-(N-(2-(1,2,4-triazol-1-yl)-5-(trifluoromethyl)phenyl)sulfamoyl)-4-ethylbenzoate: A mixture of the product from Example 28 Step 2 (100 mg, 0.438 mmol), the product from Example 19 Step 2 (127 mg, 0.482 mmol) and pyridine (35.4 μl, 0.438 mmol) in DCM (2 ml) was stirred at 35° C. over the weekend. The mixture was concentrated onto silica and purified by chromatography on silica gel (4 g cartridge, 0-10% MeOH/DCM) to afford the title compound (78 mg, 0.091 mmol, 21% yield, 53% purity) as a white solid. UPLC-MS (Method 1) m/z 455.2 (M+H)+, 453.1 (M−H)− at 1.55 min.

Step 2: 3-(N-(2-(1,2,4-triazol-1-yl)-5-(trifluoromethyl) phenyl)sulfamoyl)-4-ethylbenzoic acid: A mixture of the product from step 1 above (78 mg, 0.091 mmol, 53% purity) and LiOH (16 mg, 0.374 mmol) in THF/MeOH/water (4:1:1, 1.2 ml) was stirred at 40° C. for 4 days. The mixture was diluted with water (10 ml), adjusted to ~pH 4 using 1 M HCl(aq) and extracted with EtOAc (3×15 ml). The combined organic extracts were washed with brine (10 ml), dried by passage through a phase separator and the solvent was removed in vacuo. The crude product was purified by preparative HPLC (Waters X-Select Prep-C18, 5 μm, 19×50 mm column, 35-65% MeCN in Water (0.1% Formic acid)) to afford the title compound (34.1 mg, 0.077 mmol, 85% yield) as a white solid. UPLC-MS (Method 1) m/z 441.2 (M+H)+, 439.1 (M−H)− at 1.38 min. $^1$H NMR (500 MHz, DMSO-$d_6$) δ 13.26 (s, 1H), 10.51 (s, 1H), 8.95 (s, 1H), 8.23-8.16 (m, 2H), 8.06 (dd, J=8.0, 1.8 Hz, 1H), 7.79 (d, J=8.1 Hz, 1H), 7.74 (br s, 1H), 7.54 (d, J=8.0 Hz, 1H), 7.45 (d, J=1.8 Hz, 1H), 2.85 (q, J=7.4 Hz, 2H), 1.12 (t, J=7.4 Hz, 3H).

Example 30: 3-(N-(2-(pyrazol-1-yl)-5-(trifluoromethyl)phenyl)sulfamoyl)-4-methoxybenzoic acid

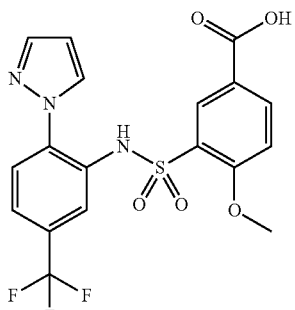

Step 1: 1-(2-nitro-4-(trifluoromethyl)phenyl)pyrazole: A mixture of 1-fluoro-2-nitro-4-(trifluoromethyl)benzene (0.5 ml, 3.57 mmol), pyrazole (268 mg, 3.93 mmol) and DIPEA (1.3 ml, 7.44 mmol) in MeCN (15 ml) was heated under reflux and stirred overnight. The mixture was concentrated onto silica and purified by chromatography on silica gel (12 g cartridge, 0-50% EtOAc/isohexane) to afford the title compound (237 mg, 0.908 mmol, 25% yield, 99% purity) as a light yellow oil. UPLC-MS (Method 1) m/z 258.1 (M+H)+ at 1.38 min. $^1$H NMR (500 MHz, DMSO-$d_6$) δ 8.51-8.46 (m, 2H), 8.22 (dd, J=8.5, 2.2 Hz, 1H), 8.09 (d, J=8.5 Hz, 1H), 7.84 (d, J=1.7 Hz, 1H), 6.65 (t, J=2.2 Hz, 1H).

Step 2: 2-(pyrazol-1-yl)-5-(trifluoromethyl)aniline: The product from Step 1 above (310 mg, 1.18 mmol) was dissolved in EtOH (5 ml) and the reaction mixture was hydrogenated in a ThalesNano H-cube® flow reactor (10% Pd/C, 30×4 mm cartridge, full hydrogen mode, RT, 1 ml/min flow rate, 1 pass). 10% Pd/C (Type 39) (126 mg, 0.118 mmol) was added to the solution and the mixture was stirred at RT under $H_2$ (4 bar pressure) overnight. The mixture was filtered through Celite® and concentrated in vacuo to afford the title compound (250 mg, 1.07 mmol, 90% yield, 97% purity) as a brown oil. UPLC-MS (Method 2) m/z 228.1 (M+H)+, 226.4 (M−H)− at 1.30 min. $^1$H NMR (500 MHz, DMSO-$d_6$) δ 8.23 (d, J=2.5 Hz, 1H), 7.81 (d, J=1.8 Hz, 1H), 7.47 (d, J=8.2 Hz, 1H), 7.22 (d, J=2.1 Hz, 1H), 6.94 (dd, J=8.2, 2.1 Hz, 1H), 6.56 (t, J=2.1 Hz, 1H), 6.12 (s, 2H).

Step 3: methyl 3-(N-(2-(pyrazol-1-yl)-5-(trifluoromethyl) phenyl)sulfamoyl)-4-methoxybenzoate: A mixture of the product from Step 2 above (125 mg, 0.550 mmol), methyl 3-(chlorosulfonyl)-4-methoxybenzoate (175 mg, 0.660 mmol) and pyridine (0.14 ml, 1.73 mmol) in DCM (3 ml) was stirred at 35° C. overnight. The mixture was concentrated onto silica and purified by chromatography on silica gel (12 g cartridge, 0-100% EtOAc/isohexane) to afford the title compound (169 mg, 0.364 mmol, 66.1% yield, 98% purity) as a white solid. UPLC-MS (Method 1) m/z 456.2 (M+H)+, 454.1 (M−H)− at 1.62 min. $^4$H NMR (500 MHz, DMSO-$d_6$) δ 11.19 (s, 1H), 8.47 (d, J=2.6 Hz, 1H), 8.24 (d, J=2.2 Hz, 1H), 8.12 (dd, J=8.8, 2.2 Hz, 1H), 8.06 (d, J=1.9 Hz, 1H), 7.84 (d, J=8.5 Hz, 1H), 7.82 (d, J=2.1 Hz, 1H), 7.59 (dd, J=8.5, 2.1 Hz, 1H), 7.21 (d, J=8.8 Hz, 1H), 6.68 (dd, J=2.6, 1.9 Hz, 1H), 3.83 (s, 3H), 3.61 (s, 3H).

Step 4: 3-(N-(2-(pyrazol-1-yl)-5-(trifluoromethyl)phenyl) sulfamoyl)-4-methoxybenzoic acid: A mixture of the product from step 3 above (169 mg, 0.364 mmol) and LiOH (64 mg, 1.50 mmol) in THF/MeOH/water (4:1:1, 6.4 ml) was stirred at 40° C. overnight. The mixture was diluted with water (10 ml), adjusted to ~pH 4 using 1 M HCl(aq) and extracted with EtOAc (3×30 ml). The combined organic extracts were washed with brine, dried by passage through a phase separator and the solvent was removed in vacuo. The residue was loaded onto silica and purified by chromatography on silica gel (4 g cartridge, 0-100% EtOAc/isohexane) to afford the title compound (29.9 mg, 0.067 mmol, 18% yield, 99% purity) as a white solid. UPLC-MS (Method 1) m/z 442.2 (M+H)$^+$, 440.1 (M–H)$^-$ at 1.45 min. $^1$H NMR (500 MHz, DMSO-$d_6$) δ 13.15 (s, 1H), 11.20 (s, 1H), 8.49 (d, J=2.6 Hz, 1H), 8.25 (d, J=2.2 Hz, 1H), 8.09 (dd, J=8.8, 2.2 Hz, 1H), 8.07 (d, J=1.9 Hz, 1H), 7.85 (d, J=8.5 Hz, 1H), 7.82 (d, J=2.1 Hz, 1H), 7.60-7.55 (m, 1H), 7.18 (d, J=8.8 Hz, 1H), 6.69 (app t, J=2.3 Hz, 1H), 3.59 (s, 3H).

Example 31: 3-(N-(2-(pyrazol-1-yl)-5-(trifluoromethyl)phenyl)sulfamoyl)-4-ethylbenzoic acid

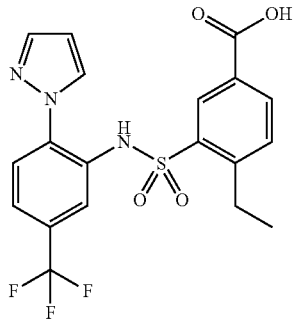

Step 1: methyl 3-(N-(2-(pyrazol-1-yl)-5-(trifluoromethyl)phenyl)sulfamoyl)-4-ethylbenzoate: A mixture of the product from Example 30 Step 2 (125 mg, 0.550 mmol), the product from Example 19 Step 2 (170 mg, 0.647 mmol) and pyridine (0.14 ml, 1.73 mmol) in DCM (3 ml) was stirred at 35° C. overnight. The mixture was concentrated onto silica and purified by chromatography on silica gel (12 g cartridge, 0-100% EtOAc/isohexane) to afford the title compound (225 mg, 0.486 mmol, 88% yield, 98% purity) as a white solid. UPLC-MS (Method 1) m/z 454.2 (M+H)$^+$, 452.1 (M–H)$^-$ at 1.80 min. $^1$H NMR (500 MHz, DMSO-$d_6$) δ 11.08 (s, 1H), 8.32 (br s, 1H), 8.17 (d, J=1.9 Hz, 1H), 8.05 (dd, J=8.0, 1.9 Hz, 1H), 7.92 (d, J=1.9 Hz, 1H), 7.82 (d, J=8.4 Hz, 1H), 7.70-7.64 (m, 2H), 7.51 (d, J=8.0 Hz, 1H), 6.61-6.56 (m, 1H), 3.84 (s, 3H), 2.75 (q, J=7.4 Hz, 2H), 1.05 (t, J=7.4 Hz, 3H).

Step 2: 3-(N-(2-(pyrazol-1-yl)-5-(trifluoromethyl)phenyl)sulfamoyl)-4-ethylbenzoic acid: A mixture of the product from Step 1 above (225 mg, 0.486 mmol) and LiOH (83 mg, 1.95 mmol) in THF/MeOH/water (4:1:1, 7.2 ml) was stirred at 40° C. overnight. The mixture was diluted with water (10 ml), adjusted to ~pH 4 using 1 M HCl(aq) and extracted with EtOAc (3×30 ml). The organic extracts were combined, washed with brine, dried by passage through a phase separator and concentrated in vacuo. The residue was loaded onto silica and purified by chromatography on silica gel (4 g cartridge, 0-100% EtOAc/isohexane) to afford the title compound (163 mg, 0.370 mmol, 76% yield) as a white solid. UPLC-MS (Method 1) m/z 440.2 (M+H)$^+$, 438.1 (M–H)$^-$ at 1.64 min. $^1$H NMR (500 MHz, DMSO-$d_6$) δ 13.29 (s, 1H), 11.09 (s, 1H), 8.34 (d, J=2.6 Hz, 1H), 8.21 (d, J=1.8 Hz, 1H), 8.03 (dd, J=8.0, 1.8 Hz, 1H), 7.94 (d, J=1.8 Hz, 1H), 7.83 (d, J=8.4 Hz, 1H), 7.66 (d, J=8.6 Hz, 1H), 7.64-7.61 (m, 1H), 7.49 (d, J=8.0 Hz, 1H), 6.60 (t, J=2.3 Hz, 1H), 2.75 (q, J=7.4 Hz, 2H), 1.05 (t, J=7.4 Hz, 3H).

Example 32: 4-ethyl-3-(N-(4-(methylsulfonyl)-[1,1'-biphenyl]-2-yl)sulfamoyl)benzoic acid

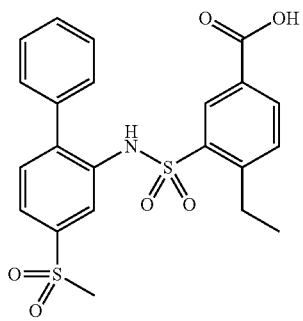 [SMILES: CCc1ccc(C(=O)O)cc1S(=O)(=O)Nc1cc(S(C)(=O)=O)ccc1-c1ccccc1]

Step 1: methyl 3-(N-(2-bromo-5-(methylsulfonyl)phenyl)sulfamoyl)-4-ethylbenzoate: A solution of 2-bromo-5-(methylsulfonyl)aniline (1 g, 4.00 mmol), the product from Example 19 Step 2 (1.26 g, 4.80 mmol) and pyridine (0.970 ml, 12.0 mmol) in DCM (6.4 ml) was stirred at RT for 3 days. The reaction mixture was partially purified by chromatography on silica gel (50 g cartridge, 0-50% EtOAc/isohexane), then purified by chromatography (40 g reverse phase C18 cartridge, 35-65% MeCN/0.1% formic acid(aq)) to afford the title compound (673 mg, 1.39 mmol, 35% yield, 98% purity) as a white solid. UPLC-MS (Method 1) m/z 474.1 (M–H)$^-$ at 1.39 min.

Step 2: methyl 4-ethyl-3-(N-(4-(methylsulfonyl)-[1,1'-biphenyl]-2-yl)sulfamoyl)benzoate: To the reaction vessel containing the product from Step 1 above (70 mg, 0.147 mmol), phenylboronic acid (24 mg, 0.197 mmol), 1 M $K_3PO_4$(aq) (0.25 ml, 0.25 mmol) and dioxane (1.47 ml) was added XPhos Pd G3 (7 mg, 8.27 μmol). The reaction mixture was degassed with $N_2$ for 10 min and then heated at 80° C. for 2 h. The reaction mixture was concentrated in vacuo and the crude product was purified by chromatography on silica gel (12 g cartridge, 10-60% EtOAc/isohexane) to afford the title compound (56.8 mg, 0.119 mmol, 81% yield, 99% purity) as a colourless oil. UPLC-MS (Method 1) m/z 474.3 (M+H)$^+$, 472.3 (M–H)$^-$ at 1.51 min.

Step 3: 4-ethyl-3-(N-(4-(methylsulfonyl)-[1,1'-biphenyl]-2-yl)sulfamoyl)benzoic acid: 1 M LiOH(aq) (0.480 ml, 0.480 mmol) was added to a solution of the product from Step 2 above (56.8 mg, 0.120 mmol) in THF (0.96 ml) at RT. The solution was stirred at RT for 17 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo to afford the title compound (44.7 mg, 0.095 mmol, 79% yield, 98% purity) as a cream solid. UPLC-MS (Method 1) m/z 460.3 (M+H)$^+$, 458.2 (M–H)$^-$ at 1.37 min. $^1$H NMR (500 MHz, DMSO-$d_6$) δ 13.21 (br s, 1H), 10.18 (br s, 1H), 8.09-8.05 (m, 1H), 8.02 (dd, J=8.0, 1.9 Hz, 1H), 7.85 (br d, J=8.1 Hz, 1H), 7.59 (d, J=1.9 Hz, 1H), 7.50 (d, J=8.1 Hz, 1H), 7.44 (d, J=8.0 Hz, 1H), 7.33-7.28 (m, 3H), 7.21-7.16 (m, 2H), 3.18 (s, 3H), 2.76 (q, J=7.4 Hz, 2H), 1.11 (t, J=7.4 Hz, 3H).

Example 33: 4-ethyl-3-(N-(3'-fluoro-4-(methylsulfonyl)-[1,1-biphenyl]-2-yl)sulfamoyl)benzoic acid

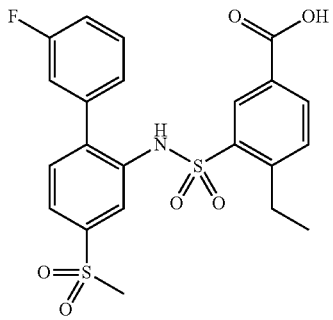 [SMILES: CCc1ccc(C(=O)O)cc1S(=O)(=O)Nc1cc(S(C)(=O)=O)ccc1-c1cccc(F)c1]

Step 1: methyl 4-ethyl-3-(N-(3'-fluoro-4-(methylsulfonyl)-[1,1'-biphenyl]-2-yl)sulfamoyl)benzoate: To the reaction vessel containing the product from Example 32 Step 1 (70 mg, 0.147 mmol), (3-fluorophenyl)boronic acid (27 mg, 0.193 mmol), 1 M $K_3PO_4$(aq) (0.25 ml, 0.25 mmol) and dioxane (1.47 ml) was added XPhos Pd G3 (7 mg, 8.27 µmol). The reaction mixture was degassed with $N_2$ for 10 min and then heated at 80° C. for 2 h. The reaction mixture was concentrated in vacuo and the crude product was purified by chromatography on silica gel (12 g cartridge, 10-50% EtOAc/isohexane) to afford the title compound (65.7 mg, 0.132 mmol, 90% yield, 99% purity) as a yellow oil. UPLC-MS (Method 1) m/z 492.5 $(M+H)^+$, 490.2 $(M-H)^-$ at 1.51 min.

Step 2: 4-ethyl-3-(N-(3'-fluoro-4-(methylsulfonyl)-[1,1'-biphenyl]-2-yl)sulfamoyl)benzoic acid: 1 M LiOH(aq) (0.535 ml, 0.535 mmol) was added to a solution of the product from Step 1 above (65.7 mg, 0.134 mmol) in THF (1.07 ml) at RT. The solution was stirred at RT for 17 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo to afford the title compound (50.4 mg, 0.100 mmol, 75% yield, 95% purity) as an off-white solid. UPLC-MS (Method 1) m/z 478.2 $(M+H)^+$, 476.2 $(M-H)^-$ at 1.37 min. $^1$H NMR (500 MHz, DMSO-$d_6$) δ 13.21 (br s, 1H), 10.27 (br s, 1H), 8.06-8.03 (m, 1H), 8.01 (dd, J=8.0, 1.9 Hz, 1H), 7.86 (br d, J=8.0 Hz, 1H), 7.64 (d, J=1.9 Hz, 1H), 7.53 (d, J=8.1 Hz, 1H), 7.43 (d, J=8.0 Hz, 1H), 7.33 (app. td, J=8.1, 6.1 Hz, 1H), 7.16-7.10 (m, 1H), 7.02-6.95 (m, 2H), 3.20 (s, 3H), 2.78 (q, J=7.4 Hz, 2H), 1.12 (t, J=7.4 Hz, 3H).

Example 34: 4-ethyl-3-(N-(5-(methylsulfonyl)-2-(thiophen-2-yl)phenyl)sulfamoyl) benzoic acid

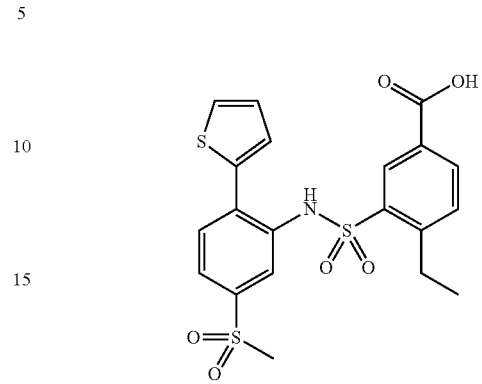

Step 1: methyl 4-ethyl-3-(N-(5-(methylsulfonyl)-2-(thiophen-2-yl)phenyl)sulfamoyl)benzoate: To the reaction vessel containing the product from Example 32 Step 1 above (70 mg, 0.147 mmol), thiophen-2-ylboronic acid (25 mg, 0.195 mmol), 1 M $K_3PO_4$(aq) (0.25 ml, 0.25 mmol) and dioxane (1.47 ml) was added XPhos Pd G3 (7 mg, 8.27 µmol). The reaction mixture was degassed with $N_2$ for 10 min and then heated to 80° C. for 2 h. The reaction mixture was concentrated in vacuo and the crude product was purified by chromatography on silica gel (12 g cartridge, 10-50% EtOAc/isohexane) to afford the title compound (69.8 mg, 0.146 mmol, 99% yield) as a colourless oil. UPLC-MS (Method 1) m/z 480.3 $(M+H)^+$, 478.2 $(M-H)^-$ at 1.48 min.

Step 2: 4-ethyl-3-(N-(5-(methylsulfonyl)-2-(thiophen-2-yl)phenyl)sulfamoyl)benzoic acid: 1 M LiOH(aq) (0.582 ml, 0.582 mmol) was added to a solution of the product from Step 1 above (69.8 mg, 0.146 mmol) in THF (1.16 ml) at RT. The solution was stirred at RT for 17 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo to afford the title compound (47.2 mg, 0.100 mmol, 69% yield, 99% purity) as a white solid. UPLC-MS (Method 1) m/z 466.2 $(M+H)^+$, 464.1 $(M-H)^-$ at 1.33 min. $^1$H NMR (500 MHz, DMSO-$d_6$) δ 13.26 (br s, 1H), 10.31 (br s, 1H), 8.19 (br s, 1H), 8.08 (d, J=8.0 Hz, 1H), 7.90-7.79 (m, 2H), 7.69 (d, J=5.1 Hz, 1H), 7.60-7.53 (m, 2H), 7.24 (br s, 1H), 7.13 (dd, J=5.1, 3.7 Hz, 1H), 3.09 (s, 3H), 2.91 (br q, J=7.0 Hz, 2H), 1.16 (t, J=7.4 Hz, 3H).

Example 35: 3-(N-(2-(pyrrol-1-yl)-5-(trifluoromethyl)phenyl)sulfamoyl)-4-methoxybenzoic acid

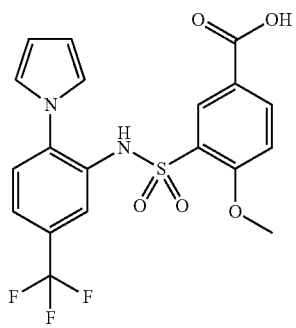 [SMILES: COc1ccc(C(=O)O)cc1S(=O)(=O)Nc1cc(C(F)(F)F)ccc1-n1cccc1]

Step 1: methyl 3-(N-(2-((tert-butoxycarbonyl)amino)-5-(trifluoromethyl)phenyl)sulfamoyl)-4-methoxybenzoate: A mixture of tert-butyl (2-amino-4-(trifluoromethyl)phenyl)carbamate (100 mg, 0.362 mmol), methyl 3-(chlorosulfonyl)-4-methoxybenzoate (105 mg, 0.398 mmol) and pyridine (90 µl, 1.11 mmol) in DCM (2 ml) was stirred at 35° C. overnight. The mixture was concentrated onto silica and purified by chromatography on silica gel (12 g cartridge, 0-50% EtOAc/isohexane) to afford the title compound (159 mg, 0.309 mmol, 85% yield, 98% purity) as a colourless oil. UPLC-MS (Method 1) m/z 405.5 (M+H—$C_4H_8$)$^+$, 503.1 (M−H)$^-$ at 1.70 min.

Step 2: methyl 3-(N-(2-amino-5-(trifluoromethyl)phenyl)sulfamoyl)-4-methoxybenzoate: A mixture of the product from Step 1 above (159 mg, 0.309 mmol) in TFA (0.5 ml) and DCM (5 ml) was stirred at RT overnight. The mixture was concentrated onto silica and purified by chromatography on silica gel (12 g cartridge, 0-100% EtOAc/isohexane) to afford the title compound (119 mg, 0.294 mmol, 95% yield) as a white foam. UPLC-MS (Method 1) m/z 405.5 (M+H)−, 403.0 (M−H)$^-$ at 1.33 min.

Step 3: methyl 3-(N-(2-(pyrrol-1-yl)-5-(trifluoromethyl)phenyl)sulfamoyl)-4-methoxybenzoate: A mixture of the product from Step 2 above (119 mg, 0.294 mmol), 2,5-dimethoxytetrahydrofuran (40 µl, 0.309 mmol) and AcOH (0.6 ml) was heated at 120° C. and stirred for 1 h and then at RT overnight. The mixture was concentrated onto silica and purified by chromatography on silica gel (12 g cartridge, 0-100% EtOAc/isohexane) to afford the title compound (95 mg, 0.180 mmol, 60% yield, 86% purity) as a pale yellow oil. UPLC-MS (Method 1) m/z 455.4 (M+H)$^+$, 453.1 (M−H)$^-$ at 1.65 min. $^1$H NMR (500 MHz, DMSO-$d_6$) δ 9.81 (s, 1H), 8.15 (dd, J=8.8, 2.3 Hz, 1H), 8.07-8.04 (m, 1H), 7.74-7.66 (m, 1H), 7.50 (d, J=8.3 Hz, 1H), 7.41 (s, 1H), 7.30 (d, J=8.8 Hz, 1H), 6.98-6.93 (m, 2H), 6.14 (t, J=2.1 Hz, 2H), 3.87 (s, 3H), 3.82 (s, 3H).

Step 4: 3-(N-(2-(pyrrol-1-yl)-5-(trifluoromethyl)phenyl)sulfamoyl)-4-methoxybenzoic acid: A mixture of the product from Step 3 above (95 mg, 0.180 mmol) and LiOH (36 mg, 0.842 mmol) in THF/MeOH/water (4:1:1, 3 ml) was stirred at 40° C. overnight. The mixture was diluted with water (10 ml), adjusted to ~pH 4 using 1 M HCl(aq) and extracted with EtOAc (3×20 ml). The combined organic extracts were washed with brine (10 ml), dried by passage through a phase separator and the solvent was removed in vacuo. The residue was loaded onto silica and partially purified by chromatography on silica gel (4 g cartridge, 0-100% EtOAc/isohexane), then purified by preparative HPLC (Waters X-Select Prep-C18, 5 µm, 19 ×50 mm column, 35-65% MeCN in Water (0.1% Formic acid)) to afford the title compound (43.4 mg, 0.098 mmol, 54% yield, 99% purity) as a white solid. UPLC-MS (Method 1) m/z 441.2 (M+H)$^+$, 439.1 (M−H)$^-$ at 1.48 min. $^1$H NMR (500 MHz, DMSO-$d_6$) δ 13.04 (s, 1H), 9.73 (s, 1H), 8.12 (dd, J=8.7, 2.2 Hz, 1H), 8.08 (d, J=2.2 Hz, 1H), 7.73-7.61 (m, 1H), 7.50 (d, J=8.3 Hz, 1H), 7.42-7.38 (m, 1H), 7.27 (d, J=8.7 Hz, 1H), 7.00-6.96 (m, 2H), 6.17 (app. t, J=2.2 Hz, 2H), 3.85 (s, 3H).

Example 36: 3-(N-(2-(pyrrol-1-yl)-5-(trifluoromethyl)phenyl)sulfamoyl)-4-ethylbenzoic acid

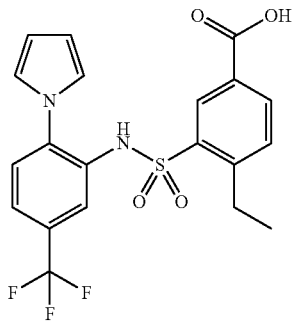 [SMILES: CCc1ccc(C(=O)O)cc1S(=O)(=O)Nc1cc(C(F)(F)F)ccc1-n1cccc1]

Step 1: methyl 3-(N-(2-((tert-butoxycarbonyl)amino)-5-(trifluoromethyl)phenyl)sulfamoyl)-4-ethylbenzoate: A mixture of tert-butyl (2-amino-4-(trifluoromethyl)phenyl)carbamate (100 mg, 0.362 mmol), the product from Example 19 Step 2 (105 mg, 0.398 mmol) and pyridine (90 µl, 1.11 mmol) in DCM (2 ml) was stirred at 35° C. overnight. The mixture was concentrated onto silica and purified by chromatography on silica gel (12 g cartridge, 0-50% EtOAc/isohexane) to afford the title compound (158 mg, 0.245 mmol, 68% yield, 78% purity) as a light brown oil UPLC-MS (Method 1) m/z 403.6 (M+H—$C_4H_8$)$^+$, 501.1 (M−H)$^-$ at 1.85 min.

Step 2: methyl 3-(N-(2-amino-5-(trifluoromethyl)phenyl)sulfamoyl)-4-ethylbenzoate: A mixture of the product from Step 1 above (158 mg, 0.267 mmol) in TFA (0.5 ml) and DCM (5 ml) was stirred at RT overnight. The mixture was concentrated onto silica and purified by chromatography on silica gel (12 g cartridge, 0-100% EtOAc/isohexane) to afford the title compound (108 mg, 0.255 mmol, 95% yield, 95% purity) as a pale yellow gum. UPLC-MS (Method 1) m/z 403.5 (M+H)$^+$, 401.1 (M−H)$^-$ at 1.52 min.

Step 3: methyl 3-(N-(2-(pyrrol-1-yl)-5-(trifluoromethyl)phenyl)sulfamoyl)-4-ethylbenzoate: A mixture of the product from Step 2 above (108 mg, 0.255 mmol), 2,5-dimethoxytetrahydrofuran (40 µl, 0.309 mmol) and AcOH (0.6 ml) was heated to 120° C. and stirred for 1 h and then at RT overnight. The mixture was concentrated onto silica and purified by chromatography on silica gel (12 g cartridge, 0-100% EtOAc/isohexane) to afford the title compound (70 mg, 0.125 mmol, 49% yield, 81% purity) as a pale yellow oil. UPLC-MS (Method 1) m/z 453.5 (M+H)$^+$, 451.1 (M−H)$^-$ at 1.79 min. $^1$H NMR (500 MHz, DMSO-$d_6$) δ 10.37 (s, 1H), 8.11 (d, J=1.9 Hz, 1H), 8.08 (dd, J=8.0, 1.9 Hz, 1H), 7.76-7.69 (m, 1H), 7.55 (d, J=8.0 Hz, 1H), 7.51 (d, J=8.4 Hz, 1H), 7.26 (d, J=2.1 Hz, 1H), 6.91 (app. t, J=2.2 Hz, 2H), 6.13 (app. t, J=2.2 Hz, 2H), 3.84 (s, 3H), 2.88 (q, J=7.4 Hz, 2H), 1.15 (t, J=7.4 Hz, 3H).

Step 4: 3-(N-(2-(pyrrol-1-yl)-5-(trifluoromethyl)phenyl) sulfamoyl)-4-ethylbenzoic acid: A mixture of the product from Step 3 above (70 mg, 0.125 mmol) and LiOH (27 mg, 0.631 mmol) in THF/MeOH/water (4:1:1, 2.4 ml) was stirred at 40° C. overnight. The mixture was diluted with water (10 ml), adjusted to ~pH 4 using 1 M HCl(aq) and extracted with EtOAc (3×20 ml). The combined organic extracts were washed with brine (10 ml), dried by passage through a phase separator and the solvent was removed in vacuo. The residue was loaded onto silica and partially purified by chromatography on silica gel (4 g cartridge, 0-100% EtOAc/isohexane), then purified by preparative HPLC (Waters X-Select Prep-C18, 5 μm, 19 ×50 mm column, 50-80% MeCN in Water (0.1% Formic acid)) to afford the title compound (31.4 mg, 0.071 mmol, 57% yield, 99% purity) as a white solid. UPLC-MS (Method 1) m/z 439.3 (M+H)$^+$, 437.1 (M–H)$^-$ at 1.62 min. $^1$H NMR (500 MHz, DMSO-d$_6$) δ 13.20 (br s, 1H), 10.33 (br s, 1H), 8.14 (br s, 1H), 8.06 (dd, J=8.1, 1.8 Hz, 1H), 7.76-7.62 (m, 1H), 7.56-7.48 (m, 2H), 7.22 (d, J=2.2 Hz, 1H), 6.97-6.92 (m, 2H), 6.16 (app. t, J=2.2 Hz, 2H), 2.89 (q, J=7.4 Hz, 2H), 1.15 (t, J=7.4 Hz, 3H).

Example 37: 4-ethyl-3-(N-(2-(pyridin-2-yl)-5-(trifluoromethyl)phenyl) sulfamoyl)benzoic acid

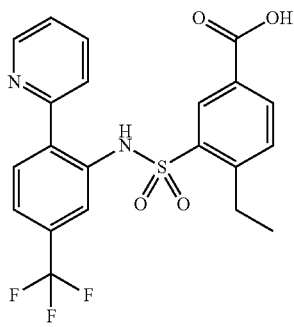 [SMILES: CCc1ccc(C(=O)O)cc1S(=O)(=O)Nc1cc(C(F)(F)F)ccc1-c1ccccn1]

Step 1: methyl 4-ethyl-3-(N-(2-(pyridin-2-yl)-5-(trifluoromethyl)phenyl)sulfamoyl)benzoate: 2-(Tributylstannyl)pyridine (0.07 ml, 0.216 mmol) was added to a solution of the product from Example 19 Step 3 (80 mg, 0.172 mmol) and tetrakis-(triphenylphosphine)palladium(0) (19.8 mg, 0.017 mmol) in toluene (1.8 ml). The resultant mixture was degassed with N$_2$ for 10 min and then heated at 90° C. for 22 h. The reaction mixture was concentrated in vacuo and the crude product was purified by chromatography on silica gel (24 g cartridge, 0-45% EtOAc/isohexane) to afford the title compound (56 mg, 0.119 mmol, 70% yield, 99% purity) as a bright yellow solid. UPLC-MS (Method 1) m/z 465.3 (M+H)$^+$, 463.2 (M–H)$^-$ at 1.85 min.

Step 2: 4-ethyl-3-(N-(2-(pyridin-2-yl)-5-(trifluoromethyl)phenyl)sulfamoyl)benzoic acid: 1 M LiOH(aq) (0.482 ml, 0.482 mmol) was added to a solution of the product from Step 1 above (56 mg, 0.121 mmol) in THF (0.96 ml) at RT. The solution was stirred at RT for 40 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over MgSO$_4$, filtered and concentrated in vacuo to afford the title compound (42.5 mg, 0.093 mmol, 77% yield, 99% purity) as a bright yellow solid. UPLC-MS (Method 1) m/z 451.3 (M+H)$^+$, 449.2 (M–H)$^-$ at 1.69 min. $^1$H NMR (500 MHz, DMSO-d$_6$) δ 13.27 (br s, 1H), 13.18 (br s, 1H), 8.78-8.75 (m, 1H), 8.29 (d, J=1.8 Hz, 1H), 8.09 (d, J=8.3 Hz, 1H), 8.05-7.99 (m, 2H), 7.97 (d, J=8.1 Hz, 1H), 7.72 (d, J=1.9 Hz, 1H), 7.59-7.50 (m, 2H), 7.44 (d, J=8.0 Hz, 1H), 2.76 (q, J=7.4 Hz, 2H), 0.97 (t, J=7.4 Hz, 3H).

Example 38: 3-(N-(5-cyano-2-(pyridin-2-yl)phenyl) sulfamoyl)-4-ethylbenzoic acid

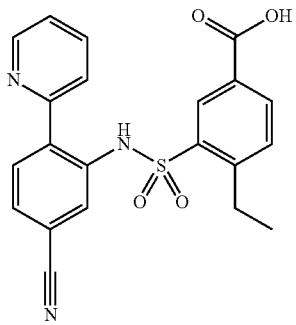 [SMILES: CCc1ccc(C(=O)O)cc1S(=O)(=O)Nc1cc(C#N)ccc1-c1ccccn1]

Step 1: methyl 3-(N-(2-bromo-5-cyanophenyl)sulfamoyl)-4-ethylbenzoate: A solution of 3-amino-4-bromobenzonitrile (0.7 g, 3.55 mmol), the product from Example 19 Step 2 (1.03 g, 3.91 mmol) and pyridine (0.862 ml, 10.7 mmol) in DCM (6 ml) was stirred at RT for 6 days. The reaction mixture was concentrated in vacuo and the crude product was partially purified by chromatography on silica gel (40 g cartridge, 0-100% EtOAc/isohexane), then purified by chromatography (40 g reverse phase C18 cartridge, 45-75% MeCN/0.1% formic acid(aq)) to afford the title compound (570 mg, 1.34 mmol, 38% yield) as a white solid. UPLC-MS (Method 1) m/z 421.2 (M–H)$^-$ at 1.52 min. $^1$H NMR (500 MHz, DMSO-d$_6$) δ 10.65 (br s, 1H), 8.21 (d, J=1.9 Hz, 1H), 8.12 (dd, J=8.0, 1.9 Hz, 1H), 7.82 (d, J=8.2 Hz, 1H), 7.68-7.61 (m, 3H), 3.84 (s, 3H), 3.03 (q, J=7.4 Hz, 2H), 1.21 (t, J=7.4 Hz, 3H).

Step 2: methyl 3-(N-(5-cyano-2-(pyridin-2-yl)phenyl)sulfamoyl)-4-ethylbenzoate: 2-(Tributylstannyl)pyridine (0.07 ml, 0.216 mmol) was added to a solution of the product from Step 1 above (80 mg, 0.189 mmol) and tetrakis-(triphenylphosphine)palladium(0) (21.8 mg, 0.019 mmol) in toluene (1.8 ml). The resultant mixture was degassed with N$_2$ for 10 min and then heated to 90° C. for 24 h. Additional 2-(tributylstannyl)pyridine (0.07 ml, 0.216 mmol) and tetrakis-(triphenylphosphine)palladium(0) (21.8 mg, 0.019 mmol) were added, the mixture was degassed with N$_2$ for 10 min and then heated to 90° C. for 24 h. The reaction mixture was concentrated in vacuo and the crude product was purified by chromatography on silica gel (24 g cartridge, 10-50% EtOAc/isohexane) to afford the title compound (16 mg, 0.038 mmol, 20% yield) as a bright yellow solid. UPLC-MS (Method 1) m/z 422.4 (M+H)$^+$, 420.3 (M–H)$^-$ at 1.65 min.

Step 3: 3-(N-(5-cyano-2-(pyridin-2-yl)phenyl)sulfamoyl)-4-ethylbenzoic acid: 1 M LiOH(aq) (0.152 ml, 0.152 mmol) was added to a solution of the product from Step 1 above (16 mg, 0.038 mmol) in THF (0.45 ml) at RT. The solution was stirred at RT for 40 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over MgSO$_4$, filtered and concentrated in vacuo to afford the title compound (11.1 mg, 0.027 mmol, 70% yield, 98% purity) as a cream solid. UPLC-MS (Method 1) m/z 408.4 (M+H)$^+$, 406.3 (M−H)$^−$ at 1.49 min. $^1$H NMR (500 MHz, DMSO-d$_6$) δ 13.30 (br s, 1H), 13.00 (br s, 1H), 8.74 (app. ddd, J=4.9, 1.8, 0.9 Hz, 1H), 8.21 (d, J=1.8 Hz, 1H), 8.04 (d, J=8.2 Hz, 1H), 8.02-7.96 (m, 2H), 7.92 (d, J=8.1 Hz, 1H), 7.78 (d, J=1.6 Hz, 1H), 7.69 (dd, J=8.1, 1.7 Hz, 1H), 7.52 (app. ddd, J=7.6, 4.9, 1.1 Hz, 1H), 7.42 (d, J=8.0 Hz, 1H), 2.73 (q, J=7.4 Hz, 2H), 0.99 (t, J=7.4 Hz, 3H).

Example 39: 3-(N-(3'-cyano-4-(methylsulfonyl)-[1,1'-biphenyl]-2-yl)sulfamoyl)-4-ethylbenzoic acid

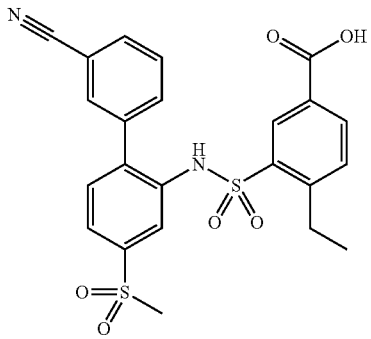 [SMILES: CCc1ccc(C(=O)O)cc1S(=O)(=O)Nc1cc(S(C)(=O)=O)ccc1-c1cccc(C#N)c1]

Step 1: methyl 3-(N-(3'-cyano-4-(methylsulfonyl)-[1,1'-biphenyl]-2-yl)sulfamoyl)-4-ethylbenzoate: To the reaction vessel containing the product from Example 32 Step 1 (70 mg, 0.147 mmol), (3-cyanophenyl)boronic acid (29 mg, 0.197 mmol), 1 M K$_3$PO$_4$(aq) (0.25 ml, 0.25 mmol) and dioxane (1.47 ml) was added XPhos Pd G3 (7 mg, 8.27 μmol). The reaction mixture was degassed with N$_2$ for 10 min and then heated to 80° C. for 3 h. The reaction mixture was concentrated in vacuo and the crude product was purified by chromatography on silica gel (10 g cartridge, 10-60% EtOAc/isohexane) to afford the title compound (94 mg, 0.147 mmol, 100% yield, 78% purity) as a white solid. UPLC-MS (Method 1) m/z 499.2 (M+H)$^+$, 497.2 (M−H)$^−$ at 1.41 min.

Step 2: 3-(N-(3'-cyano-4-(methylsulfonyl)-[1,1'-biphenyl]-2-yl)sulfamoyl)-4-ethylbenzoic acid: 1 M LiOH(aq) (0.586 ml, 0.586 mmol) was added to a solution of the product from Step 1 above (73 mg, 0.146 mmol) in THF (1.17 ml) at RT. The solution was stirred at RT for 16 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over MgSO$_4$, filtered and concentrated in vacuo. The crude product was purified by preparative HPLC (Waters X-Select Prep-C18, 5 μm, 19×50 mm column, 35-65% MeCN in Water (0.1% Formic acid)) to afford the title compound (39.4 mg, 0.081 mmol, 55% yield) as a white solid. UPLC-MS (Method 1) m/z 485.2 (M+H)$^+$, 483.2 (M−H)$^−$ at 1.26 min. $^1$H NMR (500 MHz, DMSO-d$_6$) δ 13.22 (br s, 1H), 10.33 (s, 1H), 8.04-7.95 (m, 2H), 7.93-7.80 (m, 1H), 7.75 (app. dt, J=7.1, 1.7 Hz, 1H), 7.69 (d, J=1.9 Hz, 1H), 7.61 (s, 1H), 7.55 (d, J=7.9 Hz, 1H), 7.51-7.44 (m, 2H), 7.42 (d, J=8.1 Hz, 1H), 3.21 (s, 3H), 2.76 (q, J=7.2 Hz, 2H), 1.11 (t, J=7.4 Hz, 3H).

Example 40: 3-(N-(4-cyano-[1,1'-biphenyl]-2-yl)sulfamoyl)-4-ethylbenzoic acid

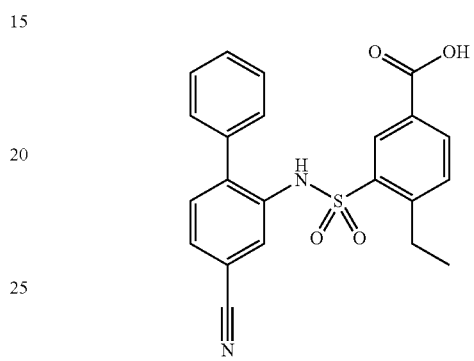

Step 1: methyl 3-(N-(4-cyano-[1,1'-biphenyl]-2-yl)sulfamoyl)-4-ethylbenzoate: To the reaction vessel containing the product from Example 38 Step 1 (70 mg, 0.165 mmol), phenylboronic acid (27 mg, 0.221 mmol), 1 M K$_3$PO$_4$(aq) (0.28 ml, 0.28 mmol) and dioxane (1.65 ml) was added XPhos Pd G3 (8 mg, 9.45 μmol). The reaction mixture was degassed with N$_2$ for 10 min and then heated to 80° C. for 2 h. The reaction mixture was concentrated in vacuo and the crude product was purified by chromatography on silica gel (24 g cartridge, 10-40% EtOAc/isohexane) to afford the title compound (67 mg, 0.159 mmol, 96% yield) as a yellow solid. UPLC-MS (Method 1) m/z 421.4 (M+H)$^+$, 419.3 (M−H)$^−$ at 1.65 min.

Step 2: 3-(N-(4-cyano-[1,1'-biphenyl]-2-yl)sulfamoyl)-4-ethylbenzoic acid: 1 M LiOH(aq) (0.637 ml, 0.637 mmol) was added to a solution of the product from Step 1 above (67 mg, 0.159 mmol) in THF (1.27 ml) at RT. The solution was stirred at RT for 18 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over MgSO$_4$, filtered and concentrated in vacuo to afford the title compound (46.4 mg, 0.112 mmol, 70% yield, 98% purity) as an off-white solid. UPLC-MS (Method 1) m/z 405.2 (M−H)$^−$ at 1.49 min. $^1$H NMR (500 MHz, DMSO-d$_6$) δ 13.20 (br s, 1H), 10.19 (br s, 1H), 8.02-7.98 (m, 2H), 7.78 (br d, J=8.0 Hz, 1H), 7.55 (d, J=1.7 Hz, 1H), 7.41 (d, J=8.0 Hz, 1H), 7.38 (d, J=8.4 Hz, 1H), 7.32-7.23 (m, 3H), 7.13-7.08 (m, 2H), 2.71 (q, J=7.4 Hz, 2H), 1.09 (t, J=7.4 Hz, 3H).

Example 41: 3-(N-(4-cyano-3'-fluoro-[1,1'-biphenyl]-2-yl)sulfamoyl)-4-ethylbenzoic acid

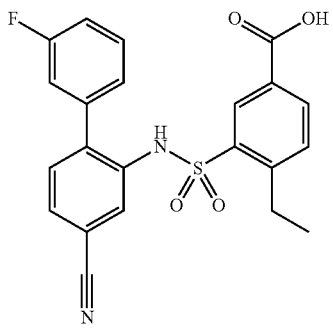

Step 1: methyl 3-(N-(4-cyano-3'-fluoro-[1,1'-biphenyl]-2-yl)sulfamoyl)-4-ethylbenzoate: To the reaction vessel containing the product from Example 38 Step 1 (70 mg, 0.165 mmol), (3-fluorophenyl)boronic acid (31 mg, 0.222 mmol), 1 M $K_3PO_4$(aq) (0.28 ml, 0.28 mmol) and dioxane (1.65 ml) was added XPhos Pd G3 (8 mg, 9.45 µmol). The reaction mixture was degassed with $N_2$ for 10 min and then heated to 80° C. for 2 h. The reaction mixture was concentrated in vacuo and the crude product was purified by chromatography on silica gel (24 g cartridge, 10-40% EtOAc/isohexane) to afford the title compound (71 mg, 0.162 mmol, 98% yield) as a yellow solid. UPLC-MS (Method 1) m/z 437.2 (M−H)$^−$ at 1.64 min.

Step 2: 3-(N-(4-cyano-3'-fluoro-[1,1'-biphenyl]-2-yl)sulfamoyl)-4-ethylbenzoic acid: 1 M LiOH(aq) (0.648 ml, 0.648 mmol) was added to a solution of the product from Step 1 above (71 mg, 0.162 mmol) in THF (1.30 ml) at RT. The solution was stirred at RT for 18 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over $MgSO_4$, filtered and concentrated in vacuo to afford the title compound (50.4 mg, 0.115 mmol, 71% yield, 97% purity) as an off-white solid. UPLC-MS (Method 1) m/z 423.2 (M−H)$^−$ at 1.49 min. $^1$H NMR (500 MHz, DMSO-$d_6$) δ 13.20 (br s, 1H), 10.28 (br s, 1H), 8.02-7.95 (m, 2H), 7.85-7.78 (m, 1H), 7.62 (d, J=1.7 Hz, 1H), 7.45 (d, J=8.0 Hz, 1H), 7.38 (d, J=8.0 Hz, 1H), 7.28 (app. td, J=8.2, 6.3 Hz, 1H), 7.10 (app. ddd, J=10.2, 8.2, 2.6 Hz, 1H), 6.94-6.87 (m, 2H), 2.73 (q, J=7.4 Hz, 2H), 1.10 (t, J=7.4 Hz, 3H).

Example 42: 3-(N-(3',4-dicyano-[1,1'-biphenyl]-2-yl)sulfamoyl)-4-ethylbenzoic acid

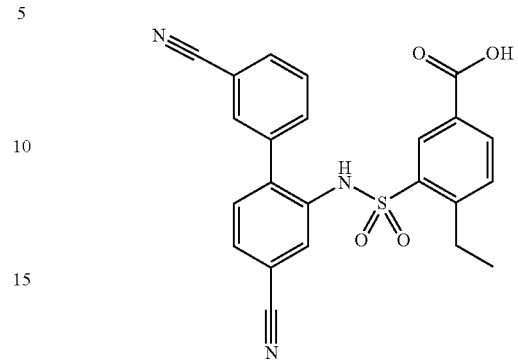

Step 1: methyl 3-(N-(3',4-dicyano-[1,1'-biphenyl]-2-yl)sulfamoyl)-4-ethylbenzoate: To the reaction vessel containing the product from Example 38 step 1 (70 mg, 0.165 mmol), (3-cyanophenyl)boronic acid (33 mg, 0.225 mmol), 1 M $K_3PO_4$(aq) (0.28 ml, 0.28 mmol) and dioxane (1.65 ml) was added XPhos Pd G3 (7 mg, 8.27 µmol). The reaction mixture was degassed with $N_2$ for 10 min and then heated to 80° C. for 2 h. The reaction mixture was concentrated in vacuo and the crude product was purified by chromatography on silica gel (24 g cartridge, 10-45% EtOAc/isohexane) to afford the title compound (63.1 mg, 0.140 mmol, 85% yield, 99% purity) as an off-white solid. UPLC-MS (Method 1) m/z 444.3 (M−H)$^−$ at 1.53 min.

Step 2: 3-(N-(3',4-dicyano-[1,1'-biphenyl]-2-yl)sulfamoyl)-4-ethylbenzoic acid: 1 M LiOH(aq) (0.566 ml, 0.566 mmol) was added to a solution of the product from Step 1 above (63 mg, 0.141 mmol) in THF (1.13 ml) at RT. The solution was stirred at RT for 22 h. The reaction mixture was concentrated in vacuo and the residue was dissolved in water (3 ml) and washed with EtOAc (3 ml). The aqueous phase was acidified using 1 M HCl(aq) until pH 4-5 and the product was extracted with EtOAc (3×3 ml). The organic extracts were combined and THF (3 ml) was added to obtain a clear solution. This was dried over $MgSO_4$, filtered and concentrated in vacuo to afford the title compound (53.1 mg, 0.119 mmol, 84% yield, 97% purity) as an off-white solid. UPLC-MS (Method 1) m/z 430.2 (M−H)$^−$ at 1.37 min. $^1$H NMR (500 MHz, DMSO-$d_6$) δ 13.22 (br s, 1H), 10.34 (br s, 1H), 7.99 (dd, J=8.0, 1.9 Hz, 1H), 7.94-7.90 (m, 1H), 7.88-7.81 (m, 1H), 7.72 (app. dt, J=7.7, 1.5 Hz, 1H), 7.67 (d, J=1.7 Hz, 1H), 7.52 (d, J=2.1 Hz, 1H), 7.48 (d, J=8.0 Hz, 1H), 7.44 (t, J=7.7 Hz, 1H), 7.41-7.35 (m, 2H), 2.69 (q, J=7.4 Hz, 2H), 1.10 (t, J=7.4 Hz, 3H).

Example 43: 3-(N-(5-cyano-2-(thiophen-2-yl)phenyl)sulfamoyl)-4-ethylbenzoic acid

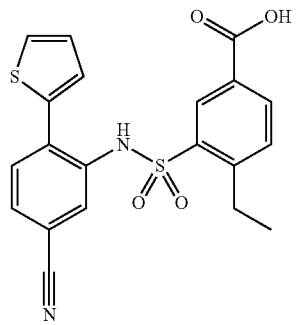

Step 1: methyl 3-(N-(5-cyano-2-(thiophen-2-yl)phenyl)sulfamoyl)-4-ethylbenzoate: To the reaction vessel containing the product from Example 38 Step 1 (70 mg, 0.165 mmol), thiophen-2-ylboronic acid (29 mg, 0.227 mmol), 1 M $K_3PO_4$(aq) (0.28 ml, 0.28 mmol) and dioxane (1.65 ml) was added XPhos Pd G3 (8 mg, 9.45 µmol). The reaction mixture was degassed with $N_2$ for 10 min and then heated to 80° C. for 2 h. The reaction mixture was concentrated in vacuo and the crude product was purified by chromatography on silica gel (24 g cartridge, 10-40% EtOAc/isohexane) to afford the title compound (29.8 mg, 0.070 mmol, 42% yield) as an off-white solid. UPLC-MS (Method 1) m/z 425.2 (M−H)⁻ at 1.61 min.

Step 2: 3-(N-(5-cyano-2-(thiophen-2-yl)phenyl)sulfamoyl)-4-ethylbenzoic acid: 1 M LiOH(aq) (0.281 ml, 0.281 mmol) was added to a solution of the product from Step 1 above (30 mg, 0.070 mmol) in THF (0.56 ml) at RT. The solution was stirred at RT for 22 h. The reaction mixture was concentrated in vacuo and the residue was dissolved in water (3 ml) and washed with EtOAc (3 ml). The aqueous phase was acidified using 1 M HCl(aq) until pH 4-5 and the product was extracted with EtOAc (3×3 ml). The organic phases were combined, dried over $MgSO_4$, filtered and concentrated in vacuo to afford the title compound (21.6 mg, 0.052 mmol, 74% yield, 99% purity) as an off-white solid. UPLC-MS (Method 1) m/z 411.2 (M−H)⁻ at 1.46 min. ¹H NMR (500 MHz, DMSO-$d_6$) δ 13.25 (br s, 1H), 10.33 (br s, 1H), 8.14 (br s, 1H), 8.06 (dd, J=8.0, 1.9 Hz, 1H), 7.83-7.72 (m, 2H), 7.66 (dd, J=5.1, 1.2 Hz, 1H), 7.55-7.49 (m, 2H), 7.22-7.18 (m, 1H), 7.09 (dd, J=5.1, 3.7 Hz, 1H), 2.88 (q, J=7.4 Hz, 2H), 1.15 (t, J=7.4 Hz, 3H).

Example 44: 4-methoxy-3-(N-(5-(methylsulfonyl)-2-(pyridin-2-yl)phenyl) sulfamoyl)benzoic acid

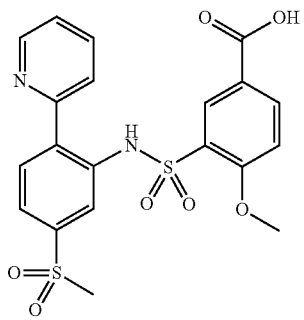 [SMILES: COc1ccc(C(=O)O)cc1S(=O)(=O)Nc1cc(S(C)(=O)=O)ccc1-c1ccccn1]

Step 1: methyl 3-(N-(2-bromo-5-(methylsulfonyl)phenyl)sulfamoyl)-4-methoxybenzoate: A solution of 2-bromo-5-(methylsulfonyl)aniline (600 mg, 2.40 mmol), methyl 3-(chlorosulfonyl)-4-methoxybenzoate (762 mg, 2.88 mmol) and pyridine (0.776 ml, 9.60 mmol) in DCM (6 ml) was stirred at RT for 68 h. The reaction mixture was concentrated in vacuo and the crude product was purified by chromatography on silica gel (80 g cartridge, 20-100% EtOAc/isohexane) to afford the title compound (579 mg, 1.17 mmol, 49% yield, 97% purity) as an cream solid. UPLC-MS (Method 1) m/z 478.2 (M+H)⁺, 476.0 (M−H)⁻ at 1.20 min. ¹H NMR (500 MHz, DMSO-$d_6$) δ 10.22 (s, 1H), 8.25 (d, J=2.2 Hz, 1H), 8.19 (dd, J=8.7, 2.3 Hz, 1H), 7.90 (d, J=8.4 Hz, 1H), 7.82 (d, J=2.2 Hz, 1H), 7.67 (dd, J=8.4, 2.2 Hz, 1H), 7.35 (d, J=8.8 Hz, 1H), 3.83 (s, 3H), 3.82 (s, 3H), 3.21 (s, 3H).

Step 2: methyl 4-methoxy-3-(N-(5-(methylsulfonyl)-2-(pyridin-2-yl)phenyl)sulfamoyl)benzoate: 2-(Tributylstannyl)pyridine (0.07 ml, 0.216 mmol) was added to a solution of the product from Step 1 above (80 mg, 0.167 mmol) and tetrakis-(triphenylphosphine)palladium(0) (19.3 mg, 0.017 mmol) in toluene (1.7 ml). The resultant mixture was degassed with $N_2$ for 10 min and then heated to 90° C. for 18 h. The reaction mixture was concentrated in vacuo and the crude product was purified by chromatography on silica gel (12 g cartridge, 10-100% EtOAc/isohexane) to afford the title compound (40.6 mg, 0.078 mmol, 47% yield, 92% purity) as a yellow solid. UPLC-MS (Method 1) m/z 477.3 (M+H)⁺, 475.1 (M−H)⁻ at 1.28 min.

Step 3: 4-methoxy-3-(N-(5-(methylsulfonyl)-2-(pyridin-2-yl)phenyl)sulfamoyl)benzoic acid: 1 M LiOH(aq) (0.336 ml, 0.336 mmol) was added to a solution of the product from Step 2 above (40 mg, 0.084 mmol) in THF (0.68 ml) at RT. The solution was stirred at RT for 20 h. The reaction mixture was concentrated in vacuo and the residue was dissolved in water (3 ml) and washed with EtOAc (3 ml). The aqueous phase was acidified using 1 M HCl(aq) until pH 4-5 and the product was extracted with EtOAc (3×3 ml). The organic phases were combined, dried over $MgSO_4$, filtered and concentrated in vacuo. The crude product was purified by preparative HPLC (Waters X-Bridge Prep-C18, 5 µm, 19×50 mm column, 10-40% MeCN in 10 mM ammonium bicarbonate(aq)) to afford the title compound (15.2 mg, 0.031 mmol, 37% yield, 95% purity) as a pale yellow solid. UPLC-MS (Method 1) m/z 463.2 (M+H)⁺, 461.2 (M−H)⁻ at 1.14 min. ¹H NMR (500 MHz, DMSO-$d_6$) δ 13.10 (br s, 2H), 8.86 (d, J=4.6 Hz, 1H), 8.33 (d, J=2.2 Hz, 1H), 8.14-8.02 (m, 5H), 7.68-7.62 (m, 1H), 7.62-7.57 (m, 1H), 7.10 (d, J=8.8 Hz, 1H), 3.40 (s, 3H), 3.13 (s, 3H).

Example 45: 3-(N-(5-cyano-2-(pyridin-2-yl)phenyl)sulfamoyl)-4-methoxybenzoic acid

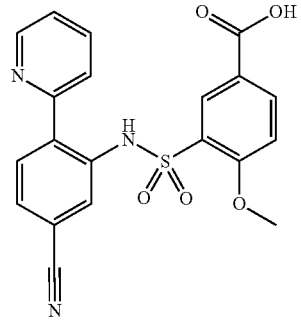

Step 1: methyl 3-(N-(2-bromo-5-cyanophenyl)sulfamoyl)-4-methoxybenzoate: A solution of 3-amino-4-bromobenzonitrile (344 mg, 1.75 mmol), methyl 3-(chlorosulfonyl)-4-methoxybenzoate (601 mg, 2.27 mmol) and pyridine (0.565 ml, 6.98 mmol) in DCM (6 ml) was stirred at RT for 68 h. The reaction mixture was concentrated in vacuo and the crude product was purified by chromatography on silica gel (40 g cartridge, 10-70% EtOAc/isohexane) to afford the title compound (301 mg, 0.665 mmol, 38% yield, 94% purity) as an off-white solid. UPLC-MS (Method 1) m/z 423.2 (M−H)⁻ at 1.36 min. ¹H NMR (500 MHz, DMSO-d₆) δ 10.23 (s, 1H), 8.23 (d, J=2.2 Hz, 1H), 8.18 (dd, J=8.7, 2.3 Hz, 1H), 7.83 (d, J=8.3 Hz, 1H), 7.73 (d, J=2.0 Hz, 1H), 7.61 (dd, J=8.3, 2.0 Hz, 1H), 7.33 (d, J=8.8 Hz, 1H), 3.83 (s, 3H), 3.79 (s, 3H).

Step 2: methyl 3-(N-(5-cyano-2-(pyridin-2-yl)phenyl)sulfamoyl)-4-methoxybenzoate: 2-(Tributylstannyl)pyridine (0.08 ml, 0.247 mmol) was added to a solution of the product from Step 1 above (80 mg, 0.188 mmol) and tetrakis-(triphenylphosphine)palladium(0) (21.7 mg, 0.019 mmol) in toluene (1.9 ml). The resultant mixture was degassed with N₂ for 10 min and then heated to 90° C. for 18 h. The reaction mixture was concentrated in vacuo and the crude product was purified by chromatography on silica gel (12 g cartridge, 10-100% EtOAc/isohexane) to afford the title compound (65.2 mg, 0.140 mmol, 75% yield, 91% purity) as a yellow solid. UPLC-MS (Method 1) m/z 424.4 (M+H)⁺, 422.2 (M−H)⁻ at 1.45 min.

Step 3: 3-(N-(5-cyano-2-(pyridin-2-yl)phenyl)sulfamoyl)-4-methoxybenzoic acid: 1 M LiOH(aq) (0.614 ml, 0.614 mmol) was added to a solution of the product from Step 2 above (65 mg, 0.154 mmol) in THF (1.23 ml) at RT. The solution was stirred at RT for 18 h. The reaction mixture was concentrated in vacuo and the residue was dissolved in water (3 ml) and washed with EtOAc (3 ml). The aqueous phase was acidified using 1 M HCl(aq) until pH 4-5 and the product was extracted with EtOAc (3×3 ml). The organic phases were combined and THF (3 ml) was added to obtain a clear solution. This was dried over MgSO₄, filtered and concentrated in vacuo. The crude product was purified by preparative HPLC (Waters X-Bridge Prep-C18, 5 μm, 19×50 mm column, 10-40% MeCN in 10 mM ammonium bicarbonate(aq)) to afford the title compound (30.5 mg, 0.071 mmol, 46% yield, 95% purity) as an off-white solid. UPLC-MS (Method 1) m/z 410.3 (M+H)⁺, 408.2 (M−H)⁻ at 1.29 min. ¹H NMR (500 MHz, DMSO-d₆) δ 13.07 (br s, 2H), 8.82 (d, J=4.9 Hz, 1H), 8.31 (d, J=2.2 Hz, 1H), 8.15-7.97 (m, 4H), 7.83 (d, J=1.7 Hz, 1H), 7.65-7.47 (m, 2H), 7.09 (d, J=8.8 Hz, 1H), 3.42 (s, 3H).

Example 46: 3-(N-(3'-chloro-4-(trifluoromethyl)-[1,1'-biphenyl]-2-yl)sulfamoyl)-4-methoxybenzoic acid

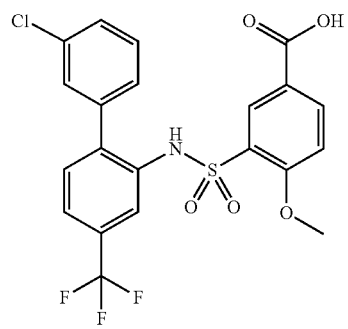 [SMILES: COc1ccc(C(=O)O)cc1S(=O)(=O)Nc1cc(C(F)(F)F)ccc1-c1cccc(Cl)c1]

Step 1: methyl 3-(N-(3'-chloro-4-(trifluoromethyl)-[1,1'-biphenyl]-2-yl)sulfamoyl)-4-methoxybenzoate: To the reaction vessel containing the product from Example 1, Step 1 (70 mg, 0.149 mmol), (3-chlorophenyl)boronic acid (42 mg, 0.269 mmol), 1 M K₃PO₄(aq) (0.25 ml, 0.25 mmol) and dioxane (1.5 ml) was added XPhos Pd G2 (6 mg, 7.63 μmol). The reaction mixture was degassed with N₂ for 10 min, heated to 80° C. for 21 h then cooled to RT and concentrated in vacuo. The crude product was partially purified by chromatography on silica gel (12 g cartridge, 0-45% EtOAc/isohexane), then purified by chromatography (12 g reverse phase C18 cartridge, 50-80% MeCN/0.1% formic acid(aq)) to afford the title compound (30.8 mg, 0.062 mmol, 40% yield, 97% purity) as a yellow oil. UPLC-MS (Method 1) m/z 500.1 (M−H)⁻ at 1.78 min.

Step 2: 3-(N-(3'-chloro-4-(trifluoromethyl)-[1,1'-biphenyl]-2-yl)sulfamoyl)-4-methoxybenzoic acid: 1 M LiOH (aq) (0.246 ml, 0.246 mmol) was added to a solution of the product from Step 1 above (30.8 mg, 0.062 mmol) in THF (0.49 ml) at RT. The solution was stirred at RT for 22 h. The reaction mixture was concentrated in vacuo. The residue was dissolved in water (3 ml) and washed with EtOAc (3 ml). The aqueous phase was acidified using 1 M HCl(aq) until pH 4-5 and the product was extracted into EtOAc (3×3 ml). The organic phases were combined, dried over MgSO₄, filtered and concentrated in vacuo to afford the title compound (23.1 mg, 0.047 mmol, 76% yield, 99% purity) as an off-white solid. UPLC-MS (Method 1) m/z 486.3 (M+H)⁺, 484.2 (M−H)⁻ at 1.62 min. ¹H NMR (500 MHz, DMSO-d₆) δ 13.00 (br s, 1H), 9.80 (br s, 1H), 8.09 (dd, J=8.7, 2.3 Hz, 1H), 8.00 (br s, 1H), 7.70-7.54 (m, 1H), 7.50-7.41 (m, 2H), 7.39-7.30 (m, 2H), 7.28-7.15 (m, 3H), 3.80 (s, 3H).

The following examples were prepared by methods analogous to Example 46, substituting appropriate starting materials and intermediates where necessary:

| Example | Structure | Name/Analytical Data |
|---|---|---|
| 47 | 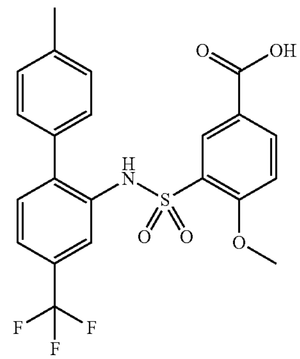 [SMILES: COc1ccc(C(=O)O)cc1S(=O)(=O)Nc1cc(C(F)(F)F)ccc1-c1ccc(C)cc1] | 4-methoxy-3-(N-(4'-methyl-4-(trifluoromethyl)-[1,1'-biphenyl]-2-yl)sulfamoyl)benzoic acid<br>UPLC-MS (Method 1) m/z 464.2 (M − H)⁻ at 1.65 min. ¹H NMR (500 MHz, DMSO-d₆) δ 13.01 (br s, 1H), 9.48 (br s, 1H), 8.09 (dd, J = 8.7, 2.2 Hz, 1H), 7.94 (d, J = 2.2 Hz, 1H), 7.65-7.57 (m, 1H), 7.45-7.39 (m, 2H), 7.18 (d, J = 8.8 Hz, 1H), 7.12 (d, J = 8.1 Hz, 2H), 7.08 (d, J = 8.0 Hz, 2H), 3.79 (s, 3H), 2.30 (s, 3H). |
| 48 | 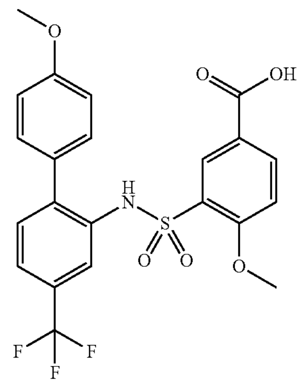 [SMILES: COc1ccc(-c2ccc(C(F)(F)F)cc2NS(=O)(=O)c2cc(C(=O)O)ccc2OC)cc1] | 4-methoxy-3-(N-(4'-methoxy-4-(trifluoromethyl)-[1,1'-biphenyl]-2-yl)sulfamoyl)benzoic acid<br>UPLC-MS (Method 1) m/z 482.2 (M + H)⁺, 480.3 (M − H)⁻ at 1.56 min. ¹H NMR (500 MHz, DMSO-d₆) δ 13.00 (br s, 1H), 9.47 (br s, 1H), 8.08 (dd, J = 8.7, 2.2 Hz, 1H), 7.95 (d, J = 2.2 Hz, 1H), 7.64-7.52 (m, 1H), 7.46-7.38 (m, 2H), 7.23-7.15 (m, 3H), 6.87-6.81 (m, 2H), 3.82 (s, 3H), 3.77 (s, 3H). |
| 49 | 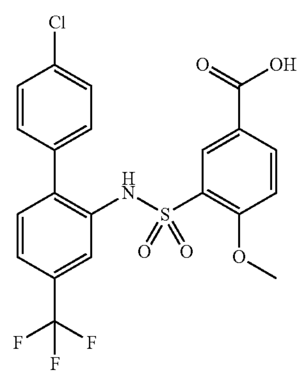 | 3-(N-(4'-chloro-4-(trifluoromethyl)-[1,1'-biphenyl]-2-yl)sulfamoyl)-4-methoxybenzoic acid<br>UPLC-MS (Method 1) m/z 484.2 (M − H)⁻ at 1.62 min. ¹H NMR (500 MHz, DMSO-d₆) δ 13.00 (br s, 1H), 9.74 (br s, 1H), 8.10 (dd, J = 8.7, 2.2 Hz, 1H), 7.94 (d, J = 2.2 Hz, 1H), 7.71-7.60 (m, 1H), 7.46 (d, J = 8.0 Hz, 1H), 7.41 (d, J = 1.9 Hz, 1H), 7.36-7.30 (m, 2H), 7.29-7.24 (m, 2H), 7.21 (d, J = 8.8 Hz, 1H), 3.85 (s, 3H). |

Example 50: 3-(N-(2-(imidazol-1-yl)-5-(trifluoromethyl)phenyl)sulfamoyl)-4-ethylbenzoic acid

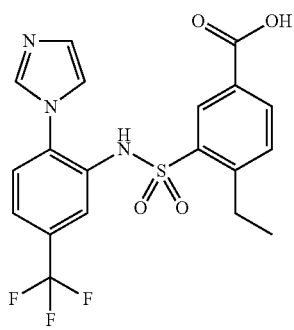 [SMILES: CCc1ccc(C(=O)O)cc1S(=O)(=O)Nc1cc(C(F)(F)F)ccc1-n1ccnc1]

To a degassed solution of Example 19 Step 3 (200 mg, 0.429 mmol) in DMSO (2.5 ml) was added imidazole (70 mg, 1.0 mmol), CuI (30 mg, 0.16 mmol), L-proline (222 mg, 1.93 mmol), K₂CO₃ (207 mg, 1.50 mmol) and NaI (10 mg, 0.067 mmol) and the mixture was stirred at 120° C. overnight. The crude product was partially purified by chromatography (40 g reverse phase C18 cartridge, 10-40% MeCN/0.1% formic acid(aq)), then purified by preparative HPLC (Waters X-Select Prep-C18, 5 μm, 19×50 mm column, 10-40% MeCN in Water (0.1% Formic acid)) to afford the title compound (13 mg, 0.030 mmol, 7% yield, 95% purity) as a white solid. UPLC-MS (Method 1) m/z 440.2 (M+H)⁺, 438.1 (M−H)⁻ at 0.90 min. ¹H NMR (500 MHz, DMSO-d₆) δ 13.08 (br s, 1H), 8.50 (br s, 1H), 8.30 (d, J=1.8 Hz, 1H), 7.99 (dd, J=7.9, 1.8 Hz, 1H), 7.72-7.24 (m, 6H), 2.91 (q, J=7.4 Hz, 2H), 1.09 (t, J=7.4 Hz, 3H). One exchangeable proton not observed.

Example 51: 3-(N-(2'-isopropyl-4-(trifluoromethyl)-[1,1'-biphenyl]-2-yl)sulfamoyl)-4-methoxybenzoic acid

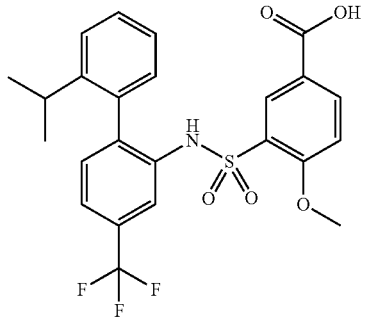 [SMILES: COc1ccc(C(=O)O)cc1S(=O)(=O)Nc1cc(C(F)(F)F)ccc1-c1ccccc1C(C)C]

A mixture of the product from Example 1 Step 2 (60 mg, 0.132 mmol), (2-isopropylphenyl)boronic acid (43.3 mg, 0.264 mmol), $Cs_2CO_3$ (95 mg, 0.291 mmol), tetrakis-(triphenylphosphine)palladium(0) (15.3 mg, 0.013 mmol), CuCl (26.2 mg, 0.264 mmol) in dioxane/water (4:1, 1.75 ml) was degassed with $N_2$ for 10 min. The resultant mixture was stirred and heated in the microwave at 100° C. for 90 min. The reaction mixture was sequentially filtered through cotton wool and a PTFE filter, then concentrated in vacuo. The crude product was purified by chromatography (12 g reverse phase C18 cartridge, 25-100% MeCN/0.1% formic acid(aq)) to afford the product as a cream solid. The product was suspended in water (3 ml) and treated with 2 M NaOH(aq) until pH>12. The aqueous phase was washed with TBME (2×3 ml) and then acidified using 1 M HCl(aq) until pH 4-5. The aqueous phase was extracted with TBME (2×5 ml), dried over $MgSO_4$, filtered, and concentrated in vacuo to afford the title compound (27.1 mg, 0.054 mmol, 41% yield, 99% purity) as a cream solid. UPLC-MS (Method 1) m/z 492.2 (M–H)⁻ at 1.79 min. $^1$H NMR (500 MHz, DMSO-$d_6$) δ 13.09 (br s, 1H), 8.94 (br s, 1H), 8.17-8.11 (m, 2H), 7.60-7.48 (m, 2H), 7.42-7.32 (m, 3H), 7.28 (d, J=8.7 Hz, 1H), 7.15 (app. td, J=7.3, 1.5 Hz, 1H), 6.90 (app. dd, J=7.6, 1.3 Hz, 1H), 3.80 (s, 3H), 2.58-2.53 (m, 1H), 1.12 (d, J=6.5 Hz, 3H), 1.00 (d, J=6.8 Hz, 3H).

Example 52: 3-(N-(4-(tetrazol-1-yl)-[1,1'-biphenyl]-2-yl)sulfamoyl)-4-ethylbenzoic acid

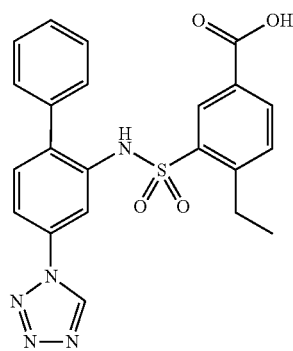 [SMILES: CCc1ccc(C(=O)O)cc1S(=O)(=O)Nc1cc(-n2cnnn2)ccc1-c1ccccc1]

Step 1: 1-(4-bromo-3-nitrophenyl)tetrazole: A solution of 4-bromo-3-nitroaniline (3.00 g, 13.8 mmol) and triethyl orthoformate (11.5 ml, 69.1 mmol) in acetic acid (54 ml) was heated to 80° C. for 1 h. Azidotrimethylsilane (2.40 ml, 18.1 mmol) was added dropwise and the resultant mixture was heated at 80° C. for 3.5 h. Additional azidotrimethylsilane (0.367 ml, 2.76 mmol) was added and the reaction heated at 80° C. for a further 1 h. The reaction was allowed to cool to RT, then concentrated in vacuo and azeotroped with toluene (100 ml). The residue was purified by chromatography on silica gel (40 g cartridge, 0-2.5% MeOH/DCM) to afford the title compound (3.30 g, 12.0 mmol, 87% yield, 98% purity) as a yellow solid. UPLC-MS (Method 1) m/z no ionisation at 1.12 min. $^1$H NMR (500 MHz, DMSO-$d_6$) δ 10.20 (s, 1H), 8.70 (d, J=2.5 Hz, 1H), 8.24 (d, J=8.7 Hz, 1H), 8.19 (dd, J=8.7, 2.5 Hz, 1H).

Step 2: 2-bromo-5-(tetrazol-1-yl)aniline: Zinc dust (2.72 g, 41.7 mmol) and ammonium chloride (2.23 g, 41.7 mmol) were added to the product from Step 1 above (1.50 g, 5.55 mmol) in THF/water (3:1, 60 ml) at RT and then stirred for 4 h. The reaction mixture was filtered through Celite®, washed with THF (50 ml) and then concentrated in vacuo. The solid was dissolved in DCM/MeOH (3:4, 70 ml) and then the organic phase was dried by passage through a phase separator and concentrated in vacuo to afford the title compound (1.63 g, 5.55 mmol, 100% yield, 82% purity) as a light brown solid. UPLC-MS (Method 1) m/z 240.1 (M+H)⁺, 238.1 (M–H)⁻ at 0.98 min. $^1$H NMR (500 MHz, DMSO-$d_6$) δ 10.02 (s, 1H), 7.60 (d, J=8.5 Hz, 1H), 7.30 (d, J=2.6 Hz, 1H), 6.97 (dd, J=8.5, 2.6 Hz, 1H), 5.86 (s, 2H).

Step 3: methyl 3-(N-(2-bromo-5-(tetrazol-1-yl)phenyl)sulfamoyl)-4-ethylbenzoate: A solution of the product from Step 2 above (500 mg, 1.71 mmol) and the product from Example 19, Step 2 (494 mg, 1.88 mmol) in pyridine (3.0 ml) was stirred at RT for 17 h. The solution was concentrated in vacuo, azeotroped with toluene (2×50 ml), and then the resultant residue was loaded onto Celite® and partially purified by chromatography on silica gel (24 g cartridge, 50% EtOAc/isohexane, then 0-1.5% MeOH/DCM), then purified by chromatography (24 g reverse phase C18 cartridge, 15-65% MeCN/0.1% formic acid(aq)) to afford the title compound (348 mg, 0.724 mmol, 42% yield, 97% purity) as a pale orange solid. $^1$H NMR (500 MHz, DMSO-$d_6$) δ 10.65 (br s, 1H), 10.11 (s, 1H), 8.28 (d, J=1.9 Hz, 1H), 8.12 (dd, J=8.0, 1.9 Hz, 1H), 7.88 (d, J=8.7 Hz, 1H), 7.85 (d, J=2.6 Hz, 1H), 7.77-7.69 (m, 1H), 7.65 (d, J=8.1 Hz, 1H), 3.82 (s, 3H), 3.08 (q, J=7.4 Hz, 2H), 1.23 (t, J=7.4 Hz, 3H).

Step 4: methyl 3-(N-(4-(tetrazol-1-yl)-[1,1'-biphenyl]-2-yl)sulfamoyl)-4-ethylbenzoate: To the reaction vessel containing the product from step 3 above (90 mg, 0.193 mmol), phenylboronic acid (31 mg, 0.254 mmol), 1 M $K_3PO_4$ (aq) (0.32 ml, 0.32 mmol) and dioxane (1.9 ml) was added XPhos Pd G3 (9 mg, 10.63 μmol). The reaction mixture was degassed with $N_2$ for 15 min and then heated to 80° C. for 16 h. The resultant reaction mixture was allowed to cool to RT, filtered through Celite®, washed with MeOH (10 ml) and then concentrated in vacuo. The crude product was purified by chromatography on silica gel (12 g cartridge, 0-50% EtOAc/isohexane) to afford the title compound (49.0 mg, 0.104 mmol, 54% yield, 98% purity) as a colourless oil. UPLC-MS (Method 1) m/z 464.4 (M+H)⁺, 462.2 (M–H)⁻ at 1.56 min.

Step 5: 3-(N-(4-(tetrazol-1-yl)-[1,1'-biphenyl]-2-yl)sulfamoyl)-4-ethylbenzoic acid: 1 M LiOH (aq) (0.423 ml, 0.423 mmol) was added to a solution of the product from Step 4 above (49.0 mg, 0.104 mmol) in THF (0.85 ml) at RT. The solution was stirred at RT for 18 h. The reaction mixture was concentrated in vacuo. The residue was dissolved in water (3 ml) and washed with EtOAc (3 ml). The aqueous phase was acidified using 1 M HCl(aq) until pH 4-5 and the product was extracted into EtOAc (3×3 ml). The organic phases were combined, dried over MgSO₄, filtered and concentrated in vacuo to afford the title compound (39.0 mg, 0.086 mmol, 81% yield, 99% purity) as an off-white solid. UPLC-MS (Method 1) m/z 450.3 (M+H)⁺, 448.2 (M−H)⁻ at 1.40 min. ¹H NMR (500 MHz, DMSO-d₆) δ 13.16 (br s, 1H), 10.20 (br s, 1H), 10.11 (s, 1H), 8.08 (br s, 1H), 7.99 (dd, J=8.0, 1.9 Hz, 1H), 7.90-7.79 (m, 1H), 7.75 (d, J=2.3 Hz, 1H), 7.47 (d, J=8.3 Hz, 1H), 7.37 (d, J=8.0 Hz, 1H), 7.31-7.23 (m, 3H), 7.20-7.11 (m, 2H), 2.76 (q, J=7.5 Hz, 2H), 1.10 (t, J=7.5 Hz, 3H).

Example 53: 4-ethyl-3-(N-(3'-fluoro-4-(tetrazol-1-yl)-[1,1'-biphenyl]-2-yl)sulfamoyl) benzoic acid

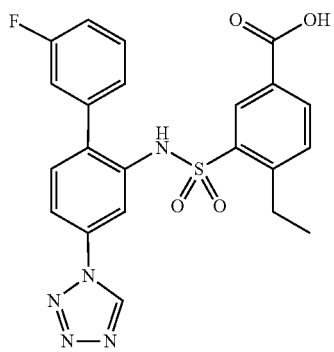 [SMILES: CCc1ccc(C(=O)O)cc1S(=O)(=O)Nc1cc(-n2cnnn2)ccc1-c1cccc(F)c1]

Step 1: methyl 4-ethyl-3-(N-(3'-fluoro-4-(tetrazol-1-yl)-[1,1'-biphenyl]-2-yl)sulfamoyl)benzoate: To the reaction vessel containing the product from Example 52 Step 3 (90 mg, 0.193 mmol), (3-fluorophenyl)boronic acid (36 mg, 0.257 mmol), 1 M K₃PO₄ (aq) (0.32 ml, 0.32 mmol) and dioxane (1.9 ml) was added XPhos Pd G3 (9 mg, 10.63 µmol). The reaction mixture was degassed with N₂ for 15 min and then heated to 80° C. for 16 h. The resultant reaction mixture was allowed to cool to RT, filtered through Celite®, washed with MeOH (10 ml) and then concentrated in vacuo. The crude product was purified by chromatography on silica gel (12 g cartridge, 0-50% EtOAc/isohexane) to afford the title compound (60.9 mg, 0.125 mmol, 65% yield, 99% purity) as a white solid. UPLC-MS (Method 1) m/z 482.1 (M+H)⁺, 480.2 (M−H)⁻ at 1.55 min.

Step 2: 4-ethyl-3-(N-(3'-fluoro-4-(tetrazol-1-yl)-[1,1'-biphenyl]-2-yl)sulfamoyl)benzoic acid: 1 M LiOH (aq) (0.506 ml, 0.506 mmol) was added to a solution of the product from step 1 above (60.9 mg, 0.125 mmol) in THF (1.01 ml) at RT. The solution was stirred at RT for 17 h. The reaction mixture was concentrated in vacuo. The residue was dissolved in water (3 ml) and washed with EtOAc (3 ml). The aqueous phase was acidified using 1 M HCl(aq) until pH 4-5 and the product was extracted into EtOAc (3×3 ml). The organic phases were combined, dried over MgSO₄, filtered and concentrated in vacuo to afford the title compound (49.3 mg, 0.104 mmol, 83% yield, 99% purity) as an off-white solid. UPLC-MS (Method 1) m/z 468.3 (M+H)⁺, 466.2 (M−H)⁻ at 1.40 min. ¹H NMR (500 MHz, DMSO-d₆) δ 13.17 (br s, 1H), 10.31 (br s, 1H), 10.14 (s, 1H), 8.06 (br s, 1H), 7.99 (dd, J=8.0, 1.9 Hz, 1H), 7.94-7.84 (m, 1H), 7.82 (d, J=2.3 Hz, 1H), 7.52 (d, J=8.4 Hz, 1H), 7.38 (d, J=8.0 Hz, 1H), 7.30 (app. td, J=8.0, 6.1 Hz, 1H), 7.14-7.07 (m, 1H), 7.01-6.91 (m, 2H), 2.79 (q, J=7.4 Hz, 2H), 1.12 (t, J=7.4 Hz, 3H).

Example 54: 4-ethyl-3-(N-(5-(methylsulfonyl)-2-(pyridin-3-yl)phenyl)sulfamoyl) benzoic acid

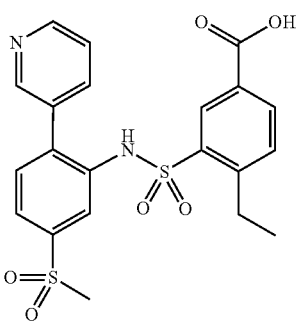

Step 1: methyl 4-ethyl-3-(N-(5-(methylsulfonyl)-2-(pyridin-3-yl)phenyl)sulfamoyl)benzoate: A mixture of the product from Example 32 Step 1 (100 mg, 0.210 mmol), pyridin-3-ylboronic acid (53 mg, 0.431 mmol), Cs₂CO₃ (156 mg, 0.479 mmol), CuCl (42.0 mg, 0.424 mmol) in dioxane/water (4:1, 2.50 ml) was degassed with N₂ for 10 min. tetrakis-(triphenylphosphine)palladium(0) (26.0 mg, 0.022 mmol) was added and the resultant mixture degassed with N₂ for 5 min. The resultant mixture was stirred and heated in the microwave at 100° C. for 90 min. The reaction mixture was filtered through Celite® and washed with MeOH (15 ml). The organic phase was concentrated in vacuo to afford the title compound (135 mg, 0.210 mmol, 100% yield, 74% purity) as a yellow gum. UPLC-MS (Method 1) m/z 475.3 (M+H)⁺, 473.2 (M−H)⁻ at 1.05 min.

Step 2: 4-ethyl-3-(N-(5-(methylsulfonyl)-2-(pyridin-3-yl)phenyl)sulfamoyl)benzoic acid: 1 M LiOH(aq) (0.840 ml, 0.840 mmol) was added to a solution of the product from Step 1 above (135 mg, 0.210 mmol) in THF (1.68 ml) at RT. The solution was stirred at RT for 18 h. The reaction mixture was concentrated in vacuo and the residue was dissolved in water (5 ml) and washed with EtOAc (5 ml). The aqueous phase was acidified using 1 M HCl(aq) until pH 4-5 and the product was extracted with EtOAc (3×5 ml). The organic phases were combined, dried over MgSO₄, filtered and concentrated in vacuo. The crude product was purified by preparative HPLC (Waters X-Bridge Prep-C18, 5 µm, 19×50 mm column, 40-50% MeCN in 10 mM ammonium bicarbonate(aq)) to afford the title compound (24.8 mg, 0.051 mmol, 24% yield, 95% purity) as a white solid. UPLC-MS (Method 1) m/z 461.2 (M+H)⁺, 459.2 (M−H)⁻ at 0.87 min. ¹H NMR (500 MHz, DMSO-d₆) δ 13.22 (br s, 1H), 10.35 (br s, 1H), 8.52 (dd, J=4.8, 1.6 Hz, 1H), 8.42 (d, J=2.3 Hz, 1H), 8.09 (s, 1H), 8.02 (dd, J=8.1, 1.9 Hz, 1H), 7.91-7.77 (m, 1H), 7.66-7.51 (m, 3H), 7.45 (d, J=8.0 Hz, 1H), 7.35 (dd, J=7.9, 4.8 Hz, 1H), 3.17 (s, 3H), 2.78 (q, J=7.4 Hz, 2H), 1.11 (t, J=7.4 Hz, 3H).

Example 55: 4-cyclopropyl-3-(N-(4-(trifluoromethyl)-[1,1'-biphenyl]-2-yl)sulfamoyl) benzoic acid

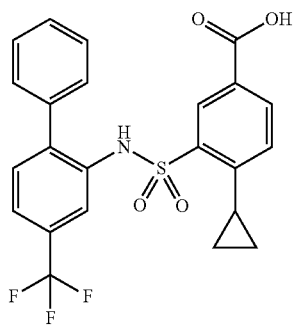 [SMILES: O=C(O)c1ccc(C2CC2)c(S(=O)(=O)Nc2cc(C(F)(F)F)ccc2-c2ccccc2)c1]

Step 1: methyl 2-nitro-4-(trifluoromethyl)-1,1'-biphenyl: A mixture of 1-bromo-2-nitro-4-(trifluoromethyl)benzene (300 μl, 1.96 mmol), phenylboronic acid (287 mg, 2.35 mmol) and $K_2CO_3$ (541 mg, 3.92 mmol) in dioxane/water (2:1, 7.5 ml) was degassed with $N_2$. $Pd(PPh_3)_4$ (113 mg, 0.0980 mmol) was added and the mixture heated to 90° C. and stirred overnight. The mixture was diluted with water (10 ml) and extracted with EtOAc (3×20 ml). The organic phases were combined and washed with brine (15 ml), dried by passage through a phase separator and concentrated in vacuo. The crude product was loaded onto silica and purified by chromatography on silica gel (12 g cartridge, 0-20% EtOAc/isohexane) to afford the title compound (468 mg, 1.63 mmol, 83% yield, 93% purity) as a pale yellow oil. UPLC-MS (Method 1) m/z no ionisation at 1.44 min.

Step 2: 4-(trifluoromethyl)-[1,1'-biphenyl]-2-amine: A mixture of the product from step 1 above (468 mg, 1.63 mmol), iron powder (2.00 g, 35.8 mmol) and ammonium chloride (105 mg, 1.955 mmol) in IPA (14 ml) and water (7 ml) was heated to 90° C. and stirred overnight and then cooled to RT. The reaction mixture was filtered through Celite®, rinsed with MeOH (100 ml) and concentrated in vacuo. The residue was loaded onto silica and purified by chromatography on silica gel (12 g cartridge, 0-50% EtOAc/isohexane) to afford the title compound (351 mg, 1.45 mmol, 89% yield, 98% purity) as a light orange oil. UPLC-MS (Method 1) m/z 238.1 (M+H)$^+$, at 1.66 min. $^1$H NMR (500 MHz, DMSO-$d_6$) δ 7.52-7.35 (m, 5H), 7.16 (d, J=7.8 Hz, 1H), 7.08 (d, J=1.9 Hz, 1H), 6.90 (dd, J=7.8, 1.9 Hz, 1H), 5.28-5.20 (m, 2H).

Step 3: methyl 4-bromo-3-(chlorosulfonyl)benzoate: A mixture of 4-bromo-3-(chlorosulfonyl)benzoic acid (2.00 g, 6.68 mmol) and thionyl chloride (20 ml) was heated under reflux for 4 h. Upon cooling to RT the mixture was concentrated in vacuo and the residue added slowly to MeOH (40 ml) at 0° C. The solvent was removed in vacuo and the resultant solid was triturated with a small amount of cold MeOH to give the title compound (1.71 g, 5.40 mmol, 81% yield, 99% purity) as a white solid. 1H NMR (500 MHz, DMSO-d6) δ 8.47 (d, J=2.0 Hz, 1H), 7.78-7.71 (m, 2H), 3.86 (s, 3H).

Step 4: methyl 4-bromo-3-(N-(4-(trifluoromethyl)-[1,1'-biphenyl]-2-yl)sulfamoyl)benzoate: To a solution of the product from Step 2 above (351 mg, 1.45 mmol) in DCM (10 ml) was added pyridine (350 μl, 4.33 mmol) and the product from Step 3 above (505 mg, 1.59 mmol). The mixture was stirred at RT overnight and the solvent was then removed in vacuo. The crude product was loaded onto silica and purified by chromatography on silica gel (14 g cartridge, 0-100% DCM/isohexane) to afford the title compound (401 mg, 0.764 mmol, 52% yield, 98% purity) as a white solid. UPLC-MS (Method 1) m/z 512.0 (M–H)$^-$, at 1.81 min.

Step 5: methyl 4-cyclopropyl-3-(N-(4-(trifluoromethyl)-[1,1'-biphenyl]-2-yl)sulfamoyl)benzoate: To a mixture of the product from Step 4 above (200 mg, 0.381 mmol) and tBuXPhos Pd G3 (30 mg, 0.038 mmol) in THF (4 ml) was added cyclopropylzinc(II) bromide (0.5 M in THF) (3.0 ml, 1.5 mmol). The mixture was stirred at RT overnight and then quenched with saturated ammonium chloride(aq) (10 ml) and extracted with EtOAc (3×20 mL). The organic phases were combined, washed with brine (15 ml), dried by passage through a phase separator and the solvent was removed in vacuo. The crude product was loaded onto silica and purified by chromatography on silica gel (24 g cartridge, 0-100% DCM/isohexane) to afford the title compound (51 mg, 0.095 mmol, 25% yield, 89% purity) as a clear colourless oil. UPLC-MS (Method 1) m/z 476.3 (M+H)$^+$, 474.1 (M–H)$^-$, at 1.86 min. $^1$H NMR (500 MHz, DMSO-$d_6$) δ 10.12 (s, 1H), 8.10 (d, J=1.9 Hz, 1H), 7.99 (dd, J=8.3, 1.9 Hz, 1H), 7.70-7.64 (m, 1H), 7.50 (d, J=8.0 Hz, 1H), 7.33-7.26 (m, 5H), 7.23 (d, J=1.9 Hz, 1H), 7.09 (d, J=8.3 Hz, 1H), 3.84 (s, 3H), 2.63-2.56 (m, 1H), 1.06-0.99 (m, 2H), 0.85-0.78 (m, 2H).

Step 6: 4-cyclopropyl-3-(N-(4-(trifluoromethyl)-[1,1'-biphenyl]-2-yl)sulfamoyl)benzoic acid: A mixture of the product from Step 5 above (51 mg, 0.095 mmol) and LiOH (9.1 mg, 0.38 mmol) in THF/MeOH/water (4:1:1, 2.1 ml) was stirred at 40° C. overnight. The mixture was diluted with water (10 ml), acidified to ~pH 4 using 1 M HCl(aq) and extracted with EtOAc (3×30 ml). The organic phases were combined, washed with brine (10 ml), dried by passage through a phase separator and the solvent was removed in vacuo. The residue was loaded onto silica and purified by chromatography on silica gel (4 g cartridge, 0-100% EtOAc/isohexane) to afford the title compound (21 mg, 0.044 mmol, 46% yield, 95% purity) as a white solid. UPLC-MS (Method 1) m/z 462.3 (M+H)$^+$, 460.2 (M–H)$^-$ at 1.70 min. $^1$H NMR (500 MHz, DMSO-$d_6$) δ 13.17 (s, 1H), 10.08 (s, 1H), 8.14 (s, 1H), 8.00-7.94 (m, 1H), 7.70-7.58 (m, 1H), 7.53-7.43 (m, 1H), 7.37-7.27 (m, 5H), 7.20 (s, 1H), 7.07 (d, J=8.3 Hz, 1H), 2.63-2.56 (m, 1H), 1.05-0.98 (m, 2H), 0.87-0.77 (m, 2H).

Example 56: 3-(N-(3'-cyano-4-tetrazol-1-yl-[1,1'-biphenyl]-2-yl)sulfamoyl)-4-ethylbenzoic acid

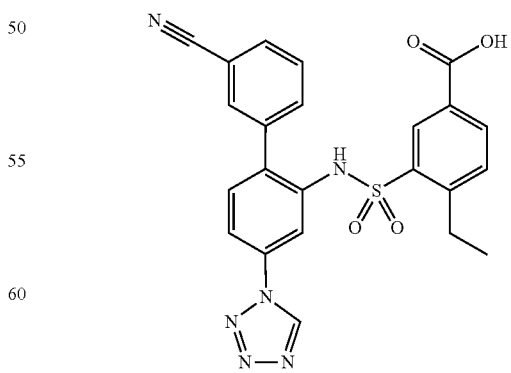

Step 1: methyl 3-(N-(3'-cyano-4-(tetrazol-1-yl)-[1,1'-biphenyl]-2-yl)sulfamoyl)-4-ethylbenzoate: To the reaction vessel containing the product from Example 52 Step 3 (90 mg, 0.174 mmol, 90% purity), (3-cyanophenyl)boronic acid (37 mg, 0.252 mmol), 1 M K$_3$PO$_4$ (aq) (320 µl, 0.32 mmol) and dioxane (1.9 ml) was added XPhos Pd G3 (10 mg, 11.8 µmol). The reaction mixture was degassed with N$_2$ for 15 min and then heated to 80° C. for 1 h. The reaction was allowed to cool to RT, filtered through Celite®, washed with MeOH (10 ml) and then concentrated in vacuo. The crude product was purified by chromatography on silica gel (12 g cartridge, 0-70% then 100% EtOAc/isohexane) to afford the title compound (61.5 mg, 0.126 mmol, 72% yield) as a cream solid. UPLC-MS (Method 1) m/z 489.3 (M+H)$^+$, 487.2 (M−H)$^−$ at 1.43 min.

Step 2: 3-(N-(3'-cyano-4-(tetrazol-1-yl)-[1,1'-biphenyl]-2-yl)sulfamoyl)-4-ethylbenzoic acid): 1 M LiOH (aq) (504 µl, 0.504 mmol) was added to a solution of the product from Step 1 above (61.5 mg, 0.126 mmol) in THF (1.01 ml) at RT. The reaction mixture was stirred at RT for 16 h, and then concentrated in vacuo to remove the THF. The residue was diluted with water (3 ml) and washed with EtOAc (3 ml). The aqueous phase was acidified using 1 M HCl(aq) until pH 4-5 and the product was extracted into EtOAc (3×3 ml). The combined organic extracts were dried over MgSO$_4$, filtered and concentrated in vacuo. The crude product was purified by preparative HPLC (Waters, Acidic (0.1% Formic acid), Acidic, Waters X-Select Prep-C18, 5 µm, 19×50 mm column, 20-50% MeCN in Water) to afford the title compound (24 mg, 0.050 mmol, 39% yield, 99% purity) as an off-white solid. UPLC-MS (Method 1) m/z 475.4 (M+H)$^+$, 473.2 (M−H)$^−$ at 1.29 min. $^1$H NMR (500 MHz, DMSO-d$_6$) δ 13.20 (br s, 1H), 10.37 (br s, 1H), 10.17 (s, 1H), 8.01-7.91 (m, 3H), 7.86 (d, J=2.3 Hz, 1H), 7.72 (app. dt, J=7.3, 1.6 Hz, 1H), 7.58-7.52 (m, 2H), 7.47-7.39 (m, 2H), 7.36 (d, J=8.0 Hz, 1H), 2.73 (q, J=7.4 Hz, 2H), 1.11 (t, J=7.4 Hz, 3H).

Example 57: 3-(N-(5-cyano-2-(pyridin-3-yl)phenyl) sulfamoyl)-4-ethylbenzoic acid

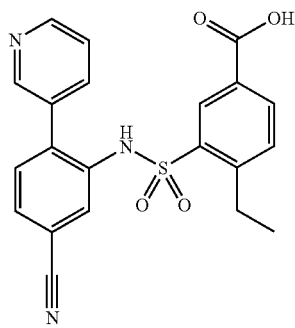

Step 1: methyl 3-(N-(5-cyano-2-(pyridin-3-yl)phenyl)sulfamoyl)-4-ethylbenzoate: A mixture of the product from Example 38 Step 1 (220 mg, 0.416 mmol, 80% purity), pyridin-3-ylboronic acid (112 mg, 0.915 mmol), Cs$_2$CO$_3$ (298 mg, 0.915 mmol), CuCl (82 mg, 0.832 mmol) in 4:1 dioxane/water (5.2 ml) was degassed with N$_2$ for 10 min. Tetrakis-(triphenylphosphine)palladium(0) (48 mg, 41.5 µmol) was added and the reaction mixture was degassed with N$_2$ for 5 min. The reaction was stirred and heated in the microwave at 100° C. for 90 min, and then filtered through Celite®, washed with MeOH (3×10 ml). The combined organic extracts were concentrated in vacuo. The crude product was purified by chromatography (24 g reverse phase C18 cartridge, 15-50% MeCN/0.1% Formic acid) to afford the title compound (125 mg, 0.291 mmol, 70% yield, 98% purity) as a pale yellow solid. UPLC-MS (Method 1) m/z 422.4 (M+H)$^+$, 420.3 (M−H)$^−$ at 1.18 min.

Step 2: 3-(N-(5-cyano-2-(pyridin-3-yl)phenyl)sulfamoyl)-4-ethylbenzoic acid: 1 M LiOH(aq) (1.2 ml, 1.20 mmol) was added to a solution of the product from Step 1 above (125 mg, 0.291 mmol, 98% purity) in THF (2.4 ml) at RT. The reaction mixture was stirred at RT for 40 h, and then concentrated in vacuo to remove the THF. The residue was diluted with water (4 ml) and washed with EtOAc (4 ml). The aqueous phase was acidified using 1 M HCl(aq) until pH 4-5 and the product was extracted into EtOAc (3×4 ml). The combined organic extracts were dried over MgSO$_4$, filtered and concentrated in vacuo to afford the title compound (63 mg, 0.152 mmol, 52% yield, 98% purity) as an off-white solid. UPLC-MS (Method 1) m/z 408.3 (M+H)$^+$, 406.3 (M−H)$^−$ at 1.00 min. $^1$H NMR (500 MHz, DMSO-d$_6$) δ 13.13 (br s, 1H), 10.36 (br s, 1H), 8.68-8.26 (m, 2H), 8.13 (s, 1H), 7.96 (d, J=7.8 Hz, 1H), 7.73-7.47 (m, 3H), 7.46-7.28 (m, 3H), 2.80 (q, J=7.4 Hz, 2H), 1.07 (t, J=7.4 Hz, 3H).

Example 58: 4-ethyl-3-(N-(2-(5-methylthiophen-2-yl)-5-(trifluoromethyl)phenyl) sulfamoyl)benzoic acid

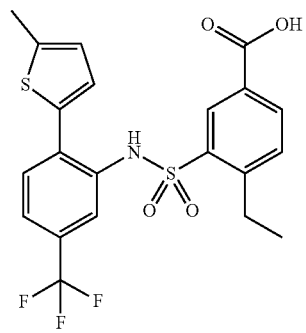 [SMILES: CCc1ccc(C(=O)O)cc1S(=O)(=O)Nc1cc(C(F)(F)F)ccc1-c1ccc(C)s1]

Step 1: methyl 4-ethyl-3-(N-(2-(5-methylthiophen-2-yl)-5-(trifluoromethyl)phenyl)-sulfamoyl)benzoate: To the reaction vessel containing the product from Example 19 Step 3 (200 mg, 0.408 mmol, 95% purity), (5-methylthiophen-2-yl)boronic acid (81 mg, 0.569 mmol), 1 M K$_3$PO$_4$(aq) (720 µl, 0.720 mmol) and dioxane (4.4 ml) was added XPhos Pd G3 (19.2 mg, 22.7 µmol). The reaction mixture was degassed with N$_2$ for 15 min and then heated to 80° C. for 3 h. Additional (5-methylthiophen-2-yl)boronic acid (81 mg, 0.569 mmol) and XPhos Pd G3 (19.2 mg, 23.0 µmol) were added, the reaction mixture was degassed with N$_2$ for 15 min and then heated to 80° C. for 3 h. The reaction mixture was allowed to cool to RT, filtered through Celite®, washed with MeOH (10 ml) and then the combined organic phase was concentrated in vacuo. The crude product was purified by chromatography on silica gel (12 g cartridge, 0-100% EtOAc/isohexane) to afford the title compound (133 mg, 0.275 mmol, 67% yield) as a light brown oil. UPLC-MS (Method 1) m/z 482.2 (M−H)$^−$ at 1.91 min.

Step 2: 4-ethyl-3-(N-(2-(5-methylthiophen-2-yl)-5-(trifluoromethyl)phenyl)sulfamoyl)benzoic acid: 1 M LiOH (aq) (1.1 ml, 1.10 mmol) was added to a solution of the product from Step 1 above (133 mg, 0.275 mmol) in THF (2.2 ml) at RT. The reaction mixture was stirred at RT for 23 h, and then concentrated in vacuo to remove the THF. The reaction mixture was diluted with water (5 ml) and washed with EtOAc (5 ml). The aqueous phase was acidified using 1 M HCl(aq) until pH 4-5 and the product was extracted into EtOAc (3×5 ml). The organic phases were combined, dried by passage through a phase separator and concentrated in vacuo to afford the title compound (122 mg, 0.255 mmol, 93% yield, 98% purity) as a cream solid. UPLC-MS (Method 1) m/z 470.3 (M+H)+, 468.2 (M−H)− at 1.77 min. $^1$H NMR (500 MHz, DMSO-d$_6$) δ 13.22 (br s, 1H), 10.20 (s, 1H), 8.14 (s, 1H), 8.08 (dd, J=7.9, 1.9 Hz, 1H), 7.73 (d, J=8.2 Hz, 1H), 7.68-7.58 (m, 1H), 7.54 (d, J=8.0 Hz, 1H), 7.31 (d, J=3.6 Hz, 1H), 6.97 (s, 1H), 6.77 (d, J=3.6 Hz, 1H), 2.89 (q, J=7.4 Hz, 2H), 2.44 (s, 3H), 1.15 (t, J=7.4 Hz, 3H).

Example 59: 4-ethyl-3-(N-(2-(5-methoxythiophen-2-yl)-5-(trifluoromethyl)phenyl) sulfamoyl)benzoic acid

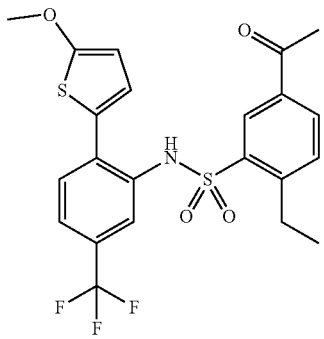 [SMILES: CCc1ccc(C(C)=O)cc1S(=O)(=O)Nc1cc(C(F)(F)F)ccc1-c1ccc(OC)s1]

Step 1: methyl 4-ethyl-3-(N-(2-(5-methoxythiophen-2-yl)-5-(trifluoromethyl)phenyl)-sulfamoyl)benzoate: To the reaction vessel containing the product from Example 19 Step 3 (100 mg, 0.208 mmol, 97% purity), 2-(5-methoxythiophen-2-yl)-4,4,5,5-tetramethyl-1,3,2-dioxaborolane (68.3 mg, 0.284 mmol), 1 M K$_3$PO$_4$(aq) (360 μl, 0.36 mmol) and dioxane (2.2 ml) was added XPhos Pd G3 (9.62 mg, 11.4 μmol). The reaction mixture was degassed with N$_2$ for 15 min and then heated to 80° C. for 1 h. Additional XPhos Pd G3 (9.62 mg, 11.4 μmol) was added, the reaction mixture was degassed with N$_2$ for 15 min and then heated to 80° C. for 1 h. The reaction mixture was allowed to cool to RT, filtered through Celite®, washed with MeOH (10 ml). The combined organic extracts were concentrated in vacuo. The crude product was purified by chromatography on silica gel (24 g cartridge, 0-30% EtOAc/isohexane) to afford the title compound (43.5 mg, 0.083 mmol, 40% yield, 95% purity) as a light brown oil. UPLC-MS (Method 1) m/z 498.2 (M−H)− at 1.86 min.

Step 2: 4-ethyl-3-(N-(2-(5-methoxythiophen-2-yl)-5-(trifluoromethyl)phenyl)sulfamoyl)-benzoic acid: 1 M LiOH (aq) (331 μl, 0.331 mmol) was added to a suspension of the product from Step 1 above (43.5 mg, 0.083 mmol, 95% purity) in THF (2 ml) at RT. MeOH was added dropwise until a solution was obtained. The reaction mixture was heated to 30° C. for 20 h, and then concentrated in vacuo to remove the THF and MeOH. The residue was diluted with water (5 ml) and then washed with EtOAc (2×5 ml). The aqueous phase was acidified using 1 M HCl(aq) until pH 6, the product was collected by filtration, washed with water (2×2 ml) and then dried in vacuo to afford the title compound (18 mg, 0.035 mmol, 43% yield, 95% purity) as a cream solid. UPLC-MS (Method 1) m/z 486.3 (M+H)+, 484.2 (M−H)− at 1.71 min. $^1$H NMR (500 MHz, DMSO-d$_6$) δ 13.15 (br s, 1H), 10.17 (br s, 1H), 8.20 (br s, 1H), 8.05 (br s, 1H), 7.75 (d, J=8.1 Hz, 1H), 7.54 (s, 2H), 7.28 (d, J=4.1 Hz, 1H), 6.83 (br s, 1H), 6.30 (d, J=4.1 Hz, 1H), 3.02-2.88 (m, 2H), 3.88 (s, 3H), 1.14 (t, J=7.4 Hz, 3H).

Example 60: 3-(N-(4-cyano-[1,1'-biphenyl]-2-yl)sulfamoyl)-4-methoxybenzoic acid

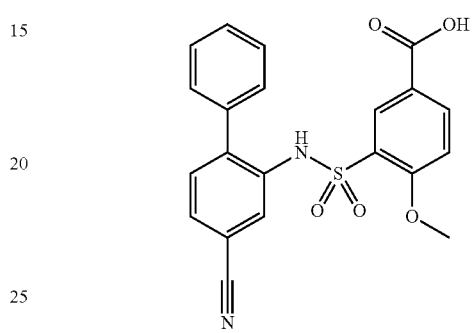

Step 1: methyl 3-(N-(4-cyano-[1,1'-biphenyl]-2-yl)sulfamoyl)-4-methoxybenzoate: A mixture of the product from Example 45 Step 1 (192 mg, 0.442 mmol, 94% purity), phenylboronic acid (73.9 mg, 0.606 mmol) and 1 M K$_3$PO$_4$aq) (750 μl, 0.750 mmol) in dioxane (4.5 ml) was degassed with N$_2$ for 15 min. XPhos Pd G3 (38 mg, 0.045 mmol) was added, the mixture degassed with N$_2$ for 5 min and then heated to 80° C. and stirred for 2 h. The mixture was filtered through Celite® rinsing with EtOAc. The filtrate was concentrated in vacuo onto silica and purified by chromatography on silica gel (12 g cartridge, 0-100% EtOAc/isohexane) to afford the title compound (125 mg, 0.287 mmol, 64% yield, 97% purity) as a light tan solid. UPLC-MS (Method 1) m/z 421.2 (M−H)− at 1.50 min. $^1$H NMR (500 MHz, DMSO-d$_6$) δ 9.69 (s, 1H), 8.10 (dd, J=8.7, 2.3 Hz, 1H), 7.95 (d, J=2.3 Hz, 1H), 7.76 (d, J=8.0 Hz, 1H), 7.59 (d, J=1.6 Hz, 1H), 7.42 (d, J=8.0 Hz, 1H), 7.35-7.24 (m, 3H), 7.23-7.15 (m, 3H), 3.83 (s, 3H), 3.78 (s, 3H).

Step 2: 3-(N-(4-cyano-[1,1'-biphenyl]-2-yl)sulfamoyl)-4-methoxybenzoic acid: A mixture of the product from Step 1 above (30 mg, 0.069 mmol, 97% purity) and LiOH (12 mg, 0.281 mmol) in THF/MeOH/water (4:1:1, 1.32 ml) was stirred at 40° C. overnight. The mixture was concentrated in vacuo and the residue acidified to pH 1 with 1 M HCl(aq). The precipitate was collected, dried in vacuo and purified by preparative HPLC (Waters, Acidic (0.1% Formic acid), Acidic, Waters X-Select Prep-C18, 5 μm, 19×50 mm column, 20-50% MeCN in Water) to afford the title compound (14.2 mg, 0.034 mmol, 50% yield, 99% purity) as a white solid. UPLC-MS (Method 1) m/z 407.1 (M−H)− at 1.34 min. $^1$H NMR (500 MHz, DMSO-d$_6$) δ 13.02 (s, 1H), 9.62 (s, 1H), 8.07 (dd, J=8.8, 2.3 Hz, 1H), 7.98 (d, J=2.3 Hz, 1H), 7.78-7.69 (m, 1H), 7.57 (d, J=1.7 Hz, 1H), 7.41 (d, J=7.9 Hz, 1H), 7.34-7.26 (m, 3H), 7.25-7.20 (m, 2H), 7.16 (d, J=8.8 Hz, 1H), 3.77 (s, 3H).

Example 61: 3-(N-(4-cyano-3'-fluoro-[1,1'-biphenyl]-2-yl)sulfamoyl)-4-methoxybenzoic acid

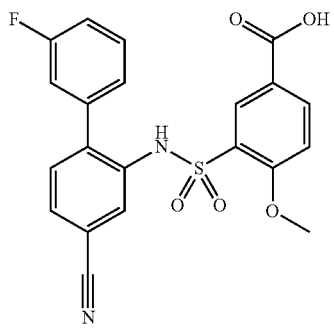 [SMILES: COc1ccc(C(=O)O)cc1S(=O)(=O)Nc1cc(C#N)ccc1-c1cccc(F)c1]

Step 1: methyl 3-(N-(4-cyano-3'-fluoro-[1,1'-biphenyl]-2-yl)sulfamoyl)-4-methoxybenzoate: A mixture of the product of Example 45 Step 1 (192 mg, 0.442 mmol), (3-fluorophenyl)boronic acid (85 mg, 0.606 mmol) and 1 M $K_3PO_4$(aq) (750 μl, 0.75 mmol) in dioxane (4.5 ml) was degassed with $N_2$ for 15 min. XPhos Pd G3 (38 mg, 0.045 mmol) was added, the mixture degassed with $N_2$ for 5 min and then heated to 80° C. and stirred for 2 h. The mixture was filtered through Celite®, rinsing with EtOAc. The filtrate was concentrated in vacuo onto silica and purified by chromatography on silica gel (12 g cartridge, 0-100% EtOAc/isohexane) to afford the title compound (169 mg, 0.38 mmol, 86% yield, 99% purity) as a beige solid. UPLC-MS (Method 1) m/z 439.1 (M–H)⁻ at 1.49 min. ¹H NMR (500 MHz, DMSO-$d_6$) δ 9.88 (s, 1H), 8.09 (dd, J=8.7, 2.3 Hz, 1H), 7.93 (d, J=2.3 Hz, 1H), 7.80 (d, J=7.9 Hz, 1H), 7.62 (d, J=1.7 Hz, 1H), 7.45 (d, J=7.9 Hz, 1H), 7.12-7.07 (m, 1H), 7.20 (d, J=8.7 Hz, 1H), 7.13-7.06 (m, 1H), 7.06-6.99 (m, 2H), 3.82 (s, 6H).

Step 2: 3-(N-(4-cyano-3'-fluoro-[1,1'-biphenyl]-2-yl)sulfamoyl)-4-methoxybenzoic acid: A mixture of the product from Step 1 above (30 mg, 0.067 mmol, 99% purity) and LiOH (12 mg, 0.281 mmol) in THF/MeOH/water (4:1:1, 1.32 ml) was stirred at 40° C. overnight. The mixture was concentrated in vacuo and the residue acidified to pH 1 with 1 M HCl(aq). The precipitate was collected, dried and purified by preparative HPLC (Waters, Acidic (0.1% Formic acid), Acidic, Waters X-Select Prep-C18, 5 μm, 19×50 mm column, 20-50% MeCN in Water) to afford the title compound (14.2 mg, 0.034 mmol, 50% yield, 99% purity) as a white solid. UPLC-MS (Method 1) m/z 425.1 (M–H)⁻ at 1.33 min. ¹H NMR (500 MHz, DMSO-$d_6$) δ 13.01 (s, 1H), 9.82 (s, 1H), 8.07 (dd, J=8.7, 2.3 Hz, 1H), 7.98-7.92 (m, 1H), 7.77 (br s, 1H), 7.61 (d, J=1.7 Hz, 1H), 7.45 (d, J=8.1 Hz, 1H), 7.35-7.27 (m, 1H), 7.17 (d, J=8.7 Hz, 1H), 7.15-7.07 (m, 1H), 7.07-7.00 (m, 2H), 3.81 (s, 3H).

Example 62: 3-(N-(5-cyano-2-(thiophen-2-yl)phenyl)sulfamoyl)-4-methoxybenzoic acid

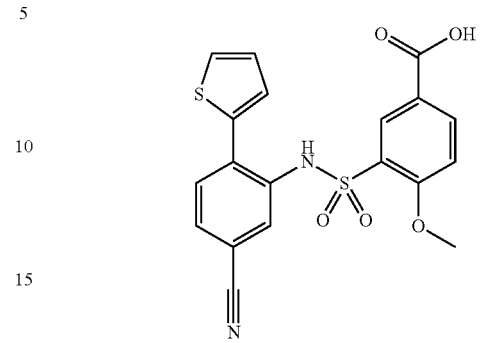

Step 1: methyl 3-(N-(5-cyano-2-(thiophen-2-yl)phenyl)sulfamoyl)-4-methoxybenzoate: A mixture of the product of Example 45 Step 1 (192 mg, 0.442 mmol), thiophen-2-ylboronic acid (87 mg, 0.606 mmol) and 1 M $K_3PO_4$(aq) (750 μl, 0.75 mmol) in dioxane (4.5 ml) was degassed with $N_2$ for 15 min. XPhos Pd G3 (38 mg, 0.045 mmol) was added, the mixture degassed with $N_2$ for 5 min and then heated to 80° C. and stirred for 2 h. The mixture was filtered through Celite®, rinsing with EtOAc. The filtrate was concentrated in vacuo onto silica and purified by chromatography on silica gel (12 g cartridge, 0-100% EtOAc/isohexane) to afford the title compound (157 mg, 0.38 mmol, 82% yield, 99% purity) as a grey solid. UPLC-MS (Method 1) m/z 427.1 (M–H)⁻ at 1.46 min. ¹H NMR (500 MHz, DMSO-$d_6$) δ 9.97 (s, 1H), 8.17 (dd, J=8.7, 2.3 Hz, 1H), 8.10 (d, J=2.3 Hz, 1H), 7.81-7.73 (m, 2H), 7.65 (d, J=5.1 Hz, 1H), 7.55 (dd, J=3.7, 1.2 Hz, 1H), 7.35 (d, J=1.6 Hz, 1H), 7.30 (d, J=8.8 Hz, 1H), 7.10 (dd, J=5.1, 3.7 Hz, 1H), 3.83 (s, 3H), 3.82 (s, 3H).

Step 2: 3-(N-(5-cyano-2-(thiophen-2-yl)phenyl)sulfamoyl)-4-methoxybenzoic acid: A mixture of the product from Step 1 above (30 mg, 69.0 μmol, 99% purity) and LiOH (12 mg, 0.281 mmol) in THF/MeOH/water (4:1:1, 1.32 ml) was stirred at 40° C. overnight. The mixture was concentrated in vacuo and the residue acidified to pH 1 with 1 M HCl(aq). The precipitate was collected, dried and purified by preparative HPLC (Waters, Acidic (0.1% Formic acid), Acidic, Waters X-Select Prep-C18, 5 μm, 19×50 mm column, 20-50% MeCN in Water) to afford the title compound (15.2 mg, 36.0 μmol, 52% yield, 99% purity) as a white solid. UPLC-MS (Method 1) m/z 413.1 (M–H)⁻ at 1.29 min. ¹H NMR (500 MHz, DMSO-$d_6$) δ 13.07 (s, 1H), 9.92 (s, 1H), 8.16-8.09 (m, 2H), 7.81-7.73 (m, 2H), 7.68-7.63 (m, 1H), 7.56 (d, J=3.6 Hz, 1H), 7.34 (s, 1H), 7.27 (d, J=8.7 Hz, 1H), 7.10 (dd, J=5.1, 3.7 Hz, 1H), 3.80 (s, 3H).

Example 63: 3-(N-(4-(tetrazol-5-yl)-[1,1'-biphenyl]-2-yl)sulfamoyl)-4-methoxybenzoic acid

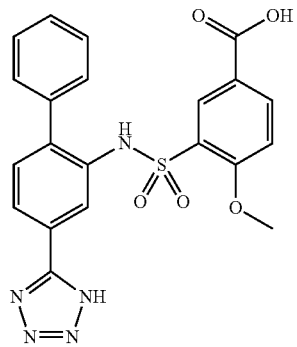 [SMILES: COc1ccc(C(=O)O)cc1S(=O)(=O)Nc1cc(-c2nnn[nH]2)ccc1-c1ccccc1]

Step 1: methyl 3-(N-(4-(tetrazol-5-yl)-[1,1'-biphenyl]-2-yl)sulfamoyl)-4-methoxybenzoate: To a mixture of the product from Example 60 Step 1 (92 mg, 0.211 mmol) and $Cu_2O$ (1 mg, 6.99 μmol) in MeOH (40 μl) and DMF (400 μl) was added trimethylsilyl azide (62 μl, 0.467 mmol). The mixture was stirred at RT for 10 min and then at 80° C. overnight. Upon cooling to RT the mixture was diluted with EtOAc (15 ml) and washed with 1 M HCl(aq) (5 ml). The organic phase was dried by passage through a phase separator and the solvent was removed in vacuo. The residue was loaded onto silica and purified by chromatography on silica gel (4 g cartridge, 0-10% MeOH/DCM) to afford the title compound (67 mg, 0.13 mmol, 61% yield, 90% purity) as a white solid. UPLC-MS (Method 1) m/z 465.8 (M+H)$^+$, 464.1 (M−H)$^−$ at 1.32 min. $^1$H NMR (500 MHz, DMSO-$d_6$) δ 17.00 (s, 1H), 9.58-9.54 (m, 1H), 8.08 (dd, J=8.8, 2.3 Hz, 1H), 7.98-7.95 (m, 2H), 7.94-7.91 (m, 1H), 7.44 (d, J=8.2 Hz, 1H), 7.32-7.27 (m, 3H), 7.27-7.22 (m, 2H), 7.17 (d, J=8.8 Hz, 1H), 3.80 (s, 3H), 3.80 (s, 3H).

Step 2: 3-(N-(4-(tetrazol-5-yl)-[1,1'-biphenyl]-2-yl)sulfamoyl)-4-methoxybenzoic acid: A mixture of the product from Step 1 above (67 mg, 0.13 mmol, 90% purity) and LiOH (25 mg, 0.585 mmol) in THF/MeOH/water (4:1:1, 2.7 ml) was stirred at 40° C. for 4 days. The mixture was diluted with water (5 ml), adjusted to pH 4 with 1 M HCl(aq) and extracted with EtOAc (3×10 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 20-50% MeCN in Water) to afford the title compound (39.4 mg, 86.0 μmol, 66% yield, 99% purity) as a white solid. UPLC-MS (Method 1) m/z 452.5 (M+H)$^+$, 450.2 (M−H)$^−$ at 1.18 min. $^1$H NMR (500 MHz, DMSO-$d_6$) δ 17.03 (s, 1H), 12.98 (s, 1H), 9.48 (s, 1H), 8.06 (dd, J=8.8, 2.2 Hz, 1H), 7.98 (d, J=2.2 Hz, 1H), 7.97-7.90 (m, 2H), 7.45 (d, J=7.9 Hz, 1H), 7.34-7.29 (m, 3H), 7.29-7.24 (m, 2H), 7.15 (d, J=8.8 Hz, 1H), 3.79 (s, 3H).

Example 64: 3-(N-(3'-fluoro-4-(tetrazol-5-yl)-[1,1'-biphenyl]-2-yl)sulfamoyl)-4-methoxybenzoic acid

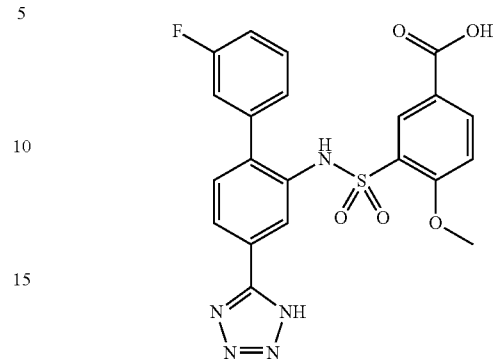

Step 1: methyl 3-(N-(3'-fluoro-4-(tetrazol-5-yl)-[1,1'-biphenyl]-2-yl)sulfamoyl)-4-methoxybenzoate: To a mixture of the product from Example 61 Step 1 (113 mg, 0.254 mmol, 99% purity) and $Cu_2O$ (1.1 mg, 7.69 μmol) in MeOH (45 μl) and DMF (450 μl) was added trimethylsilyl azide (75 μl, 0.565 mmol). The mixture was stirred at RT for 10 min and then at 80° C. overnight. Upon cooling to RT the mixture was diluted with EtOAc (15 ml) and washed with 1 M HCl(aq) (5 ml). The organic phase was dried by passage through a phase separator and the solvent removed in vacuo. The residue was loaded onto silica and purified by chromatography on silica gel (4 g cartridge, 0-10% MeOH/DCM) to afford the title compound (70 mg, 0.142 mmol, 55% yield, 98% purity) as a white solid. UPLC-MS (Method 1) m/z 484.3 (M+H)$^+$, 482.2 (M−H)$^−$ at 1.33 min. $^1$H NMR (500 MHz, DMSO-$d_6$) δ 17.04 (s, 1H), 9.78 (s, 1H), 8.08 (dd, J=8.8, 2.3 Hz, 1H), 8.00-7.91 (m, 3H), 7.49 (d, J=7.9 Hz, 1H), 7.34-7.26 (m, 1H), 7.19 (d, J=8.8 Hz, 1H), 7.12-7.04 (m, 3H), 3.85 (s, 3H), 3.80 (s, 3H).

Step 2: 3-(N-(3'-fluoro-4-(tetrazol-5-yl)-[1,1'-biphenyl]-2-yl)sulfamoyl)-4-methoxybenzoic acid: A mixture of the product from Step 1 above (70 mg, 0.142 mmol, 98% purity) and LiOH (25 mg, 0.585 mmol) in THF/MeOH/water (4:1:1, 2.7 ml) was stirred at 40° C. for 4 days. The mixture was diluted with water (5 ml), adjusted to pH 4 with 1 M HCl(aq) and extracted with EtOAc (3×10 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 20-50% MeCN in Water) to the title compound (49.7 mg, 0.105 mmol, 73% yield) as a white solid. UPLC-MS (Method 1) m/z 470.3 (M+H)$^+$, 468.1 (M−H)$^−$ at 1.18 min. $^1$H NMR (500 MHz, DMSO-$d_6$) δ 17.05 (s, 1H), 12.97 (s, 1H), 9.71 (s, 1H), 8.05 (dd, J=8.7, 2.3 Hz, 1H), 7.99-7.92 (m, 3H), 7.48 (d, J=7.9 Hz, 1H), 7.36-7.28 (m, 1H), 7.17 (d, J=8.7 Hz, 1H), 7.14-7.05 (m, 3H), 3.84 (s, 3H).

Example 65: 3-(N-(5-(tetrazol-5-yl)-2-(thiophen-2-yl)phenyl)sulfamoyl)-4-methoxybenzoic acid

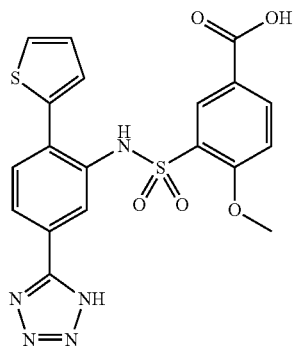 [SMILES: COc1ccc(C(=O)O)cc1S(=O)(=O)Nc1cc(-c2nnn[nH]2)ccc1-c1cccs1]

Step 1: methyl 3-(N-(5-(tetrazol-5-yl)-2-(thiophen-2-yl)phenyl)sulfamoyl)-4-methoxybenzoate: To a mixture of the product from Example 62 Step 1 (123 mg, 0.284 mmol, 99% purity) and $Cu_2O$ (1.3 mg, 9.09 µmol) in MeOH (50 µl) and DMF (500 µl) was added trimethylsilyl azide (85 µl, 0.64 mmol). The mixture was stirred at RT for 10 min and then at 80° C. overnight. Upon cooling to RT the mixture was diluted with EtOAc (15 ml) and washed with 1 M HCl(aq) (5 ml). The organic phase was dried by passage through a phase separator and the solvent removed in vacuo. The residue was loaded onto silica and purified by chromatography on silica gel (4 g cartridge, 0-10% MeOH/DCM) to afford the title compound (70 mg, 0.129 mmol, 45% yield, 87% purity) as a white solid. UPLC-MS (Method 1) m/z 472.2 $(M+H)^+$, 470.1 $(M-H)^-$ at 1.29 min. $^1H$ NMR (500 MHz, DMSO-$d_6$) δ 16.98 (s, 1H), 9.83 (s, 1H), 8.14 (dd, J=8.8, 2.2 Hz, 1H), 8.10 (d, J=2.2 Hz, 1H), 7.93 (dd, J=8.2, 1.9 Hz, 1H), 7.79 (d, J=8.1 Hz, 1H), 7.77 (d, J=1.9 Hz, 1H), 7.60 (dd, J=5.1, 1.2 Hz, 1H), 7.52 (dd, J=3.7, 1.2 Hz, 1H), 7.31 (d, J=8.8 Hz, 1H), 7.09 (dd, J=5.1, 3.7 Hz, 1H), 3.86 (s, 3H), 3.79 (s, 3H).

Step 2: 3-(N-(5-(tetrazol-5-yl)-2-(thiophen-2-yl)phenyl)sulfamoyl)-4-methoxybenzoic acid: A mixture of the product from Step 1 above (70 mg, 0.129 mmol, 87% purity) and LiOH (25 mg, 0.585 mmol) in THF/MeOH/water (4:1:1, 2.7 ml) was stirred at 40° C. for 4 days. The mixture was diluted with water (5 ml), adjusted to pH 4 with 1 M HCl(aq) and extracted with EtOAc (3×10 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 20-50% MeCN in Water) to afford the title compound (32.9 mg, 68.0 µmol, 52% yield, 95% purity) as a white solid. UPLC-MS (Method 1) m/z 458.2 $(M+H)^+$, 456.0 $(M-H)^-$ at 1.16 min. $^1H$ NMR (500 MHz, DMSO-$d_6$) δ 17.01 (s, 1H), 13.02 (s, 1H), 9.77 (s, 1H), 8.14-8.08 (m, 2H), 7.92 (dd, J=8.2, 1.9 Hz, 1H), 7.82-7.75 (m, 2H), 7.61 (dd, J=5.1, 1.2 Hz, 1H), 7.52 (dd, J=3.7, 1.2 Hz, 1H), 7.28 (d, J=8.7 Hz, 1H), 7.10 (dd, J=5.1, 3.7 Hz, 1H), 3.85 (s, 3H).

Example 66: 4-ethyl-3-(N-(2-(3-fluoropyridin-2-yl)-5-(trifluoromethyl)phenyl) sulfamoyl)benzoic acid

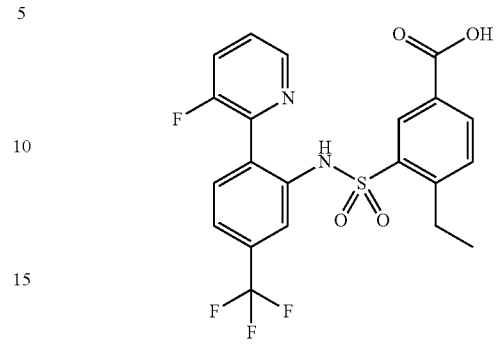

Step 1: Methyl 4-ethyl-3-(N-(2-(3-fluoropyridin-2-yl)-5-(trifluoromethyl)phenyl)sulfamoyl)-benzoate: 3-fluoro-2-(tributylstannyl)pyridine (112 mg, 0.29 mmol) in toluene (1 ml) was added to a solution of the product from Example 19 Step 3 (100 mg, 0.203 mmol, 95% purity) and $Pd(PPh_3)_4$ (25 mg, 21.6 µmol) in toluene (2.1 ml). The reaction mixture was degassed with $N_2$ for 10 min and then heated to 90° C. for 53 h. The reaction mixture was allowed to cool to RT, filtered through Celite®, washed with MeOH (10 ml), concentrated in vacuo onto Celite® and purified by chromatography on silica gel (24 g cartridge, 0-40% EtOAc/isohexane) to afford the title compound (24.1 mg, 0.033 mmol, 16% yield, 66% purity) as a yellow oil. UPLC-MS (Method 1) m/z 483.3 $(M+H)^+$, 481.2 $(M-H)^-$ at 1.83 min.

Step 2: 4-ethyl-3-(N-(2-(3-fluoropyridin-2-yl)-5-(trifluoromethyl)phenyl)sulfamoyl)benzoic acid: 1 M LiOH (aq) (131 µl, 0.131 mmol) was added to a solution of the product from Step 1 above (24 mg, 0.033 mmol, 66% purity) in THF (300 µl) at RT. The reaction mixture was stirred at RT for 24 h, and then concentrated in vacuo to remove the THF. The residue was diluted with water (3 ml) and then washed with EtOAc (3 ml). The aqueous phase was acidified using 1 M HCl(aq) until pH 4-5 and the product was extracted into EtOAc (3×3 ml). The combined organic extracts were dried over $MgSO_4$, filtered and concentrated in vacuo. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (5.9 mg, 0.013 mmol, 38% yield, 99% purity) as an off-white solid. UPLC-MS (Method 1) m/z 469.3 $(M+H)^+$, 467.2 $(M-H)^-$ at 1.66 min. $^1H$ NMR (500 MHz, DMSO-$d_6$) δ 13.19 (br s, 1H), 10.48 (br s, 1H), 8.44 (d, J=4.7 Hz, 1H), 8.11 (br s, 1H), 8.03-7.92 (m, 1H), 7.79-7.57 (m, 3H), 7.55 (s, 1H), 7.53-7.45 (m, 1H), 7.41 (d, J=7.9 Hz, 1H), 2.86-2.60 (m, 2H), 1.05 (t, J=7.4 Hz, 3H).

Example 67: 4-ethyl-3-(N-(2-(5-fluorothiophen-2-yl)-5-(trifluoromethyl)phenyl) sulfamoyl)benzoic acid

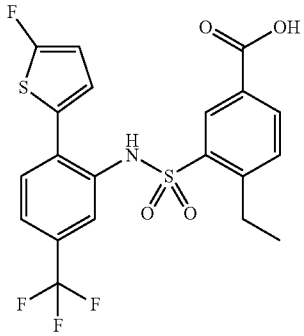 [SMILES: CCc1ccc(C(=O)O)cc1S(=O)(=O)Nc1cc(C(F)(F)F)ccc1-c1ccc(F)s1]

Step 1: methyl 4-ethyl-3-(N-(2-(5-fluorothiophen-2-yl)-5-(trifluoromethyl)phenyl)sulfamoyl)-benzoate: To the reaction vessel containing the product from Example 19 Step 3 (150 mg, 0.306 mmol, 95% purity), 2-(5-fluorothiophen-2-yl)-4,4,5,5-tetramethyl-1,3,2-dioxaborolane (88 mg, 0.386 mmol), 1 M K$_3$PO$_4$(aq) (540 µl, 0.540 mmol) and dioxane (3.2 ml) was added XPhos Pd G3 (15 mg, 17.7 µmol). The reaction mixture was degassed with N$_2$ for 10 min and then heated to 80° C. for 3.5 h. The reaction mixture was allowed to cool to RT, filtered through Celite®, washed with MeOH (15 ml), concentrated in vacuo onto Celite® and purified by chromatography on silica gel (12 g cartridge, 0-25% EtOAc/isohexane) to afford the title compound (99.1 mg, 0.199 mmol, 65% yield, 98% purity) as a colourless oil. UPLC-MS (Method 1) m/z 486.1 (M–H)⁻ at 1.87 min.

Step 2: 4-ethyl-3-(N-(2-(5-fluorothiophen-2-yl)-5-(trifluoromethyl)phenyl)sulfamoyl)benzoic acid: 1 M LiOH (aq) (820 µl, 0.820 mmol) was added to a solution of the product from Step 1 above (99.1 mg, 0.199 mmol, 98% purity) in THF (1.6 ml) at RT. The reaction mixture was stirred at RT for 20 h, and then concentrated in vacuo to remove the THF. The residue was diluted with water (4 ml) and then washed with EtOAc (4 ml). The aqueous phase was acidified using 1 M HCl(aq) until pH 4-5 and the product was extracted into EtOAc (3×4 ml). The organic phases were combined, dried over MgSO$_4$, filtered and concentrated in vacuo to afford the title compound (84.9 mg, 0.174 mmol, 87% yield, 97% purity) as an off-white solid. UPLC-MS (Method 1) m/z 472.1 (M–H)⁻ at 1.72 min. ¹H NMR (500 MHz, DMSO-d$_6$) δ 13.27 (br s, 1H), 10.29 (br s, 1H), 8.16 (br s, 1H), 8.14-8.09 (m, 1H), 7.87 (d, J=8.3 Hz, 1H), 7.73-7.62 (m, 1H), 7.60 (d, J=8.0 Hz, 1H), 7.30 (t, J=4.0 Hz, 1H), 6.83 (br s, 1H), 6.77 (dd, J=4.3, 2.2 Hz, 1H), 2.91 (q, J=7.4 Hz, 2H), 1.16 (t, J=7.4 Hz, 3H).

Example 68: 4-ethyl-3-(N-(2-(pyrimidin-2-yl)-5-(trifluoromethyl)phenyl)sulfamoyl)benzoic acid

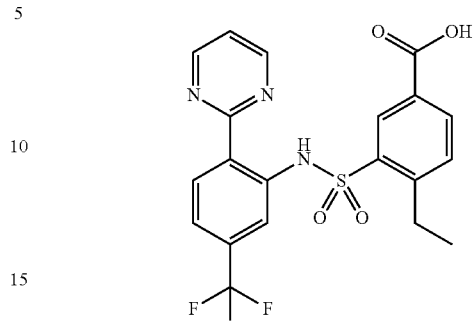

Step 1: methyl 4-ethyl-3-(N-(2-(pyrimidin-2-yl)-5-(trifluoromethyl)phenyl)sulfamoyl)-benzoate: A mixture of the product from Example 19 Step 3 (150 mg, 0.322 mmol, 98% purity) and 2-(tributylstannyl)pyrimidine (150 µl, 0.473 mmol) in dioxane (3.5 ml) was degassed with N$_2$ for 15 min. XPhos Pd G3 (27 mg, 0.032 mmol) was added. The reaction mixture was degassed with N$_2$ for 5 min and then heated to 80° C. and stirred overnight. The mixture was concentrated in vacuo onto silica and purified by chromatography on silica gel (12 g cartridge, 0-50% EtOAc/Isohexane) to afford the title compound (32 mg, 0.062 mmol, 19% yield, 90% purity) as a light yellow solid. UPLC-MS (Method 1) m/z 466.2 (M+H)⁺, 464.1 (M–H)⁻ at 1.84 min. ¹H NMR (500 MHz, DMSO-d$_6$) δ 13.16 (s, 1H), 9.09 (d, J=5.0 Hz, 2H), 8.65 (d, J=8.4 Hz, 1H), 8.40 (d, J=1.9 Hz, 1H), 8.05 (dd, J=7.8, 1.9 Hz, 1H), 7.82-7.78 (m, 1H), 7.69-7.64 (m, 1H), 7.56 (d, J=8.4 Hz, 1H), 7.53 (d, J=8.1 Hz, 1H), 3.85 (s, 3H), 2.92 (q, J=7.4 Hz, 2H), 1.01 (t, J=7.4 Hz, 3H).

Step 2: 4-ethyl-3-(N-(2-(pyrimidin-2-yl)-5-(trifluoromethyl)phenyl)sulfamoyl)benzoic acid: A mixture of the product from Step 1 above (32 mg, 0.062 mmol, 90% purity) and LiOH (11 mg, 0.257 mmol) in THF/MeOH/water (4:1:1, 1.2 ml) was stirred at 40° C. overnight. The mixture was diluted with water (3 ml) and EtOAc (5 ml) and acidified to pH 4 with 1 M HCl(aq). The phases were separated and the aqueous phase was extracted with EtOAC (3×5 ml). The combined organic extracts were washed with brine (5 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (16.5 mg, 0.036 mmol, 58% yield, 99% purity) as a light purple solid after trituration with TBME. UPLC-MS (Method 1) m/z 452.2 (M+H)⁺, 450.1 (M–H)⁻ at 1.67 min. ¹H NMR (500 MHz, DMSO-d$_6$) δ 13.26 (br s, 2H), 9.09 (d, J=5.0 Hz, 2H), 8.66-8.59 (m, 1H), 8.43 (d, J=1.8 Hz, 1H), 8.03 (dd, J=8.0, 1.8 Hz, 1H), 7.77 (d, J=1.8 Hz, 1H), 7.65 (t, J=5.0 Hz, 1H), 7.52 (d, J=8.4 Hz, 1H), 7.49 (d, J=8.0 Hz, 1H), 2.92 (q, J=7.5 Hz, 2H), 1.01 (t, J=7.4 Hz, 3H).

Example 69: 3-(N-(2-(pyrrol-2-yl)-5-(trifluoromethyl)phenyl)sulfamoyl)-4-ethylbenzoic acid

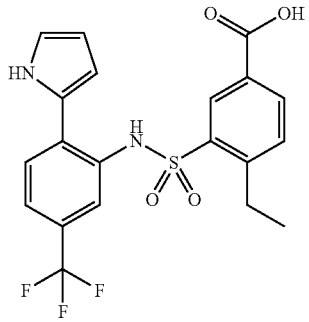 [SMILES: CCc1ccc(C(=O)O)cc1S(=O)(=O)Nc1cc(C(F)(F)F)ccc1-c1ccc[nH]1]

Step 1: methyl 4-ethyl-3-(N-(2-(pyrrol-2-yl)-5-(trifluoromethyl)phenyl)sulfamoyl)benzoate: A mixture of the product from Example 19 Step 3 (100 mg, 0.214 mmol), (1-(tert-butoxycarbonyl)pyrrol-2-yl)boronic acid (59 mg, 0.279 mmol), K$_3$PO$_4$ (137 mg, 0.643 mmol), dioxane (4 ml) and water (1 ml) was treated with XPhos Pd G3 (8.4 mg, 10.7 μmol). The reaction mixture was degassed with N$_2$ for 10 min and then heated at 80° C. for 17 h. The reaction was concentrated in vacuo. The residue was purified by chromatography on silica gel (24 g cartridge, 0-50% EtOAc/isohexane) to afford the title compound (90 mg, 0.155 mmol, 72% yield, 95% purity) as a light brown solid. UPLC-MS (Method 1) m/z 453.3 (M+H−Boc)$^+$, 551.2 (M−H)$^−$ at 1.99 min.

Step 2: 3-(N-(2-(pyrrol-2-yl)-5-(trifluoromethyl)phenyl)sulfamoyl)-4-ethylbenzoic acid: 4 M HCl in dioxane (204 μl, 0.814 mmol) was added to a solution of the product from Step 1 above (90 mg, 0.155 mmol, 95% purity) in dioxane (5 ml) and the mixture was heated to 60° C. for 16 h. Concentrated HCl(aq) (2 ml) was added and the mixture was heated to 70° C. for 16 h. The mixture was concentrated in vacuo. The residue was purified by preparative HPLC (Waters, Acidic (0.1% Formic acid), Acidic, Waters X-Select Prep-C18, 5 μm, 19×50 mm column, 10-40% MeCN in Water) to afford the title compound (8.5 mg, 0.019 mmol, 12% yield, 97% purity) as a cream solid. UPLC-MS (Method 1) m/z 439.3 (M+H)$^+$, 437.2 (M−H)$^−$ at 1.57 min. $^1$H NMR (500 MHz, DMSO-d$_6$) δ 13.11 (br s, 1H), 11.36 (br s, 1H), 9.99 (br s, 1H), 8.31 (s, 1H), 8.02 (d, J=7.6 Hz, 1H), 7.67 (d, J=8.1 Hz, 1H), 7.49 (d, J=8.0 Hz, 1H), 7.04 (s, 1H), 6.91 (q, J=2.2 Hz, 1H), 6.69 (s, 1H), 6.13 (q, J=2.7 Hz, 1H), 3.05-2.90 (m, 2H), 1.17-1.03 (m, 3H). One exchangeable proton not observed.

Example 70: 3-(N-(2-(5-chlorothiophen-2-yl)-5-(trifluoromethyl)phenyl)sulfamoyl)-4-ethylbenzoic acid

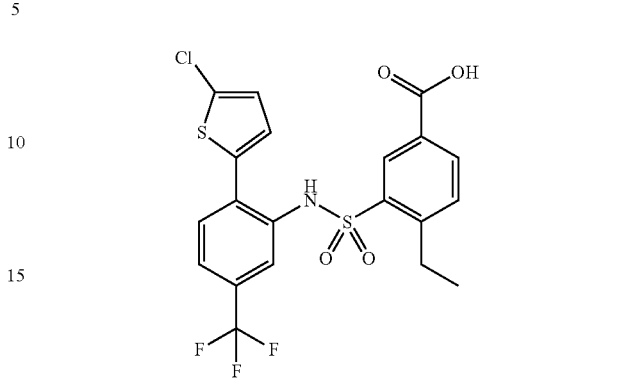

Step 1: methyl 3-(N-(2-(5-chlorothiophen-2-yl)-5-(trifluoromethyl)phenyl)sulfamoyl)-4-ethylbenzoate: Two reactions were set up simultaneously. To the reaction vessel containing the product from Example 19 Step 3 (150 mg, 0.306 mmol, 95% purity), (5-chlorothiophen-2-yl)boronic acid (105 mg, 0.647 mmol), 1 M K$_3$PO$_4$(aq) (540 μl, 0.54 mmol) and dioxane (3.2 ml) was added PdCl$_2$[P(Cy)$_3$]$_2$ (13 mg, 17.6 μmol). The reaction mixture was degassed with N$_2$ for 15 min and then heated to 80° C. for 4 h, and then allowed to cool to RT. The reaction mixture concentrated in vacuo onto Celite® and purified by chromatography on silica gel (24 g cartridge, 0-20% EtOAc/isohexane) to afford the title compound (65 mg, 0.125 mmol, 39% yield, 97% purity) as a yellow oil. UPLC-MS (Method 1) m/z 502.1 (M−H)$^−$ at 1.94 min. To the reaction vessel containing the product from Example 19 Step 3 (150 mg, 0.306 mmol, 95% purity), (5-chlorothiophen-2-yl)boronic acid (157 mg, 0.965 mmol), 1 M K$_3$PO$_4$(aq) (540 μl, 0.54 mmol) and dioxane (3.2 ml) was added PdCl$_2$[P(Cy)$_3$]$_2$ (13 mg, 17.6 μmol). The reaction mixture was degassed with N$_2$ for 15 min and then heated to 80° C. for 1.5 h. The reaction mixture was allowed to cool to RT, filtered through Celite®, washed with DCM (15 ml) and then concentrated in vacuo. The crude product was combined with the above title compound (65 mg, 0.125 mmol, 97% purity) and purified by chromatography on silica gel (40 g cartridge, 0-70% DCM/isohexane) and by chromatography on silica gel (40 g cartridge, 0-15% EtOAc/isohexane) to afford the title compound (165 mg, 0.321 mmol, 52% yield, 98% purity) as a colourless oil. UPLC-MS (Method 1) m/z 502.1 (M−H)$^−$ at 1.93 min.

Step 2: 3-(N-(2-(5-chlorothiophen-2-yl)-5-(trifluoromethyl)phenyl)sulfamoyl)-4-ethylbenzoic acid: 1 M LIOH (aq) (1.31 ml, 1.31 mmol) was added to a solution of the product from Step 1 above (165 mg, 0.321 mmol, 98% purity) in THF (2.6 ml) at RT. The reaction mixture was stirred at RT for 19 h, and then concentrated in vacuo to remove the THF. The residue was diluted with water (5 ml) and then washed with EtOAc (5 ml). The aqueous phase was acidified using 1 M HCl(aq) until pH 4-5 and the product was extracted into EtOAc (3×5 ml). The combined organic extracts were dried over MgSO$_4$, filtered and concentrated in vacuo to afford the title compound (128 mg, 0.253 mmol, 79% yield, 97% purity) as an off-white solid. UPLC-MS (Method 1) m/z 488.1 (M−H)$^−$ at 1.79 min. $^1$H NMR (500 MHz, DMSO-d$_6$) δ 13.26 (br s, 1H), 10.33 (br s, 1H), 8.15 (br s, 1H), 8.11 (dd, J=8.0, 1.8 Hz, 1H), 7.88 (d, J=8.2 Hz, 1H), 7.74-7.62 (m, 1H), 7.58 (d, J=8.0 Hz, 1H), 7.44 (d, J=4.1 Hz, 1H), 7.14 (d, J=4.0 Hz, 1H), 6.89 (br s, 1H), 2.91 (q, J=7.4 Hz, 2H), 1.16 (t, J=7.4 Hz, 3H).

Example 71: 4-ethyl-3-(N-(5-(methylsulfonyl)-2-(pyridin-2-yl)phenyl)sulfamoyl)benzoic acid

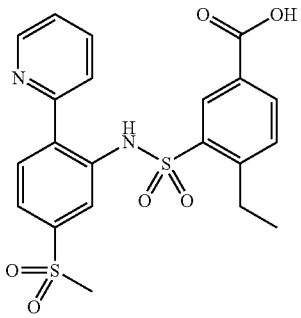 [SMILES: CCc1ccc(C(=O)O)cc1S(=O)(=O)Nc1cc(S(C)(=O)=O)ccc1-c1ccccn1]

Step 1: 5-(methylsulfonyl)-2-(pyridin-2-yl)aniline: Pyridin-2-ylzinc(II) bromide (0.5 M in THF) (14.4 ml, 7.20 mmol) was combined with 2-bromo-5-(methylsulfonyl)aniline (600 mg, 2.39 mmol) in dioxane (5 ml) and Pd(PPh$_3$)$_4$ (277 mg, 0.24 mmol) was added. The mixture was degassed with N$_2$ for 15 min and the resultant mixture was heated at 80° C. for 16 h. The mixture was concentrated in vacuo and the residue purified by chromatography on silica gel (40 g cartridge, 0-100% EtOAc/isohexane to afford the title compound (1.06 g, 2.34 mmol, 98% yield, 55% purity) as an orange oil. UPLC-MS (Method 1) m/z 249.2 (M+H)$^+$ at 0.72 min.

Step 2: methyl 4-ethyl-3-(N-(5-(methylsulfonyl)-2-(pyridin-2-yl)phenyl)sulfamoyl)benzoate: A solution of the product from Step 1 above (200 mg, 0.443 mmol, 55% purity) in DCM (3 ml) and pyridine (215 µl, 2.66 mmol) was added to a solution of the product from Example 19 Step 2 (116 mg, 0.443 mmol) in DCM (3 ml). The resultant mixture was stirred at RT for 48 h. The reaction mixture was concentrated in vacuo and the residue purified by chromatography on silica gel (24 g cartridge, 0-10% MeOH/DCM) to afford the title compound (87 mg, 0.161 mmol, 36% yield, 88% purity) as a yellow solid. UPLC-MS (Method 1) m/z 475.3 (M+H)$^+$, 473.3 (M−H)$^−$ at 1.50 min.

Step 3: 4-ethyl-3-(N-(5-(methylsulfonyl)-2-(pyridin-2-yl)phenyl)sulfamoyl)benzoic acid: 4 M HCl in dioxane (202 µl, 0.808 mmol) was added to a solution of the product from Step 2 above (87 mg, 0.161 mmol, 88% purity) in dioxane (5 ml) and the mixture was heated at 60° C. for 16 h. The mixture was concentrated in vacuo and triturated with TBME (10 ml) and MeOH (5 ml), and the solid was collected to afford the title compound (70 mg, 0.149 mmol, 92% yield, 98% purity) as a yellow solid. UPLC-MS (Method 1) m/z 461.3 (M+H)$^+$, 459.2 (M−H)$^−$ at 1.34 min. $^1$H NMR (500 MHz, DMSO-d$_6$) δ 13.31 (br s, 1H), 13.12 (br s, 1H), 8.83-8.70 (m, 1H), 8.28 (d, J=1.8 Hz, 1H), 8.13 (d, J=8.3 Hz, 1H), 8.07-7.89 (m, 4H), 7.82-7.67 (m, 1H), 7.61-7.50 (m, 1H), 7.44 (d, J=8.0 Hz, 1H), 3.18 (s, 3H), 2.75 (q, J=7.4 Hz, 2H), 0.98 (t, J=7.4 Hz, 3H).

Example 72: 4-cyclopropyl-3-(N-(2-(pyridin-2-yl)-5-(trifluoromethyl)phenyl) sulfamoyl)benzoic acid

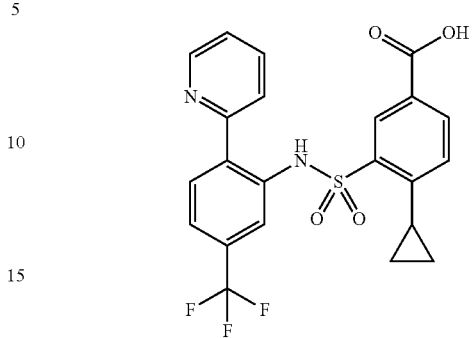

Step 1: 2-(pyridin-2-yl)-5-(trifluoromethyl)aniline: Pyridin-2-ylzinc(II) bromide (0.5 M in THF) (15 ml, 7.50 mmol) was combined with 2-bromo-5-(trifluoromethyl)aniline (600 mg, 2.50 mmol) in dioxane (5 ml) and Pd(PPh$_3$)$_4$ (289 mg, 0.25 mmol) was added. The mixture was degassed with N$_2$ for 15 min and then heated at 80° C. for 16 h. The mixture was concentrated in vacuo and the residue purified by chromatography on silica gel (40 g cartridge, 0-100% EtOAc/isohexane) to afford the title compound (364 mg, 1.36 mmol, 54% yield, 89% purity) as a red solid. UPLC-MS (Method 1) m/z 239.2 (M+H)+ at 1.33 min.

Step 2: methyl 4-bromo-3-(N-(2-(pyridin-2-yl)-5-(trifluoromethyl)phenyl)sulfamoyl)benzoate: A solution of the product from Step 1 above (180 mg, 0.673 mmol, 89% purity) in DCM (3 ml) and pyridine (326 µl, 4.04 mmol) was added to a solution of the product from Example 55 Step 3 (211 mg, 0.673 mmol, 99% purity) in DCM (3 ml) and the resultant solution was stirred at RT for 2 days. The reaction mixture was concentrated in vacuo. The residue was purified by chromatography on silica gel (24 g cartridge, 0-10% MeOH/DCM) to afford the title compound (152 mg, 0.295 mmol, 44% yield) as a yellow solid. UPLC-MS (Method 1) m/z 515.2 (M+H)$^+$ at 1.82 min.

Step 3: methyl 4-cyclopropyl-3-(N-(2-(pyridin-2-yl)-5-(trifluoromethyl)phenyl)sulfamoyl)benzoate: Cyclopropylzinc(I) bromide (0.5 M in THF) (1.88 ml, 0.944 mmol) was added to a mixture of the product from Step 2 above (152 mg, 0.295 mmol) and Pd-174 (21 mg, 0.029 mmol) in THF (4.5 ml). The mixture was degassed with N$_2$ for 15 min, then heated at 60° C. for 16 h. Additional Pd-174 (21 mg, 0.029 mmol) and cyclopropylzinc(II) bromide (0.5 M in THF) (1.88 ml, 0.944 mmol) was added. The resultant mixture was heated at 60° C. for 2 h. The mixture was concentrated in vacuo onto silica and purified by chromatography on silica gel (24 g cartridge, 0-100% EtOAc/isohexane) to afford the title compound (150 mg, 0.280 mmol, 95% yield, 89% purity) as a light yellow solid. UPLC-MS (Method 1) m/z 477.3 (M+H)$^+$, 475.2 (M−H)$^−$ at 1.84 min.

Step 4: 4-cyclopropyl-3-(N-(2-(pyridin-2-yl)-5-(trifluoromethyl)phenyl)sulfamoyl)benzoic acid: LiOH (15 mg, 0.630 mmol) was added to a solution of the product from Step 3 above (150 mg, 0.280 mmol, 89% purity) in THF (5 ml) and water (5 ml). The reaction mixture was stirred at RT overnight. The mixture was acidified to pH 6 using 10% w/v citric acid(aq) and the resultant precipitate collected by filtration to afford the title compound (125 mg, 0.262 mmol, 81% yield, 97% purity) as a yellow solid. UPLC-MS (Method 1) m/z 463.3 (M+H)$^+$, 461.2 (M−H)~ at 1.67 min.

¹H NMR (500 MHz, DMSO-d₆) δ 13.43 (br s, 1H), 13.28 (br s, 1H), 8.74 (d, J=4.9 Hz, 1H), 8.41 (d, J=1.9 Hz, 1H), 8.19-8.01 (m, 3H), 7.92 (dd, J=8.2, 1.9 Hz, 1H), 7.71 (d, J=2.0 Hz, 1H), 7.52 (d, J=20.3 Hz, 2H), 6.99 (d, J=8.3 Hz, 1H), 2.55-2.46 (m, 1H), 0.75-0.67 (m, 2H), 0.68-0.53 (m, 2H).

Example 73: 4-ethyl-3-(N-(2-(1-methyl-pyrrol-2-yl)-5-(trifluoromethyl)phenyl) sulfamoyl)benzoic acid

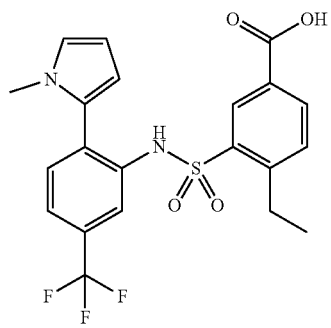 [SMILES: CCc1ccc(C(=O)O)cc1S(=O)(=O)Nc1cc(C(F)(F)F)ccc1-c1cccn1C]

Step 1: methyl-4-ethyl-3-(N-(2-(1-methyl-pyrrol-2-yl)-5-(trifluoromethyl)phenyl)sulfamoyl)benzoate. A mixture of the product from Example 19, Step 3 (150 mg, 0.322 mmol), 1-methyl-2-(4,4,5,5-tetramethyl-1,3,2-dioxaborolan-2-yl)-pyrrole (133 mg, 0.643 mmol) and K₃PO₄ (137 mg, 0.643 mmol) in dioxane (4 ml) and water (1 ml) was treated with XPhos Pd G3 (13.6 mg, 16.0 μmol). The reaction mixture was degassed with N₂ for 10 min and then heated to 80° C. for 17 h. The mixture was concentrated in vacuo and the residue purified by chromatography on silica gel (24 g cartridge, 0-50% EtOAc/isohexane) to afford the title compound (50 mg, 0.055 mmol, 17% yield, 51% purity) as a light brown solid. UPLC-MS (Method 1) m/z 465.2 (M–H)⁻ at 1.99 min.

Step 2: 4-ethyl-3-(N-(2-(1-methyl-pyrrol-2-yl)-5-(trifluoromethyl)phenyl)sulfamoyl)benzoic acid: 1 M LiOH(aq) (164 μl, 0.164 mmol) was added to a solution of the product from Step 1 above (50 mg, 0.055 mmol, 55% purity) in THF (5 ml) and water (5 ml) and the resultant mixture was stirred at RT overnight. The mixture was acidified to pH 6 using 10% w/v citric acid(aq) and concentrated in vacuo. The residue was purified by preparative HPLC (Waters, Acidic (0.1% Formic acid), Acidic, Waters X-Select Prep-C18, 5 μm, 19×50 mm column, 50-80% MeCN in Water) to afford the title compound (6 mg, 0.013 mmol, 24% yield, 99% purity) as a white solid. UPLC-MS (Method 1) m/z 453.3 (M+H)⁺, 451.2 (M–H)⁻ at 1.69 min. ¹H NMR (500 MHz, DMSO-d6) δ 13.20 (br s, 1H), 9.93 (br s, 1H), 8.17 (s, 1H), 8.02 (d, J=8.0 Hz, 1H), 7.48 (d, J=8.0 Hz, 2H), 7.41 (d, J=11.9 Hz, 2H), 6.74 (t, J=2.2 Hz, 1H), 6.04 (s, 1H), 5.99 (t, J=3.1 Hz, 1H), 3.20 (s, 3H), 2.84 (q, J=7.5 Hz, 2H), 1.13 (t, J=7.6 Hz, 3H).

Example 74: 4-cyclopropyl-3-(N-(5-(methylsulfonyl)-2-(thiophen-2-yl)phenyl)sulfamoyl) benzoic acid

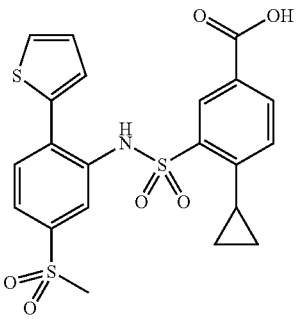 [SMILES: CS(=O)(=O)c1ccc(-c2cccs2)c(NS(=O)(=O)c2cc(C(=O)O)ccc2C2CC2)c1]

Step 1: 5-(methylsulfonyl)-2-(thiophen-2-yl)aniline: 2-bromo-5-(methylsulfonyl)aniline (50 mg, 0.200 mmol) was combined with thiophen-2-ylboronic acid (33.3 mg, 0.260 mmol) and 1 M K₃PO₄(aq) (0.340 ml, 0.340 mmol) in dioxane (2 ml). The resultant mixture was treated with XPhos Pd G3 (10 mg, 0.012 mmol) and degassed with N₂ for 10 min, then then heated at 80° C. for 16 h. In a separate vessel, 2-bromo-5-(methylsulfonyl)aniline (450 mg, 1.80 mmol) was combined with thiophen-2-ylboronic acid (300 mg, 2.35 mmol) and 1 M K₃PO₄(aq) (3.10 ml, 3.10 mmol) in dioxane (18 ml). The resultant mixture was treated with XPhos Pd G3 (76 mg, 0.090 mmol) and degassed with N₂ for 15 min and then heated at 80° C. for 30 min. The two reaction mixtures were allowed to cool to RT and were combined, filtered through Celite®, washing with EtOAc (20 ml), and then partitioned between EtOAc (10 ml) and saturated NH₄Cl(aq) (20 ml). The phases were separated, and the aqueous phase extracted with EtOAc (2×5 ml). The organic phases were combined and dried over MgSO₄ and then concentrated in vacuo. The crude product was purified by chromatography on silica gel (24 g cartridge, 0-2% MeOH/DCM) to afford the title compound (303 mg, 1.19 mmol, 60% yield) as a pale yellow solid. UPLC-MS (Method 1): m/z 254.2 (M+H)⁺ at 1.14 min. ¹H NMR (500 MHz, DMSO-d₆) δ 7.65 (dd, J=5.1, 1.1 Hz, 1H), 7.39 (d, J=8.1 Hz, 1H), 7.37 (dd, J=3.6, 1.2 Hz, 1H), 7.34 (d, J=2.0 Hz, 1H), 7.19 (dd, J=5.1, 3.6 Hz, 1H), 7.09 (dd, J=8.0, 2.0 Hz, 1H), 5.64 (s, 2H), 3.15 (s, 3H).

Step 2: methyl 4-bromo-3-(N-(5-(methylsulfonyl)-2-(thiophen-2-yl)phenyl)sulfamoyl)benzoate: To a mixture of the product Step 1 above (200 mg, 0.782 mmol), the product from Example 55 Step 3 (297 mg, 0.938 mmol) and pyridine (200 μl, 2.47 mmol) in DCM (4.5 ml) was stirred at 35° C. for 5 days. The mixture was concentrated in vacuo onto silica and purified by chromatography on silica gel (24 g cartridge, 0-100% EtOAc/isohexane) to afford the title compound (143 mg, 0.245 mmol, 31% yield, 91% purity) as a clear yellow oil. UPLC-MS (Method 1) m/z 530.0 (M+H)⁺, 528.0 (M–H)⁻ at 1.41 min. ¹H NMR (500 MHz, DMSO-d₆) δ 10.55 (s, 1H), 8.23 (d, J=1.8 Hz, 1H), 8.03-7.96 (m, 2H), 7.85 (d, J=1.3 Hz, 2H), 7.63 (dd, J=5.1, 1.3 Hz, 1H), 7.55 (dd, J=3.7, 1.2 Hz, 1H), 7.35 (t, J=1.3 Hz, 1H), 7.06 (dd, J=5.1, 3.7 Hz, 1H), 3.86 (s, 3H), 3.13 (s, 3H).

Step 3: methyl 4-cyclopropyl-3-(N-(5-(methylsulfonyl)-2-(thiophen-2-yl)phenyl)sulfamoyl)benzoate: To a mixture of the product from Step 2 above (143 mg, 0.245 mmol, 91% purity) and Pd-174 (18 mg, 0.025 mmol) in THF (5 ml) was added cyclopropylzinc(II) bromide (0.5 M in THF) (2 ml, 1.00 mmol) and the reaction mixture was heated to 60° C. and stirred overnight. The reaction mixture was concentrated in vacuo onto silica and purified by chromatography on silica gel (12 g cartridge, 0-100% EtOAc/isohexane) to the title compound (66 mg, 0.09 mmol, 36% yield, 67% purity) as a yellow solid. UPLC-MS (Method 1) m/z 514.2 (M+Na)+, 490.1 (M−H)⁻ at 1.46 min.

Step 4: 4-cyclopropyl-3-(N-(5-(methylsulfonyl)-2-(thiophen-2-yl)phenyl)sulfamoyl)benzoic acid: A mixture of the product from Step 3 above (66 mg, 0.09 mmol, 67% purity) and LiOH (16 mg, 0.374 mmol) in THF/MeOH/water (4:1:1, 3 ml) was stirred at 40° C. overnight. The mixture was diluted with water (5 ml), acidifed to pH 4 with 1 M HCl(aq) and extracted with EtOAc (3×10 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (17.1 mg, 0.035 mmol, 39% yield, 99% purity) as a white solid. UPLC-MS (Method 1) m/z 500.2 (M+Na)⁺, 476.1 (M−H)⁻ at 1.31 min. ¹H NMR (500 MHz, DMSO-$d_6$) δ 13.21 (s, 1H), 10.29 (s, 1H), 8.21 (s, 1H), 8.01 (d, J=8.2 Hz, 1H), 7.92-7.87 (m, 1H), 7.85-7.79 (m, 1H), 7.74-7.67 (m, 1H), 7.61 (d, J=3.7 Hz, 1H), 7.25-7.21 (m, 1H), 7.18-7.10 (m, 2H), 3.03 (s, 3H), 2.75-2.65 (m, 1H), 1.14-1.03 (m, 2H), 0.95-0.83 (m, 2H).

Example 75: 3-(N-(5-cyano-2-(thiophen-2-yl)phenyl)sulfamoyl)-4-cyclopropylbenzoic acid

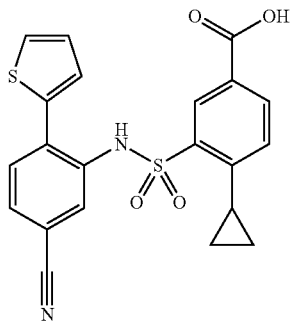 [SMILES: N#Cc1ccc(-c2cccs2)c(NS(=O)(=O)c2cc(C(=O)O)ccc2C2CC2)c1]

Step 1: 3-amino-4-(thiophen-2-yl)benzonitrile: A mixture of 3-amino-4-bromobenzonitrile (1. g, 5.08 mmol), thiophen-2-ylboronic acid (844 mg, 6.60 mmol) and 1 M $K_3PO_4$(aq) (9 ml, 9.00 mmol) in dioxane (40 ml) was degassed with $N_2$ for 15 min. XPhos Pd G3 (215 mg, 0.254 mmol) was added, the mixture was degassed with $N_2$ for 5 min and then heated to 80° C. and stirred overnight. The mixture was filtered through Celite©, rinsing with EtOAc. The filtrate was diluted with saturated $NH_4Cl$(aq) (30 ml) and extracted with EtOAc (3×50 ml). The combined organic extracts were washed with brine (20 ml), dried by passage through a phase separator and the solvent removed in vacuo. The residue was loaded onto silica and purified by chromatography on silica gel (24 g cartridge, 0-50% EtOAc/isohexane) to the title compound (841 mg, 4.12 mmol, 81% yield, 98% purity) as a yellow oil. UPLC-MS (Method 1) m/z 201.3 (M+H)⁺ at 1.34 min. ¹H NMR (500 MHz, DMSO-$d_6$) δ 7.66 (dd, J=5.1, 1.1 Hz, 1H), 7.38 (dd, J=3.6, 1.1 Hz, 1H), 7.33 (d, J=7.9 Hz, 1H), 7.19 (dd, J=5.1, 3.6 Hz, 1H), 7.14 (d, J=1.7 Hz, 1H), 6.99 (dd, J=7.9, 1.7 Hz, 1H), 5.58 (s, 2H).

Step 2: methyl 4-bromo-3-(N-(5-cyano-2-(thiophen-2-yl)phenyl)sulfamoyl)benzoate: A mixture of the product from Step 1 above (200 mg, 0.979 mmol, 98% purity), the product from Example 55 Step 3 (372 mg, 1.17 mmol) and pyridine (240 μl, 2.97 mmol) in DCM (5.5 ml) was stirred at 35° C. for 3 days. The mixture was concentrated in vacuo onto silica and purified by chromatography on silica gel (24 g cartridge, 0-100% DCM/isohexane) to afford the title compound (244 mg, 0.506 mmol, 51% yield, 99% purity) as a white foam. UPLC-MS (Method 1) m/z 475.0 (M−H)⁻ at 1.55 min. ¹H NMR (500 MHz, DMSO-$d_6$) δ 10.54 (s, 1H), 8.20 (d, J=2.1 Hz, 1H), 7.98 (dd, J=8.3, 2.1 Hz, 1H), 7.94 (d, J=8.3 Hz, 1H), 7.82-7.77 (m, 1H), 7.74 (d, J=8.1 Hz, 1H), 7.59 (dd, J=5.1, 1.2 Hz, 1H), 7.51 (dd, J=3.7, 1.2 Hz, 1H), 7.41 (d, J=1.7 Hz, 1H), 7.02 (dd, J=5.1, 3.7 Hz, 1H), 3.87 (s, 3H).

Step 3: methyl 3-(N-(5-cyano-2-(thiophen-2-yl)phenyl)sulfamoyl)-4-cyclopropylbenzoate: To a mixture of the product from Step 2 above (244 mg, 0.506 mmol, 99% purity) and Pd-174 (36 mg, 0.050 mmol) in THF (10 ml) was added cyclopropylzinc(II) bromide (0.5 M in THF) (4 ml, 2.00 mmol) and the mixture was heated to 60° C. and stirred overnight. The mixture was concentrated in vacuo onto silica and purified by chromatography on silica gel (12 g cartridge, 0-100% DCM/isohexane) to afford the title compound (58 mg, 0.077 mmol, 15% yield, 58% purity) as a white solid. UPLC-MS (Method 1) m/z 437.1 (M−H)⁻ at 1.60 min.

Step 4: 3-(N-(5-cyano-2-(thiophen-2-yl)phenyl)sulfamoyl)-4-cyclopropylbenzoic acid: A mixture of the product from Step 3 above (58 mg, 0.077 mmol, 58% purity) and LiOH (14 mg, 0.327 mmol) in THF/MeOH/water (4:1:1, 3 ml) was stirred at 40° C. overnight. The mixture was diluted with water (5 ml), acidifed to pH 4 with 1 M HCl(aq) and extracted with EtOAc (3×10 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (12.8 mg, 0.03 mmol, 38% yield, 99% purity) as a white solid. UPLC-MS (Method 1) m/z 423.1 (M−H)⁻ at 1.44 min. ⁴H NMR (500 MHz, DMSO-$d_6$) δ 13.20 (s, 1H), 10.25 (s, 1H), 8.21 (s, 1H), 8.01 (d, J=8.2 Hz, 1H), 7.84 (d, J=8.2 Hz, 1H), 7.68 (d, J=5.1 Hz, 1H), 7.66-7.63 (m, 1H), 7.58 (dd, J=3.7, 1.2 Hz, 1H), 7.13 (dd, J=5.1, 3.7 Hz, 2H), 6.94 (s, 1H), 2.76-2.66 (m, 1H), 1.10-1.04 (m, 2H), 0.88-0.83 (m, 2H).

Example 76: 4-cyclopropyl-3-(N-(2-(thiophen-2-yl)-5-(trifluoromethyl)phenyl) sulfamoyl)benzoic acid

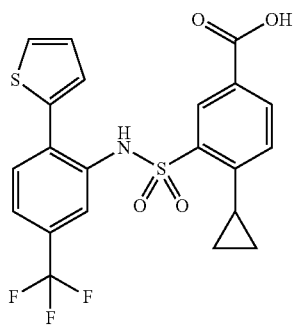 [SMILES: O=C(O)c1ccc(C2CC2)c(S(=O)(=O)Nc2cc(C(F)(F)F)ccc2-c2cccs2)c1]

Step 1: 2-(thiophen-2-yl)-5-(trifluoromethyl)aniline: A mixture of 2-bromo-5-(trifluoromethyl)aniline (597 ml, 4.17 mmol), thiophen-2-ylboronic acid (693 mg, 5.42 mmol) and 1 M $K_3PO_4$(aq) (7 ml, 7.00 mmol) in dioxane (33 ml) was degassed with $N_2$ for 15 min. XPhos Pd G3 (176 mg, 0.208 mmol) was added, the mixture was degassed with $N_2$ for 5 min and then heated to 80° C. and stirred overnight. The mixture was filtered through Celite®, rinsing with EtOAc. The filtrate was diluted with saturated $NH_4Cl$(aq) (30 ml) and extracted with EtOAc (3×50 ml). The combined organic extracts were washed with brine (20 ml), dried by passage through a phase separator and the solvent removed in vacuo. The residue was loaded onto silica and purified by chromatography on silica gel (24 g cartridge, 0-50% EtOAc/isohexane) to afford the title compound (934 mg, 3.80 mmol, 91% yield, 99% purity) as a yellow solid. UPLC-MS (Method 1) m/z 244.1 (M+H)$^+$ at 1.63 min. $^1$H NMR (500 MHz, DMSO-d$_6$) δ 7.63 (dd, J=5.2, 1.1 Hz, 1H), 7.38-7.32 (m, 2H), 7.19 (dd, J=5.2, 3.6 Hz, 1H), 7.13 (d, J=1.9 Hz, 1H), 6.88 (dd, J=8.1, 1.9 Hz, 1H), 5.55 (s, 2H).

Step 2: methyl 4-bromo-3-(N-(2-(thiophen-2-yl)-5-(trifluoromethyl)phenyl)sulfamoyl)benzoate: A mixture of the product from Step 1 above (200 mg, 0.814 mmol, 99% purity), the product from Example 55 Step 3 (309 mg, 0.977 mmol) and pyridine (200 µl, 2.47 mmol) in DCM (4.5 ml) was stirred at 35° C. for 3 days. The mixture was concentrated in vacuo onto silica and purified by chromatography on silica gel (24 g cartridge, 0-100% DCM/isohexane) to the title compound (243 mg, 0.462 mmol, 57% yield, 99% purity) as a white solid. UPLC-MS (Method 1) m/z 518.0 (M–H)$^-$ at 1.77 min. $^1$H NMR (500 MHz, DMSO-d$_6$) δ 10.49 (s, 1H), 8.20 (d, J=2.0 Hz, 1H), 8.03-7.95 (m, 2H), 7.79 (d, J=8.2 Hz, 1H), 7.72-7.67 (m, 1H), 7.60 (dd, J=5.1, 1.2 Hz, 1H), 7.51 (dd, J=3.7, 1.2 Hz, 1H), 7.12 (d, J=2.0 Hz, 1H), 7.04 (dd, J=5.1, 3.7 Hz, 1H), 3.86 (s, 3H).

Step 3: methyl 4-cyclopropyl-3-(N-(2-(thiophen-2-yl)-5-(trifluoromethyl)phenyl)sulfamoyl)benzoate: To a mixture of the product from Step 2 above (243 mg, 0.462 mmol, 99% purity) and Pd-174 (33 mg, 0.046 mmol) in THF (9 ml) was added cyclopropylzinc(II) bromide (0.5 M in THF) (3.7 ml, 1.85 mmol). The reaction mixture was heated to 60° C. and stirred overnight. The mixture was concentrated in vacuo onto silica and purified by chromatography on silica gel (12 g cartridge, 0-100% DCM/isohexane) to afford the title compound (64 mg, 0.121 mmol, 26% yield, 91% purity) as a white solid. UPLC-MS (Method 1) m/z 482.2 (M+H)$^+$, 480.1 (M–H)$^-$ at 1.82 min.

Step 4: 4-cyclopropyl-3-(N-(2-(thiophen-2-yl)-5-(trifluoromethyl)phenyl)sulfamoyl)benzoic acid: A mixture of the product from Step 3 above (64 mg, 0.121 mmol, 91% purity) and LiOH (21 mg, 0.491 mmol) in THF/MeOH/water (4:1:1, 3 ml) was stirred at 40° C. overnight. The mixture was diluted with water (5 ml), acidifed to pH 4 with 1 M HCl(aq) and extracted with EtOAc (3×10 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (17.6 mg, 0.037 mmol, 30% yield, 99% purity) as a white solid. UPLC-MS (Method 1) m/z 468.2 (M+H)$^+$, 466.1 (M–H)$^-$ at 1.66 min. $^1$H NMR (500 MHz, DMSO-d$_6$) δ 13.22 (s, 1H), 10.30 (s, 1H), 8.22 (s, 1H), 8.00 (d, J=8.2 Hz, 1H), 7.84-7.74 (m, 2H), 7.69-7.65 (m, 1H), 7.58 (d, J=3.7 Hz, 1H), 7.16-7.08 (m, 3H), 2.69-2.63 (m, 1H), 1.07-1.01 (m, 2H), 0.89-0.81 (m, 2H).

Example 77: 3-(N-(2-(5-cyanothiophen-2-yl)-5-(trifluoromethyl)phenyl)sulfamoyl)-4-ethylbenzoic acid

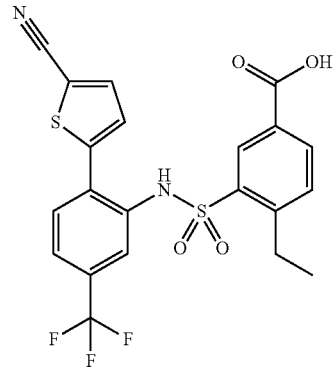 [SMILES: CCc1ccc(C(=O)O)cc1S(=O)(=O)Nc1cc(C(F)(F)F)ccc1-c1ccc(C#N)s1]

Step 1: methyl 3-(N-(2-(5-cyanothiophen-2-yl)-5-(trifluoromethyl)phenyl)sulfamoyl)-4-ethylbenzoate: To the reaction vessel containing the product from Example 19 Step 3 (150 mg, 0.306 mmol, 95% purity), (5-cyanothiophen-2-yl)boronic acid (98 mg, 0.643 mmol), 1 M $K_3PO_4$(aq) (540 µl, 0.54 mmol) and dioxane (2.2 ml) was added XPhos Pd G3 (12 mg, 14.2 µmol). The reaction mixture was degassed with $N_2$ for 15 min and then heated to 80° C. for 23 h. Additional (5-cyanothiophen-2-yl)boronic acid (49 mg, 0.321 mmol) and XPhos Pd G3 (12 mg, 14.2 µmol) were added, the reaction mixture was degassed with $N_2$ for 10 min and then heated to 80° C. for 2 h. Additional (5-cyanothiophen-2-yl)boronic acid (24 mg, 0.157 mmol) and XPhos Pd G3 (6 mg, 7.10 µmol) were added, the reaction mixture was degassed with $N_2$ for 10 min and then heated to 80° C. for 1 h. The reaction mixture was allowed to cool to RT, concentrated in vacuo onto Celite® and purified by chromatography on silica gel (12 g cartridge, 0-50% EtOAc/isohexane) to afford the title compound (151 mg, 0.284 mmol, 93% yield, 93% purity) as an orange oil. UPLC-MS (Method 1) m/z 493.1 (M–H)$^-$ at 1.76 min.

Step 2: 3-(N-(2-(5-cyanothiophen-2-yl)-5-(trifluoromethyl)phenyl)sulfamoyl)-4-ethylbenzoic acid: 1 M LiOH (aq) (1.14 ml, 1.14 mmol) was added to a solution of the product from Step 1 above (151 mg, 0.284 mmol, 93% purity) in THF (2.3 ml) at RT. The reaction mixture was stirred at RT for 18 h, and then concentrated in vacuo to remove the THF. The residue was diluted with water (5 ml) and then washed with EtOAc (5 ml). The aqueous phase was acidified using 1 M HCl(aq) until pH 4-5 and the product was extracted into EtOAc (3×5 ml). The combined organic extracts were dried over MgSO$_4$, filtered and concentrated in vacuo. The crude product was purified by preparative HPLC (Waters, Acidic (0.1% Formic acid), Acidic, Waters X-Select Prep-C18, 5 μm, 19×50 mm column, 50-80% MeCN in Water) to afford the title compound (71.8 mg, 0.142 mmol, 50% yield, 95% purity) as an off-white solid. UPLC-MS (Method 1) m/z 479.2 (M–H)$^-$ at 1.61 min. $^1$H NMR (500 MHz, DMSO-d$_6$) δ 13.25 (br s, 1H), 10.43 (br s, 1H), 8.16 (br s, 1H), 8.09 (d, J=8.0 Hz, 1H), 7.97 (d, J=8.2 Hz, 1H), 7.94 (d, J=4.0 Hz, 1H), 7.67 (d, J=4.1 Hz, 2H), 7.56 (d, J=8.0 Hz, 1H), 6.99 (s, 1H), 2.95-2.83 (m, 2H), 1.13 (t, J=7.4 Hz, 3H).

Example 78: 4-methoxy-3-(N-(5-(methylsulfonyl)-2-(thiophen-2-yl)phenyl)sulfamoyl) benzoic acid

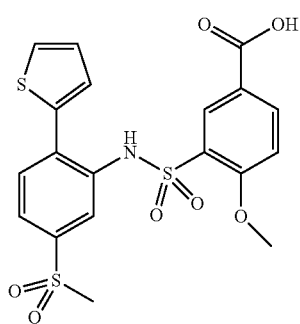 [SMILES: COc1ccc(C(=O)O)cc1S(=O)(=O)Nc1cc(S(C)(=O)=O)ccc1-c1cccs1]

Step 1: methyl 4-methoxy-3-(N-(5-(methylsulfonyl)-2-(thiophen-2-yl)phenyl)sulfamoyl)benzoate: A mixture of the product from Example 74 Step 1 (97 mg, 0.383 mmol), methyl 3-(chlorosulfonyl)-4-methoxybenzoate (122 mg, 0.459 mmol) and pyridine (93 μl, 1.15 mmol) in DCM (3 ml) was stirred at 35° C. for 5 days. The reaction mixture was concentrated in vacuo onto silica and purified by chromatography on silica gel (12 g cartridge, 0-100% EtOAc/isohexane) to afford the title compound (143 mg, 0.297 mmol, 78% yield) as a pale yellow solid. UPLC-MS (Method 2) m/z 480.1 (M–H)$^-$ at 1.14 min.

Step 2: 4-methoxy-3-(N-(5-(methylsulfonyl)-2-(thiophen-2-yl)phenyl)sulfamoyl)benzoic acid: 1 M LiOH (aq) (2.97 ml, 2.97 mmol) was added to a solution of the product from Step 1 above (143 mg, 0.297 mmol) in THF (3 ml) and the solution was stirred at RT overnight. The mixture was adjusted to pH 6 with 1 M citric acid(aq) and the precipitate was collected by filtration and dried in vacuo to afford the title compound (60 mg, 0.122 mmol, 41% yield, 95% purity) as a white solid. MS (Method 1) m/z 468.6 (M+H)$^+$, 466.1 (M–H)$^-$ at 1.17 min. $^1$H NMR (500 MHz, DMSO-d$_6$) δ 13.1 (br s, 1H), 9.89 (br s, 1H), 8.21-8.07 (m, 2H), 7.87 (d, J=8.2 Hz, 1H), 7.82 (m, 1H), 7.69 (d, J=5.2 Hz, 1H), 7.59 (d, J=3.6 Hz, 1H), 7.44 (s, 1H), 7.32 (d, J=8.8 Hz, 1H), 7.14 (dd, J=5.1, 3.6 Hz, 1H), 3.84 (s, 3H), 3.09 (s, 3H).

Example 79: 4-methoxy-3-(N-(2-(5-methylthiophen-2-yl)-5-(trifluoromethyl)phenyl) sulfamoyl)benzoic acid

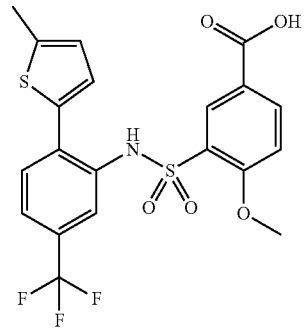

Step 1: 2-(5-methylthiophen-2-yl)-5-(trifluoromethyl)aniline: A mixture of 2-bromo-5-(trifluoromethyl)aniline (233 μl, 1.62 mmol), (5-methylthiophen-2-yl)boronic acid (300 mg, 2.11 mmol) and 1 M K$_3$PO$_4$(aq) (2.7 ml, 2.70 mmol) in dioxane (13 ml) was degassed with N$_2$ for 15 min. XPhos Pd G3 (70 mg, 0.083 mmol) was added, the mixture was degassed with N$_2$ for 5 min and then heated to 80° C. and stirred overnight. The reaction mixture was filtered through Celite®, rinsing with EtOAc. The filtrate was diluted with saturated NH$_4$Cl(aq) (15 ml) and extracted with EtOAc (3×25 ml). The combined organic extracts were washed with brine (10 ml), dried by passage through a phase separator and the solvent removed in vacuo. The residue was loaded onto silica and purified by chromatography on silica gel (12 g cartridge, 0-100% DCM/isohexane) to afford the title compound (318 mg, 1.14 mmol, 70% yield, 92% purity) as a beige solid. UPLC-MS (Method 1) m/z 258.1 (M+H)$^+$ at 1.75 min.

Step 2: methyl 4-methoxy-3-(N-(2-(5-methylthiophen-2-yl)-5-(trifluoromethyl)phenyl)sulfamoyl)benzoate: A mixture of the product from Step 1 above (118 mg, 0.422 mmol, 92% purity), methyl 3-(chlorosulfonyl)-4-methoxybenzoate (135 mg, 0.506 mmol) and pyridine (100 μl, 1.24 mmol) in DCM (2.5 ml) was stirred at 35° C. for 4 days. The mixture was concentrated in vacuo onto silica and purified by chromatography on silica gel (12 g cartridge, 0-100% EtOAc/isohexane) to afford the title compound (153 mg, 0.284 mmol, 67% yield, 90% purity) as a clear colourless oil. UPLC-MS (Method 1) m/z 486.1 (M+H)$^+$, 484.1 (M–H)$^-$ at 1.77 min. $^1$H NMR (500 MHz, DMSO-d$_6$) δ 9.82 (s, 1H), 8.18 (dd, J=8.7, 2.3 Hz, 1H), 8.06 (d, J=2.3 Hz, 1H), 7.73 (d, J=8.2 Hz, 1H), 7.61 (dd, J=8.2, 2.0 Hz, 1H), 7.35-7.29 (m, 2H), 7.16 (d, J=2.0 Hz, 1H), 6.77 (dd, J=3.6, 1.3 Hz, 1H), 3.86 (s, 3H), 3.82 (s, 3H), 2.42 (s, 3H).

Step 3: 4-methoxy-3-(N-(2-(5-methylthiophen-2-yl)-5-(trifluoromethyl)phenyl)sulfamoyl)benzoic acid: A mixture of the product from Step 2 above (153 mg, 0.284 mmol) and LiOH (54 mg, 1.26 mmol, 90% purity) in THF/MeOH/water (4:1:1, 6 ml) was stirred at 40° C. overnight. The mixture was diluted with water (5 ml), acidified to pH 4 with 1 M HCl(aq) and extracted with EtOAc (3×10 ml). The combined organic extracts were washed with brine (10 ml), dried by passage through a phase separator and the solvent removed in vacuo. The residue was loaded onto silica and purified by chromatography on silica gel (12 g cartridge, 0-100% EtOAc/isohexane) to afford the title compound (85.4 mg, 0.179 mmol, 63% yield, 99% purity) as a white solid after trituration with TBME. UPLC-MS (Method 1) m/z 472.2 (M+H)⁺, 470.1 (M−H)⁻ at 1.61 min. ¹H NMR (500 MHz, DMSO-d₆) δ 13.05 (s, 1H), 9.75 (s, 1H), 8.16 (dd, J=8.7, 2.2 Hz, 1H), 8.07 (d, J=2.1 Hz, 1H), 7.73 (d, J=8.3 Hz, 1H), 7.60 (dd, J=8.3, 2.0 Hz, 1H), 7.32 (d, J=3.6 Hz, 1H), 7.30 (d, J=8.7 Hz, 1H), 7.15 (d, J=2.1 Hz, 1H), 6.79 (dd, J=3.6, 1.3 Hz, 1H), 3.85 (s, 3H), 2.43 (s, 3H).

Example 80: 3-(N-(5-cyano-2-(5-methylthiophen-2-yl)phenyl)sulfamoyl)-4-ethylbenzoic acid

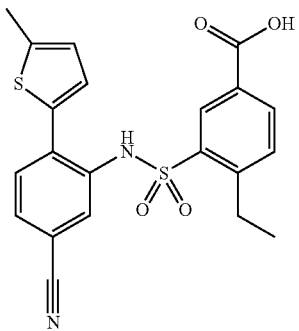 [SMILES: CCc1ccc(C(=O)O)cc1S(=O)(=O)Nc1cc(C#N)ccc1-c1ccc(C)s1]

Step 1: 3-amino-4-(5-methylthiophen-2-yl)benzonitrile: A mixture of 3-amino-4-bromobenzonitrile (700 mg, 3.55 mmol), (5-methylthiophen-2-yl)boronic acid (656 mg, 4.62 mmol) and 1 M K₃PO₄(aq) (6 ml, 6.00 mmol) in dioxane (27 ml) was degassed with N₂ for 15 min. XPhos Pd G3 (150 mg, 0.178 mmol) was added, the mixture was degassed with N₂ for 5 min and then heated to 80° C. and stirred for 2 h. The mixture was filtered through Celite©, rinsing with EtOAc. The filtrate was diluted with saturated NH₄Cl(aq) (30 ml) and extracted with EtOAc (3×50 ml). The combined organic extracts were washed with brine (20 ml), dried by passage through a phase separator and the solvent removed in vacuo. The residue was loaded onto silica and purified by chromatography on silica gel (24 g cartridge, 0-50% EtOAc/isohexane) to the title compound (682 mg, 2.83 mmol, 80% yield, 89% purity) as a yellow solid. UPLC-MS (Method 1) m/z 215.1 (M+H)⁺ at 1.48 min. ¹H NMR (500 MHz, DMSO-d₆) δ 7.27 (d, J=7.9 Hz, 1H), 7.17 (d, J=3.5 Hz, 1H), 7.11 (d, J=1.7 Hz, 1H), 6.97 (dd, J=7.9, 1.7 Hz, 1H), 6.89-6.86 (m, 1H), 5.54 (s, 2H), 2.48 (s, 3H).

Step 2: methyl 3-(N-(5-cyano-2-(5-methylthiophen-2-yl)phenyl)sulfamoyl)-4-ethylbenzoate: A mixture of the product from Step 1 above (100 mg, 0.415 mmol, 89% purity), the product from Example 19 Step 2 (143 mg, 0.54 mmol) and pyridine (100 µl, 1.24 mmol) in DCM (2.5 ml) was stirred at 35° C. for 3 days. The mixture was concentrated in vacuo onto silica and purified by chromatography on silica gel (12 g cartridge, 0-50% EtOAc/isohexane) to afford the title compound (56 mg, 0.122 mmol, 29% yield, 96% purity) as a yellow oil. UPLC-MS (Method 1) m/z 439.1 (M−H)⁻ at 1.69 min. ¹H NMR (500 MHz, DMSO-d₆) δ 10.31 (s, 1H), 8.15-8.05 (m, 2H), 7.80-7.71 (m, 1H), 7.67 (d, J=8.1 Hz, 1H), 7.53 (d, J=8.1 Hz, 1H), 7.28 (d, J=3.6 Hz, 1H), 7.27 (d, J=1.7 Hz, 1H), 6.74-6.70 (m, 1H), 3.85 (s, 3H), 2.87 (q, J=7.4 Hz, 2H), 2.40 (s, 3H), 1.14 (t, J=7.4 Hz, 3H).

Step 3: 3-(N-(5-cyano-2-(5-methylthiophen-2-yl)phenyl)sulfamoyl)-4-ethylbenzoic acid: A mixture of the product from Step 2 above (56 mg, 0.122 mmol, 96% purity) and LiOH (21 mg, 0.491 mmol) in THF/MeOH/water (4:1:1, 2.4 ml) was stirred at 40° C. overnight. The mixture was diluted with water (5 ml), acidified to pH 4 with 1 M HCl(aq) and extracted with EtOAc (3×10 ml). The combined organic extracts were washed with brine (10 ml), dried by passage through a phase separator and the solvent removed in vacuo. The residue was loaded onto silica and purified by chromatography on silica gel (4 g cartridge, 0-5% MeOH/DCM) to the title compound (22.4 mg, 0.05 mmol, 41% yield, 96% purity) as a white solid after trituration with TBME. UPLC-MS (Method 1) m/z 425.1 (M−H)⁻ at 1.53 min. ¹H NMR (500 MHz, DMSO-d₆) δ 13.24 (s, 1H), 10.26 (s, 1H), 8.11 (d, J=1.8 Hz, 1H), 8.07 (dd, J=8.0, 1.8 Hz, 1H), 7.75 (d, J=8.2 Hz, 1H), 7.68 (d, J=8.2 Hz, 1H), 7.52 (d, J=8.0 Hz, 1H), 7.30 (d, J=3.6 Hz, 1H), 7.22 (d, J=1.7 Hz, 1H), 6.73 (dd, J=3.6, 1.2 Hz, 1H), 2.87 (q, J=7.4 Hz, 2H), 2.41 (s, 3H), 1.15 (t, J=7.4 Hz, 3H).

Example 81: 3-(N-(5-cyano-2-(5-methylthiophen-2-yl)phenyl)sulfamoyl)-4-methoxybenzoic acid

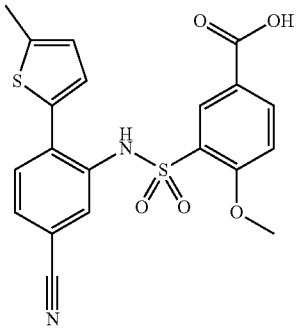

Step 1: methyl 3-(N-(5-cyano-2-(5-methylthiophen-2-yl)phenyl)sulfamoyl)-4-methoxybenzoate: A mixture of the product from Example 80 Step 1 (100 mg, 0.415 mmol, 89% purity), methyl 3-(chlorosulfonyl)-4-methoxybenzoate (144 mg, 0.54 mmol) and pyridine (100 µl, 1.24 mmol) in DCM (2.5 ml) was stirred at 35° C. for 3 days. The mixture was concentrated in vacuo onto silica and purified by chromatography on silica gel (12 g cartridge, 0-100% EtOAc/isohexane) to afford the title compound (91 mg, 0.197 mmol, 47% yield, 96% purity) as a yellow oil. UPLC-MS (Method 1) m/z 443.3 (M+H)⁺, 441.1 (M−H)⁻ at 1.55 min. ¹H NMR (500 MHz, DMSO-d₆) δ 9.89 (s, 1H), 8.20-8.15 (m, 1H), 8.08-8.05 (m, 1H), 7.73-7.68 (m, 2H), 7.35 (d, J=3.7 Hz, 1H), 7.33-7.28 (m, 2H), 6.77 (dd, J=3.7, 1.2 Hz, 1H), 3.85 (s, 3H), 3.83 (s, 3H), 2.40 (s, 3H).

Step 2: 3-(N-(5-cyano-2-(5-methylthiophen-2-yl)phenyl)sulfamoyl)-4-methoxybenzoic acid: A mixture of the product from Step 1 above (91 mg, 0.197 mmol, 96% purity) and LiOH (34 mg, 0.795 mmol) in THF/MeOH/water (4:1:1, 4.2 ml) was stirred at 40° C. overnight. The mixture was diluted with water (5 ml), acidified to pH 4 with 1 M HCl(aq) and extracted with EtOAc (3×10 ml). The combined organic extracts were washed with brine (10 ml), dried by passage through a phase separator and the solvent removed in vacuo. The residue was loaded onto silica and purified by chromatography on silica gel (4 g cartridge, 0-5% MeOH/DCM) to afford the title compound (56.8 mg, 0.127 mmol, 64% yield, 96% purity) as a white solid after trituration with TBME and hexane. UPLC-MS (Method 1) m/z 427.1 (M−H)− at 1.38 min. ¹H NMR (500 MHz, DMSO-d₆) δ 13.07 (s, 1H), 9.84 (s, 1H), 8.15 (dd, J=8.7, 2.2 Hz, 1H), 8.07 (d, J=2.2 Hz, 1H), 7.72 (s, 2H), 7.35 (d, J=3.7 Hz, 1H), 7.33-7.25 (m, 2H), 6.77 (dd, J=3.7, 1.3 Hz, 1H), 3.84 (s, 3H), 2.41 (s, 3H).

Example 82: 4-cyclopropyl-3-(N-(5-(methylsulfonyl)-2-(pyridin-2-yl)phenyl)sulfamoyl) benzoic acid

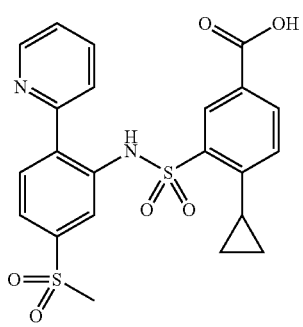 [SMILES: CS(=O)(=O)c1ccc(-c2ccccn2)c(NS(=O)(=O)c2cc(C(=O)O)ccc2C2CC2)c1]

Step 1: 5-(methylsulfonyl)-2-(pyridin-2-yl)aniline: Pyridin-2-ylzinc(II) bromide (0.5 M in THF (14.4 ml, 7.20 mmol) was combined with 2-bromo-5-(methylsulfonyl)aniline (600 mg, 2.39 mmol) in dioxane (5 ml) and Pd(PPh$_3$)$_4$ (277 mg, 0.24 mmol) was added. The resultant mixture was degassed with N$_2$ for 15 min and then heated at 80° C. for 16 h. The mixture was concentrated in vacuo and the residue purified by chromatography on silica gel (40 g cartridge, 0-100% EtOAc/isohexane) to afford the title compound (1.06 g, 2.34 mmol, 98% yield, 55% purity) as an orange oil. UPLC-MS (Method 1) m/z 249.2 (M+H)$^+$ at 0.72 min.

Step 2: methyl 4-bromo-3-(N-(5-(methylsulfonyl)-2-(pyridin-2-yl)phenyl)sulfamoyl)benzoate: A solution of the product from Step 1 above (250 mg, 0.55 mmol, 55% purity) in DCM (3 ml) and pyridine (269 µl, 3.32 mmol) was added to a solution of the product from Example 55 Step 3 (174 mg, 0.554 mmol, 99% purity) in DCM (3 ml) and the resultant solution was stirred at RT for 2 days. The reaction mixture was concentrated in vacuo and the residue purified by chromatography on silica gel (24 g cartridge, 0-10% MeOH/DCM) to afford the title compound (310 mg, 0.443 mmol, 80% yield, 75% purity) as a tan solid. UPLC-MS (Method 1) m/z 525.1 (M+H)$^+$, 522.8 (M-H)$^-$ at 1.45 min.

Step 3: methyl 4-cyclopropyl-3-(N-(5-(methylsulfonyl)-2-(pyridin-2-yl)phenyl)sulfamoyl)benzoate: Cyclopropylzinc(II) bromide (0.5 M in THF) (2.84 ml, 1.42 mmol) was added to a mixture of the product from Step 2 above (310 mg, 0.443 mmol) and Pd-174 (32 mg, 0.044 mmol) in THF (4.5 ml). The mixture was degassed under N$_2$ for 15 min and then heated at 60° C. for 16 h. Additional Pd-174 (32 mg, 0.044 mmol) and cyclopropylzinc(II) bromide (0.5 M in THF) (2.84 ml, 1.42 mmol) was added and the mixture heated at 60° C. for 2 h. The mixture was concentrated in vacuo onto silica and purified by chromatography on silica gel (24 g cartridge, 0-100% EtOAc/isohexane) to afford the title compound (310 mg, 0.382 mmol, 86% yield, 60% purity) as a brown oil. UPLC-MS (Method 1) m/z 487.3 (M+H)$^+$, 485.1 (M-H)~ at 1.48 min.

Step 4: 4-cyclopropyl-3-(N-(5-(methylsulfonyl)-2-(pyridin-2-yl)phenyl)sulfamoyl)benzoic acid: LiOH (27 mg, 1.15 mmol) was added to a solution of the product from Step 3 above (310 mg, 0.382 mmol, 60% purity) in THF (5 ml) and water (5 ml) and the resultant mixture was stirred at RT overnight. The mixture was acidified to pH 6 using 10% w/v citric acid(aq) and concentrated in vacuo. The residue was purified by preparative HPLC (Waters, Acidic (0.1% Formic acid), Acidic, Waters X-Select Prep-C18, 5 µm, 19×50 mm column, 35-65% MeCN in Water) to afford the title compound (180 mg, 0.373 mmol, 98% yield, 98% purity) as a yellow solid. UPLC-MS (Method 1) m/z 473.3 (M+H)$^+$, 471.2 (M-H)$^-$ at 1.33 min. $^1$H NMR (500 MHz, DMSO-d$_6$) δ 13.30 (br s, 2H), 8.72 (d, J=4.8 Hz, 1H), 8.42 (d, J=1.9 Hz, 1H), 8.19-8.04 (m, 2H), 8.04-7.93 (m, 2H), 7.89 (d, J=8.2 Hz, 1H), 7.60-7.45 (m, 2H), 6.95 (d, J=8.3 Hz, 1H), 3.11 (s, 3H), 2.71-2.55 (m, 1H), 0.82-0.67 (m, 2H), 0.67-0.49 (m, 2H).

Example 83: 3-(N-(5-cyano-2-(pyridin-2-yl)phenyl) sulfamoyl)-4-cyclopropylbenzoic acid

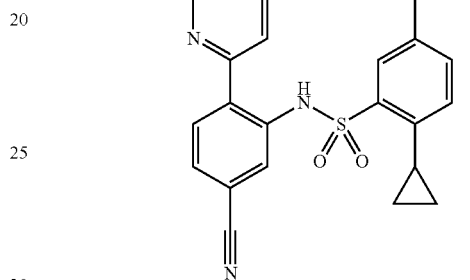

Step 1: 3-amino-4-(pyridin-2-yl)benzonitrile: Pyridin-2-ylzinc(II) bromide (0.5 M in THF) (18.3 ml, 9.14 mmol) was combined with 3-amino-4-bromobenzonitrile (600 mg, 3.05 mmol) in dioxane (5 ml) and Pd(PPh$_3$)$_4$ (352 mg, 0.305 mmol) was added. The resultant mixture was degassed with N$_2$ for 15 min and then heated at 80° C. for 16 h. The mixture was concentrated in vacuo and the residue purified by chromatography on silica gel (40 g cartridge, 0-100% EtOAc/isohexane) to afford the title compound (1.0 g, 3.02 mmol, 99% yield, 59% purity) as an orange solid. UPLC-MS (Method 1) m/z 196.5 (M+H)$^+$ at 0.96 min.

Step 2: methyl 4-bromo-3-(N-(5-cyano-2-(pyridin-2-yl)phenyl)sulfamoyl)benzoate: A solution of the product from Step 1 above (200 mg, 0.604 mmol, 59% purity) in DCM (3 ml) and pyridine (293 µl, 3.63 mmol) was added to a solution of the product from Example 55 Step 3 (190 mg, 0.604 mmol) in DCM (3 ml) and the resultant mixture was stirred at RT for 2 days. The reaction mixture was concentrated in vacuo and the residue purified by chromatography on silica gel (24 g cartridge, 0-10% MeOH/DCM) to afford the title compound (96 mg, 0.179 mmol, 30% yield, 88% purity) as a yellow oil. UPLC-MS (Method 1) m/z 474.1 (M+H)$^+$, 472.1 (M-H)$^-$ at 1.61 min.

Step 3: methyl 3-(N-(5-cyano-2-(pyridin-2-yl)phenyl)sulfamoyl)-4-cyclopropylbenzoate: Cyclopropylzinc(II) bromide (0.5 M in THF) (1.14 ml, 0.57 mmol) was added to a mixture of the product from Step 2 above (96 mg, 0.179 mmol, 88% purity) and Pd-174 (13 mg, 0.018 mmol) in THF (4.5 ml). The mixture was degassed with N$_2$ for 15 min and then heated at 60° C. for 16 h. Additional Pd-174 (13 mg, 0.018 mmol) and cyclopropylzinc(II) bromide (0.5 M in THF) (1.14 ml, 0.57 mmol) was added and the mixture heated at 60° C. for 2 h. The mixture was concentrated in vacuo onto silica and purified by chromatography on silica gel (24 g cartridge, 0-100% EtOAc/isohexane) to afford the title compound (80 mg, 0.173 mmol, 97% yield, 94% purity) as a yellow solid. UPLC-MS (Method 1) m/z 434.3 (M+H)$^+$, 432.2 (M−H)$^-$ at 1.64 min.

Step 4: 3-(N-(5-cyano-2-(pyridin-2-yl)phenyl)sulfamoyl)-4-cyclopropylbenzoic acid: LiOH (12 mg, 0.520 mmol) was added to a solution of the product from Step 3 above (80 mg, 0.173 mmol, 94% purity) in THF (5 ml) and water (5 ml) and the resultant mixture was stirred at RT overnight. The mixture was acidified to pH 6 using 10% w/v citric acid(aq) and then concentrated in vacuo. The residue was purified by preparative HPLC (Waters, Acidic (0.1% Formic acid), Acidic, Waters X-Select Prep-C18, 5 µm, 19×50 mm column, 35-65% MeCN in Water) to afford the title compound (11.8 mg, 0.028 mmol, 16% yield, 98% purity) as a yellow solid. UPLC-MS (Method 1) m/z 420.4 (M+H)$^+$, 418.3 (M−H)$^-$ at 1.47 min. $^1$H NMR (500 MHz, DMSO-d$_6$) δ 13.27 (br s, 2H), 8.71 (d, J=4.9 Hz, 1H), 8.37 (d, J=1.9 Hz, 1H), 8.18-7.95 (m, 3H), 7.90 (dd, J=8.3, 1.8 Hz, 1H), 7.72 (s, 1H), 7.60-7.44 (m, 2H), 6.96 (d, J=8.3 Hz, 1H), 2.68-2.54 (m, 1H), 0.79-0.73 (m, 2H), 0.67-0.61 (m, 2H).

Example 84: 4-ethyl-3-(N-(5-(methylsulfonyl)-2-(5-methylthiophen-2-yl)phenyl)sulfamoyl) benzoic acid

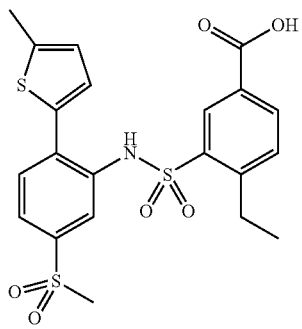 [SMILES: CCc1ccc(C(=O)O)cc1S(=O)(=O)Nc1cc(S(C)(=O)=O)ccc1-c1ccc(C)s1]

Step 1: 5-(methylsulfonyl)-2-(5-methylthiophen-2-yl)aniline: To the reaction vessel containing 2-bromo-5-(methylsulfonyl)aniline (700 mg, 2.80 mmol), (5-methylthiophen-2-yl)boronic acid (517 mg, 3.64 mmol), 1 M K$_3$PO$_4$ (aq) (4.8 ml, 4.80 mmol) and dioxane (19 ml) was added XPhos Pd G3 (118 mg, 0.140 mmol). The reaction mixture was degassed with N$_2$ for 15 min and then heated to 80° C. for 18 h. The reaction was allowed to cool to RT, filtered through Celite®, washed with MeOH (5 ml) and then concentrated in vacuo. The crude product was purified by chromatography on silica gel (24 g cartridge, 0-50% EtOAc/isohexane) to afford the title compound (585 mg, 1.99 mmol, 71% yield, 91% purity) as a pale yellow solid. $^1$H NMR (500 MHz, DMSO-d$_6$) δ 7.34 (d, J=8.0 Hz, 1H), 7.31 (d, J=2.0 Hz, 1H), 7.16 (d, J=3.5 Hz, 1H), 7.07 (dd, J=8.0, 2.0 Hz, 1H), 6.90-6.84 (m, 1H), 5.61 (s, 2H), 3.13 (s, 3H), 2.49 (d, J=1.1 Hz, 3H).

Step 2: methyl 4-ethyl-3-(N-(5-(methylsulfonyl)-2-(5-methylthiophen-2-yl)phenyl)sulfamoyl)benzoate: A solution of the product from Step 1 above (110 mg, 0.374 mmol, 91% purity), the product from Example 19 Step 2 (128 mg, 0.487 mmol) and pyridine (120 µl, 1.48 mmol) in DCM (1.5 ml) was stirred at RT for 6.5 days. The reaction mixture was concentrated in vacuo onto Celite® and purified by chromatography on silica gel (12 g cartridge, 0-40% THF/isohexane) and by chromatography (24 g reverse phase C18 cartridge, 15-80% MeCN/0.1% Formic acid) to afford the title compound (110 mg, 0.223 mmol, 60% yield) as an off-white foam. UPLC-MS (Method 1) m/z 494.2 (M+H)$^+$, 492.2 (M−H)– at 1.56 min.

Step 3: 4-ethyl-3-(N-(5-(methylsulfonyl)-2-(5-methylthiophen-2-yl)phenyl)sulfamoyl)benzoic acid: 1 M LiOH (aq) (890 µl, 0.890 mmol) was added to a solution of the product from Step 2 above (110 mg, 0.223 mmol) in THF (1.78 ml) at RT. The reaction mixture was stirred at RT for 21 h, and then concentrated in vacuo to remove the THF. The residue was diluted with water (6 ml) and washed with EtOAc (6 ml). The aqueous phase was acidified using 1 M HCl(aq) until pH 4-5 and the product was extracted into EtOAc (3×8 ml). Following the addition of THF (4 ml) to obtain a clear solution, the combined organic extracts were dried over MgSO$_4$, filtered and concentrated in vacuo to afford the title compound (87.6 mg, 0.181 mmol, 81% yield, 99% purity) as an off-white solid. UPLC-MS (Method 1) m/z 480.3 (M+H)$^+$, 478.1 (M−H)$^-$ at 1.41 min. $^1$H NMR (500 MHz, DMSO-d$_6$) δ 13.24 (br s, 1H), 10.24 (br s, 1H), 8.15 (br s, 1H), 8.07 (d, J=8.0 Hz, 1H), 7.86-7.75 (m, 1H), 7.55 (d, J=8.0 Hz, 1H), 7.35 (d, J=3.6 Hz, 1H), 7.24 (br s, 1H), 6.78 (dd, J=3.6, 1.3 Hz, 1H), 3.09 (s, 3H), 2.90 (br q, J =6.7 Hz, 3H), 2.44 (d, J=1.0 Hz, 3H), 1.16 (t, J=7.4 Hz, 3H).

Example 85: 4-methoxy-3-(N-(5-(methylsulfonyl)-2-(5-methylthiophen-2-yl)phenyl)sulfamoyl)benzoic acid

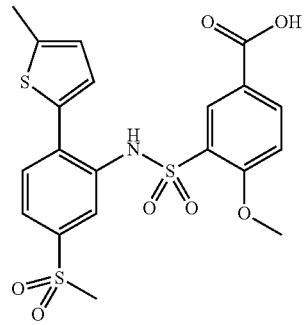

Step 1: methyl 4-methoxy-3-(N-(5-(methylsulfonyl)-2-(5-methylthiophen-2-yl)phenyl)sulfamoyl)benzoate: A solution of the product from Example 84 Step 1 (110 mg, 0.374 mmol, 91% purity), methyl-3-(chlorosulfonyl)-4-methoxybenzoate (129 mg, 0.487 mmol) and pyridine (120 µl, 1.48 mmol) in DCM (1.5 ml) was stirred at RT for 6.5 days. The reaction mixture was concentrated in vacuo and the crude product was purified by chromatography on silica gel (24 g cartridge, 20-60% EtOAc/isohexane), followed by chromatography (24 g reverse phase C18 cartridge, 15-65% MeCN/0.1% Formic acid) to afford the title compound (129 mg, 0.260 mmol, 70% yield) as an off-white solid. UPLC-MS (Method 1) m/z 496.2 (M+H)$^+$, 494.2 (M−H)$^-$ at 1.41 min.

Step 2: 4-methoxy-3-(N-(5-(methylsulfonyl)-2-(5-methylthiophen-2-yl)phenyl)sulfamoyl)benzoic acid: 1 M LiOH (aq) (1.04 ml, 1.04 mmol) was added to a solution of the product from Step 1 above (129 mg, 0.260 mmol) in THF (2.1 ml) at RT. The reaction mixture was stirred at RT for 21 h, and then concentrated in vacuo to remove the THF. The residue was diluted with water (7 ml) and then washed with EtOAc (7 ml). The aqueous phase was acidified using 1 M HCl(aq) until pH 4-5 and the product was extracted into EtOAc (3×8 ml). Following the addition of THF (8 ml) to obtain a clear solution, the combined organic extracts were dried over MgSO$_4$, filtered and concentrated in vacuo to afford the title compound (105 mg, 0.208 mmol, 80% yield, 96% purity) as a yellow solid. UPLC-MS (Method 1) m/z 482.2 (M+H)$^+$, 480.1 (M–H)$^-$ at 1.26 min. $^1$H NMR (500 MHz, DMSO-d$_6$) δ 13.02 (br s, 1H), 9.81 (br s, 1H), 8.18-8.11 (m, 1H), 8.08 (br s, 1H), 7.83-7.72 (m, 2H), 7.43-7.35 (m, 2H), 7.31 (d, J=8.7 Hz, 1H), 6.80 (dd, J=3.7, 1.3 Hz, 1H), 3.87 (s, 3H), 3.07 (s, 3H), 2.43 (d, J=1.1 Hz, 3H).

Example 86: 4-cyclopropyl-3-(N-(2-(5-methylthiophen-2-yl)-5-(trifluoromethyl)phenyl)sulfamoyl)benzoic acid

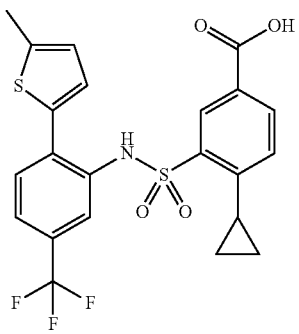 [SMILES: Cc1ccc(-c2ccc(C(F)(F)F)cc2NS(=O)(=O)c2cc(C(=O)O)ccc2C2CC2)s1]

Step 1: methyl 4-bromo-3-(N-(2-(5-methylthiophen-2-yl)-5-(trifluoromethyl)phenyl)sulfamoyl)benzoate: A mixture of the product from Example 79 Step 1 (200 mg, 0.715 mmol, 92% purity), the product from Example 55 Step 3 (272 mg, 0.858 mmol) and pyridine (180 μl, 2.23 mmol) in DCM (4 ml) was stirred at 35° C. for 4 days. The mixture was concentrated in vacuo onto silica and purified by chromatography on silica gel (24 g cartridge, 0-50% EtOAc/isohexane) to afford the title compound (223 mg, 0.401 mmol, 56% yield, 96% purity) as a white solid. UPLC-MS (Method 1) m/z 532.0 (M–H)$^-$ at 1.85 min. $^1$H NMR (500 MHz, DMSO-d$_6$) δ 10.42 (s, 1H), 8.21-8.13 (m, 1H), 8.00 (d, J=8.1 Hz, 1H), 7.96 (d, J=8.3 Hz, 1H), 7.73-7.67 (m, 2H), 7.28-7.24 (m, 1H), 7.19-7.15 (m, 1H), 6.66 (dd, J=3.6, 1.3 Hz, 1H), 3.86 (s, 3H), 2.37 (s, 3H).

Step 2: methyl 4-cyclopropyl-3-(N-(2-(5-methylthiophen-2-yl)-5-(trifluoromethyl)phenyl)sulfamoyl)benzoate: To a mixture of the product from Step 1 above (223 mg, 0.401 mmol, 96% purity) and Pd-174 (29 mg, 0.04 mmol) in THF (7 ml) was added cyclopropylzinc(II) bromide (0.5 M in THF) (3.2 ml, 1.60 mmol) and the mixture was heated to 60° C. and stirred overnight. Additional cyclopropylzinc(II) bromide (0.5 M in THF) (3.2 ml, 1.60 mmol) and Pd-174 (15 mg, 0.021 mmol) were added and stirring at 60° C. was continued for 5 h. The mixture was concentrated in vacuo onto silica and purified by chromatography on silica gel (12 g cartridge, 0-50% EtOAc/isohexane) to afford the title compound (138 mg, 0.175 mmol, 43% yield, 63% purity) as a brown oil. UPLC-MS (Method 1) m/z 494.1 (M–H)$^-$ at 1.88 min.

Step 3: 4-cyclopropyl-3-(N-(2-(5-methylthiophen-2-yl)-5-(trifluoromethyl)phenyl)sulfamoyl)benzoic acid: A mixture of the product from Step 2 above (138 mg, 0.175 mmol, 63% purity) and LiOH (30 mg, 0.702 mmol) in THF/MeOH/water (4:1:1, 3.6 ml) was stirred at 40° C. overnight. The mixture was diluted with water (5 ml), acidified to pH 4 with 1 M HCl(aq) and extracted with EtOAc (3×10 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 50-80% MeCN in Water) to afford the title compound (31.8 mg, 0.065 mmol, 37% yield, 99% purity) as a white solid. UPLC-MS (Method 1) m/z 482.0 (M+H)$^+$, 480.1 (M–H)– at 1.74 min. $^1$H NMR (500 MHz, DMSO-d$_6$) δ 13.19 (s, 1H), 10.18 (s, 1H), 8.18 (s, 1H), 8.03-7.98 (m, 1H), 7.77 (d, J=8.2 Hz, 1H), 7.64-7.61 (m, 1H), 7.35 (d, J=3.6 Hz, 1H), 7.12 (d, J=8.2 Hz, 1H), 6.96 (s, 1H), 6.80-6.76 (m, 1H), 2.75-2.65 (m, 1H), 2.45 (s, 3H), 1.09-1.03 (m, 2H), 0.88-0.83 (m, 2H).

Example 87: 3-(N-(2-(5-chlorothiophen-2-yl)-5-(trifluoromethyl)phenyl)sulfamoyl)-4-methoxybenzoic acid

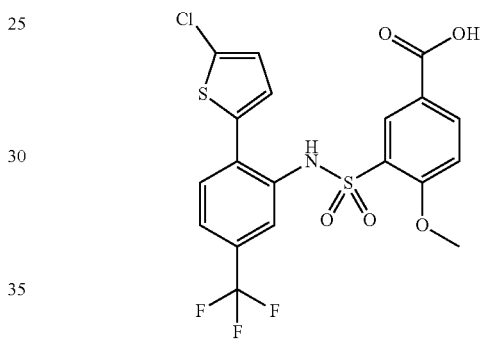

Step 1: 2-(5-chlorothiophen-2-yl)-5-(trifluoromethyl)aniline: To the reaction vessel containing 2-bromo-5-(trifluoromethyl)aniline (420 μl, 2.93 mmol), (5-chlorothiophen-2-yl)boronic acid (1.42 g, 8.75 mmol), 1 M K$_3$PO$_4$(aq) (5 ml, 5.00 mmol) and dioxane (20 ml) was added PdCl$_2$[P(Cy)$_3$]$_2$ (100 mg, 0.135 mmol). The reaction mixture was degassed with N$_2$ for 15 min and then heated to 80° C. for 19 h. The reaction mixture was allowed to cool to RT, filtered through Celite®, washed with EtOAc (5 ml) and then concentrated in vacuo. The crude product was purified by chromatography on silica gel (24 g cartridge, 0-10% EtOAc/isohexane) to afford the title compound (681 mg, 2.21 mmol, 75% yield, 90% purity) as a dark yellow oil. UPLC-MS (Method 1) m/z 278.1 (M+H)$^+$ at 1.86 min. $^1$H NMR (500 MHz, DMSO-d$_6$) δ 7.31 (dd, J=8.0, 0.9 Hz, 1H), 7.20 (d, J=3.9 Hz, 1H), 7.18 (d, J=3.9 Hz, 1H), 7.12 (d, J=1.9 Hz, 1H), 6.90-6.85 (m, 1H), 5.62 (br s, 2H).

Step 2: methyl 3-(N-(2-(5-chlorothiophen-2-yl)-5-(trifluoromethyl)phenyl)sulfamoyl)-4-methoxybenzoate: A solution of the product from Step 1 above (120 mg, 0.389 mmol, 90% purity), methyl 3-(chlorosulfonyl)-4-methoxybenzoate (134 mg, 0.506 mmol) and pyridine (160 μl, 1.98 mmol) in DCM (1.5 ml) was stirred at RT for 51 h. The reaction mixture was concentrated in vacuo and the crude product was purified by chromatography on silica gel (24 g cartridge, 0-30% EtOAc/isohexane) to afford the title compound (115 mg, 0.223 mmol, 57% yield, 98% purity) as a pale yellow solid. UPLC-MS (Method 1) m/z 504.1 (M–H)$^-$ at 1.78 min.

Step 3: 3-(N-(2-(5-chlorothiophen-2-yl)-5-(trifluoromethyl)phenyl)sulfamoyl)-4-methoxybenzoic acid: 1 M LiOH (aq) (910 µl, 0.91 mmol) was added to a solution of the product from Step 2 above (115 mg, 0.223 mmol, 98% purity) in THF (1.8 ml) at RT. The reaction mixture was stirred at RT over the weekend, and then concentrated in vacuo to remove the THF. The residue was diluted with water (6 ml) and then washed with DCM (6 ml). The aqueous phase was acidified using 1 M HCl(aq) until pH 4-5 and the product was extracted into EtOAc (3×6 ml). The combined organic extracts were dried over MgSO$_4$, filtered and concentrated in vacuo to afford the title compound (93.1 mg, 0.182 mmol, 82% yield, 96% purity) as a pale yellow solid. UPLC-MS (Method 1) m/z 490.1 (M−H)$^-$ at 1.62 min. $^1$H NMR (500 MHz, DMSO-d$_6$) δ 13.07 (br s, 1H), 9.97 (br s, 1H), 8.18 (dd, J=8.7, 2.2 Hz, 1H), 8.07 (d, J=2.2 Hz, 1H), 7.88 (d, J=8.3 Hz, 1H), 7.66 (br d, J=8.3 Hz, 1H), 7.45 (d, J=4.0 Hz, 1H), 7.35 (d, J=8.8 Hz, 1H), 7.14 (d, J=4.0 Hz, 1H), 7.06 (br s, 1H), 3.88 (s, 3H).

Example 88: 3-(N-(2-(5-chlorothiophen-2-yl)-5-(methylsulfonyl)phenyl)sulfamoyl)-4-methoxybenzoic acid

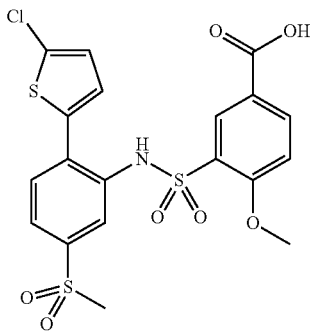 [SMILES: COc1ccc(C(=O)O)cc1S(=O)(=O)Nc1cc(S(C)(=O)=O)ccc1-c1ccc(Cl)s1]

Step 1: 2-(5-chlorothiophen-2-yl)-5-(methylsulfonyl)aniline: To the reaction vessel containing 2-bromo-5-(methylsulfonyl)aniline (700 mg, 2.80 mmol), (5-chlorothiophen-2-yl)boronic acid (1.35 g, 8.31 mmol), 1 M K$_3$PO$_4$(aq) (4.8 ml, 4.80 mmol) and dioxane (19 ml) was added PdCl$_2$[P(Cy)$_3$]$_2$ (99 mg, 0.134 mmol). The reaction mixture was degassed with N$_2$ for 15 min and then heated to 80° C. for 19 h. The reaction mixture was allowed to cool to RT, filtered through Celite®, washed with EtOAc (5 ml) and then concentrated in vacuo. The crude product was purified by chromatography on silica gel (24 g cartridge, 0-1% MeOH/DCM) to afford the title compound (664 mg, 1.75 mmol, 63% yield, 76% purity) as a pale yellow solid. UPLC-MS (Method 1) m/z 288.2 (M+H)$^+$ at 1.37 min. $^1$H NMR (500 MHz, DMSO-d$_6$) δ 7.36 (d, J=8.0 Hz, 1H), 7.33 (d, J=1.9 Hz, 1H), 7.22 (d, J=3.9 Hz, 1H), 7.19 (d, J=3.9 Hz, 1H), 7.09 (dd, J=8.0, 2.0 Hz, 1H), 5.72 (br s, 2H), 3.14 (s, 3H).

Step 2: methyl 3-(N-(2-(5-chlorothiophen-2-yl)-5-(methylsulfonyl)phenyl)sulfamoyl)-4-methoxybenzoate: A solution of the product from Step 1 above (120 mg, 0.317 mmol, 76% purity), methyl 3-(chlorosulfonyl)-4-methoxybenzoate (126 mg, 0.475 mmol) and pyridine (150 µl, 1.86 mmol) in DCM (1.5 ml) was stirred at RT for 6 days, and then concentrated in vacuo. The crude product was purified by chromatography on silica gel (40 g cartridge, 0-70% EtOAc/isohexane) and by chromatography (24 g reverse phase C18 cartridge, 15-65% MeCN/0.1% Formic acid) to afford the title compound (139 mg, 0.267 mmol, 84% yield, 99% purity) as an off-white foam. UPLC-MS (Method 1) m/z 516.1 (M+H)$^+$, 514.2 (M−H)$^-$ at 1.44 min.

Step 3: 3-(N-(2-(5-chlorothiophen-2-yl)-5-(methylsulfonyl)phenyl)sulfamoyl)-4-methoxybenzoic acid: 1 M LiOH (aq) (1.08 ml, 1.08 mmol) was added to a solution of the product from Step 2 above (139 mg, 0.267 mmol, 99% purity) in THF (2.2 ml) at RT. The reaction mixture was stirred at RT over the weekend, and then concentrated in vacuo to remove the THF. The residue was diluted with water (7 ml) and then washed with TBME (7 ml). The aqueous phase was acidified using 1 M HCl(aq) until pH 4-5 and the product was extracted into EtOAc (3×7 ml). The combined organic extracts were dried over MgSO$_4$, filtered and concentrated in vacuo to afford the title compound (106 mg, 0.207 mmol, 77% yield, 98% purity) as an off-white solid. UPLC-MS (Method 1) m/z 502.2 (M+H)$^+$, 500.1 (M−H)− at 1.29 min. $^1$H NMR (500 MHz, DMSO-d$_6$) δ 13.08 (br s, 1H); 10.02 (br s, 1H), 8.18 (dd, J=8.7, 2.2 Hz, 1H), 8.08 (d, J=2.2 Hz, 1H), 7.94 (d, J=8.3 Hz, 1H), 7.83 (br d, J=8.4 Hz, 1H), 7.50 (d, J=4.1 Hz, 1H), 7.36 (br d, J=8.7 Hz, 1H), 7.31 (br s, 1H), 7.15 (d, J=4.0 Hz, 1H), 3.90 (s, 3H), 3.07 (s, 3H).

Example 89: 3-(N-(2-(5-chlorothiophen-2-yl)-5-(methylsulfonyl)phenyl)sulfamoyl)-4-ethylbenzoic acid

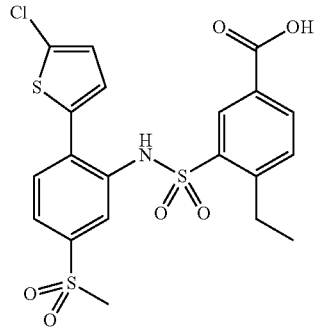 [SMILES: CCc1ccc(C(=O)O)cc1S(=O)(=O)Nc1cc(S(C)(=O)=O)ccc1-c1ccc(Cl)s1]

Step 1: methyl 4-ethyl-3-(N-(5-(methylsulfonyl)-2-(5-methylthiophen-2-yl)phenyl)sulfamoyl)benzoate: A solution of the product from Example 88 Step 1 (120 mg, 0.317 mmol, 76% purity), the product from Example 19 Step 2 (125 mg, 0.475 mmol) and pyridine (150 µl, 1.86 mmol) in DCM (1.5 ml) was stirred at RT for 10 days. The reaction mixture was concentrated in vacuo and the crude product was purified by chromatography on silica gel (24 g cartridge, 0-50% EtOAc/isohexane) and by chromatography (24 g reverse phase C18 cartridge, 15-85% MeCN/0.1% Formic acid) to afford the title compound (87.3 mg, 0.168 mmol, 53% yield, 99% purity) as an off-white solid. UPLC-MS (Method 1) m/z 514.3 (M+H)$^+$, 512.0 (M−H)$^-$ at 1.60 min.

Step 2: 3-(N-(2-(5-chlorothiophen-2-yl)-5-(methylsulfonyl)phenyl)sulfamoyl)-4-ethylbenzoic acid: 1 M LiOH (aq) (670 µl, 0.67 mmol) was added to a solution of the product from Step 1 above (87 mg, 0.168 mmol, 99% purity) in THF (1.3 ml) at RT. The reaction mixture was stirred at RT for 18 h, and then concentrated in vacuo to remove the THF. The residue was diluted with water (4 ml) and then washed with TBME (4 ml). The aqueous phase was acidified using 1 M HCl(aq) until pH 4-5 and the product was extracted into EtOAc (3×4 ml). The combined organic extracts were dried over MgSO$_4$, filtered and concentrated in vacuo to afford the title compound (69.8 mg, 0.138 mmol, 82% yield, 99% purity) as an off-white solid. UPLC-MS (Method 1) m/z 500.2 (M+H)$^+$, 498.0 (M–H)$^-$ at 1.45 min. $^1$H NMR (500 MHz, DMSO-d$_6$) δ 13.28 (br s, 1H), 10.36 (br s, 1H), 8.17 (br s, 1H), 8.14-8.06 (m, 1H), 7.93 (d, J=8.3 Hz, 1H), 7.88-7.78 (m, 1H), 7.58 (d, J=8.1 Hz, 1H), 7.47 (d, J=4.1 Hz, 1H), 7.17 (br s, 1H), 7.14 (d, J=4.0 Hz, 1H), 3.08 (s, 3H), 2.90 (q, J=7.4 Hz, 2H), 1.16 (t, J=7.4 Hz, 3H).

Example 90: 3-(N-(2-(5-chlorothiophen-2-yl)-5-cyanophenyl)sulfamoyl)-4-methoxybenzoic acid

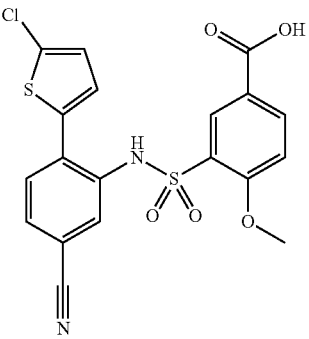 [SMILES: CCc1ccc(C(=O)O)cc1S(=O)(=O)Nc1cc(C#N)ccc1-c1ccc(Cl)s1]

Step 1: 3-amino-4-(5-chlorothiophen-2-yl)benzonitrile: To the reaction vessel containing 3-amino-4-bromobenzonitrile (700 mg, 3.55 mmol), (5-chlorothiophen-2-yl)boronic acid (1.73 g, 10.7 mmol), 1 M K$_3$PO$_4$(aq) (6 ml, 6.00 mmol) and dioxane (24 ml) was added PdCl$_2$[P(Cy)$_3$]$_2$ (131 mg, 0.178 mmol). The reaction mixture was degassed with N$_2$ for 15 min and then heated to 80° C. for 105 min. The reaction mixture was allowed to cool to RT, filtered through Celite®, rinsing with MeOH (10 ml) and then concentrated in vacuo. The crude product was purified by chromatography on silica gel (24 g cartridge, 0-30% EtOAc/isohexane) to afford the title compound (702 mg, 2.87 mmol, 81% yield, 96% purity) as a yellow solid. UPLC-MS (Method 1) m/z 235.2 (M+H)$^+$ at 1.58 min. $^1$H NMR (500 MHz, DMSO-d$_6$) δ 7.31 (d, J=7.9 Hz, 1H), 7.23 (d, J=3.9 Hz, 1H), 7.19 (d, J=3.9 Hz, 1H), 7.13 (d, J=1.7 Hz, 1H), 6.99 (dd, J=7.9, 1.7 Hz, 1H), 5.65 (br s, 2H).

Step 2: methyl 3-(N-(2-(5-chlorothiophen-2-yl)-5-cyanophenyl)sulfamoyl)-4-methoxybenzoate: A solution of the product from Step 1 above (110 mg, 0.45 mmol, 96% purity), methyl 3-(chlorosulfonyl)-4-methoxybenzoate (155 mg, 0.585 mmol) and pyridine (180 μl, 2.23 mmol) in DCM (1.5 ml) was stirred at RT for 6 days. The reaction mixture was concentrated in vacuo and the crude product was purified by chromatography on silica gel (24 g cartridge, 0-40% EtOAc/isohexane) and by chromatography (24 g reverse phase C18 cartridge, 15-65% MeCN/0.1% Formic acid) to afford the title compound (138 mg, 0.292 mmol, 65% yield, 98% purity) as a yellow solid. UPLC-MS (Method 1) m/z 461.1 (M–H)$^-$ at 1.57 min.

Step 3: 3-(N-(2-(5-chlorothiophen-2-yl)-5-cyanophenyl)sulfamoyl)-4-methoxybenzoic acid: 1 M LiOH (aq) (1.17 ml, 1.17 mmol) was added to a solution of the product from Step 2 above (138 mg, 0.292 mmol, 98% purity) in THF (2.3 ml) at RT. The reaction mixture was stirred at RT for 18 h, and then concentrated in vacuo to remove the THF. The residue was diluted with water (6 ml) and then washed with TBME (6 ml). The aqueous phase was acidified using 1 M HCl(aq) until pH 4-5 and the product was extracted into EtOAc (3×6 ml). The combined organic extracts were dried over MgSO$_4$, filtered and concentrated in vacuo to afford the title compound (118 mg, 0.249 mmol, 85% yield, 95% purity) as a yellow solid. UPLC-MS (Method 1) m/z 447.1 (M–H)$^-$ at 1.41 min. $^1$H NMR (500 MHz, DMSO-d$_6$) δ 13.09 (br s, 1H), 10.02 (br s, 1H), 8.18 (dd, J=8.7, 2.2 Hz, 1H), 8.08 (d, J=2.2 Hz, 1H), 7.86 (d, J=8.2 Hz, 1H), 7.78 (br d, J=8.4 Hz, 1H), 7.48 (d, J=4.1 Hz, 1H), 7.33 (d, J=8.8 Hz, 1H), 7.25 (d, J=1.7 Hz, 1H), 7.13 (d, J=4.1 Hz, 1H), 3.87 (s, 3H).

Example 91: 3-(N-(2-(5-chlorothiophen-2-yl)-5-cyanophenyl)sulfamoyl)-4-ethylbenzoic acid

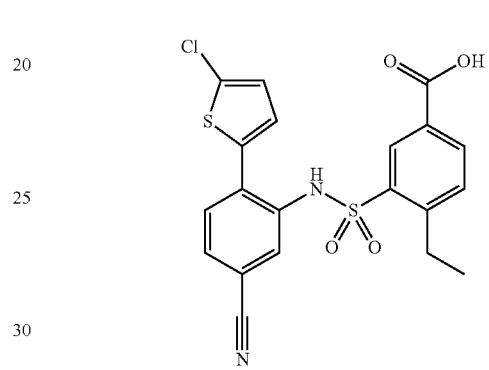

Step 1: Methyl 3-(N-(2-(5-chlorothiophen-2-yl)-5-cyanophenyl)sulfamoyl)-4-ethylbenzoate: A solution of the product from Example 90 Step 1 (110 mg, 0.45 mmol, 96% purity), the product from Example 19 Step 2 (154 mg, 0.585 mmol) and pyridine (180 μl, 2.23 mmol) in DCM (1.5 ml) was stirred at RT for 6 days. The reaction mixture was concentrated in vacuo and the crude product was purified by chromatography on silica gel (24 g cartridge, 0-40% EtOAc/isohexane) and by chromatography (24 g reverse phase C18 cartridge, 15-80% MeCN/0.1% Formic acid) to afford the title compound (144 mg, 0.312 mmol, 69% yield) as an off-white solid. UPLC-MS (Method 1) m/z 459.2 (M–H)$^-$ at 1.73 min.

Step 2: 3-(N-(2-(5-chlorothiophen-2-yl)-5-cyanophenyl)sulfamoyl)-4-ethylbenzoic acid: 1 M LiOH (aq) (1.25 ml, 1.25 mmol) was added to a solution of the product from Step 1 above (144 mg, 0.312 mmol) in THF (2.5 ml) at RT. The reaction mixture was stirred at RT for 16 h, and then concentrated in vacuo to remove the THF. The residue was diluted with water (7 ml) and then washed with TBME (7 ml). The aqueous phase was acidified using 1 M HCl(aq) until pH 4-5 and the product was extracted into EtOAc (3×7 ml). Following the addition of THF (10 ml) to obtain a clear solution, the combined organic extracts were dried over MgSO$_4$, filtered and concentrated in vacuo to afford the title compound (107 mg, 0.236 mmol, 76% yield, 99% purity) as an off-white solid. UPLC-MS (Method 1) m/z 445.2 (M–H)$^-$ at 1.58 min. $^1$H NMR (500 MHz, DMSO-d$_6$) δ 13.26 (br s, 1H), 10.39 (br s, 1H), 8.14 (br s, 1H), 8.09 (dd, J=8.0, 1.8 Hz, 1H), 7.82 (d, J=8.1 Hz, 1H), 7.78 (br s, 1H), 7.55 (d, J=8.0 Hz, 1H), 7.42 (d, J=4.1 Hz, 1H), 7.16 (d, J=1.6 Hz, 1H), 7.10 (d, J=4.0 Hz, 1H), 2.89 (q, J=7.4 Hz, 2H), 1.15 (t, J=7.4 Hz, 3H).

Example 92: 4-cyclopropyl-3-(N-(3'-fluoro-4-(trifluoromethyl)-[1,1'-biphenyl]-2-yl)sulfamoyl)benzoic acid

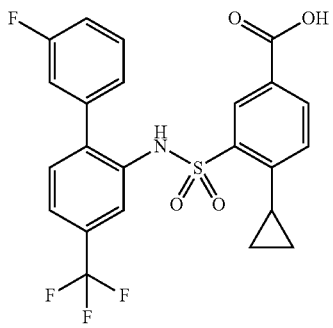 [SMILES: O=C(O)c1ccc(C2CC2)c(S(=O)(=O)Nc2cc(C(F)(F)F)ccc2-c2cccc(F)c2)c1]

Step 1: 3'-fluoro-4-(trifluoromethyl)-[1,1'-biphenyl]-2-amine: A mixture of 2-bromo-5-(trifluoromethyl)aniline (149 µl, 1.04 mmol), 3-fluorophenylboronic acid (189 mg, 1.35 mmol) and $K_3PO_4$ (663 mg, 3.12 mmol) in dioxane/water (3:1, 7.5 ml) was degassed under $N_2$ for 15 min. XPhos Pd G3 (41 mg, 0.052 mmol) was added and the mixture was heated to 80° C. and stirred overnight. The mixture was diluted with water (10 ml) and extracted with EtOAc (3×20 ml). The combined organic extracts were washed with brine (15 ml), dried by passage through a phase separator and concentrated in vacuo. The residue was purified by chromatography on silica gel (24 g cartridge, 0-50% EtOAc/isohexane) to afford the title compound (210 mg, 0.815 mmol, 78% yield, 99% purity) as a dark green oil. UPLC-MS (Method 1) m/z 256.2 $(M+H)^+$ at 1.69 min Step 2: methyl 4-bromo-3-(N-(3'-fluoro-4-(trifluoromethyl)-[1,1'-biphenyl]-2-yl)sulfamoyl)benzoate: A solution of the product from Step 1 above (150 mg, 0.582 mmol, 99% purity) in DCM (3 ml) and pyridine (282 µl, 3.49 mmol) was added to the product from Example 55 Step 3 (182 mg, 0.582 mmol) and the mixture was stirred at RT for 3 days. The solvent was removed in vacuo. The residue was purified by chromatography on silica gel (24 g cartridge, 0-50% EtOAc/isohexane) to afford the title compound (190 mg, 0.357 mmol, 61% yield) as a cream solid. UPLC-MS (Method 1) m/z 532.0 $(M-H)^-$ at 1.77 min.

Step 3: methyl 4-cyclopropyl-3-(N-(3'-fluoro-4-(trifluoromethyl)-[1,1'-biphenyl]-2-yl)sulfamoyl)benzoate: To a solution of the product from Step 2 above (190 mg, 0.357 mmol) in THE (4.5 ml) was added Pd-174 (26 mg, 0.036 mmol) and cyclopropylzinc bromide (0.5 M in THF) (2.86 ml, 1.43 mmol). The mixture was heated to 70° C. overnight. The reaction mixture was concentrated in vacuo onto silica. The residue was purified by chromatography on silica gel (24 g cartridge, 0-100% EtOAc/isohexane) to afford the title compound (69 mg, 0.12 mmol, 32% yield, 82% purity) as a colourless oil. UPLC-MS (Method 1) m/z 492.2 $(M-H)^-$ at 1.82 min.

Step 4: 4-cyclopropyl-3-(N-(3'-fluoro-4-(trifluoromethyl)-[1,1'-biphenyl]-2-yl)sulfamoyl)benzoic acid: LiOH (8.24 mg, 0.344 mmol) was added to a solution of the product from Step 3 above (69 mg, 0.12 mmol, 82% purity) in THE (5 ml) and water (5 ml) and the mixture was stirred at RT overnight. The mixture was acidified to pH 6 using 10% w/v citric acid(aq) and then concentrated in vacuo. The residue was purified by preparative HPLC (Waters, Acidic (0.1% Formic acid), Acidic, Waters X-Select Prep-C18, 5 µm, 19×50 mm column, 50-80% MeCN in Water) to afford the title compound (24.4 mg, 7.88 µmol, 44% yield, 98% purity) as a white solid. UPLC-MS (Method 1) m/z 480.3 $(M+H)^+$, 478.2 $(M-H)^-$ at 1.69 min. $^1$H NMR (500 MHz, DMSO-$d_6$) δ 13.17 (br s, 1H), 10.17 (br s, 1H), 8.11 (s, 1H), 7.97 (d, J=8.2 Hz, 1H), 7.68 (s, 1H), 7.52 (d, J=8.1 Hz, 1H), 7.41-7.31 (m, 1H), 7.29 (s, 1H), 7.20-6.97 (m, 4H), 2.65-2.56 (m, 1H), 1.10-0.97 (m, 2H), 0.85-0.74 (m, 2H).

Example 93: 4-cyclopropyl-3-(N-(3'-fluoro-4-(methylsulfonyl)-[1,1'-biphenyl]-2-yl)sulfamoyl)benzoic acid

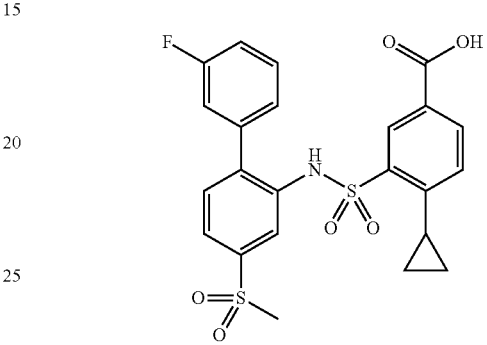

Step 1: 3'-fluoro-4-(methylsulfonyl)-[1,1'-biphenyl]-2-amine: A mixture of 2-bromo-5-(methylsulfonyl)aniline (250 mg, 1.00 mmol), 3-fluorophenylboronic acid (182 mg, 1.30 mmol) and $K_3PO_4$ (637 mg, 3.12 mmol) in dioxane/water (3:1, 7.5 ml) was degassed under $N_2$ for 15 min. XPhos Pd G3 (39 mg, 0.050 mmol) was added and the mixture was heated to 80° C. and stirred overnight. The mixture was diluted with water (10 ml) and extracted with EtOAc (3×20 ml). The combined organic extracts were washed with brine (15 ml), dried by passage through a phase separator and concentrated in vacuo. The residue was purified by chromatography on silica gel (24 g cartridge, 0-50% EtOAc/isohexane) to afford the title compound (230 mg, 0.867 mmol, 87% yield) as a cream solid. UPLC-MS (Method 1) m/z 266.2 $(M+H)^+$ at 1.20 min Step 2: Methyl 4-bromo-3-(N-(3'-fluoro-4-(methylsulfonyl)-[1,1'-biphenyl]-2-yl)sulfamoyl)benzoate: A solution of the product from Step 1 above (150 mg, 0.565 mmol) in DCM (3 ml) and pyridine (274 µl, 3.39 mmol) was added to the product from Example 55 Step 3 (177 mg, 0.565 mmol) and the mixture was stirred at RT for 3 days. The solvent was removed in vacuo. The residue was purified by chromatography on silica gel (24 g cartridge, 0-50% EtOAc/isohexane) to afford the title compound (110 mg, 0.203 mmol, 36% yield) as a yellow solid. UPLC-MS (Method 1) m/z 542.0 $(M-H)^-$ at 1.45 min.

Step 3: Methyl 4-cyclopropyl-3-(N-(3'-fluoro-4-(methylsulfonyl)-[1,1'-biphenyl]-2-yl)sulfamoyl)benzoate: To a solution of the product from Step 2 above (110 mg, 0.203 mmol) in THE (4.5 ml) was added Pd-174 (15 mg, 0.02 mmol) and cyclopropylzinc bromide (0.5 M in THF) (1.62 ml, 0.811 mmol). The mixture was heated to 70° C. overnight. The reaction mixture was concentrated in vacuo onto silica. The residue was purified by chromatography on silica gel (24 g cartridge, 0-100% EtOAc/isohexane) to afford the title compound (80 mg, 0.14 mmol, 68% yield, 88% purity) as a colourless oil. UPLC-MS (Method 1) m/z 502.2 $(M-H)^-$ at 1.82 min.

Step 4: 4-cyclopropyl-3-(N-(3'-fluoro-4-(methylsulfonyl)-[1,1'-biphenyl]-2-yl)sulfamoyl)benzoic acid: LiOH (10 mg, 0.419 mmol) was added to a solution of the product from Step 3 above (80 mg, 0.14 mmol, 88% purity) in THF (5 ml) and water (5 ml) and the mixture was stirred at RT overnight. The mixture was acidified to pH 6 using 10% w/v citric acid(aq) and then concentrated in vacuo. The residue was purified by preparative HPLC (Waters, Acidic (0.1% Formic acid), Acidic, Waters X-Select Prep-C18, 5 μm, 19×50 mm column, 35-65% MeCN in Water) to afford the title compound (19.4 mg, 0.039 mmol, 27% yield, 98% purity) as a white solid. UPLC-MS (Method 1) m/z 511.9 (M+Na)$^+$, 488.2 (M−H)$^-$ at 1.39 min. $^1$H NMR (500 MHz, DMSO-d$_6$) δ 13.12 (br s, 1H), 10.21 (br s, 1H), 8.15 (d, J=9.6 Hz, 1H), 7.93 (d, J=8.3 Hz, 1H), 7.85-7.70 (m, 1H), 7.62 (s, 1H), 7.52 (s, 1H), 7.39-7.31 (m, 1H), 7.21-7.07 (m, 3H), 7.02 (s, 1H), 3.12 (s, 3H), 2.67-2.56 (m, 1H), 1.08-0.95 (m, 2H), 0.81 (d, J=5.2 Hz, 2H).

Example 94: 3-(N-(4-cyano-3'-fluoro-[1,1-biphenyl]-2-yl)sulfamoyl)-4-cyclopropylbenzoic acid

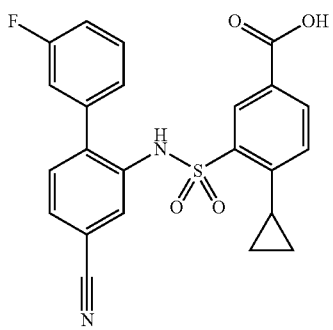 [SMILES: N#Cc1ccc(-c2cccc(F)c2)c(NS(=O)(=O)c2cc(C(=O)O)ccc2C2CC2)c1]

Step 1: 2-amino-3'-fluoro-[1,1'-biphenyl]-4-carbonitrile: A mixture of 3-amino-4-bromobenzonitrile (250 mg, 1.27 mmol), 3-fluorophenylboronic acid (231 mg, 1.65 mmol) and K$_3$PO$_4$ (808 mg, 3.81 mmol) in dioxane/water (3:1, 7.5 ml) was degassed under N$_2$ for 15 min. XPhos Pd G3 (50 mg, 0.063 mmol) was added and the mixture was heated to 80° C. and stirred overnight. The mixture was diluted with water (10 ml) and extracted with EtOAc (3×20 ml). The combined organic extracts were washed with brine (15 ml), dried by passage through a phase separator and concentrated in vacuo. The residue was purified by chromatography on silica gel (24 g cartridge, 0-50% EtOAc/isohexane) to afford the title compound (256 mg, 1.21 mmol, 95% yield) as a pale brown solid. UPLC-MS (Method 1) m/z 213.3 (M+H)$^+$ at 1.42 min.

Step 2: methyl 4-bromo-3-(N-(4-cyano-3'-fluoro-[1,1'-biphenyl]-2-yl)sulfamoyl)benzoate: A solution of the product from Step 1 above (150 mg, 0.707 mmol) in DCM (3 ml) and pyridine (343 μl, 4.24 mmol) was added the product from Example 55 Step 3 (222 mg, 0.707 mmol) and the mixture was stirred at RT for 3 days. The solvent was removed in vacuo. The residue was purified by chromatography on silica gel (24 g cartridge, 0-50% EtOAc/isohexane) to afford the title compound (190 mg, 0.388 mmol, 55% yield) as a cream solid. UPLC-MS (Method 1) m/z 489.1 (M−H)$^-$ at 1.55 min.

Step 3: methyl 3-(N-(4-cyano-3'-fluoro-[1,1'-biphenyl]-2-yl)sulfamoyl)-4-cyclopropylbenzoate: To a solution of the product from Step 2 above (190 mg, 0.388 mmol) in THF (4.5 ml) was added Pd-174 (28 mg, 0.039 mmol) and cyclopropylzinc bromide (0.5 M in THF) (3.11 ml, 1.55 mmol). The mixture was heated to 70° C. overnight. The reaction mixture was concentrated in vacuo onto silica. The residue was purified by chromatography on silica gel (24 g cartridge, 0-100% EtOAc/isohexane) to afford the title compound (140 mg, 0.158 mmol, 41% yield, 51% purity) as a cream solid. UPLC-MS (Method 1) m/z 449.2 (M−H)$^-$ at 1.64 min.

Step 4: 3-(N-(4-cyano-3'-fluoro-[1,1'-biphenyl]-2-yl)sulfamoyl)-4-cyclopropylbenzoic acid: LiOH (11 mg, 0.475 mmol) was added to a solution of the product from Step 3 above (140 mg, 0.158 mmol, 51% purity) in THF (5 ml) and water (5 ml) and the mixture was stirred at RT overnight. The mixture was acidified to pH 6 using 10% w/v citric acid(aq) and then concentrated in vacuo. The residue was purified by preparative HPLC (Waters, Acidic (0.1% Formic acid), Acidic, Waters X-Select Prep-C18, 5 μm, 19×50 mm column, 35-65% MeCN in Water) to afford the title compound (16 mg, 0.036 mmol, 22% yield, 96% purity) as a white solid. UPLC-MS (Method 1) m/z 437.2 (M+H)$^+$, 435.2 (M−H)$^-$ at 1.69 min. UPLC-MS (Method 1) m/z 437.6 (M+H)$^+$ at 1.49 min. $^1$H NMR (500 MHz, DMSO-d$_6$) δ 13.17 (br s, 1H), 10.23 (br s, 1H), 8.08 (d, J=1.9 Hz, 1H), 7.94 (dd, J=8.2, 1.9 Hz, 1H), 7.79-7.71 (m, 1H), 7.52 (d, J=1.7 Hz, 1H), 7.47 (d, J=8.0 Hz, 1H), 7.34-7.27 (m, 1H), 7.13-7.06 (m, 1H), 7.02 (dd, J=8.0 Hz, 3H), 2.65-2.55 (m, 1H), 1.04-0.95 (m, 2H), 0.83-0.75 (m, 2H).

Example 95: 3-(N-(5-cyano-2-(5-methylthiophen-2-yl)phenyl)sulfamoyl)-4-cyclopropylbenzoic acid

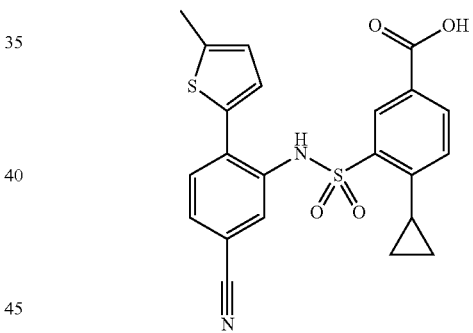

Step 1: Methyl 4-bromo-3-(N-(5-cyano-2-(5-methylthiophen-2-yl)phenyl)sulfamoyl)benzoate: A mixture of the product from Example 80 Step 1 (200 mg, 0.831 mmol, 89% purity), the product from Example 55 Step 3 (342 mg, 1.08 mmol) and pyridine (200 μl, 2.47 mmol) in DCM (5 ml) was stirred at 35° C. for 4 days. The mixture was concentrated in vacuo onto silica and purified by chromatography on silica gel (12 g cartridge, 0-100% EtOAc/isohexane) to afford the title compound (213 mg, 0.381 mmol, 45% yield, 88% purity) as a yellow foam. UPLC-MS (Method 1) m/z 489.0 (M−H)$^-$ at 1.63 min.

Step 2: methyl 3-(N-(5-cyano-2-(5-methylthiophen-2-yl)phenyl)sulfamoyl)-4-cyclopropylbenzoate: To a mixture of the product from Step 1 above (213 mg, 0.381 mmol, 88% purity) and Pd-174 (28 mg, 0.039 mmol) in THF (6 ml) was added cyclopropylzinc(II) bromide (0.5 M in THF) (3.10 ml, 1.55 mmol) and the mixture was heated to 60° C. and stirred for 4 h. The mixture was loaded onto silica and purified by chromatography on silica gel (12 g cartridge, 0-50% EtOAc/isohexane) to afford the title compound (103 mg, 0.127 mmol, 32% yield, 56% purity) as a yellow oil. UPLC-MS (Method 1) m/z 451.1 (M–H)⁻ at 1.69 min.

Step 3: 3-(N-(5-cyano-2-(5-methylthiophen-2-yl)phenyl)sulfamoyl)-4-cyclopropylbenzoic acid: A mixture of the product from Step 2 above (103 mg, 0.127 mmol, 56% purity) and LiOH (22 mg, 0.514 mmol) in THF/MeOH/water (4:1:1, 2.7 ml) was stirred at 40° C. overnight. The mixture was diluted with water (5 ml), acidified to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (24.6 mg, 0.056 mmol, 43% yield, 99% purity) as a light yellow solid. UPLC-MS (Method 1) m/z 439.4 (M+H)⁺, 437.1 (M–H)⁻ at 1.53 min. ¹H NMR (500 MHz, DMSO-d₆) δ 13.20 (s, 1H), 10.23 (s, 1H), 8.22-8.16 (m, 1H), 7.99 (d, J=8.3 Hz, 1H), 7.73 (d, J=5.5 Hz, 2H), 7.36 (d, J=3.7 Hz, 1H), 7.19-7.16 (m, 1H), 7.09 (d, J=8.3 Hz, 1H), 6.75 (dd, J=3.7, 1.2 Hz, 1H), 2.68-2.65 (m, 1H), 2.42 (s, 3H), 1.06-1.00 (m, 2H), 0.87-0.81 (m, 2H).

Example 96: 3-(N-(4-cyano-[1,1'-biphenyl]-2-yl)sulfamoyl)-4-cyclopropylbenzoic acid

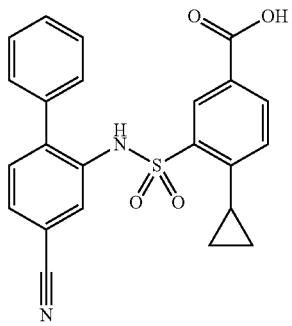 [SMILES: N#Cc1ccc(-c2ccccc2)c(NS(=O)(=O)c2cc(C(=O)O)ccc2C2CC2)c1]

Step 1: 2-amino-[1,1'-biphenyl]-4-carbonitrile: A mixture of 3-amino-4-bromobenzonitrile (250 mg, 1.27 mmol), phenylboronic acid (200 mg, 1.64 mmol) and 1 M K₃PO₄(aq) (2.2 ml, 2.20 mmol) in dioxane (10 ml) was degassed with N₂ for 15 min. XPhos Pd G3 (54 mg, 0.064 mmol) was added and the mixture was degassed with N₂ for 5 min and then heated to 80° C. and stirred for 90 min and then at RT overnight. The reaction mixture was diluted with water (5 ml) and saturated NH₄Cl(aq) (15 ml) and extracted with EtOAc (3×20 ml). The combined organic extracts were washed with brine (10 ml), dried by passage through a phase separator and the solvent removed in vacuo. The residue was loaded onto silica and purified by chromatography on silica gel (12 g cartridge, 0-50% EtOAc/isohexane) to afford the title compound (240 mg, 1.24 mmol, 97% yield) as a yellow oil. UPLC-MS (Method 1) m/z 195.1 (M+H)⁺ at 1.37 min.

Step 2: methyl 4-bromo-3-(N-(4-cyano-[1,1'-biphenyl]-2-yl)sulfamoyl)benzoate: A mixture of the product from Step 1 above (240 mg, 1.20 mmol), the product from Example 55 Step 3 (493 mg, 1.56 mmol) and pyridine (300 μl, 3.71 mmol) in DCM (7 ml) was stirred at 35° C. for 4 days. The mixture was concentrated in vacuo onto silica and purified by chromatography on silica gel (12 g cartridge, 0-50% EtOAc/isohexane) to afford the title compound (417 mg, 0.867 mmol, 72% yield, 98% purity) as a yellow oil. UPLC-MS (Method 1) m/z 469.0 (M–H)⁻ at 1.59 min.

Step 3: methyl 3-(N-(4-cyano-[1,1'-biphenyl]-2-yl)sulfamoyl)-4-cyclopropylbenzoate: To a mixture of the product from Step 2 above (200 mg, 0.416 mmol, 98% purity) and Pd-174 (30 mg, 0.042 mmol) in THF (6 ml) was added cyclopropylzinc(II) bromide (0.5 M in THF) (3.3 ml, 1.65 mmol) and the mixture was heated to 60° C. and stirred for 4 h. The mixture was loaded onto silica and purified by chromatography on silica gel (12 g cartridge, 0-50% EtOAc/isohexane) to afford the title compound (101 mg, 0.163 mmol, 39% yield, 70% purity) as a brown oil. UPLC-MS (Method 1) m/z 431.2 (M–H)⁻ at 1.64 min.

Step 4: 3-(N-(4-cyano-[1,1'-biphenyl]-2-yl)sulfamoyl)-4-cyclopropylbenzoic acid: A mixture of the product from Step 3 above (101 mg, 0.163 mmol, 70% purity) and LiOH (28 mg, 0.654 mmol) in THF/MeOH/water (4:1:1, 3.3 ml) was stirred at 40° C. for overnight. The mixture was diluted with water (5 ml), acidified to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (35.5 mg, 0.084 mmol, 51% yield, 99% purity) as a white solid. UPLC-MS (Method 1) m/z 417.1 (M–H)⁻ at 1.48 min. ¹H NMR (500 MHz, DMSO-d₆) δ 13.18 (s, 1H), 10.12 (s, 1H), 8.11-8.07 (m, 1H), 7.95 (dd, J=8.2, 1.9 Hz, 1H), 7.83-7.71 (m, 1H), 7.46 (d, J=8.0 Hz, 1H), 7.42 (d, J=1.7 Hz, 1H), 7.32-7.27 (m, 3H), 7.27-7.21 (m, 2H), 7.03 (d, J=8.2 Hz, 1H), 2.58-2.53 (m, 1H), 1.04-0.96 (m, 2H), 0.83-0.77 (m, 2H).

Example 97: 3-(N-(5-cyano-2-(pyridin-3-yl)phenyl)sulfamoyl)-4-cyclopropylbenzoic acid

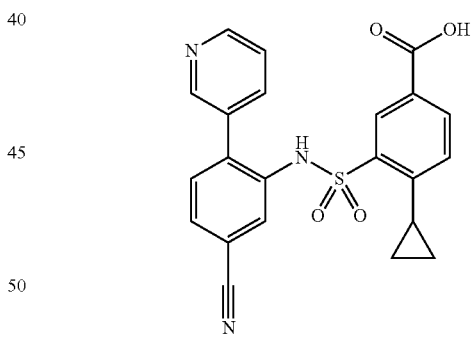

Step 1: 3-amino-4-(pyridin-3-yl)benzonitrile: A mixture of 3-amino-4-bromobenzonitrile (250 mg, 1.27 mmol), pyridin-3-ylboronic acid (200 mg, 1.63 mmol) and 1 M K₃PO₄(aq) (2.2 ml, 2.20 mmol) in dioxane (10 ml) was degassed with N₂ for 15 min. XPhos Pd G3 (54 mg, 0.064 mmol) was added and the mixture was degassed with N₂ for 5 min, heated to 80° C. for 90 min and then allowed to cool to RT overnight. The mixture was diluted with water (5 ml) and saturated NH₄Cl(aq) (15 ml) and extracted with EtOAc (3×20 ml). The combined organic extracts were washed with brine (10 ml), dried by passage through a phase separator and the solvent removed in vacuo. The residue was loaded onto silica and purified by chromatography on silica gel (12 g cartridge, 0-100% EtOAc/isohexane) to afford the title compound (208 mg, 0.756 mmol, 59% yield, 71% purity) as a yellow oil. UPLC-MS (Method 1) m/z 196.1 (M+H)⁺ at 0.49 min.

Step 2: methyl 4-bromo-3-(N-(5-cyano-2-(pyridin-3-yl)phenyl)sulfamoyl)benzoate: A mixture of the product from Step 1 above (208 mg, 0.756 mmol, 71% purity), the product from Example 55 Step 3 (311 mg, 0.983 mmol) and pyridine (180 µl, 2.23 mmol) in DCM (4.5 ml) was stirred at 35° C. for 4 days. The mixture was concentrated in vacuo onto silica and purified by chromatography on silica gel (12 g cartridge, 0-5% MeOH/DCM) and then by chromatography on 24 g reverse phase cartridge (5-50% MeCN/Water 0.1% Formic Acid) to afford the title compound (51 mg, 0.108 mmol, 14% yield) as a yellow solid. UPLC-MS (Method 1) m/z 472.1 (M+H)⁺, 470.0 (M−H)⁻ at 1.09 min.

Step 3: methyl 3-(N-(5-cyano-2-(pyridin-3-yl)phenyl)sulfamoyl)-4-cyclopropylbenzoate: To a mixture of the product from Step 2 above (51 mg, 0.108 mmol) and Pd-174 (8 mg, 0.011 mmol) in THF (6 ml) was added cyclopropylzinc(II) bromide (0.5 M in THF) (900 µl, 0.450 mmol) and the mixture was heated to 60° C. and stirred for 4 h. The residue was loaded onto silica and purified by chromatography on silica gel (4 g cartridge, 0-100% EtOAc/isohexane) to afford the title compound (41 mg, 0.095 mmol, 88% yield) as a brown oil. UPLC-MS (Method 1) m/z 434.2 (M+H)⁺, 432.1 (M−H)⁻ at 1.15 min.

Step 4: 3-(N-(5-cyano-2-(pyridin-3-yl)phenyl)sulfamoyl)-4-cyclopropylbenzoic acid: A mixture of the product from Step 3 above (41 mg, 0.095 mmol) and LiOH (16 mg, 0.374 mmol) in THF/MeOH/water (4:1:1, 2.1 ml) was stirred at 40° C. overnight. The mixture was diluted with water (5 ml), acidified to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 20-50% MeCN in Water) to afford the title compound (1.9 mg, 4.48 µmol, 4% yield, 99% purity) as a white solid. UPLC-MS (Method 1) m/z 420.2 (M+H)⁺, 418.1 (M−H)⁻ at 0.97 min. ¹H NMR (500 MHz, DMSO-d₆) δ 13.18 (s, 1H), 10.29 (s, 1H), 8.51-8.42 (m, 2H), 8.17-8.06 (m, 1H), 7.94 (d, J=8.3 Hz, 1H), 7.87-7.76 (m, 1H), 7.72-7.62 (m, 1H), 7.57-7.50 (m, 1H), 7.46 (d, J=1.6 Hz, 1H), 7.37-7.30 (m, 1H), 7.08-6.94 (m, 1H), 2.55-2.54 (m, 1H), 1.00 (d, J=8.2 Hz, 2H), 0.81 (s, 2H).

Example 98: 4-cyclopropyl-3-(N-(2-(pyridin-3-yl)-5-(trifluoromethyl)phenyl) sulfamoyl)benzoic acid

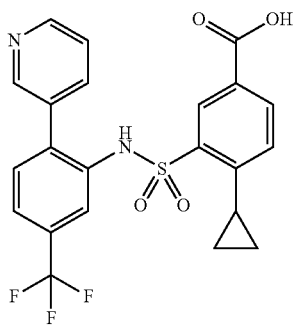

Step 1: 2-(pyridin-3-yl)-5-(trifluoromethyl)aniline: A mixture of 2-bromo-5-(trifluoromethyl)aniline (149 µl, 1.04 mmol), pyridin-3-ylboronic acid (166 mg, 1.35 mmol) and 1 M K₃PO₄(aq) (1.8 ml, 1.80 mmol) in dioxane (8 ml) was degassed with N₂ for 15 min. XPhos Pd G3 (44 mg, 0.052 mmol) was added and the mixture was degassed with N₂ for 5 min and then heated to 80° C. and stirred for 90 min and then at RT overnight. Upon cooling to RT the mixture was diluted with water (5 ml) and saturated NH₄Cl(aq) (15 ml) and extracted with EtOAc (3×20 ml). The combined organic extracts were washed with brine (10 ml), dried by passage through a phase separator and the solvent removed in vacuo. The residue was loaded onto silica and purified by chromatography on silica gel (12 g cartridge, 0-100% EtOAc/isohexane) to the title compound (216 mg, 0.716 mmol, 68% yield, 79% purity) as a yellow oil. UPLC-MS (Method 1) m/z 239.1 (M+H)⁺ at 0.87 min.

Step 2: Methyl 4-bromo-3-(N-(2-(pyridin-3-yl)-5-(trifluoromethyl)phenyl)sulfamoyl)benzoate: A mixture the product from Step 1 above (216 mg, 0.716 mmol, 79% purity), the product from Example 55 Step 3 (295 mg, 0.931 mmol) and pyridine (180 µl, 2.23 mmol) in DCM (4.5 ml) was stirred at 35° C. for 4 days. The mixture was concentrated in vacuo onto silica and purified by chromatography on silica gel (12 g cartridge, 0-5% MeOH/DCM) and then by chromatography on 24 g reverse phase cartridge (5-50% MeCN/Water 0.1% Formic Acid) to afford the title compound (81 mg, 0.141 mmol, 19% yield, 90% purity) as a yellow solid. UPLC-MS (Method 1) m/z 515.1 (M+H)⁺, 513.0 (M−H)⁻ at 1.32 min.

Step 3: Methyl 4-cyclopropyl-3-(N-(2-(pyridin-3-yl)-5-(trifluoromethyl)phenyl)sulfamoyl)benzoate: To a mixture of the product from Step 2 above (81 mg, 0.141 mmol, 90% purity) and Pd-174 (10 mg, 0.014 mmol) in THF (6 ml) was added cyclopropylzinc(II) bromide (0.5 M in THF) (1.1 ml, 0.550 mmol) and the mixture was heated to 60° C. and stirred for 4 h. The residue was loaded onto silica and purified by chromatography on silica gel (4 g cartridge, 0-100% EtOAc/isohexane) to afford the title compound (50 mg, 0.10 mmol, 70% yield, 95% purity) as a brown oil. UPLC-MS (Method 1) m/z 477.1 (M+H)⁺, 475.1 (M−H)⁻ at 1.37 min.

Step 4: 4-cyclopropyl-3-(N-(2-(pyridin-3-yl)-5-(trifluoromethyl)phenyl)sulfamoyl)benzoic acid: A mixture the product from Step 3 above (50 mg, 0.10 mmol, 95% purity) and LiOH (17 mg, 0.398 mmol) in THF/MeOH/water (4:1:1, 2.1 ml) was stirred at 40° C. overnight. The mixture was diluted with water (5 ml), acidified to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 20-50% MeCN in Water) to afford the title compound (15.5 mg, 0.033 mmol, 33% yield, 99% purity) as a light yellow solid. UPLC-MS (Method 1) m/z 463.1 (M+H)⁺, 461.1 (M−H)⁻ at 1.20 min. ¹H NMR (500 MHz, DMSO-d₆) δ 13.19 (s, 1H), 10.25 (s, 1H), 8.55-8.49 (m, 2H), 8.15-8.12 (m, 1H), 7.97 (dd, J=8.2, 1.9 Hz, 1H), 7.76-7.70 (m, 1H), 7.70-7.64 (m, 1H), 7.57 (d, J=8.0 Hz, 1H), 7.39 (dd, J=7.9, 4.8 Hz, 1H), 7.25-7.22 (m, 1H), 7.07 (d, J=8.2 Hz, 1H), 2.63-2.58 (m, 1H), 1.07-0.99 (m, 2H), 0.85-0.78 (m, 2H).

Example 99: 3-(N-(2-pyrrol-1-yl-5-(trifluoromethyl)phenyl)sulfamoyl)-4-cyclopropylbenzoic acid

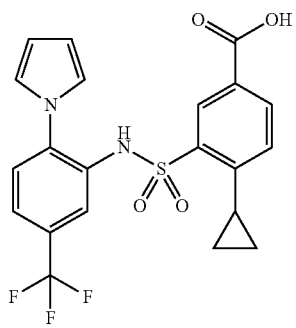 [SMILES: O=C(O)c1ccc(C2CC2)c(S(=O)(=O)Nc2cc(C(F)(F)F)ccc2-n2cccc2)c1]

Step 1: methyl 4-bromo-3-(N-(2-((tert-butoxycarbonyl)amino)-5-(trifluoromethyl)phenyl)sulfamoyl)benzoate: A mixture of tert-butyl (2-amino-4-(trifluoromethyl)phenyl)carbamate (200 mg, 0.724 mmol), the product from Example 55 Step 3 (300 mg, 0.947 mmol) and pyridine (180 µl, 2.23 mmol) in DCM (4.5 ml) was stirred at 35° C. overnight. The mixture was concentrated in vacuo onto silica and was purified by chromatography on silica gel (12 g cartridge, 0-50% EtOAc/isohexane) to afford the title compound (412 mg, 0.596 mmol, 82% yield, 80% purity) as a white foam. UPLC-MS (Method 1) m/z 453.1 (M+H-Boc)$^+$, 551.0 (M–H)$^-$ at 1.80 min.

Step 2: methyl 3-(N-(2-amino-5-(trifluoromethyl)phenyl)sulfamoyl)-4-bromobenzoate: A mixture of the product from Step 1 above (412 mg, 0.596 mmol, 80% purity) in TFA (1.1 ml) and DCM (11 ml) was stirred at RT overnight. The mixture was concentrated in vacuo onto silica and purified by chromatography on silica gel (12 g cartridge, 0-100% EtOAc/isohexane) to afford the title compound (303 mg, 0.535 mmol, 90% yield, 80% purity) as a light orange oil. UPLC-MS (Method 1) m/z 453.0 (M+H)$^+$, 451.0 (M–H)$^-$ at 1.44 min. 5 Step 3: methyl 3-(N-(2-(pyrrol-1-yl)-5-(trifluoromethyl)phenyl)sulfamoyl)-4-bromobenzoate: A mixture of the product from Step 2 above (303 mg, 0.535 mmol, 80% purity) and 2,5-dimethoxytetrahydrofuran (100 µl, 0.772 mmol) in AcOH (1 ml) was heated to 120° C. and stirred for 2 h. Upon cooling to RT the mixture was concentrated in vacuo onto silica and purified by chromatography on silica gel (12 g cartridge, 0-50% EtOAc/isohexane) to afford the title compound (104 mg, 0.141 mmol, 26% yield, 68% purity) as a pale brown solid. UPLC-MS (Method 1) m/z 503.0 (M+H)$^+$, 501.0 (M–H)$^-$ at 1.72 min.

Step 4: methyl 3-(N-(2-(pyrrol-1-yl)-5-(trifluoromethyl)phenyl)sulfamoyl)-4-cyclopropylbenzoate: To a mixture of the product from Step 3 above (104 mg, 0.141 mmol, 68% purity) and Pd-174 (10 mg, 0.014 mmol) in THF (6 ml) was added cyclopropylzinc(II) bromide (0.5 M in THF) (1.1 ml, 0.550 mmol) and the mixture was heated to 60° C. and stirred for 4 h. The residue was loaded onto silica and purified by chromatography on silica gel (4 g cartridge, 0-50% EtOAc/isohexane) to afford the title compound (42 mg, 0.059 mmol, 41% yield, 65% purity) as a yellow oil. UPLC-MS (Method 1) m/z 465.0 (M+H)$^+$, 463.1 (M–H)$^-$ at 1.77 min.

Step 5: 3-(N-(2-(pyrrol-1-yl)-5-(trifluoromethyl)phenyl)sulfamoyl)-4-cyclopropylbenzoic acid: A mixture of the product from Step 4 above (42 mg, 0.059 mmol, 65% purity) and LiOH (10 mg, 0.234 mmol) in THF/MeOH/water (4:1:1, 1.2 ml) was stirred at 40° C. overnight. The mixture was diluted with water (5 ml), acidified to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (15.1 mg, 0.033 mmol, 56% yield, 99% purity) as a white solid. UPLC-MS (Method 1) m/z 451.1 (M+H)$^+$, 449.1 (M–H)$^-$ at 1.61 min. $^1$H NMR (500 MHz, DMSO-d$_6$) δ 13.20 (s, 1H), 10.30 (s, 1H), 8.23-8.19 (m, 1H), 8.01 (d, J=7.9 Hz, 1H), 7.75-7.65 (m, 1H), 7.59-7.51 (m, 1H), 7.17-7.09 (m, 2H), 7.08-7.05 (m, 2H), 6.20-6.17 (m, 2H), 2.72-2.65 (m, 1H), 1.10-1.05 (m, 2H), 0.88-0.84 (m, 2H).

Example 100: 3-(N-(5-cyano-2-(5-fluorothiophen-2-yl)phenyl)sulfamoyl)-4-methoxybenzoic acid

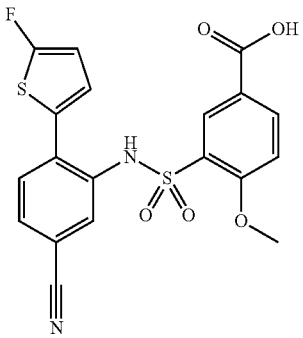

Step 1: 3-amino-4-(5-fluorothiophen-2-yl)benzonitrile: A mixture of 3-amino-4-bromobenzonitrile (700 mg, 3.55 mmol), 2-(5-fluorothiophen-2-yl)-4,4,5,5-tetramethyl-1,3,2-dioxaborolane (972 mg, 4.26 mmol) and K$_3$PO$_4$ (2.26 g, 10.7 mmol) in dioxane (5 ml) and water (1 ml) was degassed with N$_2$ for 15 min. XPhos Pd G3 (150 mg, 0.180 mmol) was added, the mixture was degassed with N$_2$ for 5 min and then heated to 80° C. for 2 h. The reaction was concentrated in vacuo. The residue was purified by chromatography on silica gel (40 g cartridge, 0-50% EtOAc/isohexane) to afford the title compound (750 mg, 3.33 mmol, 94% yield, 97% purity) as a tan solid. UPLC-MS (Method 1) m/z 219.2 (M+H)$^+$ at 1.45 min.

Step 2: methyl 3-(N-(5-cyano-2-(5-fluorothiophen-2-yl)phenyl)sulfamoyl)-4-methoxybenzoate: A solution of the product from Step 1 above (150 mg, 0.667 mmol, 97% purity) in DCM (3 ml) and pyridine (324 µl, 4.00 mmol) were added to a solution of methyl-3-(chlorosulfonyl)-4-methoxybenzoate (176 mg, 0.667 mmol) in DCM (3 ml) and the solution was stirred at RT for 2 days. The reaction mixture was concentrated in vacuo. The residue was purified by chromatography on silica gel (24 g cartridge, 0-50% EtOAc/isohexane) to afford the title compound (171 mg, 0.381 mmol, 57% yield) as a pale brown solid. UPLC-MS (Method 1) m/z 445.1 (M–H)$^-$ at 1.50 min.

Step 3: 3-(N-(5-cyano-2-(5-fluorothiophen-2-yl)phenyl)sulfamoyl)-4-methoxybenzoic acid: 1 M LiOH(aq) (1.14 ml, 1.14 mmol) was added to a solution of the product from Step 2 above (171 mg, 0.381 mmol) in THF (5 ml) and the mixture was stirred at RT overnight. The mixture was acidified to pH 6 using 10% w/v citric acid(aq) and the Example 101: 3-(N-(5-cyano-2-(5-fluorothiophen-2-yl)phenyl)sulfamoyl)-4-ethylbenzoic acid

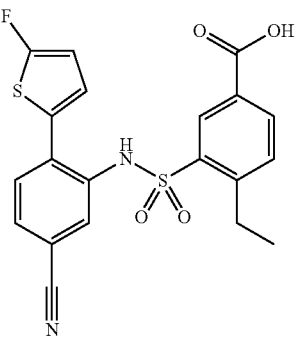

Step 1: methyl 3-(N-(5-cyano-2-(5-fluorothiophen-2-yl)phenyl)sulfamoyl)-4-ethylbenzoate: A solution of the product from Example 100 Step 1 (150 mg, 0.667 mmol, 97% purity) in DCM (3 ml) and pyridine (324 μl, 4.00 mmol) were added to a solution of the product from Example 19 Step 2 (175 mg, 0.667 mmol) in DCM (3 ml) and the solution was stirred at RT for 2 days. The reaction mixture was concentrated in vacuo. The residue was purified by chromatography on silica gel (24 g cartridge, 0-50% EtOAc/isohexane) to afford the title compound (135 mg, 0.292 mmol, 44% yield, 96% purity) as a light brown solid. UPLC-MS (Method 1) m/z 443.2 (M−H)⁻ at 1.65 min.

Step 2: 3-(N-(5-cyano-2-(5-fluorothiophen-2-yl)phenyl)sulfamoyl)-4-ethylbenzoic acid: 1 M LiOH(aq) (875 μl, 0.875 mmol) was added to a solution of the product from Step 1 above (135 mg, 0.292 mmol, 96% purity) in THF (5 ml) and the mixture was stirred at RT overnight. The mixture was acidified to pH 6 using 10% w/v citric acid(aq) and the resultant precipitate was collected. The residue was purified by preparative HPLC (Waters, Acidic (0.1% Formic acid), Acidic, Waters X-Select Prep-C18, 5 μm, 19×50 mm column, 35-65% MeCN in Water) to afford the title compound (59.7 mg, 0.137 mmol, 47% yield, 99% purity) as a white solid. UPLC-MS (Method 1) m/z 429.3 (M−H)⁻ at 1.58 min. ¹H NMR (500 MHz, DMSO-d₆) δ 13.28 (br s, 1H), 10.36 (br s, 1H), 8.17 (s, 1H), 8.10 (d, J=8.1 Hz, 1H), 7.83 (d, J=8.1 Hz, 2H), 7.58 (d, J=8.0 Hz, 1H), 7.30 (t, J=4.1 Hz, 1H), 7.11 (s, 1H), 6.75 (dd, J=4.3, 2.2 Hz, 1H), 2.91 (d, J=7.5 Hz, 2H), 1.16 (t, J=7.4 Hz, 3H).

Example 102: 3-(N-(5-cyano-2-(5-fluorothiophen-2-yl)phenyl)sulfamoyl)-4-cyclopropylbenzoic acid

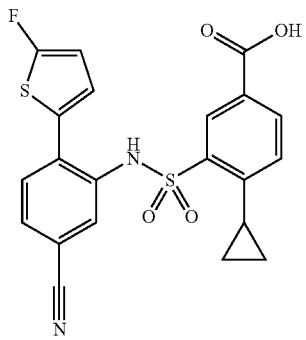

Step 1: methyl 4-bromo-3-(N-(5-cyano-2-(5-fluorothiophen-2-yl)phenyl)sulfamoyl)benzoate: A solution of the product from Example 100 Step 1 (200 mg, 0.889 mmol, 97% purity) in DCM (3 ml) and pyridine (431 μl, 5.33 mmol) was added to the product from Example 55 Step 3 (279 mg, 0.889 mmol) and the solution was stirred at RT for 2 days. The solvent was removed in vacuo. The residue was purified by chromatography on silica gel (24 g cartridge, 0-50% EtOAc/isohexane) to afford the title compound (159 mg, 0.315 mmol, 35% yield, 98% purity) as a brown oil. UPLC-MS (Method 1) m/z 495.1 (M−H)⁻ at 1.60 min.

Step 2: methyl 3-(N-(5-cyano-2-(5-fluorothiophen-2-yl)phenyl)sulfamoyl)-4-cyclopropylbenzoate: To a solution of the product from Step 1 above (159 mg, 0.315 mmol, 98% purity) in THF (4.5 ml) was added Pd-174 (23 mg, 0.031 mmol) and cyclopropylzinc bromide (0.5 M in THF) (2.52 ml, 1.26 mmol). The mixture was heated to 70° C. overnight. The reaction mixture was concentrated in vacuo onto silica. The residue was purified by chromatography on silica gel (24 g cartridge, 0-100% EtOAc/isohexane) to afford the title compound (89 mg, 0.175 mmol, 55% yield, 90% purity) as a cream solid. UPLC-MS (Method 1) m/z 455.2 (M−H)⁻ at 1.64 min.

Step 3: 3-(N-(5-cyano-2-(5-fluorothiophen-2-yl)phenyl)sulfamoyl)-4-cyclopropylbenzoic acid: 1 M LiOH(aq) (526 μl, 0.526 mmol) was added to a solution of the product from Step 2 above (89 mg, 0.175 mmol, 90% purity) in THF (5 ml) and stirred at RT overnight. The mixture was acidified to pH 6 using 10% w/v citric acid(aq) and the resultant precipitate was collected to afford the title compound (22.9 mg, 0.051 mmol, 29% yield, 99% purity) as a white solid. UPLC-MS (Method 1) m/z 441.2 (M−H)⁻ at 1.50 min. ¹H NMR (500 MHz, DMSO-d₆) δ 13.24 (br s, 1H), 10.34 (br s, 1H), 8.22 (s, 1H), 8.02 (d, J=8.2 Hz, 1H), 7.86 (d, J=8.2 Hz, 2H), 7.33 (t, J=4.1 Hz, 1H), 7.12 (d, J=14.8 Hz, 2H), 6.75 (dd, J=4.3, 2.2 Hz, 1H), 2.70-2.60 (m, 1H), 1.12-0.96 (m, 2H), 0.87 (d, J=5.3 Hz, 2H).

Example 103: 4-cyclopropyl-3-(N-(5-(methylsulfonyl)-2-(5-methylthiophen-2-yl)phenyl)sulfamoyl)benzoic acid

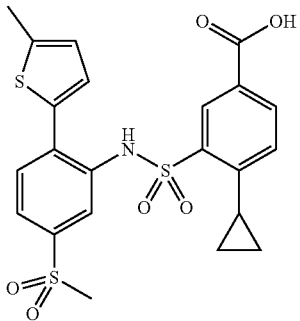 [SMILES: Cc1ccc(-c2ccc(S(C)(=O)=O)cc2NS(=O)(=O)c2cc(C(=O)O)ccc2C2CC2)s1]

Step 1: methyl 4-bromo-3-(N-(5-(methylsulfonyl)-2-(5-methylthiophen-2-yl)phenyl)sulfamoyl)benzoate: A solution of the product from Example 84 Step 1 (200 mg, 0.681 mmol, 91% purity), the product from Example 55 Step 3 (277 mg, 0.885 mmol) and pyridine (220 μl, 2.72 mmol) in DCM (2.5 ml) was stirred at RT for 11 days, and then was concentrated in vacuo. The crude product was purified by chromatography on silica gel (24 g cartridge, 0-50% EtOAc/isohexane) to afford the title compound (222 mg, 0.387 mmol, 57% yield, 95% purity) as an off-white solid. UPLC-MS (Method 1) m/z 543.8 (M+H)$^+$, 541.9 (M−H)$^-$ at 1.51 min.

Step 2: methyl 4-cyclopropyl-3-(N-(5-(methylsulfonyl)-2-(5-methylthiophen-2-yl)phenyl)sulfamoyl)benzoate: To a mixture of the product from Step 1 above (222 mg, 0.387 mmol, 95% purity) and Pd-174 (27.9 mg, 0.039 mmol) in THF (5.4 ml) was added cyclopropylzinc(II) bromide (0.5 M in THF) (2.71 ml, 1.36 mmol). The reaction mixture was heated to 60° C. and stirred for 2 h. Additional cyclopropylzinc(II) bromide (0.5 M in THF) (2.71 ml, 1.36 mmol) was added and then heated to 80° C. for 18 h. The reaction mixture was allowed to cool to RT and quenched with saturated NH$_4$Cl(aq) (2 ml). The phases were separated. The organic phase was dried by passage through a phase separator and then concentrated in vacuo. The crude product was purified by chromatography on silica gel (24 g cartridge, 0-60% EtOAc/isohexane) to the title compound (37.9 mg, 0.075 mmol, 19% yield, 67% purity) as a yellow solid. UPLC-MS (Method 1) m/z 506.3 (M+H)$^+$, 504.2 (M−H)$^-$ at 1.56 min.

Step 3: 4-cyclopropyl-3-(N-(5-(methylsulfonyl)-2-(5-methylthiophen-2-yl)phenyl)sulfamoyl)benzoic acid: 1 M LiOH(aq) (300 μl, 0.30 mmol) was added to a solution of the product from Step 2 above (37.9 mg, 0.075 mmol, 67% purity) in THF (600 μl) at RT. The reaction mixture was stirred at RT for 18 h, and then concentrated in vacuo to remove the THF. The residue was diluted with water (2 ml) and then washed with TBME (2 ml). The aqueous phase was acidified using 1 M HCl(aq) until pH 4-5 and the product was extracted into EtOAc (3×2 ml). Following the addition of THF (10 ml) to obtain a clear solution, the combined organic extracts were dried over MgSO$_4$, filtered and concentrated in vacuo to afford the title compound (27.7 mg, 0.055 mmol, 74% yield, 98% purity) as a pale yellow solid. UPLC-MS (Method 1) m/z 492.3 (M+H)$^+$, 490.2 (M−H)$^-$ at 1.41 min. $^1$H NMR (500 MHz, DMSO-d$_6$) δ 13.19 (br s, 1H), 10.23 (br s, 1H), 8.18 (br s, 1H), 8.00 (br d, J=7.9 Hz, 1H), 7.85-7.76 (m, 2H), 7.39 (d, J=3.7 Hz, 1H), 7.25 (br s, 1H), 7.13 (br d, J=8.3 Hz, 1H), 6.79 (dd, J=3.6, 1.3 Hz, 1H), 3.03 (s, 3H), 2.75-2.65 (m, 1H), 2.45 (s, 3H), 1.10-1.01 (m, 2H), 0.93-0.81 (m, 2H).

Example 104: 3-(N-(5-carbamoyl-2-(pyridin-2-yl)phenyl)sulfamoyl)-4-ethylbenzoic acid

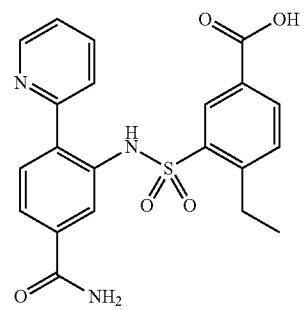 [SMILES: CCc1ccc(C(=O)O)cc1S(=O)(=O)Nc1cc(C(N)=O)ccc1-c1ccccn1]

Step 1: methyl 3-(N-(5-cyano-2-(pyridin-2-yl)phenyl)sulfamoyl)-4-ethylbenzoate: A solution of the product from Example 83 Step 1 (400 mg, 1.59 mmol, 78% purity) in DCM (3 ml) and pyridine (776 μl, 9.59 mmol) was added to a solution of the product from Example 19 Step 2 (420 mg, 1.59 mmol) in DCM (3 ml) and the solution was stirred at RT for 4 days. The reaction mixture was concentrated in vacuo. The residue was purified by chromatography on silica gel (40 g cartridge, 0-100% EtOAc/Isohexane) to afford the title compound (551 mg, 1.25 mmol, 79% yield, 96% purity) as a yellow solid. UPLC-MS (Method 1) m/z 422.4 (M+H)$^+$, 420.3 (M−H)$^-$ at 1.66 min.

Step 2: methyl 3-(N-(5-carbamoyl-2-(pyridin-2-yl)phenyl)sulfamoyl)-4-ethylbenzoate: A solution of the product from Step 1 above (490 mg, 1.11 mmol) in DMSO (10 ml, 141 mmol) was cooled to 0° C. before adding 27% H$_2$O$_2$(aq) (0.380 ml, 3.35 mmol) followed by K$_2$CO$_3$ (309 mg, 2.23 mmol). The mixture was treated with water (3 ml) and stirred at RT for 10 min. The mixture was diluted with saturated NH$_4$Cl(aq) (10 ml) and extracted with EtOAc (20 ml). The organic phase was dried over MgSO$_4$, filtered, and concentrated in vacuo to afford the title compound (500 mg, 1.00 mmol, 90% yield, 88% purity) as a yellow solid. UPLC-MS (Method 1) m/z 440.3 (M+H)$^+$, 438.3 (M−H)$^-$ at 1.29 min.

Step 3: 3-(N-(5-carbamoyl-2-(pyridin-2-yl)phenyl)sulfamoyl)-4-ethylbenzoic acid: 1 M LiOH(aq) (292 μl, 0.292 mmol) was added to a solution of the product from Step 2 above (45 mg, 0.097 mmol, 88% purity) in THF (5 ml) and the mixture was stirred at RT overnight. The mixture was acidified to pH 6 using 10% w/v citric acid(aq) and the resultant precipitate was collected to afford the title compound (31.2 mg, 0.073 mmol, 74% yield, 99% purity) as a yellow solid. UPLC-MS (Method 1) m/z 426.4 (M+H)$^+$, 424.3 (M−H)$^-$ at 1.16 min. $^1$H NMR (500 MHz, DMSO-d$_6$) δ 12.74 (br s, 1H), 8.71 (dd, J=4.5, 1.6 Hz, 1H), 8.20 (d, J=1.8 Hz, 1H), 8.05 (s, 1H), 8.01 (d, J=1.7 Hz, 1H), 7.98-7.92 (m, 2H), 7.88 (t, J=8.1 Hz, 2H), 7.69 (d, J=8.2 Hz, 1H), 7.47 (t, J=3.7 Hz, 2H), 7.38 (d, J=8.0 Hz, 1H), 2.72 (q, J=7.4 Hz, 2H), 0.98 (t, J=7.4 Hz, 3H). One exchangeable proton not observed.

Example 105: 3-(N-(2-(5-fluorothiophen-2-yl)-5-(methylsulfonyl)phenyl)sulfamoyl)-4-methoxybenzoic acid

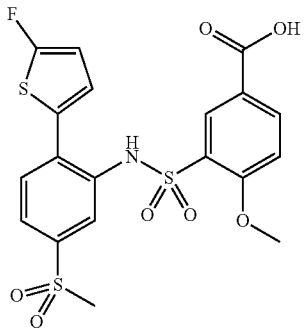

Step 1: 2-(5-fluorothiophen-2-yl)-5-(methylsulfonyl)aniline: To a reaction vessel containing 2-bromo-5-(methylsulfonyl)aniline (700 mg, 2.80 mmol), 2-(5-fluorothiophen-2-yl)-4,4,5,5-tetramethyl-1,3,2-dioxaborolane (766 mg, 3.36 mmol), $K_3PO_4$ (1.19 g, 5.60 mmol) in water (1 ml) and dioxane (6 ml) was added XPhos Pd G3 (118 mg, 0.140 mmol). The reaction mixture was degassed with $N_2$ for 15 min and then heated at 80° C. for 35 min. The reaction mixture was allowed to cool to RT, filtered through Celite®, washed with MeOH (7 ml) and concentrated in vacuo. The crude product was purified by chromatography on silica gel (24 g cartridge, 100% DCM) to afford the title compound (755 mg, 2.67 mmol, 95% yield, 96% purity) as a brown solid. UPLC-MS (Method 1) m/z 272.1 (M+H)$^+$ at 1.24 min. $^1$H NMR (500 MHz, DMSO-$d_6$) δ 7.34 (d, J=8.0 Hz, 1H), 7.32 (d, J=1.9 Hz, 1H), 7.08 (dd, J=8.0, 1.9 Hz, 1H), 7.04 (t, J=3.8 Hz, 1H), 6.80 (dd, J=4.1, 2.4 Hz, 1H), 5.70 (br s, 2H), 3.14 (s, 3H).

Step 2: methyl 3-(N-(2-(5-fluorothiophen-2-yl)-5-(methylsulfonyl)phenyl)sulfamoyl)-4-methoxybenzoate: A solution of the product from Step 1 above (120 mg, 0.425 mmol, 96% purity), methyl 3-(chlorosulfonyl)-4-methoxybenzoate (146 mg, 0.552 mmol) and pyridine (140 μl, 1.73 mmol) in DCM (1.5 ml) was stirred at RT for 11 days. The reaction mixture was directly purified by chromatography on silica gel (24 g cartridge, 0-70% EtOAc/isohexane) to afford the title compound (146 mg, 0.289 mmol, 68% yield, 99% purity) as a yellow solid. UPLC-MS (Method 1) m/z 500.2 (M+H)$^+$, 498.1 (M−H)$^-$ at 1.36 min.

Step 3: 3-(N-(2-(5-fluorothiophen-2-yl)-5-(methylsulfonyl)phenyl)sulfamoyl)-4-methoxybenzoic acid: 1 M LiOH(aq) (1.16 ml, 1.16 mmol) was added to a solution of the product from Step 2 above (146 mg, 0.289 mmol, 99% purity) in THF (2.3 ml) at RT. The reaction mixture was stirred at RT for 17 h, and then concentrated in vacuo to remove the THF. The residue was diluted with water (7 ml) and then washed with TBME (7 ml). The aqueous phase was acidified using 1 M HCl(aq) until pH 4-5 and extracted with EtOAc (3×7 ml). The combined organic extracts were dried over $MgSO_4$, filtered and concentrated in vacuo to afford the title compound (112 mg, 0.224 mmol, 77% yield, 97% purity) as an off-white solid. UPLC-MS (Method 1) m/z 486.2 (M+H)$^+$, 484.2 (M−H)$^-$ at 1.21 min. $^1$H NMR (500 MHz, DMSO-$d_6$) δ 13.08 (br s, 1H), 9.99 (br s, 1H), 8.19 (dd, J=8.7, 2.2 Hz, 1H), 8.09 (d, J=2.2 Hz, 1H), 7.95 (d, J=8.3 Hz, 1H), 7.82 (br d, J=8.5 Hz, 1H), 7.41-7.33 (m, 2H), 7.28 (br s, 1H), 6.79 (dd, J=4.3, 2.2 Hz, 1H), 3.91 (s, 3H), 3.06 (s, 3H).

Example 106: 4-ethyl-3-(N-(2-(5-fluorothiophen-2-yl)-5-(methylsulfonyl)phenyl) sulfamoyl)benzoic acid

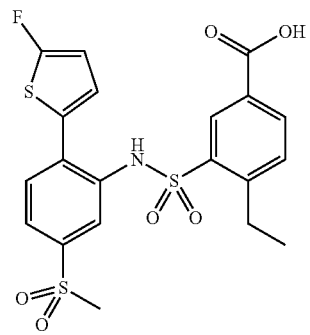 [SMILES: CCc1ccc(C(=O)O)cc1S(=O)(=O)Nc1cc(S(C)(=O)=O)ccc1-c1ccc(F)s1]

Step 1: methyl 4-ethyl-3-(N-(2-(5-fluorothiophen-2-yl)-5-(methylsulfonyl)phenyl)sulfamoyl)-benzoate: A solution of the product from Example 105 Step 1 (120 mg, 0.425 mmol, 96% purity), the product from Example 19 Step 2 (145 mg, 0.552 mmol) and pyridine (140 μl, 1.73 mmol) in DCM (1.5 ml) was stirred at RT for 11 days. The reaction mixture was directly purified by chromatography on silica gel (24 g cartridge, 0-50% EtOAc/isohexane) to afford the title compound (153 mg, 0.289 mmol, 68% yield, 94% purity) as a yellow solid. UPLC-MS (Method 1) m/z 498.2 (M+H)$^+$, 496.2 (M−H)$^-$ at 1.53 min.

Step 2: 4-ethyl-3-(N-(2-(5-fluorothiophen-2-yl)-5-(methylsulfonyl)phenyl)sulfamoyl)benzoic acid: 1 M LiOH(aq) (1.16 ml, 1.16 mmol) was added to a solution of the product from Step 1 above (153 mg, 0.289 mmol, 94% purity) in THF (2.3 ml) at RT. The reaction mixture was stirred at RT for 17 h, and then concentrated in vacuo to remove the THF. The residue was diluted with water (7 ml) and then washed with TBME (7 ml). The aqueous phase was acidified using 1 M HCl(aq) until pH 4-5 and extracted with EtOAc (3×7 ml). The combined organic extracts were dried over $MgSO_4$, filtered and concentrated in vacuo to afford the title compound (116 mg, 0.233 mmol, 81% yield, 97% purity) as an off-white solid. UPLC-MS (Method 1) m/z 484.3 (M+H)$^+$, 482.1 (M−H)~ at 1.37 min. $^1$H NMR (500 MHz, DMSO-$d_6$) δ 13.29 (br s, 1H), 10.33 (br s, 1H), 8.19 (br s, 1H), 8.11 (dd, J=7.9, 1.9 Hz, 1H), 7.94 (d, J=8.3 Hz, 1H), 7.89-7.78 (m, 1H), 7.60 (d, J=8.0 Hz, 1H), 7.35 (t, J=4.0 Hz, 1H), 7.12 (br s, 1H), 6.79 (dd, J=4.3, 2.2 Hz, 1H), 3.08 (s, 3H), 2.91 (q, J=7.5 Hz, 2H), 1.17 (t, J=7.5

Example 107: 3-(N-(5-cyano-2-(pyrrol-1-yl)phenyl)sulfamoyl)-4-ethylbenzoic acid

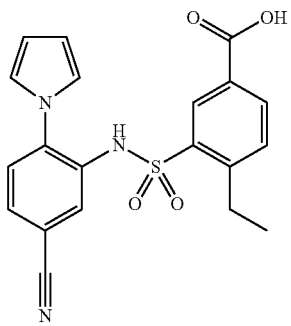 [SMILES: CCc1ccc(C(=O)O)cc1S(=O)(=O)Nc1cc(C#N)ccc1-n1cccc1]

Step 1: tert-butyl (4-cyano-2-nitrophenyl)carbamate: To a mixture of 4-amino-3-nitrobenzonitrile (1.00 g, 6.13 mmol), DIPEA (1.20 ml, 6.87 mmol) and DMAP (38.0 mg, 0.311 mmol) in DCM (15 ml) at 0° C. was slowly added Boc$_2$O (1.50 g, 6.87 mmol) in DCM (10 ml). The mixture was warmed to RT and stirred for 3 days. The mixture was sequentially washed with 5% citric acid(aq) (20 ml) and brine (20 ml) and the organic phase was dried by passage through a phase separator. The filtrate was concentrated in vacuo onto silica and purified by chromatography on silica gel (40 g cartridge, 0-40% EtOAc/isohexane) to afford the title compound (943 mg, 3.55 mmol, 57% yield, 99% purity) as a pale yellow solid after trituration with hexane and small amounts of TBME. UPLC-MS (Method 1) m/z 262.1 (M−H)$^-$ at 1.57 min. $^1$H NMR (500 MHz, DMSO-d$_6$) δ 10.05 (s, 1H), 8.50 (d, J=2.0 Hz, 1H), 8.09 (dd, J=8.6, 2.0 Hz, 1H), 7.86 (d, J=8.6 Hz, 1H), 1.46 (s, 9H).

Step 2: tert-butyl (2-amino-4-cyanophenyl)carbamate: A mixture of the product from Step 1 above (943 mg, 3.55 mmol, 99% purity), iron (4 g, 71.6 mmol) and NH$_4$Cl (228 mg, 4.26 mmol) in IPA/water (2:1, 45 ml) was heated to 90° C. and stirred overnight. Upon cooling to RT the reaction mixture was filtered through Celite®, rinsing with EtOAc and the filtrate was concentrated in vacuo. The residue was extracted with DCM (2×50 ml) and the combined organic phases were dried by passage through a phase separator. The residue was loaded onto silica and purified by chromatography on silica gel (24 g cartridge, 0-100% EtOAc/isohexane) to the title compound (571 mg, 2.42 mmol, 68% yield, 99% purity) as a yellow solid. $^1$H NMR (500 MHz, DMSO-d$_6$) δ 8.60 (s, 1H), 7.58 (d, J=8.3 Hz, 1H), 7.00 (d, J=2.0 Hz, 1H), 6.94 (dd, J=8.3, 2.0 Hz, 1H), 5.39 (s, 2H), 1.47 (s, 9H).

Step 3: methyl 3-(N-(2-((tert-butoxycarbonyl)amino)-5-cyanophenyl)sulfamoyl)-4-ethylbenzoate: A mixture of the product from Step 2 above (200 mg, 0.849 mmol, 99% purity), the product from Example 19 Step 2 (245 mg, 0.934 mmol, 95% purity) and pyridine (200 μl, 2.47 mmol) in DCM (5 ml) was stirred at 35° C. overnight. The reaction mixture was concentrated in vacuo onto silica and purified by chromatography on silica gel (12 g cartridge, 0-50% EtOAc/isohexane) to afford the title compound (425 mg, 0.795 mmol, 94% yield, 86% purity) as a yellow solid. UPLC-MS (Method 1) m/z 360.1 (M+H-Boc)$^+$, 458.1 (M−H)$^-$ at 1.67 min. $^1$H NMR (500 MHz, DMSO-d$_6$) δ 9.96 (s, 1H), 8.45 (s, 1H), 8.27 (d, J=1.9 Hz, 1H), 8.08 (dd, J=8.0, 1.9 Hz, 1H), 7.90 (d, J=8.7 Hz, 1H), 7.65 (d, J=8.7 Hz, 1H), 7.58 (d, J=8.1 Hz, 1H), 7.48 (d, J=2.0 Hz, 1H), 3.86 (s, 3H), 2.78 (q, J=7.5 Hz, 2H), 1.39 (s, 9H), 1.11 (t, J=7.4 Hz, 3H).

Step 4: methyl 3-(N-(2-amino-5-cyanophenyl)sulfamoyl)-4-ethylbenzoate: A mixture of the product from Step 3 above (425 mg, 0.795 mmol, 86% purity) and TFA (1.50 ml, 19.5 mmol) in DCM (6 ml) was stirred at RT overnight. The mixture was concentrated in vacuo onto Celite® and purified by chromatography on 24 g reverse phase cartridge (20-65% MeCN/Water 0.1% Formic acid) to afford the title compound (199 mg, 0.537 mmol, 67% yield, 97% purity) as a light pink foam. UPLC-MS (Method 1) m/z 360.2 (M+H)$^+$, 358.0 (M−H)$^-$ at 1.26 min. $^1$H NMR (500 MHz, DMSO-d$_6$) δ 9.71 (s, 1H), 8.30 (d, J=1.9 Hz, 1H), 8.11 (dd, J=8.0, 1.9 Hz, 1H), 7.62 (d, J=8.0 Hz, 1H), 7.29 (dd, J=8.5, 2.0 Hz, 1H), 6.88 (d, J=2.0 Hz, 1H), 6.69 (d, J=8.5 Hz, 1H), 5.96 (s, 2H), 3.86 (s, 3H), 2.95 (q, J=7.4 Hz, 2H), 1.16 (t, J=7.4 Hz, 3H).

Step 5: methyl 3-(N-(5-cyano-2-(pyrrol-1-yl)phenyl)sulfamoyl)-4-ethylbenzoate: A mixture of the product from Step 4 above (199 mg, 0.537 mmol, 97% purity), 2,5-dimethoxytetrahydrofuran (90 μl, 0.695 mmol) and AcOH (900 μl) was heated to 120° C. for 90 min. Upon cooling to RT, the reaction mixture was concentrated in vacuo onto silica and purified by chromatography on silica gel (12 g cartridge, 0-100% EtOAc/isohexane) to afford the title compound (91.8 mg, 0.209 mmol, 38% yield, 93% purity) as a beige solid. UPLC-MS (Method 1) m/z 410.1 (M+H)$^+$, 408.1 (M−H)$^-$ at 1.57 min. $^1$H NMR (500 MHz, DMSO-d$_6$) δ 10.41 (s, 1H), 8.08-8.03 (m, 2H), 7.88-7.79 (m, 1H), 7.55 (d, J=1.9 Hz, 1H), 7.51 (d, J=8.6 Hz, 1H), 7.47 (d, J=8.3 Hz, 1H), 6.87 (t, J=2.2 Hz, 2H), 6.09 (t, J=2.2 Hz, 2H), 3.85 (s, 3H), 2.85 (q, J=7.4 Hz, 2H), 1.15 (t, J=7.4 Hz, 3H).

Step 6: 3-(N-(5-cyano-2-(pyrrol-1-yl)phenyl)sulfamoyl)-4-ethylbenzoic acid: A mixture of the product from Step 5 above (91.8 mg, 0.209 mmol) and LiOH (36 mg, 0.842 mmol) in THF/MeOH/water (4:1:1, 3.6 ml) was stirred at 40° C. overnight. The reaction mixture was diluted with water (5 ml), adjusted to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (58.7 mg, 0.147 mmol, 70% yield, 99% purity) as a white solid. UPLC-MS (Method 1) m/z 396.0 (M+H)$^+$, 394.1 (M−H)$^-$ at 1.41 min. $^1$H NMR (500 MHz, DMSO-d$_6$) δ 13.22 (s, 1H), 10.36 (s, 1H), 8.10-8.07 (m, 1H), 8.04 (dd, J=8.0, 1.9 Hz, 1H), 7.83 (br s, 1H), 7.52-7.45 (m, 3H), 6.92-6.87 (m, 2H), 6.11 (t, J=2.2 Hz, 2H), 2.86 (q, J=7.4 Hz, 2H), 1.15 (t, J=7.4 Hz, 3H).

Example 108: 4-ethyl-3-(N-(5-(methylsulfonyl)-2-(pyrrol-1-yl)phenyl)sulfamoyl)benzoic acid

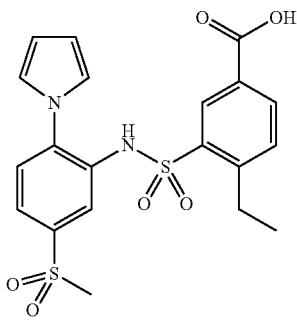 [SMILES: CCc1ccc(C(=O)O)cc1S(=O)(=O)Nc1cc(S(C)(=O)=O)ccc1-n1cccc1]

Step 1: tert-butyl (4-(methylsulfonyl)-2-nitrophenyl)carbamate: To a mixture of 4-(methylsulfonyl)-2-nitroaniline (2 g, 9.25 mmol), DIPEA (1.80 ml, 10.3 mmol) and DMAP (57.0 mg, 0.467 mmol) in DCM (20 ml) at 0° C. was added slowly Boc$_2$O (2.34 ml, 10.1 mmol) in DCM (17.5 ml). The mixture was warmed to RT and stirred overnight. The reaction mixture was sequentially washed with 5% citric acid(aq) (10 ml) and brine (10 ml) and the organic phase was dried by passage through a phase separator. The filtrate was concentrated in vacuo onto silica and purified by chromatography on silica gel (40 g cartridge, 0-50% EtOAc/isohexane) to afford the title compound (1.66 g, 5.20 mmol, 56% yield, 99% purity) as a pale yellow solid after trituration with hexane and small amounts of TBME. UPLC-MS (Method 1) m/z 315.0 (M−H)⁻ at 1.41 min. $^1$H NMR (500 MHz, DMSO-d$_6$) δ 10.06 (s, 1H), 8.41 (d, J=2.2 Hz, 1H), 8.17 (dd, J=8.7, 2.2 Hz, 1H), 7.95 (d, J=8.7 Hz, 1H), 3.29 (s, 3H), 1.47 (s, 9H).

Step 2: tert-butyl (2-amino-4-(methylsulfonyl)phenyl)carbamate: A mixture of the product from Step 1 above (1.66 g, 5.20 mmol), iron (5.80 g, 104 mmol) and NH$_4$Cl (333 mg, 6.23 mmol) in IPA/water (2:1, 66 ml) was heated to 90° C. and stirred overnight. Upon cooling to RT the mixture was filtered through Celite®, rinsing with EtOAc and the filtrate was concentrated in vacuo. The residue was extracted with DCM (2×50 ml). The combined organic extracts were dried by passage through a phase separator and the solvent removed in vacuo. The residue was loaded onto silica and purified by chromatography on silica gel (40 g cartridge, 0-100% EtOAc/isohexane) to afford the title compound (1.11 g, 3.80 mmol, 73% yield, 98% purity) as a yellow solid. UPLC-MS (Method 1) m/z 287.0 (M+H)⁺, 285.0 (M−H)⁻ at 1.02 min. $^1$H NMR (500 MHz, DMSO-d$_6$) δ 8.58 (s, 1H), 7.61 (d, J=8.4 Hz, 1H), 7.21 (d, J=2.2 Hz, 1H), 7.04 (dd, J=8.4, 2.2 Hz, 1H), 5.45 (s, 2H), 3.08 (s, 3H), 1.48 (s, 9H).

Step 3: methyl 3-(N-(2-((tert-butoxycarbonyl)amino)-5-(methylsulfonyl)phenyl)sulfamoyl)-4-ethylbenzoate: A mixture of the product from Step 2 above (300 mg, 1.03 mmol, 98% purity), the product from Example 19 Step 2 (297 mg, 1.13 mmol, 95% purity) and pyridine (250 µl, 3.09 mmol) in DCM (6 ml) was stirred at 35° C. overnight. The reaction mixture was concentrated in vacuo onto silica and purified by chromatography on silica gel (24 g cartridge, 0-100% EtOAc/isohexane) to afford the title compound (602 mg, 0.928 mmol, 90% yield, 79% purity) as a yellow solid. UPLC-MS (Method 1) m/z 535.1 (M+Na)+, 511.1 (M−H)⁻ at 1.55 min.

Step 4: methyl 3-(N-(2-amino-5-(methylsulfonyl)phenyl)sulfamoyl)-4-ethylbenzoate: A mixture of the product from Step 3 above (602 mg, 0.928 mmol, 79% purity) and TFA (1.70 ml, 22.1 mmol) in DCM (7 ml) was stirred at RT overnight. The reaction mixture was concentrated in vacuo onto Celite® and purified by chromatography (24 g reverse phase cartridge, 5-50% MeCN/Water 0.1% Formic acid) to afford the title compound (337 mg, 0.809 mmol, 87% yield, 99%) as a pale orange foam. UPLC-MS (Method 1) m/z 435.1 (M+Na)⁺, 411.0 (M−H)⁻ at 1.13 min. $^1$H NMR (500 MHz, DMSO-d$_6$) δ 9.70 (s, 1H), 8.30 (d, J=1.9 Hz, 1H), 8.10 (dd, J=8.0, 1.9 Hz, 1H), 7.62 (d, J=8.0 Hz, 1H), 7.38 (dd, J=8.6, 2.2 Hz, 1H), 6.99 (d, J=2.2 Hz, 1H), 6.75 (d, J=8.6 Hz, 1H), 5.96 (s, 2H), 3.84 (s, 3H), 2.96 (q, J=7.4 Hz, 2H), 2.84 (s, 3H), 1.17 (t, J=7.4 Hz, 3H).

Step 5: methyl 4-ethyl-3-(N-(5-(methylsulfonyl)-2-(pyrrol-1-yl)phenyl)sulfamoyl)benzoate: A mixture of the product from Step 4 above (337 mg, 0.809 mmol, 99% purity), 2,5-dimethoxytetrahydrofuran (140 µl, 1.08 mmol) and AcOH (1.4 ml) was heated to 120° C. for 90 min. Upon cooling to RT the mixture was concentrated in vacuo onto silica and purified by chromatography on silica gel (12 g cartridge, 0-100% EtOAc/isohexane) to afford the title compound (161 mg, 0.313 mmol, 38% yield, 90% purity) as a white solid. UPLC-MS (Method 1) m/z 485.2 (M+Na)⁺, 461.0 (M−H)⁻ at 1.45 min. $^1$H NMR (500 MHz, DMSO-d$_6$) δ 10.41 (s, 1H), 8.13 (d, J=1.9 Hz, 1H), 8.08 (dd, J=8.0, 1.9 Hz, 1H), 7.92-7.87 (m, 1H), 7.56 (dd, J=8.2, 2.2 Hz, 2H), 7.51 (d, J=2.2 Hz, 1H), 6.94 (t, J=2.2 Hz, 2H), 6.15 (t, J=2.2 Hz, 2H), 3.84 (s, 3H), 3.17 (s, 3H), 2.88 (q, J=7.4 Hz, 2H), 1.16 (t, J=7.4 Hz, 3H).

Step 6: 4-ethyl-3-(N-(5-(methylsulfonyl)-2-(pyrrol-1-yl)phenyl)sulfamoyl)benzoic acid: A mixture of the product from Step 5 above (161 mg, 0.313 mmol, 90% purity) and LiOH (54.0 mg, 1.26 mmol) in THF/MeOH/water (4:1:1, 6 ml) was stirred at 40° C. overnight. The mixture was diluted with water (5 ml), adjusted to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 35-65% MeCN in Water) to afford the title compound (106 mg, 0.236 mmol, 75% yield, 99% purity) as a white solid. UPLC-MS (Method 1) m/z 471.4 (M+Na)⁺, 447.1 (M−H)⁻ at 1.30 min. $^1$H NMR (500 MHz, DMSO-d$_6$) δ 13.23 (s, 1H), 10.36 (s, 1H), 8.14 (d, J=1.8 Hz, 1H), 8.06 (dd, J=8.0, 1.8 Hz, 1H), 7.92-7.84 (m, 1H), 7.57 (d, J=8.3 Hz, 1H), 7.54 (d, J=8.0 Hz, 1H), 7.48 (d, J=2.2 Hz, 1H), 6.96 (t, J=2.2 Hz, 2H), 6.17 (t, J=2.2 Hz, 2H), 3.15 (s, 3H), 2.89 (q, J=7.4 Hz, 2H), 1.16 (t, J=7.4 Hz, 3H).

Example 109: 3-(N-(5-cyano-2-(pyrrol-1-yl)phenyl) sulfamoyl)-4-cyclopropylbenzoic acid

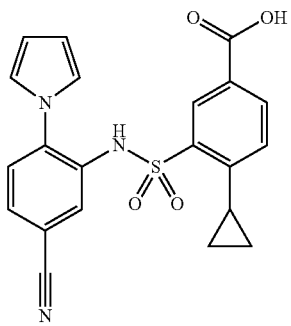 [SMILES: N#Cc1ccc(-n2cccc2)c(NS(=O)(=O)c2cc(C(=O)O)ccc2C2CC2)c1]

Step 1: methyl 4-bromo-3-(N-(2-((tert-butoxycarbonyl)amino)-5-cyanophenyl)sulfamoyl)benzoate: A mixture of the product from Example 107 Step 2 (371 mg, 1.56 mmol, 99% purity), the product from Example 55 Step 3 (549 mg, 1.73 mmol, 99% purity) and pyridine (400 µl, 4.95 mmol) in DCM (9 ml) was stirred at 35° C. overnight. The mixture was concentrated in vacuo onto silica and purified by chromatography on silica gel (24 g cartridge, 0-50% EtOAc/isohexane) to afford the title compound (855 mg, 1.01 mmol, 63% yield, 60% purity) as a pale yellow foam. UPLC-MS (Method 1) m/z 410.0 (M+H-Boc)$^+$, 508.0 (M-H)$^-$ at 1.61 min.

Step 2: methyl 3-(N-(2-amino-5-cyanophenyl)sulfamoyl)-4-bromobenzoate: A mixture of the product from Step 1 above (855 mg, 1.01 mmol, 60% purity) and TFA (1.80 ml, 23.4 mmol) in DCM (7.2 ml) was stirred at RT overnight. The mixture was concentrated in vacuo onto Celite® and purified by chromatography (24 g reverse phase cartridge, 20-65% MeCN/Water 0.1% Formic acid) to afford the title compound (335 mg, 0.776 mmol, 77% yield, 95% purity) as a light pink foam. UPLC-MS (Method 1) m/z 410.2 (M+H)$^+$, 408.0 (M-H)$^-$ at 1.18 min. $^1$H NMR (500 MHz, DMSO-d$_6$) δ 10.00 (s, 1H), 8.37 (d, J=1.8 Hz, 1H), 8.09-7.99 (m, 2H), 7.30 (dd, J=8.5, 2.0 Hz, 1H), 7.00 (d, J=2.0 Hz, 1H), 6.70 (d, J=8.5 Hz, 1H), 6.00 (s, 2H), 3.87 (s, 3H).

Step 3: methyl 4-bromo-3-(N-(5-cyano-2-(pyrrol-1-yl)phenyl)sulfamoyl)benzoate: A mixture of the product from Step 2 above (335 mg, 0.776 mmol, 95% purity), 2,5-dimethoxytetrahydrofuran (140 µl, 1.08 mmol) and AcOH (1.4 ml) was heated to 120° C. for 90 min. Upon cooling to RT, the reaction mixture was concentrated in vacuo onto silica and purified by chromatography on silica gel (12 g cartridge, 0-100% EtOAc/isohexane) to afford the title compound (180 mg, 0.364 mmol, 46% yield, 93% purity) as a beige solid. UPLC-MS (Method 1) m/z 460.1 (M+H)$^+$, 458.0 (M-H)$^-$ at 1.51 min. $^1$H NMR (500 MHz, DMSO-d$_6$) δ 10.54 (s, 1H), 8.11 (d, J=2.0 Hz, 1H), 7.96 (dd, J=8.3, 2.2 Hz, 1H), 7.91 (d, J=8.3 Hz, 1H), 7.90-7.85 (m, 1H), 7.65 (d, J=2.0 Hz, 1H), 7.50 (d, J=8.3 Hz, 1H), 6.93 (t, J=2.2 Hz, 2H), 5.98 (t, J=2.2 Hz, 2H), 3.87 (s, 3H).

Step 4: methyl 3-(N-(5-cyano-2-(pyrrol-1-yl)phenyl)sulfamoyl)-4-cyclopropylbenzoate: To a mixture of the product from Step 3 above (180 mg, 0.364 mmol, 93% purity) and Pd-174 (26 mg, 0.036 mmol) in THF (6 ml) was added cyclopropylzinc(II) bromide (0.5 M in THF) (2.90 ml, 1.45 mmol) and the mixture was heated to 60° C. and stirred for 90 min, and then at RT overnight. The mixture was concentrated in vacuo onto silica and purified by chromatography on silica gel (12 g cartridge, 0-100% EtOAc/isohexane) to afford the title compound (91 mg, 0.181 mmol, 49% yield, 84% purity) as a pale yellow oil. UPLC-MS (Method 1) m/z 422.1 (M+H)$^+$, 420.1 (M-H)$^-$ at 1.57 min.

Step 5: 3-(N-(5-cyano-2-(pyrrol-1-yl)phenyl)sulfamoyl)-4-cyclopropylbenzoic acid: A mixture of the product from Step 4 above (91 mg, 0.181 mmol, 84% purity) and LiOH (31 mg, 0.725 mmol) in THF/MeOH/water (4:1:1, 3 ml) was stirred at 40° C. for 3 h. The mixture was diluted with water (5 ml), acidified to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 µm, 19×50 mm column, 35-65% MeCN in Water) to afford the title compound (35 mg, 0.085 mmol, 46% yield, 98% purity) as a white solid. UPLC-MS (Method 1) m/z 408.1 (M+H)$^+$, 406.1 (M-H)$^-$ at 1.41 min. $^1$H NMR (500 MHz, DMSO-d$_6$) δ 13.20 (s, 1H), 10.33 (s, 1H), 8.17 (d, J=1.9 Hz, 1H), 7.99 (dd, J=8.0, 1.9 Hz, 1H), 7.87-7.78 (m, 1H), 7.52 (d, J=8.3 Hz, 1H), 7.36 (d, J=1.9 Hz, 1H), 7.11 (d, J=8.3 Hz, 1H), 7.02 (t, J=2.2 Hz, 2H), 6.14 (t, J=2.2 Hz, 2H), 2.65-2.61 (m, 1H), 1.10-1.02 (m, 2H), 0.91-0.84 (m, 2H).

Example 110: 4-cyclopropyl-3-(N-(5-(methylsulfonyl)-2-(pyrrol-1-yl)phenyl)sulfamoyl) benzoic acid

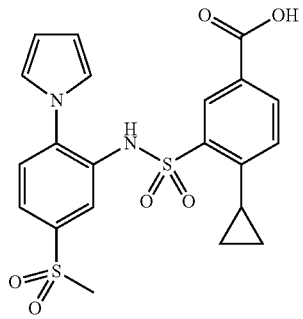 [SMILES: CS(=O)(=O)c1ccc(-n2cccc2)c(NS(=O)(=O)c2cc(C(=O)O)ccc2C2CC2)c1]

Step 1: methyl 4-bromo-3-(N-(2-((tert-butoxycarbonyl)amino)-5-(methylsulfonyl)phenyl)sulfamoyl)benzoate: A mixture of the product from Example 108 Step 2 (810 mg, 2.77 mmol, 98% purity), the product from Example 55 Step 3 (966 mg, 3.05 mmol, 99% purity) and pyridine (700 µl, 8.65 mmol) in DCM (16 ml) was stirred at 35° C. overnight. The mixture was concentrated in vacuo onto silica and purified by chromatography on silica gel (40 g cartridge, 0-100% EtOAc/isohexane) to afford the title compound (1.74 g, 1.95 mmol, 70% yield, 63% purity) as a yellow solid. UPLC-MS (Method 1) m/z 463.1 (M+H-Boc)$^+$, 561.0 (M-H)$^-$ at 1.49 min.

Step 2: methyl 3-(N-(2-amino-5-(methylsulfonyl)phenyl)sulfamoyl)-4-bromobenzoate: A mixture of the product from Step 1 above (1.74 g, 1.95 mmol) and TFA (3.60 ml, 46.7 mmol) in DCM (14 ml) was stirred at RT for 4 h. The mixture was concentrated in vacuo onto Celite® and purified by chromatography (24 g reverse phase cartridge, 5-50% MeCN/Water 0.1% Formic acid) to afford the title compound (902 mg, 1.91 mmol, 98% yield, 98% purity) as a pale orange solid. UPLC-MS (Method 1) m/z 463.3 (M+H)$^+$, 461.2 (M-H)$^-$ at 1.05 min. $^1$H NMR (500 MHz, DMSO-d$_6$) δ 9.99 (s, 1H), 8.36 (d, J=2.0 Hz, 1H), 8.08-8.00

(m, 2H), 7.40 (dd, J=8.6, 2.2 Hz, 1H), 7.09 (d, J=2.2 Hz, 1H), 6.76 (d, J=8.6 Hz, 1H), 6.00 (s, 2H), 3.85 (s, 3H), 2.87 (s, 3H).

Step 3: methyl 4-bromo-3-(N-(5-(methylsulfonyl)-2-(pyrrol-1-yl)phenyl)sulfamoyl)benzoate: A mixture of the product from Step 2 above (902 mg, 1.91 mmol, 98% purity), 2,5-dimethoxytetrahydrofuran (350 μl, 2.70 mmol) and AcOH (3.5 ml) was heated to 120° C. for 90 min. Upon cooling to RT, the mixture was concentrated in vacuo onto silica and purified by chromatography on silica gel (24 g cartridge, 0-100% EtOAc/isohexane) to afford the title compound (325 mg, 0.525 mmol, 27% yield, 83% purity) as a white solid. UPLC-MS (Method 1) m/z 513.1 (M+H)$^+$, 511.0 (M−H)$^-$ at 1.39 min. $^1$H NMR (500 MHz, DMSO-d$_6$) δ 10.55 (s, 1H), 8.15 (d, J=1.9 Hz, 1H), 8.01-7.90 (m, 3H), 7.59 (d, J=8.3 Hz, 1H), 7.56 (d, J=2.2 Hz, 1H), 6.98 (t, J=2.2 Hz, 2H), 6.04 (t, J=2.2 Hz, 2H), 3.86 (s, 3H), 3.19 (s, 3H).

Step 4: methyl 4-cyclopropyl-3-(N-(5-(methylsulfonyl)-2-(pyrrol-1-yl)phenyl)sulfamoyl)benzoate: To a mixture of the product from Step 3 above (325 mg, 0.525 mmol, 83% purity) and Pd-174 (37 mg, 0.051 mmol) in THF (8 ml) was added cyclopropylzinc(II) bromide (0.5 M in THF) (4 ml, 2.00 mmol) and the mixture was heated to 60° C. and stirred for 90 min and then at RT overnight. The reaction mixture was concentrated in vacuo onto silica and purified by chromatography on silica gel (12 g cartridge, 0-100% EtOAc/isohexane) to afford the title compound (257 mg, 0.325 mmol, 64% yield, 60% purity) as a brown oil. UPLC-MS (Method 1) m/z 497.0 (M+Na)$^+$, 473.1 (M−H)$^-$ at 1.44 min.

Step 5: 4-cyclopropyl-3-(N-(5-(methylsulfonyl)-2-(pyrrol-1-yl)phenyl)sulfamoyl)benzoic acid: A mixture of the product from Step 4 above (257 mg, 0.325 mmol, 60% purity) and LiOH (56 mg, 1.31 mmol) in THF/MeOH/water (4:1:1, 6 ml) was stirred at 40° C. for 3 h. The mixture was diluted with water (5 ml), acidified to pH 4 with 1 M HCl(aq) and extracted with EtOAc (3×15 ml). The combined organic extracts were washed with brine (10 ml), dried by passage through a phase separator and the solvent removed in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (41 mg, 0.088 mmol, 27% yield, 98% purity) as a white solid. UPLC-MS (Method 1) m/z 483.5 (M+Na)$^+$, 459.0 (M−H)$^-$ at 1.39 min. $^1$H NMR (500 MHz, DMSO-d$_6$) δ 13.20 (s, 1H), 10.34 (s, 1H), 8.20 (s, 1H), 8.00 (d, J=8.3 Hz, 1H), 7.92-7.81 (m, 1H), 7.60 (d, J=8.0 Hz, 1H), 7.42-7.39 (m, 1H), 7.14 (d, J=8.3 Hz, 1H), 7.08 (t, J=2.2 Hz, 2H), 6.19 (t, J=2.2 Hz, 2H), 3.09 (s, 3H), 2.72-2.64 (m, 1H), 1.11-1.06 (m, 2H), 0.91-0.86 (m, 2H).

Example 111: 3-(N-(2-(5-chlorothiophen-2-yl)-5-cyanophenyl)sulfamoyl)-4-cyclopropylbenzoic acid

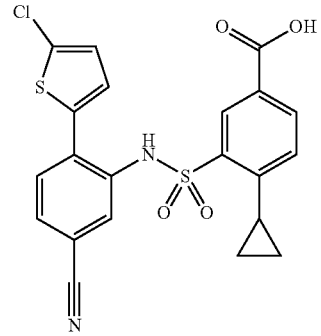 [SMILES: N#Cc1ccc(-c2ccc(Cl)s2)c(NS(=O)(=O)c2cc(C(=O)O)ccc2C2CC2)c1]

Step 1: methyl 4-bromo-3-(N-(2-(5-chlorothiophen-2-yl)-5-cyanophenyl)sulfamoyl)benzoate: A solution of the product from Example 90 Step 1 (200 mg, 0.818 mmol, 96% purity), the product from Example 55 Step 3 (333 mg, 1.06 mmol) and pyridine (270 μl, 3.34 mmol) in DCM (2.5 ml) was stirred at RT for 7 days. The reaction mixture was concentrated in vacuo. The crude product was purified by chromatography on silica gel (24 g cartridge, 0-35% EtOAc/isohexane) to afford the title compound (365 mg, 0.642 mmol, 78% yield, 90% purity) as an orange solid. UPLC-MS (Method 1) m/z 510.9 (M−H)$^-$ at 1.67 min.

Step 2: methyl 3-(N-(2-(5-chlorothiophen-2-yl)-5-cyanophenyl)sulfamoyl)-4-cyclopropylbenzoate: To a mixture of the product from Step 1 above (365 mg, 0.642 mmol, 90% purity) and Pd-174 (46.3 mg, 0.064 mmol) in THF (9 ml) was added cyclopropylzinc(II) bromide (0.5 M in THF) (4.49 ml, 2.25 mmol). The reaction mixture was heated to 60° C. and stirred for 2 h. Additional Pd-174 (46.3 mg, 0.064 mmol) was added and the reaction was heated at 60° C. for 2 h. Additional cyclopropylzinc(II) bromide (0.5 M in THF) (4.49 ml, 2.25 mmol) was added and the reaction heated at 60° C. for 18 h. The reaction mixture was allowed to cool to RT and quenched with saturated NH$_4$Cl(aq) (2 ml). The phases were separated and the organic phase was filtered through Celite®, rinsing with MeOH (9 ml) and then concentrated in vacuo. The crude product was purified by chromatography on silica gel (24 g cartridge, 0-25% EtOAc/isohexane) and by chromatography (24 g reverse phase cartridge, 15-65% MeCN/0.1% Ammonium Bicarbonate (aq)) to afford the title compound (34.1 mg, 0.071 mmol, 11% yield, 98% purity) as an orange oil. UPLC-MS (Method 1) m/z 471.2 (M−H)$^-$ at 1.73 min.

Step 3: 3-(N-(2-(5-chlorothiophen-2-yl)-5-cyanophenyl)sulfamoyl)-4-cyclopropylbenzoic acid: 1 M LiOH(aq) (290 μl, 0.29 mmol) was added to a solution of the product from Step 2 above (34 mg, 0.07 mmol, 98% purity) in THF (580 μl) at RT. The reaction mixture was stirred at RT for 21 h, and then concentrated in vacuo to remove the THF. The residue was diluted with water (2 ml) and washed with TBME (2 ml). The aqueous phase was acidified using 1 M HCl(aq) until pH 4-5 and the product was extracted into EtOAc (3×2 ml). The combined organic extracts were dried over MgSO$_4$, filtered and concentrated in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (11.3 mg, 0.024 mmol, 35% yield, 99% purity) as an off-white solid. UPLC-MS (Method 1) m/z 457.1 (M−H)⁻ at 1.57 min. ¹H NMR (500 MHz, DMSO-d₆) δ 13.23 (br s, 1H), 10.36 (br s, 1H), 8.20 (d, J=1.9 Hz, 1H), 8.01 (dd, J=8.3, 1.9 Hz, 1H), 7.86 (d, J=8.2 Hz, 1H), 7.77 (br s, 1H), 7.46 (d, J=4.1 Hz, 1H), 7.16 (d, J=1.7 Hz, 1H), 7.14-7.08 (m, 2H), 2.71-2.57 (m, 1H), 1.08-0.99 (m, 2H), 0.91-0.82 (m, 2H).

Example 112: 3-(N-(4-cyano-3',5-difluoro-[1,1'-biphenyl]-2-yl)sulfamoyl)-4-methoxybenzoic acid

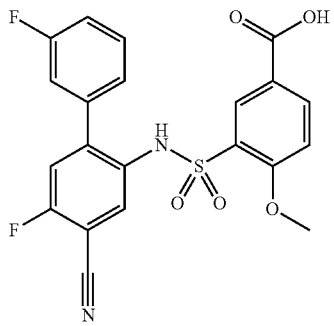 [SMILES: COc1ccc(C(=O)O)cc1S(=O)(=O)Nc1cc(C#N)c(F)cc1-c1cccc(F)c1]

Step 1: 2-amino-3',5-difluoro-[1,1'-biphenyl]-4-carbonitrile: To a reaction vessel containing 5-amino-4-bromo-2-fluorobenzonitrile (150 mg, 0.698 mmol), (3-fluorophenyl)boronic acid (117 mg, 0.837 mmol), K₃PO₄ (193 mg, 0.907 mmol) and 5:1 dioxane:water (6 ml) was added Xphos Pd G3 (59 mg, 0.070 mmol). The reaction mixture was degassed with N₂ for 15 min and heated to 80° C. for 2 h. The reaction mixture was filtered through Celite® and concentrated in vacuo. The crude product was purified by chromatography on silica gel (12 g cartridge, 0-100% EtOAc/isohexane) to afford the title compound (140 mg, 0.601 mmol, 86% yield, 99% purity) as a brown oil. UPLC-MS (Method 2) m/z 231.8 (M+H)⁺, 229.1 (M−H)⁻ at 1.44 min.

Step 2: methyl 3-(N-(4-cyano-3',5-difluoro-[1,1'-biphenyl]-2-yl)sulfamoyl)-4-methoxybenzoate: Methyl 3-(chlorosulfonyl)-4-methoxybenzoate (177 mg, 0.669 mmol) was added to a solution of pyridine (148 µl, 1.82 mmol) and the product from Step 1 above (140 mg, 0.608 mmol) in DCM (1 ml). The reaction mixture was stirred at RT for 2 days, and then concentrated in vacuo. The residue was purified by chromatography on silica gel (12 g cartridge, 0-100% EtOAc/isohexane) to afford the title compound (233 mg, 0.502 mmol, 83% yield, 99% purity) as a white solid. UPLC-MS (Method 2) m/z 457.2 (M−H)⁻ at 1.39 min.

Step 3: 3-(N-(4-cyano-3',5-difluoro-[1,1'-biphenyl]-2-yl)sulfamoyl)-4-methoxybenzoic acid: 1 M LiOH(aq) (2 ml, 2.00 mmol) was added to a solution of the product from Step 2 above (233 mg, 0.502 mmol) in THF (4 ml). The reaction mixture was stirred at RT for 3 days then concentrated in vacuo. 1 M HCl(aq) was added until pH 4-5. The crude product precipitated out as a white solid and was isolated by filtration. The crude product was purified by chromatography on a 24 g reverse phase cartridge (0-100% MeCN/Water 0.1% Formic Acid) to afford the title compound (138 mg, 0.295 mmol, 58% yield, 95% purity) as a white solid. UPLC-MS (Method 1) m/z 445.0 (M+H)⁺, 443.2 (M−H)⁻ at 1.37 min. ¹H NMR (500 MHz, DMSO-d₆) δ13.0 (br s, 1H), 9.88 (br s, 1H), 8.05 (dd, J=8.7, 2.2 Hz, 1H), 7.91 (s, 1H), 7.72 (d, J=6.2 Hz, 1H), 7.50 (d, J=9.8 Hz, 1H), 7.34-7.26 (m, 1H), 7.17-7.04 (m, 4H), 3.83 (s, 3H).

Example 113: 3-(N-(2-(5-chlorothiophen-2-yl)-5-(trifluoromethyl)phenyl)sulfamoyl)-4-cyclopropyl-benzoic acid

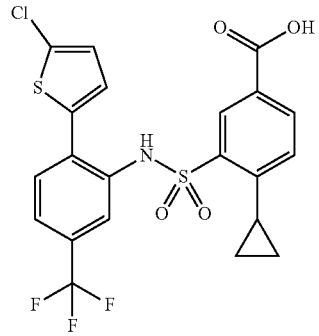 [SMILES: O=C(O)c1ccc(C2CC2)c(S(=O)(=O)Nc2cc(C(F)(F)F)ccc2-c2ccc(Cl)s2)c1]

Step 1: methyl 4-bromo-3-(N-(2-(5-chlorothiophen-2-yl)-5-(trifluoromethyl)phenyl)-sulfamoyl)benzoate: A solution of the product from Example 87 Step 1 (200 mg, 0.648 mmol, 90% purity), the product from Example 55 Step 3 (264 mg, 0.843 mmol) and pyridine (210 µl, 2.60 mmol) in DCM (2.5 ml) was stirred at RT for 6 days. The reaction mixture was concentrated in vacuo. The crude product was purified by chromatography on silica gel (24 g cartridge, 0-20% EtOAc/isohexane) to afford the title compound (288 mg, 0.472 mmol, 73% yield, 91% purity) as an orange solid. UPLC-MS (Method 1) m/z 554.0 (M−H)⁻ at 1.87 min.

Step 2: methyl 3-(N-(2-(5-chlorothiophen-2-yl)-5-(trifluoromethyl)phenyl)sulfamoyl)-4-cyclopropylbenzoate: To a mixture of the product from Step 1 above (288 mg, 0.472 mmol, 91% purity) and Pd-174 (34.1 mg, 0.047 mmol) in THF (6.6 ml) was added cyclopropylzinc(II) bromide (0.5 M in THF) (3.31 ml, 1.65 mmol). The reaction mixture was heated to 60° C. and stirred for 2 h. Additional Pd-174 (34.1 mg, 0.047 mmol) was added and the reaction was heated at 60° C. for 2 h. Additional cyclopropylzinc(II) bromide (0.5 M in THF) (3.31 ml, 1.65 mmol) was added and the reaction was heated at 60° C. for 18 h. The reaction mixture was allowed to cool to RT and quenched with saturated NH₄Cl (aq) (2 ml).

The phases were separated. The organic phase was dried by passage through a phase separator and concentrated in vacuo. The crude product was purified by chromatography (40 g reverse phase C18 cartridge, 15-70% MeCN/0.1% Ammonium Bicarbonate(aq)) to afford the title compound (25.3 mg, 0.038 mmol, 8% yield, 78% purity) as a yellow oil. UPLC-MS (Method 1) m/z 514.1 (M−H)⁻ at 1.92 min. A second product was isolated: methyl 4-cyclopropyl-3-(N-(2-(5-cyclopropylthiophen-2-yl)-5-(trifluoromethyl)phenyl)-sulfamoyl)benzoate (59 mg, 0.095 mmol, 20% yield, 84% purity) as an orange oil. UPLC-MS (Method 1) m/z 520.2 (M−H)⁻ at 1.99 min.

Step 3: 3-(N-(2-(5-chlorothiophen-2-yl)-5-(trifluoromethyl)phenyl)sulfamoyl)-4-cyclopropylbenzoic acid: 1 M LiOH(aq) (160 µl, 0.16 mmol) was added to a solution of the product from Step 2 above (25.3 mg, 0.038 mmol, 78% purity) in THF (320 µl) at RT. The reaction mixture was stirred at RT for 20 h, and then concentrated in vacuo to remove the THF. The residue was diluted with water (2 ml) and washed with TBME (2 ml). The aqueous phase was acidified using 1 M HCl(aq) until pH 4-5 and extracted with EtOAc (3×2 ml). The combined organic extracts were dried over MgSO₄, filtered and concentrated in vacuo. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (4.2 mg, 8.28 µmol, 22% yield, 99% purity) as an off-white solid. UPLC-MS (Method 1) m/z 500.2 (M−H)⁻ at 1.78 min. ¹H NMR (500 MHz, DMSO-$d_6$) δ 13.19 (br s, 1H), 10.32 (br s, 1H), 8.29-8.10 (m, 1H), 8.08-7.95 (m, 1H), 7.89 (d, J=8.2 Hz, 1H), 7.79-7.54 (m, 1H), 7.46 (d, J=4.1 Hz, 1H), 7.13 (br d, J=4.1 Hz, 2H), 7.03-6.84 (m, 1H), 2.80-2.58 (m, 1H), 1.13-0.97 (m, 2H), 0.93-0.76 (m, 2H).

Example 114: 4-cyclopropyl-3-(N-(2-(5-cyclopropylthiophen-2-yl)-5-(trifluoromethyl) phenyl)sulfamoyl)benzoic acid

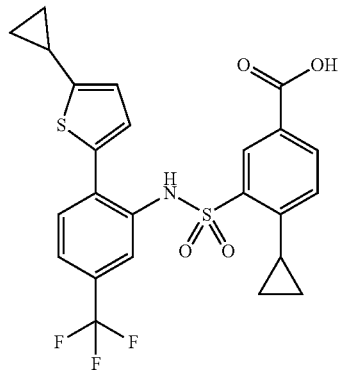 [SMILES: O=C(O)c1ccc(C2CC2)c(S(=O)(=O)Nc2cc(C(F)(F)F)ccc2-c2ccc(C3CC3)s2)c1]

Step 1: 4-cyclopropyl-3-(N-(2-(5-cyclopropylthiophen-2-yl)-5-(trifluoromethyl)phenyl)-sulfamoyl)benzoic acid: 1 M LiOH(aq) (380 µl, 0.38 mmol) was added to a solution of the second product from Example 113 Step 2 (59 mg, 0.095 mmol, 84% purity) in THF (760 µl) at RT. The reaction mixture was stirred at RT for 24 h, and then concentrated in vacuo to remove the THF. The residue was diluted with water (3 ml) and washed with TBME (3 ml). The aqueous phase was acidified using 1 M HCl(aq) until pH 4-5 and extracted with EtOAc (3×3 ml). The combined organic extracts were dried over MgSO₄, filtered and concentrated in vacuo. The crude product was purified by preparative HPLC (Waters, Acidic (0.1% Formic acid), Acidic, Waters X-Select Prep-C18, 5 µm, 19×50 mm column, 50-80% MeCN in Water) to afford the title compound (17.0 mg, 0.033 mmol, 35% yield, 99% purity) as an off-white solid. UPLC-MS (Method 1) m/z 506.2 (M−H)⁻ at 1.85 min. ¹H NMR (500 MHz, DMSO-$d_6$) δ 13.19 (br s, 1H), 10.19 (br s, 1H), 8.21 (br s, 1H), 8.01 (br d, J=8.2 Hz, 1H), 7.76 (d, J=8.2 Hz, 1H), 7.69-7.54 (m, 1H), 7.36 (d, J=3.8 Hz, 1H), 7.12 (br d, J=8.3 Hz, 1H), 6.99 (br s, 1H), 6.77 (d, J=3.7 Hz, 1H), 2.72-2.65 (m, 1H), 2.14-2.08 (m, 1H), 1.08-0.98 (m, 4H), 0.88-0.79 (m, 2H), 0.70-0.64 (m, 2H).

Example 115: 4-cyclopropyl-3-(N-(2-(5-cyclopropylthiophen-2-yl)-5-(methylsulfonyl) phenyl)sulfamoyl)benzoic acid

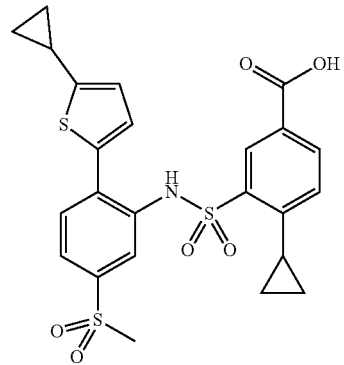 [SMILES: CS(=O)(=O)c1ccc(-c2ccc(C3CC3)s2)c(NS(=O)(=O)c2cc(C(=O)O)ccc2C2CC2)c1]

Step 1: methyl 4-bromo-3-(N-(2-(5-chlorothiophen-2-yl)-5-(methylsulfonyl)phenyl)-sulfamoyl)benzoate: A solution of the product from Example 88 Step 1 (252 mg, 0.665 mmol, 76% purity), the product from Example 55 Step 3 (271 mg, 0.865 mmol) and pyridine (220 µl, 2.72 mmol) in DCM (2.5 ml) was stirred at RT for 11 days. The reaction mixture was concentrated in vacuo. The crude product was purified by chromatography on silica gel (24 g cartridge, 0-50% EtOAc/isohexane) to afford the title compound (247 mg, 0.394 mmol, 59% yield, 90% purity) as a yellow foam. UPLC-MS (Method 1) m/z 564.0 (M−H)⁻ at 1.55 min.

Step 2: methyl 4-cyclopropyl-3-(N-(2-(5-cyclopropylthiophen-2-yl)-5-(methylsulfonyl)-phenyl)sulfamoyl)benzoate: To a mixture of the product from Step 1 above (247 mg, 0.394 mmol, 90% purity) and Pd-174 (28.4 mg, 0.039 mmol) in THF (6.6 ml) was added cyclopropylzinc(II) bromide (0.5 M in THF) (2.75 ml, 1.38 mmol) and the reaction mixture was heated to 60° C. and stirred for 2 h. Additional Pd-174 (28.4 mg, 0.039 mmol) was added and the reaction was heated at 60° C. for 2 h. Additional cyclopropylzinc(II) bromide (0.5 M in THF) (2.75 ml, 1.38 mmol) was added and the reaction was heated at 60° C. for 18 h. The reaction mixture was allowed to cool to RT and quenched with saturated NH₄Cl(aq) (2 ml). The phases were separated. The organic phase was dried by passage through a phase separator and concentrated in vacuo. The crude product was purified by chromatography (40 g reverse phase C18 cartridge, 15-55% MeCN/0.1% Ammonium Bicarbonate(aq)) to afford the title compound (98.6 mg, 0.152 mmol, 39% yield, 82% purity) as a yellow oil. UPLC-MS (Method 1) m/z 532.1 (M+H)⁺, 530.2 (M−H)⁻ at 1.65 min.

Step 3: 4-cyclopropyl-3-(N-(2-(5-cyclopropylthiophen-2-yl)-5-(methylsulfonyl)phenyl)-sulfamoyl)benzoic acid: 1 M LiOH(aq) (610 µl, 0.61 mmol) was added to a solution of the product from Step 2 above (98.6 mg, 0.152 mmol, 82% purity) in THF (1.22 ml) at RT. The reaction mixture was stirred at RT for 24 h, and then concentrated in vacuo to remove the THF. The residue was diluted with water (5 ml) and washed with TBME (5 ml). The aqueous phase was acidified using 1 M HCl(aq) until pH 4-5 and extracted with EtOAc (3×5 ml). The combined organic extracts were dried over MgSO₄, filtered and concentrated in vacuo. The crude product was purified by preparative HPLC (Waters, Acidic (0.1% Formic acid), Acidic, Waters X-Select Prep-C18, 5 µm, 19×50 mm column, 35-65% MeCN in Water) to afford the title compound (8.3 mg, 0.016 mmol, 10% yield, 97% purity) as a cream solid. UPLC-MS (Method 1) m/z 518.3 (M+H)⁺, 516.2 (M−H)⁻ at 1.50 min. ¹H NMR (500 MHz, DMSO-d₆) δ 13.16 (br s, 1H), 10.24 (br s, 1H), 8.33-8.15 (m, 1H), 8.09-7.91 (m, 1H), 7.89-7.70 (m, 2H), 7.41 (d, J=3.8 Hz, 1H), 7.37-7.23 (m, 1H), 7.20-7.03 (m, 1H), 6.78 (d, J=3.8 Hz, 1H), 3.03 (s, 3H), 2.79-2.59 (m, 1H), 2.16-2.06 (m, 1H), 1.12-0.95 (m, 4H), 0.94-0.76 (m, 2H), 0.71-0.63 (m, 2H).

Example 116: 4-cyclopropyl-3-(N-(2-(5-fluorothiophen-2-yl)-5-(methylsulfonyl)-phenyl)sulfamoyl) benzoic acid

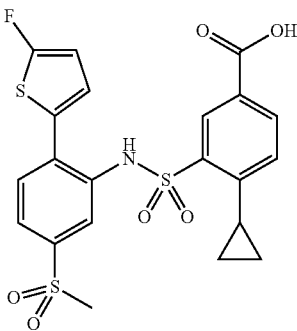 [SMILES: CS(=O)(=O)c1ccc(-c2ccc(F)s2)c(NS(=O)(=O)c2cc(C(=O)O)ccc2C2CC2)c1]

Step 1: 2-(5-fluorothiophen-2-yl)-5-(methylsulfonyl)aniline: To the reaction vessel containing 2-bromo-5-(methylsulfonyl)aniline (700 mg, 2.80 mmol), 2-(5-fluorothiophen-2-yl)-4,4,5,5-tetramethyl-1,3,2-dioxaborolane (766 mg, 3.36 mmol), K₃PO₄ (1.18 g, 5.60 mmol) in water (1 ml) and 1,4-dioxane (5 ml) was added XPhos Pd G3 (118 mg, 0.14 mmol). The reaction mixture was degassed with N₂ for 15 min and then heated at 80° C. for 35 min. The reaction mixture was allowed to cool to RT, filtered through Celite®, rinsing with MeOH (7 ml) and then concentrated in vacuo. The crude product was purified by chromatography on silica gel (24 g cartridge, 100% DCM) to afford the title compound (755 mg, 2.67 mmol, 95% yield) as a brown solid. UPLC-MS (Method 1) m/z 272.1 (M+H)⁺ at 1.24 min. ¹H NMR (500 MHz, DMSO-d₆) δ 7.34 (d, J=8.0 Hz, 1H), 7.32 (d, J=1.9 Hz, 1H), 7.08 (dd, J=8.0, 1.9 Hz, 1H), 7.04 (t, J=3.8 Hz, 1H), 6.80 (dd, J=4.1, 2.4 Hz, 1H), 5.70 (br s, 2H), 3.14 (s, 3H).

Step 2: methyl 4-bromo-3-(N-(2-(5-fluorothiophen-2-yl)-5-(methylsulfonyl)phenyl)sulfamoyl)benzoate: A solution of the product from Step 1 above (200 mg, 0.708 mmol), the product from Example 55 Step 3 (288 mg, 0.92 mmol) and pyridine (230 μl, 2.84 mmol) in DCM (2.5 ml) was stirred at RT for 11 days. The reaction mixture was purified by chromatography on silica gel (24 g cartridge, 0-50% EtOAc/isohexane) to afford the title compound (248 mg, 0.448 mmol, 63% yield) as a yellow solid. UPLC-MS (Method 1) m/z 548.1 (M+H)⁺ at 1.47 min.

Step 3: methyl 4-cyclopropyl-3-(N-(2-(5-fluorothiophen-2-yl)-5-(methylsulfonyl)phenyl)sulfamoyl)benzoate: A solution of the product from Step 2 above (248 mg, 0.448 mmol) and Pd-174 (32.3 mg, 0.045 mmol) in THF (6.4 ml) was degassed with N₂ for 10 min. Cyclopropylzinc(II) bromide (0.5 M in THF) (3.2 ml, 1.60 mmol) was added and then the reaction mixture was heated to 60° C. and stirred for 3.75 h. Additional cyclopropylzinc(II) bromide (0.5 M in THF) (3.2 ml, 1.60 mmol) was added and then the reaction was heated to 60° C. and stirred for 2 h. Additional Pd-174 (32.3 mg, 0.045 mmol) was added and then the reaction was heated to 60° C. and stirred for 17 h. The reaction mixture was allowed to cool to RT and then quenched with saturated NH₄Cl(aq) (3 ml). The phases were separated. The organic phase was filtered through Celite®, rinsing with MeOH (10 ml) and concentrated in vacuo. The crude product was purified by chromatography on silica gel (24 g cartridge, 0-50% EtOAc/isohexane) and by chromatography on (24 g reverse phase cartridge, 15-50% MeCN/10 mM Ammonium Bicarbonate) to afford the title compound (38 mg, 0.074 mmol, 16% yield) as an off-white solid. UPLC-MS (Method 1) m/z 510.3 (M+H)⁺, 508.1 (M−H)⁻ at 1.52 min.

Step 4: 4-cyclopropyl-3-(N-(2-(5-fluorothiophen-2-yl)-5-(methylsulfonyl)phenyl)sulfamoyl)benzoic acid: 1 M LiOH (aq) (300 μl, 0.30 mmol) was added to a solution of the product from Step 3 above (38 mg, 0.075 mmol) in THF (600 μl) at RT. The reaction mixture was stirred at RT for 20 h, and then concentrated in vacuo to remove the THF. The residue was diluted with water (2 ml) and then washed with TBME (2 ml). The aqueous phase was acidified using 1 M HCl until pH 4-5 and extracted with EtOAc (3×2 ml). The combined organic extracts were dried over MgSO₄ and then concentrated in vacuo to afford the title compound (25.6 mg, 0.049 mmol, 66% yield) as an off-white solid. UPLC-MS (Method 1) m/z 518.2 (M+Na)⁺, 494.2 (M−H)⁻ at 1.37 min. ¹H NMR (500 MHz, DMSO-d₆) δ 13.20 (br s, 1H), 10.33 (br s, 1H), 8.20 (br s, 1H), 8.01 (br d, J=8.1 Hz, 1H), 7.94 (d, J=8.3 Hz, 1H), 7.90-7.68 (m, 1H), 7.36 (t, J=4.0 Hz, 1H), 7.28-7.03 (m, 2H), 6.83-6.70 (m, 1H), 3.01 (s, 3H), 2.80-2.61 (m, 1H), 1.12-1.01 (m, 2H), 0.97-0.78 (m, 2H).

Example 117: 3-(N-(2-(5-fluorothiophen-2-yl)-5-(trifluoromethyl)phenyl)sulfamoyl)-4-methoxybenzoic acid

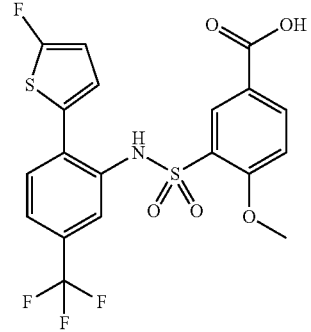 [SMILES: COc1ccc(C(=O)O)cc1S(=O)(=O)Nc1cc(C(F)(F)F)ccc1-c1ccc(F)s1]

Step 1: 2-(5-fluorothiophen-2-yl)-5-(trifluoromethyl)aniline: To the reaction vessel containing 2-bromo-5-(trifluoromethyl)aniline (420 μl, 2.93 mmol), 2-(5-fluorothiophen-2-yl)-4,4,5,5-tetramethyl-1,3,2-dioxaborolane (803 mg, 3.52 mmol), K₃PO₄ (1.24 g, 5.84 mmol) in water (1 ml) and 1,4-dioxane (5 ml) was added XPhos Pd G3 (124 mg, 0.146 mmol). The reaction mixture was degassed with N₂ for 15 min and then heated at 80° C. for 1 h. The reaction mixture was allowed to cool to RT and then concentrated in vacuo onto Celite®. The crude product was purified by chromatography on silica gel (12 g cartridge, 0-5% EtOAc/isohexane) to afford the title compound (728 mg, 2.76 mmol, 94% yield) as a brown oil. UPLC-MS (Method 1) m/z 262.2 (M+H)⁺ at 1.74 min. ¹H NMR (500 MHz, DMSO-d₆) δ 7.30

(d, J=8.0 Hz, 1H), 7.11 (d, J=1.9 Hz, 1H), 7.00 (t, J=3.8 Hz, 1H), 6.88 (dd, J=8.1, 1.9 Hz, 1H), 6.79 (dd, J=4.1, 2.4 Hz, 1H), 5.60 (br s, 2H).

Step 2: methyl 3-(N-(2-(5-fluorothiophen-2-yl)-5-(trifluoromethyl)phenyl)sulfamoyl)-4-methoxybenzoate: A solution of the product from Step 1 above (100 mg, 0.379 mmol), methyl 3-(chlorosulfonyl)-4-methoxybenzoate (130 mg, 0.493 mmol) and pyridine (130 µl, 1.61 mmol) in DCM (1 ml) was stirred at RT for 4 days. The reaction mixture was purified by chromatography on silica gel (12 g cartridge, 0-30% EtOAc/isohexane), and then by chromatography on (24 g reverse phase cartridge, 15-80% MeCN/Water 0.1% Formic acid) to afford the title compound (154 mg, 0.315 mmol, 83% yield) as a white solid. UPLC-MS (Method 1) m/z 488.1 (M–H)⁻ at 1.71 min.

Step 3: 3-(N-(2-(5-fluorothiophen-2-yl)-5-(trifluoromethyl)phenyl)sulfamoyl)-4-methoxybenzoic acid: 1 M LiOH (aq) (1.26 ml, 1.26 mmol) was added to a solution of the product of Step 2 above (154 mg, 0.315 mmol) in THF (2.52 ml) at RT. The reaction mixture was stirred at RT for 25 h, and then concentrated in vacuo to remove the THF. The residue was diluted with water (8 ml) and then washed with TBME (8 ml). The aqueous phase was acidified using 1 M HCl until pH 4-5 and then extracted with EtOAc (3×8 ml). The combined organic extracts were dried over MgSO₄ and then concentrated in vacuo to afford the title compound (95 mg, 0.20 mmol, 64% yield) as an off-white solid. UPLC-MS (Method 1) m/z 474.2 (M–H)⁻ at 1.56 min. ¹H NMR (500 MHz, DMSO-d₆) δ 13.08 (br s, 1H), 9.93 (br s, 1H), 8.18 (dd, J=8.7, 2.2 Hz, 1H), 8.07 (d, J=2.2 Hz, 1H), 7.87 (d, J=8.3 Hz, 1H), 7.64 (br d, J=8.3 Hz, 1H), 7.36 (d, J=8.8 Hz, 1H), 7.31 (app. t, J=4.0 Hz, 1H), 7.01 (br s, 1H), 6.77 (dd, J=4.3, 2.2 Hz, 1H), 3.89 (s, 3H).

Example 118: 3-(N-(5-cyano-2-(5-cyanothiophen-2-yl)phenyl)sulfamoyl)-4-ethylbenzoic acid

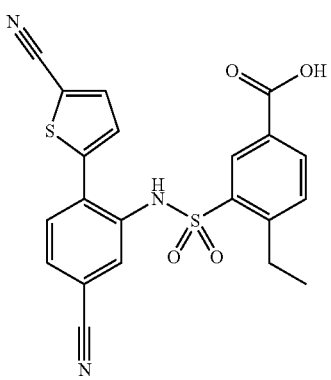 [SMILES: CCc1ccc(C(=O)O)cc1S(=O)(=O)Nc1cc(C#N)ccc1-c1ccc(C#N)s1]

Step 1: Methyl 3-(N-(2-bromo-5-cyanophenyl)sulfamoyl)-4-ethylbenzoate: A solution of 3-amino-4-bromobenzonitrile (1 g, 5.08 mmol) in DCM (3 ml) and pyridine (2.46 ml, 30.5 mmol) were added to a solution of the product from Example 19 Step 2 (1.33 g, 5.08 mmol) in DCM (3 ml) and the resultant solution was stirred at RT for 48 h. The mixture was concentrated in vacuo. The residue was purified by chromatography on silica gel (40 g cartridge, 0-50% EtOAc/isohexane followed by 0-100% DCM/isohexane) to afford crude product. The crude product was purified by column chromatography (40 g reverse phase C18 cartridge, 15-70% MeCN in 0.1% formic acid(aq)) to afford the title compound (0.669 g, 1.58 mmol, 31% yield) as a white solid. UPLC-MS (Method 1): m/z 421.2 (M–H)⁻ at 1.52 min.

Step 2: methyl 3-(N-(5-cyano-2-(5-cyanothiophen-2-yl)phenyl)sulfamoyl)-4-ethylbenzoate: To the reaction vessel containing the product from Step 1 above (150 mg, 0.354 mmol), (5-cyanothiophen-2-yl)boronic acid (108 mg, 0.709 mmol), 1 M K₃PO₄(aq) (600 µl, 0.60 mmol) and dioxane (3.5 ml) was added XPhos Pd G3 (15 mg, 0.018 mmol). The reaction mixture was degassed with N₂ for 15 min and heated at 80° C. for 1 h. Additional XPhos Pd G3 (15 mg, 0.018 mmol) and (5-cyanothiophen-2-yl)boronic acid (54 mg, 0.353 mmol) were added. The reaction mixture was degassed with N₂ for 10 min and heated at 80° C. for 2 h. The reaction mixture was allowed to cool to RT and concentrated in vacuo onto Celite®. The crude product was purified by chromatography on silica gel (12 g cartridge, 0-100% EtOAc/isohexane) to afford the title compound (154 mg, 0.334 mmol, 94% yield, 98% purity) as a yellow solid. UPLC-MS (Method 2) m/z 450.0 (M–H)⁻ at 2.08 min.

Step 3: 3-(N-(5-cyano-2-(5-cyanothiophen-2-yl)phenyl)sulfamoyl)-4-ethylbenzoic acid: 1 M LiOH(aq) (1.4 ml, 1.40 mmol) was added to a solution of the product from Step 2 above (154 mg, 0.341 mmol) in THF (2.8 ml). The reaction mixture was stirred at RT overnight and then concentrated in vacuo. The residue was redissolved in water (12 ml) and washed with EtOAc (12 ml). The aqueous phase was acidified using 1 M HCl until pH 4-5 and the product extracted into EtOAc (2×12 ml). The combined organic extracts were passed through a phase separator and concentrated in vacuo. The crude product was purified by chromatography (24 g reverse phase C18 cartridge, 0-100% MeCN/Water 0.1% Formic acid) to afford the title compound (78 mg, 0.169 mmol, 50% yield) as a pale brown solid. UPLC-MS (Method 1) m/z 436.5 (M–H)⁻ at 1.42 min. ¹H NMR (500 MHz, DMSO-d₆) δ 13.3 (br s, 1H), 10.5 (br s, 1H), 8.14 (s, 1H), 8.09 (d, J=8.0 Hz, 1H), 7.94-7.91 (m, 2H), 7.81 (s, 1H), 7.65 (d, J=4.1 Hz, 1H), 7.55 (d, J=8.0 Hz, 1H), 7.30-7.26 (m, 1H), 2.89 (q, J=7.4 Hz, 2H), 1.15 (t, J=7.4 Hz, 3H).

Example 119: 3-(N-(5-cyano-2-(5-cyanothiophen-2-yl)phenyl)sulfamoyl)-4-methoxybenzoic acid

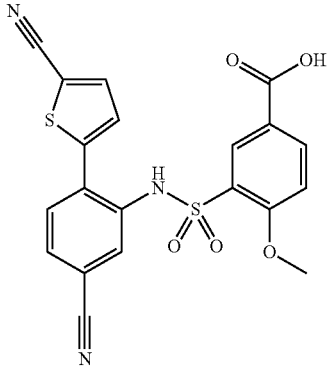 [SMILES: COc1ccc(C(=O)O)cc1S(=O)(=O)Nc1cc(C#N)ccc1-c1ccc(C#N)s1]

Step 1: Methyl 3-(N-(2-bromo-5-cyanophenyl)sulfamoyl)-4-methoxybenzoate: A mixture of 3-amino-4-bromobenzonitrile (1 g, 5.08 mmol), methyl 3-(chlorosulfonyl)-4-methoxybenzoate (1.5 g, 5.67 mmol) and pyridine (1.2 ml, 14.8 mmol) in DCM (35 ml) was stirred at 35° C. overnight. The mixture was concentrated in vacuo onto silica and purified by chromatography on silica gel (40 g cartridge, 0-100% EtOAc/isohexane) and then triturated with TBME to afford the title compound (573 mg, 1.32 mmol, 26% yield, 98% purity) as a beige solid. UPLC-MS (Method 1): m/z 423.1 (M−H)⁻ at 1.35 min. $^1$H NMR (500 MHz, DMSO-d$_6$) δ 10.23 (s, 1H), 8.22 (d, J=2.3 Hz, 1H), 8.18 (dd, J=8.7, 2.3 Hz, 1H), 7.83 (d, J=8.3 Hz, 1H), 7.73 (d, J=2.0 Hz, 1H), 7.62 (dd, J=8.3, 2.0 Hz, 1H), 7.33 (d, J=8.7 Hz, 1H), 3.83 (s, 3H), 3.79 (s, 3H).

Step 2: Methyl 3-(N-(5-cyano-2-(5-cyanothiophen-2-yl)phenyl)sulfamoyl)-4-methoxybenzoate: To the reaction vessel containing the product from Step 1 above (150 mg, 0.346 mmol, 98% purity), (5-cyanothiophen-2-yl)boronic acid (108 mg, 0.705 mmol), 1 M K$_3$PO$_4$(aq) (600 µl, 0.60 mmol) and dioxane (3.5 ml, 0.353 mmol) was added XPhos Pd G3 (15 mg, 0.018 mmol). The reaction mixture was degassed with N$_2$ for 15 min and then heated at 80° C. for 1 h. Additional XPhos Pd G3 (15 mg, 0.018 mmol) and (5-cyanothiophen-2-yl)boronic acid (54 mg, 0.355 mmol) were added. The reaction mixture was degassed with N$_2$ for 10 min and heated at 80° C. for 2 h. The reaction was allowed to cool to RT and then concentrated in vacuo onto Celite®. The crude product was purified by chromatography on silica gel (12 g cartridge, 0-100% EtOAc/isohexane) to afford the title compound (153 mg, 0.334 mmol, 95% yield) as a yellow solid. UPLC-MS (Method 2) m/z 452.2 (M−H)⁻ at 1.11 min.

Step 3: 3-(N-(5-cyano-2-(5-cyanothiophen-2-yl)phenyl)sulfamoyl)-4-ethylbenzoic acid: 1 M LiOH(aq) (1.35 ml, 1.35 mmol) was added to a solution of the product from Step 2 above (153 mg, 0.337 mmol) in THF (3 ml). The reaction mixture was stirred at RT overnight, and then concentrated in vacuo. The residue was redissolved in water (12 ml) and washed with EtOAc (12 ml). The aqueous phase was acidified using 1 M HCl until pH 1-2 and the product was extracted into EtOAc (2×12 ml). The combined organic extracts were passed through a phase separator and concentrated in vacuo. The crude product was purified by chromatography (24 g reverse phase cartridge, 0-100% MeCN/Water 0.1% Formic acid) to afford the title compound (36 mg, 0.078 mmol, 23% yield) as a white solid. UPLC-MS (Method 1) m/z 438.2 (M−H)⁻ at 1.23 min. $^1$H NMR (500 MHz, DMSO-d$_6$) δ 13.1 (br s, 1H), 10.2 (br s, 1H), 8.17 (d, J=8.8 Hz, 1H), 8.08 (s, 1H), 7.97-7.91 (m, 2H), 7.82 (s, 1H), 7.70 (d, J=4.1 Hz, 1H), 7.37 (s, 1H), 7.33 (d, J=8.8 Hz, 1H), 3.86 (s, 3H).

Example 120: 3-(N-(2-(5-cyanothiophen-2-yl)-5-(methylsulfonyl)phenyl)sulfamoyl)-4-ethylbenzoic acid

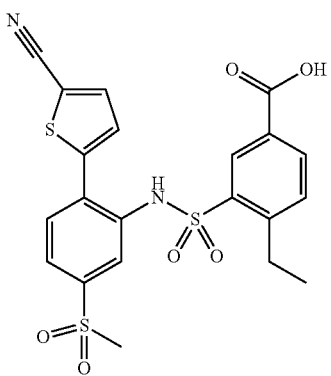 [SMILES: CCc1ccc(C(=O)O)cc1S(=O)(=O)Nc1cc(S(C)(=O)=O)ccc1-c1ccc(C#N)s1]

Step 1: Methyl 3-(N-(2-bromo-5-(methylsulfonyl)phenyl)sulfamoyl)-4-ethylbenzoate: 2-bromo-5-(methylsulfonyl)aniline (600 mg, 2.40 mmol) was added to a solution of methyl 3-(chlorosulfonyl)-4-ethylbenzoate (756 mg, 2.88 mmol) and pyridine (0.78 ml, 9.64 mmol) in DCM (1.6 ml). The resultant mixture was stirred at RT for 4 days. The reaction mixture was concentrated in vacuo and azeotroped with toluene (50 ml) and then concentrated onto Celite® with MeCN (50 ml). The crude product was purified by chromatography on (40 g reverse phase cartridge, 10-65% MeCN/Water 0.1% Formic Acid) to the title compound (626 mg, 1.29 mmol, 54% yield, 98% purity) as an off-white solid. UPLC-MS (Method 1): m/z 476.2 (M+H)⁺, 474.0 (M−H)⁻ at 1.39 min.

Step 2: methyl 3-(N-(2-(5-cyanothiophen-2-yl)-5-(methylsulfonyl)phenyl)sulfamoyl)-4-ethylbenzoate: To the reaction vessel containing the product from Step 1 above (150 mg, 0.315 mmol, 98% purity), (5-cyanothiophen-2-yl)boronic acid (100 mg, 0.654 mmol), 1 M K$_3$PO$_4$(aq) (530 µl, 0.53 mmol) and dioxane (3.5 ml, 0.315 mmol) was added XPhos Pd G3 (13 mg, 0.015 mmol). The reaction mixture was degassed with N$_2$ for 15 min and then heated at 80° C. for 1 h. Additional XPhos Pd G3 (13 mg, 0.015 mmol) and (5-cyanothiophen-2-yl)boronic acid (50 mg, 0.327 mmol) were added. The reaction mixture was degassed with N$_2$ for 10 min and then heated at 80° C. for 2 h. The reaction was allowed to cool to RT and then concentrated in vacuo onto Celite®. The crude product was purified by chromatography on silica gel (12 g cartridge, 0-10% MeOH/DCM followed by 20% MeOH (0.7 M NH$_3$) in DCM) to afford the title compound (117 mg, 0.23 mmol, 73% yield) as a dark yellow solid. LC-MS (Method 4) m/z 503.0 (M−H)⁻ at 1.88 min.

Step 3: 3-(N-(2-(5-cyanothiophen-2-yl)-5-(methylsulfonyl)phenyl)sulfamoyl)-4-ethylbenzoic acid: 1 M LiOH(aq) (930 µl, 0.93 mmol) was added to a solution of the product from Step 2 above (117 mg, 0.232 mmol) in THF (2 ml). The reaction mixture was stirred at RT overnight, and then concentrated in vacuo. The residue was redissolved in water (12 ml) and washed with EtOAc (12 ml). The aqueous phase was acidified using 1 M HCl until pH 1-2 and the product was extracted into EtOAc (2×12 ml). The combined organic extracts were passed through a phase separator and concentrated in vacuo. The crude product was purified by chromatography on (24 g reverse phase cartridge, 0-100% MeCN/Water 0.1% Formic acid) to afford the title compound (45 mg, 0.087 mmol, 38% yield) as a white solid. LC-MS (Method 3) m/z 489.5 (M−H)⁻ at 1.29 min. $^1$H NMR (500 MHz, DMSO-d$_6$) δ 13.3 (br s, 1H), 10.5 (br s, 1H), 8.18 (s, 1H), 8.10 (d, J=8.0 Hz, 1H), 8.03 (d, J=8.3 Hz, 1H), 7.95 (d, J=4.1 Hz, 1H), 7.88 (s, 1H), 7.69 (d, J=4.1 Hz, 1H), 7.58 (d, J=8.0 Hz, 1H), 7.28 (s, 1H), 3.12 (s, 3H), 2.90 (q, J=7.5 Hz, 2H), 1.15 (t, J=7.5 Hz, 3H).

Example 121: 3-(N-(5-cyano-2-(pyrrol-1-yl)phenyl)sulfamoyl)-4-methoxybenzoic acid

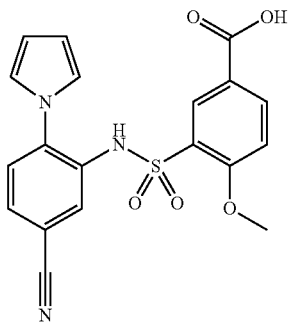 [SMILES: COc1ccc(C(=O)O)cc1S(=O)(=O)Nc1cc(C#N)ccc1-n1cccc1]

Step 1: methyl 3-(N-(2-((tert-butoxycarbonyl)amino)-5-cyanophenyl)sulfamoyl)-4-methoxybenzoate: A mixture of the product from Example 107 Step 2 (414 mg, 1.76 mmol, 99% purity), methyl 3-(chlorosulfonyl)-4-methoxybenzoate (511 mg, 1.93 mmol) and pyridine (430 µl, 5.32 mmol) in DCM (10 ml) was stirred at 35° C. for 3 days. The mixture was concentrated in vacuo onto silica and purified by chromatography on silica gel (40 g cartridge, 0-100% EtOAc/isohexane) to afford the title compound (903 mg, 1.68 mmol, 96% yield, 86% purity) as a yellow solid. UPLC-MS (Method 1) m/z 484.3 (M+Na)$^+$, 460.3 (M−H)$^−$ at 1.53 min. $^1$H NMR (500 MHz, DMSO-$d_6$) δ 9.93 (s, 1H), 8.49 (s, 1H), 8.20-8.14 (m, 2H), 7.93 (d, J=8.6 Hz, 1H), 7.63 (dd, J=8.6, 2.0 Hz, 1H), 7.55 (d, J=2.0 Hz, 1H), 7.38 (d, J=8.5 Hz, 1H), 3.88 (s, 3H), 3.82 (s, 3H), 1.43 (s, 9H).

Step 2: methyl 3-(N-(2-amino-5-cyanophenyl)sulfamoyl)-4-methoxybenzoate: A solution of the product from Step 1 above (903 mg, 1.68 mmol, 86% purity) in TFA/DCM (1:4, 15 ml) was stirred at RT for 2 h 30 min. The mixture was concentrated in vacuo onto Celite® and purified by chromatography on (120 g reverse phase cartridge, 10-50% MeCN/Water 0.1% Formic acid) to afford the title compound (526 mg, 1.37 mmol, 81% yield, 94% purity) as a white solid. UPLC-MS (Method 1) m/z 362.7 (M+H)$^+$, 360.2 (M−H)$^−$ at 1.08 min. $^1$H NMR (500 MHz, DMSO-$d_6$) δ 9.59 (s, 1H), 8.20-8.15 (m, 2H), 7.38 (d, J=9.3 Hz, 1H), 7.26 (dd, J=8.5, 2.0 Hz, 1H), 7.05 (d, J=2.0 Hz, 1H), 6.67 (d, J=8.5 Hz, 1H), 5.95 (s, 2H), 3.96 (s, 3H), 3.82 (s, 3H).

Step 3: methyl 3-(N-(5-cyano-2-(pyrrol-1-yl)phenyl)sulfamoyl)-4-methoxybenzoate: A mixture of the product from Step 2 above (526 mg, 1.37 mmol, 95% purity), 2,5-dimethoxytetrahydrofuran (250 µl, 1.93 mmol) and AcOH (2.5 ml) was heated to 120° C. for 90 min. Upon cooling to RT, the mixture was concentrated in vacuo onto silica and purified by chromatography on silica gel (24 g cartridge, 0-100% EtOAc/isohexane) to afford the title compound (198 mg, 0.462 mmol, 33% yield, 96% purity) as a white solid after trituration with TBME. UPLC-MS (Method 1) m/z 412.3 (M+H)$^+$, 410.3 (M−H)$^−$ at 1.43 min. $^1$H NMR (500 MHz, DMSO-$d_6$) δ 9.90 (s, 1H), 8.13 (dd, J=8.7, 2.3 Hz, 1H), 8.02 (d, J=2.3 Hz, 1H), 7.83 (dd, J=8.3, 2.0 Hz, 1H), 7.60 (d, J=2.0 Hz, 1H), 7.48 (d, J=8.3 Hz, 1H), 7.27 (d, J=8.8 Hz, 1H), 6.95 (t, J=2.2 Hz, 2H), 6.12 (t, J=2.2 Hz, 2H), 3.87 (s, 3H), 3.82 (s, 3H).

Step 4: 3-(N-(5-cyano-2-(pyrrol-1-yl)phenyl)sulfamoyl)-4-methoxybenzoic acid: A mixture of the product from Step 3 above (198 mg, 0.462 mmol, 96% purity) and LiOH (79 mg, 1.85 mmol) in THF/MeOH/water (4:1:1, 7.8 ml) was stirred at 40° C. overnight. The mixture was diluted with water (10 ml), acidified to pH 4 with 1 M HCl(aq) and extracted with EtOAc (3×20 ml). The combined organic extracts were washed with brine (10 ml), dried by passage through a phase separator and the solvent removed in vacuo. The residue was loaded onto silica and purified by chromatography on silica gel (12 g cartridge, 0-100% EtOAc/isohexane) and then by preparative HPLC (Waters, Acidic (0.1% Formic acid), Acidic, Waters X-Select Prep-C18, 5 µm, 19×50 mm column, 20-50% MeCN in Water) to afford the title compound (85.8 mg, 0.214 mmol, 46% yield, 99% purity) as a white solid. UPLC-MS (Method 1) m/z 398.7 (M+H)$^+$, 396.2 (M−H)$^−$ at 1.28 min. $^1$H NMR (500 MHz, DMSO-$d_6$) δ 13.04 (s, 1H), 9.84 (s, 1H), 8.11 (dd, J=8.8, 2.2 Hz, 1H), 8.04 (d, J=2.2 Hz, 1H), 7.81 (d, J=8.4 Hz, 1H), 7.58 (d, J=1.9 Hz, 1H), 7.48 (d, J=8.4 Hz, 1H), 7.25 (d, J=8.8 Hz, 1H), 6.97 (t, J=2.2 Hz, 2H), 6.14 (t, J=2.2 Hz, 2H), 3.86 (s, 3H).

Example 122: 4-cyclopropyl-3-(N-(2-(5-fluorothiophen-2-yl)-5-(trifluoromethyl)phenyl) sulfamoyl) benzoic acid

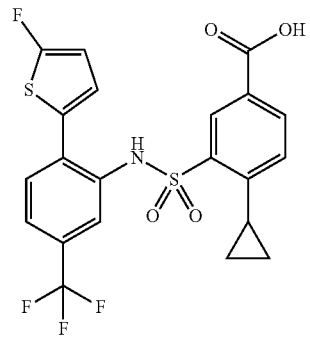

Step 1: Methyl 4-cyclopropyl-3-(N-(2-(5-fluorothiophen-2-yl)-5-(trifluoromethyl)phenyl)sulfamoyl)benzoate: A solution of the product from Example 117 Step 1 (100 mg, 0.379 mmol), the product from Example 132 Step 5 (129 mg, 0.46 mmol) and pyridine (130 µl, 1.60 mmol) in DCM (1.5 ml) was stirred at RT for 47 h. The reaction mixture was purified by chromatography on silica gel (12 g cartridge, 0-25% EtOAc/isohexane) to afford the title compound (141 mg, 0.281 mmol, 74% yield) as a cream solid. UPLC-MS (Method 1) m/z 500.2 (M+H)$^+$, 498.2 (M−H)$^−$ at 1.86 min.

Step 2: 4-cyclopropyl-3-(N-(2-(5-fluorothiophen-2-yl)-5-(trifluoromethyl)phenyl)sulfamoyl)benzoic acid: 1 M LiOH (aq) (1.13 ml, 1.13 mmol) was added to a solution of the product from Step 5 above (141 mg, 0.281 mmol) in THF (2.26 ml) at RT. The reaction mixture was stirred at RT for 22 h, and then concentrated in vacuo to remove the THF. The residue was diluted with water (7 ml) and then washed with TBME (7 ml). The aqueous phase was acidified using 1 M HCl until pH 4-5 and then the product was extracted into EtOAc (3×7 ml). The combined organic extracts were dried over MgSO$_4$ and concentrated in vacuo to afford the title compound (112 mg, 0.227 mmol, 81% yield) as an off-white solid. UPLC-MS (Method 1) m/z 484.1 (M−H)$^−$ at 1.72 min. $^1$H NMR (500 MHz, DMSO-$d_6$) δ 13.22 (br s, 1H), 10.28 (br s, 1H), 8.18 (d, J=1.9 Hz, 1H), 8.03 (dd, J=8.2, 1.9 Hz, 1H), 7.89 (d, J=8.3 Hz, 1H), 7.66 (br d, J=8.3 Hz, 1H), 7.32 (t, J=4.0 Hz, 1H), 7.15 (d, J=8.3 Hz, 1H), 6.87 (br s, 1H), 6.77 (dd, J=4.2, 2.2 Hz, 1H), 2.73-2.64 (m, 1H), 1.11-1.03 (m, 2H), 0.90-0.83 (m, 2H).

Example 123: 3-(N-(2-(5-chlorothiophen-2-yl)-5-(methylsulfonyl)phenyl)sulfamoyl)-4-cyclopropyl-benzoic acid

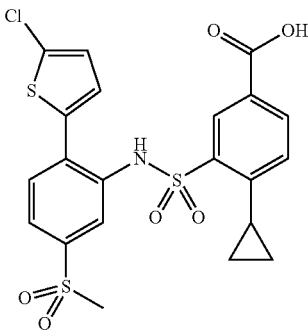 [SMILES: CS(=O)(=O)c1ccc(-c2ccc(Cl)s2)c(NS(=O)(=O)c2cc(C(=O)O)ccc2C2CC2)c1]

Step 1: Methyl 3-(N-(2-(5-chlorothiophen-2-yl)-5-(methylsulfonyl)phenyl)sulfamoyl)-4-cyclopropylbenzoate: A solution of the product Example 88 Step 1 (140 mg, 0.370 mmol, 76% purity), the product from Example 132 Step 5 (100 mg, 0.357 mmol) and pyridine (0.120 ml, 1.48 mmol) in DCM (1.5 ml) was stirred at RT for 72 h. The reaction mixture was purified by chromatography on silica gel (24 g cartridge, 0-50% EtOAc/isohexane) to afford the title compound (91.8 mg, 0.140 mmol, 38% yield, 80% purity) as a yellow solid. UPLC-MS (Method 1): m/z 548.2 (M+Na)$^+$, 524.1 (M−H)$^−$ at 1.60 min.

Step 2: 3-(N-(2-(5-chlorothiophen-2-yl)-5-(methylsulfonyl)phenyl)sulfamoyl)-4-cyclopropylbenzoic acid: 1 M LiOH(aq) (0.560 ml, 0.560 mmol) was added to a solution of the product from Step 1 above (91.8 mg, 0.140 mmol, 80% purity) in THF (1.12 ml) at RT. The resultant mixture was stirred at RT over the weekend. The reaction mixture was concentrated in vacuo. The residue was diluted water (5 ml) and then washed with TBME (5 ml). The aqueous phase was acidified using 1 M HCl(aq) until pH 4-5 and then extracted with EtOAc (3×5 ml). Following the addition of THF (4 ml), the combined organic phase was concentrated in vacuo. The crude product was purified by chromatography (24 g reverse phase cartridge, 5-40% MeCN/10 mM Ammonium Bicarbonate) to afford the title compound (53.9 mg, 0.104 mmol, 75% yield, 99% purity) as an off-white solid. UPLC-MS (Method 1): m/z 534.2 (M+Na)$^+$, 510.1 (M−H)$^−$ at 1.45 min. $^1$H NMR (500 MHz, DMSO-d$_6$) δ 13.20 (br s, 1H), 10.36 (br s, 1H), 8.19 (br s, 1H), 8.01 (br d, J=7.9 Hz, 1H), 7.95 (d, J=8.3 Hz, 1H), 7.91-7.72 (m, 1H), 7.50 (d, J=4.0 Hz, 1H), 7.23 (br s, 1H), 7.14 (br d, J=4.2 Hz, 2H), 3.03 (s, 3H), 2.79-2.61 (m, 1H), 1.16-0.99 (m, 2H), 0.97-0.76 (m, 2H).

Example 124: 3-(N-(2-(5-cyanothiophen-2-yl)-5-(methylsulfonyl)phenyl)sulfamoyl)-4-cyclopropyl-benzoic acid

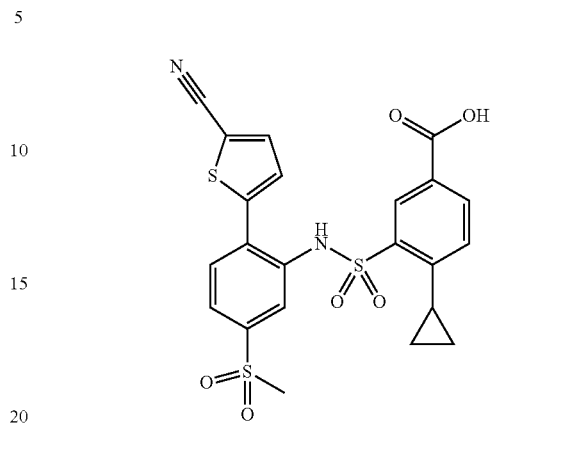

Step 1: 5-(2-amino-4-(methylsulfonyl)phenyl)thiophene-2-carbonitrile: To a reaction vessel containing 2-bromo-5-(methylsulfonyl)aniline (250 mg, 1.00 mmol), (5-cyanothiophen-2-yl)boronic acid (310 mg, 2.03 mmol), 1 M K$_3$PO$_4$ (aq) (1.70 ml, 1.70 mmol) and dioxane (5 ml) was added XPhos Pd G3 (42 mg, 0.050 mmol). The resultant reaction mixture was degassed with N$_2$ for 15 min and then heated at 80° C. for 2 h. Additional XPhos Pd G3 (42 mg, 0.050 mmol) and (5-cyanothiophen-2-yl)boronic acid (160 mg, 1.05 mmol) were added and the reaction mixture was degassed with N$_2$ for 10 min and heated at 80° C. for 4 h. The reaction was allowed to cool to RT. The mixture was concentrated in vacuo onto Celite® and purified by chromatography on silica gel (12 g cartridge, 40-100% EtOAc/isohexane) to the title compound (169 mg, 0.498 mmol, 50% yield, 82% purity) as a dark yellow solid. UPLC-MS (Method 4): m/z 277.0 (M−H)$^−$ at 1.71 min.

Step 2: Methyl 3-(N-(2-(5-cyanothiophen-2-yl)-5-(methylsulfonyl)phenyl)sulfamoyl)-4-cyclopropylbenzoate: The product from Example 132 Step 5 (180 mg, 0.655 mmol) was added to a solution of pyridine (150 μl, 1.86 mmol) and the product from Step 4 above (169 mg, 0.61 mmol, 82% purity) in DCM (1 ml). The resultant solution was stirred at RT for 3 days. Additional pyridine (150 μl, 1.86 mmol) and DCM (1 ml) was added to the reaction mixture. The solution was stirred at RT for 2 days. The reaction mixture was concentrated in vacuo and purified by chromatography on silica gel (12 g cartridge, 0-100% EtOAc/isohexane) to afford the title compound (77 mg, 0.119 mmol, 20% yield, 80% purity) as a yellow oil and an additional batch of the title compound (173 mg, 0.127 mmol, 26% yield, 38% purity). UPLC-MS (Method 2): m/z 515.1 (M−H)$^−$ at 1.16 min.

Step 3: 3-(N-(2-(5-cyanothiophen-2-yl)-5-(methylsulfonyl)phenyl)sulfamoyl)-4-cyclopropylbenzoic acid: 1 M LiOH(aq) (360 μl, 0.360 mmol) was added to a solution of the product from Step 2 above (77 mg, 0.119 mmol, 80% purity) in THF (1 ml). In a separate vesseal, 1 M LiOH(aq) (420 μl, 0.420 mmol) was added to a solution of the product from Step 2 above (173 mg, 0.127 mmol, 38% purity) in THF (1 ml). The reaction mixtures were both stirred at RT overnight, then each was concentrated in vacuo. Each residue was dissolved in water (12 ml) and washed with EtOAc (12 ml). The aqueous phase was acidified using 1 M HCl(aq) until pH 4-5 and extracted with EtOAc (2×12 ml). The organic phases from each reaction were combined and dried by passage through a phase separator and concentrated in vacuo. The residue from each reaction was combined and partially purified by chromatography (24 g reverse phase C18 cartridge, 20-50% MeCN/Water 0.1% formic acid(aq)), then purified by preparative HPLC (Waters, Acidic (0.1% Formic acid), Acidic, Waters X-Select Prep-C18, 5 μm, 19×50 mm column, 20-50% MeCN in Water) to afford the title compound (5 mg, 9.45 μmol, 8% yield, 95% purity) as a white solid. UPLC-MS (Method 1): m/z 500.9 (M–H)$^-$ at 1.29 min. $^1$H NMR (500 MHz, DMSO-$d_6$) δ 13.2 (br s, 1H), 10.5 (br s, 1H), 8.20 (s, 1H), 8.04 (d, J=8.3 Hz, 1H), 8.00 (d, J=8.3 Hz, 1H), 7.94 (d, J=4.0 Hz, 1H), 7.89-7.81 (m, 1H), 7.71 (d, J=4.1 Hz, 1H), 7.37 (s, 1H), 7.12 (d, J=8.3 Hz, 1H), 3.08 (s, 3H), 2.80-2.65 (m, 1H), 1.12-0.98 (m, 2H), 0.93-0.81 (m, 2H).

Example 125: 3-(N-(2-(5-cyanothiophen-2-yl)-5-(trifluoromethyl)phenyl)sulfamoyl)-4-methoxybenzoic acid

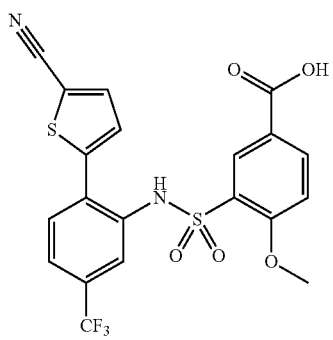 [SMILES: COc1ccc(C(=O)O)cc1S(=O)(=O)Nc1cc(C(F)(F)F)ccc1-c1ccc(C#N)s1]

Step 1: 5-(2-amino-4-(trifluoromethyl)phenyl)thiophene-2-carbonitrile: To a reaction vessel containing 2-bromo-5-(trifluoromethyl)aniline (0.3 ml, 2.09 mmol), (5-cyanothiophen-2-yl)boronic acid (650 mg, 4.25 mmol), 1 M $K_3PO_4$ (aq) (3.5 ml, 3.50 mmol) and dioxane (10 ml) was added XPhos Pd G3 (90 mg, 0.106 mmol). The reaction mixture was degassed with $N_2$ for 15 min and heated at 80° C. for 1 h. Additional XPhos Pd G3 (90 mg, 0.106 mmol) and (5-cyanothiophen-2-yl)boronic acid (320 mg, 2.09 mmol) was added, the reaction mixture was degassed with $N_2$ for 10 min and heated at 80° C. for 1 h. The reaction mixture was allowed to cool to RT, filtered through Celite® and concentrated in vacuo. The crude product was purified by chromatography on silica gel (12 g cartridge, 5-100% EtOAc/isohexane) to afford the title compound (546 mg, 1.87 mmol, 89% yield, 92% purity) as a dark yellow solid. UPLC-MS (Method 2): m/z 267.1 (M–H)$^-$ at 1.56 min.

Step 2: Methyl 3-(N-(2-(5-cyanothiophen-2-yl)-5-(trifluoromethyl)phenyl)sulfamoyl)-4-methoxybenzoate: Methyl 3-(chlorosulfonyl)-4-methoxybenzoate (300 mg, 1.13 mmol) was added to a solution of pyridine (250 μl, 3.09 mmol) and the product from Step 1 above (273 mg, 1.02 mmol, 92% purity) in DCM (1 ml). The resultant solution was stirred at RT for 2 days. The reaction mixture was concentrated in vacuo and purified by chromatography on silica gel (12 g cartridge, 0-100% Ethyl acetate/Isohexane) to the title compound (337 mg, 0.611 mmol, 60% yield, 90% purity) as a yellow oil. UPLC-MS (Method 2): m/z 495.1 (M–H)$^-$ at 1.29 min.

Step 3: 3-(N-(2-(5-cyanothiophen-2-yl)-5-(trifluoromethyl)phenyl)sulfamoyl)-4-methoxybenzoic acid: 1 M LiOH (aq) (2 ml, 2.00 mmol) was added to a solution of the product from Step 2 above (337 mg, 0.679 mmol, 90% purity) in THF (4 ml). The reaction mixture was stirred at RT overnight and then concentrated in vacuo. The residue was dissolved in water (12 ml) and washed with EtOAc (12 ml). The aqueous phase was acidified using 1 M HCl(aq) until pH 4-5 and then extracted into EtOAc (2×12 ml). The combined organic phases were dried by passage through a phase separator and concentrated in vacuo. The residue was purified by chromatography (24 g reverse phase cartridge, 15-60% MeCN/Water 0.1% Formic Acid) to afford the crude product. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (70 mg, 0.138 mmol, 20% yield, >95% purity) as a white solid. UPLC-MS (Method 1): m/z 481.1 (M–H)$^-$ at 1.45 min. $^1$H NMR (500 MHz, DMSO-$d_6$) δ 13.09 (br s, 1H), 10.14 (br s, 1H), 8.18 (d, J=8.7 Hz, 1H), 8.07 (s, 1H), 8.00-7.93 (m, 2H), 7.79-7.63 (m, 2H), 7.35 (d, J=8.8 Hz, 1H), 7.16 (s, 1H), 3.88 (s, 3H).

Example 126: 3-(N-(5-cyano-2-(5-cyanothiophen-2-yl)phenyl)sulfamoyl)-4-cyclopropylbenzoic acid

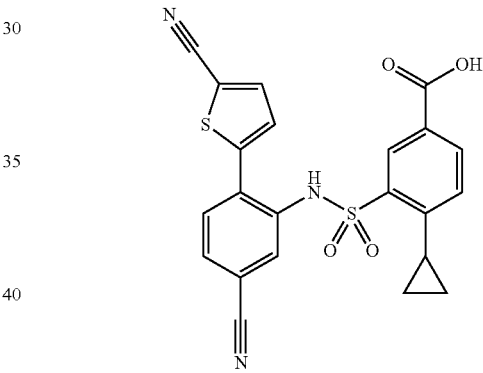

Step 1: 5-(2-amino-4-cyanophenyl)thiophene-2-carbonitrile: To the reaction vessel containing 3-amino-4-bromobenzonitrile (250 mg, 1.27 mmol), (5-cyanothiophen-2-yl)boronic acid (390 mg, 2.55 mmol), 1 M $K_3PO_4$(aq) (2.1 ml, 2.10 mmol) and dioxane (5 ml) was added XPhos Pd G3 (54 mg, 0.064 mmol). The reaction mixture was degassed with $N_2$ for 15 min and heated at 80° C. for 1 h. Additional XPhos Pd G3 (54 mg, 0.064 mmol) and (5-cyanothiophen-2-yl)boronic acid (190 mg, 1.24 mmol) was added, the reaction mixture was degassed with $N_2$ for 10 min and heated at 80° C. for 1 h. The reaction mixture was allowed to cool to RT, filtered through Celite® and concentrated in vacuo. The crude product was purified by chromatography on silica gel (12 g cartridge, 10-100% EtOAc/isohexane) to afford the title compound (163 mg, 0.673 mmol, 53% yield, 93% purity) as a yellow solid. UPLC-MS (Method 2): m/z 224.4 (M–H)$^-$ at 1.27 min.

Step 2: Methyl 3-(N-(5-cyano-2-(5-cyanothiophen-2-yl)phenyl)sulfamoyl)-4-cyclopropylbenzoate: The product from Example 132 Step 5 (220 mg, 0.801 mmol) was added to a solution of pyridine (180 μl, 2.23 mmol) and the product from Step 1 above (163 mg, 0.724 mmol, 93% purity) in DCM (1 ml). The resultant solution was stirred for 1 day. Additional pyridine (180 μl, 2.23 mmol) and DCM (1 ml) was added to the reaction mixture which was then stirred at RT for 8 days. The reaction mixture was concentrated in vacuo and purified by chromatography on silica gel (12 g cartridge, 0-100% Ethyl acetate/Isohexane) to afford the title compound (222 mg, 0.450 mmol, 62% yield, 94% purity) as a bright yellow oil. UPLC-MS (Method 2): m/z 462.3 (M−H)⁻ at 1.29 min.

Step 3: 3-(N-(5-cyano-2-(5-cyanothiophen-2-yl)phenyl)sulfamoyl)-4-cyclopropylbenzoic acid: 1 M LiOH(aq) (1.5 ml, 1.50 mmol) was added to a solution of the product from Step 2 above (222 mg, 0.479 mmol, 94% purity) in THF (3 ml). The reaction mixture was stirred at RT overnight. The reaction mixture was concentrated in vacuo. The residue was dissolved in water (12 ml) and washed with EtOAc (12 ml). The aqueous phase was acidified using 1 M HCl(aq) until pH 4-5 and extracted with EtOAc (2×12 ml). The combined organic phases were dried by passage through a phase separator and concentrated in vacuo. The crude product was purified by chromatography (24 g reverse phase cartridge, 15-80% MeCN/Water 0.1% Formic Acid) and by preparative HPLC (Waters, Acidic (0.1% Formic acid), Acidic, Waters X-Select Prep-C18, 5 μm, 19×50 mm column, 35-65% MeCN in Water) to afford the title compound (62 mg, 0.131 mmol, 27% yield, >95% purity) as a white solid. UPLC-MS (Method 2): m/z 448.2 (M−H)⁻ at 1.40 min. ¹H NMR (500 MHz, DMSO-d₆) δ 13.2 (br, s, 1H), 10.50 (br, s, 1H), 8.20 (s, 1H), 8.01 (dd, J=8.3, 1.9 Hz, 1H), 7.95 (d, J=8.2 Hz, 1H), 7.91 (d, J=4.1 Hz, 1H), 7.80 (s, 1H), 7.66 (d, J=4.1 Hz, 1H), 7.30 (d, J=1.7 Hz, 1H), 7.09 (d, J=8.3 Hz, 1H), 2.73-2.58 (m, 1H), 1.12-0.98 (m, 2H), 0.92-0.80 (m, 2H).

Example 127: 3-(N-(2-(5-cyanothiophen-2-yl)-5-(trifluoromethyl)phenyl)sulfamoyl)-4-cyclopropylbenzoic acid

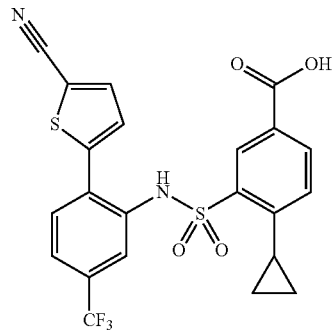 [SMILES: N#Cc1ccc(-c2ccc(C(F)(F)F)cc2NS(=O)(=O)c2cc(C(=O)O)ccc2C2CC2)s1]

Step 1: Methyl 3-(N-(2-(5-cyanothiophen-2-yl)-5-(trifluoromethyl)phenyl)sulfamoyl)-4-cyclopropylbenzoate: The product from Example 132 Step 5 (310 mg, 1.13 mmol) was added to a solution of pyridine (250 μl, 3.09 mmol) and the product Example 125 Step 1 above (273 mg, 1.02 mmol, 92% purity) in DCM (2 ml). The resultant solution was stirred at RT for 9 days. The reaction mixture was concentrated in vacuo and purified by chromatography on silica gel (24 g cartridge, 0-100% Ethyl acetate/Isohexane) to afford the title compound (415 mg, 0.705 mmol, 69% yield, 86% purity) as a dark yellow oil. UPLC-MS (Method 2): m/z 505.2 (M−H)⁻ at 1.42 min.

Step 2: 3-(N-(2-(5-cyanothiophen-2-yl)-5-(trifluoromethyl)phenyl)sulfamoyl)-4-cyclopropylbenzoic acid: 1 M LiOH(aq) (2.5 ml, 2.50 mmol) was added to a solution of the product from Step 1 above (415 mg, 0.819 mmol) in THF (5 ml). The reaction mixture was stirred at RT overnight and then concentrated in vacuo. The residue was dissolved in water (12 ml) and washed with EtOAc (12 ml). The aqueous phase was acidified using 1 M HCl(aq) until pH 4-5 and then extracted with EtOAc (2×12 ml). The combined organic phases were dried by passage through a phase separator and concentrated in vacuo. The crude product was purified by chromatography (24 g reverse phase cartridge, 15-80% MeCN/Water 0.1% Formic Acid) and by preparative HPLC (Waters, Acidic (0.1% Formic acid), Acidic, Waters X-Select Prep-C18, 5 μm, 19×50 mm column, 50-80% MeCN in Water) to afford the title compound (77 mg, 0.149 mmol, 18% yield) as a white solid. UPLC-MS (Method 2): m/z 491.1 (M−H)⁻ at 1.61 min. ¹H NMR (500 MHz, DMSO-d₆) δ 13.2 (br s, 1H) 10.3 (br s, 1H), 8.18 (s, 1H), 8.02 (dd, J=8.2, 1.9 Hz, 1H), 7.98 (d, J=8.2 Hz, 1H), 7.95 (d, J=4.0 Hz, 1H), 7.74-7.67 (m, 2H), 7.13 (d, J=8.3 Hz, 1H), 7.05 (s, 1H), 2.72-2.61 (m, 1H), 1.15-1.03 (m, 2H), 0.93-0.80 (m, 2H).

Example 128: 4-ethyl-3-(N-(2-(thiazol-2-yl)-5-(trifluoromethyl)phenyl)sulfamoyl)benzoic acid

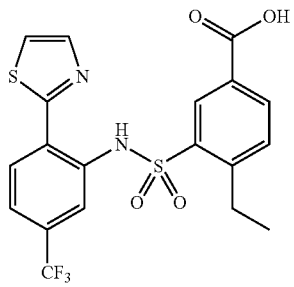 [SMILES: CCc1ccc(C(=O)O)cc1S(=O)(=O)Nc1cc(C(F)(F)F)ccc1-c1nccs1]

Step 1: 2-(4,4,5,5-tetramethyl-1,3,2-dioxaborolan-2-yl)-5-(trifluoromethyl)aniline: A mixture of 2-bromo-5-(trifluoromethyl)aniline (0.300 ml, 2.09 mmol), 4,4,4',4',5,5,5',5'-octamethyl-2,2'-bi(1,3,2-dioxaborolane) (639 mg, 2.52 mmol) and potassium acetate (621 mg, 6.32 mmol) in dioxane (7.40 ml) was degassed with N₂ for 5 min before [Pd(dppf)Cl₂]-DCM complex (85 mg, 0.105 mmol) was added and the mixture was then degassed with N₂ for further 5 min.

The reaction was heated at 80° C. for 2 h. The reaction was allowed to cool RT, filtered through Celite®, washed with DCM (8 ml) and concentrated in vacuo. The crude product was purified by chromatography on silica gel (12 g cartridge, 0-10% EtOAc/isohexane) to the title compound (234 mg, 0.489 mmol, 23% yield, 60% purity) as a colourless oil. ¹H NMR (500 MHz, Chloroform-d) δ 7.77 (d, J=7.7 Hz, 1H), 7.12 (s, 1H), 7.08 (d, J=7.7 Hz, 1H), 1.36 (s, 12H). Two exchangeable protons not observed.

Step 2: 2-(thiazol-2-yl)-5-(trifluoromethyl)aniline: To a reaction vessel containing the product from Step 1 above (346 mg, 0.723 mmol, 60% purity) and 2-bromothiazole (0.085 ml, 0.940 mmol) in dioxane (3.00 ml) was added XPhos Pd G3 (30.6 mg, 0.036 mmol). The resultant reaction mixture was degassed with N₂ for 5 min. 1 M K₃PO₄(aq) (1.81 ml, 1.81 mmol) was added, the mixture was degassed for a further 5 min and then heated to 80° C. for 2 h. The resultant mixture was allowed to cool to RT, filtered through Celite®, washing with EtOAc (3 ×10 ml) and concentrated in vacuo. The crude product was purified by chromatography on silica gel (24 g cartridge, 0-10% EtOAc/isohexane) to afford the title compound (32 mg, 0.131 mmol, 18% yield, >95% purity) as a pale green solid. UPLC-MS (Method 1) m/z 245.2 (M+H)$^+$ at 1.64 min. $^1$H NMR (500 MHz, DMSO-d$_6$) δ 7.97 (d, J=3.3 Hz, 1H), 7.80 (q, J=2.3 Hz, 2H), 7.38 (s, 2H), 7.19 (d, J=1.9 Hz, 1H), 6.88 (dd, J=8.4, 1.9 Hz, 1H).

Step 3: Methyl 4-ethyl-3-(N-(2-(thiazol-2-yl)-5-(trifluoromethyl)phenyl)sulfamoyl)benzoate: To a solution of the product from Step 2 above (32 mg, 0.131 mmol, >95% purity) and the product from Example 19 Step 2 (37.9 mg, 0.144 mmol) in DCM (1 ml, 0.131 mmol) was added pyridine (0.042 ml, 0.524 mmol) and the mixture was stirred at RT for 3 days. The reaction mixture was concentrated in vacuo then purified by chromatography on silica gel (12 g cartridge, 0-50% EtOAc/isohexane) to afford the title compound (52 mg, 0.111 mmol, 84% yield) as a colourless solid. UPLC-MS (Method 2): m/z 471.7 (M+H)$^+$, 469.2 (M−H)$^-$ at 1.42 min.

Step 4: 4-ethyl-3-(N-(2-(thiazol-2-yl)-5-(trifluoromethyl)phenyl)sulfamoyl)benzoic acid: LiOH (7.79 mg, 0.325 mmol) was added to a solution of the product from Step 3 above (0.051 g, 0.108 mmol) in THF (3 ml, 0.108 mmol) and water (1 ml) at RT. The resultant mixture was stirred at RT for 96 h. The reaction mixture was concentrated in vacuo to remove the THF.

The residue was acidified with 10% w/v citric acid(aq) and the precipitate was collected under filtration to afford the title compound (42.5 mg, 0.089 mmol, 82% yield, 96% purity) as a white solid. UPLC-MS (Method 1): m/z 457.3 (M+H)$^+$, 455.2 (M−H)$^-$ at 1.75 min. $^1$H NMR (500 MHz, DMSO-d$_6$) δ 13.35 (br s, 1H), 12.54 (br s, 1H), 8.48-8.38 (m, 1H), 8.19 (s, 1H), 8.14 (d, J=8.2 Hz, 1H), 8.07 (d, J=10.3 Hz, 2H), 7.63 (s, 1H), 7.55 (d, J=8.3 Hz, 2H), 2.98-2.88 (m, 2H), 1.04 (t, J=7.4 Hz, 3H).

Example 129: 4-ethyl-3-(N-(2-(thiazol-5-yl)-5-(trifluoromethyl)phenyl)sulfamoyl)benzoic acid

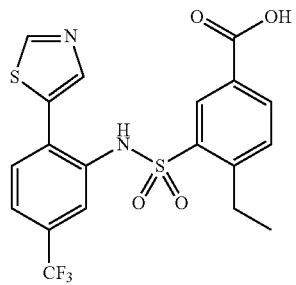 [SMILES: CCc1ccc(C(=O)O)cc1S(=O)(=O)Nc1cc(C(F)(F)F)ccc1-c1cncs1]

Step 1: 2-(thiazol-4-yl)-5-(trifluoromethyl)aniline: To a reaction vessel containing the product from Example 128 Step 1 (204 mg, 0.426 mmol, 60% purity), 4-bromothiazole (50 μl, 0.561 mmol), 1 M K$_3$PO$_4$(aq) (750 μl, 0.750 mmol) and dioxane (3.00 ml) was added XPhos Pd G3 (20 mg, 0.024 mmol). The resultant reaction mixture was degassed with N$_2$ for 10 min and then heated to 80° C. for 1.5 h. The resultant mixture was allowed to cool to RT, filtered, washed with DCM (5 ml) and concentrated in vacuo. The crude product was purified by chromatography on silica gel (12 g cartridge, 0-20% EtOAc/isohexane) to the title compound (80 mg, 0.308 mmol, 72% yield, 94% purity) as a tan solid. UPLC-MS (Method 1): m/z 245.2 (M+H)$^+$ (ES$^+$), at 1.46 min. $^1$H NMR (500 MHz, DMSO-d$_6$) δ 9.29 (d, J=1.9 Hz, 1H), 8.14 (d, J=2.0 Hz, 1H), 7.76 (dd, J=8.2, 1.1 Hz, 1H), 7.12-7.08 (m, 1H), 6.89-6.85 (m, 1H), 6.53 (br s, 2H).

Step 2: Methyl 4-ethyl-3-(N-(2-(thiazol-5-yl)-5-(trifluoromethyl)phenyl)sulfamoyl)benzoate: To a solution of the product from Step 1 above (75 mg, 0.307 mmol, 94% purity) and the product from Example 19 Step 2 (89 mg, 0.338 mmol) in DCM (1.5 ml, 0.307 mmol) was added pyridine (0.099 ml, 1.23 mmol) and the mixture was stirred at RT for 3 days. The reaction mixture was concentrated in vacuo then purified by chromatography on silica gel (12 g cartridge, 0-50% EtOAc/isohexane) to afford the title compound (130 mg, 0.268 mmol, 87% yield, 97% purity) as a colourless solid. UPLC-MS (Method 2): m/z 471.4 (M+H)$^+$, 469.2 (M−H)$^-$ at 1.69 min.

Step 3: 4-ethyl-3-(N-(2-(thiazol-5-yl)-5-(trifluoromethyl)phenyl)sulfamoyl)benzoic acid: LiOH (0.019 g, 0.804 mmol) was added to a solution of the product from Step 2 above (0.130 g, 0.268 mmol, 97% purity) in THF (3 ml, 0.268 mmol) and water (1 ml) at RT. The resultant mixture was stirred at RT for 96 h. The reaction mixture was concentrated in vacuo to remove the THF. The residue was acidified with 10% w/v citric acid(aq) and the resultant precipitate was collected under filtration to afford the title compound (66.6 mg, 0.144 mmol, 54% yield, 99% purity) as a white solid. UPLC-MS (Method 1) m/z 457.3 (M+H)$^+$, 455.2 (M−H)$^-$ at 1.67 min. $^1$H NMR (500 MHz, DMSO-d$_6$) δ 13.30 (br s, 1H), 12.00 (s, 1H), 9.49 (s, 1H), 8.45 (s, 1H), 8.33 (d, J=1.9 Hz, 1H), 8.09 (d, J=8.2 Hz, 1H), 8.03 (dd, J=8.0, 1.8 Hz, 1H), 7.66 (s, 1H), 7.55-7.45 (m, 2H), 2.84 (q, J=7.6 Hz, 2H), 1.02 (t, J=7.4 Hz, 3H).

Example 130: 4-ethyl-3-(N-(4-fluoro-2-(pyrrol-1-yl)-5-(trifluoromethyl)phenyl) sulfamoyl)benzoic acid

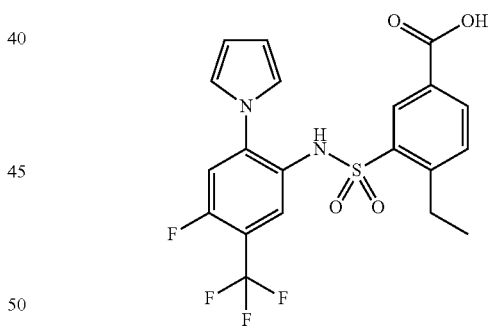

Step 1: Tert-butyl (5-fluoro-2-nitro-4-(trifluoromethyl)phenyl)carbamate: 5-fluoro-2-nitro-4-(trifluoromethyl)aniline (1.51 g, 6.74 mmol) was dissolved in DCM (3 ml) and treated with a solution of BOC$_2$O (1.72 ml, 7.41 mmol) in DCM (2 ml). The resultant mixture was stirred at RT for 18 h. The mixture was concentrated in vacuo, dissolved in THF (2.5 ml) and then heated at 65° C. for 24 h. The mixture was concentrated in vacuo and treated portionwise with 1 M LiHMDS in THF (6.74 ml, 6.74 mmol) with cooling, then stirred at RT for 2 h. Additional 1 M LiHMDS in THF (6.74 ml, 6.74 mmol) was added and stirring continued for 18 h. The mixture was quenched by portionwise addition to a cooled solution of acetic acid (1.6 ml, 27.9 mmol) in THF (5 ml). The mixture was concentrated in vacuo onto silica and purified by chromatography on silica gel (40 g cartridge, 0-25% DCM/Isohexane) to afford the title compound (888 mg, 2.74 mmol, 41% yield) as a pale yellow solid. UPLC-MS (Method 1): m/z 323.2 (M–H)⁻ at 1.92 min.

Step 2: Tert-butyl (2-amino-5-fluoro-4-(trifluoromethyl)phenyl)carbamate: A solution of the product from Step 1 above (0.888 g, 2.74 mmol) in MeOH (80 ml) was hydrogenated in the H-Cube (10% Pt/C, 30×4 mm, Full hydrogen, 25° C., 1 ml/min). The resultant solution was concentrated in vacuo to afford the title compound (0.844 g, 2.44 mmol, 89% yield, 85% purity) as a orange-brown foam. $^1$H NMR (500 MHz, DMSO-$d_6$) δ 8.71 (s, 1H), 7.60 (d, J=13.2 Hz, 1H), 6.99 (d, J=7.3 Hz, 1H), 5.26 (s, 2H), 1.49 (s, 9H).

Step 3: Methyl 3-(N-(2-((tert-butoxycarbonyl)amino)-4-fluoro-5-(trifluoromethyl)phenyl)sulfamoyl)-4-ethylbenzoate: The product from Step 2 above (250 mg, 0.722 mmol, 85% purity) was combined with the product from Example 19 Step 2 (250 mg, 0.952 mmol) in DCM (2 ml) and treated with pyridine (100 µl, 1.24 mmol). THF (2 ml) was added and the resultant clear solution allowed to stand at RT for 2 days. The mixture was diluted with PhMe (1 ml) and concentrated in vacuo, azeotroping with PhMe (1 ml). The crude product was purified by chromatography on silica gel (12 g cartridge, 0-30% EtOAc/isohexane) to afford the title compound (342 mg, 0.644 mmol, 89% yield, 98% purity) as a brown viscous oil. UPLC-MS (Method 1) m/z 421.4 (M+H-Boc)⁺, 519.2 (M–H)⁻ at 1.92 min.

Step 4: 2-((2-ethyl-5-(methoxycarbonyl)phenyl)sulfonamido)-5-fluoro-4-(trifluoromethyl)benzenaminium trifluoroacetate: The product from Step 3 above (342 mg, 0.644 mmol, 98% purity) was dissolved in DCM (2.5 ml) and treated with trifluoroacetic acid (500 µl, 6.49 mmol). The resultant mixture was allowed to stand for 18 h. The mixture was treated with PhMe (2 ml) and concentrated in vacuo to afford the title compound (258 mg, 0.454 mmol, 71% yield, 94% purity) as a brown solid. UPLC-MS (Method 1): m/z 421.4 (M+H)⁺, 419.3 (M–H)⁻ at 1.56 min.

Step 5: methyl 4-ethyl-3-(N-(4-fluoro-2-(pyrrol-1-yl)-5-(trifluoromethyl)phenyl)sulfamoyl)benzoate: The product from Step 4 above (258 mg, 0.454 mmol, 94% purity) was combined with sodium acetate (100 mg, 1.22 mmol) and 2,5-dimethoxytetrahydrofuran (100 µl, 0.772 mmol) in AcOH (2 ml). The mixture was heated to 120° C. and the resultant clear solution was allowed to stand at 120° C. for 2 h. n-Heptane (3 ml) was added and the mixture concentrated in vacuo. The crude product was purified by chromatography on silica gel (12 g cartridge, 0-50% EtOAc/isohexane) to afford the title compound (183 mg, 0.354 mmol, 78% yield, 91% purity) as an orange-brown oil. UPLC-MS (Method 1): m/z 471.4 (M+H)⁺, 469.2 (M–H)⁻ at 1.79 min.

Step 6: 4-ethyl-3-(N-(4-fluoro-2-(pyrrol-1-yl)-5-(trifluoromethyl)phenyl)sulfamoyl)benzoic acid: 1 M LiOH(aq) (1.4 ml, 1.40 mmol) was added to a solution of the product from Step 5 above (183 mg, 0.354 mmol, 91% purity) in THF (2.8 ml). The reaction mixture was stirred at RT overnight and then concentrated in vacuo. The residue was dissolved in water (12 ml) and washed with EtOAc (12 ml). The aqueous phase was acidified using 1 M HCl(aq) until pH 1-2 and the product was extracted with EtOAc (2×12 ml). The combined organic phases were dried by passage through a phase separator and concentrated in vacuo. The crude product was purified by preparative HPLC (Waters, Acidic (0.1% Formic acid), Acidic, Waters X-Select Prep-C18, 5 µm, 19×50 mm column, 40-70% MeCN in Water) to afford the title compound (58 mg, 0.121 mmol, 34% yield, >95% purity) as a white solid. UPLC-MS (Method 1): m/z 457.1 (M+H)⁺, 455.2 (M–H)⁻ at 1.65 min. $^1$H NMR (500 MHz, DMSO-$d_6$) δ 13.22 (br s, 1H), 10.31 (br s, 1H), 8.11-8.08 (m, 1H), 8.05 (dd, J=8.0, 1.9 Hz, 1H), 7.59 (d, J=11.4 Hz, 1H), 7.51 (d, J=8.0 Hz, 1H), 7.22 (d, J=7.3 Hz, 1H), 7.03 (t, J=2.2 Hz, 2H), 6.16 (t, J=2.2 Hz, 2H), 2.88 (q, J=7.4 Hz, 2H), 1.16 (t, J=7.4 Hz, 3H).

Example 131: 3-(N-(4-chloro-2-(pyrrol-1-yl)-5-(trifluoromethyl)phenyl)sulfamoyl)-4-ethylbenzoic acid

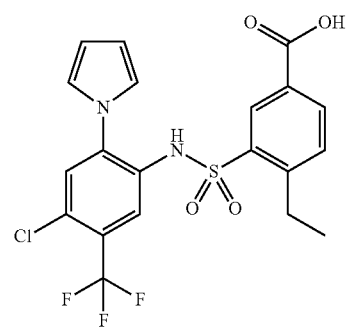

Step 1: Tert-butyl (5-chloro-2-nitro-4-(trifluoromethyl)phenyl)carbamate: 5-chloro-2-nitro-4-(trifluoromethyl)aniline (1.23 g, 5.11 mmol) was dissolved in DCM (3 ml) and treated with a solution of Boc₂O (1.31 ml, 5.63 mmol) in DCM (2 ml). The resultant mixture was stirred at RT for 18 h. The mixture was concentrated in vacuo, dissolved in THF (2.5 ml), heated at 65° C. for 48 h and then cooled to RT. The mixture was concentrated in vacuo onto silica and purified by chromatography on silica gel (40 g cartridge, 0-25% DCM/Isohexane) to afford the title compound (1.17 g, 3.43 mmol, 51% yield) as a white solid. UPLC-MS (Method 1): m/z 339.1 (M–H)⁻ at 1.99 min.

Step 2: Tert-butyl (2-amino-5-chloro-4-(trifluoromethyl)phenyl)carbamate: A solution of the product from Step 1 above (1.17 g, 3.43 mmol) in MeOH (80 ml) was hydrogenated in the H-Cube (10% Pt/C, 30×4 mm, Full hydrogen, 25° C., 1 ml/min). The resulatant solution was concentrated in vacuo to afford the title compound (1.05 g, 3.04 mmol, 89% yield, 90% purity) as a yellow foam. $^1$H NMR (500 MHz, DMSO-$d_6$) δ 8.70 (s, 1H), 7.74 (s, 1H), 7.12 (s, 1H), 5.54 (s, 2H), 1.49 (s, 9H).

Step 3: Methyl 3-(N-(2-((tert-butoxycarbonyl)amino)-4-chloro-5-(trifluoromethyl)phenyl)sulfamoyl)-4-ethylbenzoate: The product from Step 2 above (250 mg, 0.724 mmol, 90% purity) was combined with the product from Example 19 Step 2 (250 mg, 0.952 mmol) in DCM (2 ml) and the resultant suspension treated with pyridine (100 µl, 1.24 mmol). THF (2 ml) was added and the resultant clear solution allowed to stand at RT for 2 days. The mixtures were diluted with PhMe (1 ml) and concentrated in vacuo, azeotroping with PhMe (1 ml). The crude product was purified by chromatography on silica gel (12 g cartridge, 0-30% EtOAc/isohexane) to afford the title compound (379 mg, 0.685 mmol, 95% yield, 97% purity) as a brown viscous oil. UPLC-MS (Method 1): m/z 437.3 (M+H-Boc)⁺, 535.2 (M–H)⁻ at 1.99 min.

Step 4: 5-chloro-2-((2-ethyl-5-(methoxycarbonyl)phenyl)sulfonamido)-4-(trifluoromethyl)benzenaminium trifluoroacetamide: The product from Step 3 above (379 mg, 0.685 mmol, 97% purity) was dissolved in DCM (2.5 ml) and treated with trifluoroacetic acid (500 µl, 6.49 mmol). The resultant mixture was allowed to stand for 18 h. The mixture was treated with PhMe (2 ml) and concentrated in vacuo to afford the title compound (297 mg, 0.512 mmol, 75% yield, 95% purity) as a brown solid. UPLC-MS (Method 1): m/z 437.3 (M+H)+, 435.2 (M−H)− at 1.61 min.

Step 5: Methyl 3-(N-(4-chloro-2-(pyrrol-1-yl)-5-(trifluoromethyl)phenyl)sulfamoyl)-4-ethylbenzoate: The product from Step 4 above (297 mg, 0.512 mmol, 95% yield) was combined with sodium acetate (100 mg, 1.22 mmol) and 2,5-dimethoxytetrahydrofuran (100 µl, 0.772 mmol) in AcOH (2 ml). The mixture was heated to 120° C. and the resultant clear solution was allowed to stand at 120° C. for 2 h. n-Heptane (3 ml) was added and the mixtures concentrated in vacuo. The crude product was purified by chromatography on silica gel (12 g cartridge, 0-50% EtOAc/isohexane) to afford the title compound (220 mg, 0.402 mmol, 62% yield, 89% purity) as an orange-brown oil. UPLC-MS (Method 1) m/z 487.3 (M+H)+−, 485.2 (M−H)− at 1.88 min.

Step 6: 3-(N-(4-chloro-2-(pyrrol-1-yl)-5-(trifluoromethyl)phenyl)sulfamoyl)-4-ethylbenzoic acid: 1 M LiOH (aq) (1.6 ml, 1.60 mmol) was added to a solution of the product from Step 5 above (220 mg, 0.402 mmol, 89% purity) in THF (3.2 ml). The reaction mixture was stirred at RT overnight. The reaction mixture was concentrated in vacuo. The residue was dissolved in water (12 ml) and washed with EtOAc (12 ml). The aqueous phase was acidified using 1 M HCl(aq) until pH 1-2 and the product was extracted with EtOAc (2×12 ml). The combined organic phases were dried by passage through a phase separator and concentrated in vacuo. The crude product was purified by preparative HPLC (Waters, Acidic (0.1% Formic acid), Acidic, Waters X-Select Prep-C18, 5 µm, 19×50 mm column, 40-70% MeCN in Water) to afford the title compound (72 mg, 0.145 mmol, 36% yield, >95% purity) as a white solid. UPLC-MS (Method 1): m/z 473.1 (M+H)+, 471.2 (M−H)− at 1.74 min. 1H NMR (500 MHz, DMSO-d6) δ 13.26 (br s, 1H), 10.44 (s, 1H), 8.13 (d, J=1.8 Hz, 1H), 8.08 (dd, J=8.0, 1.9 Hz, 1H), 7.72 (s, 1H), 7.55 (d, J=8.0 Hz, 1H), 7.30 (s, 1H), 7.03 (t, J=2.2 Hz, 2H), 6.17 (t, J=2.2 Hz, 2H), 2.90 (q, J=7.4 Hz, 2H), 1.16 (t, J=7.4 Hz, 3H).

Example 132: 3-(N-(4-chloro-5-cyano-2-(pyridin-2-yl)phenyl)sulfamoyl)-4-cyclopropylbenzoic acid

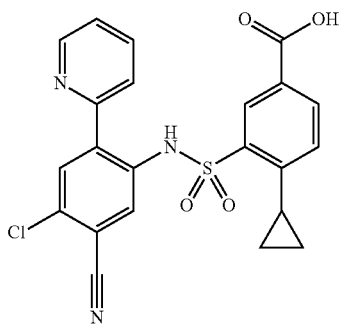 [SMILES: N#Cc1cc(NS(=O)(=O)c2cc(C(=O)O)ccc2C2CC2)c(-c2ccccn2)cc1Cl]

Step 1: 4-bromo-2-chloro-5-nitrobenzonitrile: 4-bromo-2-chlorobenzonitrile (1.00 g, 4.62 mmol) was dissolved in conc H2SO4 (4.92 ml, 92 mmol) and cooled to 0° C. before adding nitric acid (6.07 ml, 92 mmol). The mixture was kept at 0° C. for 30 min before stirring at RT overnight. The mixture was diluted with water (5 ml) and extracted with DCM (20 ml). The organic phase was dried over MgSO4, filtered and concentrated in vacuo. The crude product was purified by chromatography on silica gel (40 g cartridge, 0-50% TBME/Isohexane) to afford the title compound (1.06 g, 3.85 mmol, 83% yield, 95% purity) as a pale yellow solid. UPLC-MS (Method 1): m/z no ionisation at 1.37 min. 1H NMR (500 MHz, DMSO-d6) δ 8.81 (s, 1H), 8.52 (s, 1H).

Step 2: 5-amino-4-bromo-2-chlorobenzonitrile: The product from Step 1 above (1.40 g, 5.35 mmol, 95% purity) was dissolved in acetic acid (10 ml, 175 mmol) and iron (0.299 g, 5.35 mmol) was added with vigorous stirring. The resultant mixture was stirred at RT for 3 h. The mixture was filtered through Celite® and concentrated in vacuo. The crude product was purified by chromatography on silica gel (40 g cartridge, 0-50% TBME/Isohexane) to afford the title compound (0.650 g, 2.67 mmol, 50% yield, 95% purity) as a cream solid. 1H NMR (500 MHz, DMSO-d6) δ 7.79 (s, 1H), 7.17 (s, 1H), 5.98 (s, 2H).

Step 3: 5-amino-2-chloro-4-(pyridin-2-yl)benzonitrile: Pyridin-2-ylzinc(II) bromide (6.48 ml, 3.24 mmol) was added to a solution of the product from Step 2 above (0.250 g, 1.08 mmol, 95% purity) in dioxane (5 ml, 58.5 mmol) and Pd(PPh3)4 (0.125 g, 0.108 mmol) was added. The mixture was degassed under nitrogen and heated at 80° C. for 16 h. The mixture was concentrated onto silica and purified by chromatography on silica gel (40 g cartridge, 0-100% EtOAc/isohexane) to afford crude product which was triturated with TBME to afford the title compound (0.150 g, 0.542 mmol, 50% yield, 83% purity) as a tan solid. UPLC-MS (Method 1): m/z 230.2 (M+H)+, at 1.33 min.

Step 4: Methyl 3-(benzylthio)-4-cyclopropylbenzoate: To a degassed mixture of methyl 3-bromo-4-cyclopropylbenzoate (850 mg, 3.33 mmol), DIPEA (1.2 ml, 6.87 mmol) and XantPhos Pd G3 (300 mg, 0.316 mmol) in dioxane (13 ml) was added phenylmethanethiol (425 µl, 3.62 mmol) and the mixture was heated to 100° C. and stirred overnight. The mixture was cooled to RT, concentrated in vacuo onto silica and purified by chromatography on silica gel (40 g cartridge, 20-70% DCM/isohexane) to afford the title compound (600 mg, 1.91 mmol, 58% yield, 95% purity) as a orange oil. 1H NMR (500 MHz, DMSO-d6) δ 7.86 (d, J=1.8 Hz, 1H), 7.67 (dd, J=8.1, 1.8 Hz, 1H), 7.40-7.35 (m, 2H), 7.35-7.29 (m, 2H), 7.28-7.22 (m, 1H), 7.04 (d, J=8.1 Hz, 1H), 4.27 (s, 2H), 3.83 (s, 3H), 2.21-2.12 (m, 1H), 1.06-0.99 (m, 2H), 0.75-0.68 (m, 2H).

Step 5: Methyl 3-(chlorosulfonyl)-4-cyclopropylbenzoate: A mixture of the product from Step 4 above (600 mg, 1.91 mmol), AcOH (110 µl, 1.92 mmol) and water (250 µl, 13.9 mmol) in MeCN (9 ml) at −10° C. was treated with 1,3-dichloro-5,5-dimethylimidazolidine-2,4-dione (565 mg, 2.87 mmol). The mixture was stirred at −10° C. for 3 h. The mixture was diluted with water (50 ml) and extracted with DCM (2×50 ml). The organic phases were combined, dried over MgSO4, filtered, concentrated in vacuo onto silica and then purified by chromatography on silica gel (40 g cartridge, 0-50% DCM/Isohexane) to afford the title compound (440 mg, 1.52 mmol, 80% yield, 95% purity) as a pale yellow oil. 1H NMR (500 MHz, DMSO-d6) δ 8.36 (d, J=2.0 Hz, 1H), 7.77 (dd, J=8.2, 2.1 Hz, 1H), 6.84 (d, J=8.2 Hz, 1H), 3.84 (s, 3H), 3.22-3.01 (m, 1H), 1.08-0.98 (m, 2H), 0.79-0.70 (m, 2H).

Step 6: Methyl 3-(N-(4-chloro-5-cyano-2-(pyridin-2-yl)phenyl)sulfamoyl)-4-cyclopropylbenzoate: A solution of the product from Step 3 (0.100 g, 0.361 mmol, 83% purity) in DCM (3 ml, 46.6 mmol) and pyridine (0.175 ml, 2.17 mmol) was added the product from Step 5 above (0.109 g, 0.398 mmol) and the solution was stirred at RT for 48 h, then at 60° C. overnight, then at 90° C. overnight. The solvent was removed in vacuo. The crude product was purified by chromatography on silica gel (24 g cartridge, 0-100% EtOAc/Isohexane) to afford the title compound (0.052 g, 0.111 mmol, 31% yield) as a brown solid. UPLC-MS (Method 1): m/z 468.3 (M+H)$^+$, 466.2 (M−H)$^-$ at 1.75 min.

Step 7: 3-(N-(4-chloro-5-cyano-2-(pyridin-2-yl)phenyl)sulfamoyl)-4-cyclopropylbenzoic acid: LiOH (7.98 mg, 0.333 mmol) was added to a solution of the product from Step 5 above (0.052 g, 0.111 mmol) in THF (3 ml, 0.111 mmol) and water (1 ml) at RT. The resultant mixture was stirred at RT for 24 h. The reaction mixture was concentrated in vacuo to remove the THF. The residue was acidified with 10% w/v citric acid(aq) and the precipitate was collected under filtration to give the title compound (34.8 mg, 0.074 mmol, 67% yield, 97% purity) as a pale yellow solid. UPLC-MS (Method 1): m/z 454.3 (M+H)$^+$, 452.2 (M−H)$^-$ at 1.60 min. $^1$H NMR (500 MHz, DMSO-d$_6$) δ 13.31 (br s, 1H), 13.16 (br s, 1H), 8.73 (d, J=4.9 Hz, 1H), 8.31 (d, J=1.7 Hz, 1H), 8.27 (s, 1H), 8.08 (s, 1H), 8.03 (d, J=8.2 Hz, 1H), 7.95-7.90 (m, 1H), 7.85 (s, 1H), 7.54 (s, 1H), 6.99 (d, J=8.3 Hz, 1H), 2.51 (m, 1H), 0.83-0.69 (m, 2H), 0.71-0.56 (m, 2H).

Example 133: 3-(N-(5-chloro-4-cyano-3'-fluoro-[1,1'-biphenyl]-2-yl)sulfamoyl)-4-cyclopropylbenzoic acid

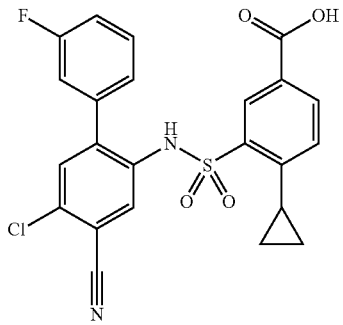 [SMILES: N#Cc1cc(NS(=O)(=O)c2cc(C(=O)O)ccc2C2CC2)c(-c2cccc(F)c2)cc1Cl]

Step 1: 2-amino-5-chloro-3'-fluoro-[1,1'-biphenyl]-4-carbonitrile: The product from Example 132 Step 2 (0.200 g, 0.864 mmol) was dissolved in dioxane (5 ml) and water (1 ml) before adding (3-fluorophenyl)boronic acid (0.133 g, 0.950 mmol), K$_3$PO$_4$ (0.550 g, 2.59 mmol) followed by Pd(PPh$_3$)$_4$ (0.050 g, 0.043 mmol). The mixture was degassed for 5 min under nitrogen and then heated at 80° C. for 2 h. The mixture was concentrated onto silica and the crude product was purified by chromatography on silica gel (24 g cartridge, 0-70% EtOAc/isohexane) to afford the title product (0.200 g, 0.649 mmol, 75% yield, 80% purity) as a cream solid. UPLC-MS (Method 1): m/z 247.2 (M+H)$^+$, at 1.58 min.

Step 2: Methyl 3-(N-(5-chloro-4-cyano-3'-fluoro-[1,1'-biphenyl]-2-yl)sulfamoyl)-4-cyclopropylbenzoate: A solution of the product from Step 1 above (0.100 g, 0.324 mmol, 80% purity) in dry THF (5 ml) was cooled to 0° C. before adding dropwise 1 M LiHMDS in THF (0.422 ml, 0.422 mmol). The mixture was stirred at 0° C. for 10 min before adding the product from Example 132 Step 5 (0.098 g, 0.357 mmol) and the solution was stirred at RT for 1 h. The mixture was quenched with MeOH (1 ml) and concentrated onto silica gel. The crude product was purified by chromatography on silica gel (24 g cartridge, 0-50% EtOAc/isohexane) to afford the title compound (0.103 g, 0.178 mmol, 55% yield, 84% purity) as a brown oil. UPLC-MS (Method 1) m/z 483.2 (M−H)$^-$ at 1.75 min.

Step 3: 3-(N-(5-chloro-4-cyano-3'-fluoro-[1,1'-biphenyl]-2-yl)sulfamoyl)-4-cyclopropylbenzoic acid: LiOH (0.013 g, 0.535 mmol) was added to a solution of the product from Step 2 (0.103 g, 0.178 mmol, 84% purity) in THF (3 ml) and water (1 ml) at RT. The resultant mixture was stirred at RT for 24 h. The reaction mixture was concentrated in vacuo to remove the THF. The residue was acidified with 10% w/v citric acid (aq) and the precipitate was collected under filtration. The precipitate was purified by chromatography on silica gel (24 g cartridge, 0-50% EtOAc/DCM) to afford crude product. The crude product was purified by chromatography (24 g reverse phase cartridge, 15-80% MeCN/Water 0.1% Formic Acid) to afford the title compound (23.4 mg, 0.048 mmol, 27% yield, 97% purity) as a white solid. UPLC-MS (Method 1): m/z 469.1 (M−H)$^-$ at 1.61 min. $^1$H NMR (500 MHz, DMSO-d$_6$) δ 13.45 (br s, 1H), 10.30 (br s, 1H), 8.04 (s, 1H), 7.98-7.87 (m, 1H), 7.68 (s, 2H), 7.29 (s, 1H), 7.15-6.84 (m, 4H), 2.51 (m, 1H), 1.02 (m, 2H), 0.80 (m, 2H).

Example 134: 3-(N-(4-chloro-2-(5-chlorothiophen-2-yl)-5-cyanophenyl)sulfamoyl)-4-cyclopropylbenzoic acid

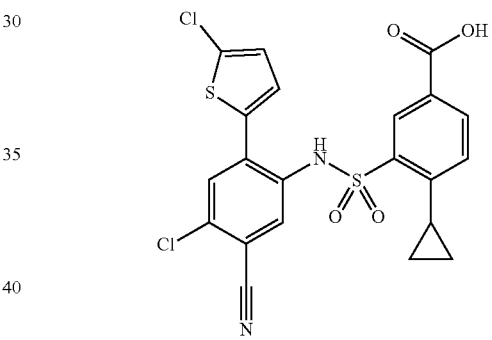

Step 1: 5-amino-2-chloro-4-(5-chlorothiophen-2-yl)benzonitrile: To the reaction vessel containing the product from Example 132 Step 2 (0.20 g, 0.864 mmol), (5-chlorothiophen-2-yl)boronic acid (0.417 g, 2.57 mmol), K$_3$PO$_4$ (0.315 g, 1.48 mmol) and dioxane (10 ml) and water (1 ml) was added PdCl$_2$[P(Cy)$_3$]$_2$ (0.032 g, 0.043 mmol). The resultant reaction mixture was degassed with N$_2$ for 10 min and then heated at 80° C. for 6 h. The reaction mixture was allowed to cool to RT, filtered through Celite®, washed with EtOAc (5 ml) and then concentrated in vacuo. The crude product was purified by chromatography on silica gel (24 g cartridge, 0-50% EtOAc/Isohexane) to the title compound (0.240 g, 0.785 mmol, 91% yield, 88% purity) as a yellow solid. UPLC-MS (Method 1): m/z 269.3 (M+H)$^+$ at 1.73 min.

Step 2: Methyl 3-(N-(4-chloro-2-(5-chlorothiophen-2-yl)-5-cyanophenyl)sulfamoyl)-4-cyclopropylbenzoate: A solution of the product from Step 1 above (0.100 g, 0.327 mmol, 88% purity) in dry THF (5 ml) was cooled to 0° C. before adding dropwise 1 M LiHMDS in THF (0.425 ml, 0.425 mmol). The mixture was stirred at RT for 10 min before adding the product from Example 132 Step 5 (0.099 g, 0.360 mmol) and the solution was stirred at RT for 1 h. The mixture was quenched with MeOH (1 ml) and concentrated onto silica gel. The crude product was purified by chromatography on silica gel (24 g cartridge, 0-50% EtOAc/isohexane) to afford the title compound (0.130 g, 0.218 mmol, 67% yield, 85% purity) as a brown solid. UPLC-MS (Method 1): 504.8 (M–H)⁻ at 1.81 min.

Step 3: 3-(N-(4-chloro-2-(5-chlorothiophen-2-yl)-5-cyanophenyl)sulfamoyl)-4-cyclopropylbenzoic acid: LiOH (0.016 g, 0.653 mmol) was added to a solution of the product from Step 2 above (0.130 g, 0.218 mmol) in THF (3 ml) and water (1 ml) at RT. The resultant mixture was stirred at RT for 24 h. The reaction mixture was concentrated in vacuo to remove the THF. The residue was acidified with 10% w/v citric acid (aq) and the precipitate was collected under filtration. The precipitate was purified by chromatography on silica gel (24 g cartridge, 0-50% EtOAc/DCM) to afford the crude product. The crude product was purified by chromatography (24 g reverse phase cartridge, 15-80% MeCN/Water 0.1% Formic Acid) to the title compound (44.9 mg, 0.089 mmol, 41% yield, 98% purity) as a white solid. UPLC-MS (Method 1): m/z 492.1 (M–H)⁻ at 1.70 min. ¹H NMR (500 MHz, DMSO-d₆) δ 13.40 (br s, 1H), 10.40 (br s, 1H), 8.22 (s, 1H), 8.10 (s, 1H), 8.02 (d, J=8.2 Hz, 1H), 7.59 (d, J=4.1 Hz, 1H), 7.26 (s, 1H), 7.12 (dd, J=10.9, 6.2 Hz, 2H), 2.64 (m, 1H), 1.04 (m, 2H), 0.87 (m, 2H).

Preparation of Aniline Intermediates

The following anilines were prepared and then used for the synthesis of the bespoke analogues detailed.

Preparation of Intermediate 1: 4-(5-methylisoxazol-4-yl)-[1,1'-biphenyl]-2-amine

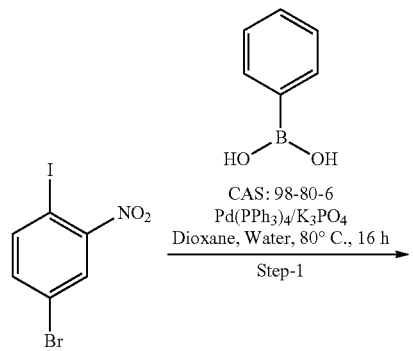

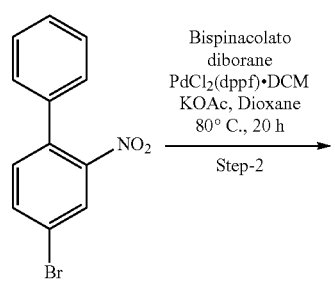

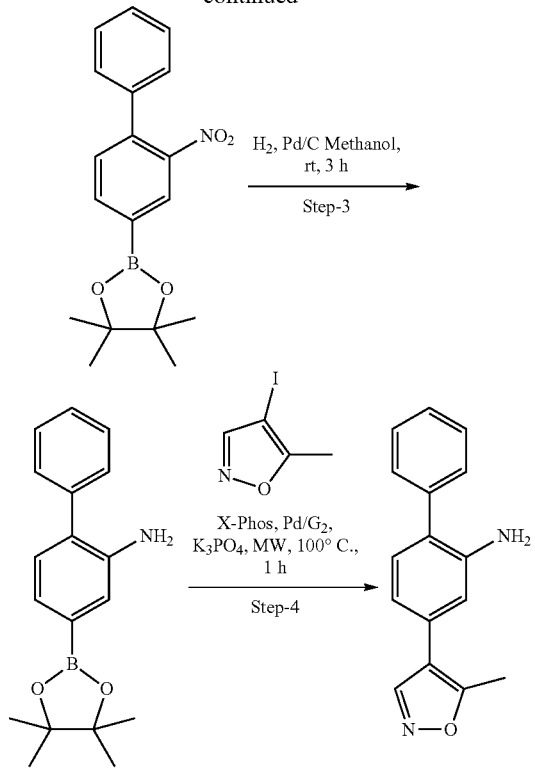

Step-1: Synthesis of 4-bromo-2-nitro-1,1'-biphenyl. To a stirred solution of 4-bromo-1-iodo-2-nitrobenzene (10 g, 0.031 mol, 1 eq) in dioxane: water (100 mL: 10 mL, 5 Vol) was added phenyl boronic acid (1.7 g, 0.013 mol, 0.9 eq) and tripotassium phosphate (1 M solution in Water) (25 mL, 1.6 eq). The reaction mixture was purged with N₂ gas for 30 min. Tetrakis (0.87 g, 0.001 mol, 0.05 eq) was added to the reaction mixture and stirred at 80° C. for 16 h, cooled and poured into water (200 mL) then extracted with ethyl acetate (2×100 mL). The combined organic layer was dried over sodium sulfate and concentrated under reduced pressure. The obtained crude was purified by column chromatography (60-120 Silica gel) using hexanes eluent to give title bromide as a yellow solid (14 g, 91.96%).

Step-2: Synthesis of 4,4,5,5-tetramethyl-2-(2-nitro-[1,1'-biphenyl]-4-yl)-1,3,2-dioxaborolane. To a solution Step-1 bromide (8 g, 0.028 mole, 1 eq) and potassium acetate (8.5 g, 0.84 mole, 3 eq) in dioxane (160 mL) was added Bispinacolato diborane (8.06 g, 0.03176 mole, 1.1 eq) at room temperature and stirred for 15 min. The reaction mixture was purged with N₂ for 20 min and then [Pd(dppf)Cl₂]-DCM (0.633 g, 0.000866 mole, 0.03 eq) was added. The resulting reaction mixture was stirred at 80° C. for 20 hrs, cooled, diluted with water (100 mL) and filtered through a celite bed. The filtrate was extracted with EtOAc (3×30 mL). The combined organic layer was dried over sodium sulphate and concentrated under reduced pressure. The crude was purified by column chromatography using 20% EtOAc in Hexane as eluent to give title dioxaborolane (3.5 g, 39.83%).

Step-3: Synthesis of 4-(4,4,5,5-tetramethyl-1,3,2-dioxaborolan-2-yl)-[1,1'-biphenyl]-2-amine. To a solution of Step-2 dioxaborolane (3.0 g, 1.011 mmol, 1 eq) in MeOH (30 ml) was added with 10% Pd—C(0.75 g, 25% W/W). The solution was stirred under hydrogen atmosphere for 3 h at room temperature. After completion of reaction as indicated by TLC (50% Ethyl acetate in Hexane), reaction mixture was filtered through celite and the filtrate was concentrated under reduced vacuum to give title amine (3.5 g, quantitative) as a light brown solid. UPLC-MS (Method 1) m/z 296.3 (M+H)+ at 2.99 min.

Step-4: Synthesis of 4-(5-methylisoxazol-4-yl)-[1,1'-biphenyl]-2-amine. To a stirred solution of Step-3 amine (0.25 g, 1.21 mmol, 1 eq) in dioxane: water (4 mL: 1 mL) was added 4-iodo-5-methylisoxazole (0.422 g, 1.44 mmol, 1.2 eq) and potassium phosphate (0.66 g, 1.56 mmol, 1.3 eq). The reaction mixture was purged with $N_2$ gas for 30 min. X-Phos Pd $G_2$ (0.188 g, 0.240 mmol, 0.1 eq) was added and stirred at 110° C. for 1 h, cooled, poured into water (80 mL) and extracted with ethyl acetate (2×80 mL). The combined organic layer was dried over sodium sulfate and concentrated under reduced pressure. The obtained crude was purified by neutral alumina using 5% EtOAc in Hexane as eluent to get title amine (0.146 g, 68%, LCMS 100%) as an off white solid. UPLC-MS (Method 1) m/z 251.2 (M+H)+ at 2.38 min. $^1$H NMR (500 MHz, DMSO-$d_6$) δ 8.77 (s, 1H), 7.48 (m, 4H), 7.32 (m, 1H), 7.06 (d, 1H), 6.93 (d, 1H), 6.79 (dd, 1H), 4.92 (s, 2H), 2.59 (s, 3H).

Preparation of Intermediate-2: 4-(5-methylisothiazol-4-yl)-[1,1'-biphenyl]-2-amine

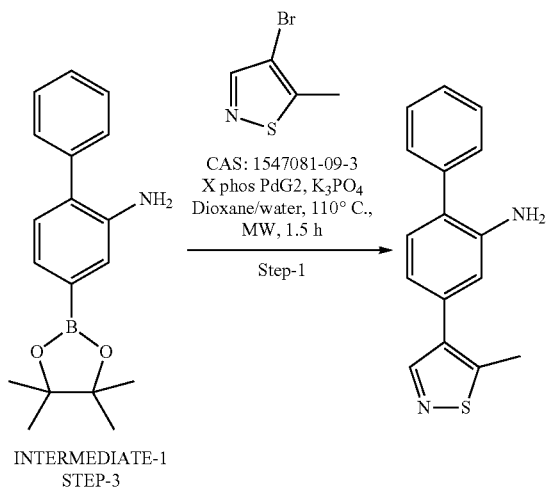

INTERMEDIATE-1
STEP-3

To a solution of 4-(4,4,5,5-tetramethyl-1,3,2-dioxaborolan-2-yl)-[1,1'-biphenyl]-2-amine (INTERMEDIATE-1, Step-3) (1.38 g, 0.0047 mole, 1.2 eq) and 4-bromo-5-methylisothiazole (0.75, 0.0039 mole, 1 eq) in dioxane: water (9:1 mL) was added $K_3PO_4$ (1.08 g, 0.00513 mole, 1.3 eq) at room temperature. The reaction mixture was purged with $N_2$ for 30 min and X-Phos-Pd-G2 (0.33 g, 0.00039 mole, 0.1 eq) was added. The resulting reaction mixture was stirred at 110° C. for 1.5 h in microwave, cooled, diluted with water (75 mL) and extracted with ethyl acetate (3×100 mL). The combined organic layer was washed with brine (10 mL), dried over anhydrous $Na_2SO_4$ and concentrated under reduced pressure. The resulting crude material was purified by column chromatography on neutral alumina using (8% ethyl acetate in hexane) as eluent to give title amine as a white solid (0.490 g, 39.38%). UPLC-MS (Method 1) m/z 267.2 (M+H)+ at 2.53 min. $^1$H NMR (500 MHz, DMSO-$d_6$) δ 8.56 (s, 1H), 7.47 (m, 4H), 7.35 (m, 1H), 7.09 (d, 1H), 6.91 (d, 1H), 6.76 (dd, 1H), 4.95 (s, 2H), 2.61 (s, 3H).

Preparation of Intermediate-3: 4-(isothiazol-5-yl)-[1,1'-biphenyl]-2-amine

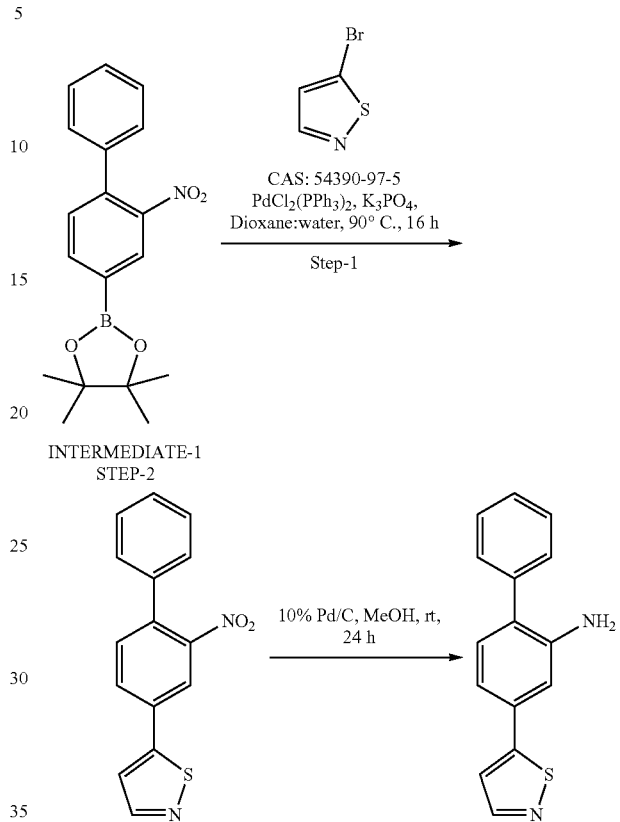

Step-1: Synthesis of 5-(2-nitro-[1,1'-biphenyl]-4-yl)isothiazole. To a stirred solution of 4,4,5,5-tetramethyl-2-(2-nitro-[1,1'-biphenyl]-4-yl)-1,3,2-dioxaborolane (INTERMEDIATE-1, STEP-2) (0.7 g, 4.26 mmol, 1 eq) in dioxane: water (6 mL: 2 mL) was added 5-bromoisothiazole (1.6 g, 5.12 mmol, 1.2 eq) and tripotassium phosphate (2.7 g, 1.27 mmol, 3 eq). The reaction mixture was purged with $N_2$ gas for 30 min. $PdCl_2(pph)_3$ (0.149 g, 0.21 mmol, 0.05 eq) was added and stirred at 90° C. for 16 h, cooled, poured into water (50 mL) then extracted with Ethyl acetate (2×20 mL). The combined organic layer was dried over sodium sulfate and concentrated under reduced pressure. The obtained crude was purified by flash column chromatography (200-400 Silica gel) using 4% EtOAc in Hexane as eluent to give title isothiazole as a yellow solid (0.450 g, 74%). UPLC-MS (Method 1) m/z 283.2 (M+H)+ at 2.60 min. $^1$H NMR (500 MHz, DMSO-$d_6$) δ 8.68 (d, 1H), 8.40 (d, 1H), 8.10 (dd, 1H), 8.03 (d, 1H), 7.69 (d, 1H), 7.47 (m, 3H), 7.38 (m, 2H).

Step-2: Synthesis of 4-(isothiazol-5-yl)-[1,1'-biphenyl]-2-amine. To a solution of Step-1 isothiazole (0.450 g, 1.59 mmol) in MeOH (5 mL) was added Pd—C(10% WNV, 50% moisture) (0.150 g, 20%) under nitrogen atmosphere at room temperature. The resulting reaction mixture was purged $H_2$ gas at room temperature for 24 h. After completion of reaction as indicated by TLC (10% EtOAc in Hexane as mobile phase), the reaction mixture was filtered through a celite bed. The celite bed was washed with ethyl acetate (50 mL). The filtrate was concentrated under vacuum to get crude which was purified by trituration using diethyl ether (20 ml) and pentane (10 mL) to give title amine (0.250 g, 62%) as a yellow solid. UPLC-MS (Method 1) m/z 253.2 (M+H)$^+$ at 2.63 min. $^1$H NMR (500 MHz, DMSO-d$_6$) δ 8.58 (d, 1H), 7.67 (s, 1H), 7.47 (m, 4H), 7.38 (m, 1H), 7.11 (m, 2H), 7.02 (d, 1H), 5.09 (s, 2H).

Preparation of Intermediate-4: 4-(1H-pyrazol-4-yl)-[1,1'-biphenyl]-2-amine

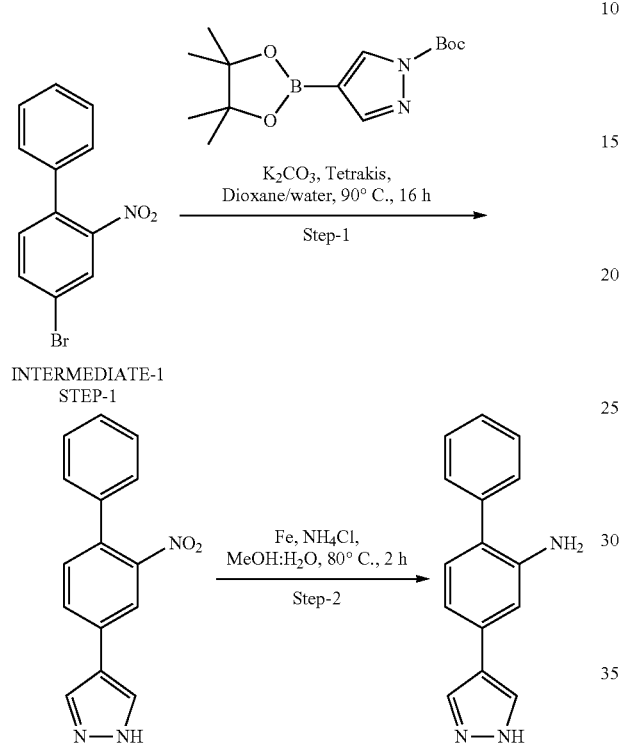

Step-1: Synthesis of 4-(2-nitro-[1,1'-biphenyl]-4-yl)-1H-pyrazole. To a stirred solution of 4-bromo-2-nitro-1,1'-biphenyl (INTERMEDIATE-1, STEP-1) (1 g, 0.0036 mol, 1 eq) in dioxane: water (20 mL, 9:1, 20 vol) was added tert-butyl 4-(4,4,5,5-tetramethyl-1,3,2-dioxaborolan-2-yl)-1H-pyrazole-1-carboxylate (2.23 g, 0.0075 mol, 2.1 eq) and potassium carbonate (1.4 g, 0.010 mol, 3 eq). The reaction mixture was purged with N$_2$ gas for 30 min. Tetrakis (0.208 g, 0.0001 mol, 0.05 eq) was added to the reaction mixture and stirred at 90° C. for 16 h, cooled, poured into water (10 mL) and extracted with ethyl acetate (3×20 mL). The combined organic layer was dried over sodium sulfate and concentrated under reduced pressure. The obtained crude was purified by column chromatography (200-400 Silica gel) using 5% ethyl acetate in hexane as eluent to give title pyrazole as a yellow solid (0.8 g, 83.31%). UPLC-MS (Method 1) m/z 266.1 (M+H)$^+$ at 2.55 min.

Step-2: Synthesis of 4-(1H-pyrazol-4-yl)-[1,1'-biphenyl]-2-amine. To a solution of Step-1 pyrazole (0.8 g, 0.0021 mol, 1 eq) in methanol: water (8:2 mL) was added Fe powder (0.61 g, 0.0109 mol, 5 eq) and NH$_4$Cl (0.57 g, 0.0109 mol, 5 eq). The reaction mixture was stirred at 80° C. for 2 h, cooled, poured into water (500 mL) and filtered through celite bed. The celite bed was washed with DCM (20 mL). The filtrate was concentrated under reduced pressure. The crude was treated with 1 N HCl (10 mL) and extracted with EtOAc (2×10 mL). The aqueous layer was basified with sat NaHCO$_3$ solution and extracted with ethyl acetate (3×20 mL). The combined organic layer was dried over sodium sulphate and concentrated under reduced pressure to give title amine as a white solid (0.45 g, 87.37%). UPLC-MS (Method 1) m/z 236.2 (M+H)$^+$ at 2.27 min. $^1$H NMR (500 MHz, DMSO-d$_6$) δ 12.92 (s, 1H), 8.06 (s, 1H), 7.98 (s, 1H), 7.43 (m, 4H), 7.32 (m, 1H), 6.98 (m, 2H), 6.35 (d, 1H), 4.76 (s, 2H).

Preparation of Intermediate-5: 3'-fluoro-4-(5-methylisoxazol-4-yl)-[1,1'-biphenyl]-2-amine

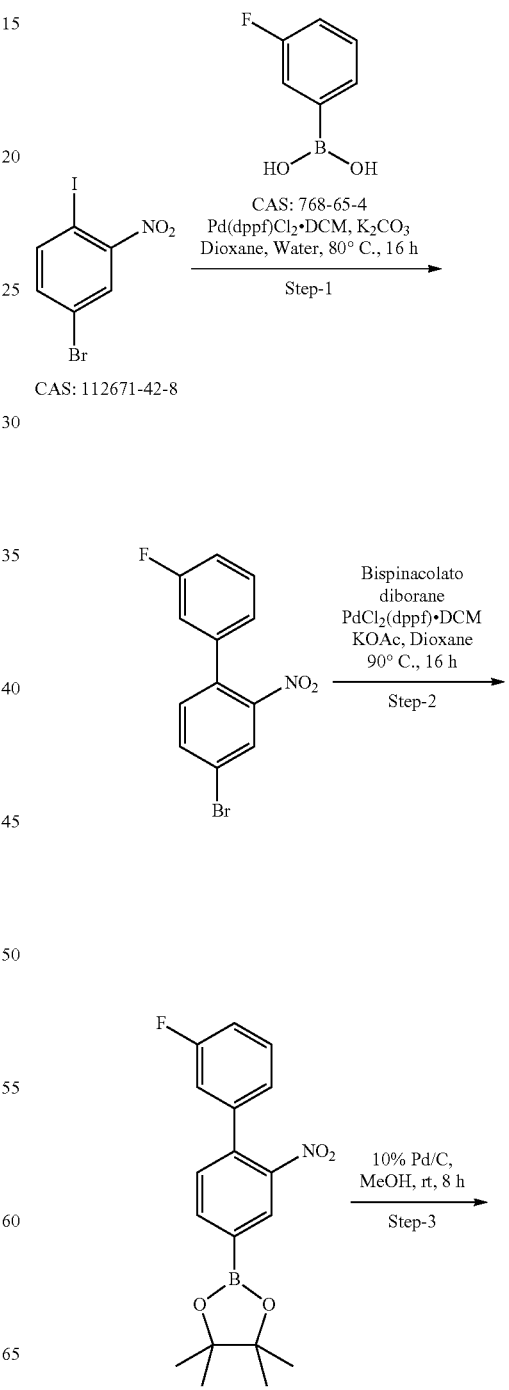

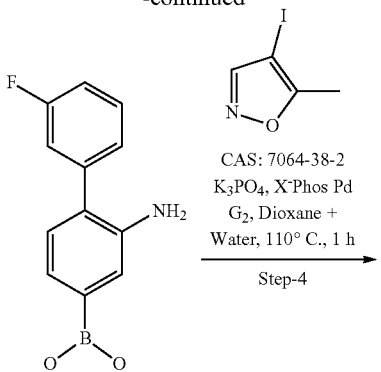

Step-1: Synthesis of 4-bromo-3'-fluoro-2-nitro-1,1'-biphenyl. To a stirred solution of 4-bromo-1-iodo-2-nitrobenzene (5.0 g, 15.24 mmol, 1 eq) in dioxane: water (60 mL: 20 mL) was added (3-fluorophenyl)boronic acid (2.34 g, 16.77 mmol, 1.2 eq) and potassium carbonate (6.32 g, 45.74 mmol, 3 eq). The reaction mixture was purged with $N_2$ gas for 30 min. Pd(dppf)Cl$_2$]-DCM (0.622 g, 0.76 mmol, 0.05 eq) was added to the reaction mixture and stirred at 80° C. for 16 h, cooled, poured into water (250 mL) and extracted with Ethyl acetate (2×250 mL). The combined organic layer was dried over sodium sulfate and concentrated under reduced pressure. The obtained crude was purified by flash column chromatography (200-400 Silica gel) using 20% EtOAc in Hexane as eluent to give title bromide (8 g, 88.43%) as a yellow solid.

Step-2: Synthesis of 2-(3'-fluoro-2-nitro-[1,1'-biphenyl]-4-yl)-4,4,5,5-tetramethyl-1,3,2-dioxaborolane. To a stirred solution of Step-1 bromide (2.0 g, 6.75 mmol, 1 eq) in Dioxane: 30 mL was added bis pinacolato diborane (1.9 g, 7.43 mmol, 1.1 eq) and potassium acetate (1.99 g, 20.26 mmol, 3 eq). The reaction mixture was purged with $N_2$ gas for 30 min. Pd(dppf)Cl$_2$ DCM (0.275 g, 0.337 mmol, 0.05 eq) was added to the reaction mixture and stirred at 80° C. for 16 h, cooled, poured into water (250 mL) and extracted with Ethyl acetate (2×200 mL). The combined organic layer was dried over sodium sulfate and concentrated under reduced pressure. The obtained crude was purified by flash column chromatography (200-400 Silica gel) using 5% EtOAc in Hexane as eluent to give title dioxaborolane (5 g, Quantitative) as solid.

Step-3: Synthesis of 3'-fluoro-4-(4,4,5,5-tetramethyl-1,3,2-dioxaborolan-2-yl)-[1,1'-biphenyl]-2-amine. To a solution of Step-2 dioxaborolane (0.5 g, 1.45 mmol) in MeOH (5 mL) was added Pd—C(10% W/W, 50% moisture) (0.150 g, 20%) under nitrogen atmosphere at room temperature. The resulting reaction mixture was purged $H_2$ gas at room temperature for 4 h. After completion of reaction as indicated by TLC (30% EtOAc in Hexane as mobile phase), the reaction mixture was filtered through a celite bed. The celite bed was washed with ethyl acetate (50 mL). The filtrate was concentrated under vacuum to get crude which was purified by trituration using diethyl ether (30 ml) and pentane (10 mL) to get yielding title amine (0.400 g, LCMS: 90%) as yellow solid.

Step-4: Synthesis of 3'-fluoro-4-(5-methylisoxazol-4-yl)-[1,1'-biphenyl]-2-amine. To a stirred solution of Step-3 amine (0.5 g, 2.40 mmol, 1 eq) in Dioxane: water (4 mL: 1 mL) was added 4-iodo-5-methylisoxazole (0.902 g, 2.88 mmol, 1.2 eq) and potassium phosphate (0.66 g, 3.12 mmol, 1.3 eq). The reaction mixture was purged with $N_2$ gas for 30 min. X-Phos Pd G$_2$ (0.188 g, 0.240 mmol, 0.1 eq) was added to the reaction mixture and stirred at 110° C. for 1 h, cooled, poured into water (80 mL) and extracted with Ethyl acetate (2×80 mL). The combined organic layer was dried over sodium sulfate and concentrated under reduced pressure. The obtained crude was purified by neutral alumina using 5% EtOAc in Hexane as eluent to give title amine. (0.25 g, LCMS 100%) as off white solid. UPLC-MS (Method 1) m/z 269.2 $(M+H)^+$ at 2.43 min. $^1$H NMR (500 MHz, DMSO-$d_6$) δ 8.77 (s, 1H), 7.48 (m, 1H), 7.29 (m, 2H), 7.18 (m, 1H), 7.09 (d, 1H), 6.94 (d, 1H), 6.79 (dd, 1H), 5.05 (s, 2H), 2.51 (s, 3H).

Preparation of Intermediate-6: 3'-fluoro-4-(5-methylisothiazol-4-yl)-[1,1'-biphenyl]-2-amine

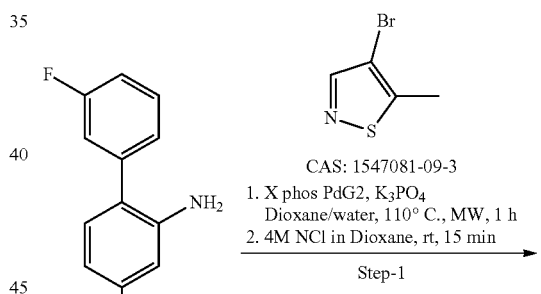

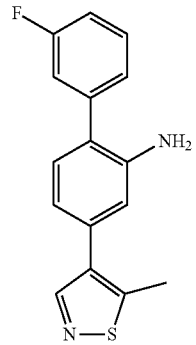 [SMILES: Cc1oncc1-c1ccc(-c2cccc(F)c2)c(N)c1]

To a solution of 3'-fluoro-4-(4,4,5,5-tetramethyl-1,3,2-dioxaborolan-2-yl)-[1,1'-biphenyl]-2-amine (INTERMEDIATE-5, STEP-3) (1.0 g, 0.0034 mole, 1.2 eq) and 4-bromo-5-methylisothiazole (0.500 g, 0.0028 mole, 1 eq) in dioxane: water (10:3 mL) was added $K_3PO_4$ (0.782 g, 0.0036 mole, 1.3 eq) at room temperature and stirred for 15 min. The reaction mixture was purged with $N_2$ for 30 min and X-Phos-Pd-G2 (0.223 g, 0.00028 mole, 0.1 eq) was added. The resulting reaction mixture was stirred at 110° C. for 1 h in microwave, cooled, diluted with water (75 mL) and extracted with ethyl acetate (3×50 mL). The combined organic layer was washed with brine (10 mL), dried over anhydrous $Na_2SO_4$ and concentrated under reduced pressure. The resulting crude material was purified by column chromatography on neutral alumina using 15% ethyl acetate in hexane as eluent to give title amine as gummy liquid white solid (0.3 g). This was dissolved in DCM (5 mL) and 4 M HCl in dioxane (0.2 mL) was added. The reaction mixture was stirred for 15 min and concentrated under reduced pressure. The residue was triturated with diethyl ether (20 mL) and solid was dried under high vacuum to get title amine hydrochloride salt (0.28 g, 30.87%). UPLC-MS (Method 1) m/z 285.2 (M+H)$^+$ at 2.56 min. $^1$H NMR (500 MHz, DMSO-$d_6$) δ 8.55 (s, 1H), 7.50 (m, 1H), 7.29 (m, 2H), 7.17 (m, 1H), 7.13 (d, 1H), 6.91 (d, 1H), 6.77 (dd, 1H), 5.05 (s, 2H), 2.60 (s, 3H).

Preparation of Intermediate-7: 3'-fluoro-4-(isothiazol-5-yl)-[1,1'-biphenyl]-2-amine

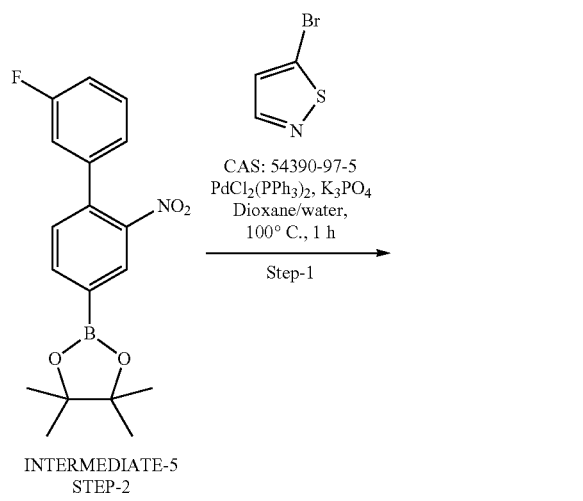

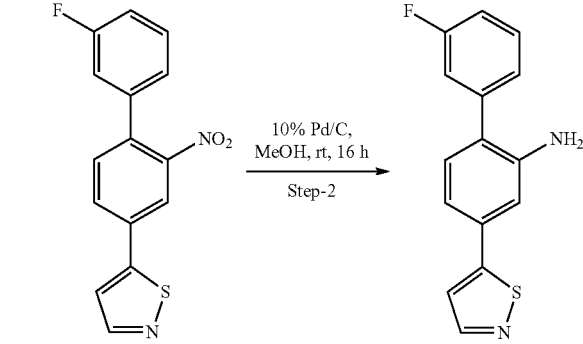

Step-1: Synthesis of 5-(3'-fluoro-2-nitro-[1,1'-biphenyl]-4-yl)isothiazole. To a stirred solution of 5-bromoisothiazole (0.60 g, 3.65 mmol, 1 eq) in dioxane: water (9 mL: 1 mL) was added 2-(3'-fluoro-2-nitro-[1,1'-biphenyl]-4-yl)-4,4,5,5-tetramethyl-1,3,2-dioxaborolane (INTERMEDIATE-5, STEP-2) (1.38 g, 4.00 mmol, 1.1 eq) and potassium phosphate (2.32 g, 10.9 mmol, 3 eq). The reaction mixture was purged with $N_2$ gas for 30 min. $PdCl_2(PPh_3)_2$ (0.12 g, 0.182 mmol, 0.05 eq) was added to the reaction mixture and stirred at 100° C. for 1 h, cooled, poured into water (100 mL) and extracted with Ethyl acetate (2×35 mL). The combined organic layer was dried over sodium sulfate and concentrated under reduced pressure. The obtained crude was purified by flash column chromatography (200-400 Silica gel) using 5% EtOAc in Hexane as eluent to give title isothiazole (0.62 g, LCMS: 85%). UPLC-MS (Method 1) m/z 301.1 (M+H)$^+$ at 2.58 min.

Step-2: Synthesis of 3'-fluoro-4-(isothiazol-5-yl)-[1,1'-biphenyl]-2-amine. To a solution of Step-1 isothiazole (0.65 g, 2.16 mmol, 1 eq) in MeOH (30 mL) was added Pd—C(10% W/W, 50% moisture) (0.65 g, 20%) under nitrogen atmosphere at room temperature. The resulting reaction mixture was purged $H_2$ gas at room temperature for 16 h. After completion of reaction as indicated by TLC (10% EtOAc in Hexane as mobile phase), the reaction mixture was filtered through a celite bed. The celite bed was washed with methanol (100 mL). The filtrate was concentrated under vacuum to get crude which was purified by reverse phase chromatography 27% acetonitrile in water as eluent to give title amine as yellow solid (0.6 g). UPLC-MS (Method 1) m/z 271.2 (M+H)$^+$ at 2.51 min. $^1$H NMR (500 MHz, DMSO-$d_6$) δ 8.58 (d, 1H), 7.67 (s, 1H), 7.51 (m, 1H), 7.28 (m, 2H), 7.20 (m, 1H), 7.14 (m, 2H), 7.00 (dd, 1H), 5.20 (s, 2H).

Preparation of Intermediate-8: 3'-fluoro-4-(1H-pyrazol-4-yl)-[1,1'-biphenyl]-2-amine

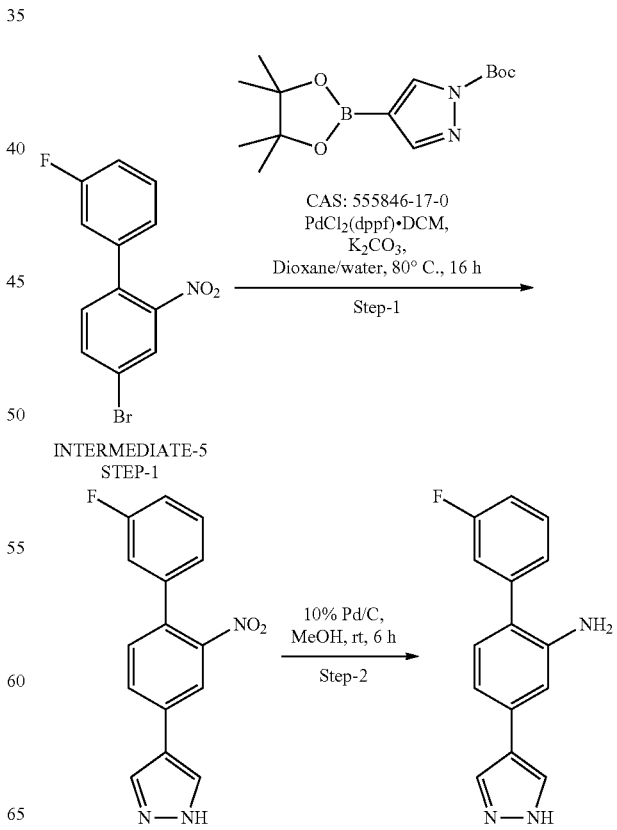

Step-1: Synthesis of 4-(3'-fluoro-2-nitro-[1,1'-biphenyl]-4-yl)-1H-pyrazole. To a stirred solution of 4-bromo-3'-fluoro-2-nitro-1,1'-biphenyl (INTERMEDIATE-5, STEP-1) (2 g, 3.37 mmol, 1 eq) in dioxane: water (18 mL: 6 mL) was added tert-butyl 4-(4,4,5,5-tetramethyl-1,3,2-dioxaborolan-2-yl)-1H-pyrazole-1-carboxylate (2.4 g, 4.05 mmol, 1.2 eq) and potassium carbonate (2.8 g, 10.1 mmol, 3 eq). The reaction mixture was purged with $N_2$ gas for 30 min. Pd(dppf)$Cl_2$·DCM (0.28 g, 0.33 mmol, 0.05 eq) was added to the reaction mixture and stirred at 80° C. for 16 h, cooled, poured into water (50 mL) and extracted with Ethyl acetate (2×40 mL). The combined organic layer was dried over sodium sulfate and concentrated under reduced pressure. The obtained crude was purified by flash column chromatography (200-400 Silica gel) using 20% EtOAc in Hexane as eluent to give title pyrazole as a yellow solid (0.8 g). UPLC-MS (Method 1) m/z 284.2 (M+H)$^+$ at 2.60 min.

Step-2: Synthesis of 3'-fluoro-4-(1H-pyrazol-4-yl)-[1,1'-biphenyl]-2-amine. To a solution of Step-1 pyrazole (0.8 g, 2.82 mmol) in MeOH (6 mL) was added Pd—C(10% W/W, 50% moisture) (0.1 g, 20%) under nitrogen atmosphere at room temperature. The resulting reaction mixture was purged $H_2$ gas at room temperature for 6 h. After completion of reaction as indicated by TLC (50% EtOAc in Hexane as mobile phase), the reaction mixture was filtered through a celite bed. The celite bed was washed with ethyl acetate (50 mL). The filtrate was concentrated under vacuum to get crude which was purified by trituration using diethyl ether (20 ml) and pentane (10 mL) to give title amine as a yellow solid (0.6 g). UPLC-MS (Method 1) m/z 254.1 (M+H)$^+$ at 2.40 min. $^1$H NMR (500 MHz, DMSO-$d_6$) δ 12.95 (s, 1H), 7.93 (bs, 2H), 7.48 (m, 1H), 7.27 (m, 2H), 7.14 (m, 1H), 6.99 (m, 2H), 6.88 (dd, 1H), 4.88 (s, 2H).

Preparation of Intermediate-9: 5-(5-methylisoxazol-4-yl)-2-(pyridin-3-yl) aniline

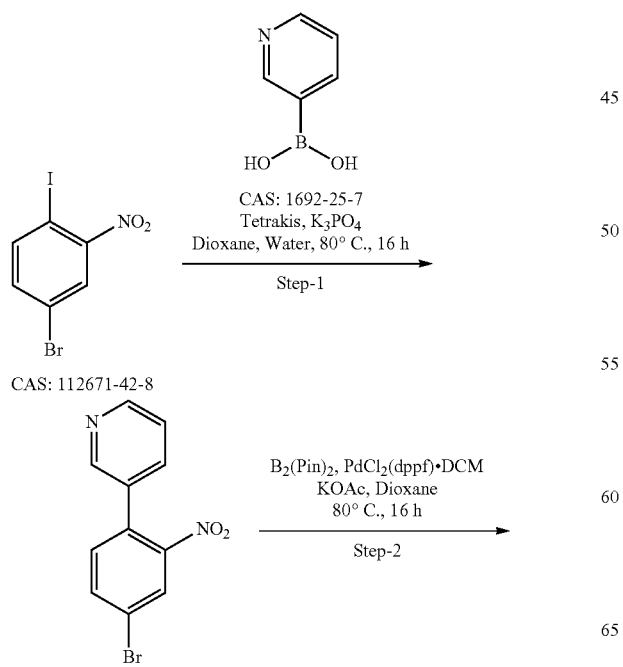

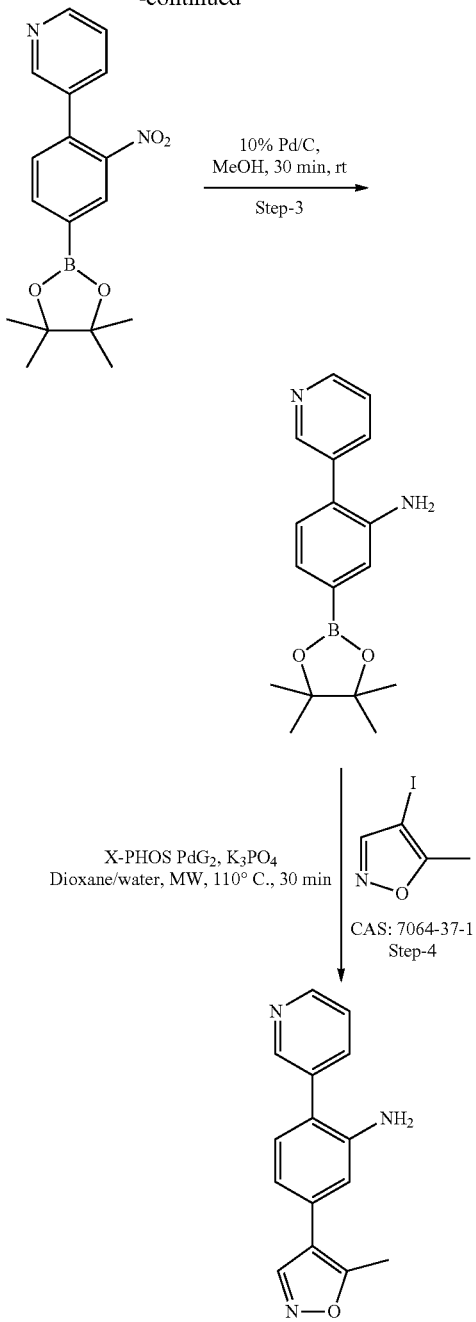

Step-1: Synthesis of 3-(4-bromo-2-nitrophenyl)pyridine. To a stirred solution of 4-bromo-1-iodo-2-nitrobenzene (10 g, 0.030 mole, 1 eq) and pyridin-3-ylboronic acid (5.6 g, 0.045 mole, 1.5 eq) in dioxane: water (100 mL: 10 mL, 10 vol) was slowly added $K_3PO_4$ (19.48 g, 0.091 mole, 3 eq) portion wise. The reaction mixture was purged with $N_2$ gas for 30 min at room temperature. After that Tetrakis (1.76 g, 0.0015 mol, 0.05 eq) was added and further heated at 80° C. for 16 h. After completion of reaction as indicated by TLC (30% ethyl acetate in hexane), reaction mixture was poured into water (100 mL) and extracted with Ethyl acetate (2×50 mL). The combined organic layer was dried over sodium sulfate and concentrated under reduced pressure to give title pyridine as a brown oil (6.5 g, 75.95%). UPLC-MS (Method 1) m/z 279.1/281.1 (M+H)$^+$ at 2.38 min.

Step-2: Synthesis of 3-(2-nitro-4-(4,4,5,5-tetramethyl-1,3,2-dioxaborolan-2-yl)phenyl) pyridine. To a stirred solution of Step-1 pyridine (3 g, 0.010 mol, 1 eq) and bispinacolato diborane (3 g, 0.011 mol, 1.1 eq) in dioxane (60 mL, 20 Vol) was added potassium acetate (3.17 g, 0.032 mol, 3 eq) portion wise under nitrogen atmosphere. The reaction mixture was purged with $N_2$ gas for 30 min at room temperature. $PdCl_2$(dppf)·DCM (0.235 g, 0.00032 mol, 0.03 eq) was added and stirred at 80° C. for 16 h, cooled, through a bed of celite and washed with ethyl acetate (30 mL). The filtrate was concentrated under reduced pressure to give crude title pyridine as viscous brown oil (7 g, quantitative). This material used as such for next step.

Step-3: Synthesis of 2-(pyridin-3-yl)-5-(4,4,5,5-tetramethyl-1,3,2-dioxaborolan-2-yl)aniline To a solution of Pd/C (4.0 g,) in methanol (50 mL, 10 vol) was added Step-2 pyridine (5 g, 0.015 mol, 1 eq) under nitrogen atmosphere. The resulting reaction mixture was purged with $H_2$ gas for 30 min at room temperature. After completion of reaction as indicated by TLC (50% Ethyl acetate in Hexane), the reaction mixture was filtered through celite and washed with methanol (100 mL). The filtrate was concentrated under reduced pressure to give crude title aniline as a brown solid (3.7 g, 81.8%). This material is used as such for next step.

Step-4: 5-(5-methylisoxazol-4-yl)-2-(pyridin-3-yl)aniline. To a stirred solution of Step-3 aniline (0.400 g, 0.0013 mol, 1.1 eq) and 4-iodo-5-methylisoxazole in dioxane: water (5:1 mL) was added $K_3PO_4$ (0.344 g, 0.0016 mol, 1.3 eq) portion wise. The reaction mixture was purged with $N_2$ gas for 30 min at room temperature. X-PHOS Pd G2 (0.105 g, 0.0001 mol, 0.1 eq) was added and then reaction mixture was stirred at 110° C. for 30 min in microwave, cooled, poured into water (100 mL) and extracted with ethyl acetate (2×100 mL). The combined organic layer was dried over sodium sulfate and concentrated under reduced pressure. The obtained crude material was purified by prep HPLC purification (using A: 0.05% $NH_3$ in water, B: Acetonitrile: 0.05% $NH_3$ in water). The fractions were lyophilized to give title aniline as a white solid (0.127 g, 27.5%). UPLC-MS (Method 1) m/z 252.3 (M+H)$^+$ at 1.48 min. $^1$H NMR (500 MHz, DMSO-$d_6$) δ 8.78 (s, 1H), 8.62 (d, 1H), 8.54 (dd, 1H), 7.85 (m, 1H), 7.46 (m, 1H), 7.09 (d, 1H), 6.94 (s, 1H), 6.81 (dd, 1H), 5.07 (s, 2H), 2.61 (s, 3H).

Preparation of Intermediate-10: 5-(5-methylisothiazol-4-yl)-2-(pyridin-3-yl)aniline

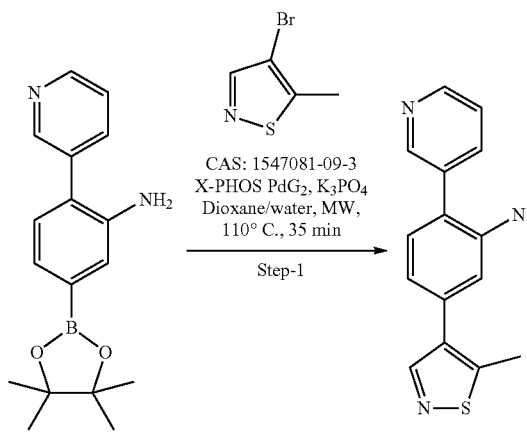

INTERMEDIATE-9
STEP-3

To a solution of 2-(pyridin-3-yl)-5-(4,4,5,5-tetramethyl-1,3,2-dioxaborolan-2-yl)aniline (INTERMEDIATE-9, STEP-3) (0.5 g, 0.0016 mol, 1.2 eq) and $K_3PO_4$ (0.385 g, 0.00182 mole, 1.3 eq) in dioxane: water (5.4: 0.6 mL) was added 4-bromo-5-methylisothiazole (0.25, 0.0014 mole, 1 eq) at room temperature. The reaction mixture was purged with $N_2$ for 30 min and X-PHOS·PdG$_2$ (0.118 g, 0.00014 mole, 0.1 eq) was added. The resulting reaction mixture was stirred at 110° C. for 35 min in microwave, cooled, diluted with water (25 mL) and extracted with ethyl acetate (3×25 mL). The combined organic layer was washed with brine (10 mL), dried over anhydrous $Na_2SO_4$. The solvent was evaporated under reduced pressure. The resulting crude material was purified by manual column chromatography on neutral silica using 30% ethyl acetate in hexane as eluent to give title aniline as a pale yellow solid (0.383 g, 74.9%). UPLC-MS (Method 1) m/z 268.2 (M+H)$^+$ at 1.67 min. $^1$H NMR (500 MHz, DMSO-$d_6$) δ 8.65 (m, 1H), 8.55 (m, 2H), 7.88 (m, 1H), 7.47 (m, 1H), 7.11 (d, 1H), 6.92 (d, 1H), 6.78 (dd, 1H), 5.10 (s, 2H), 2.61 (s, 3H).

Preparation of Intermediate-11: 5-(isothiazol-5-yl)-2-(pyridin-3-yl)aniline. HCl salt

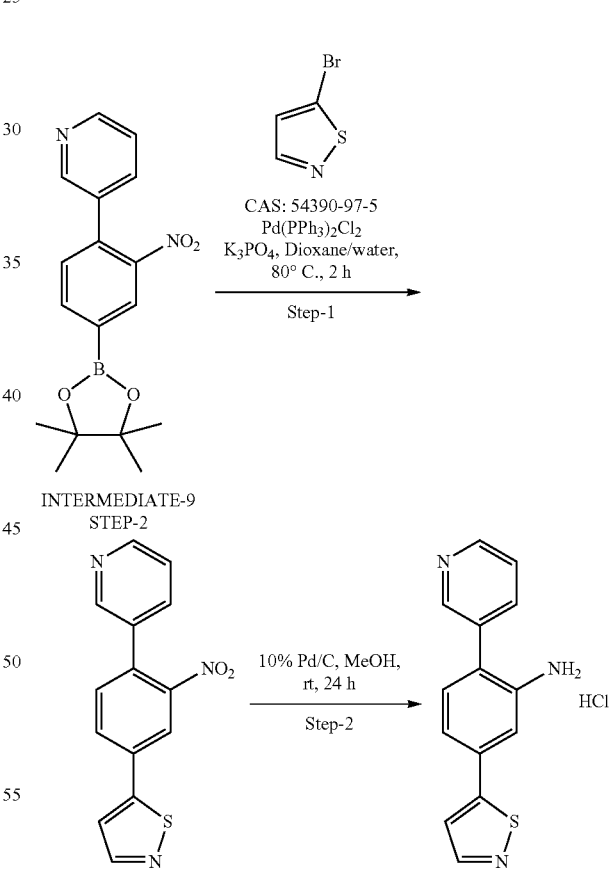

Step-1: Synthesis of 5-(3-nitro-4-(pyridin-3-yl)phenyl) isothiazole. To a solution of 3-(2-nitro-4-(4,4,5,5-tetramethyl-1,3,2-dioxaborolan-2-yl)phenyl)pyridine (INTERMEDIATE-9, STEP-2) (1.4 g, 4.39 mmol, 1.2 eq) in dioxane: water (6: 2 mL) was added $K_3PO_4$ (2.32 g, 10.97 mmol, 3 eq). The reaction mixture was purged with $N_2$ gas for 30 min and 5-bromoisothiazole (0.6 g, 3.65 mmol, 1 eq) was added at room temperature. Pd(PPh$_3$)$_2$Cl$_2$ (0.128 g, 0.182 mmole, 0.05 eq) was added and resulting reaction mixture was stirred at 80° C. for 2 h, cooled, diluted with water (50 mL) and extracted with ethyl acetate (3×15 mL). The combined organic layer was washed with brine solution (10 mL), dried over anhydrous sodium sulphate and concentrated under reduced pressure to get crude title isothiazole (1.3 g, LCMS: 88.77%). UPLC-MS (Method 1) m/z 284.2 (M+H)+ at 1.93 min. This crude material has been used as such for next step.

Step-2: Synthesis of 5-(isothiazol-5-yl)-2-(pyridin-3-yl) aniline hydrochloride salt. To a solution of Step-1 isothiazole (0.8 g, 2.82 mmol) in MeOH (6 mL) was added Pd—C(10% WNW, 50% moisture) (0.1 g, 20%) under nitrogen atmosphere at room temperature. The resulting reaction mixture was purged $H_2$ gas at room temperature for 24 h. After completion of reaction as indicated by TLC (50% EtOAc in Hexane as mobile phase), the reaction mixture was filtered through a celite bed. The celite bed was washed with ethyl acetate (50 mL). The filtrate was concentrated under vacuum to get crude which was purified by trituration using diethyl ether (20 ml) and pentane (10 mL) to give title aniline (0.6 g) as a yellow solid. UPLC-MS (Method 1) m/z 254.2 (M+H)+ at 1.88 min. $^1$H NMR (500 MHz, DMSO-$d_6$) δ 9.02 (d, 1H), 8.88 (d, 1H), 8.62 (m, 2H), 8.11 (m, 1H), 7.76 (s, 1H), 7.29 (d, 1H), 7.23 (s, 1H), 7.17 (d, 1H), 4.5-5.7 (b).

Preparation of Intermediate-12: 5-(1H-pyrazol-4-yl)-2-(pyridin-3-yl)aniline

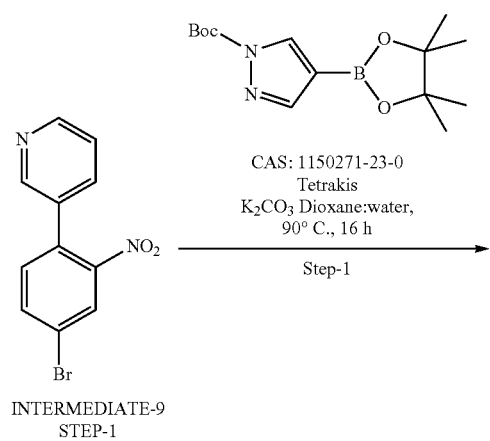

INTERMEDIATE-9
STEP-1

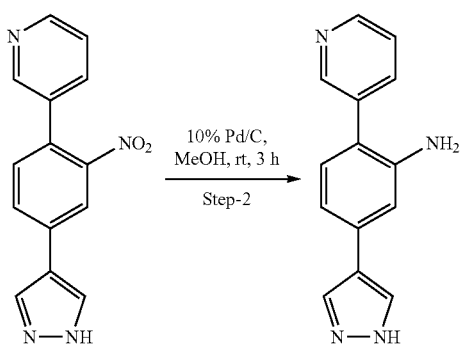

Step-1: Synthesis of 3-(2-nitro-4-(1H-pyrazol-4-yl)phenyl)pyridine. To a solution of 3-(4-bromo-2-nitrophenyl)pyridine (INTERMEDIATE-9, STEP-1) (2.00 g, 0.00716 mole, 1.0 eq) and tert-butyl 4-(4,4,5,5-tetramethyl-1,3,2-dioxaborolan-2-yl)-1H-pyrazole-1-carboxylate (4.42 g, 0.0150 mole, 2.1 eq) in dioxane: water (10 mL:1 mL) was added $K_2CO_3$ (2.96 g, 0.0214 mole, 3 eq) was added at room temperature. The reaction mixture was purged with $N_2$ for 30 min and tetrakis (0.413 g, 0.0035 mole, 0.05 eq) was added. The resulting reaction mixture was stirred at 90° C. for 16 hr, cooled, diluted with water (100 mL) and extracted with ethyl acetate (3×100 mL). The combined organic layer was washed with brine (30 mL), dried over anhydrous $Na_2SO_4$ and concentrated under reduced pressure. The resulting crude material was purified by combi flash chromatography (230-400) silica using (50% ethyl acetate in hexane) as eluent to give title pyridine as a white solid (0.78 g, 40.6%). UPLC-MS (Method 1) m/z 267.2 (M+H)+ at 1.55 min Step-2: Synthesis of 5-(1H-pyrazol-4-yl)-2-(pyridin-3-yl) aniline. To a suspension of 10% Pd/C (50% wet) (0.400 g, 20 W/W) in MeOH (15 ml) was added Step-1 pyridine (0.450 g, 0.0012 mol, 1.0 eq). The mixture was purged with $H_2$ gas for 3 h. After completion of reaction as indicated by TLC (70% EtOAc in hexane), reaction mixture was filtered through a celite bed and was washed with methanol (20 mL). The filtrate was concentrated under reduced pressure further purified by prep HPLC to give title aniline (0.2 g, 50.1%). UPLC-MS (Method 1) m/z 237.2 (M+H)+ at 1.40 min. $^1$H NMR (500 MHz, DMSO-$d_6$) δ 12.93 (s, 1H), 8.62 (s, 1H), 8.52 (d, 1H), 7.93 (s, 2H), 7.84 (d, 1H), 7.44 (m, 1H), 7.00 (m. 2H), 6.91 (d, 1H), 4.90 (s, 2H).

Preparation of Intermediate-13: 5-(5-methylisoxazol-4-yl)-2-(pyridin-2-yl)aniline

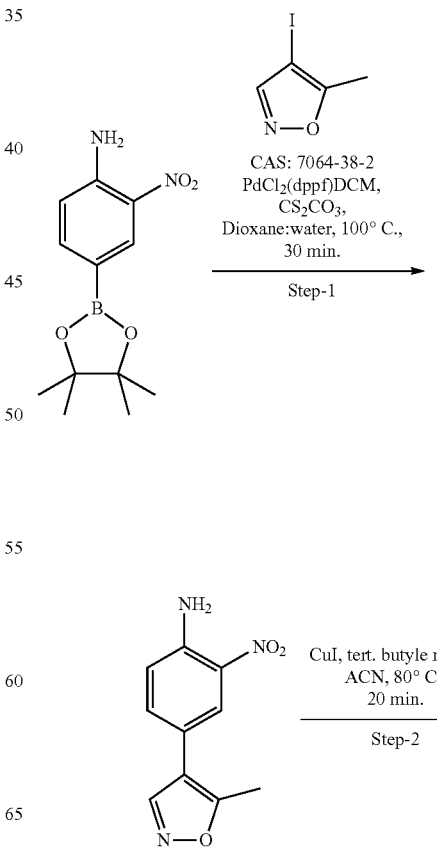

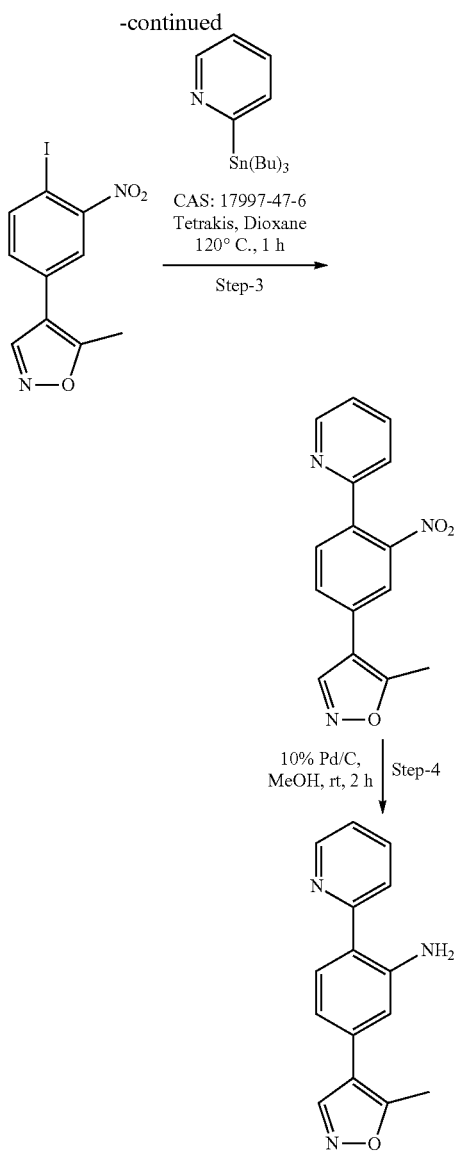

Step-1: Synthesis of 4-(5-methylisoxazol-4-yl)-2-nitroaniline. To a solution of 2-nitro-4-(4,4,5,5-tetramethyl-1,3,2-dioxaborolan-2-yl)aniline (1.00 g, 0.0048 mole, 1 eq) and Cs₂CO₃ (2.73 g, 0.0084 mole, 2 eq) in dioxane: water (9:3 mL) was added 4-iodo-5-methylisoxazole (1.2 g, 0.0048 mole, 1 eq) at room temperature and stirred for 15 min. The reaction mixture was purged with N₂ for 30 min and PdCl₂(dppf)DCM (0.392 g, 0.00048 mole, 0.1 eq) added. The resulting reaction mixture was stirred at 100° C. for 30 min, cooled, diluted with water (100 mL) and filtered through a celite bed. The filtrate was extracted with ethyl acetate (3×100 mL). The combined organic layer was dried over anhydrous Na₂SO₄ and concentrated under reduced pressure. The resulting crude material was purified by trituration using 5 ml DCM and 20 ml pentane to give title aniline. as a brown solid (1.9 g, 96.00%). UPLC-MS (Method 1) m/z 220.2 (M+H)⁺ at 2.27 min.

This material used as such for next step.

Step-2: Synthesis of 4-(4-iodo-3-nitrophenyl)-5-methylisoxazole. To a solution of Step-1 aniline (1.9 g, 0.0867 mole, 1 eq) and CuI (3.2 g, 0.0173 mole, 2 eq) in acetonitrile (30 mL) was added tert butyl nitrite (1.33 mL, 0.0130 mole, 1.5 eq). The resulting reaction mixture was stirred at 80° C. for 20 min. After completion of reaction as indicated by TLC (30% Ethyl acetate in Hexane), the reaction mixture was diluted with water (100 mL) and filtered through a celite bed. The filtrate was extracted with ethyl acetate (3×100 mL). The combined organic layer was dried over anhydrous Na₂SO₄ concentrated under reduced pressure. The resulting crude material was purified by column chromatography on silica using 20% ethyl acetate in hexane as eluent to give title isoxazole as an orange solid (2.45 g, 69.38%).

Step-3: Synthesis of 5-methyl-4-(3-nitro-4-(pyridin-2-yl)phenyl)isoxazole. A solution of Step-2 isoxazole (0.1 g, 0.00030 mol, 1 eq) and 2-tributyl stannyl pyridine (0.167 g, 0.00045 mole, 1.5 eq) in dioxane (1 mL) was mixed at room temperature and stirred for 15 min. The reaction mixture was purged with N₂ and Tetrakis (0.035 g, 0.000030 mole, 0.1 eq) was added. The resulting reaction mixture was stirred at 120° C. for 1 h in microwave, cooled, diluted with water (25 mL) and extracted with ethyl acetate (3×25 mL). The organic extracts were combined and washed with brine (10 mL), dried over anhydrous Na₂SO₄. The solvent was evaporated under reduced pressure. The resulting crude material was purified by column chromatography on neutral silica using (30% ethyl acetate in hexane) as eluent to afford the title isoxazole as a yellow solid (0.16 g, 46.32%). UPLC-MS (Method 1) m/z 282.2 (M+H)⁺ at 2.33 min.

Step-4: Synthesis of 5-(5-methylisoxazol-4-yl)-2-(pyridin-2-yl)aniline. To a suspension of 10% Pd/C (50% wet) (0.16 g, 20 W/W) in MeOH (15 ml) was added Step-3 isoxazole (0.16 g, 0.00057 mol, 1.0 eq). The above reaction mixture was purged with H₂ gas for 30 min, then filtered through a celite bed and the bed was washed with methanol (50 mL). The filtrate was concentrated under reduced pressure. And crude was purified by neutral silica eluted by (15% EtOAC) to give title aniline (0.072 g, 50%). UPLC-MS (Method 1) m/z 252.3 (M+H)⁺ at 1.96 min. ¹H NMR (500 MHz, DMSO-d₆) δ 8.91 (s, 1H), 8.75 (d, 1H), 8.24 (t, 1H), 8.07 (d, 1H), 7.68 (m, 2H), 7.25 (s, 1H), 7.16 (dd, 1H), 3.8-4.8 (b, 2H), 2.64 (s, 3H).

Preparation of Intermediate-14: 5-(5-methylisoxazol-4-yl)-2-(pyridin-3-yl) aniline

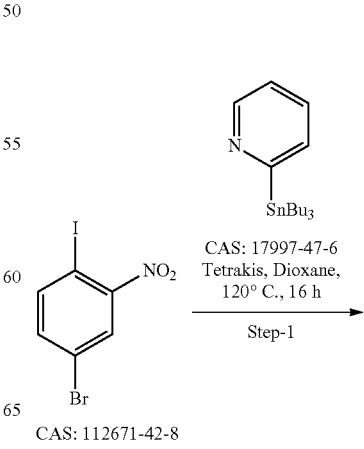

-continued

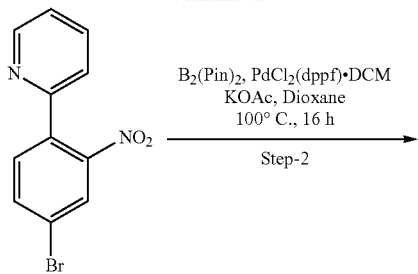

B₂(Pin)₂, PdCl₂(dppf)·DCM
KOAc, Dioxane
100° C., 16 h
Step-2

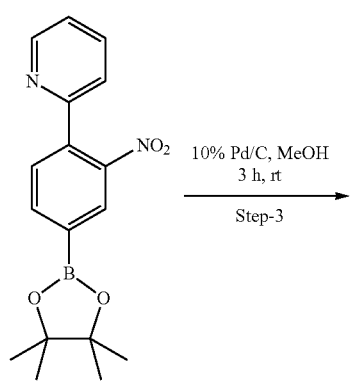

10% Pd/C, MeOH
3 h, rt
Step-3

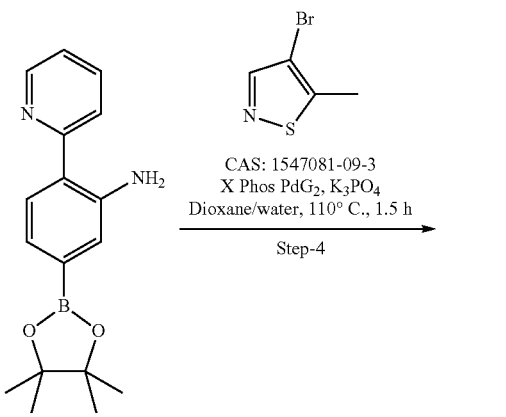

CAS: 1547081-09-3
X Phos PdG₂, K₃PO₄
Dioxane/water, 110° C., 1.5 h
Step-4

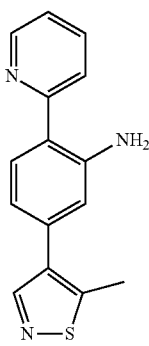 [SMILES: Cc1oncc1-c1ccc(-c2ccccn2)c(N)c1]

Step-1: Synthesis of 2-(4-bromo-2-nitrophenyl)pyridine. A stirred solution of 4-bromo-1-iodo-2-nitrobenzene (0.5 g, 0.0015 mole, 1 eq) and 2-(tributylstannyl)pyridine (0.839 g, 0.0022 mole, 1.5 eq) in dioxane (10 ml, 20 Vol) was purged with $N_2$ gas for 30 min at room temperature. Tetrakis (0.175 g, 0.0001 mole, 0.1 eq) was added and the mixture heated at 120° C. for 16 h, cooled, poured into water (100 mL) and extracted with ethyl acetate (2×100 mL). The combined organic layer was dried over sodium sulfate and concentrated under reduced pressure. The crude was further purified by manual column chromatography using 20% ethyl acetate in hexane as eluent to give title pyridine as a yellow solid (3.70 g, 88.09%). UPLC-MS (Method 1) m/z 279.1/281.1 (M+H)⁺ at 2.74 min.

Step-2: Synthesis of 2-(2-nitro-4-(4,4,5,5-tetramethyl-1,3,2-dioxaborolan-2-yl)phenyl) pyridine. To a stirred solution of Step-1 pyridine (1.5 g, 0.053 mol, 1 eq) and bispinacolato diborane (2.04 g, 0.080 mol, 1.5 eq) in dioxane (15 mL, 10 Vol) was added potassium acetate (1.56 g, 0.0159 mol, 3 eq) portion wise under nitrogen atmosphere. The reaction mixture was purged with $N_2$ gas for 30 min at room temperature. Then PdCl₂(dppf)·DCM (0.387 g, 0.00053 mol, 0.1 eq) was added and the reaction was stirred at 100° C. for 16 h. After completion of reaction as indicated by TLC (30% ethyl acetate in hexane, 3 times), reaction mixture was diluted with water (100 mL) and filtered through a celite bed. The filtrate was extracted with ethyl acetate (3×200 mL). The combined organic layer was dried over sodium sulphate and concentrated under reduced pressure. The crude was purify by column chromatography using 12% ethyl acetate in hexane as eluent to give title pyridine as a brown liquid (2 g, quantitative).

Step-3: Synthesis of 2-(pyridin-2-yl)-5-(4,4,5,5-tetramethyl-1,3,2-dioxaborolan-2-yl)aniline. To a suspension of 10% Pd/C (50% wet) (1.20 g, 20 W/W) in MeOH (25 ml) was added Step-2 pyridine (2.00 g, 0.0061 mol, 1.0 eq). The mixture was purged with $H_2$ gas at room temperature for 3 h, then filtered through a celite bed and the bed was washed with methanol (20 mL). The filtrate was concentrated under reduced pressure. The crude was purified by trituration to give title aniline. (1.8 g, 88%). UPLC-MS (Method 1) m/z 297.3 (M+H)⁺ at 2.50 min.

Step-4: Synthesis of 5-(5-methylisothiazol-4-yl)-2-(pyridin-2-yl)aniline. A solution of Step-3 aniline (0.75 g, 0.0047 mole, 1.2 eq), 4-bromo-5-methylisothiazole (1.4 g, 0.0039 mole, 1 eq) and K₃PO₄ (1.07 g, 0.0050 mole, 1.3 eq) in dioxane: water (9:1 mL) was stirred at room temperature. The reaction mixture was purged with $N_2$ for 30 min and X-Phos-Pd-G2 (0.318 g, 0.00039 mole, 0.1 eq) was added. The resulting reaction mixture was stirred at 110° C. for 1.5 h in microwave, cooled, diluted with water (75 mL) and extracted with ethyl acetate (3×100 mL). The organic extracts were combined and washed with brine (10 mL), dried over anhydrous Na₂SO₄ and concentrated under reduced pressure. The resulting crude material was purified by manual column chromatography by neutral alumina using (8% ethyl acetate in hexane) as eluent to get title aniline as a yellow solid (0.176 g, 26%). UPLC-MS (Method 1) m/z 268.2 (M+H)⁺ at 1.91 min. ¹H NMR (500 MHz, DMSO-d₆) δ 8.62 (d, 1H), 8.59 (s, 1H), 7.88 (m, 2H), 7.66 (d, 1H), 7.30 (m, 1H), 6.92 (d, 1H), 6.77 (m, 3H), 2.61 (s, 3H).

Preparation of Intermediate-15: 5-(isothiazol-5-yl)-2-(pyridin-2-yl)aniline

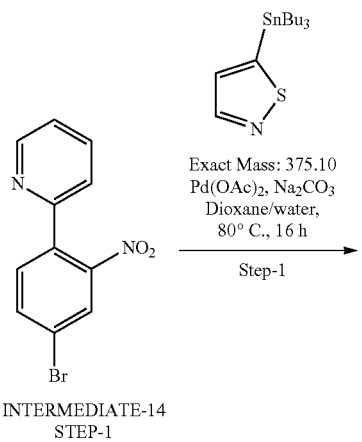

INTERMEDIATE-14
STEP-1

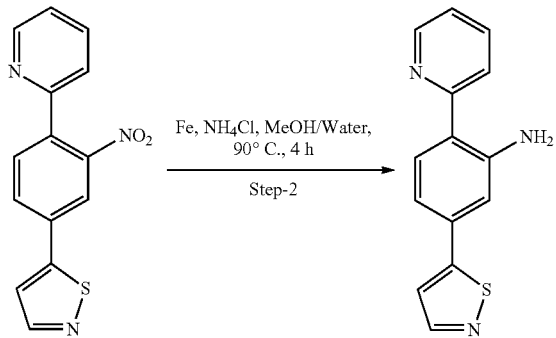

Step-1A: Synthesis of 5-(tributylstannyl)isothiazole. To a stirred solution of 5-bromo-1,2-thiazole (1.0 g, 0.0060 mole, 1 eq) in THF (50 mL, 50 Vol) was slowly added n-BuLi (1.6 M in THF) (0.585 g, 0.0091 mole, 1.5 eq) at −78° C. drop wise. The reaction mixture was stirred at −78° C. for 30 min. Tributyl tin chloride (2.98 g, 0.0091 mole, 1.5 eq) was slowly added at −78° C. The reaction mixture was stirred at −78° C. for 1 h. After completion of reaction as indicated by TLC (10% Ethyl acetate in Hexane), reaction mixture was poured into sat. Ammonium chloride solution (250 mL) and extracted with EtOAc (2×250 mL). The combined organic layer was dried over sodium sulfate and concentrated under reduced pressure to give title stannyl as a brown liquid (2.0 g, 86.95%). This material used as such for next step.

Step-1: Synthesis of 5-(3-nitro-4-(pyridin-2-yl)phenyl)isothiazole. To a solution of 2-(4-bromo-2-nitrophenyl)pyridine (INTERMEDIATE-14, STEP-1) (1 g, 0.0035 mole, 1 eq) in 1,4-dioxane (15 mL) was added 5-(tributylstannyl) isothiazole (1.34 g, 0.0035 mole, 1 eq), $Na_2CO_3$ (1.14 g, 0.0107 mole, 3.0 eq). The reaction mixture was purged with nitrogen for 30 min. Then Pd(OAc)$_2$ (0.057 g, 0.00025 mole, 0.07 eq) and X-Phos (0.24 g, 0.00050 mole, 0.14 eq) were added and stirred at 80° C. temperature for 16 h, cooled, poured into water (100 mL) and extracted with EtOAc (2×70 mL). The combined organic layer was dried over sodium sulphate and concentrated under reduced pressure. The obtained crude was purified by column chromatography (using silica) using 20% EtOAc in Hexane as eluent to give title isothiazole as a light brown solid (0.48 g, 47.5%). UPLC-MS (Method 1) m/z 284.0 (M+H)$^+$ at 1.98 min.

Step-2: Synthesis of 5-(isothiazol-5-yl)-2-(pyridin-2-yl) aniline. To a solution of Step-1 isothiazole (0.44 g, 0.0015 mol, 1 eq) in methanol: water (9:1 mL) was added Fe powder (0.434 g, 0.0077 mol, 5 eq) and NH$_4$Cl (0.415 g, 0.0077 mol, 5 eq). The reaction mixture was stirred at 90° C. for 4 h, cooled, poured into water (100 mL) and filtered through a celite bed. The filtrate was extracted with EtOAc (3×50 mL) and the combined organic layer dried over sodium sulphate and concentrated under reduced pressure. The obtained crude was purified by column chromatography (neutral alumina) using 20% EtOAc in Hexane as eluent to give title aniline as a yellow solid (0.24 g, 61.1%). UPLC-MS (Method 1) m/z 254.1 (M+H)$^+$ at 2.44 min. $^1$H NMR (500 MHz, DMSO-d$_6$) δ 8.63 (d, 1H), 8.60 (d, 1H), 7.82 (s, 2H), 7.72 (m, 2H), 7.36 (m, 1H), 7.14 (d, 1H), 7.00 (dd, 1H), 6.91 (s, 2H).

Preparation of Intermediate-16: 5-(1H-pyrazol-4-yl)-2-(pyridin-2-yl)aniline

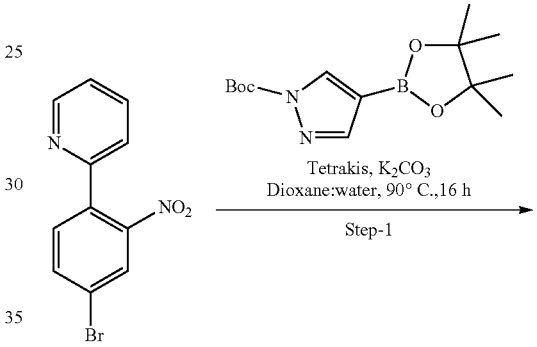

INTERMEDIATE-14
STEP-1

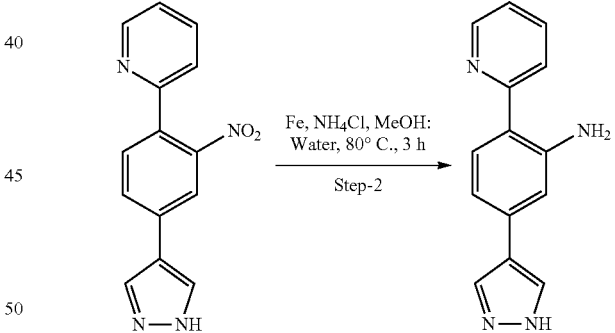

Step-1: Synthesis of 2-(2-nitro-4-(1H-pyrazol-4-yl)phenyl)pyridine. To a solution of 2-(4-bromo-2-nitrophenyl) pyridine (INTERMEDIATE-14, STEP-1) (1.5 g, 0.0053 mole, 1.0 eq) (and tert-butyl 4-(4,4,5,5-tetramethyl-1,3,2-dioxaborolan-2-yl)-1H-pyrazole-1-carboxylate (3.31 g, 0.0011 mole, 2.1 eq) in Dioxane: Water (10 mL: 1 mL) was added K$_2$CO$_3$ (2.22 g, 0.0161 mole, 3 eq) at room temperature. The reaction mixture was purged with N$_2$ for 30 min. Tetrakis (0.310 g, 0.0002 mole, 0.05 eq) was added and resulting reaction mixture was stirred at 90° C. for 16 h, COOLED, diluted with water (50 mL) and extracted with ethyl acetate (3×100 mL). The combined organic layer was dried over anhydrous Na$_2$SO$_4$ and concentrated under reduced pressure. The resulting crude material was purified by column chromatography (60-120) silica using (50% ethyl acetate in hexane) as eluent to afford the title pyridine as a yellow solid (1.5 g, 38.7%). UPLC-MS (Method 1) m/z 267.2 (M+H)$^+$ at 2.13 min.

Step-2: Synthesis of 5-(1H-pyrazol-4-yl)-2-(pyridin-2-yl)aniline. To a solution of Step-1 pyridine (0.60 g, 0.0017 mol, 1.0 eq) in MeOH was added Fe powder (0.498 g, 0.0089 mol, 5 eq.) and NH$_4$Cl (0.476 g, 0.0089 mol, 5 eq). The mixture was stirred at 80° C. for 3 h, diluted with water (20 mL) and extracted with ethyl acetate (3×50 mL). The combined organic layer was dried over anhydrous Na$_2$SO$_4$ and concentrated under reduced pressure. The crude was further purified by prep HPLC purification to give title aniline (0.137 g, 25.7%). UPLC-MS (Method 1) m/z 237.3 (M+H)$^+$ at 1.37 min. $^1$H NMR (500 MHz, DMSO-d$_6$) δ 12.96 (s, 1H), 8.58 (d, 1H), 7.87 (b, 1H), 7.83 (m, 3H), 7.55 (d, 1H), 7.26 (m, 1H), 6.98 (s, 1H), 6.87 (d. 1H), 6.64 (m, 2H).

Preparation of Intermediate-17: 5-(5-methylisoxazol-4-yl)-2-(thiophen-2-yl)aniline

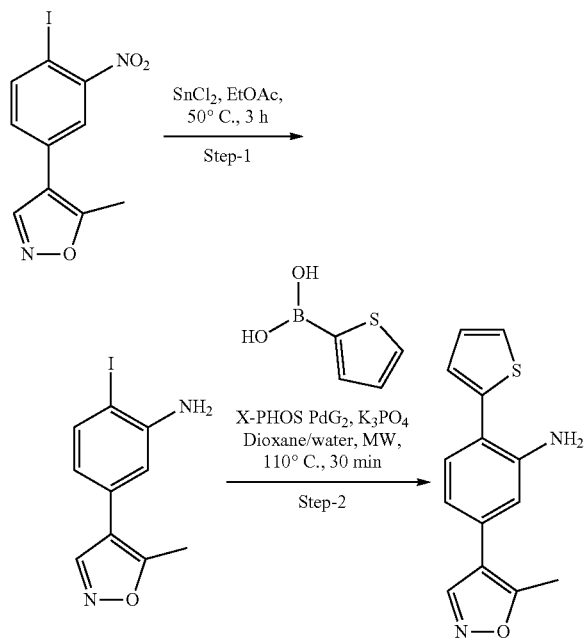

Step-1: Synthesis of 2-iodo-5-(5-methylisoxazol-4-yl)aniline. To a solution 4-(4-iodo-3-nitrophenyl)-5-methylisoxazole (INTERMEDIATE-13, STEP-2) (3 g, 1.67 mmol) in ethyl acetate (25 mL) was added SnCl$_2$ (3.1 g, 8.30 mmol, 5 eq). The reaction mixture was stirred at 50° C. for 3 h, cooled and poured into sat NaHCO$_3$ solution (50 mL). The precipitated solid was filtered through celite and the filtrate was extracted with Ethyl acetate (2×100 mL). The combined organic layer was dried over sodium sulfate and concentrated under reduced pressure give title aniline as a yellow solid (2.8 g). This material used as such for next step without purification.

Step-2: Synthesis of 5-(5-methylisoxazol-4-yl)-2-(thiophen-2-yl)aniline. To a stirred solution of Step-1 aniline (0.800 g, 2.67 mol, 1 eq) and thiophen-2-ylboronic acid (0.800 g, 5.35 mol, 1.1 eq) in dioxane: water (9:3 mL) was added K$_3$PO$_4$ (0737 g, 3.47 mol, 1.3 eq) portion wise. The reaction mixture was purged with N$_2$ gas for 30 min at room temperature. X-PHOS Pd G2 (0.210 g, 0.26 mol, 0.1 eq) was added and reaction mixture was stirred at 110° C. for 30 min in microwave, cooled, poured into water (100 mL) and extracted with Ethyl acetate (2×100 mL). The combined organic layer was dried over sodium sulfate and concentrated under reduced pressure. The obtained crude material was purified by manual column chromatography (neutral alumina) using 25% EtOAc in Hexane as eluent to give title aniline as a white solid (0.126 g, 27.5%). UPLC-MS (Method 1) m/z 257.2 (M+H)$^+$ at 2.53 min. $^1$H NMR (500 MHz, DMSO-d$_6$) δ 8.78 (s, 1H), 7.56 (d, 1H), 7.25 (m, 2H), 7.18 (m, 1H), 6.96 (s, 1H), 6.78 (d, 1H), 5.21 (s, 2H), 2.58 (s, 3H).

Preparation of Intermediate-18: 5-(5-methylisothiazol-4-yl)-2-(pyridin-3-yl)aniline

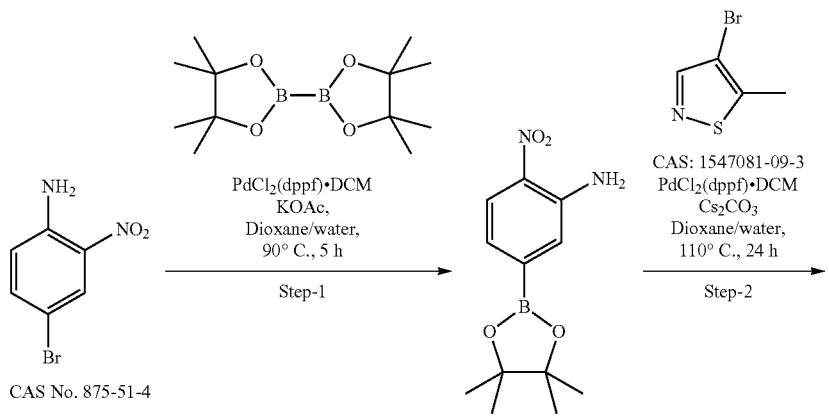

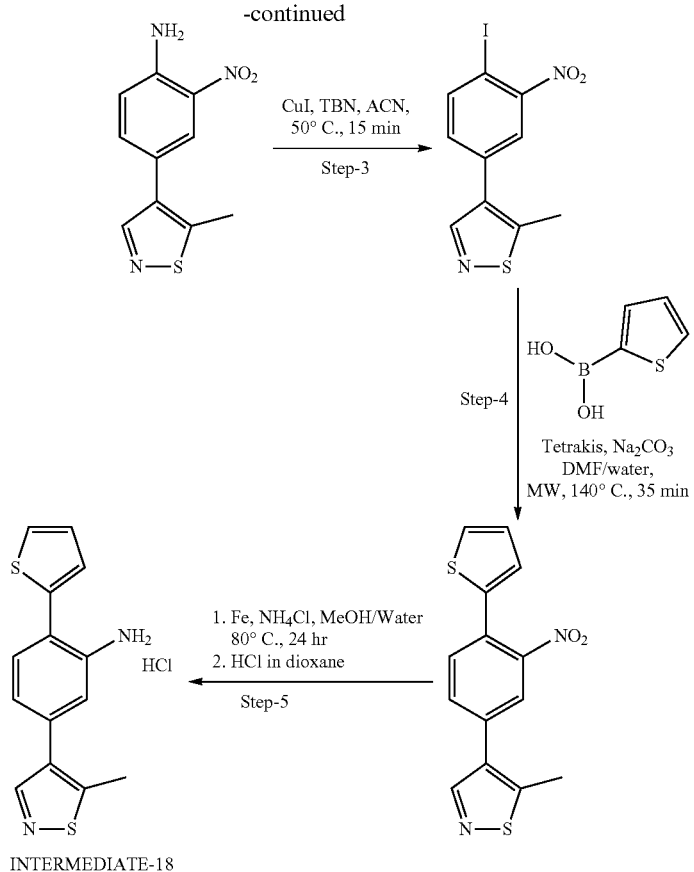

INTERMEDIATE-18

Step-1: Synthesis of 2-nitro-5-(4,4,5,5-tetramethyl-1,3,2-dioxaborolan-2-yl)aniline. To a solution of 4-bromo-2-nitro aniline (CAS: 875-51-4) (4.0 g, 0.0184 mole, 1 eq) and potassium acetate (5.4 g, 0.0541 mole, 2.9 eq) in dioxane (100 mL) was added 4,4,4',4',5,5,5',5'-octamethyl-2,2'-bi(1,3,2-dioxaborolane) (5.15, 0.02028 mole, 1.1 eq) at room temperature. The reaction mixture was purged with $N_2$ for 30 min and $PdCl_2$(dppf)·DCM (0.405 g, 0.00055 mole, 0.03 eq) was added. The resulting reaction mixture was stirred at 90° C. for 5 h, cooled, diluted with water (500 mL) and extracted with ethyl acetate (3×100 mL). The combined organic layer was washed with brine solution (50 mL), dried over anhydrous $Na_2SO_4$ and concentrated under reduced pressure. The resulting crude material was purified by manual column chromatography on silica using 20% ethyl acetate in hexane as eluent to give title aniline as an orange solid (12 g, 82.20%).

Step-2: Synthesis of 4-(5-methylisothiazol-4-yl)-2-nitroaniline. To a solution of Step-1 aniline (0.75 g, 0.0028 mole, 1 eq) and $Cs_2CO_3$ (2.73 g, 0.0084 mole, 3 eq) in Dioxane:Water (6:2 mL) was added 4-bromo-5-methylisothiazole (0.5, 0.0028 mole, 1 eq) at room temperature. The reaction mixture was purged with $N_2$ for 30 min and $PdCl_2$(dppf)·DCM (0.228 g, 0.00028 mole, 0.1 eq) was added. The resulting reaction mixture was stirred at 110° C. for 24 h, cooled, diluted with water (50 mL) and extracted with ethyl acetate (3×50 mL). The combined organic layer was washed with brine solution (10 mL), dried over anhydrous $Na_2SO_4$ and concentrated under reduced pressure. The resulting crude material was purified by flash column chromatography on silica using (2% ethyl acetate in hexane) as eluent to give title aniline as a yellow solid (2.4 g, 59.9%). UPLC-MS (Method 1) m/z 236.2 (M+H)$^+$ at 2.32 min. $^1$H NMR (500 MHz, DMSO-$d_6$) δ 8.61 (s, 1H), 8.05 (d, 1H), 7.60 (m, 3H), 7.13 (d, 1H), 2.90 (s, 3H).

Step-3: Synthesis of 4-(4-iodo-3-nitrophenyl)-5-methylisothiazole. To a solution of Step-2 aniline (2.4 g, 0.0102 mole, 1 eq) and CuI (3.88 g, 0.0204 mole, 2 eq) in acetonitrile (30 mL) was added tert-butyl nitrite (1.67 mL, 0.0153 mole, 1.5 eq). The resulting reaction mixture was stirred at 50° C. for 15 min, cooled, diluted with water (50 mL) and extracted with ethyl acetate (3×50 mL). The combined organic layer was washed with brine (20 mL), dried over anhydrous $Na_2SO_4$ and concentrated under reduced pressure. The resulting crude material was purified by flash column chromatography on silica using (5% ethyl acetate in hexane) as eluent to get afford the title isothiazole as a yellow solid (2.45 g, 69.4%). $^1$H NMR (500 MHz, DMSO-$d_6$) δ 8.70 (s, 1H), 8.18 (d, 1H), 8.10 (d, 1H), 7.58 (dd, 1H), 2.62 (s, 3H).

Step-4: Synthesis of 5-methyl-4-(3-nitro-4-(thiophen-2-yl)phenyl)isothiazole. To a solution of Step-3 isothiazole (0.5 g, 0.0014 mol, 1 eq) and $Na_2CO_3$ (0.371 g, 0.0035 mole, 2.5 eq) in DMF: Water (5:1 mL) was added thiophen-2-ylboronic acid (0.556, 0.0014 mole, 3 eq) at room temperature. The reaction mixture was purged with $N_2$ for 30 min and tetrakis (0.161 g, 0.00014 mole, 0.1 eq) was added. The resulting reaction mixture was stirred at 140° C. for 35 min in microwave, cooled, diluted with water (25 mL) and extracted with ethyl acetate (3×25 mL). The combined organic layer was washed with brine (10 mL), dried over anhydrous $Na_2SO_4$ and concentrated under reduced pressure. The resulting crude material was purified by column chromatography on silica using (20% ethyl acetate in hexane) as eluent to afford the title isothiazole as an orange solid (0.4 g, 92.5%). UPLC-MS (Method 1) m/z 303.3 (M+H)$^+$ at 2.74 min.

Step-5: Synthesis of 5-(5-methylisothiazol-4-yl)-2-(thiophen-2-yl)aniline hydrochloride salt. A solution of Step-4 isothiazole (0.4 g, 0.0132 mole, 1 eq), iron powder (0.369 g, 0.0662 mole, 5.0 eq) and ammonium chloride (0.354 g, 0.06625 mole 5 eq) in Methanol: Water (5:1, 10 mL) was stirred at 80° C. for 24 h. After completion of reaction as indicated by TLC (30% EtOAc in hexane), reaction mixture was filtered through celite and the filtrate was concentrated under reduced pressure. The crude was purified by column chromatography using neutral alumina (20% ethyl acetate in hexane) as eluent to give title aniline as yellow gummy liquid (0.31 g). The above isolated material was dissolved in DCM (10 mL) and 4 N HCl in Dioxane (1 mL) was added. The reaction mixture was stirred at room temperature for 15 min. The reaction mixture was concentrated under reduced pressure and residue was triturated with DCM (10 mL) and decanted. The solid was dried under high vacuum to give title hydrochloride salt as a yellow solid (0.229 g, 77.9%). UPLC-MS (Method 1) m/z 273.2 (M+H)$^+$ at 2.67 min. $^1$H NMR (500 MHz, DMSO-d$_6$) δ 8.54 (s, 1H), 7.57 (d, 1H), 7.27 (m, 2H), 7.18 (m, 1H), 6.94 (s, 1H), 6.77 (dd, 1H), 5.24 (s, 2H), 2.60 (s, 3H).

Preparation of Intermediate-19: 5-(isothiazol-5-yl)-2-(thiophen-2-yl)aniline

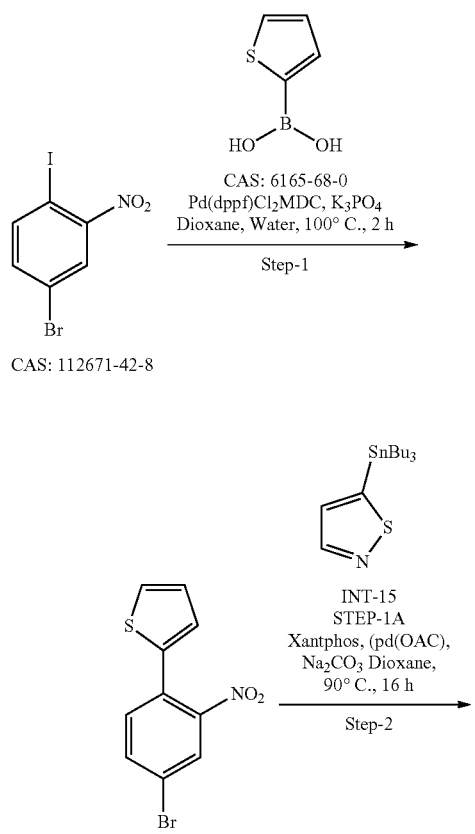

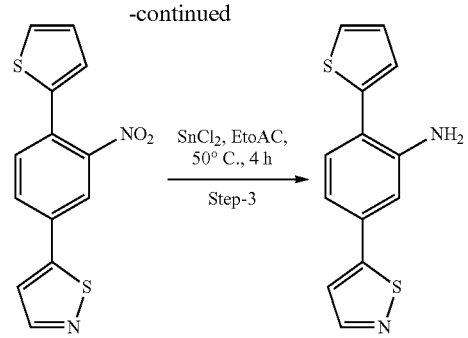

Step-1: Synthesis of 2-(4-bromo-2-nitrophenyl)thiophene. To a stirred solution of 4-bromo-1-iodo-2-nitrobenzene (3.0 g, 9.14 mole, 1 eq) and thiophen-2-ylboronic acid (1.76 g, 13.7 mole, 1.5 eq) in dioxane: water (30 mL: 10 mL, 10 Vol) was slowly added K$_3$PO$_4$ (3.8 g, 0.45 mole, 3 eq) portion wise. The reaction mixture was purged with N$_2$ gas for 30 min at room temperature. Pd(dppf)Cl$_2$ DCM (0.38 g, 0.45 mol, 0.05 eq) was added and further heated at 100° C. for 2 h, cooled, poured into water (100 mL) and extracted with Ethyl acetate (2×150 mL). The combined organic layer was dried over sodium sulfate and concentrated under reduced pressure. The obtained crude was purified by flash column chromatography (200-400 Silica gel) using 1.2% EtOAc in Hexane as eluent to give title thiophene as solid (1.7 g).

Step-2: Synthesis of 5-(3-nitro-4-(thiophen-2-yl)phenyl)isothiazole. To a solution of Step-1 thiophene (0.6 g, 0.0021 mole, 1.0 eq) and 5-(tributylstannyl)isothiazole (1.18 g, 0.0031 mole, 1.5 eq) (INTERMEDIATE-15, STEP-1A) in dioxane (10 mL) was added Na$_2$CO$_3$ (0.67 g, 0.0063 mole, 3 eq) at room temperature. The reaction mixture was purged with N$_2$ for 30 min. Xantphos (0.14 g, 0.0003 mole, 0.14 eq) and Pd(OAc) (0.033 g, 0.0002 mol, 0.07 eq) were added and stirred at 90° C. for 16 hr, cooled, diluted with water (50 mL) and extracted with ethyl acetate (2×50 mL). The combined organic was dried over anhydrous Na$_2$SO$_4$ and concentrated uner reduced pressure. The resulting crude material was purified by combi flash chromatography (230-400) silica using (14% ethyl acetate in hexane) as eluent to give title isothiazole as a brown solid (0.450 g, 97.8%). UPLC-MS (Method 1) m/z 289.1 (M+H)$^+$ at 2.98 min.

Step-3: Synthesis of 5-(isothiazol-5-yl)-2-(thiophen-2-yl) aniline. To a solution of Step-2 isothiazole (0.450 g, 0.0015 mol, 1.0 eq) in ethyl acetate (5 mL) was added SnCl$_2$ (1.47 g, 0.0078 mol, 5 eq). The reaction mixture was stirred at 50° C. for 4 h, cooled, diluted with water (50 mL), filtered through celite and extracted with ethyl acetate (3×50 mL). The organic layer was dried over anhydrous Na$_2$SO$_4$ concentrated under reduced pressure. The crude was further purified by combi flash chromatography (230-400) silica using (10% ethyl acetate in hexane) as eluent to give title aniline (0.210 g, 52.1%). UPLC-MS (Method 1) m/z 259.4 (M+H)$^+$ at 2.67 min. $^1$H NMR (500 MHz, DMSO-d$_6$) δ 8.58 (s, 1H), 7.67 (d, 1H), 7.60 (d, 1H), 7.33 (d, 1H), 7.28 (d, 1H), 7.17 (m, 2H), 7.00 (dd, 1H), 5.37 (s, 2H).

Preparation of Intermediate-20: 5-(1H-pyrazol-4-yl)-2-(thiophen-2-yl)aniline

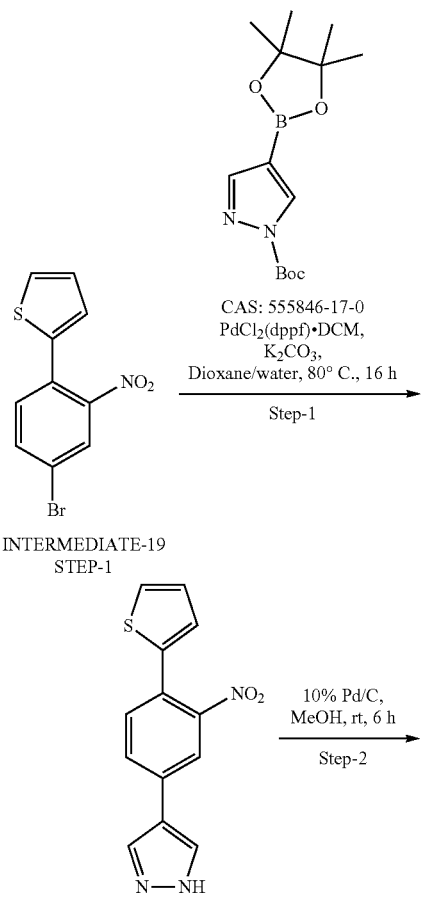

INTERMEDIATE-19
STEP-1

Step-1: Synthesis of 4-(3-nitro-4-(thiophen-2-yl)phenyl)-1H-pyrazole. To a stirred solution of 2-(4-bromo-2-nitrophenyl)thiophene (INTERMEDIATE-19, STEP-1) (0.8 g, 2.81 mmol, 1 eq) in dioxane: Water (9 mL: 3 mL) was added tert-butyl 4-(4,4,5,5-tetramethyl-1,3,2-dioxaborolan-2-yl)-1H-pyrazole-1-carboxylate (0.993 g, 3.38 mmol, 1.2 eq) and potassium carbonate (1.1 g, 8.45 mmol, 3 eq). The reaction mixture was purged with $N_2$ gas for 30 min. Pd(dppf)$Cl_2$·DCM (0.114 g, 0.14 mmol, 0.05 eq) was added to the reaction mixture and stirred at 80° C. for 16 h, cooled, poured into water (50 mL) and extracted with Ethyl acetate (2×40 mL). The combined organic layer was dried over sodium sulfate and concentrated under reduced pressure. The obtained crude was purified by flash column chromatography (200-400 Silica gel) using 20% EtOAc in Hexane as eluent to give title pyrazole as a yellow solid (0.65 g). UPLC-MS (Method 1) m/z 272.2 (M+H)$^+$ at 2.55 min. $^1$H NMR (500 MHz, DMSO-$d_6$) δ 13.16 (s, 1H), 8.44 (s, 1H), 8.18 (d, 1H), 8.12 (s, 1H), 7.96 (dd, 1H), 7.70 (m, 1H), 7.63 (d, 1H), 7.14 (m, 2H).

Step-2: Synthesis of 5-(1H-pyrazol-4-yl)-2-(thiophen-2-yl)aniline. To a solution of Step-1 pyrazole (0.65 g, 2.39 mmol) in MeOH (8 mL) was added Pd—C(10% W/W, 50% moisture) (0.250 g, 20%) under nitrogen atmosphere at room temperature. The resulting reaction mixture was purged with $H_2$ gas at room temperature for 3 h. After completion of reaction as indicated by TLC (50% EtOAc in Hexane as mobile phase), the reaction mixture was filtered through a celite bed. The celite bed was washed with ethyl acetate (50 mL). The filtrate was concentrated under vacuum to get crude which was purified by reverse phase column chromatography using 20% EtOAc in Hexane as eluent to give title aniline as a solid (0.18 g). UPLC-MS (Method 1) m/z 242.2 (M+H)$^+$ at 2.31 min. $^1$H NMR (500 MHz, DMSO-$d_6$) δ 12.94 (s, 1H), 8.06 (s, 1H), 7.80 (s, 1H), 7.52 (d, 1H), 7.24 (d, 1H), 7.14 (m, 2H), 7.02 (s, 1H), 6.87 (dd, 1H), 5.06 (s, 2H).

Preparation of Intermediate-21: 2-(5-methylthiophen-2-yl)-5-(5-methylisoxazol-4-yl)aniline

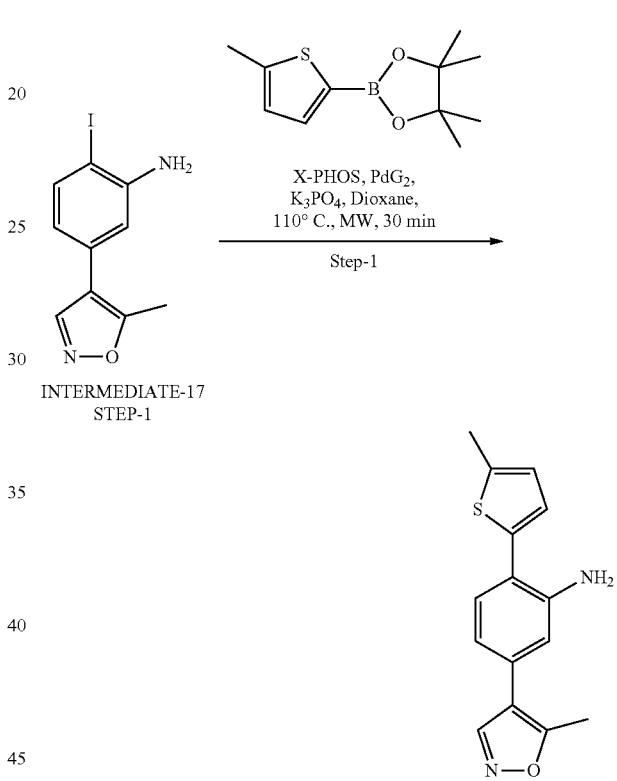

INTERMEDIATE-17
STEP-1

To a stirred solution of 2-iodo-5-(5-methylisoxazol-4-yl)aniline (INTERMEDIATE-17, STEP-1) (0.8 g, 2.675 mmol, 1 eq) in dioxane: water (9 mL: 3 mL) was added 4,4,5,5-tetramethyl-2-(5-methylthiophen-2-yl)-1,3,2-dioxaborolane (0.66 g, 5.35 mmol, 2 eq) and potassium phosphate tri basic (0.73 g, 3.47 mmol, 1.3 eq). The reaction mixture was purged with $N_2$ gas for 30 min. X-PHOS Pd-$G_2$ (0.210 g, 0.26 mmol, 0.1 eq) was added to the reaction mixture and stirred at 110° C. for 30 min in microwave, cooled, poured into water (80 mL) and extracted with ethyl acetate (2×80 mL). The combined organic layer was dried over sodium sulfate and concentrated under reduced pressure. The obtained crude was purified by manual column chromatography (neutral alumina) using 7% EtOAc in hexane as eluent to give title aniline (0.220 g, 28.4%). UPLC-MS (Method 1) m/z 271.2 (M+H)$^+$ at 2.68 min. $^1$H NMR (500 MHz, DMSO-$d_6$) δ 8.76 (s, 1H), 7.19 (d, 1H), 7.05 (d, 1H), 6.93 (d, 1H), 6.83 (m, 1H), 6.76 (dd, 1H), 5.18 (s, 2H), 2.53 (s, 3H), 2.47 (s, 3H).

Preparation of Intermediate-22: 5-(5-methylisothiazol-4-yl)-2-(5-methylthiophen-2-yl)aniline

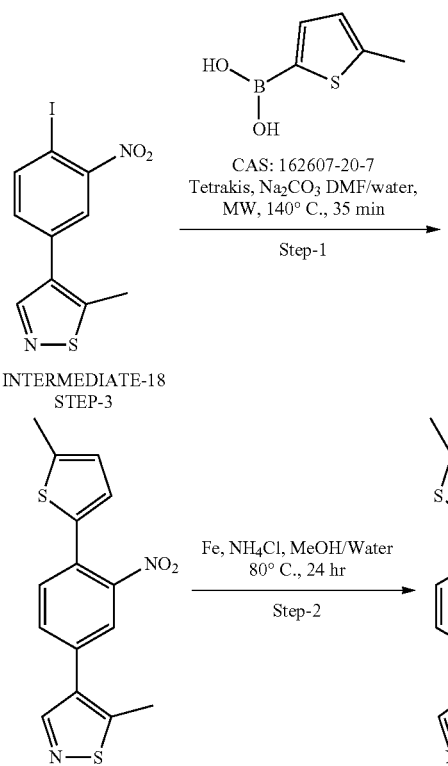

Step-1: Synthesis of 5-methyl-4-(4-(5-methylthiophen-2-yl)-3-nitrophenyl)isothiazole. To a solution of 4-(4-iodo-3-nitrophenyl)-5-methylisothiazole (INTERMEDIATE-18. STEP-3) (0.5 g, 0.0014 mole, 1 eq) and $Na_2CO_3$ (0.381 g, 0.0036 mole, 2.5 eq) in DMF: Water (5:1 mL) was added (5-methylthiophen-2-yl)boronic acid (0.617, 0.0043 mole, 3 eq) at room temperature. The reaction mixture was purged with $N_2$ for 30 min and tetrakis (0.166 g, 0.00014 mole, 0.1 eq) was added. The resulting reaction mixture was stirred at 140° C. for 35 min in microwave, cooled, diluted with water (25 mL) and extracted with ethyl acetate (3×25 mL). The combined organic layer was washed with brine solution (10 mL), dried over anhydrous $Na_2SO_4$ and concentrated under reduced pressure. The resulting crude material was purified by column chromatography on silica using (20% ethyl acetate in hexane) as eluent to give isothiazole as an orange solid (0.4 g, 87.52%). UPLC-MS (Method 1) m/z 317.2 $(M+H)^+$ at 2.88 min.

Step-2: Synthesis of 5-(5-methylisothiazol-4-yl)-2-(5-methylthiophen-2-yl)aniline. A stirred solution of Step-1 isothiazole (0.4 g, 0.0022 mole, 1 eq), iron powder (0.6 g, 0.0110 mole, 5.0 eq) and ammonium chloride (0.59 g, 0.011 mole, 5 eq) in Methanol: Water (5:1, 10 mL) was stirred at 80° C. for 24 h. After completion of reaction as indicated by TLC (30% EtOAc in hexane), reaction mixture was filtered through celite and filtrate was concentrated under reduced pressure. The crude was purified by flash column chromatography using neutral alumina (20% ethyl acetate in hexane) as eluent. The fractions were concentrated and residue was triturated by using MDC (1 mL) and n-Pentane (20 mL) to give title aniline as a yellow solid (0.129 g, 20.4%). UPLC-MS (Method 1) m/z 287.2 $(M+H)^+$ at 2.77 min. $^1H$ NMR (500 MHz, DMSO-$d_6$) δ 8.54 (s, 1H), 7.20 (d, 1H), 7.07 (d, 1H), 6.92 (d, 1H), 6.84 (m, 1H), 6.74 (dd, 1H), 5.20 (s, 2H), 2.59 (s, 3H), 2.48 (s, 3H).

Preparation of Intermediate-23: 5-(isothiazol-5-yl)-2-(5-methylthiophen-2-yl)aniline

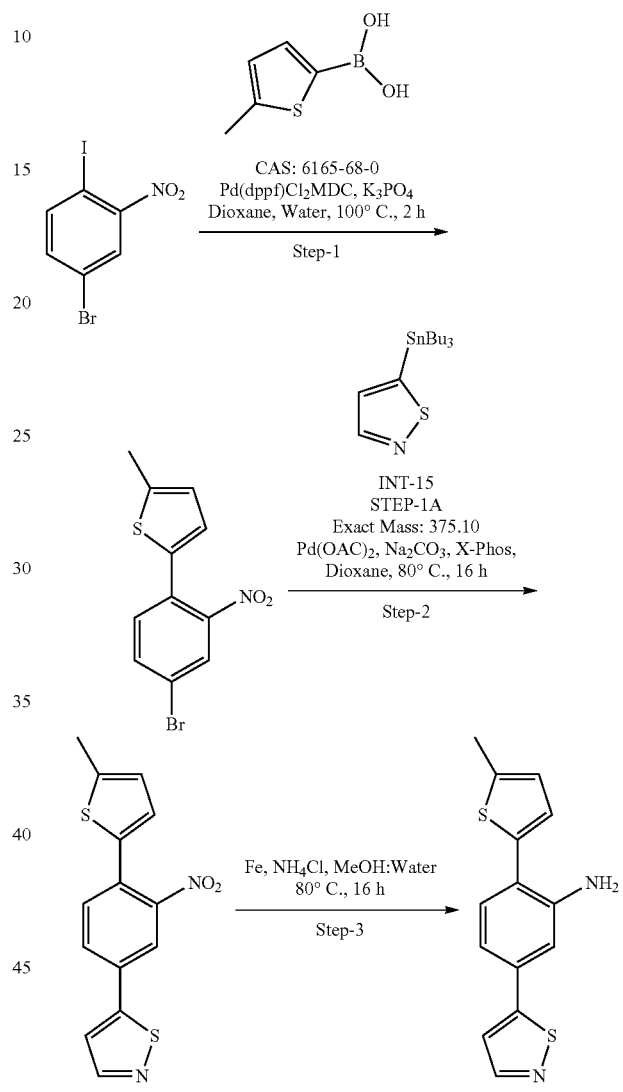

Step-1: Synthesis of 2-(4-bromo-2-nitrophenyl)-5-methylthiophene. To a stirred solution of 4-bromo-1-iodo-2-nitrobenzene (3.0 g, 9.14 mole, 1 eq) and (5-chlorothiophen-2-yl)boronic acid (1.76 g, 13.7 mole, 1.5 eq) in dioxane: water (30 mL: 10 mL, 10 Vol) was slowly added $K_3PO_4$ (3.8 g, 0.45 mole, 3 eq) portion wise. The reaction mixture was purged with $N_2$ gas for 30 min at room temperature. Then Pd(dppf)$Cl_2$·DCM (0.38 g, 0.45 mol, 0.05 eq) was added and further heated at 100° C. for 2 h, cooled, poured into water (100 mL) and extracted with Ethyl acetate (2×150 mL). The combined organic layer was dried over sodium sulfate and concentrated under reduced pressure. The obtained crude was purified by flash column chromatography (200-400 Silica gel) using 1.2% EtOAc in Hexane as eluent to give title thiophene as a solid (1.7 g).

Step-2: Synthesis of 5-(4-(5-methylthiophen-2-yl)-3-nitrophenyl)isothiazole. To a solution of Step-1 Ithiophene (1 g, 0.0033 mole, 1 eq) in 1,4-dioxane (20 mL) was added 5-(tributylstannyl)isothiazole (INTERMEDIATE-15, STEP-1A) 2.2 g, 0.0066 mole, 2 eq), Na$_2$CO$_3$ (1.05 g, 0.0099 mole, 3.0 eq). The reaction mixture was purged with nitrogen for 30 min. Pd(OAc)$_2$ (0.052 g, 0.00023 mole, 0.07 eq) and X-PHOS (0.2 g, 0.0046 mole, 0.14 eq) were added and stirred at 80° C. temperature for 16 h, cooled, poured into water (100 mL) and extracted with EtOAc (2×50 mL). The combined organic layer was dried over sodium sulphate and concentrated under reduced pressure to give title isothiazole (1.2 g, Quantitative). This material used as such for next step without purification.

Step-3: Synthesis of 5-(isothiazol-5-yl)-2-(5-methylthiophen-2-yl)aniline. To a solution of Step-2 isothiazole (1.2 g, 0.0039 mol, 1 eq) in methanol: water (10:2 mL) was added Fe powder (1.1 g, 0.0198 mol, 5 eq) and NH$_4$Cl (1.0 g, 0.0198 mol, 5 eq). The reaction mixture was stirred at 80° C. for 16 h. After completion of reaction as indicated by TLC (30% EtOAc in hexane), reaction mixture was poured into water (100 mL) and filtered through celite. The filtrate was extracted with EtOAc (3×50 mL), the combined organic layer was dried over sodium sulphate and concentrated under reduced pressure. The obtained crude was purified by column chromatography (using neutral alumina) using 10% EtOAc in Hexane as eluent to give title aniline as a yellow solid (0.38 g, 35.2%). UPLC-MS (Method 1) m/z 273.2 (M+H)$^+$ at 2.35 min. $^1$H NMR (500 MHz, DMSO-d$_6$) δ 8.58 (s, 1H), 7.65 (d, 1H), 7.23 (d, 1H), 7.13 (d, 1H), 7.11 (d, 1H), 6.99 (dd, 1H), 6.85 (dd, 1H), 5.34 (s, 2H), 2.48 (s, 3H).

Preparation of Intermediate-24: 2-(5-methylthiophen-2-yl)-5-(1H-pyrazol-4-yl)aniline Step-1 Synthesis of 4-(4-(5-methylthiophen-2-yl)-3-nitrophenyl)-1H-pyrazole. To a stirred solution of 2-(4-bromo-2-nitrophenyl)-5-methylthiophene (INTERMEDIATE-23, STEP-1) (1 g, 3.35 mmol, 1 eq) in dioxane: water (9 mL: 1 mL) was added tert-butyl 4-(4,4,5,5-tetramethyl-1,3,2-dioxaborolan-2-yl)-1H-pyrazole-1-carboxylate (2.1 g, 7.04 mmol, 2.1 eq) and potassium carbonate (1.4 g, 10.05 mmol, 3 eq). The reaction mixture was purged with N$_2$ gas for 30 min. Pd(PPh$_3$)$_4$ (0.20 g, 0.16 mmol, 0.05 eq) was added to the reaction mixture and stirred at 90° C. for 16 h, cooled, poured into water (50 mL) and extracted with ethyl acetate (2×40 mL). The combined organic layer was dried over sodium sulfate and concentrated under reduced pressure. The obtained crude was purified by flash column chromatography (200-400 Silica gel) using 40% EtOAc in Hexane as eluent to give title pyrazole as a yellow solid (1.3 g). UPLC-MS (Method 1) m/z 286.2 (M+H)$^+$ at 2.64 min Step-2: Synthesis of 2-(5-methylthiophen-2-yl)-5-(1H-pyrazol-4-yl) aniline. To a solution Step-1 pyrazole (0.5 g, 1.67 mmol) in ethyl acetate (5 mL) was added SnCl$_2$ (1.57 g, 8.30 mmol, 5 eq). The reaction mixture was stirred at 40° C. for 4 h, cooled, poured into water (50 mL) and extracted with Ethyl acetate (2×100 mL). The combined organic layer was dried over sodium sulfate and concentrated under reduced pressure. The obtained crude was purified by neutral alumina using 20% EtOAc in Hexane as eluent to give title aniline as a yellow solid (0.28 g). UPLC-MS (Method 1) m/z 256.2 (M+H)$^+$ at 2.16 min. $^1$H NMR (500 MHz, DMSO-d$_6$) δ 12.92 (s, 1H), 8.00 (bs, 1H), 7.79 (bs, 1H), 7.10 (d, 1H), 6.99 (m, 2H), 6.85 (d, 1H), 6.81 (m, 1H), 5.02 (s, 2H), 2.46 (s, 3H).

Preparation of Intermediate-25: 2-(5-chlorothiophen-2-yl)-5-(5-methylisoxazol-4-yl)aniline

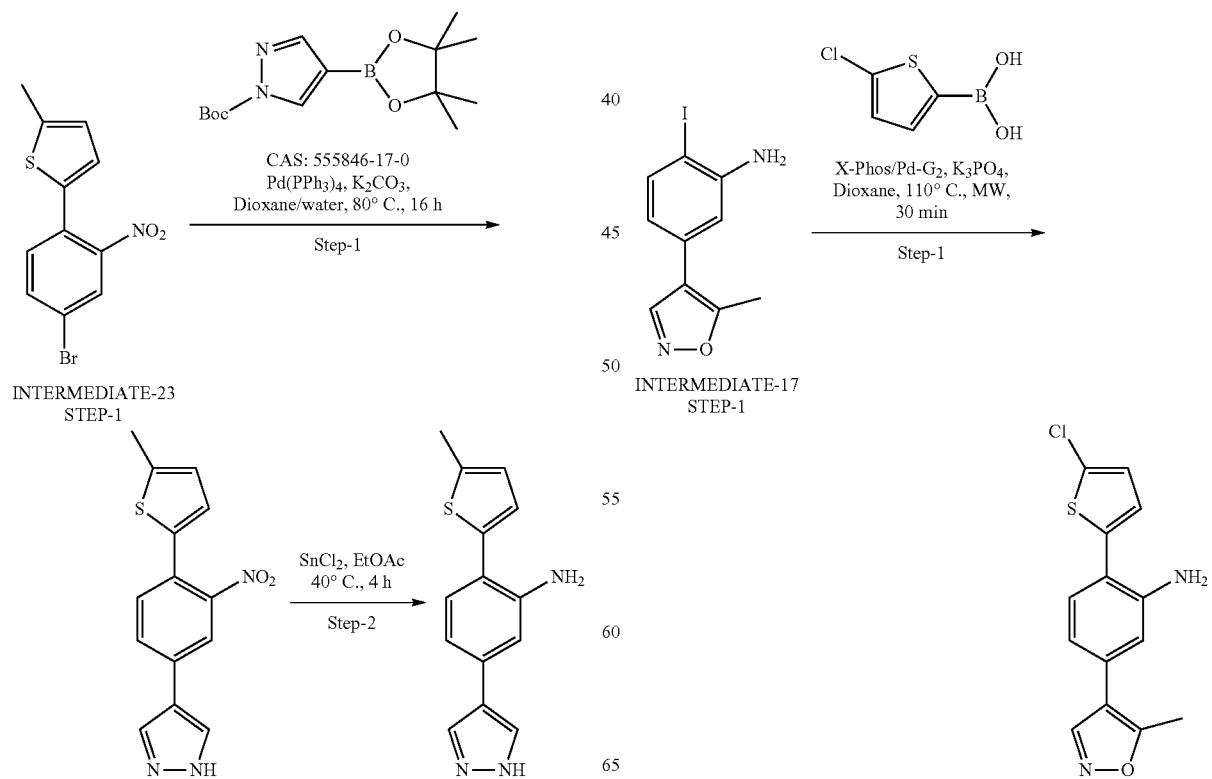

To a stirred solution of 2-iodo-5-(5-methylisoxazol-4-yl) aniline (INTERMEDIATE-17, STEP-1) 0.8 g, 2.675 mmol, 1 eq) in dioxane: Water (9 mL: 3 mL) was added (5-chlorothiophen-2-yl)boronic acid (0.66 g, 5.35 mmol, 2 eq) and potassium phosphate tri basic (0.73 g, 3.47 mmol, 1.3 eq). The reaction mixture was purged with $N_2$ gas for 30 min. X-PHOIS Pd-$G_2$ (0.210 g, 0.26 mmol, 0.1 eq) was added to the reaction mixture and stirred at 110° C. for 30 min in microwave, cooled, poured into water (80 mL) and extracted with ethyl acetate (2×80 mL). The combined organic layer was dried over sodium sulfate and concentrated under reduced pressure. The obtained crude was purified by manual column chromatography (neutral alumina) using 7% EtOAc in hexane as eluent to give title aniline 0.220 g, 28.4%). UPLC-MS (Method 1) m/z 291.3/293.3 (M+H)$^+$ at 2.88 min. $^1$H NMR (500 MHz, DMSO-$d_6$) δ 8.75 (s, 1H), 7.20 (d, 1H), 7.14 (m, 2H), 6.96 (s, 1H), 6.78 (d, 1H), 5.30 (s, 2H), 2.58 (s, 3H).

Preparation of Intermediate-26: 2-(5-chlorothiophen-2-yl)-5-(5-methylisothiazol-4-yl) aniline

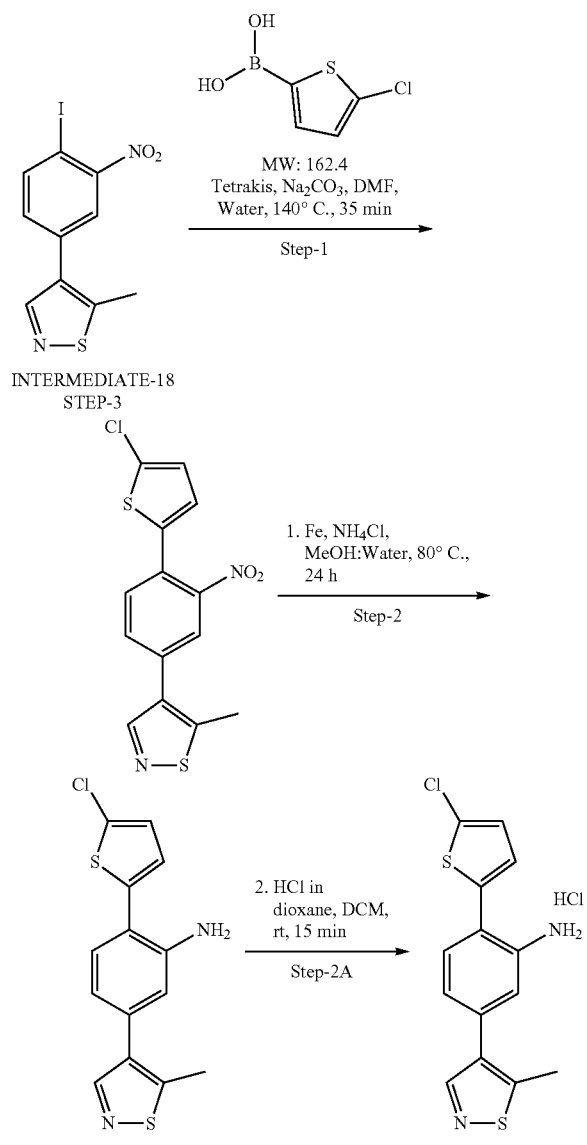

Step-1: Synthesis of 4-(4-(5-chlorothiophen-2-yl)-3-nitrophenyl)-5-methylisothiazole. To a stirred solution of 4-(4-iodo-3-nitrophenyl)-5-methylisothiazole (INTERMEDIATE-17, STEP-3) (0.5 g, 0.0014 mol, 1 eq) and (5-chlorothiophen-2-yl)boronic acid (1.1 g, 0.0072 mol, 5 eq) in DMF: water (5 mL: 2 mL, 10 Vol) was added $Na_2CO_3$ (0.38 g, 0.0036 mol, 2.5 eq) portion wise. The reaction mixture was purged with $N_2$ gas for 15 min at room temperature. Tetrakis (0.16 g, 0.0001 mol, 0.1 eq) was added and reaction mixture was stirred at 140° C. in microwave for 35 min. After completion of reaction as indicated by TLC (20% ethyl acetate in hexane), the reaction mixture was poured into water (100 mL) and extracted with Ethyl acetate (2×100 mL). The combined organic layer was dried over sodium sulfate and concentrated under reduced pressure. The crude was purified by flash chromatography neutral alumina using 10% EtOAc in Hexane as eluent to give title isothiazole as a brown oil (0.690 g, quantitative). UPLC-MS (Method 1) m/z 337.1/339.1 (M+H)$^+$ at 2.98 min.

Step-2: Synthesis of 2-(5-chlorothiophen-2-yl)-5-(5-methylisothiazol-4-yl) aniline hydrochloride salt. To a solution of Step-1 isothiazole (0.65 g, 0.0020 mol, 1 eq) in methanol: water (8:2 mL, 10 vol) was added Fe powder (0.56 g, 0.0103 mol, 5 eq) and (0.55 g, 0.010 mol, 5 eq). The reaction mixture was stirred at 80° C. for 24 h. After completion of reaction as indicated by TLC (20% EtOAc in hexane), reaction mixture was poured into water (500 mL) and filtered through celite. The celite bed was washed with ethyl acetate (50 mL). The layers were separated and the organic layer was dried over sodium sulphate and concentrated under reduced pressure. The obtained crude was purified by column chromatography (neutral alumina) using 10% EtOAc in Hexane to give title aniline as a brown sticky solid (0.25 g).

Step-2A: The above isolated crude material was dissolved in DCM (10 mL) and 4 N HCl in Dioxane (1 mL) was added. The reaction mixture was stirred at room temperature for 15 min. The reaction mixture was concentrated under reduced pressure and residue was triturated with DCM (10 mL) and decanted. The solid was dried under high vacuum to give title hydrochloride salt as a brown solid (0.195 g, 30.81%) UPLC-MS (Method 1) m/z 307.1/309.1 (M+H)$^+$ at 3.00 min. $^1$H NMR (500 MHz, DMSO-$d_6$) δ 8.60 (s, 1H), 7.38 (d, 1H), 7.31 (m, 2H), 7.21 (d, 1H), 7.12 (bd, 1H), 7.00-5.50 (bs, 2H), 2.61 (s, 3H).

Preparation of Intermediate-27: 2-(5-chlorothiophen-2-yl)-5-(isothiazol-5-yl)aniline

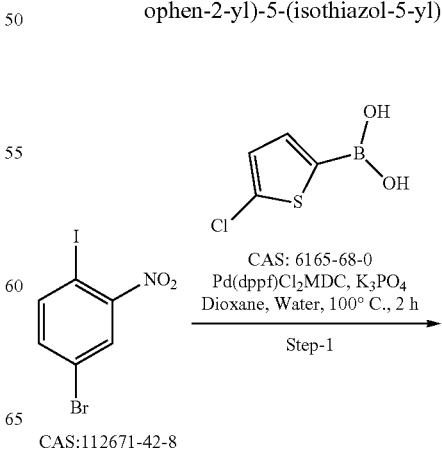

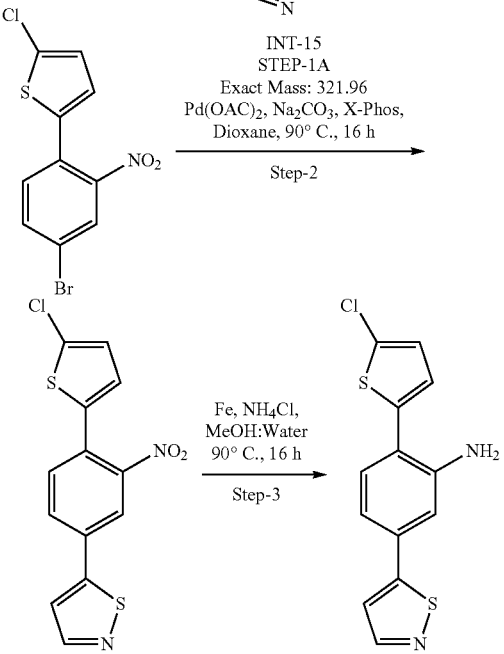

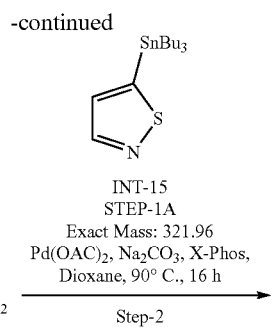

Step-1 Synthesis of 2-(4-bromo-2-nitrophenyl)-5-fluorothiophene. To a stirred solution of 4-bromo-1-iodo-2-nitrobenzene (3.0 g, 9.14 mole, 1 eq) and (5-chlorothiophen-2-yl)boronic acid (1.76 g, 13.7 mole, 1.5 eq) in dioxane:water (30 mL: 10 mL, 10 Vol) was slowly added $K_3PO_4$ (3.8 g, 0.45 mole, 3 eq) portion wise. The reaction mixture was purged with $N_2$ gas for 30 min at room temperature. Then Pd(dppf)Cl$_2$ DCM (0.38 g, 0.45 mol, 0.05 eq) was added and further heated at 100° C. for 2 h, cooled, poured into water (100 mL) and extracted with Ethyl acetate (2×150 mL). The combined organic layer was dried over sodium sulfate and concentrated under reduced pressure. The obtained crude was purified by flash column chromatography (200-400 Silica gel) using 1.2% EtOAc in Hexane as eluent to give title thiophene as a solid (1.7 g).

Step-2: Synthesis of 5-(4-(5-chlorothiophen-2-yl)-3-nitrophenyl)isothiazole. To a solution of Step-1 thiophene (1.6 g, 0.0053 mole, 1 eq) in 1,4-dioxane (20 mL) was added 5-(tributylstannyl)isothiazole (INTERMEDIATE-15, STEP-1A) (2.0 g, 0.0053 mole, 1 eq), Na$_2$CO$_3$ (1.6 g, 0.0159 mole, 3.0 eq). The reaction mixture was purged with nitrogen for 30 min. Pd(OAc)$_2$ (0.08 g, 0.00037 mole, 0.07 eq) and X-PHOS (0.35 g, 0.0074 mole, 0.14 eq) was added and stirred at 90° C. temperature for 16 h, cooled, poured into water (500 mL) and extracted with EtOAc (2×500 mL). The combined organic layer was dried over sodium sulphate and concentrated under reduced pressure to give title isothiazole as a yellow liquid (1.0 g, 50%).

This material used as such for next step without purification.

Step-3: Synthesis of 2-(5-chlorothiophen-2-yl)-5-(isothiazol-5-yl)aniline. To a solution of Step-2 isothiazole (0.9 g, 0.0027 mol, 1 eq) in methanol: water (8:2 mL) was added Fe powder (0.7 g, 0.0013 mol, 5 eq) and NH$_4$Cl (0.7 g, 0.0013 mol, 5 eq). The reaction mixture was stirred at 90° C. for 16 h, cooled, poured into water (500 mL) and filtered through celite. The filtrate was extracted with EtOAc (3×300 mL) and the combined organic layer, dried over sodium sulphate and concentrated under reduced pressure. The obtained crude was purified by column chromatography (using neutral alumina) using 5% EtOAc in Hexane as eluent to give title aniline as a white solid (0.14 g, 18%). UPLC-MS (Method 1) m/z 293.1/295.1 (M+H)$^+$ at 3.09 min. $^1$H NMR (500 MHz, DMSO-d$_6$) δ 8.58 (s, 1H), 7.67 (s, 1H), 7.25 (d, 1H), 7.16 (m, 3H), 7.00 (dd, 1H), 5.44 (s, 2H).

Preparation of Intermediate-28: 2-{5-Chlorothiophen-2-Yl}-5-(1H-pyrazol-4-yl)aniline

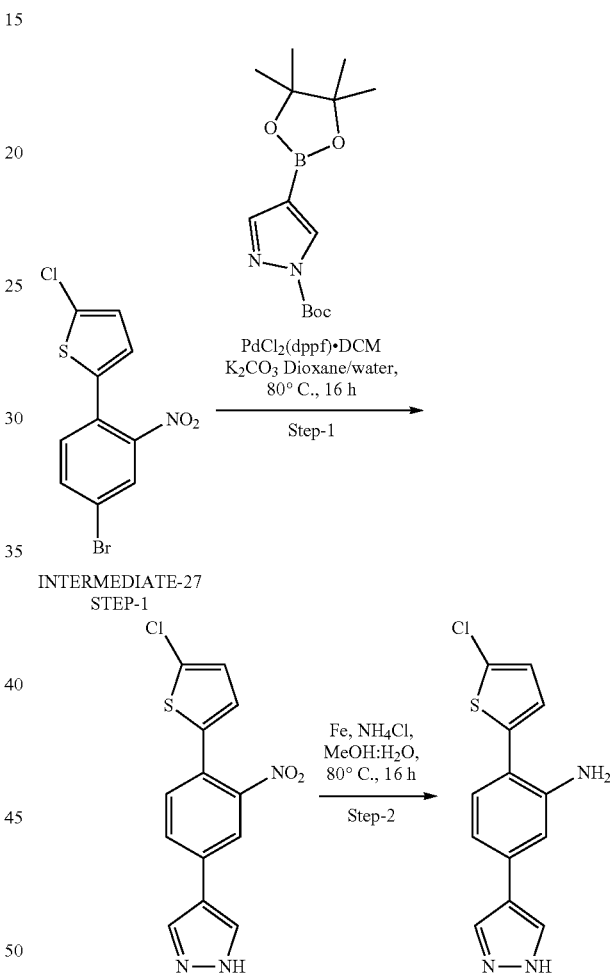

Step-1: Synthesis of 4-(4-(5-chlorothiphen-2-yl)-3-nitrophenyl)-1H-pyrazole. To a stirred solution of 2-(4-bromo-2-nitrophenyl)-5-chlorothiophene (INTERMEDIATE-27, STEP-1) (0.6 g, 0.0016 mol, 1 eq) in dioxane: water (12 mL, 9:3, 20 vol) was added tert-butyl 4-(4,4,5,5-tetramethyl-1,3,2-dioxaborolan-2-yl)-1H-pyrazole-1-carboxylate (1.4 g, 0.0049 mol, 3 eq) and potassium carbonate (0.68 g, 0.0049 mol, 3 eq). The reaction mixture was purged with N$_2$ gas for 30 min. Pd(dppf)Cl$_2$·DCM (0.066 g, 0.0001 mol, 0.05 eq) was added to the reaction mixture and stirred at 80° C. for 16 h, cooled, poured into water (50 mL) and extracted with DCM (3×20 mL). The combined organic layer was dried over sodium sulfate and concentrated under reduced pressure to give crude title pyrazole as yellow solid (0.46 g, 45%).

This material used as such for next step.

Step-2: Synthesis of 2-(5-Chlorothiophen-2-yl)-5-(1H-pyrazol-4-yl)aniline. To a solution of Step-1 pyrazole (0.380 g, 0.936 mmol, 1 eq) in methanol: water (9:3 mL) was added Fe powder (0.261 g, 4.681 mmol, 5 eq) and NH$_4$Cl (0.250 g, 4.681 mol, 5 eq). The reaction mixture was stirred at 80° C. for 16 h. After completion of reaction as indicated by TLC (50% EtOAc in hexane), reaction mixture was poured into water (100 mL) and filtered through celite. The celite bed was washed with DCM (3×50 mL). The filtrate was concentrated under reduced pressure. The crude purified by column chromatography using neutral alumina using 30% EtOAc in Hexane as eluent to give title aniline as a white solid (0.180 g, 87.4%). UPLC-MS (Method 1) m/z 276.1/278.1 (M+H)$^+$ at 2.35 min. $^1$H NMR (500 MHz, DMSO-d$_6$) δ 12.95 (s, 1H), 8.05 (s, 1H), 7.79 (s, 1H), 7.10 (m, 3H), 7.01 (s, 1H), 6.86 (d, 1H), 5.13 (s, 2H).

Preparation of Intermediate-29: 2-(5-fluorothiophen-2-yl)-5-(5-methylisoxazol-4-yl)aniline

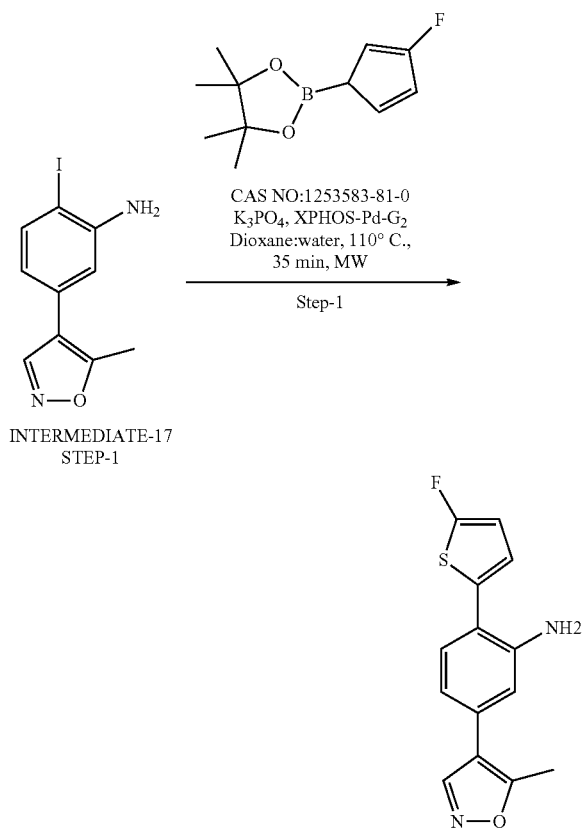

To stirred a solution of 2-iodo-5-(5-methylisoxazol-4-yl)aniline (INTERMEDIATE-17, STEP-1) (0.8 g, 0.00267 mole, 1 eq) and Phenyl 2-(3-fluorocyclopenta-2,4-dien-1-yl)-4,4,5,5-tetramethyl-1,3,2-dioxaborolane (3 g, 0.133 mole, 5 eq) in 9:1 dioxane: water was added K$_3$PO$_4$ (0.738 g, 0.347 mole, 1.3 eq). The reaction mixture was purged with N$_2$ for 30 min. XPHOS-Pd-G2 (0.210 g, 0.000267 mole, 0.1 eq) was added to the reaction mixture and further stirred at 110° C. for 35 min in microwave. After completion of reaction as indicated by TLC (Mobile phase: 30% ethyl acetate: Hexane), reaction mixture was diluted with water (30 mL) and extracted with ethyl acetate (3×30 mL). The combined organic layer was dried over Na$_2$SO$_4$ and concentrated under reduced pressure. The crude was purified by manual column chromatography on neutral silica using (30% ethyl acetate in hexane) as eluent to give title aniline as a pale yellow solid (0.207 g, 28.3%). UPLC-MS (Method 1) m/z 275.2 (M+H)$^+$ at 2.74 min. $^1$H NMR (500 MHz, DMSO-d$_6$) δ 8.77 (s, 1H), 7.18 (d, 1H), 6.93 (m, 2H), 6.77 (m, 2H), 5.27 (s, 2H), 2.57 (s, 3H).

Preparation of Intermediate-30: 2-(5-fluorothiophen-2-yl)-5-(5-methylisothiazol-4-yl)aniline

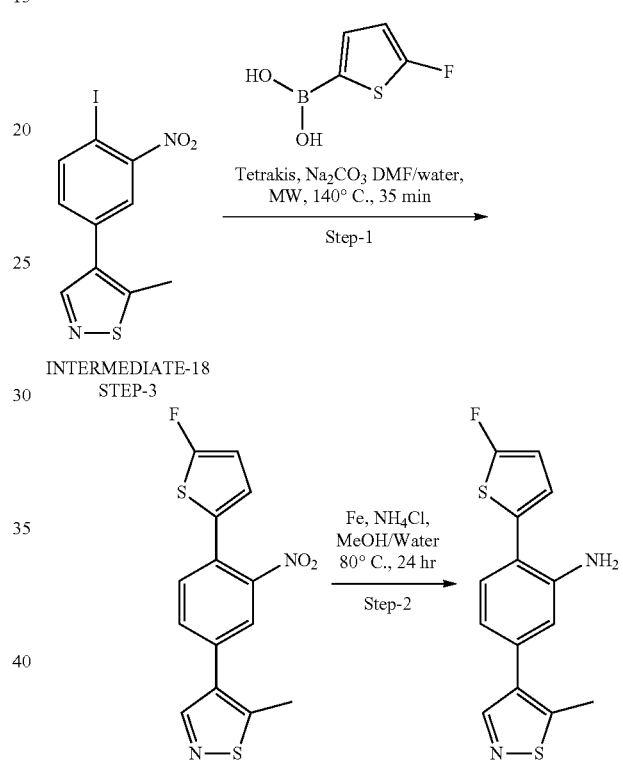

Step-1: Synthesis of 4-(4-(5-fluorothiophen-2-yl)-3-nitrophenyl)-5-methylisothiazole. To a solution of 4-(4-iodo-3-nitrophenyl)-5-methylisothiazole (INTERMEDIATE-18. STEP-3) (0.5 g, 0.0014 mole, 1 eq) and Na$_2$CO$_3$ (0.381 g, 0.0036 mole, 2.5 eq) in DMF: Water (5:1 mL) was added (5-fluorothiophen-2-yl)boronic acid (0.634, 0.0043 mole, 3 eq) at room temperature. The reaction mixture was purged with N$_2$ for 30 min and added tetrakis (0.166 g, 0.00014 mole, 0.1 eq) was added. The resulting reaction mixture was stirred at 140° C. for 35 min in microwave, cooled, diluted with water (25 mL) and extracted with ethyl acetate (3×25 mL). The combined organic layer was washed with brine solution (10 mL), dried over anhydrous Na$_2$SO$_4$ and concentrated under reduced pressure to give title isothiazole as an orange solid (0.2 g, 67.4%). UPLC-MS (Method 1) m/z 321.1 (M+H)$^+$ at 2.88 min Step-2: Synthesis of 2-(5-fluorothiophen-2-yl)-5-(5-methylisothiazol-4-yl)aniline. A solution of Step-1 isothiazole (0.65 g, 2.03 mmol, 1 eq), iron powder (0.566 g, 10.15 mole, 5.0 eq) and ammonium chloride (0.542 g, 10.15 m mole, 5 eq) in Methanol: Water (5:1, 10 mL) was stirred at 80° C. for 24 h. After completion of reaction as indicated by TLC (30% EtOAc in hexane), reaction mixture was filtered through celite and the filtrate was concentrated under reduced pressure. The filtrated was extracted using EtOAc (2×30 mL). The combined organic layer was dried over sodium sulfate and concentrated under reduced pressure. The crude was purified by flash column chromatography using neutral alumina (20% ethyl acetate in hexane) as eluent. The fracrions were concentrated and residue was triturated by using MDC (1 mL) and n-Pentane (20 mL) to give title aniline as yellow solid (0.200 g, 33.9%). UPLC-MS (Method 1) m/z 291.1 (M+H)$^+$ at 2.32 min. $^1$H NMR (500 MHz, DMSO-d$_6$) δ 8.59 (s, 1H), 7.33 (d, 1H), 7.31 (m, 2H), 7.22 (bs, 1H), 7.06 (m, 2H), 6.81 (m, 1H), 6.00-4.50 (bs, 2H), 2.79 (s, 3H).

Preparation of Intermediate-31: 2-(5-fluorothiophen-2-yl)-5-(isothiazol-5-yl)aniline

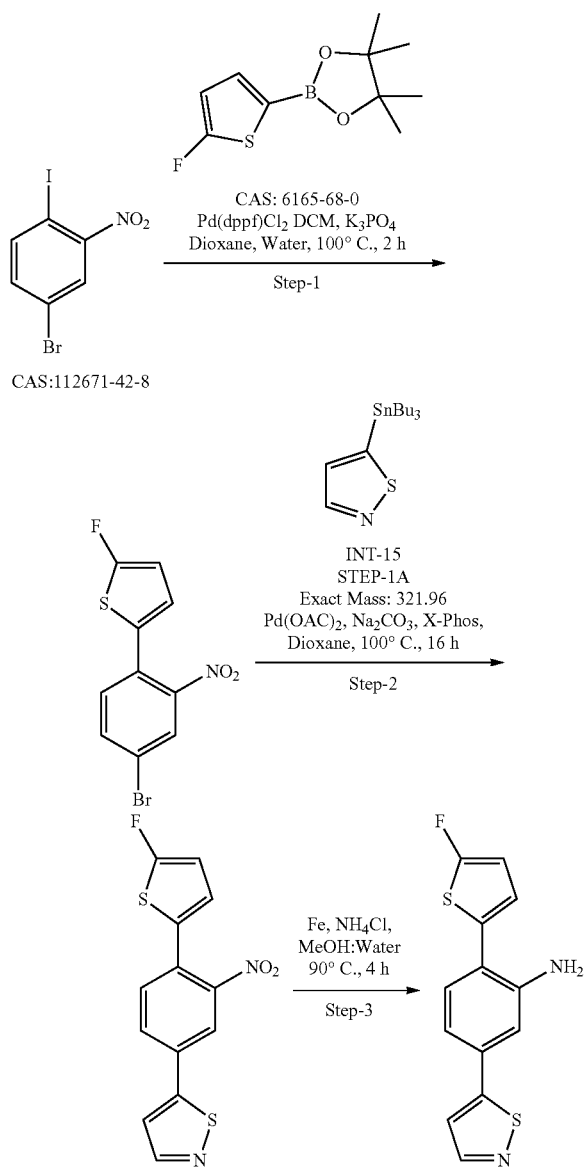

Step-1: Synthesis of 2-(4-bromo-2-nitrophenyl)-5-fluorothiophene. To a stirred solution of 4-bromo-1-iodo-2-nitrobenzene (3.0 g, 9.14 mole, 1 eq) and 2-(5-fluorothiophen-2-yl)-4,4,5,5-tetramethyl-1,3,2-dioxaborolane (1.76 g, 13.7 mole, 1.5 eq) in dioxane: water (30 mL: 10 mL, 10 Vol) was slowly added K$_3$PO$_4$ (3.8 g, 0.45 mole, 3 eq) portion wise. The reaction mixture was purged with N$_2$ gas for 30 min at room temperature. Pd(dppf)Cl$_2$·DCM (0.38 g, 0.45 mol, 0.05 eq) was added and heated at 100° C. for 2 h. After completion of reaction as indicated by TLC (100% in hexane), the reaction mixture was poured into water (100 mL) and extracted with Ethyl acetate (2×150 mL). The combined organic layer was dried over sodium sulfate and concentrated under reduced pressure. The obtained crude was purified by flash column chromatography (200-400 Silica gel) using 1.2% EtOAc in Hexane as eluent to give title thiophene as a solid (1.7 g).

Step-2: Synthesis of 5-(4-(5-fluorothiophen-2-yl)-3-nitrophenyl)isothiazole. To a solution of Step-1 thiophene (1.0 g, 0.0033 mole, 1 eq) in 1,4-dioxane (15 mL) was added 5-(tributylstannyl)isothiazole INTERMEDIATE-15, STEP-3) (2.86 g, 0.0076 mole, 2.3 eq), Na$_2$CO$_3$ (1.05 g, 0.0096 mole, 3.0 eq). The reaction mixture was purged with nitrogen for 20 min, then Pd(OAc)$_2$ (0.052 g, 0.00023 mole, 0.07 eq) and X-PHOS (0.221 g, 0.00046 mole, 0.14 eq) was added and stirred at 100° C. temperature for 16 h. After completion of reaction as indicated by TLC (20% Ethyl acetate in Hexane), reaction mixture was poured into water (100 mL) and extracted with EtOAc (2×100 mL). The combined organic layer was dried over sodium sulphate and concentrated under reduced pressure. The crude was purified by manual column chromatography using 10% EtOAc in Hexane to give title isothiazole as a yellow liquid (0.35 g, 17.9%). This material used as such for next step.

Step-3: Synthesis of 2-(5-fluorothiophen-2-yl)-5-(isothiazol-5-yl)aniline. To a solution of Step-2 isothiazole (0.35 g, 0.0011 mol, 1 eq) in methanol: water (10 mL, 5:1 mL) was added Fe powder (0.32 g, 0.0057 mol, 5 eq) and NH$_4$Cl (0.3 g, 0.0057 mol, 5 eq). The reaction mixture was stirred at 90° C. for 4 h, cooled, poured into water (100 mL) and filtered through celite. The filtrate was extracted with EtOAc (3×100 mL) and the combined organic layer, dried over sodium sulphate and concentrated under reduced pressure. The obtained crude was purified by column chromatography (using neutral alumina) using 5% EtOAc in Hexane as eluent to give title aniline as a light yellow solid (0.17 g, 53.9%). UPLC-MS (Method 1) m/z 277.1 (M+H)$^+$ at 2.58 min. $^1$H NMR (500 MHz, DMSO-d$_6$) δ 8.48 (s, 1H), 7.67 (s, 1H), 7.23 (d, 1H), 7.14 (s, 1H), 7.00 (m, 2H), 6.78 (m, 1H), 5.42 (s, 2H).

Preparation of Intermediate-32: 2-{5-Fluorothiophen-2-Yl}-5-(1H-pyrazol-4-yl)aniline

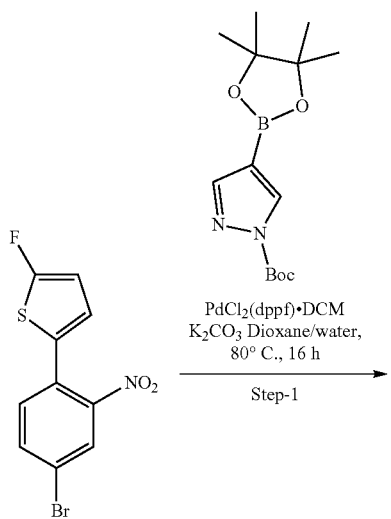

INTERMEDIATE-31
STEP-1

Step-1: Synthesis of 4-(4-(5-fluorothiphen-2-yl)-3-nitrophenyl)-1H-pyrazole. To a stirred solution of 2-(4-bromo-2-nitrophenyl)-5-fluoroothiophene (INTERMEDIATE-31, STEP-1) (0.5 g, 0.0016 mol, 1 eq) in dioxane: water (12 mL, 9:3, 20 vol) was added tert-butyl 4-(4,4,5,5-tetramethyl-1,3,2-dioxaborolan-2-yl)-1H-pyrazole-1-carboxylate (1.04 g, 0.0034 mol, 2.1 eq) and potassium carbonate (0.68 g, 0.0049 mol, 3 eq). The reaction mixture was purged with $N_2$ gas for 30 min. Tetrakis (0.095 g, 0.0001 mol, 0.05 eq) was added to the reaction mixture and stirred at 90° C. for 24 h, cooled, poured into water (50 mL) and extracted with DCM (3×20 mL). The combined organic layer was dried over sodium sulfate and concentrated under reduced pressure. The crude was purified by manual column chromatography using 20% EtOAC in Hexane as eluent to give title pyrazole as a yellow solid (2.0 g, quantitative). This material used as such for next step.

Step-2: Synthesis of 2-{5-fluorothiophen-2-yl}-5-(1H-pyrazol-4-yl)aniline. To a solution of Step-1 pyrazole (2.0 g, 0.0061 mol, 1 eq) in methanol: water (15:5 mL) was added Fe powder (1.91 g, 0.034 mol, 5 eq) and $NH_4Cl$ (1.83 g, 0.034 mol, 5 eq). The reaction mixture was stirred at 80° C. for 16 h, cooled, poured into water (100 mL) and filtered through celite. The celite bed was washed with DCM (3×50 mL). The filtrate was concentrated under reduced pressure. The crude purified by column chromatography using neutral alumina using 30% EtOAc in Hexane as eluent to give title aniline as a white solid (GLD3-X-0032) (0.280 g, 15.6%). UPLC-MS (Method 1) m/z 260.1 (M+H)$^+$ at 2.50 min. $^1$H NMR (500 MHz, DMSO-$d_6$) δ 12.95 (s, 1H), 8.07 (s, 1H), 7.79 (s, 1H), 7.09 (d, 1H), 7.00 (s, 1H), 6.86 (m, 2H), 6.73 (s, 1H), 5.10 (s, 2H).

Preparation of Intermediate-33: 5-(5-methylisoxazol-4-yl)-2-(1H-pyrrol-1-yl)aniline

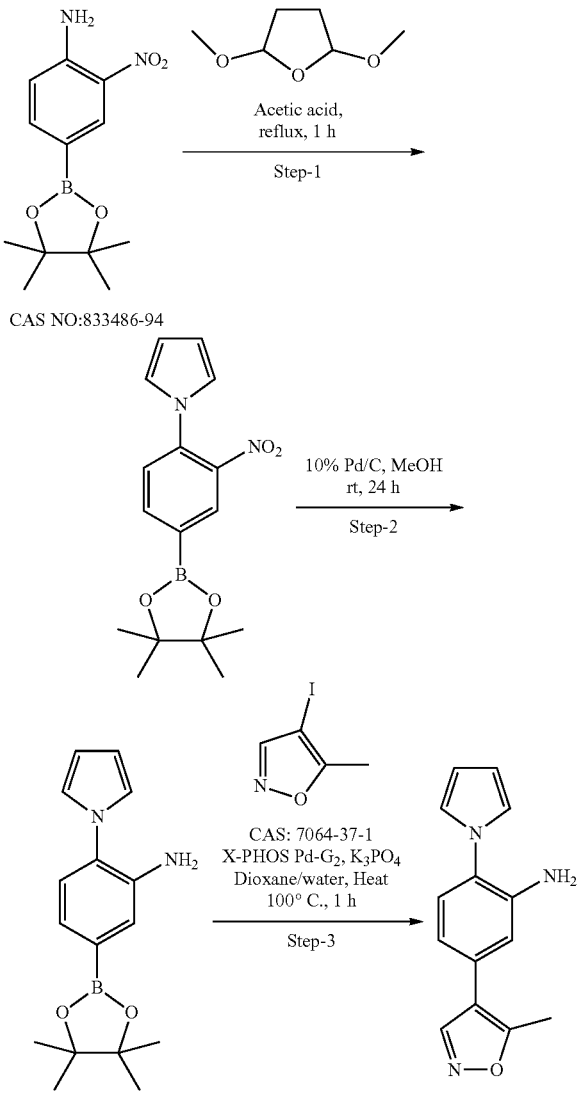

CAS NO:833486-94

Step 1: Synthesis of 1-(2-nitro-4-(4,4,5,5-tetramethyl-1,3,2-dioxaborolan-2-yl)phenyl)-1H-pyrrole. A solution of 2-nitro-4-(4,4,5,5-tetramethyl-1,3,2-dioxaborolan-2-yl)aniline (1.5 g, 0.0056 mole, 1 eq) and 2,5-dimethoxytetrahydrofuran (1.07 g, 0.0068 mole, 1.2 eq) in acetic acid (15 mL) was refluxed for 3 h, cooled, diluted with water (25 mL) and extracted with ethyl acetate (3×25 mL). The combined organic layer was washed with brine solution (10 mL), dried over anhydrous $Na_2SO_4$ and concentrated under reduced pressure to give title pyrrole as a brown solid (1.72 g, 96.4%).

Step 2: Synthesis of 2-(1H-pyrrol-1-yl)-5-(4,4,5,5-tetramethyl-1,3,2-dioxaborolan-2-yl)aniline. To a suspension of 10% Pd/C (50% wet) (0.5 g, 20 WIW) in MeOH (20 mL) was added Step-1 pyrrole (1.72 g, 0.0057 mole, 1.0 eq). The above reaction mixture was purged with $H_2$ gas for 24 h, then filtered through a celite bed and the bed was washed with methanol (20 mL). The filtrate was concentrated under reduced pressure to give title aniline (1.5 g, 98.4%). UPLC-MS (Method 1) m/z 285.3 (M+H)$^+$ at 2.61 min.

Step 3: Synthesis of (5-methylisoxazol-4-yl)-2-(1H-pyrrol-1-yl)aniline. To a solution of Step-2 aniline (0.407 g, 0.00119 mole, 1 eq) and $K_3PO_4$ (0.330 g, 0.0115 mole, 1.3 eq) in dioxane: water (6:2 mL), was added 4-iodo-5-methylisoxazole (0.250 g, 0.01196 mole, 1 eq) at room temperature. The reaction mixture was purged with $N_2$ for 30 min and X-PHOS Pd-G2 (0.094 g, 0.001196 mole, 0.1 eq) was added. The resulting reaction mixture was stirred at 100° C. for 1 h in microwave, cooled, diluted with water (50 mL) and extracted with ethyl acetate (3×50 mL). The combined organic layers were dried over anhydrous $Na_2SO_4$ and concentrated under reduced pressure. The resulting crude material was purified by column chromatography on neutral silica using 20% ethyl acetate in hexane as eluent to give title aniline as a pale yellow solid (0.12 g, 42.0%). UPLC-MS (Method 1) m/z 240.1 (M+H)$^+$ at 2.35 min. $^1$H NMR (500 MHz, DMSO-$d_6$) δ 8.79 (s, 1H), 7.10 (d, 1H), 6.99 (s, 1H), 6.91 (m, 2H), 6.77 (dd, 1H), 6.25 (m, 2H), 4.94 (s, 2H), 2.58 (s, 3H).

Preparation of Intermediate-34: 5-(5-methylisothiazol-4-yl)-2-(1H-pyrrol-1-yl)aniline

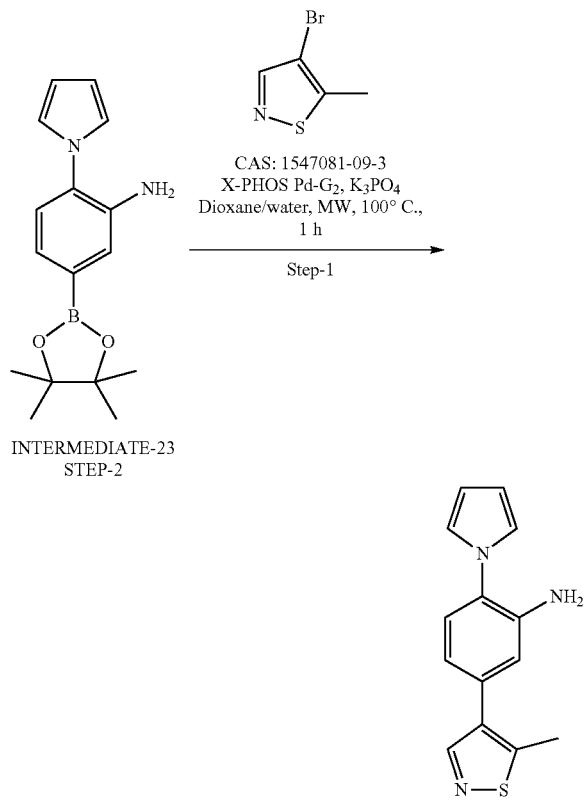

To a solution of 2-(1H-pyrrol-1-yl)-5-(4,4,5,5-tetramethyl-1,3,2-dioxaborolan-2-yl)aniline (INTERMEDIATE-33, STEP-2) (0.7 g, 0.0024 mol, 1.2 eq) and $K_3PO_4$ (0.56 g, 0.0026 mole, 1.3 eq) in dioxane: water (5.4:0.6 mL) was added 4-bromo-5-methylisothiazole (0.38, 0.0020 mole, 1 eq) at room temperature. The reaction mixture was purged with $N_2$ for 30 min and X-PHOS Pd-G2 (0.173 g, 0.0002 mole, 0.1 eq) was added. The resulting reaction mixture was stirred at 110° C. for 1 h in microwave, cooled, diluted with water (25 mL) and extracted with ethyl acetate (3×25 mL). The combined organic layer was washed with brine (10 mL), dried over anhydrous $Na_2SO_4$ concentrated under reduced pressure. The resulting crude material was purified by manual column chromatography on Neutral alumina using 6% ethyl acetate in hexane as eluent to give title aniline as a pale yellow solid (0.332 g, 74.9%). UPLC-MS (Method 1) m/z 256.2 (M+H)$^+$ at 2.54 min. $^1$H NMR (500 MHz, DMSO-$d_6$) δ 8.55 (s, 1H), 7.11 (d, 1H), 6.94 (m, 3H), 6.76 (dd, 1H), 6.25 (m, 2H), 4.96 (s, 2H), 2.60 (s, 3H).

Preparation of Intermediate-35; 5-(isothiazol-5-yl)-2-(1H-pyrrol-1-yl)aniline

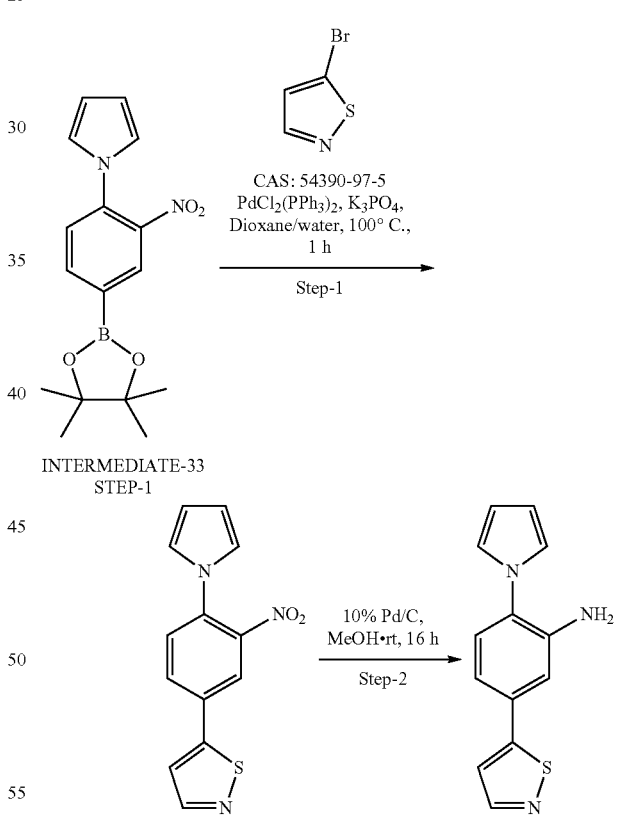

Step-1: Synthesis of 5-(3-nitro-4-(1H-pyrrol-1-yl)phenyl)isothiazole. To a stirred solution of 5-bromoisothiazole (0.60 g, 3.65 mmol, 1 eq) in dioxane: water (9 mL: 1 mL) was added 1-(2-nitro-4-(4,4,5,5-tetramethyl-1,3,2-dioxaborolan-2-yl)phenyl)-1H-pyrrole (INTERMEDIATE-33, STEP-1) (1.26 g, 4.01 mmol, 1.0 eq) and potassium phosphate (1.21 g, 5.70 mmol, 3 eq). The reaction mixture was purged with $N_2$ gas for 30 min. $PdCl_2(PPh_3)_2$ (0.12 g, 0.18 mmol, 0.05 eq) was added to the reaction mixture and stirred at 100° C. for 1 h, cooled, poured into water (100 mL) and extracted with Ethyl acetate (2×35 mL). The combined organic layer was dried over sodium sulfate and concentrated under reduced pressure. The obtained crude was purified by flash column chromatography (200-400 Silica gel) using 7% EtOAc in Hexane as eluent to give title isothiazole as yellow solid (0.65 g). UPLC-MS (Method 1) m/z 272.2 (M+H)$^+$ at 2.39 min. $^1$H NMR (500 MHz, DMSO-d$_6$) δ 8.68 (d, 1H), 8.48 (d, 1H), 8.14 (dd, 1H), 8.02 (d, 1H), 7.78 (d, 1H), 7.00 (m, 2H), 6.33 (m, 2H).

Step-2: Synthesis of 5-(isothiazol-5-yl)-2-(1H-pyrrol-1-yl)aniline. To a solution of Step-1 isothiazole (0.62 g, 2.28 mmol) in MeOH (25 mL) was added Pd—C(10% W/W, 50% moisture) (0.62 g, 20%) under nitrogen atmosphere at room temperature. The resulting reaction mixture was purged H$_2$ gas at room temperature for 16 h. After completion of reaction as indicated by TLC (10% EtOAc in Hexane as mobile phase), the reaction mixture was filtered through celite. The celite bed was washed with methanol (100 mL). The filtrate was concentrated under vacuum to get crude which was purified by prep-HPLC to give title aniline as a yellow solid (0.34 g). UPLC-MS (Method 1) m/z 242.1 (M+H)$^+$ at 2.37 min. $^1$H NMR (500 MHz, DMSO-d$_6$) δ 8.59 (s, 1H), 7.68 (d, 1H), 7.19 (d, 1H), 7.14 (d, 1H), 7.02 (m, 1H), 6.94 (m, 2H), 6.27 (m, 2H), 5.12 (s, 2H).

Preparation of Intermediate-36: 5-(1H-pyrazol-4-yl)-2-(1H-pyrrol-1-yl)aniline

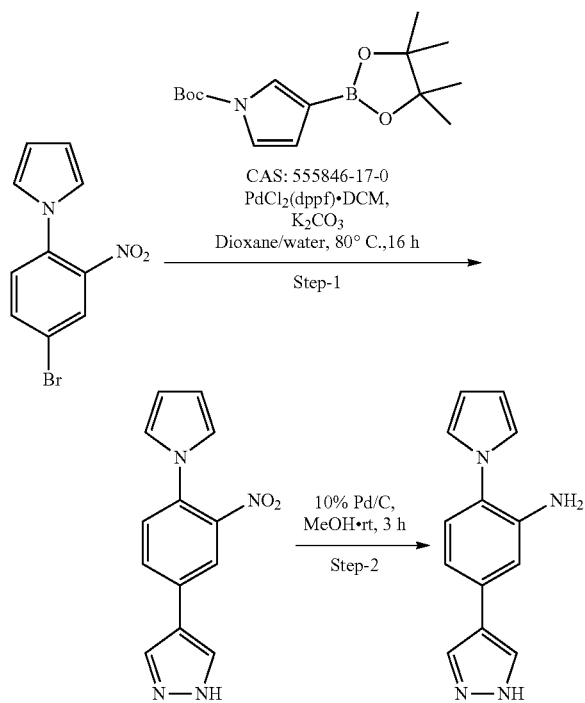

Step-1: Synthesis of 4-(3-nitro-4-(1H-pyrrol-1-yl)phenyl)-1H-pyrazole. To a stirred solution of 1-(4-bromo-2-nitrophenyl)-1H-pyrrol (1 g, 3.74 mmol, 1 eq) in dioxane:water (30 ml: 10 ml) was added tert-butyl 4-(4,4,5,5-tetramethyl-1,3,2-dioxaborolan-2-yl)-1H-pyrazole-1-carboxylate (1.2 g, 4.11 mmol, 1.2 eq) and potassium carbonate (1.5 g, 1.12 mmol, 3 eq). The reaction mixture was purged with N$_2$ gas for 30 min. Pd(dppf)Cl$_2$-DCM (0.15 g, 0.18 mmol, 0.05 eq) was added to the reaction mixture and stirred at 80° C. for 16 h, cooled, poured into water (50 mL) and extracted with Ethyl acetate (2×40 mL). The combined organic layer was dried over sodium sulfate and concentrated under reduced pressure. The obtained crude was purified by flash column chromatography (200-400 Silica gel) using 20% EtOAc in Hexane as eluent to give title pyrazole as a yellow solid (0.25 g). UPLC-MS (Method 1) m/z 255.2 (M+H)$^+$ at 2.36 min. $^1$H NMR (500 MHz, DMSO-d$_6$) δ 13.16 (s, 1H), 8.43 (s, 1H), 8.27 (d, 1H), 8.12 (s, 1H), 8.02 (dd, 1H), 7.62 (d, 1H), 6.94 (s, 2H), 6.26 (s, 2H).

Step-2: Synthesis of 5-(1H-pyrazol-4-yl)-2-(1H-pyrrol-1-yl)aniline. To a solution of Step-1 pyrazole (0.6 g, 2.86 mmol, 1 eq) in MeOH (6 mL) was added Pd—C(10% W/W, 50% moisture) (0.06 g, 20%) under nitrogen atmosphere at room temperature. The resulting reaction mixture was purged H$_2$ gas at room temperature for 3 h. After completion of reaction as indicated by TLC (50% EtOAc in Hexane as mobile phase), the reaction mixture was filtered through celite. The celite bed was washed with ethyl acetate (50 mL). The filtrate was concentrated under vacuum to get crude which was purified by trituration using diethyl ether (20 ml) and pentane (10 mL) to give title aniline as a yellow solid (0.25 g). UPLC-MS (Method 1) m/z 225.2 (M+H)$^+$ at 1.89 min. $^1$H NMR (500 MHz, DMSO-d$_6$) δ 12.94 (s, 1H), 7.93 (s, 2H), 7.04 (d, 1H), 7.00 (d, 1H), 6.88 (m, 3H), 6.23 (m, 2H), 4.75 (s, 2H).

Example 135: 4-cyclopropyl-3-(N-(4-(isothiazol-5-yl)-[1,1'-biphenyl]-2-yl)sulfamoyl)benzoic acid

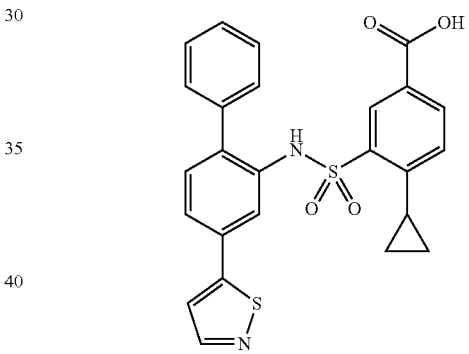

Step 1: A solution of 4-(isothiazol-5-yl)-[1,1'-biphenyl]-2-amine (INTERMEDIATE-3) (101 mg, 0.40 mmol) in DCM (2 ml) was treated with a solution of the product from Example 132 Step 5 (132 mg, 0.48 mmol) in DCM (0.5 ml) followed by pyridine (0.081 ml, 1.00 mmol) and the mixture was stirred at RT for 18 h. The mixture was concentrated in vacuo then diluted with water (1 ml) and MeOH (1 ml). 6 M NaOH(aq) (0.333 ml, 2.00 mmol) was added and the mixture was stirred at RT overnight. Formic acid (0.128 ml, 3.33 mmol) was added followed by DMSO (1.5 ml).

Step 2: The mixture was filtered and the resultant solid was sequentially washed with water (1 ml), DCM/MeOH (1:1, 2 ml), and then triturated with MeOH (5 ml) and filtered to afford the title compound (136 mg, 0.285 mmol, 71% yield, 95% purity). UPLC-MS (Method 1): m/z 476.6 (M+H)$^+$, 474.7 (M−H)$^−$ at 1.64 min. $^1$H NMR (500 MHz, DMSO-d$_6$) δ 13.22 (s, 1H), 9.98 (s, 1H), 8.58 (d, J=1.8 Hz, 1H), 8.23 (d, J=1.9 Hz, 1H), 8.03 (dd, J=8.2, 1.9 Hz, 1H), 7.73 (dd, J=8.0, 1.9 Hz, 1H), 7.64 (d, J=1.8 Hz, 1H), 7.47-7.28 (m, 6H), 7.20-7.07 (m, 2H), 2.76-2.61 (m, 1H), 1.11-1.01 (m, 2H), 0.89-0.78 (m, 2H).

The following examples were prepared by methods analogous to Example 135, substituting appropriate starting materials and intermediates where necessary:

| Example | Structure | Name/Analytical Data |
|---|---|---|
| 136 | 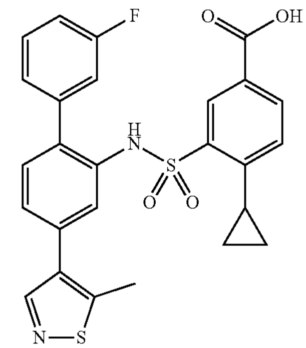 [SMILES: Cc1sncc1-c1ccc(-c2cccc(F)c2)c(NS(=O)(=O)c2cc(C(=O)O)ccc2C2CC2)c1] | 4-cyclopropyl-3-(N-(3'-fluoro-4-(5-methylisothiazol-4-yl)-[1,1'-biphenyl]-2-yl)sulfamoyl)benzoic acid (using INTERMEDIATE-6); <br> UPLC-MS (Method 1): m/z 509.4 (M + H)+, 507.2 (M − H)⁻ at 1.66 min. 1H NMR (500 MHz, DMSO-d6) δ 13.20 (s, 1H), 10.01 (s, 1H), 8.46 (s, 1H), 8.18 (d, J = 1.9 Hz, 1H), 7.97 (dd, J = 8.2, 1.9 Hz, 1H), 7.57-7.49 (m, 1H), 7.47-7.33 (m, 2H), 7.21-7.10 (m, 3H), 7.10-7.02 (m, 2H), 2.71-2.57 (m, 1H), 2.40 (s, 3H), 1.10-0.98 (m, 2H), 0.87-0.77 (m, 2H). |
| 137 | 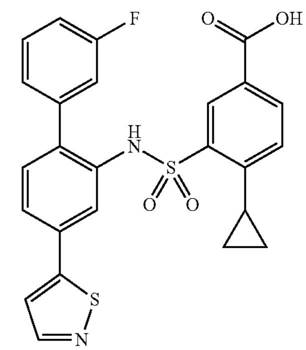 [SMILES: O=C(O)c1ccc(C2CC2)c(S(=O)(=O)Nc2cc(-c3ccns3)ccc2-c2cccc(F)c2)c1] | 4-cyclopropyl-3-(N-(3'-fluoro-4-(isothiazol-5-yl)-[1,1'-biphenyl]-2-yl)sulfamoyl)benzoic acid (using INTERMEDIATE-7); <br> UPLC-MS (Method 1): m/z 494.7 (M + H)⁺, 493.3 (M − H)⁻ at 1.63 min. ¹H NMR (500 MHz, DMSO-d₆) δ 13.20 (s, 1H), 10.07 (s, 1H), 8.59 (d, J = 1.8 Hz, 1H), 8.17 (d, J = 1.8 Hz, 1H), 8.01 (dd, J = 8.2, 1.9 Hz, 1H), 7.75 (dd, J = 8.0, 1.9 Hz, 1H), 7.69 (d, J = 1.8 Hz, 1H), 7.46 (d, J = 8.0 Hz, 1H), 7.43-7.33 (m, 1H), 7.23-7.07 (m, 5H), 2.74-2.61 (m, 1H), 1.13-1.03 (m, 2H), 0.91-0.82 (m, 2H). |
| 138 | 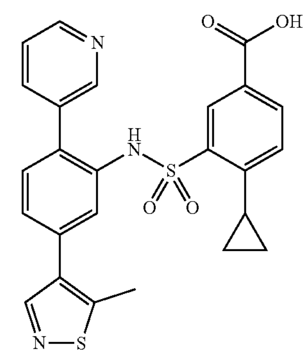 [SMILES: Cc1sncc1-c1ccc(-c2cccnc2)c(NS(=O)(=O)c2cc(C(=O)O)ccc2C2CC2)c1] | 4-cyclopropyl-3-(N-(5-(5-methylisothiazol-4-yl)-2-(pyridin-3-yl)phenyl)sulfamoyl)benzoic acid (using INTERMEDIATE-10); <br> UPLC-MS (Method 1): m/z 491.9 (M + H)⁺, 490.3 (M − H)⁻ at 1.09 min. ¹H NMR (500 MHz, DMSO-d₆) δ 13.23 (s, 1H), 10.09 (s, 1H), 8.57 (d, J = 2.3 Hz, 1H), 8.53 (dd, J = 4.8, 1.6 Hz, 1H), 8.43 (s, 1H), 8.20 (d, J = 1.8 Hz, 1H), 7.98 (dd, J = 8.2, 1.9 Hz, 1H), 7.78 (dt, J = 7.9, 2.0 Hz, 1H), 7.55 (dd, J = 7.9, 1.8 Hz, 1H), 7.48 (d, J = 7.9 Hz, 1H), 7.45-7.35 (m, 1H), 7.09 (d, J = 8.2 Hz, 1H), 7.02 (d, J = 1.8 Hz, 1H), 2.70-2.59 (m, 1H), 2.37 (s, 3H), 1.12-0.99 (m, 2H), 0.91-0.78 (m, 2H). |
| 139 | 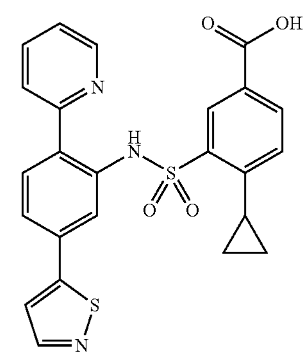 [SMILES: O=C(O)c1ccc(C2CC2)c(S(=O)(=O)Nc2cc(-c3ccns3)ccc2-c2ccccn2)c1] | 4-cyclopropyl-3-(N-(5-(isothiazol-5-yl)-2-(pyridin-2-yl)phenyl)sulfamoyl)benzoic acid (using INTERMEDIATE-15); <br> UPLC-MS (Method 1): m/z 477.7 (M + H)⁺, 475.9 (M − H)⁻ at 1.62 min. ¹H NMR (500 MHz, DMSO-d₆) δ 13.83-13.17 (m, 2H), 8.78-8.70 (m, 1H), 8.62 (d, J = 1.8 Hz, 1H), 8.57 (d, J = 1.9 Hz, 1H), 8.16-8.01 (m, 3H), 7.94 (dd, J = 8.1, 1.9 Hz, 1H), 7.76 (d, J = 1.8 Hz, 1H), 7.67 (d, J = 1.9 Hz, 1H), 7.59-7.47 (m, 2H), 7.03 (d, J = 8.3 Hz, 1H), 2.66-2.56 (m, 1H), 0.78-0.70 (m, 2H), 0.68-0.59 (m, 2H). |

| Example | Structure | Name/Analytical Data |
|---|---|---|
| 140 | 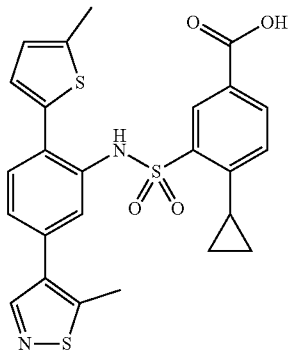 [SMILES: Cc1ccc(-c2ccc(-c3cnsc3C)cc2NS(=O)(=O)c2cc(C(=O)O)ccc2C2CC2)s1] | 4-cyclopropyl-3-(N-(5-(5-methylisothiazol-4-yl)-2-(5-methylthiophen-2-yl)phenyl)sulfamoyl)benzoic acid (using INTERMEDIATE-22); UPLC-MS (Method 1): m/z 510.7 (M + H)+, 509.3 (M − H)− at 1.73 min. $^1$H NMR (500 MHz, DMSO-d$_6$) δ 13.21 (s, 1H), 10.04 (s, 1H), 8.35 (s, 1H), 8.26 (d, J = 1.9 Hz, 1H), 8.00 (dd, J = 8.2, 1.9 Hz, 1H), 7.63 (d, J = 8.1 Hz, 1H), 7.52-7.43 (m, 1H), 7.29 (d, J = 3.5 Hz, 1H), 7.14 (d, J = 8.2 Hz, 1H), 6.88-6.83 (m, 1H), 6.81-6.74 (m, 1H), 2.84-2.68 (m, 1H), 2.46 (s, 3H), 2.30 (s, 3H), 1.12-1.03 (m, 2H), 0.89-0.81 (m, 2H). |
| 141 | 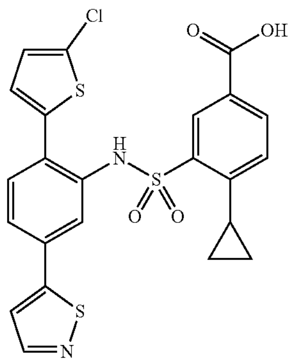 | 3-(N-(2-(5-chlorothiophen-2-yl)-5-(isothiazol-5-yl)phenyl)sulfamoyl)-4-cyclopropylbenzoic acid (using INTERMEDIATE-27); UPLC-MS (Method 1): m/z 516.7 (M + H)+, 515.3 (M − H)− at 1.71 min. $^1$H NMR (500 MHz, DMSO-d$_6$) δ 13.23 (s, 1H), 10.23 (s, 1H), 8.56 (d, J = 1.7 Hz, 1H), 8.24 (d, J = 1.9 Hz, 1H), 8.08 (dd, J = 8.3, 1.9 Hz, 1H), 7.82 (d, J = 8.2 Hz, 1H), 7.78-7.71 (m, 1H), 7.60 (d, J = 1.8 Hz, 1H), 7.47 (d, J = 4.0 Hz, 1H), 7.21 (d, J = 8.3 Hz, 1H), 7.15 (d, J = 4.0 Hz, 1H), 6.87 (d, J = 1.9 Hz, 1H), 2.86-2.67 (m, 1H), 1.17-1.08 (m, 2H), 0.96-0.86 (m, 2H). |
| 142 | 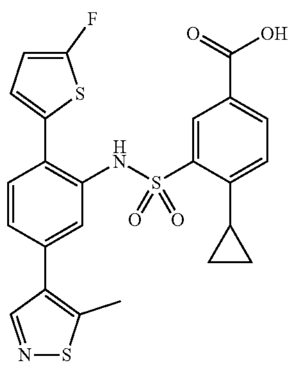 | 4-cyclopropyl-3-(N-(2-(5-fluorothiophen-2-yl)-5-(5-methylisothiazol-4-yl)phenyl)sulfamoyl)benzoic acid (using INTERMEDIATE-30); UPLC-MS (Method 1): m/z 514.6 (M + H)+, 513.2 (M − H)− at 1.67 min. $^1$H NMR (500 MHz, DMSO-d$_6$) δ 13.24 (s, 1H), 10.16 (s, 1H), 8.32 (s, 1H), 8.26 (d, J = 1.9 Hz, 1H), 8.02 (dd, J = 8.2, 1.9 Hz, 1H), 7.73 (d, J = 8.2 Hz, 1H), 7.60-7.44 (m, 1H), 7.22 (t, J = 4.0 Hz, 1H), 7.19-7.13 (m, 1H), 6.80 (d, J = 1.9 Hz, 1H), 6.75 (dd, J = 4.2, 2.3 Hz, 1H), 2.80-2.69 (m, 1H), 2.27 (s, 3H), 1.18-1.06 (m, 2H), 0.94-0.80 (m, 2H). |
| 143 | 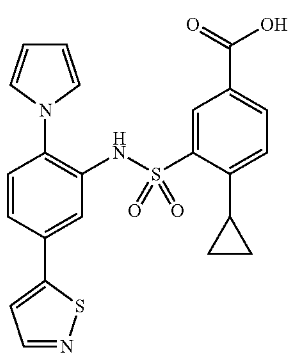 [SMILES: O=C(O)c1ccc(C2CC2)c(S(=O)(=O)Nc2cc(-c3ccns3)ccc2-n2cccc2)c1] | 4-cyclopropyl-3-(N-(5-(isothiazol-5-yl)-2-(pyrrol-1-yl)phenyl)sulfamoyl)benzoic acid (using INTERMEDIATE-35); UPLC-MS (Method 1): m/z 465.5 (M + H)+, 463.9 (M − H)− at 1.56 min. $^1$H NMR (500 MHz, DMSO-d$_6$) δ 13.24 (s, 1H), 10.20 (s, 1H), 8.57 (d, J = 1.8 Hz, 1H), 8.28 (d, J = 1.8 Hz, 1H), 8.07 (dd, J = 8.2, 1.9 Hz, 1H), 7.77 (dd, J = 8.3, 2.1 Hz, 1H), 7.61 (d, J = 1.8 Hz, 1H), 7.48 (d, J = 8.3 Hz, 1H), 7.22 (d, J = 8.3 Hz, 1H), 7.08 (t, J = 2.2 Hz, 2H), 7.02 (d, J = 2.1 Hz, 1H), 6.21 (t, J = 2.2 Hz, 2H), 2.80-2.66 (m, 1H), 1.17-1.07 (m, 2H), 0.98-0.86 (m, 2H). |

| Example | Structure | Name/Analytical Data |
|---|---|---|
| 144 | 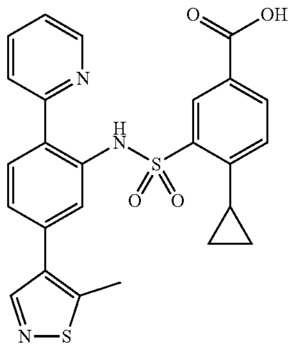 [SMILES: Cc1sncc1-c1ccc(-c2ccccn2)c(NS(=O)(=O)c2cc(C(=O)O)ccc2C2CC2)c1] | 4-cyclopropyl-3-(N-(5-(5-methylisothiazol-4-yl)-2-(pyridin-2-yl)phenyl)sulfamoyl)benzoic acid (using INTERMEDIATE-14); UPLC-MS (Method 1): m/z 491.8 (M + H)$^+$, 489.8 (M − H)$^-$ at 1.64 min. $^1$H NMR (500 MHz, DMSO-d$_6$) δ 13.61-13.16 (m, 2H), 8.76-8.67 (m, 1H), 8.54 (s, 1H), 8.44 (d, J = 1.9 Hz, 1H), 8.08-7.98 (m, 3H), 7.93 (dd, J = 8.2, 1.9 Hz, 1H), 7.56 (d, J = 1.8 Hz, 1H), 7.52-7.45 (m, 1H), 7.36 (dd, J = 8.2, 1.8 Hz, 1H), 7.01 (d, J = 8.2 Hz, 1H), 5.76 (s, 1H), 2.60-2.54 (m, 1H), 2.53 (s, 3H), 0.78-0.71 (m, 2H), 0.68-0.61 (m, 2H). |

The following examples were prepared by methods analogous to Example 135 substituting appropriate starting materials and intermediates where necessary. The solid was further purified by trituration with EtOH and water to afford:

| Example | Structure | Name/Analytical Data |
|---|---|---|
| 145 | 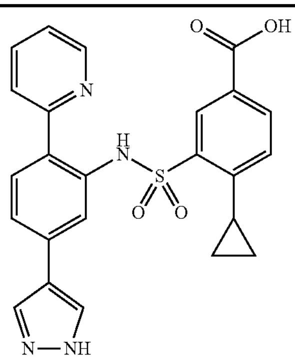 | 3-(N-(5-(pyrazol-4-yl)-2-(pyridin-2-yl)phenyl)sulfamoyl)-4-cyclopropylbenzoic acid (using INTERMEDIATE-16); UPLC-MS (Method 1): m/z 460.6 (M + H)$^+$, 459.3 (M − H)$^-$ at 1.35 min. $^1$H NMR (500 MHz, DMSO-d$_6$) δ 13.53 (s, 2H), 8.79-8.58 (m, 2H), 8.20-7.78 (m, 6H), 7.60-7.49 (m, 1H), 7.43 (s, 1H), 7.31 (s, 1H), 6.92 (d, J = 8.1 Hz, 1H), 2.64-2.56 (m, 1H), 2.55 (s, 1H), 0.78-0.64 (m, 2H), 0.64-0.54 (m, 2H). |

The following examples were prepared by methods analogous to Example 135, substituting appropriate starting materials and intermediates where necessary. The isolated solid was suspended in THF (1 ml) and a solution of NaOH (96 mg, 2.4 mmol) in water (1 ml) was added. The mixtures were heated to 50° C. and stirred for 16 h. The resultant solids were filtered to afford:

| Example | Structure | Name/Analytical Data |
|---|---|---|
| 146 | 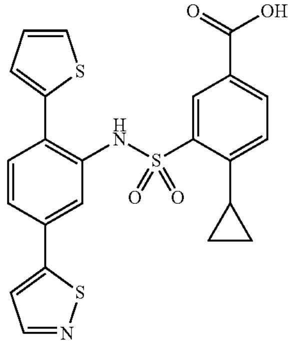 [SMILES: O=C(O)c1ccc(C2CC2)c(S(=O)(=O)Nc2cc(-c3ccns3)ccc2-c2cccs2)c1] | 4-cyclopropyl-3-(N-(5-(isothiazol-5-yl)-2-(thiophen-2-yl)phenyl)sulfamoyl)benzoic acid (using INTERMEDIATE-19); UPLC-MS (Method 1): m/z 482.4 (M + H)$^+$, 480.8 (M − H)$^-$ at 1.61 min. $^1$H NMR (500 MHz, DMSO-d$_6$) δ 13.22 (s, 1H), 10.15 (s, 1H), 8.55 (d, J = 1.8 Hz, 1H), 8.28 (d, J = 1.9 Hz, 1H), 8.08 (dd, J = 8.3, 1.9 Hz, 1H), 7.80-7.70 (m, 2H), 7.67 (dd, J = 5.2, 1.2 Hz, 1H), 7.60 (dd, J = 3.7, 1.2 Hz, 1H), 7.57 (d, J = 1.8 Hz, 1H), 7.21 (d, J = 8.3 Hz, 1H), 7.15 (dd, J = 5.1, 3.6 Hz, 1H), 6.88 (d, J = 1.9 Hz, 1H), 2.85-2.72 (m, 1H), 1.19-1.08 (m, 2H), 0.97-0.87 (m, 2H). |

| Example | Structure | Name/Analytical Data |
|---|---|---|
| 147 | 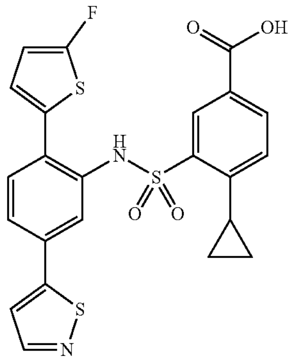 [SMILES: O=C(O)c1ccc(C2CC2)c(S(=O)(=O)Nc2cc(-c3ccns3)ccc2-c2ccc(F)s2)c1] | 4-cyclopropyl-3-(N-(2-(5-fluorothiophen-2-yl)-5-(isothiazol-5-yl)phenyl)sulfamoyl)benzoic acid (using INTERMEDIATE-31); UPLC-MS (Method 1): m/z 500.3 (M + H)$^+$, 499.2 (M − H)$^-$ at 1.64 min. $^1$H NMR (500 MHz, DMSO-d$_6$) δ 13.23 (s, 1H), 10.19 (s, 1H), 8.55 (d, J = 1.9 Hz, 1H), 8.25 (s, 1H), 8.13-8.00 (m, 1H), 7.81 (d, J = 8.2 Hz, 1H), 7.78-7.69 (m, 1H), 7.58 (d, J = 1.8 Hz, 1H), 7.32 (t, J = 4.0 Hz, 1H), 7.22 (d, J = 8.3 Hz, 1H), 6.83 (s, 1H), 6.81-6.73 (m, 1H), 2.85-2.68 (m, 1H), 1.21-1.05 (m, 2H), 1.01-0.85 (m, 2H). |

The following examples were prepared by methods analogous to Example 135 Step 1, substituting appropriate starting materials and intermediates where necessary. The DMSO solutions were purified by preparative HPLC (Waters, Acidic (0.1% Formic acid), Acidic, Waters X-Select Prep-C18, 5 μm, 19×50 mm column, MeCN/Water gradient) to afford:

| Example | Structure | Name/Analytical Data |
|---|---|---|
| 148 | 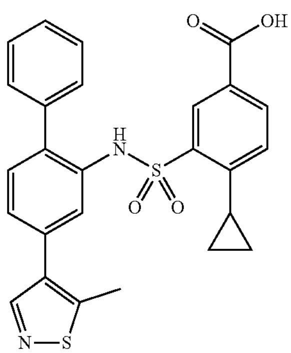 [SMILES: Cc1sncc1-c1ccc(-c2ccccc2)c(NS(=O)(=O)c2cc(C(=O)O)ccc2C2CC2)c1] | 4-cyclopropyl-3-(N-(4-(5-methylisothiazol-4-yl)-[1,1'-biphenyl]-2-yl)sulfamoyl)benzoic acid (using INTERMEDIATE-2); UPLC-MS (Method 1): m/z 490.9 (M + H)$^+$, 489.3 (M − H)$^-$ at 1.67 min. $^1$H NMR (500 MHz, DMSO-d$_6$) δ 13.18 (s, 1H), 9.91 (s, 1H), 8.42 (s, 1H), 8.24 (d, J = 1.9 Hz, 1H), 7.97 (dd, J = 8.2, 1.9 Hz, 1H), 7.52-7.43 (m, 1H), 7.42-7.28 (m, 6H), 7.09 (d, J = 8.3 Hz, 1H), 7.00 (d, J = 1.8 Hz, 1H), 2.75-2.60 (m, 1H), 2.37 (s, 3H), 1.07-0.97 (m, 2H), 0.89-0.75 (m, 2H). |
| 149 | 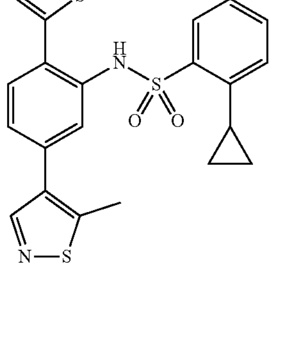 | 3-(N-(2-(5-chlorothiophen-2-yl)-5-(5-methylisothiazol-4-yl)phenyl)sulfamoyl)-4-cyclopropylbenzoic acid (using INTERMEDIATE-26); UPLC-MS (Method 1): m/z 530.8 (M + H)$^+$, 528.8 (M − H)$^-$ at 1.74 min. $^1$H NMR (500 MHz, DMSO-d$_6$) δ 13.21 (s, 1H), 10.19 (s, 1H), 8.34 (s, 1H), 8.31-8.21 (m, 1H), 8.06-7.93 (m, 1H), 7.75 (d, J = 8.1 Hz, 1H), 7.53 (d, J = 1.6 Hz, 1H), 7.39 (d, J = 4.0 Hz, 1H), 7.19-7.02 (m, 2H), 6.93-6.79 (m, 1H), 2.85-2.66 (m, 1H), 2.29 (s, 3H), 1.17-0.97 (m, 2H), 0.96-0.65 (m, 2H). |

| Example | Structure | Name/Analytical Data |
|---|---|---|
| 150 | 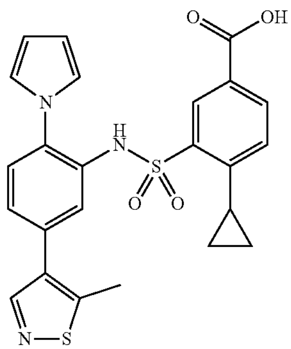 [SMILES: Cc1sncc1-c1ccc(-n2cccc2)c(NS(=O)(=O)c2cc(C(=O)O)ccc2C2CC2)c1] | 4-cyclopropyl-3-(N-(5-(5-methylisothiazol-4-yl)-2-(pyrrol-1-yl)phenyl)sulfamoyl)benzoic acid (using INTERMEDIATE-34); UPLC-MS (Method 1): m/z 479.7 (M + H)⁺, 477.8 (M − H)⁻ at 1.60 min. ¹H NMR (500 MHz, DMSO-d₆) δ 13.22 (s, 1H), 10.12 (s, 1H), 8.38 (s, 1H), 8.29 (d, J = 1.9 Hz, 1H), 8.06-7.96 (m, 1H), 7.60-7.38 (m, 2H), 7.15 (d, J = 8.3 Hz, 1H), 7.05 (t, J = 2.2 Hz, 2H), 6.95 (s, 1H), 6.19 (t, J = 2.2 Hz, 2H), 2.81-2.66 (m, 1H), 2.32 (s, 3H), 1.16-1.00 (m, 2H), 0.94-0.83 (m, 2H). |

Example 151: 4-cyclopropyl-3-(N-(2-(isothiazol-3-yl)-5-(trifluoromethyl)phenyl) sulfamoyl)benzoic acid

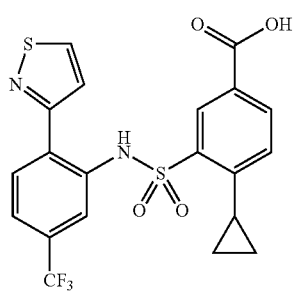

Step 1: 2-(isothiazol-3-yl)-5-(trifluoromethyl)aniline: To a reaction vessel containing 3-bromoisothiazole (114 mg, 0.697 mmol), the product from Example 128 Step 1 (250 mg, 0.697 mmol), 1 M K₃PO₄(aq) (1.20 ml, 1.20 mmol) and dioxane (4.80 ml) was added XPhos Pd G3 (29.5 mg, 0.035 mmol). The resultant reaction mixture was degassed with N₂ for 10 min and then heated to 80° C. for 1 h. The reaction mixture was concentrated in vacuo. The crude product was purified by chromatography on silica gel (12 g cartridge, 0-15% EtOAc/isohexane) to afford the title compound (154 mg, 0.580 mmol, 83% yield, 92% purity) as a light brown solid. UPLC-MS (Method 1): m/z 245.2 (M+H)⁺ (ES⁺), at 1.57 min. ¹H NMR (500 MHz, DMSO-d₆) δ 9.16 (d, J=4.8 Hz, 1H), 8.00 (d, J=4.9 Hz, 1H), 7.95 (d, J=8.2 Hz, 1H), 7.16 (d, J=1.9 Hz, 1H), 7.12 (br s, 2H), 6.86 (dd, J=8.4, 1.9 Hz, 1H).

Step 2: Methyl 4-cyclopropyl-3-(N-(2-(isothiazol-3-yl)-5-(trifluoromethyl)phenyl)sulfamoyl)benzoate: A solution of the product from Step 1 above (80 mg, 0.301 mmol, 92% purity), the product from Example 132 Step 5 (87 mg, 0.301 mmol) and pyridine (0.120 ml, 1.49 mmol) in DCM (1.0 ml) was stirred at RT for 46 h. The reaction mixture was purified by chromatography on silica gel (12 g cartridge, 0-50% EtOAc/isohexane) to afford the title compound (125 mg, 0.259 mmol, 86% yield) as an off-white solid. UPLC-MS (Method 1): m/z 483.3 (M+H)⁺, 481.2 (M−H)⁻ at 1.86 min.

Step 3: 4-cyclopropyl-3-(N-(2-(isothiazol-3-yl)-5-(trifluoromethyl)phenyl)sulfamoyl)benzoic acid: 1 M LiOH(aq) (1.04 ml, 1.04 mmol) was added to a solution of the product from Step 2 above (125 mg, 0.259 mmol) in THF (2.08 ml) at RT. The resultant mixture was stirred at RT for 23 h. The reaction mixture was concentrated in vacuo to remove the THF. The residue was diluted with water (6 ml) and then washed with TBME (6 ml). The aqueous phase was acidified using 1 M HCl(aq) until pH 4-5 and extracted with EtOAc (3×6 ml). The combined organic phase was dried by passage through a phase separator and concentrated in vacuo to afford the title compound (105 mg, 0.217 mmol, 84% yield, 97% purity) as an off-white solid. UPLC-MS (Method 1): m/z 469.3 (M+H)⁺, 467.2 (M−H)⁻ at 1.70 min. ¹H NMR (500 MHz, DMSO-d₆) δ 13.29 (br s, 1H), 12.15 (br s, 1H), 9.27 (d, J=4.9 Hz, 1H), 8.47 (d, J=1.9 Hz, 1H), 8.21 (d, J=8.3 Hz, 1H), 8.11 (d, J=4.5 Hz, 1H), 7.96 (d, J=8.2 Hz, 1H), 7.65 (d, J=1.8 Hz, 1H), 7.56-7.40 (m, 1H), 7.05 (d, J=8.3 Hz, 1H), 2.61-2.52 (m, 1H), 0.81-0.75 (m, 2H), 0.70-0.63 (m, 2H).

Example 152: 3-(N-(5-cyano-2-(3-fluoropyridin-2-yl)phenyl)sulfamoyl)-4-cyclopropylbenzoic acid

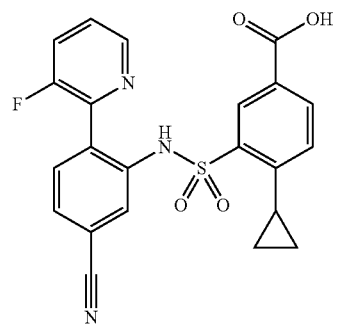

Step 1: 3-amino-4-(4,4,5,5-tetramethyl-1,3,2-dioxaborolan-2-yl)benzonitrile: A mixture of 3-amino-4-bromobenzonitrile (500 mg, 2.54 mmol), 4,4,4',4',5,5,5',5'-octamethyl-2,2'-bi(1,3,2-dioxaborolane) (773 mg, 3.05 mmol), potassium acetate (747 mg, 7.61 mmol) and [Pd(dppf)Cl₂]-DCM complex (104 mg, 0.127 mmol) was evacuated and purged with N₂ 3 times. Dioxane (5 ml) and was added and the mixture was purged with N₂ for 5 min. The reaction was heated at 80° C. for 3 h then cooled to RT. The reaction was filtered through Celite®, washed with EtOAc (10 m), and the filtrate concentrated in vacuo to afford the title compound (683 mg, 1.93 mmol, 76% yield, 69% purity) as dark brown gum. UPLC-MS (Method 1): no ionisation at 0.60 min.

Step 2: 3-amino-4-(3-fluoropyridin-2-yl)benzonitrile: To a mixture of the product from Step 1 above (150 mg, 0.369 mmol), 2-bromo-3-fluoropyridine (71.4 mg, 0.406 mmol) in dioxane (3 ml) was added [Pd(dppf)Cl$_2$]-DCM complex (15 mg, 0.018 mmol). The resultant reaction mixture was degassed with N$_2$ for 5 min. 1 M K$_3$PO$_4$(aq) (0.922 ml, 0.922 mmol) was added and the reaction mixture was degassed for a further 5 min. The reaction was heated at 80° C. for 16 h and then cooled to RT. The mixture was filtered through Celite®, washed with EtOAc (2×10 ml) and the filtrate concentrated in vacuo. The crude product was purified by chromatography on silica gel (24 g cartridge, 0-50% EtOAc/isohexane) to afford the title compound (140 mg, 0.368 mmol, 100% yield, 56% purity) as a light yellow oil. UPLC-MS (Method 1): m/z 214.3 (M+H)$^+$ (ES$^+$), at 1.08 min. $^1$H NMR (500 MHz, DMSO-d$_6$) δ 8.57-8.52 (m, 1H), 7.92-7.84 (m, 1H), 7.57-7.50 (m, 1H), 7.43 (dd, J=7.9, 2.7 Hz, 1H), 7.16 (d, J=1.7 Hz, 1H), 7.01 (dd, J=7.9, 1.7 Hz, 1H), 6.04 (s, 2H).

Step 3: Methyl 3-(N-(5-cyano-2-(3-fluoropyridin-2-yl)phenyl)sulfamoyl)-4-cyclopropylbenzoate: To a mixture of the product from Step 2 above (142 mg, 0.360 mmol) and the product from Example 132 Step 5 (99 mg, 0.360 mmol) in DCM (750 µl) at RT was added pyridine (200 µl, 2.47 mmol). The resultant solution was stirred at RT for 5 days. The reaction was concentrated in vacuo and the crude product was purified by chromatography on silica gel (24 g cartridge, 0-100% EtOAc/isohexane) to afford the title compound (115 mg, 0.252 mmol, 70% yield, 99% purity) as a pale yellow solid. UPLC-MS (Method 1): m/z 452.3 (M+H)$^+$, 450.2 (M−H)$^-$ at 1.33 min.

Step 4: 3-(N-(5-cyano-2-(3-fluoropyridin-2-yl)phenyl)sulfamoyl)-4-cyclopropylbenzoic acid: A mixture of the product from Step 3 above (105 mg, 0.233 mmol) and LiOH (22.7 mg, 0.930 mmol) in THF/MeOH/water (4:1:1, 3 ml) was stirred at RT overnight. Reaction was concentrated in vacuo and the residue was adjusted to ~pH 4 with 1 M HCl(aq). The precipitate was filtered, washed with water and dried to the title product (100 mg, 0.224 mmol, 96% yield, 98% purity) as a white solid. UPLC-MS (Method 1): m/z 438.3 (M+H)$^+$, 436.3 (M−H)$^-$ at 1.41 min. $^1$H NMR (500 MHz, DMSO-d$_6$) δ 13.22 (s, 1H), 10.54 (s, 1H), 8.46-8.41 (m, 1H), 8.12-8.07 (m, 1H), 7.93 (dd, J=8.2, 1.9 Hz, 1H), 7.84-7.77 (m, 1H), 7.76-7.71 (m, 1H), 7.71-7.64 (m, 2H), 7.51-7.44 (m, 1H), 6.98 (d, J=8.3 Hz, 1H), 2.48-2.44 (m, 1H), 0.96-0.87 (m, 2H), 0.76-0.67 (m, 2H).

Example 153: 3-(N-(5-cyano-2-(6-fluoropyridin-2-yl)phenyl)sulfamoyl)-4-cyclopropylbenzoic acid Step 1: 3-amino-4-(6-fluoropyridin-2-yl)benzonitrile: To a mixture of the product from Example 152 Step 1 (150 mg, 0.522 mmol), 2-bromo-6-fluoropyridine (101 mg, 0.575 mmol) in dioxane (3 ml) was added [Pd(dppf)Cl$_2$]-DCM complex (21 mg, 0.026 mmol). The resultant reaction mixture was degassed with N$_2$ for 5 min. 1 M K$_3$PO$_4$(aq) (1.31 ml, 1.31 mmol) was added and the reaction mixture was degassed for a further 5 min. The reaction was heated at 80° C. for 2 h. The reaction mixture was cooled to RT, filtered through Celite®, washed with EtOAc (2×10 ml) and filtrate was concentrated in vacuo. The crude product was purified by chromatography on silica gel (24 g cartridge, 0-50% EtOAc/isohexane) to afford the title compound (112 mg, 0.499 mmol, 96% yield, 95% purity) as a light yellow solid. UPLC-MS (Method 2): m/z 214.3 (M+H)$^+$, 212.1 (M−H)$^-$ at 1.24 min. $^1$H NMR (500 MHz, Chloroform-d) δ 7.96-7.92 (m, 1H), 7.61 (d, J=8.0 Hz, 1H), 7.58 (dd, J=7.7, 2.4 Hz, 1H), 7.04 (dd, J=8.0, 1.6 Hz, 1H), 7.03-7.01 (m, 1H), 6.95-6.92 (m, 1H), 5.82 (s, 2H).

Step 2: Methyl 3-(N-(5-cyano-2-(6-fluoropyridin-2-yl)phenyl)sulfamoyl)-4-cyclopropylbenzoate: To a mixture of the product from Step 1 above (112 mg, 0.499 mmol) and the product from Example 132 Step 5 (131 mg, 0.476 mmol) in DCM (750 µl) at RT was added pyridine (250 µl, 3.09 mmol). The resultant solution was stirred at RT for 4 days. The reaction was concentrated in vacuo and the crude product was purified by chromatography on silica gel (24 g cartridge, 0-100% EtOAc/isohexane) to afford the title compound (114 mg, 0.253 mmol, 53% yield) as a white solid. UPLC-MS (Method 2): m/z 452.7 (M+H)$^+$, 450.2 (M−H)$^-$ at 1.46 min.

Step 3: 3-(N-(5-cyano-2-(6-fluoropyridin-2-yl)phenyl)sulfamoyl)-4-cyclopropylbenzoic acid: A mixture of the product from Step 2 above (104 mg, 0.230 mmol) and LiOH (23 mg, 0.921 mmol) in THF/MeOH/water (4:1:1, 4 ml) was stirred at RT overnight. The reaction was concentrated in vacuo and the residue was adjusted to ~pH 4 with 1 M HCl(aq). The resultant precipitate was filtered, washed with water and dried to give the title compound (97 mg, 0.217 mmol, 94% yield, 98% purity) as a white solid. UPLC-MS (Method 2): m/z 438.3 (M+H)$^+$, 436.3 (M−H)$^-$ at 0.95 min. $^1$H NMR (500 MHz, DMSO-d$_6$) δ 13.24 (s, 1H), 10.95 (s, 1H), 8.20 (d, J=1.8 Hz, 1H), 8.05 (app. q, J=8.2 Hz, 1H), 7.94 (dd, J=8.2, 1.9 Hz, 1H), 7.86 (d, J=8.1 Hz, 1H), 7.78 (s, 1H), 7.71-7.63 (m, 2H), 7.23-7.17 (m, 1H), 7.01 (d, J=8.3 Hz, 1H), 2.53-2.52 (m, 1H), 0.96-0.89 (m, 2H), 0.78-0.71 (m, 2H).

Example 154: 3-(N-(5-cyano-4-fluoro-2-(pyridin-2-yl)phenyl)sulfamoyl)-4-cyclopropylbenzoic acid

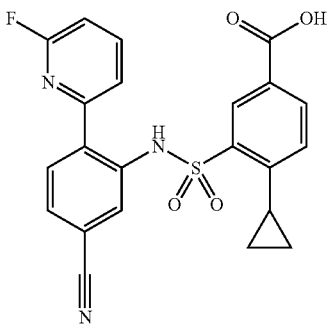 [SMILES: N#Cc1ccc(-c2cccc(F)n2)c(NS(=O)(=O)c2cc(C(=O)O)ccc2C2CC2)c1]

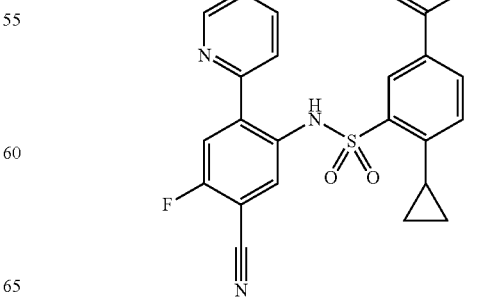

Step 1: 5-amino-2-fluoro-4-(pyridin-2-yl)benzonitrile: 0.5 M pyridin-2-ylzinc(II) bromide in THF (4.7 ml, 2.35 mmol) was added to a solution of 5-amino-4-bromo-2-fluorobenzonitrile (250 mg, 1.16 mmol) in dioxane (1.2 ml) and Pd(PPh$_3$)$_4$ (130 mg, 0.112 mmol). The mixture was degassed under nitrogen for 10 min then stirred at 80° C. for 3 h. The reaction mixture was allowed to cool to RT and left to stand overnight. The reaction mixture was concentrated in vacuo onto silica. The crude product was partially purified by chromatography on silica gel (24 g cartridge, 0-100% EtOAc/isohexane) to afford the title compound (410 mg), contaminated with triphenylphosphine oxide and pyridine. UPLC-MS (Method 1): m/z 214.5 (M+H)$^+$ (ES$^+$) at 1.20 min.

Step 2: 5-amino-2-fluoro-4-(pyridin-2-yl)benzonitrile: The product from Step 1 (330 mg) was treated with DCM (5 ml) and MeOH (1 ml). The resultant pale yellow precipitate was collected by filtration. The filtrate was concentrated in vacuo and the resultant residue combined with the precipitate then purified by chromatography on silica gel (40 g cartridge, 0-100% EtOAc/isohexane) to afford the title compound (128 mg, 0.360 mmol, 23% yield, 60% purity) as a yellow solid. UPLC-MS (Method 1): m/z 214.6 (M+H)$^+$ (ES$^+$), at 1.15 min. $^1$H NMR (500 MHz, DMSO-d$_6$) δ 8.71-8.66 (m, 1H), 8.00-7.92 (m, 2H), 7.75 (d, J=11.0 Hz, 1H), 7.47-7.39 (m, 1H), 7.16 (d, J=5.8 Hz, 1H), 6.83 (s, 2H).

Step 3: Methyl 3-(N-(5-cyano-4-fluoro-2-(pyridin-2-yl)phenyl)sulfamoyl)-4-cyclopropylbenzoate: To a mixture of the product from Step 2 (142 mg, 0.400 mmol) and the product from Example 132 Step 5 (110 mg, 0.400 mmol) in DCM (750 μl) at RT was added pyridine (200 μl, 2.47 mmol). The resultant solution was stirred at RT for 5 days. The reaction was concentrated in vacuo and the crude product was purified by chromatography on silica gel (12 g cartridge, 0-100% EtOAc/isohexane) to afford the title compound (32 mg, 0.071 mmol, 18% yield) as a pale yellow solid. UPLC-MS (Method 2): m/z 452.3 (M+H)$^+$, 450.3 (M−H)$^-$ at 1.55 min.

Step 4: 3-(N-(5-cyano-4-fluoro-2-(pyridin-2-yl)phenyl)sulfamoyl)-4-cyclopropylbenzoic acid: A mixture of the product from Step 3 above (32 mg, 0.071 mmol) and LiOH (6.93 mg, 0.284 mmol) in THF/MeOH/water (4:1:1, 2 ml) was stirred at RT overnight. The reaction was concentrated in vacuo and the residue was adjusted to ~pH 4 with 1 M HCl(aq). The resultant precipitate was filtered, washed with water and dried to afford the title compound (16 mg, 0.036 mmol, 51% yield, 99% purity) as a white solid. UPLC-MS (Method 2): m/z 438.4 (M+H)$^+$, 436.2 (M−H)$^-$ at 0.97 min. $^1$H NMR (500 MHz, DMSO-d$_6$) δ 13.27 (s, 1H), 12.68 (s, 1H), 8.73-8.67 (m, 1H), 8.24-8.18 (m, 1H), 8.09-8.03 (m, 1H), 8.01-7.91 (m, 2H), 7.92-7.86 (m, 1H), 7.86-7.79 (m, 1H), 7.53-7.48 (m, 1H), 6.97-6.91 (m, 1H), 2.49-2.44 (m, 1H), 0.82-0.74 (m, 2H), 0.68-0.59 (m, 2H).

Example 155: 4-cyclopropyl-3-(N-(4-fluoro-2-(pyrrol-1-yl)-5-(trifluoromethyl)phenyl) sulfamoyl)benzoic acid

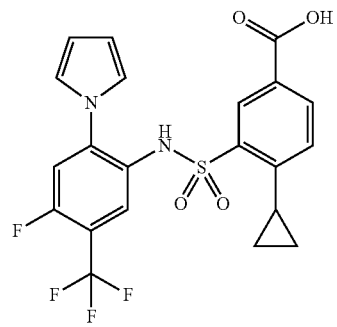 [SMILES: O=C(O)c1ccc(C2CC2)c(S(=O)(=O)Nc2cc(C(F)(F)F)c(F)cc2-n2cccc2)c1]

Step 1: Methyl 3-(N-(2-((tert-butoxycarbonyl)amino)-4-fluoro-5-(trifluoromethyl)phenyl)sulfamoyl)-4-cyclopropylbenzoate: The product from Example 132 Step 5 (170 mg, 0.588 mmol) was added to a solution of pyridine (140 μl, 1.73 mmol) and the product from Example 130 Step 2 (165 mg, 0.477 mmol) in DCM (1 ml). The resultant solution was stirred at RT for 4 days. The reaction mixture was concentrated in vacuo and purified by chromatography on silica gel (24 g cartridge, 0-100% Ethyl acetate/Isohexane) to afford the title compound (292 mg, 0.422 mmol, 89% yield, 77% purity) as a dark brown oil. UPLC-MS (Method 2): m/z 433.4 (M+H-Boc)$^+$, 531.2 (M−H)$^-$ at 1.52 min.

Step 2: 2-((2-cyclopropyl-5-(methoxycarbonyl)phenyl)sulfonamido)-5-fluoro-4-(trifluoromethyl)benzenaminium trifluoroacetate: The product from Step 1 above (292 mg, 0.422 mmol, 77% purity) was dissolved in DCM (2.5 ml) and treated with TFA (330 μl, 4.28 mmol). The resultant mixture was stirred at RT for 18 h. The mixture was treated with PhMe (2 ml) and concentrated in vacuo to afford the title compound (269 mg, 0.369 mmol, 87% yield, 75% purity) as a brown oil. UPLC-MS (Method 2): m/z 433.3 (M+H)$^+$, 431.2 (M−H)$^-$ at 1.44 min.

Step 3: Methyl 4-cyclopropyl-3-(N-(4-fluoro-2-(pyrrol-1-yl)-5-(trifluoromethyl)phenyl)sulfamoyl)benzoate: The product from Step 2 above (269 mg, 0.369 mmol, 75% purity) was combined with sodium acetate (46 mg, 0.561 mmol) and 2,5-dimethoxytetrahydrofuran (100 μl, 0.772 mmol) in AcOH (2 ml). The mixture was heated to 120° C. and the resultant clear solution was stirred for 2 h. n-Heptane (3 ml) was added and the mixture concentrated in vacuo. The crude product was purified by chromatography on silica gel (24 g cartridge, 0-50% EtOAc/isohexane) to afford the title compound (132 mg, 0.246 mmol, 67% yield, 90% purity) as a brown oil. UPLC-MS (Method 2): m/z 483.3 (M+H)$^+$, 481.3 (M−H)$^-$ at 1.45 min.

Step 4: 4-cyclopropyl-3-(N-(4-fluoro-2-(pyrrol-1-yl)-5-(trifluoromethyl)phenyl)sulfamoyl)benzoic acid: 1 M LiOH (aq) (740 μl, 0.740 mmol) was added to a solution of the product from Step 3 above (132 mg, 0.246 mmol, 90% purity) in THF (1.5 ml). The reaction mixture was stirred at RT for 2 days and then concentrated in vacuo. The residue was dissolved in water (12 ml) and washed with EtOAc (12 ml). The aqueous phase was acidified using 1 M HCl(aq) until pH 4-5 and then extracted with EtOAc (2×12 ml). The combined organic phases were dried by passage through a phase separator and concentrated in vacuo. The crude product was purified by chromatography on (24 g reverse phase cartridge, 15-70% MeCN/Water 0.1% Formic Acid) to afford the title compound (52 mg, 0.105 mmol, 43% yield, >95% purity) as a white solid. UPLC-MS (Method 1): m/z 467.2 (M−H)⁻ at 1.64 min. ¹H NMR (500 MHz, DMSO-d₆) δ 13.22 (br s, 1H), 10.29 (br s, 1H), 8.16 (d, J=1.9 Hz, 1H), 8.01 (dd, J=8.2, 1.9 Hz, 1H), 7.64 (d, J=11.4 Hz, 1H), 7.16 (t, J=2.2 Hz, 2H), 7.13 (d, J=8.3 Hz, 1H), 7.08 (d, J=7.3 Hz, 1H), 6.20 (t, J=2.2 Hz, 2H), 2.71-2.61 (m, 1H), 1.13-1.04 (m, 2H), 0.92-0.83 (m, 2H).

Example 156: 3-(N-(4-chloro-2-(pyrrol-1-yl)-5-(trifluoromethyl)phenyl)sulfamoyl)-4-cyclopropylbenzoic acid

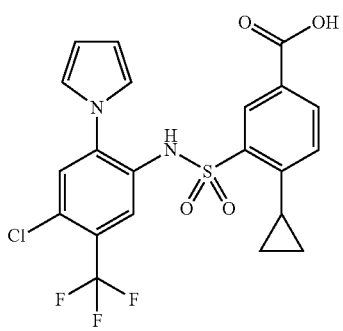 [SMILES: O=C(O)c1ccc(C2CC2)c(S(=O)(=O)Nc2cc(C(F)(F)F)c(Cl)cc2-n2cccc2)c1]

Step 1: Methyl 3-(N-(2-((tert-butoxycarbonyl)amino)-4-chloro-5-(trifluoromethyl)phenyl)sulfamoyl)-4-cyclopropylbenzoate: The product from Example 132 Step 5 (150 mg, 0.519 mmol) was added to a solution of pyridine (120 µl, 1.48 mmol) and the product from Example 131 Step 2 (150 mg, 0.435 mmol) in DCM (1 ml). The resultant solution was stirred at RT for 4 days. The reaction mixture was concentrated in vacuo and purified by chromatography on silica gel (24 g cartridge, 0-100% Ethyl acetate/Isohexane) to afford the title compound (280 mg, 0.485 mmol, 112% yield, 95% purity) as a pale brown oil. UPLC-MS (Method 2): m/z 449.6 (M+H-Boc)⁺, 547.1 (M−H)⁻ at 1.53 min.

Step 2: 5-chloro-2-((2-cyclopropyl-5-(methoxycarbonyl)phenyl)sulfonamido)-4-(trifluoromethyl)benzenaminium trifluoroacetate: The product from Step 1 above (280 mg, 0.485 mmol, 95% purity) was dissolved in DCM (2.5 ml) and treated with TFA (370 µl, 4.80 mmol). The resultant mixture was stirred at RT for 18 h. The mixture was treated with PhMe (2 ml) and concentrated in vacuo to afford the title compound (238 mg, 0.389 mmol, 80% yield, 92% purity) as a brown solid. UPLC-MS (Method 2): m/z 449.3 (M+H)⁺, 447.2 (M−H)⁻ at 1.35 min.

Step 3: Methyl 3-(N-(4-chloro-2-(pyrrol-1-yl)-5-(trifluoromethyl)phenyl)sulfamoyl)-4-cyclopropylbenzoate: The product from Step 2 above (238 mg, 0.389 mmol, 92% purity) was combined with sodium acetate (50 mg, 0.610 mmol) and 2,5-dimethoxytetrahydrofuran (110 µl, 0.849 mmol) in AcOH (2 ml). The mixture was heated to 120° C. and the resultant clear solution was stirred for 2 h. n-Heptane (3 ml) was added and the mixture concentrated in vacuo. The crude product was purified by chromatography on silica gel (24 g cartridge, 0-50% EtOAc/isohexane) to afford the title compound (115 mg, 0.207 mmol, 53% yield, 90% purity) as a brown oil. UPLC-MS (Method 2): m/z 499.3 (M+H)⁺, 497.3 (M−H)⁻ at 1.49 min.

Step 4: 3-(N-(4-chloro-2-(pyrrol-1-yl)-5-(trifluoromethyl)phenyl)sulfamoyl)-4-cyclopropylbenzoic acid: 1 M LiOH(aq) (700 µl, 0.700 mmol) was added to a solution of the product from Step 3 above (115 mg, 0.207 mmol, 90% purity) in THF (1.5 ml). The reaction mixture was stirred at RT for 2 days. The reaction mixture was concentrated in vacuo. The residue was dissolved in water (12 ml) and washed with EtOAc (12 ml). The aqueous phase was acidified using 1 M HCl(aq) until pH 1-2 and then extracted with EtOAc (2×12 ml). The combined organic phases were dried by passage through a phase separator and concentrated in vacuo. The crude product was purified by chromatography on (24 g reverse phase cartridge, 15-70% MeCN/Water 0.1% Formic Acid) to afford the title compounds (42 mg, 0.082 mmol, 40% yield, >95% purity) as a white solid. UPLC-MS (Method 1): m/z 483.2 (M−H)⁻ at 1.74 min. ¹H NMR (500 MHz, DMSO-d₆) δ 13.24 (s, 1H), 10.40 (s, 1H), 8.20 (d, J=1.9 Hz, 1H), 8.02 (dd, J=8.2, 1.9 Hz, 1H), 7.76 (s, 1H), 7.19 (s, 1H), 7.16-7.12 (m, 3H), 6.21 (t, J=2.2 Hz, 2H), 2.72-2.60 (m, 1H), 1.13-1.05 (m, 2H), 0.91-0.83 (m, 2H).

Example 157: 3-(N-(5-cyano-4-fluoro-2-(pyrrol-1-yl)phenyl)sulfamoyl)-4-cyclopropylbenzoic acid

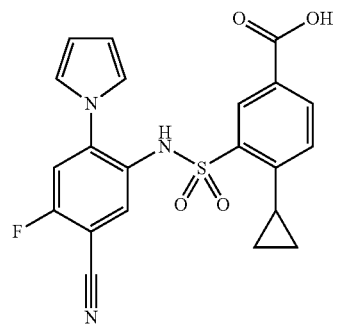 [SMILES: N#Cc1cc(NS(=O)(=O)c2cc(C(=O)O)ccc2C2CC2)c(-n2cccc2)cc1F]

Step 1: Tert-butyl (2-amino-4-cyano-5-fluorophenyl)carbamate: A solution of tert-butyl (4-cyano-5-fluoro-2-nitrophenyl)carbamate (250 mg, 0.889 mmol) in 1:1 EtOH/MeOH (8 ml) was treated with 5% Pd/C (Type 87L) (240 mg, 0.045 mmol). The solution was hydrogenated at a pressure of 1 bar for 4 h. The reaction mixture was filtered through Celite® and concentrated in vacuo to afford the title compound (226 mg, 0.765 mmol, 86% yield, 85% purity) as a brown oil. UPLC-MS (Method 2): m/z 250.2 (M−H)⁻ at 1.32 min.

Step 2: Methyl 3-(N-(2-((tert-butoxycarbonyl)amino)-5-cyano-4-fluorophenyl)sulfamoyl)-4-cyclopropylbenzoate: The product from Example 132 Step 5 (150 mg, 0.519 mmol) was added to a solution of pyridine (114 µl, 1.41 mmol) and the product from Step 1 above (150 mg, 0.507 mmol, 85% purity) in DCM (1 ml). The resultant solution was stirred at RT for 3 days. The reaction mixture was concentrated in vacuo and purified by chromatography on silica gel (12 g cartridge, 0-50% Ethyl acetate/Isohexane) to afford the title compound (288 mg, 0.559 mmol, 110% yield, 95% purity) as a dark yellow oil. UPLC-MS (Method 2): m/z 390.5 (M+H-Boc)⁺, 488.2 (M−H)⁻ at 1.38 min.

Step 3: 4-cyano-2-((2-cyclopropyl-5-(methoxycarbonyl)phenyl)sulfonamido)-5-fluorobenzenaminium trifluoroacetate: The product from Step 2 above (288 mg, 0.494 mmol) was dissolved in DCM (2.5 ml) and treated with TFA (380 µl, 4.93 mmol). The resultant mixture was stirred at RT for 18 h. The mixture was treated with PhMe (2 ml) and concentrated in vacuo to afford the title compound (243 mg, 0.405 mmol, 82% yield, 84% purity) as a brown oil. UPLC-MS (Method 2): m/z 388.3 (M–H)⁻ at 1.08 min.

Step 4: Methyl 3-(N-(5-cyano-4-fluoro-2-(pyrrol-1-yl)phenyl)sulfamoyl)-4-cyclopropylbenzoate: The product from Step 3 above (243 mg, 0.405 mmol, 84% purity) was combined with sodium acetate (50 mg, 0.610 mmol) and 2,5-dimethoxytetrahydrofuran (110 µl, 0.849 mmol) in AcOH (2 ml). The mixture was heated to 120° C. and the resultant clear solution was stirred for 2 h. n-Heptane (3 ml) was added and the mixture concentrated in vacuo. The crude product was purified by chromatography on silica gel (24 g cartridge, 0-40% EtOAc/isohexane) to afford the title compound (148 mg, 0.320 mmol, 79% yield, 95% purity) as a yellow oil. UPLC-MS (Method 2): m/z 438.3 (M–H)⁻ at 1.37 min.

Step 5: 3-(N-(5-cyano-4-fluoro-2-(pyrrol-1-yl)phenyl)sulfamoyl)-4-cyclopropylbenzoic acid: 1 M LiOH(aq) (960 µl, 0.960 mmol) was added to a solution of the product from Step 4 above (148 mg, 0.320 mmol, 95% purity) in THF (2 ml). The reaction mixture was stirred at RT for 2 days. The reaction mixture was concentrated in vacuo. The residue was dissolved in water (12 ml) and washed with EtOAc (12 ml). The aqueous phase was acidified using 1 M HCl(aq) until pH 4-5 and then extracted with EtOAc (2×12 ml). The combined organic phases were dried by passage through a phase separator and concentrated in vacuo. The crude product was purified by chromatography on 24 g reverse phase cartridge (15-70% MeCN/10 mM Ammonium Bicarbonate) to afford the title compound (60 mg, 0.134 mmol, 42% yield, >95% purity) as a white solid. UPLC-MS (Method 1): m/z 426.2 (M+H)⁺, 424.4 (M–H)⁻ at 1.46 min. ¹H NMR (500 MHz, DMSO-d₆) δ 13.15 (br s, 1H), 10.30 (br s, 1H), 8.18-8.13 (m, 1H), 7.95 (dd, J=8.3, 1.9 Hz, 1H), 7.58 (d, J=10.2 Hz, 1H), 7.47 (d, J=6.7 Hz, 1H), 7.14-7.09 (m, 2H), 7.05 (d, J=8.3 Hz, 1H), 6.13 (t, J=2.2 Hz, 2H), 2.72-2.60 (m, 1H), 1.12-1.00 (m, 2H), 0.91-0.82 (m, 2H).

Example 158: 3-(N-(4-chloro-2-(pyrrol-1-yl)-5-(trifluoromethyl)phenyl)sulfamoyl)-4-methoxybenzoic acid

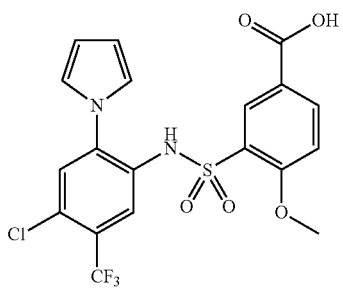 [SMILES: COc1ccc(C(=O)O)cc1S(=O)(=O)Nc1cc(C(F)(F)F)c(Cl)cc1-n1cccc1]

Step 1: Methyl 3-(N-(2-((tert-butoxycarbonyl)amino)-4-chloro-5-(trifluoromethyl)phenyl)sulfamoyl)-4-methoxybenzoate: Methyl 3-(chlorosulfonyl)-4-methoxybenzoate (190 mg, 0.718 mmol) was added to a solution of pyridine (160 µl, 1.98 mmol) and the product from Example 131 Step 2 (200 mg, 0.579 mmol) in DCM (1 ml). The resultant solution was stirred at RT for 2 days. The reaction mixture was concentrated in vacuo and purified by chromatography on silica gel (24 g cartridge, 0-50% Ethyl acetate/Isohexane) to afford the title compound (342 mg, 0.628 mmol, 108% yield, 99% purity) as a dark purple oil, which solidified on standing. UPLC-MS (Method 2): m/z 537.1 (M–H)⁻ at 1.89 min.

Step 2: 5-chloro-2-((2-methoxy-5-(methoxycarbonyl)phenyl)sulfonamido)-4-(trifluoromethyl)benzenaminium trifluoroacetate: The product from Step 1 above (342 mg, 0.628 mmol, 99% purity) was dissolved in DCM (3 ml) and treated with TFA (500 µl, 6.49 mmol). The resultant mixture was stirred at RT overnight. The mixture was treated with PhMe (2 ml) and concentrated in vacuo to afford the title compound (285 mg, 0.479 mmol, 76% yield, 93% purity) as a light brown solid. UPLC-MS (Method 1): m/z 439.2 (M+H)⁺, 437.1 (M–H)⁻ at 1.35 min.

Step 3: Methyl 3-(N-(4-chloro-2-(pyrrol-1-yl)-5-(trifluoromethyl)phenyl)sulfamoyl)-4-methoxybenzoate: The product from Step 2 above (285 mg, 0.479 mmol, 93% purity) was combined with sodium acetate (50 mg, 0.610 mmol) and 2,5-dimethoxytetrahydrofuran (87 µl, 0.671 mmol) in AcOH (2 ml). The mixture was heated to 120° C. and the resultant clear solution was stirred for 2 h. n-Heptane (3 ml) was added and the mixture concentrated in vacuo. The crude product was purified by chromatography on silica gel (24 g cartridge, 0-40% EtOAc/isohexane) to afford the title compound (146 mg, 0.239 mmol, 50% yield, 80% purity) as pale brown solid. UPLC-MS (Method 2): m/z 489.1 (M+H)⁺, 487.1 (M–H)⁻ at 1.47 min.

Step 4: 3-(N-(4-chloro-2-(pyrrol-1-yl)-5-(trifluoromethyl)phenyl)sulfamoyl)-4-methoxybenzoic acid: 1 M LiOH (aq) (720 µl, 0.720 mmol) was added to a solution of the product from Step 3 above (146 mg, 0.239 mmol, 80% purity) in THF (1.5 ml). The reaction mixture was stirred at RT for 2 days. The reaction mixture was concentrated in vacuo. The residue was dissolved in water (12 ml) and washed with EtOAc (12 ml). The aqueous phase was acidified using 1 M HCl(aq) until pH 4-5 and then extracted with EtOAc (2×12 ml). The combined organic phases were dried by passage through a phase separator and concentrated in vacuo. The crude product was purified by chromatography (24 g reverse phase cartridge, 15-70% MeCN/Water 0.1% Formic Acid) to afford the title compound (61 mg, 0.122 mmol, 51% yield, >95% purity) as a white solid. UPLC-MS (Method 1) m/z 475.4 (M+H)⁺, 473.1 (M–H)⁻ at 1.60 min. ¹H NMR (500 MHz, DMSO-d₆) δ 13.07 (br s, 1H), 9.95 (br s, 1H), 8.14 (dd, J=8.7, 2.2 Hz, 1H), 8.08 (d, J=2.2 Hz, 1H), 7.71 (s, 1H), 7.49 (s, 1H), 7.28 (d, J=8.8 Hz, 1H), 7.06 (t, J=2.2 Hz, 2H), 6.17 (t, J=2.2 Hz, 2H), 3.87 (s, 3H).

Example 159: 3-(N-(5-cyano-2-(thiazol-4-yl)phenyl)sulfamoyl)-4-cyclopropylbenzoic acid

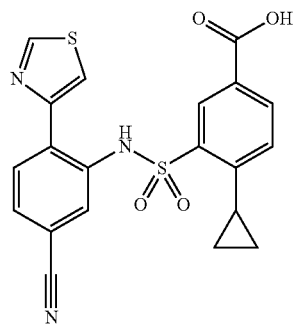 [SMILES: N#Cc1ccc(-c2cscn2)c(NS(=O)(=O)c2cc(C(=O)O)ccc2C2CC2)c1]

Step 1: 3-amino-4-(thiazol-4-yl)benzonitrile: To a reaction vessel containing the products from Example 152 Step 1 (254 mg, 0.656 mmol), 4-bromothiazole (0.060 ml, 0.677 mmol), 1 M K$_3$PO$_4$(aq) (1.13 ml, 1.13 mmol) and dioxane (4.52 ml) was added XPhos Pd G3 (28 mg, 0.033 mmol). The resultant reaction mixture was degassed with N$_2$ for 10 min and then heated to 80° C. for 3 h. The reaction mixture was concentrated in vacuo and then the crude product was purified by chromatography on silica gel (12 g cartridge, 0-20% EtOAc/isohexane) to afford the title compound (63.6 mg, 0.275 mmol, 42% yield, 87% purity) as an orange solid. UPLC-MS (Method 1): m/z 202.3 (M+H)$^+$ (ES$^+$), at 1.13 min.

Step 2: Methyl 3-(N-(5-cyano-2-(thiazol-4-yl)phenyl)sulfamoyl)-4-cyclopropylbenzoate: A solution of the product from Step 1 above (63.6 mg, 0.275 mmol, 87% purity), the product from Example 132 Step 5 (83 mg, 0.289 mmol) and pyridine (0.110 ml, 1.36 mmol) in DCM (1.0 ml) was stirred at RT for 22 h. The reaction mixture was purified directly by chromatography on silica gel (12 g cartridge, 0-40% then 40-100% EtOAc/isohexane) to afford the title compound (58.5 mg, 0.133 mmol, 48% yield) as a cream solild. UPLC-MS (Method 1): m/z 440.3 (M+H)$^+$, 438.2 (M−H)$^−$ at 1.63 min.

Step 3: 3-(N-(5-cyano-2-(thiazol-4-yl)phenyl)sulfamoyl)-4-cyclopropylbenzoic acid: 1 M LiOH(aq) (0.530 ml, 0.530 mmol) was added to a solution of the product from Step 2 above (58.5 mg, 0.133 mmol) in THF (1.06 ml) at RT. The resultant mixture was stirred at RT over the weekend. The reaction mixture was concentrated in vacuo. The residue was diluted with water (6 ml) and then washed with EtOAc (6 ml). The aqueous phase was acidified using 1 M HCl until pH 4-5 and then extracted with EtOAc (3×6 ml). The combined organic phase was dried by passage through a phase separotor and concentrated in vacuo to the title compound (51.1 mg, 0.115 mmol, 87% yield, 96% purity) as an off-white solid. UPLC-MS (Method 1): m/z 426.3 (M+H)$^+$, 424.3 (M−H)$^−$ at 1.46 min. $^1$H NMR (500 MHz, DMSO-d6) δ 13.31 (br s, 1H), 12.14 (br s, 1H), 9.44 (d, J=1.9 Hz, 1H), 8.51 (br s, 1H), 8.38 (d, J=1.9 Hz, 1H), 8.09 (d, J=8.2 Hz, 1H), 7.95 (dd, J=8.2, 1.9 Hz, 1H), 7.69 (d, J=1.7 Hz, 1H), 7.63 (br d, J=8.2 Hz, 1H), 7.02 (d, J=8.3 Hz, 1H), 2.59-2.50 (m, 1H), 0.85-0.77 (m, 2H), 0.72-0.64 (m, 2H).

Example 160: 4-cyclopropyl-3-(N-(2-(5-fluorothiophen-2-yl)-5-(5-methylisoxazol-4-yl)phenyl)sulfamoyl)benzoic acid

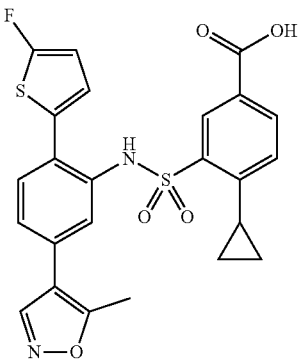

Step 1: Methyl 4-cyclopropyl-3-(N-(2-(5-fluorothiophen-2-yl)-5-(5-methylisoxazol-4-yl)phenyl)sulfamoyl)benzoate: A solution of 2-(5-fluorothiophen-2-yl)-5-(5-methylisoxazol-4-yl)aniline (INTERMEDIATE-29) (68.6 mg, 0.250 mmol) in DCM (2 ml) and pyridine (0.061 ml, 0.750 mmol) was treated with a solution of the product from Example 132 Step 5 (82 mg, 0.300 mmol) in DCM (0.5 ml) and the mixture was stirred at RT for 3.5 days. The reaction mixture was diluted with 4.5 M NH$_4$OH(aq) (1 ml), dried by passage through a phase separator and purified by chromatography on silica gel (12 g cartridge, 0-50% EtOAc/isohexane) to afford the title compound (114 mg, 0.214 mmol, 85% yield, 96% purity) as an orange gum. UPLC-MS (Method 1): m/z 513.7 (M+H)$^+$, 511.3 (M−H)$^−$ at 1.72 min.

Step 2: 4-cyclopropyl-3-(N-(2-(5-fluorothiophen-2-yl)-5-(5-methylisoxazol-4-yl)phenyl)sulfamoyl)benzoic acid: To a solution of the the product from Step 1 above (114 mg, 0.222 mmol, 96% purity) in dioxane (5 ml) was added 6 M HCl(aq) (0.371 ml, 2.22 mmol) and the mixture was heated at 55° C. for 5 h. 6 M HCl(aq) (0.375 ml, 2.25 mmol) was added, the temperature was increased to 70° C. and stirring maintained for a further 3 days. Conc. HCl (0.500 ml, 5.85 mmol) was added and the resultant mixture was heated at 70° C. for 23 h. Additional conc. HCl (0.500 ml, 5.85 mmol) was added and heated at 70° C. for 6 h. conc. HCl (0.500 ml, 5.85 mmol) was added and heated at 70° C. for 16 h. The reaction mixture was allowed to cool to RT and then concentrated in vacuo. The solid was azeotroped with MeCN (3×10 ml) and then isolated by filtration to afford the title compound (79 mg, 0.153 mmol, 71% yield, 96% purity) as a light tan solid. UPLC-MS (Method 1): m/z 499.3 (M+H)$^+$, 497.2 (M−H)$^−$ at 1.61 min. $^1$H NMR (500 MHz, DMSO-d$_6$) δ 13.23 (br s, 1H), 10.14 (br s, 1H), 8.64 (s, 1H), 8.24 (d, J=1.9 Hz, 1H), 8.01 (dd, J=8.2, 1.9 Hz, 1H), 7.70 (d, J=8.2 Hz, 1H), 7.51 (br d, J=8.1 Hz, 1H), 7.18 (t, J=4.0 Hz, 1H), 7.15 (d, J=8.3 Hz, 1H), 6.81 (d, J=1.9 Hz, 1H), 6.72 (app. dd, J=4.1, 2.3 Hz, 1H), 2.79-2.66 (m, 1H), 2.21 (s, 3H), 1.12-1.06 (m, 2H), 0.92-0.84 (m, 2H).

Example 161: 3-(N-(4-chloro-5-cyano-2-(pyrrol-1-yl)phenyl)sulfamoyl)-4-cyclopropylbenzoic acid

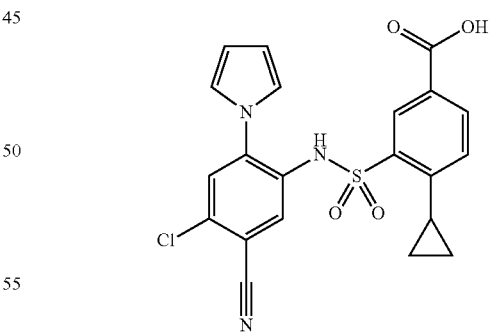

Step 1: Tert-butyl (5-chloro-4-cyano-2-nitrophenyl)carbamate: 4-amino-2-chloro-5-nitrobenzonitrile (0.5 g, 2.53 mmol) was dissolved in THF (2 ml) and cooled to 0° C. before the addition of 1 M LiHDMS in THF (2.5 ml, 2.50 mmol). The reaction mixture was allowed to warm to RT and stirred for 10 min then cooled to 0° C. before the addition of di-tert-butyl dicarbonate (0.6 g, 2.75 mmol). The resultant solution was allowed to warm to RT and stirred overnight. The reaction mixture was quenched by portionwise addition to a cooled solution of acetic acid (1 ml) in THF (4 ml). The reaction mixture was concentrated in vacuo and purified by chromatography on silica gel (40 g cartridge, 0-100% EtOAc/Isohexane) and then on silica gel (40 g cartridge, 0-100% DCM/Isohexane) to afford (443 mg, 1.49 mmol, 59% yield, 100%) as a white solid. UPLC-MS (Method 2): m/z 296.1 (M−H)⁻ at 1.70 min.

Step 2: Tert-butyl (2-amino-5-chloro-4-cyanophenyl)carbamate: A solution of the product from Step 1 above (443 mg, 1.49 mmol) in 1:1 EtOH/THF (10 ml) was treated with 5% Pd/C (Type 87L, 5% Pd, 60% water) (400 mg, 0.075 mmol). The solution was hydrogenated at a pressure of 1 bar for 6 h. The reaction mixture was filtered through Celite® and concentrated in vacuo onto silica. The crude product was purified by chromatography on silica gel (24 g cartridge, 0-100% EtOAc/isohexane) to afford the title compound (292 mg, 0.982 mmol, 66% yield, 90% purity) as a brown oil. UPLC-MS (Method 2): m/z 266.1 (M−H)⁻ at 1.41 min.

Step 3: Methyl 3-(N-(2-((tert-butoxycarbonyl)amino)-4-chloro-5-cyanophenyl)sulfamoyl)-4-cyclopropylbenzoate: The product from Example 132 Step 5 (150 mg, 0.519 mmol) was added to a solution of pyridine (130 μl, 1.61 mmol) and the product from Step 2 above (150 mg, 0.504 mmol, 90% purity) in DCM (1 ml). The resultant solution was stirred at RT for 2 days. The reaction mixture was concentrated in vacuo and purified by chromatography on silica gel (24 g cartridge, 0-100% Ethyl acetate/Isohexane) to afford the title compound (310 mg, 0.558 mmol, 111% yield, 91% purity) as a brown oil. UPLC-MS (Method 2): m/z 504.2 (M−H)⁻ at 1.53 min.

Step 4: 5-chloro-4-cyano-2-((2-cyclopropyl-5-(methoxycarbonyl)phenyl)sulfonamido)benzenaminium trifluoroacetate: The product from Step 3 above (310 mg, 0.558 mmol, 91% purity) was dissolved in DCM (3 ml) and treated with TFA (430 μl, 5.58 mmol). The resultant mixture was stirred at RT overnight. The mixture was treated with PhMe (2 ml) and concentrated in vacuo to afford (242 mg, 0.400 mmol, 72% yield, 86% purity) as an orange foam. UPLC-MS (Method 2): m/z 404.2 (M−H)⁻ at 1.19 min.

Step 5: Methyl 3-(N-(4-chloro-5-cyano-2-(pyrrol-1-yl)phenyl)sulfamoyl)-4-cyclopropylbenzoate: The product from Step 4 above (242 mg, 0.400 mmol, 86% purity) was combined with sodium acetate (50 mg, 0.610 mmol) and 2,5-dimethoxytetrahydrofuran (110 μl, 0.849 mmol) in AcOH (2 ml). The mixture was heated to 120° C. and the resultant clear solution was stirred for 1 h. The crude product was concentrated in vacuo onto silica and purified by chromatography on silica gel (24 g cartridge, 0-40% EtOAc/isohexane) to afford the title compound (84 mg, 0.162 mmol, 41% yield, 88% purity) as a brown oil. UPLC-MS (Method 2): m/z 456.4./458.6 (M+H)⁺, 454.2 (M−H)⁻ at 1.44 min.

Step 6: 3-(N-(4-chloro-5-cyano-2-(pyrrol-1-yl)phenyl)sulfamoyl)-4-cyclopropylbenzoic acid: 1 M LiOH(aq) (500 μl, 0.500 mmol) was added to a solution of the product from Step 5 above (84 mg, 0.162 mmol, 88% purity) in THF (1 ml). The reaction mixture was stirred at RT for 3 days and then concentrated in vacuo. The residue was dissolved in water (12 ml) and washed with EtOAc (12 ml). The aqueous phase was acidified using 1 M HCl(aq) until pH 4-5 and then extracted with EtOAc (2×12 ml). The combined organic phase was dried by passage through a phase separator and concentrated in vacuo. The crude product was purified by chromatography (24 g reverse phase cartridge, 15-65% MeCN/Water 0.1% Formic Acid) to afford the title compound (35 mg, 0.075 mmol, 46% yield, >95% purity) as a white solid. UPLC-MS (Method 1): m/z 442.6 (M+H)⁺, 440.2 (M−H)⁻ at 1.55 min. ¹H NMR (500 MHz, DMSO-d₆) δ 13.20 (br s, 1H), 10.41 (br s, 1H), 8.17 (d, J=1.9 Hz, 1H), 7.99 (dd, J=8.3, 1.9 Hz, 1H), 7.76 (s, 1H), 7.51 (s, 1H), 7.15-7.04 (m, 3H), 6.14 (t, J=2.2 Hz, 2H), 2.71-2.58 (m, 1H), 1.15-0.99 (m, 2H), 0.97-0.73 (m, 2H).

Example 162: 3-(N-(4-fluoro-2-(pyrrol-1-yl)-5-(trifluoromethyl)phenyl)sulfamoyl)-4-methoxybenzoic acid

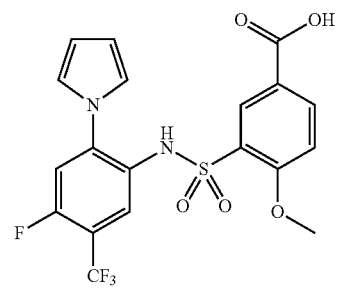

Step 1: Methyl 3-(N-(2-((tert-butoxycarbonyl)amino)-4-fluoro-5-(trifluoromethyl)phenyl)sulfamoyl)-4-methoxybenzoate: Methyl 3-(chlorosulfonyl)-4-methoxybenzoate (150 mg, 0.567 mmol) was added to a solution of pyridine (130 μl, 1.61 mmol) and the product of Example 130 Step 2 (214 mg, 0.509 mmol) in DCM (1 ml). The resultant solution was stirred at RT for 3 days. The reaction mixture was concentrated in vacuo and purified by chromatography on silica gel (24 g cartridge, 0-50% Ethyl acetate/Isohexane) to afford the title compound (350 mg, 0.509 mmol, 100% yield, 76% purity) as a red oil. UPLC-MS (Method 2): m/z 521.3 (M−H)⁻ at 1.42 min.

Step 2: 5-fluoro-2-((2-methoxy-5-(methoxycarbonyl)phenyl)sulfonamido)-4-(trifluoromethyl)benzenaminium trifluoroacetate: The product from Step 1 above (348 mg, 0.506 mmol, 76% purity) was dissolved in DCM (3 ml) and treated with TFA (480 μl, 6.23 mmol). The resultant mixture was stirred at RT overnight. The mixture was treated with PhMe (2 ml) and concentrated in vacuo to afford the title compound (273 mg, 0.438 mmol, 86% yield, 86% purity) as a brown solid. UPLC-MS (Method 2): m/z 423.3 (M+H)⁺, 421.3 (M−H)⁻ at 1.32 min.

Step 3: Methyl 3-(N-(4-fluoro-2-(pyrrol-1-yl)-5-(trifluoromethyl)phenyl)sulfamoyl)-4-methoxybenzoate: The product from Step 2 above (273 mg, 0.438 mmol, 86% purity) was combined with sodium acetate (72 mg, 0.878 mmol) and 2,5-dimethoxytetrahydrofuran (100 μl, 0.772 mmol) in AcOH (2 ml). The mixture was heated to 120° C. and the resultant clear solution was stirred for 1 h. The crude product was concentrated in vacuo onto silica and purified by chromatography on silica gel (24 g cartridge, 0-40% EtOAc/isohexane) to afford the title compound (170 mg, 0.255 mmol, 58% yield, 71% purity) as a brown oil. UPLC-MS (Method 2): m/z 473.3 (M+H)⁺, 471.2 (M−H)⁻ at 1.45 min.

Step 4: 3-(N-(4-fluoro-2-(pyrrol-1-yl)-5-(trifluoromethyl)phenyl)sulfamoyl)-4-methoxybenzoic acid: 1 M LiOH(aq) (770 μl, 0.770 mmol) was added to a solution of the product from Step 3 above (170 mg, 0.255 mmol, 71% purity) in THF (1.5 ml). The reaction mixture was stirred at RT overnight. Additional 1 M LiOH(aq) (770 μl, 0.770 mmol) was added and the solution was stirred at RT overnight. The reaction mixture was concentrated in vacuo. The residue was dissolved in water (12 ml) and washed with EtOAc (12 ml). The aqueous phase was acidified using 1 M HCl(aq) until pH 4-5 and then extracted with EtOAc (2×12 ml). The combined organic phases were dried by passage through a phase separator and concentrated in vacuo. The crude product was purified by chromatography (24 g reverse phase cartridge, 15-70% MeCN/Water 0.1% Formic Acid) to afford the title compound (59 mg, 0.122 mmol, 48% yield, >95% purity) as a white solid. UPLC-MS (Method 2): m/z 459.3 (M+H)$^+$, 457.2 (M−H)$^−$ at 1.49 min. $^1$H NMR (500 MHz, DMSO-d$_6$) δ 13.04 (br s, 1H), 9.90 (br s, 1H), 8.12 (dd, J=8.7, 2.2 Hz, 1H), 8.04 (d, J=2.2 Hz, 1H), 7.58 (d, J=11.4 Hz, 1H), 7.35 (d, J=7.3 Hz, 1H), 7.27 (d, J=8.8 Hz, 1H), 7.09 (t, J=2.2 Hz, 2H), 6.16 (t, J=2.2 Hz, 2H), 3.88 (s, 3H).

Example 163: 3-(N-(5-cyano-2-(thiazol-2-yl)phenyl)sulfamoyl)-4-cyclopropylbenzoic acid

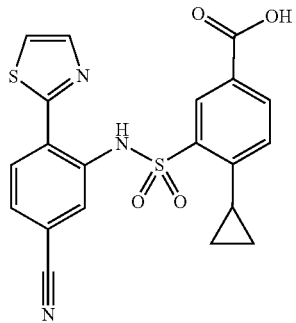 [SMILES: N#Cc1ccc(-c2nccs2)c(NS(=O)(=O)c2cc(C(=O)O)ccc2C2CC2)c1]

Step 1: 3-amino-4-(thiazol-2-yl)benzonitrile: To a reaction vessel containing the product from Example 152 Step 1 (252 mg, 0.650 mmol), 2-bromothiazole (0.061 ml, 0.677 mmol), 1 M K$_3$PO$_4$(aq) (1.13 ml, 1.13 mmol) and dioxane (4.52 ml) was added XPhos Pd G3 (28 mg, 0.033 mmol). The resultant reaction mixture was degassed with N$_2$ for 10 min and then heated to 80° C. for 3 h. Additional 2-bromothiazole (0.061 ml, 0.677 mmol) was added and heated at 80° C. for 16 h. The reaction mixture was concentrated in vacuo and the crude product was purified by chromatography on silica gel (12 g cartridge, 0-20% EtOAc/isohexane) to afford the title compound (61 mg, 0.302 mmol, 46% yield) as an orange solid. UPLC-MS (Method 1): m/z 202.3 (M+H)$^+$ (ES$^+$), at 1.34 min.

Step 2: Methyl 3-(N-(5-cyano-2-(thiazol-2-yl)phenyl)sulfamoyl)-4-cyclopropylbenzoate: A solution of the product from Step 1 above (60.7 mg, 0.302 mmol), the product from Example 132 Step 5 (92 mg, 0.317 mmol) and pyridine (0.120 ml, 1.49 mmol) in DCM (1.0 ml) was stirred at RT for 19 h. The reaction mixture was purified directly by chromatography on silica gel (12 g cartridge, 0-15%, 15-45% then 45-100% EtOAc/isohexane) to afford the title compound (69 mg, 0.157 mmol, 52% yield) as a cream solid. UPLC-MS (Method 1): m/z 440.3 (M+H)$^+$, 438.2 (M−H)$^−$ at 1.71 min.

Step 3: 3-(N-(5-cyano-2-(thiazol-2-yl)phenyl)sulfamoyl)-4-cyclopropylbenzoic acid: 1 M LiOH(aq) (0.630 ml, 0.630 mmol) was added to a solution of the product from Step 2 above (68.9 mg, 0.157 mmol) in THF (1.26 ml) at RT. The resultant mixture was stirred at RT over the weekend. The reaction mixture was concentrated in vacuo. The residue was diluted with water (7 ml) and then washed with TBME (7 ml). The aqueous phase was acidified using 1 M HCl(aq) until pH 4-5 and then extracted with EtOAc (2×7 ml). The combined organic phase was dried by passage through a phase separator and concentrated in vacuo. The crude product was purified by chromatography (24 g reverse phase cartridge, 15-80% MeCN/Water 0.1% Formic Acid) to afford the title compound (52 mg, 0.121 mmol, 77% yield, 99% purity) as an off-white solid. UPLC-MS (Method 1): m/z 426.3 (M+H)$^+$, 424.3 (M−H)$^−$ at 1.55 min. $^1$H NMR (500 MHz, DMSO-d$_6$) δ 13.35 (br s, 1H), 12.66 (br s, 1H), 8.49 (d, J=1.8 Hz, 1H), 8.21-8.09 (m, 2H), 8.05 (br s, 1H), 7.99 (br d, J=8.2 Hz, 1H), 7.76-7.44 (m, 2H), 7.08 (br d, J=8.2 Hz, 1H), 2.71-2.54 (m, 1H), 0.89-0.80 (m, 2H), 0.77-0.67 (m, 2H).

Example 164: 3-(N-(2-(5-chlorothiophen-2-yl)-5-(5-methylisoxazol-4-yl)phenyl)sulfamoyl)-4-cyclopropylbenzoic acid

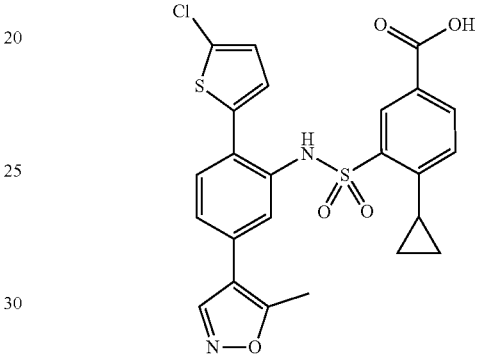

Step 1: Methyl 3-(N-(2-(5-chlorothiophen-2-yl)-5-(5-methylisoxazol-4-yl)phenyl)sulfamoyl)-4-cyclopropylbenzoate: A solution of 2-(5-chlorothiophen-2-yl)-5-(5-methylisoxazol-4-yl)aniline (INTERMEDIATE-25) (72.7 mg, 0.25 mmol) in DCM (2 ml) and pyridine (0.061 ml, 0.750 mmol) was treated with a solution of the product from Example 132 Step 5 (82 mg, 0.300 mmol) in DCM (0.5 ml) and the resultant mixture was stirred at RT for 3.5 days. The reaction mixture was diluted with 4.5 M NH$_4$OH(aq) (1 ml), dried by passage through a phase separator and purified by chromatography on silica gel (12 g cartridge, 0-50% EtOAc/isohexane) to afford the title compound (119 mg, 0.218 mmol, 87% yield, 97% purity) as a yellow gum. UPLC-MS (Method 1): m/z 529.3 (M+H)$^+$, 527.3 (M−H)$^−$ at 1.78 min.

Step 2: 3-(N-(2-(5-chlorothiophen-2-yl)-5-(5-methylisoxazol-4-yl)phenyl)sulfamoyl)-4-cyclopropylbenzoic acid: To a solution of the product from Step 1 above (119 mg, 0.225 mmol, 97% purity) in dioxane (5 ml) was added 6 M HCl(aq) (0.375 ml, 2.25 mmol) and the mixture was heated at 55° C. for 5 h. Additional 6 M HCl(aq) (0.375 ml, 2.25 mmol) was added, the temperature was increased to 70° C. and stirring maintained for a further 3 days. Conc. HCl (0.500 ml, 5.85 mmol) was added and the resultant mixture was heated at 70° C. for 23 h. Additional conc. HCl (0.500 ml, 5.85 mmol) was added and heated at 70° C. for 6 h. conc. HCl (0.500 ml, 5.85 mmol) was added and heated at 70° C. for 16 h. The reaction mixture was allowed to cool to RT and then concentrated in vacuo. The solid was azeotroped with MeCN (3×10 ml) and then isolated by filtration. The crude product and filtrate were combined and purified by chromatography (24 g reverse phase cartridge, 15-80% MeCN/Water 0.1% Formic Acid) to afford the title compound (62 mg, 0.120 mmol, 55% yield, 99% purity) as an off-white solid. UPLC-MS (Method 1): m/z 515.2 (M+H)$^+$, 513.1

(M–H)⁻ at 1.68 min. ¹H NMR (500 MHz, DMSO-d₆) δ 13.22 (br s, 1H), 10.17 (br s, 1H), 8.66 (s, 1H), 8.24 (br s, 1H), 8.01 (br d, J=8.2 Hz, 1H), 7.71 (d, J=8.2 Hz, 1H), 7.59-7.44 (m, 1H), 7.35 (d, J=4.0 Hz, 1H), 7.14 (br d, J=8.3 Hz, 1H), 7.09 (d, J=4.0 Hz, 1H), 6.85 (br s, 1H), 2.79-2.65 (m, 1H), 2.23 (s, 3H), 1.14-1.02 (m, 2H), 0.93-0.81 (m, 2H).

Example 165: 3-(N-(5-cyano-2-(pyridazin-3-yl)phenyl)sulfamoyl)-4-cyclopropylbenzoic acid

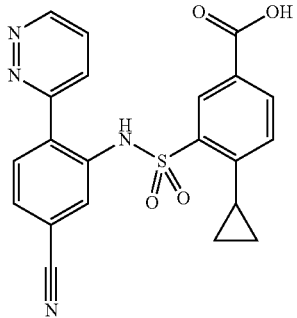 [SMILES: N#Cc1ccc(-c2cccnn2)c(NS(=O)(=O)c2cc(C(=O)O)ccc2C2CC2)c1]

Step 1: 3-amino-4-(pyridazin-3-yl)benzonitrile: To a reaction vessel containing the product from Example 152 Step 1 (236 mg, 0.445 mmol), 3-bromopyridazine (80 mg, 0.503 mmol), 1 M K₃PO₄(aq) (760 µl, 0.760 mmol) and dioxane (5 ml) was added [Pd(dppf)Cl₂] DCM complex (20 mg, 0.024 mmol). The resultant reaction mixture was degassed with N₂ for 10 min and then heated to 80° C. for 1 h. The reaction mixture was filtered through Celite® and concentrated in vacuo onto silica. The crude product was purified by chromatography on silica gel (24 g cartridge, 0-100% EtOAc/isohexane) to afford the title compound (34 mg, 0.173 mmol, 39% yield) as a brown solid. UPLC-MS (Method 2): m/z 197.3 (M+H)⁺, at 0.80 min.

Step 2: Methyl 3-(N-(5-cyano-2-(pyridazin-3-yl)phenyl)sulfamoyl)-4-cyclopropylbenzoate: The product from Example 132 Step 5 (52 mg, 0.180 mmol) was added to a solution of pyridine (42 µl, 0.519 mmol) and the product from Step 1 above (34 mg, 0.173 mmol) in DCM (0.5 ml). The resultant solution was stirred at RT for 3 days. The reaction mixture was concentrated in vacuo and purified by chromatography on silica gel (12 g cartridge, 0-50% Ethyl acetate/Isohexane) to afford the title compound (42 mg, 0.095 mmol, 55% yield, 98% purity) as a yellow solid. UPLC-MS (Method 2): m/z 435.4 (M+H)⁺, 433.2 (M–H)⁻ at 1.13 min.

Step 3: 3-(N-(5-cyano-2-(pyridazin-3-yl)phenyl)sulfamoyl)-4-cyclopropylbenzoic acid: 1 M LiOH(aq) (300 µl, 0.300 mmol) was added to a solution of the product from Step 2 above (42 mg, 0.095 mmol, 98% purity) in THF (0.6 ml). The reaction mixture was stirred at RT overnight. The reaction mixture was concentrated in vacuo. The residue was dissolved in water (12 ml) and washed with EtOAc (12 ml). The aqueous phase was acidified using 1 M HCl(aq) until pH 4-5 and then extracted with EtOAc (2×12 ml) with THF (5 ml) added to solubilise the product. The combined organic phase was dried by passage through a phase separator and concentrated in vacuo to afford (27 mg, 0.061 mmol, 64% yield, >95% purity) as an off white solid. UPLC-MS (Method 1): m/z 421.4 (M+H)⁺, 419.3 (M–H)⁻ at 1.25 min. ¹H NMR (500 MHz, DMSO-d₆) δ 13.31 (br s, 1H), 12.08 (br s, 1H), 9.28 (dd, J=5.0, 1.5 Hz, 1H), 8.28 (d, J=1.9 Hz, 1H), 8.18 (dd, J=8.7, 1.6 Hz, 1H), 8.04 (d, J=8.1 Hz, 1H), 7.95 (dd, J=8.2, 1.9 Hz, 1H), 7.88 (dd, J=8.7, 5.0 Hz, 1H), 7.80 (d, J=8.2 Hz, 1H), 7.71 (d, J=1.6 Hz, 1H), 7.04 (d, J=8.3 Hz, 1H), 2.53-2.52 (m, 1H), 0.91-0.79 (m, 2H), 0.75-0.65 (m, 2H).

Example 166: 3-(N-(2-(5-chlorothiophen-2-yl)-5-cyano-4-fluorophenyl)sulfamoyl)-4-cyclopropylbenzoic acid

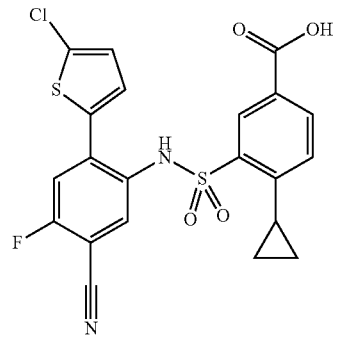 [SMILES: N#Cc1cc(NS(=O)(=O)c2cc(C(=O)O)ccc2C2CC2)c(-c2ccc(Cl)s2)cc1F]

Step 1: 5-amino-4-(5-chlorothiophen-2-yl)-2-fluorobenzonitrile: To a mixture of 5-amino-4-bromo-2-fluorobenzonitrile (100 mg, 0.465 mmol), (5-chlorothiophen-2-yl)boronic acid (227 mg, 1.40 mmol), and PdCl₂[P(Cy)₃]₂ (17.2 mg, 0.023 mmol) in dioxane (4 ml) in a microwave vial was added 1 M K₃PO₄(aq) (0.465 ml, 0.465 mmol). The resultant mixture was degassed with N₂ for 15 min, then sealed. The reaction mixture was stirred with microwave heating at 100° C. for 30 min, then at 110° C. for 30 min, then at 130° C. for 30 min, then at 130° C. for a further 90 min. The reaction mixture was cooled and filtered through Celite®, washed with EtOAc (5 ml), and the filtrate was concentrated in vacuo. The crude product was purified by chromatography on silica gel (40 g cartridge, 0-100% DCM/isohexane) to afford the title compound (114 mg, 0.329 mmol, 71% yield, 73% purity) as a yellow solid. UPLC-MS (Method 2): m/z no ionisation at 1.59 min. ¹H NMR (500 MHz, DMSO-d₆) δ 7.40 (d, J=10.2 Hz, 1H), 7.36 (d, J=4.0 Hz, 1H), 7.23 (d, J=4.0 Hz, 1H), 7.16 (d, J=6.0 Hz, 1H). Two exchangeable protons not observed.

Step 2: Methyl 3-(N-(2-(5-chlorothiophen-2-yl)-5-cyano-4-fluorophenyl)sulfamoyl)-4-cyclopropylbenzoate: To a mixture of the product from Step 1 above (114 mg, 0.329 mmol, 73% purity) and the product from Example 132 Step 5 (95 mg, 0.346 mmol) in DCM (700 µL) at RT was added pyridine (173 µl, 2.14 mmol). The resultant solution was stirred at RT for 5 days then concentrated in vacuo. The crude product was purified by chromatography on silica gel (24 g cartridge, 0-100% EtOAc/isohexane) to afford the title compound (106 mg, 0.149 mmol, 45% yield, 69% purity) as a yellow gum. UPLC-MS (Method 2): m/z 489.2 (M–H)⁻ at 1.47 min.

Step 3: 3-(N-(2-(5-chlorothiophen-2-yl)-5-cyano-4-fluorophenyl)sulfamoyl)-4-cyclopropylbenzoic acid: A mixture of methyl 3the product from Step 2 above (106 mg, 0.216 mmol, 69% purity) and LiOH (21.1 mg, 0.864 mmol) in THF/MeOH/water (4:1:1, 4 ml) was stirred at RT overnight. The reaction was concentrated in vacuo and the residue was adjusted to ~pH 4 with 1 M HCl(aq). The precipitate was filtered, washed with water and dried to give an orange gum. The crude product was purified by chromatography on silica gel (40 g cartridge, 0-10% MeOH/DCM) and then by preparative HPLC (Waters, Acidic (0.1% Formic acid), Acidic, Waters X-Select Prep-C18, 5 μm, 19×50 mm column, 20-50% MeCN in Water) to afford the title compound (30 mg, 0.060 mmol, 28% yield, 95% purity) as a pale yellow powder. UPLC-MS (Method 2): m/z 475.1 (M–H)⁻ at 1.09 min. ¹H NMR (500 MHz, DMSO-$d_6$) δ 13.22 (s, 1H), 10.35 (s, 1H), 8.22 (s, 1H), 8.01 (d, J=8.2 Hz, 1H), 7.96 (d, J=10.7 Hz, 1H), 7.61 (d, J=4.1 Hz, 1H), 7.19 (d, J=6.3 Hz, 1H), 7.14 (d, J=4.1 Hz, 1H), 7.10 (d, J=8.4 Hz, 1H), 2.72-2.61 (m, 1H), 1.05 (d, J=7.4 Hz, 2H), 0.91-0.81 (m, 2H).

Example 167: 4-cyclopropyl-3-(N-(5-(5-methylisoxazol-4-yl)-2-(pyridin-3-yl)phenyl)sulfamoyl) benzoic acid

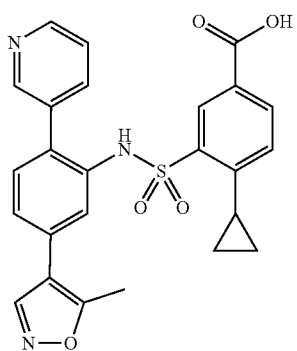 [SMILES: Cc1oncc1-c1ccc(-c2cccnc2)c(NS(=O)(=O)c2cc(C(=O)O)ccc2C2CC2)c1]

Step 1: Methyl 4-cyclopropyl-3-(N-(5-(5-methylisoxazol-4-yl)-2-(pyridin-3-yl)phenyl)sulfamoyl)benzoate: To a solution of 5-(5-methylisoxazol-4-yl)-2-(pyridin-3-yl)aniline (INTERMEDIATE-9) (17 mg, 0.068 mmol) and the product from Example 132 Step 5 (22.3 mg, 0.081 mmol) in DCM (2.5 ml) was added pyridine (0.016 ml, 0.203 mmol) and the mixture was stirred at RT for 4 days. The reaction mixture was diluted with 4.5 M NH₄OH(aq) (1 ml), dried by passage through a phase separator and concentrated in vacuo. The crude product was purified by chromatography on silica gel (12 g cartridge, 0-100% EtOAc/isohexane) to afford the title compound (22 mg, 0.045 mmol, 66% yield) as a colourless solid. UPLC-MS (Method 1): m/z 490.4 (M+H)⁺, 488.3 (M–H)⁻ at 1.16 min.

Step 2: 4-cyclopropyl-3-(N-(5-(5-methylisoxazol-4-yl)-2-(pyridin-3-yl)phenyl)sulfamoyl)benzoic acid: To a solution of the product from Step 1 above (22 mg, 0.045 mmol) in dioxane (2 ml) was added 6 M HCl(aq) (0.075 ml, 0.449 mmol) and the mixture was heated at 55° C. for 5 h. Additional 6 M HCl(aq) (0.375 ml, 2.25 mmol) was added, the temperature was increased to 70° C. and stirring maintained for a further 3 days. Conc. HCl (0.200 ml, 2.34 mmol) was added and the resultant mixture was heated at 70° C. for 23 h. Additional conc. HCl (0.100 ml, 1.17 mmol) was added and heated at 70° C. for 5.5 h. Additional conc. HCl (0.100 ml, 1.17 mmol) was added and heated at 70° C. for 18 h. The reaction mixture was allowed to cool to RT and then concentrated in vacuo. The resultant solid was azeotroped with MeOH (5 ml) and then MeCN (3×5 ml). The solid was triturated with MeCN (2 ml), isolated by filtration and then washed with MeCN (5 ml) to afford the title compound (16 mg, 0.033 mmol, 73% yield, 98% purity) as a light tan solid. UPLC-MS (Method 1): m/z 476.3 (M+H)⁺, 474.2 (M–H)⁻ at 1.00 min. ¹H NMR (500 MHz, DMSO-$d_6$) δ 13.24 (br s, 1H), 10.19 (br s, 1H), 8.75 (br s, 1H), 8.74-8.71 (m, 1H), 8.71-8.66 (m, 1H), 8.18-8.14 (m, 1H), 8.13-8.04 (m, 1H), 8.01-7.94 (m, 1H), 7.79-7.64 (m, 1H), 7.59 (d, J=7.9 Hz, 1H), 7.51 (d, J=8.0 Hz, 1H), 7.12-7.05 (m, 2H), 2.62-2.55 (m, 1H), 2.33 (s, 3H), 1.14-0.97 (m, 2H), 0.92-0.75 (m, 2H).

Example 168: 3-(N-(5-cyano-2-(pyridin-2-yl)phenyl)sulfamoyl)-4-cyclobutylbenzoic acid

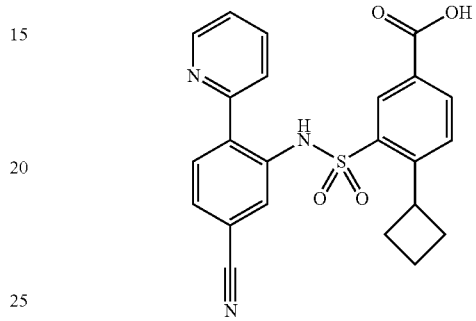

Step 1: methyl 4-bromo-3-(N-(5-cyano-2-(pyridin-2-yl)phenyl)sulfamoyl)benzoate: A mixture of the product from Example 83 Step 1 (260 mg, 1.33 mmol), the product from Example 55 Step 3 (464 mg, 1.47 mmol) and pyridine (350 μl, 4.33 mmol) in DCM (6 ml) was stirred at 35° C. overnight. The mixture concentrated in vacuo onto silica and purified by chromatography on silica gel (24 g cartridge, 0-100% EtOAc/isohexane) and triturated with TBME to afford the title compound (494 mg, 1.05 mmol, 79% yield) as a yellow solid. UPLC-MS (Method 2): m/z 472.3 (M+H)⁺, 470.2 (M–H)⁻ at 1.61 min.

Step 2: Methyl 3-(N-(5-cyano-2-(pyridin-2-yl)phenyl)sulfamoyl)-4-cyclobutylbenzoate: To a flame-dried flask was added Mg turnings (154 mg, 6.35 mmol) and iodine (10 mg, 0.039 mmol). A small portion (~0.5 ml) of a solution of bromocyclobutane (400 μl, 4.25 mmol) in THF (4 ml) was added and the mixture was heated to reflux with a heat gun. Once the brown colour disappeared the remaining solution was added at a rate that reflux was maintained. Upon complete addition the mixture was stirred at RT for 30 min. The mixture was slowly added to 2 M $ZnCl_2$ in methyltetrahydrofuran (3.2 ml, 6.40 mmol) at 0° C. and then warmed to RT and stirred for 1 h. A solution of the product from Step 1 above (200 mg, 0.423 mmol) in THF (2 ml) and $PdCl_2$ (dppf)·DCM (69 mg, 0.084 mmol) were added and the mixture was heated to 70° C. for 4 h and then at RT overnight. The mixture was quenched with saturated NH4Cl (aq) (20 ml) and extracted with EtOAc (3×20 ml). The combined organic phase was washed with brine (20 ml), dried by passage through a phase separator and concentrated in vacuo. The residue was loaded onto silica and purified by chromatography on silica gel (24 g cartridge, 0-10% MeOH/DCM) to afford the title compound (222 mg, 0.377 mmol, 89% yield, 76% purity) as a brown solid. UPLC-MS (Method 1):m/z 448.4 (M+H)⁺, 446.1 (M–H)⁻ at 1.77 min.

Step 3: 3-(N-(5-cyano-2-(pyridin-2-yl)phenyl)sulfamoyl)-4-cyclobutylbenzoic acid: A mixture of the product from Step 2 above (222 mg, 0.377 mmol, 76% purity) and LiOH (65 mg, 1.52 mmol) in THF/MeOH/water (4:1:1, 6 ml) was stirred at 40° C. overnight. The mixture was diluted with water (10 ml), acidifed to ~pH 4 with 1 M HCl(aq) and extracted with EtOAc (3×20 ml). The combined organic phase was washed with brine (15 ml), dried by passage through a phase separator and concentrated in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (63 mg, 0.143 mmol, 38% yield, 99% purity) as pale yellow solid. UPLC-MS (Method 1): m/z 434.4 (M+H)$^+$, 432.3 (M−H)$^−$ at 1.61 min. $^1$H NMR (500 MHz, DMSO-$d_6$) δ 13.34 (s, 2H), 8.82 (d, J=4.9 Hz, 1H), 8.29 (d, J=1.8 Hz, 1H), 8.11-8.05 (m, 2H), 8.05-8.00 (m, 2H), 7.78 (d, J=8.2 Hz, 1H), 7.74 (d, J=1.8 Hz, 1H), 7.66 (d, J=8.2 Hz, 1H), 7.59-7.53 (m, 1H), 4.07-3.95 (m, 1H), 2.06-1.95 (m, 2H), 1.95-1.87 (m, 2H), 1.84-1.70 (m, 2H).

Example 169: 3-(N-(5-cyano-2-(pyrimidin-2-yl) phenyl)sulfamoyl)-4-cyclopropylbenzoic acid

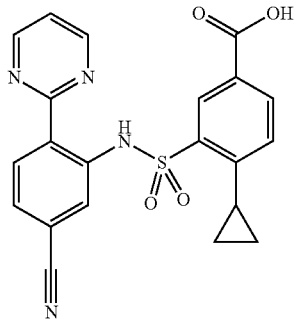 [SMILES: N#Cc1ccc(-c2ncccn2)c(NS(=O)(=O)c2cc(C(=O)O)ccc2C2CC2)c1]

Step 1: 3-amino-4-(pyrimidin-2-yl)benzonitrile: To a reaction vessel containing the product from Example 152 Step 1 (685 mg, 1.26 mmol), 2-bromopyrimidine (220 mg, 1.38 mmol), 1 M K$_3$PO$_4$(aq) (2.2 ml, 2.20 mmol) and dioxane (10 ml) was added [Pd(dppf)Cl$_2$].DCM (52 mg, 0.064 mmol). The resultant reaction mixture was degassed with N$_2$ for 10 min and then heated to 80° C. for 1 h. The reaction mixture was filtered through Celite® and concentrated in vacuo onto silica. The crude product was purified by chromatography on silica gel (24 g cartridge, 0-100% EtOAc/isohexane) then on silica gel (24 g cartridge, 0-5% MeOH/DCM) to afford the title compound (129 mg, 0.605 mmol, 48% yield, 92% purity) as a bright yellow solid. UPLC-MS (Method 2): m/z 197.3 (M+H)$^+$, at 1.1 min.

Step 2: Methyl 3-(N-(5-cyano-2-(pyrimidin-2-yl)phenyl)sulfamoyl)-4-cyclopropylbenzoate: The product from Example 132 Step 5 (200 mg, 0.692 mmol) was added to a solution of pyridine (160 μl, 1.99 mmol) and the product from Step 1 above (129 mg, 0.605 mmol, 92% purity) in DCM (1 ml). The resultant solution was stirred at RT overnight. The reaction mixture was concentrated in vacuo and purified by chromatography on silica gel (12 g cartridge, 0-100% Ethyl acetate/Isohexane) to afford the title compound (201 mg, 0.245 mmol, 41% yield, 53% purity) as a white solid. UPLC-MS (Method 2): m/z 435.4 (M+H)$^+$, 433.2 (M−H)$^−$ at 1.57 min.

Step 3: 3-(N-(5-cyano-2-(pyrimidin-2-yl)phenyl)sulfamoyl)-4-cyclopropylbenzoic acid: 1 M LiOH(aq) (740 μl, 0.740 mmol) was added to a solution of the product from Step 2 above (201 mg, 0.245 mmol, 53% purity) in THF (1.5 ml). The reaction mixture was stirred at RT overnight. The reaction mixture was concentrated in vacuo. The residue was dissolved in water (12 ml) and washed with EtOAc (12 ml). The aqueous phase was acidified with 1 M HCl(aq) until pH 4-5 and then extracted with EtOAc (2×12 ml), with THF (5 ml) added to solubilise the product. The combined organic phase was dried by passage through a phase separator and concentrated in vacuo. The crude product was purified by chromatography (24 g reverse phase cartridge, 5-40% MeCN/10 mM Ammonium Bicarbonate) to afford the title compound (84 mg, 0.190 mmol, 77% yield, >95% purity) as a pale green solid. UPLC-MS (Method 1): m/z 421.5 (M+H)$^+$, 419.2 (M−H)$^−$ at 1.46 min. $^1$H NMR (500 MHz, DMSO-$d_6$) δ 13.3 (br s, 1H), 9.06 (d, J=4.9 Hz, 2H), 8.56-8.42 (m, 2H), 7.94 (dd, J=8.2, 1.9 Hz, 1H), 7.75 (d, J=1.7 Hz, 1H), 7.64 (t, J=5.0 Hz, 1H), 7.61-7.55 (m, 1H), 7.02 (d, J=8.2 Hz, 1H), 2.72-2.62 (m, 1H), 0.89-0.77 (m, 2H), 0.72-0.60 (m, 2H). One exchangeable proton not observed.

Example 170: 3-(N-(5-cyano-2-(isothiazol-3-yl) phenyl)sulfamoyl)-4-cyclopropylbenzoic acid

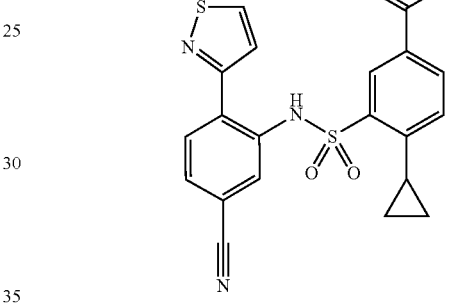

Step 1: 3-amino-4-(isothiazol-3-yl)benzonitrile: To a reaction vessel containing the product from Example 152 Step 1 (236 mg, 0.706 mmol), 3-bromoisothiazole (127 mg, 0.776 mmol), 1 M K$_3$PO$_4$(aq) (1.24 ml, 1.24 mmol) and dioxane (4.96 ml) was added XPhos Pd G3 (30 mg, 0.035 mmol). The resultant reaction mixture was degassed with N$_2$ for 10 min and then heated to 80° C. for 2 h. The reaction mixture was allowed to cool to RT, filtered through Celite©, washed with MeOH (10 ml) and then concentrated in vacuo. The crude product was purified by chromatography on silica gel (12 g cartridge, 0-25% EtOAc/isohexane) to afford the title compound (104 mg, 0.511 mmol, 72% yield, 99% purity) as a yellow solid. UPLC-MS (Method 1): m/z 202.2 (M+H)$^+$ (ES$^+$), at 1.26 min. $^1$H NMR (500 MHz, DMSO-$d_6$) δ 9.17 (d, J=4.8 Hz, 1H), 8.02 (d, J=4.8 Hz, 1H), 7.94 (d, J=8.1 Hz, 1H), 7.19 (d, J=1.7 Hz, 1H), 7.14 (br s, 2H), 6.97 (dd, J=8.1, 1.7 Hz, 1H).

Step 2: Methyl 3-(N-(5-cyano-2-(isothiazol-3-yl)phenyl)sulfamoyl)-4-cyclopropylbenzoate: A solution of the product from Step 1 above (100 mg, 0.492 mmol, 99% purity), the product from Example 132 Step 5 (149 mg, 0.517 mmol) and pyridine (0.200 ml, 2.47 mmol) in DCM (3 ml) was stirred at RT for 4 days. Additional product from Example 132 Step 5 (78 mg, 0.271 mmol) and pyridine (0.200 ml, 2.47 mmol) were added and the reaction stirred at RT for 4 h. The reaction mixture was purified directly by chromatography on silica gel (12 g cartridge, 0-50% EtOAc/isohexane, followed by 3% MeOH/DCM flush) to afford the title compound (107 mg, 0.245 mmol, 50% yield) as a yellow solid. UPLC-MS (Method 1): m/z 440.4 (M+H)$^+$, 438.2 (M−H)$^−$ at 1.67 min.

Step 3: 3-(N-(5-cyano-2-(isothiazol-3-yl)phenyl)sulfamoyl)-4-cyclopropylbenzoic acid: 1 M LiOH(aq) (0.970 ml, 0.970 mmol) was added to a suspension of the product from Step 2 above (106 mg, 0.241 mmol) in THF (1.94 ml) at RT. The resultant solution was stirred at RT for 17 h. The reaction mixture was concentrated in vacuo. The residue was diluted with water (6 ml) and then washed with TBME (6 ml). The aqueous phase was acidified with 1 M HCl(aq) until pH 4-5 and then EtOAc (6 ml) and THF (4 ml) were added. The aqueous phase was separated and extracted with EtOAc (2×6 ml). The combined organic phase was dried by passage through a phase separator and concentrated in vacuo to afford the title compound (88 mg, 0.203 mmol, 84% yield, 98% purity) as a cream solid. UPLC-MS (Method 1): m/z 426.3 (M+H)$^+$, 424.2 (M–H)$^-$ at 1.51 min. $^1$H NMR (500 MHz, DMSO-d$_6$) δ 13.34 (br s, 1H), 12.06 (br s, 1H), 9.26 (d, J=4.9 Hz, 1H), 8.43 (d, J=1.8 Hz, 1H), 8.19 (d, J=8.1 Hz, 1H), 8.08 (d, J=4.9 Hz, 1H), 7.97 (dd, J=8.2, 1.9 Hz, 1H), 7.70-7.66 (m, 2H), 7.06 (d, J=8.3 Hz, 1H), 2.58-2.52 (m, 1H), 0.86-0.76 (m, 2H), 0.72-0.66 (m, 2H).

Example 171: 3-(N-(4-chloro-5-(methylsulfonyl)-2-(pyridin-2-yl)phenyl)sulfamoyl)-4-cyclopropylbenzoic acid

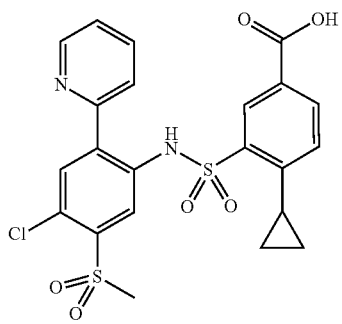 [SMILES: CS(=O)(=O)c1cc(NS(=O)(=O)c2cc(C(=O)O)ccc2C2CC2)c(-c2ccccn2)cc1Cl]

Part A; Preparation of Intermediate 38; 4-chloro-5-(methylsulfonyl)-2-(pyridin-2-yl)aniline

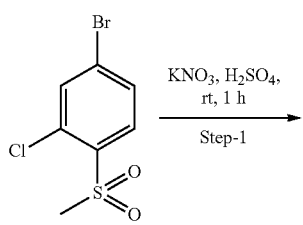

CAS: 648905-09-3

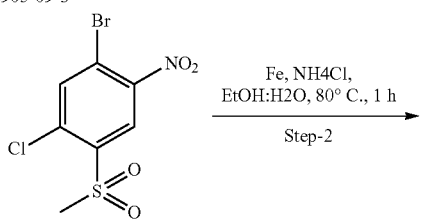

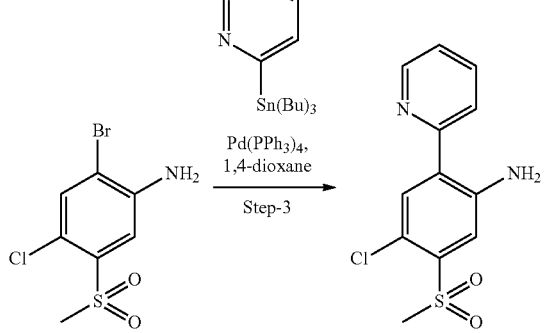

Step-1: Synthesis of 1-bromo-5-chloro-4-(methylsulfonyl)-2-nitrobenzene. To a solution of 4-bromo-2-chloro-1-(methylsulfonyl)benzene (5 g, 0.0185 mol, 1 eq) in H$_2$SO$_4$ (50 mL) was added potassium nitrate (5.6 g, 0.055 mol, 3 eq) at 0° C. The reaction mixture was stirred at room temperature for 1 h and quenched with sat solution of NaHCO$_3$ (500 mL) and extracted with EtOAc (3×100 mL). The combined organic layer was dried over sodium sulphate and concentrated under reduced pressure to give title nitrobenzene as a brown solid (5 g, 86.15%).

Step-2: Synthesis of 2-bromo-4-chloro-5-(methylsulfonyl)aniline. To a solution of Step-1 nitrobenzene (3.0 g, 0.00959 mol, 1 eq) in ethanol: water (50:50 mL) was added Fe powder (2.67 g, 0.0477 mol, 5 eq) and NH$_4$Cl (2.5 g, 0.0477 mol, 5 eq). The reaction mixture was stirred at 80° C. for 1 h, cooled, poured into water (120 mL) and filtered through a celite bed. The filtrate was extracted with EtOAc (3×50 mL). The combined organic layer was dried over sodium sulphate and concentrated under reduced pressure to give title aniline (3.2 g, quantitative). UPLC-MS (Method 1) m/z 282.3/284.3 (M+H)$^+$ at 1.69 min. $^1$H NMR (500 MHz, DMSO-d$_6$) δ 7.74 (d, 1H), 7.49 (d, 1H), 6.09 (s, 2H), 3.31 (s, 3H).

Step-3; Synthesis of 4-chloro-5-(methylsulfonyl)-2-(pyridin-2-yl)aniline. A mixture of Step-2 aniline (1 g, 0.00353 mol, 1 eq) and 2-(tributylstannyl)pyridine (1.04 g, 0.00282 mole, 0.8 eq) in dioxane (10 mL) was purged with N$_2$ for 25 min at room temperature. Tetrakis (0.205 g, 0.000176 mole, 0.05 eq) was added. The resulting reaction mixture was stirred at 120° C. for 1 h in microwave irradiation, cooled, diluted with water (25 mL) and extracted with ethyl acetate (3×25 mL). The combined organic layer was washed with brine (10 mL), dried over anhydrous Na$_2$SO$_4$. The solvent was evaporated under reduced pressure. The resulting crude material was triturated using dichlormethane (20 mL) and pentane (20 mL) to give title aniline as an off white (1 g, 50.18%). UPLC-MS (Method 1) m/z 283.3/285.3 (M+H)$^+$ at 1.81 min. $^1$H NMR (500 MHz, DMSO-d$_6$) δ 8.68 (d, 1H), 7.95 (m, 2H), 7.85 (s, 1H), 7.55 (s, 1H), 7.42 (m, 1H), 7.24 (s, 2H), 3.35 (s, 3H).

Part B; Step 1: Methyl 3-(N-(4-chloro-5-(methylsulfonyl)-2-(pyridin-2-yl)phenyl)sulfamoyl)-4-cyclopropylbenzoate The product from Example 132 Step 5 (107 mg, 0.371 mmol) was dissolved in pyridine (1 ml, 12.4 mmol) and stirred for 5 min. 4-chloro-5-(methylsulfonyl)-2-(pyridin-2-yl)aniline (INTERMEDIATE-38) (100 mg, 0.354 mmol) was added to the solution and then the resultant mixture was stirred at RT for 40 h. The solid was isolated by filtration, washed with DCM (3 ml) and then dried in vacuo to afford the title compound (114 mg, 0.217 mmol, 61% yield, 99% purity) as a yellow solid. UPLC-MS (Method 1): m/z 521.2 (M+H)⁺, 519.1 (M−H)⁻ at 1.58 min.

Step 2: 3-(N-(4-chloro-5-(methylsulfonyl)-2-(pyridin-2-yl)phenyl)sulfamoyl)-4-cyclopropylbenzoic acid: 1 M LiOH(aq) (0.870 ml, 0.870 mmol) was added to a suspension of the product from Step 1 above (114 mg, 0.217 mmol) in THF (1.74 ml) at RT. The resultant solution was stirred at RT for 20 h. The reaction mixture was concentrated in vacuo. The residue was diluted with water (6 ml) and then washed with TBME (6 ml). The aqueous phase was acidified with 1 M HCl(aq) until pH 4-5 and then extracted with EtOAc (3×6 ml). The combined organic phase was dried by passage through a phase separator, concentrated in vacuo and the solid was slurried in MeCN and concentrated in vacuo. The crude product was suspended in water (3 ml) and then dissolved in 1 M LiOH(aq). The aqueous phase was acidified using 1 M HCl until pH 4-5 and the solid was isolated by filtration and dried in vacuo to afford the title compound (82 mg, 0.160 mmol, 74% yield, 99% purity) as a yellow solid. UPLC-MS (Method 1): m/z 507.2 (M+H)⁺, 505.1 (M−H)⁻ at 1.43 min. ¹H NMR (500 MHz, DMSO-d₆) δ 13.24 (br s, 2H), 8.79-8.71 (m, 1H), 8.39 (d, J=1.9 Hz, 1H), 8.24 (br s, 1H), 8.20-8.10 (m, 2H), 8.04 (br t, J=7.9 Hz, 1H), 7.94 (dd, J=8.3, 1.9 Hz, 1H), 7.56 (br t, J=6.3 Hz, 1H), 7.01 (d, J=8.3 Hz, 1H), 3.33 (s, 3H), 2.57-2.52 (m, 1H), 0.79-0.73 (m, 2H), 0.68-0.62 (m, 2H).

Example 172: 4-cyclopropyl-3-(N-(4-fluoro-5-(methylsulfonyl)-2-(pyridin-2-yl)phenyl)sulfamoyl)benzoic acid

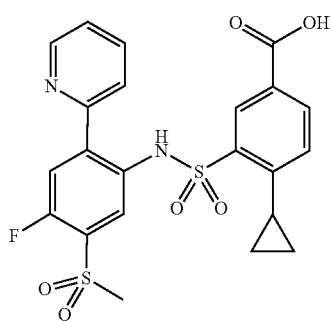 [SMILES: CS(=O)(=O)c1cc(NS(=O)(=O)c2cc(C(=O)O)ccc2C2CC2)c(-c2ccccn2)cc1F]

Part A; Preparation of intermediate 37; 4-fluoro-5-(methylsulfonyl)-2-(pyridin-2-yl)aniline

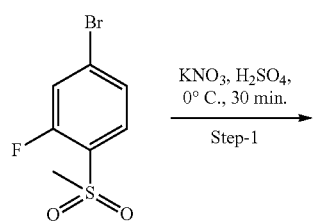

CAS No. 648904-84-1

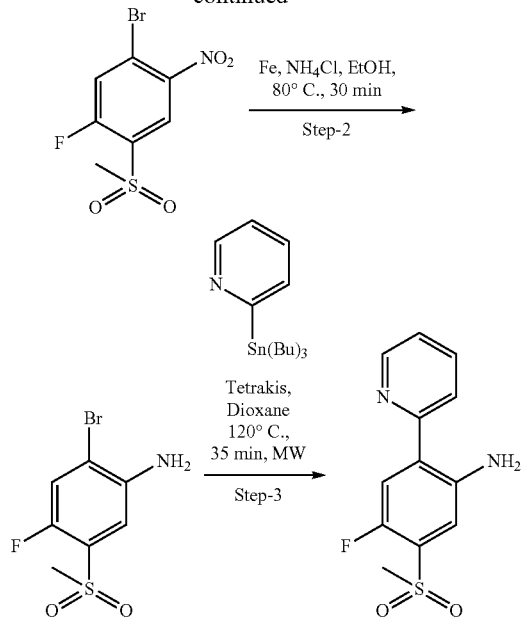

Step-1: Synthesis of 1-bromo-5-fluoro-4-(methylsulfonyl)-2-nitrobenzene. To a stirred solution of 4-bromo-2-fluoro-1-(methylsulfonyl)benzene (5 g, 0.0198 mol, 1 eq) in conc.H₂SO₄ (50 mL, 10 Vol) was added potassium nitrate (6.01 g, 0.059 mol, 3 eq) portion wise at 0° C. The reaction mixture was stirred at 0° C. for 30 min, then poured into ice cold water (200 mL). The precipitated solid was filtered washed with water (100 mL). The solid material was dried under vacuum to get title nitrobenzene as white solid (6.2 g, quantitative).

Step-2: Synthesis of 2-bromo-4-fluoro-5-(methylsulfonyl)aniline. Step-1 nitrobenzene (3 g, 0.0101 mole, 1 eq), iron powder (2.83 g, 0.051 mole, 5.0 eq) and ammonium chloride (2.70 g, 0.051 mole, 5 eq) in ethanol: water (5:1) (30 mL) was stirred at 80° C. for 30 min. The mixture was cooled, diluted with water (50 mL) and filtered through celite. The filtrate was extracted with ethyl acetate (3×50 mL). The combined organic layer was washed with brine (30 mL), dried over anhydrous Na₂SO₄. The solvent was evaporated under reduced pressure to give title aniline as a brown solid (2.69 g, 92.70%). UPLC-MS (Method 1) m/z 266.3/268.3 (M+H)⁺ at 1.72 min. ¹H NMR (500 MHz, DMSO-d₆) δ 7.65 (d, 1H), 7.26 (d, 1H), 5.76 (s, 2H), 3.20 (s, 3H).

Step-3: Synthesis of 4-fluoro-5-(methylsulfonyl)-2-(pyridin-2-yl)aniline. To a solution of Step-2 nitrobenzene (0.5 g, 0.00187 mol, 1 eq) in dioxane (8 mL) was added 2-(tributylstannyl)pyridine (1.037 g, 0.00280 mol, 1.5 eq) at room temperature. The reaction mixture was purged with N₂ for 15 min and tetrakis (0.535 g, 0.0000935 mol, 0.05 eq) was added. The resulting reaction mixture was stirred at 120° C. for 45 min in microwave, cooled, diluted with water (200 mL) and extracted with ethyl acetate (3×50 mL). The combined organic layer was washed with brine (100 mL), dried over anhydrous Na₂SO₄ and concentrated under reduced pressure. The resulting crude material was purified by combi flash on neutral allumina using 23% ethyl acetate in hexane as eluent to give title aniline as an off white solid (0.940 g, 37.75%). UPLC-MS (Method 1) m/z 267.3 (M+H)⁺ at 2.59 min. ¹H NMR (500 MHz, DMSO-d₆) δ 8.67 (d, 1H), 7.94 (m, 2H), 7.72 (d, 1H), 7.40 (m, 1H), 7.29 (d, 1H), 6.96 (s, 2H), 3.35 (s, 3H).

Part B; Step 1: Methyl 4-cyclopropyl-3-(N-(4-fluoro-5-(methylsulfonyl)-2-(pyridin-2-yl)phenyl)sulfamoyl)benzoate The product from Example 132 Step 5 (114 mg, 0.394 mmol) was dissolved in pyridine (1 ml, 12.4 mmol) and stirred for 5 min. 4-fluoro-5-(methylsulfonyl)-2-(pyridin-2-yl)aniline (INTERMEDIATE-37) (100 mg, 0.376 mmol) was added to the solution and then the resultant mixture was stirred at RT for 4 days. The solid was isolated by filtration, washed with DCM (3 ml) and then dried in vacuo to afford (145 mg, 0.285 mmol, 76% yield, 99% purity) as a pale yellow solid. UPLC-MS (Method 1): m/z 505.3 (M+H)⁺, 503.1 (M−H)⁻ at 1.51 min.

Step 2: 4-cyclopropyl-3-(N-(4-fluoro-5-(methylsulfonyl)-2-(pyridin-2-yl)phenyl)sulfamoyl)benzoic acid: 1 M LiOH (aq) (1.14 ml, 1.14 mmol) was added to a suspension of the product from Step 1 above (145 mg, 0.285 mmol, 99% purity) in THF (2.28 ml) at RT. The resultant solution was stirred at RT for 17 h. The reaction mixture was concentrated in vacuo. The residue was diluted with water (7 ml) and then washed with TBME (7 ml). The aqueous phase was acidified with 1 M HCl(aq) until pH 4-5 and then EtOAc (7 ml) and THF (7 ml) were added. The aqueous phase was separated and extracted with EtOAc (2×7 ml). The combined organic phase was dried by passage through a phase separator and concentrated in vacuo to afford the title compound (132 mg, 0.263 mmol, 92% yield, 98% purity) as a bright yellow solid. UPLC-MS (Method 1): m/z 491.3 (M+H)⁺, 489.1 (M−H)⁻ at 1.36 min. ¹H NMR (500 MHz, DMSO-d₆) δ 13.22 (br s, 1H), 12.81 (br s, 1H), 8.76-8.67 (m, 1H), 8.28 (d, J=1.9 Hz, 1H), 8.07 (d, J=11.1 Hz, 1H), 8.01 (dd, J=5.9, 1.8 Hz, 2H), 7.94-7.88 (m, 2H), 7.56-7.47 (m, 1H), 6.97 (d, J=8.3 Hz, 1H), 3.31 (s, 3H), 2.56-2.50 (m, 1H), 0.81-0.74 (m, 2H), 0.67-0.59 (m, 2H).

Example 173: 4-(tert-butyl)-3-(N-(5-cyano-2-(pyridin-2-yl)phenyl)sulfamoyl) benzoic acid

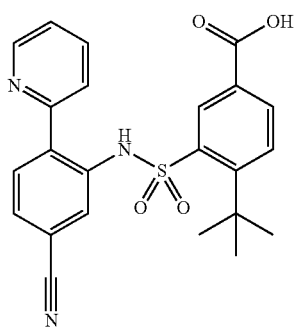 [SMILES: CC(C)(C)c1ccc(C(=O)O)cc1S(=O)(=O)Nc1cc(C#N)ccc1-c1ccccn1]

Step 1: 3-bromo-4-(tert-butyl)benzoic acid: To a mixture of 4-(tert-butyl)benzoic acid (10.0 g, 56.1 mmol), nitric acid (37 ml), water (28 ml), AcOH (170 ml) and bromine (5.20 ml, 101 mmol) was added silver nitrate (9.63 g, 56.7 mmol) in water (29 ml) via a dropping funnel over 30 min. Upon complete addition the mixture was stirred at RT overnight. The mixture was poured onto ice-water and stirred until all the ice melted. The precipitate was isolated by filtration, dissolved in EtOAc (600 ml), then sequentially washed with water (200 ml) and brine (200 ml). The organic phase was passed through a phase separator and then concentrated in vacuo to afford the title compound (13.4 g, 21.9 mmol, 39% yield, 42% purity) as a yellow solid. UPLC-MS (Method 1): m/z 255.1 (M−H)⁻ at 1.73 min.

Step 2: methyl 3-bromo-4-(tert-butyl)benzoate: A mixture of the product from Step 1 above (13.4 g, 21.9 mmol, 42% purity), iodomethane (2.70 ml, 43.4 mmol) and K₂CO₃ (6.06 g, 43.8 mmol) in DMF (20 ml) was stirred at RT for 2 h. The mixture was filtered and then the filtrate was concentrated in vacuo. The residue was dissolved in DCM (100 ml) and washed using 1 M HCl(aq) (100 ml) and brine (3×100 ml). The organic phase was passed through a phase separator and concentrated onto silica gel and purified by chromatography on silica gel (80 g cartridge, 0-10% EtOAc/isohexane) and by chromatography (330 g reverse phase C18 cartridge, 35-95% MeCN/0.1% v/v formic acid(aq)) to afford the title compound (4.19 g, 15.0 mmol, 68% yield, 97% purity) as a pale yellow oil. UPLC-MS (Method 1) m/z no ionisation at 1.98 min. ¹H NMR (500 MHz, DMSO-d₆) δ 8.09 (d, J=1.9 Hz, 1H), 7.88 (dd, J=8.3, 1.9 Hz, 1H), 7.63 (d, J=8.3 Hz, 1H), 3.85 (s, 3H), 1.48 (s, 9H).

Step 3: methyl 3-(benzylthio)-4-(tert-butyl)benzoate: A mixture of the product from Step 2 above (4.19 g, 15.0 mmol, 97% purity), DIPEA (5.50 ml, 31.5 mmol), Pd₂(dba)₃ (1.38 g, 1.51 mmol) and XantPhos (1.30 g, 2.25 mmol) in dioxane (70 ml) was sparged with N₂ for 15 min. Benzyl mercaptan (1.90 ml, 16.1 mmol) was added and the mixture was heated to 100° C. and stirred for 18 h and then at RT over the weekend. Additional benzyl mercaptan (1.90 ml, 16.1 mmol) was added and the mixture was heated to 100° C. and stirred for 5 h. Additional Pd₂(dba)₃ (1.38 g, 1.51 mmol) and XantPhos (1.30 g, 2.25 mmol) were added and stirring at 100° C. was continued overnight. Additional DIPEA (5.50 ml, 31.5 mmol) was added and stirring at 100° C. was continued overnight. Upon cooling to RT the mixture was filtered through Celite®, concentrated onto silica gel and purified by chromatography on silica gel (120 g cartridge, 0-100% DCM/isohexane) to afford the title compound (1.18 g, 2.85 mmol, 19% yield, 76% purity) as a pale yellow oil. UPLC-MS (Method 1): m/z 315.2 (M+H)⁺, 313.2 (M−H)⁻ at 2.06 min.

Step 4: methyl 4-(tert-butyl)-3-(chlorosulfonyl)benzoate: To a solution of the product from Step 3 above (1.18 g, 2.85 mmol, 76% purity) in AcOH (0.21 ml), water (1.5 ml) and MeCN (20 ml) at −10° C. was added 1,3-dichloro-5,5-dimethylimidazolidine-2,4-dione (843 mg, 4.28 mmol). The resultant mixture was stirred at −10° C. for 2 h. The mixture was concentrated to ~5 ml and extracted with DCM (2×40 ml). The organic phases were combined, passed through a phase separator, concentrated onto silica gel, and purified by chromatography on silica gel (40 g cartridge, 0-100% DCM/isohexane) to afford the title compound (697 mg, 2.28 mmol, 80% yield, 95% purity) as a white solid. ¹H NMR (500 MHz, DMSO-d₆) δ 8.76 (d, J=2.2 Hz, 1H), 7.79 (dd, J=8.3, 2.2 Hz, 1H), 7.55 (d, J=8.3 Hz, 1H), 3.84 (s, 3H), 1.53 (s, 9H).

Step 5: 3-amino-4-(pyridin-2-yl)benzonitrile: A mixture of 3-amino-4-bromobenzonitrile (1.35 g, 6.85 mmol), Pd(PPh₃)₄ (792 mg, 0.685 mmol), 2-(tributylstannyl)pyridine (3.33 ml, 10.3 mmol) in dioxane (5 ml) was placed under three vacuum-N₂ cycles before sparging with N₂ for 5 min. The reaction was heated at 80° C. for 16 h. The resultant mixture was allowed to cool to RT and then concentrated onto silica gel and purified by chromatography on silica gel (40 g cartridge, 0-10% EtOAc/DCM). The solid was triturated with TBME/isohexane (1:3) to afford the title compound (1.08 g, 5.48 mmol, 80% yield, 99% purity) as an orange solid. UPLC-MS (Method 1) m/z 196.2 (M+H)⁺ at 1.00 min. ¹H NMR (500 MHz, DMSO-d₆) δ 8.66 (ddd, J=4.9, 1.9, 0.9 Hz, 1H), 7.94 (td, J=7.8, 1.9 Hz, 1H), 7.88 (dt, J=8.2, 1.1 Hz, 1H), 7.74 (d, J=8.1 Hz, 1H), 7.39 (ddd, J=7.4, 4.9, 1.2 Hz, 1H), 7.15 (d, J=1.7 Hz, 1H), 7.04-6.91 (m, 3H).

Step 6: methyl 4-(tert-butyl)-3-(N-(5-cyano-2-(pyridin-2-yl)phenyl)sulfamoyl)benzoate: A mixture of the product from Step 4 above (233 mg, 761 μmol, 95% purity), the product from Step 5 above (100 mg, 507 μmol, 99% purity) and pyridine (122 μL, 1.52 mmol) in DCM (2 ml) was heated to 35° C. and stirred for 3 days. The mixture was concentrated onto silica gel and purified by chromatography on silica gel (12 g cartridge, 0-100% EtOAc/isohexane) to afford the title compound (119 mg, 251 μmol, 50% yield, 95% purity) as a pale-yellow solid. UPLC-MS (Method 1) m/z 450.4 (M+H)$^+$, 448.3 (M–H)$^-$ at 1.81 min.

Step 7: 4-(tert-butyl)-3-(N-(5-cyano-2-(pyridin-2-yl)phenyl)sulfamoyl)benzoic acid: A mixture of the product from Step 6 above (119 mg, 251 μmol, 95% purity) and LiOH (42 mg, 1.00 mmol) in THF/MeOH/water (4:1:1, 4.2 ml) was stirred at 40° C. overnight. The mixture was diluted with water (5 ml), acidified to ~pH 4 using 1 M HCl(aq), and extracted with EtOAc (3×15 ml). The organic phases were combined, washed with brine (10 ml), passed through a phase separator, and concentrated in vacuo. The residue was loaded onto silica gel and purified by chromatography on silica gel (12 g cartridge, 0-100% EtOAc/isohexane) to afford the title compound (15 mg, 32.8 μmol, 13% yield, 96% purity) as a light-yellow solid. UPLC-MS (Method 1) m/z 436.4 (M+H)$^+$, 434.3 (M–H)$^-$ at 1.65 min. $^1$H NMR (500 MHz, DMSO-d$_6$) δ 13.18 (s, 1H), 13.15 (s, 1H), 8.70 (d, J=4.9 Hz, 1H), 8.31 (s, 1H), 8.11 (d, J=8.2 Hz, 1H), 8.05-7.99 (m, 2H), 7.96 (dd, J=8.6, 1.8 Hz, 1H), 7.78-7.71 (m, 2H), 7.70 (d, J=8.2 Hz, 1H), 7.54-7.50 (m, 1H), 1.46 (s, 9H).

Example 175: 4-cyano-3-(N-(5-cyano-2-(pyridin-2-yl)phenyl)sulfamoyl)benzoic acid

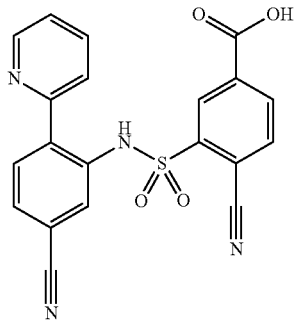 [SMILES: N#Cc1ccc(-c2ccccn2)c(NS(=O)(=O)c2cc(C(=O)O)ccc2C#N)c1]

Step 1: methyl 3-(benzylthio)-4-cyanobenzoate: A mixture of methyl 3-bromo-4-cyanobenzoate (1 g, 4.17 mmol), Pd$_2$(dba)$_3$ (0.37 g, 1.58 mmol), DIPEA (1.5 ml, 8.59 mmol) and dioxane (12 ml) was sparged with N$_2$ for 15 min before benzyl mercaptan (0.52 ml, 4.4 mmol) was added. The mixture was heated to 100° C. and stirred overnight. Upon cooling to RT, the mixture was filtered through Celite®. The filtrate was loaded onto silica and purified by chromatography on silica gel (40 g cartridge, 0-50% DCM/isohexane followed by 0-30% EtOAc/isohexane) to afford the title compound (878 mg, 2.94 mmol, 71% yield, 95% purity) as an orange solid. $^1$H NMR (500 MHz, DMSO-d$_6$) δ 8.06-8.03 (m, 1H), 7.96 (d, J=8.0 Hz, 1H), 7.87-7.80 (m, 1H), 7.45-7.39 (m, 2H), 7.37-7.31 (m, 2H), 7.30-7.24 (m, 1H), 4.48 (s, 2H), 3.90 (s, 3H).

Step 2: methyl 3-(chlorosulfonyl)-4-cyanobenzoate: To a solution of the product from Step 1 above (878 mg, 2.94 mmol, 95% purity), acetic acid (170 μl, 2.97 mmol) and water (340 μl) in MeCN (15 ml) at –10° C. was added 1,3-dichloro-5,5-dimethylimidazolidine-2,4-dione (870 mg, 4.42 mmol) in 4 portions. The mixture was stirred at –10° C. for 2 h. The mixture was concentrated in vacuo to ~2 ml, diluted with water (20 ml) and extracted with DCM (2×30 ml). The combined organic extracts were passed through a phase separator and the solvent removed in vacuo. The residue was loaded onto silica and purified by chromatography on silica gel (40 g cartridge, 0-100% DCM/isohexane) to afford the title compound (562 mg, 2.06 mmol, 70% yield, 95% purity) as a brown solid. $^1$H NMR (500 MHz, DMSO-d$_6$) δ 8.39 (d, J=1.7 Hz, 1H), 8.02 (dd, J=7.9, 1.7 Hz, 1H), 7.96 (d, J=7.9 Hz, 1H), 3.91 (s, 3H).

Step 3: Methyl 4-cyano-3-(N-(5-cyano-2-(pyridin-2-yl)phenyl)sulfamoyl)benzoate: The product from Step 2 above (150 mg, 549 μmol, 95% purity) was added to a solution of pyridine (120 μl, 1.49 mmol) and the product from Example 173 Step 5 (100 mg, 507 μmol, 99% purity) in DCM (1 ml). The resultant solution was stirred at RT for 3 days. The reaction mixture was concentrated onto silica and purified by chromatography on silica gel (12 g cartridge, 0-100% EtOAc/DCM) to afford the title compound (140 mg, 278 μmol, 55% yield, 83% purity) as a pale brown solid. UPLC-MS (Method 1) m/z 419.4 (M+H)$^+$ at 1.47 min.

Step 4: 4-cyano-3-(N-(5-cyano-2-(pyridin-2-yl)phenyl)sulfamoyl)benzoic acid: To a solution of the product from Step 3 above (140 mg, 278 μmol, 83% purity) in THF (1.8 ml) was added 1 M LiOH(aq) (900 μl, 900 μmol). The reaction mixture was stirred at RT for 2 h, concentrated in vacuo to remove THF and then acidified to pH 4-5 using 1 M HCl(aq). A precipitate formed and was collected by filtration to afford the title compound (114 mg, 276 μmol, 100% yield, 98% purity) as a yellow solid. UPLC-MS (Method 2) m/z 405.4 (M+H)$^+$ at 0.70 min. $^1$H NMR (500 MHz, DMSO-d$_6$) δ 13.92 (br s, 1H), 13.21 (br s, 1H), 8.62 (d, J=4.9 Hz, 1H), 8.18-8.16 (m, 1H), 8.16-8.12 (m, 1H), 8.01 (t, J=8.4 Hz, 2H), 7.96-7.89 (m, 2H), 7.81 (dd, J=14.5, 8.1 Hz, 2H), 7.46 (dd, J=7.6, 5.0 Hz, 1H).

Example 176: 3-(N-(5-cyano-3-methyl-2-(pyridin-2-yl)phenyl)sulfamoyl)-4-cyclopropylbenzoic acid

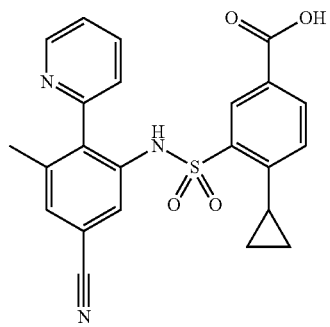 [SMILES: Cc1cc(C#N)cc(NS(=O)(=O)c2cc(C(=O)O)ccc2C2CC2)c1-c1ccccn1]

Step 1: 4-bromo-3-methyl-5-nitrobenzonitrile: To a mixture of 4-bromo-3-methylbenzonitrile (10.0 g, 51.0 mmol) and concentrated sulfuric acid (32 ml), cooled in an ice-bath at –10° C., was added a mixture of concentrated sulfuric acid (38 ml) and concentrated nitric acid (38 ml), dropwise over 1 h. The temperature of the reaction was maintained below 15° C. during this addition. The reaction was stirred for 4 h and then poured into water (80 ml) to afford a yellow precipitate which was isolated by filtration. The solid was azeotroped with MeCN (3×50 ml) and then purified by chromatography on silica gel (80 g cartridge, 10-30% TBME/isohexane) to afford a 2:1 mixture of regioisomers (10 g) with the desired as the major. A sample (1 g) was purified by chromatography on silica gel (80 g cartridge, 10% TBME/isohexane) to afford the title compound (710 mg, 2.89 mmol, 6% yield, 98% purity). Another sample (1.5 g) was purified by chromatography on silica gel (80 g cartridge, 10% TBME/isohexane) to afford the title compound (1.00 g, 4.15 mmol, 8% yield). $^1$H NMR (500 MHz, CDCl$_3$) δ 7.83 (s, 1H), 7.73 (s, 1H), 2.61 (s, 3H).

Step 2: 3-methyl-5-nitro-4-(pyridin-2-yl)benzonitrile: A mixture of the product from Step 1 above (330 mg, 1.34 mmol, 98% purity), Pd(PPh$_3$)$_4$ (155 mg, 0.134 mmol), pyridin-2-ylzinc(II) bromide (0.5 M in THF) (8.05 ml, 4.03 mmol) in dioxane (15 ml, 175 mmol) was sparged with N$_2$ for 5 min. The reaction was heated at 100° C. for 16 h. The reaction was allowed to cool to RT and diluted with EtOAc (50 ml). The organic phase was washed with water (50 ml), dried over MgSO$_4$, filtered, and concentrated in vacuo. The residue was purified by chromatography on silica gel (24 g cartridge, 0-50% then 50% EtOAc/isohexane) to afford the title compound (70 mg, 0.246 mmol, 18% yield, 84% purity) as a yellow solid. UPLC-MS (Method 6) m/z 240.6 (M+H)$^+$ at 0.56 min.

Step 3: 3-amino-5-methyl-4-(pyridin-2-yl)benzonitrile: To a mixture of the product from Step 2 above (70 mg, 0.246 mmol, 84% purity) and NH$_4$Cl (15.8 mg, 0.295 mmol) in IPA (10 ml) and water (3 ml) was added iron (137 mg, 2.46 mmol). The reaction mixture was heated at 90° C. for 4 h. The suspension was cooled to RT, filtered through Celite® and concentrated in vacuo. The residue was dissolved in 0.1 M HCl(aq) (100 ml) and washed with EtOAc (50 ml). The aqueous phase was neutralised with saturated NaHCO$_3$(aq) (50 ml) and extracted with EtOAc (5×50 ml). The organic phases were combined, dried over MgSO$_4$, filtered, and concentrated in vacuo to afford the title compound (35 mg, 0.161 mmol, 66% yield, 96% purity) as a brown oil. UPLC-MS (Method 7) m/z 210.7 (M+H)$^+$ at 0.50 min.

Step 4: methyl 3-(N-(5-cyano-3-methyl-2-(pyridin-2-yl)phenyl)sulfamoyl)-4-cyclopropylbenzoate: To a solution of the product from Step 3 above (35 mg, 0.161 mmol, 96% purity) and pyridine (67 μl, 0.825 mmol) in DCM (5 ml) was added the product from Example 132 Step 5 (58 mg, 0.201 mmol, 95% purity) at 0° C. The mixture was allowed to warm to RT and stirred at RT for 19 h. The reaction mixture was diluted with DCM (50 ml) and washed with aqueous 0.5 M HCl(aq) (2×50 ml), water (50 ml) and brine (50 ml). The organic phase was dried over MgSO$_4$, filtered, and concentrated in vacuo. The crude product was purified by chromatography on silica gel (12 g cartridge, 0-15%, 15-45% then 45-100% EtOAc/isohexane) to afford the title compound (59 mg, 0.131 mmol, 81% yield, 99% purity) as a cream solid. UPLC-MS (Method 7) m/z 448.4 (M–H)$^-$ at 0.65 min.

Step 5: 3-(N-(5-cyano-3-methyl-2-(pyridin-2-yl)phenyl)sulfamoyl)-4-cyclopropylbenzoic acid: LiOH (9.40 mg, 392 μmol) in water (1 ml) was added to a solution of the product from Step 4 above (59 mg, 131 μmol, 99% purity) in THF (3 ml) at RT and stirred for 24 h. The reaction mixture was concentrated in vacuo to remove THF. The residue was acidified with 10% w/v citric acid(aq) and the precipitate was isolated by filtration, washed with water (5 ml) and dried in vacuo to afford the title compound (18 mg, 40.5 μmol, 31% yield, 97% purity) as a white solid. UPLC-MS (Method 2) m/z 434.4 (M–H)$^-$ at 0.84 min. $^1$H NMR (500 MHz, DMSO-d$_6$) δ 13.23 (s, 1H), 9.93 (s, 1H), 8.54-8.49 (m, 1H), 8.14 (s, 1H), 7.97 (d, J=8.0 Hz, 1H), 7.76-7.67 (m, 2H), 7.42 (d, J=1.6 Hz, 1H), 7.34-7.27 (m, 1H), 7.10 (d, J=7.8 Hz, 1H), 7.03 (d, J=8.2 Hz, 1H), 2.47-2.39 (m, 1H), 2.00 (s, 3H), 0.97-0.90 (m, 2H), 0.79-0.72 (m, 2H).

Example 177: 3-(N-(2-(5-chlorothiophen-2-yl)-5-cyano-3-methylphenyl)sulfamoyl)-4-cyclopropylbenzoic acid

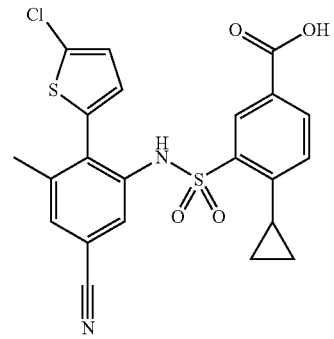 [SMILES: Cc1cc(C#N)cc(NS(=O)(=O)c2cc(C(=O)O)ccc2C2CC2)c1-c1ccc(Cl)s1]

Step 1: 4-(5-chlorothiophen-2-yl)-3-methyl-5-nitrobenzonitrile: To a mixture of Example 176 Step 1 (320 mg, 1.33 mmol), K$_3$PO$_4$ (507 mg, 2.39 mmol), (5-chlorothiophen-2-yl)boronic acid (647 mg, 3.98 mmol) in 1,4-dioxane (10 ml) and water (1 ml), was added PdCl$_2$[P(Cy)$_3$]$_2$ (49 mg, 66.4 μmol). The resultant mixture was sparged with N$_2$ for 10 min and then heated at 80° C. for 16 h. The reaction mixture was allowed to cool to RT, filtered through Celite®, washed with EtOAc (5 ml) and concentrated in vacuo. The residue was dissolved in EtOAc (100 ml) and then washed with saturated NaHCO$_3$(aq) (50 ml) and water (50 ml). The organic phase was dried over MgSO$_4$, filtered, and concentrated in vacuo. The crude product was purified by chromatography on silica gel (24 g cartridge, 0-20% EtOAc/isohexane) to afford the title compound (90 mg, 299 μmol, 23% yield, 93% purity) as a pale-yellow solid. UPLC-MS (Method 7) m/z 279.4 (M+H)$^+$ at 0.72 min. $^1$H NMR (500 MHz, CDCl$_3$) δ 7.93 (s, 1H), 7.78 (s, 1H), 6.97 (d, J=3.8 Hz, 1H), 6.75 (d, J=3.8 Hz, 1H), 2.40 (s, 3H).

Step 2: 3-amino-4-(5-chlorothiophen-2-yl)-5-methylbenzonitrile: To a mixture of the product from Step 1 above (90 mg, 299 μmol, 93% purity) and NH$_4$Cl (22.4 mg, 418 μmol) in IPA (3 ml) and water (1 ml) was added iron (167 mg, 2.99 mmol). The reaction mixture was heated at 90° C. for 20 h. The suspension was cooled to RT, filtered through Celite®, washed with MeOH (10 ml) and concentrated in vacuo. The residue was dissolved in saturated NaHCO$_3$(aq) (50 ml) and extracted with DCM (5×50 ml). The organic phases were combined, dried over MgSO$_4$, filtered, and concentrated in vacuo to afford the title compound (58 mg, 218 μmol, 73% yield, 93% purity) as a pale brown oil. UPLC-MS (Method 7) m/z no ionisation at 0.70 min. $^1$H NMR (500 MHz, CDCl$_3$) δ 7.00 (d, J=3.8 Hz, 1H), 6.94 (s, 1H), 6.86 (s, 1H), 6.75 (d, J=3.8 Hz, 1H), 2.17 (s, 3H), 1.80-1.52 (br s, 2H).

Step 3: methyl 3-(N-(2-(5-chlorothiophen-2-yl)-5-cyano-3-methylphenyl)sulfamoyl)-4-cyclopropylbenzoate: To a solution of the product from Step 2 above (58 mg, 218 μmol, 93% purity) and pyridine (78 μL, 966 μmol) in dry DCM (5 ml) was added the product from Example 132 Step 5 (69 mg, 239 μmol, 95% purity) at 0° C. The mixture was allowed to warm to RT and stirred at RT for 30 h. The reaction mixture was diluted with DCM (50 ml) and washed with aqueous 0.5 M HCl(aq) (2×50 ml), water (50 ml) and brine (50 ml). The organic phase was dried over MgSO$_4$, filtered, and concentrated in vacuo. The crude product was purified by chromatography on silica gel (12 g cartridge, 0-15%, 15-45% then 45-100% EtOAc/isohexane) to afford the title compound (75 mg, 134 μmol, 62% yield, 87% purity) as a cream solid. UPLC-MS (Method 1) m/z 485.3 (M−H)⁻ at 1.83 min.

Step 4: 3-(N-(2-(5-chlorothiophen-2-yl)-5-cyano-3-methylphenyl)sulfamoyl)-4-cyclopropylbenzoic acid: LiOH (9.65 mg, 403 μmol) in water (1 ml) was added to a solution of the product from Step 3 above (75 mg, 134 μmol, 87% purity) in THF (3 ml) at RT and stirred for 24 h. The reaction mixture was concentrated in vacuo to remove THF. The residue was acidified with 10% w/v citric acid(aq) and the precipitate was isolated by filtration, washed with water (3 ml) and dried in vacuo. The solid was dissolved in MeCN (3 ml) and stirred at 0° C. for 2 h. The solid was isolated by filtration and dried in vacuo to afford the title compound (14 mg, 28.3 μmol, 21% yield, 94% purity) as a white solid. UPLC-MS (Method 1) m/z 471.2 (M−H)⁻ at 0.72 min. ¹H NMR (500 MHz, DMSO-d$_6$) δ 13.22 (s, 1H), 10.06 (s, 1H), 8.20 (s, 1H), 8.02 (d, J=8.2 Hz, 1H), 7.72 (s, 1H), 7.47-7.38 (m, 1H), 7.10 (d, J=8.3 Hz, 1H), 7.00 (d, J=3.8 Hz, 1H), 6.67 (d, J=3.8 Hz, 1H), 2.62-2.53 (m, 1H), 2.13 (s, 3H), 1.06-0.98 (m, 2H), 0.88-0.79 (m, 2H).

Example 178: 3-(N-(4-chloro-5-cyano-2-(thiazol-4-yl)phenyl)sulfamoyl)-4-cyclopropylbenzoic acid

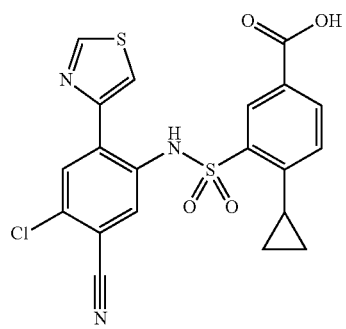 [SMILES: N#Cc1cc(NS(=O)(=O)c2cc(C(=O)O)ccc2C2CC2)c(-c2cscn2)cc1Cl]

Step 1: 5-amino-2-chloro-4-(4,4,5,5-tetramethyl-1,3,2-dioxaborolan-2-yl)benzonitrile: A mixture of the product from Example 132 Step 2 (740 mg, 3.04 mmol, 95% purity), bis(pinacolato)diboron (770 mg, 3.03 mmol), KOAc (900 mg, 9.17 mmol) and Pd(dppf)Cl$_2$ (220 mg, 301 μmol) in dioxane (5 ml) was placed under three vacuum-N$_2$ cycles before bubbling with N$_2$ gas for 5 min. The reaction was heated at 80° C. overnight. The reaction mixture was allowed to cool to RT, concentrated onto silica and purified by chromatography on silica gel (24 g cartridge, 0-50% EtOAc/isohexane) to afford the title compound (330 mg, 1.06 mmol, 35% yield, 90% purity) as a yellow solid. UPLC-MS (Method 1) m/z 197.6 (M+H+2H$_2$O-pinacol)⁺ at 0.98 min.

Step 2: 5-amino-2-chloro-4-(thiazol-4-yl)benzonitrile: The product from step 1 above (100 mg, 322 μmol, 90% purity), 4-bromothiazole (32 μl, 0.36 mmol), 1 M K$_3$PO$_4$(aq) (550 μl, 550 μmol) and dioxane (3 ml) was treated with [Pd(dppf)Cl$_2$]-DCM complex (13 mg, 15.9 μmol). The resultant solution was degassed with N$_2$ for 10 min, then heated at 80° C. for 1 h. The reaction mixture was concentrated onto silica and purified by chromatography on silica gel (24 g cartridge, 0-50% EtOAc/isohexane) to afford the title compound (85 mg, 322 μmol, quant. yield, 89% purity) as a yellow solid. UPLC-MS (Method 1) m/z 235.8 (M+H)⁺ at 1.35 min.

Step 3: Methyl 3-(N-(4-chloro-5-cyano-2-(thiazol-4-yl)phenyl)sulfamoyl)-4-cyclopropylbenzoate: The product from Example 132 Step 5 (100 mg, 346 μmol, 95% purity) was added to a solution of pyridine (80 μl, 0.99 mmol) and the product from Step 2 above (85 mg, 322 μmol, 89% purity) in DCM (1 ml). The resultant solution was stirred at RT overnight. The reaction mixture was concentrated onto silica and purified by chromatography on silica gel (24 g cartridge, 0-10% EtOAc/DCM) to afford the title compound (124 mg, 244 μmol, 76% yield, 93% purity) as a white solid. UPLC-MS (Method 1) m/z 474.5 (M+H)⁺ at 1.74 min.

Step 4: 3-(N-(4-chloro-5-cyano-2-(thiazol-4-yl)phenyl)sulfamoyl)-4-cyclopropylbenzoic acid: To a solution of the product from Step 3 above (124 mg, 244 μmol, 93% purity) in THF (1.5 ml) was added 1 M LiOH(aq) (750 μl, 750 μmol). The reaction mixture was stirred at RT for 3 days, concentrated in vacuo to remove THF, then acidified to pH 4-5 using 1 M HCl(aq). A precipitate formed and was collected by filtration to afford the title compound (114 mg, 235 μmol, 96% yield, 95% purity) as a white solid. UPLC-MS (Method 1) m/z 460.3 (M+H)⁺ at 1.59 min. ¹H NMR (500 MHz, DMSO-d$_6$) δ 13.33 (br s, 1H), 12.11 (br s, 1H), 9.44 (d, J=1.9 Hz, 1H), 8.65 (s, 1H), 8.36 (d, J=1.9 Hz, 1H), 8.30 (s, 1H), 7.95 (dd, J=8.2, 1.9 Hz, 1H), 7.79 (s, 1H), 7.03 (d, J=8.3 Hz, 1H), 2.58-2.53 (m, 1H), 0.88-0.80 (m, 2H), 0.74-0.66 (m, 2H).

Example 179: 3-(N-(4-chloro-5-cyano-2-(pyrimidin-2-yl)phenyl)sulfamoyl)-4-cyclopropylbenzoic acid

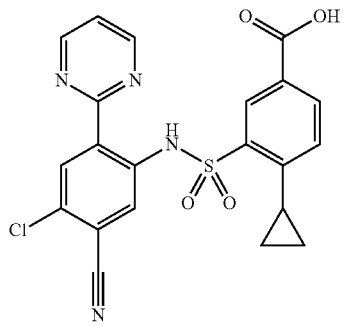 [SMILES: N#Cc1cc(NS(=O)(=O)c2cc(C(=O)O)ccc2C2CC2)c(-c2ncccn2)cc1Cl]

Step 1: 5-amino-2-chloro-4-(pyrimidin-2-yl)benzonitrile: A mixture of the product from Example 178 Step 1 (100 mg, 322 μmol, 90% purity), 2-bromopyrimidine (56 mg, 352 μmol), 1 M K$_3$PO$_4$(aq) (550 μl, 550 μmol) and dioxane (3 ml) was treated with Pd(dppf)Cl$_2$-DCM complex (13 mg, 15.9 μmol). The resultant solution was degassed with N$_2$ for 10 min, then heated at 80° C. for 1 h. The reaction mixture was concentrated onto silica and purified by chromatography on silica gel (12 g cartridge, 0-50% EtOAc/isohexane) to afford the title compound (111 mg, 322 μmol, 100% yield, 67% purity) as a yellow solid. UPLC-MS (Method 1) m/z 231.2 (M+H)⁺ at 1.39 min.

Step 2: Methyl 3-(N-(4-chloro-5-cyano-2-(pyrimidin-2-yl)phenyl)sulfamoyl)-4-cyclopropylbenzoate: The product from Example 132 Step 5 (100 mg, 346 μmol, 95% purity)

was added to a solution of pyridine (80 µl, 0.99 mmol) and the product from Step 1 above (111 mg, 322 µmol, 67% purity) in DCM (1 ml). The resultant solution was stirred at RT overnight. Additional DCM (1 ml) was added and the reaction mixture was stirred at RT for 3 days. A mixture of the product from Example 132 Step 5 (50 mg, 173 µmol, 95% purity) and pyridine (200 µl, 2.48 mmol) was added to the reaction mixture, which was subsequently stirred at RT for 3 days. The reaction mixture was concentrated onto silica and purified by chromatography on silica gel (24 g cartridge, 0-10% EtOAc/DCM) to afford the title compound (120 mg, 182 µmol, 57% yield, 71% purity) as a beige solid. UPLC-MS (Method 1) m/z 469.1 (M+H)+ at 1.79 min.

Step 3: 3-(N-(4-chloro-5-cyano-2-(pyrimidin-2-yl)phenyl)sulfamoyl)-4-cyclopropylbenzoic acid: To a solution of the product from Step 2 above (120 mg, 182 µmol, 71% purity) in THF (1.2 ml) was added 1 M LiOH(aq) (600 µl, 600 µmol). The reaction mixture stirred at RT overnight and concentrated in vacuo. The residue was dissolved in water (12 ml) and washed with EtOAc (12 ml). The aqueous phase was acidified using 1 M HCl(aq) until pH 4-5 and extracted with EtOAc (2×12 ml). The combined extracts were passed through a phase separator and concentrated in vacuo. The crude product was purified by chromatography (24 g reverse phase C18 cartridge, 15-85% (0.1% formic acid in MeCN)/0.1% formic acid(aq)) to afford the title compound (40 mg, 84 µmol, 46% yield, 95% purity) as a fluffy white solid. UPLC-MS (Method 1) m/z 455.3 (M+H)+ at 1.65 min. $^1$H NMR (500 MHz, DMSO-d$_6$) δ 13.20 (br s, 2H), 9.08 (d, J=5.0 Hz, 2H), 8.60 (s, 1H), 8.44 (d, J=1.8 Hz, 1H), 7.97 (dd, J=8.2, 1.9 Hz, 1H), 7.87 (s, 1H), 7.68 (t, J=5.0 Hz, 1H), 7.06 (d, J=8.3 Hz, 1H), 2.67-2.58 (m, 1H), 0.89-0.79 (m, 2H), 0.76-0.64 (m, 2H).

Example 180: 3-(N-(4-chloro-5-cyano-2-(isothiazol-3-yl)phenyl)sulfamoyl)-4-cyclopropylbenzoic acid

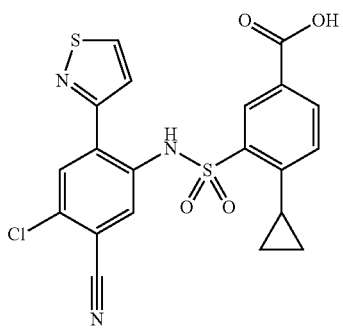 [SMILES: N#Cc1cc(NS(=O)(=O)c2cc(C(=O)O)ccc2C2CC2)c(-c2ccsn2)cc1Cl]

Step 1: 5-amino-2-chloro-4-(isothiazol-3-yl)benzonitrile: A mixture of the product from Example 178 Step 1 (100 mg, 322 µmol, 90% purity), 3-bromoisothiazole (31 µl, 352 µmol), 1 M K$_3$PO$_4$(aq) (550 µl, 550 µmol) and dioxane (3 ml) was treated with Pd(dppf)Cl$_2$-DCM complex (13 mg, 15.9 µmol). The resultant solution was degassed with N$_2$ for 10 min, then heated at 80° C. for 1 h. The reaction mixture was concentrated onto silica and purified by chromatography on silica gel (24 g cartridge, 0-40% EtOAc/isohexane) to afford the title compound (57 mg, 227 µmol, 70% yield, 94% purity) as a yellow solid. UPLC-MS (Method 1) m/z 236.1 (M+H)+ at 1.43 min Step 2: Methyl 3-(N-(4-chloro-5-cyano-2-(isothiazol-3-yl)phenyl)sulfamoyl)-4-cyclopropylbenzoate: The product from Example 132 Step 5 (70 mg, 242 µmol, 95% purity) was added to a solution of pyridine (55 µl, 681 µmol) and the product from Step 1 above (57 mg, 227 µmol, 94% purity) in DCM (1 ml). The resultant solution was stirred at RT for 3 days. A mixture of the product from Example 132 Step 5 (38 mg, 131 µmol, 95% purity) and pyridine (100 µl, 1.24 mmol) was added to the reaction mixture, which was subsequently stirred overnight. The reaction mixture was concentrated onto silica and purified by chromatography on silica gel (24 g cartridge, 0-10% EtOAc/DCM) to afford the title compound (90 mg, 0.13 mmol, 58% yield, 70% purity) as a pale-yellow solid. UPLC-MS (Method 1) m/z 474.1 (M+H)+ at 1.80 min Step 3: 3-(N-(4-chloro-5-cyano-2-(isothiazol-3-yl)phenyl)sulfamoyl)-4-cyclopropylbenzoic acid: To a solution of the product from Step 3 above (90 mg, 0.13 mmol, 70% yield) in THF (1 ml) was added 1 M LiOH(aq) (400 µl, 400 µmol). The reaction mixture stirred at RT overnight, concentrated in vacuo to remove THF, then acidified to pH 4-5 using 1 M HCl(aq). A precipitate formed and was collected by filtration to afford the title compound (64 mg, 0.13 mmol, 100% yield, 95% purity) as a white solid. UPLC-MS (Method 1) m/z 460.3 (M+H)+ at 1.65 min. $^1$H NMR (500 MHz, DMSO-d$_6$) δ 13.34 (br s, 1H), 11.99 (br s, 1H), 9.26 (d, J=4.8 Hz, 1H), 8.40 (d, J=1.8 Hz, 1H), 8.36 (s, 1H), 8.16 (d, J=4.7 Hz, 1H), 7.97 (dd, J=8.2, 1.9 Hz, 1H), 7.79 (s, 1H), 7.06 (d, J=8.3 Hz, 1H), 2.59-2.52 (m, 1H), 0.91-0.79 (m, 2H), 0.77-0.67 (m, 2H).

Example 181: 3-(N-(5-cyano-4-fluoro-2-(isothiazol-3-yl)phenyl)sulfamoyl)-4-cyclopropylbenzoic acid

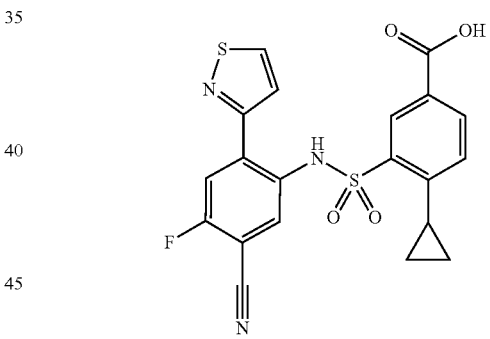

Step 1: 5-amino-2-fluoro-4-(4,4,5,5-tetramethyl-1,3,2-dioxaborolan-2-yl)benzonitrile: In the first reaction vessel a mixture of 5-amino-4-bromo-2-fluorobenzonitrile (700 mg, 3.26 mmol), bis(pinacolato)diboron (909 mg, 3.58 mmol) and KOAc (960 mg, 9.78 mmol) in dioxane (4 ml) was degassed with N$_2$ for 5 min. In the second reaction vessel Pd(dppf)Cl$_2$ (240 mg, 328 µmol) in dioxane (1 ml) was degassed with N$_2$ for 5 min. Both reaction mixtures were heated to 80° C. before addition of the second reaction vessel to the first. The resultant reaction mixture was degassed with N$_2$ for 5 min and stirred at 80° C. for 1 h. The reaction mixture was allowed to cool to RT, concentrated onto silica and purified by chromatography on silica gel (24 g cartridge, 0-50% EtOAc/isohexane) to afford the title compound (736 mg, 2.71 mmol, 83% yield, 96% purity) as an orange oil. UPLC-MS (Method 1) m/z 181.2 (M+H+2H$_2$O-pinacol)+ at 0.76 min.

Step 2: 5-amino-2-fluoro-4-(isothiazol-3-yl)benzonitrile: A mixture of the product from Step 1 above (200 mg, 736

μmol, 96% purity), 3-bromoisothiazole (65 μl, 0.74 mmol), 1 M K₃PO₄(aq) (1.30 ml, 1.30 mmol) and dioxane (6 ml) was treated with Pd(dppf)Cl₂·DCM complex (30 mg, 37 μmol). The resultant solution was degassed with N₂ for 10 min, then heated at 80° C. for 1 h. The reaction mixture was concentrated onto silica and purified by chromatography on silica gel (40 g cartridge, 0-40% EtOAc/isohexane) to afford the title compound (81 mg, 364 μmol, 50% yield, 99% purity) as a yellow solid. UPLC-MS (Method 1) m/z 220.2 (M+H)⁺ at 1.32 min.

Step 3: Methyl 3-(N-(5-cyano-4-fluoro-2-(isothiazol-3-yl)phenyl)sulfamoyl)-4-cyclopropylbenzoate: The product from Example 132 Step 5 (110 mg, 400 μmol, 95% purity) was added to a solution of pyridine (88.1 μl, 1.09 mmol) and the product from Step 2 above (81 mg, 364 μmol, 99% purity) in DCM (1 ml). The resultant solution was stirred at RT for 4 days. The reaction mixture was concentrated onto silica and purified by chromatography on silica gel (24 g cartridge, 0-10% EtOAc/DCM) to afford the title compound (153 mg, 249 μmol, 69% yield, 75% purity) as a pale-yellow solid. UPLC-MS (Method 1) m/z 458.4 (M+H)⁺ at 1.72 min.

Step 4: 3-(N-(5-cyano-4-fluoro-2-(isothiazol-3-yl)phenyl)sulfamoyl)-4-cyclopropylbenzoic acid: To a solution of the product from Step 3 above (153 mg, 249 μmol, 75% purity) in THF (1.5 ml) was added 1 M LiOH(aq) (750 μl, 750 μmol). The reaction mixture stirred at RT overnight, concentrated in vacuo for the removal of THF and acidified to pH 4-5 using 1 M HCl(aq). A precipitate formed and was collected by filtration and purified by chromatography (24 g reverse phase C18 cartridge, 15-65% (0.1% formic acid in MeCN)/0.1% formic acid(aq)) to afford the title compound (91 mg, 0.19 mmol, 78% yield, 95% purity) as a white solid. UPLC-MS (Method 1) m/z 444.3 (M+H)⁺ at 1.56 min. ¹H NMR (500 MHz, DMSO-d₆) δ 13.28 (br s, 1H), 11.63 (br s, 1H), 9.23 (d, J=4.8 Hz, 1H), 8.33 (d, J=1.8 Hz, 1H), 8.16 (d, J=10.2 Hz, 1H), 8.05 (d, J=4.9 Hz, 1H), 7.95 (dd, J=8.2, 1.9 Hz, 1H), 7.75 (d, J=5.8 Hz, 1H), 7.03 (d, J=8.3 Hz, 1H), 2.57-2.52 (m, 1H), 0.90-0.84 (m, 2H), 0.76-0.69 (m, 2H).

Example 182: 3-(N-(5-cyano-4-fluoro-2-(pyrimidin-2-yl)phenyl)sulfamoyl)-4-cyclopropylbenzoic acid

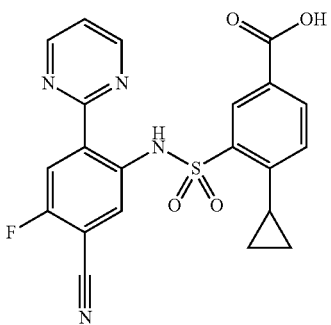 [SMILES: N#Cc1cc(NS(=O)(=O)c2cc(C(=O)O)ccc2C2CC2)c(-c2ncccn2)cc1F]

Step 1: 5-amino-2-fluoro-4-(pyrimidin-2-yl)benzonitrile: A mixture of the product from Example 181 Step 1 (165 mg, 607 μmol, 96% purity), 2-bromopyrimidine (100 mg, 629 μmol), 1 M K₃PO₄(aq) (1 ml, 1 mmol) and dioxane (5 ml) was treated with Pd(dppf)Cl₂·DCM complex (25 mg, 30.6 μmol). The resultant solution was degassed with N₂ for 10 min, then heated at 80° C. for 1 h. The reaction mixture was concentrated onto silica and purified by chromatography on silica gel (12 g cartridge, 0-40% EtOAc/isohexane) to afford the title compound (120 mg, 560 μmol, 92% yield) as a bright yellow solid. UPLC-MS (Method 1) m/z 215.2 (M+H)⁺ at 1.25 min.

Step 2: Methyl 3-(N-(5-cyano-4-fluoro-2-(pyrimidin-2-yl)phenyl)sulfamoyl)-4-cyclopropylbenzoate: The product from Step 1 above (120 mg, 560 μmol) was added to a solution of pyridine (140 μl, 1.73 mmol) and the product from Example 132 Step 5 (170 mg, 588 μmol, 95% purity) in DCM (2 ml). The resultant solution was stirred at RT overnight. The reaction mixture was acidified using 1 M HCl(aq) (12 ml) and extracted with DCM (2×10 ml). The combined organic phases were passed through a phase separator and concentrated in vacuo. The crude product was dissolved in the minimum quantity of DCM, then isohexane was added until a precipitate formed. The precipitate was collected by filtration to afford the title compound (120 mg, 236 μmol, 42% yield, 89% purity) as a pale brown solid. UPLC-MS (Method 1) m/z 453.4 (M+H)⁺ at 1.69 min.

Step 3: 3-(N-(5-cyano-4-fluoro-2-(pyrimidin-2-yl)phenyl)sulfamoyl)-4-cyclopropylbenzoic acid: To a solution of the product from Step 2 above (120 mg, 236 μmol, 89% purity) in THF (1.4 ml) was added 1 M LiOH(aq) (700 μl, 700 μmol). The reaction mixture stirred at RT overnight, concentrated in vacuo and the residue was dissolved in water (12 ml), washing with EtOAc (12 ml). The aqueous phase was acidified using 1 M HCl(aq) until pH 4-5 and extracted with EtOAc (2×12 ml). The combined extracts were passed through a phase separator and concentrated in vacuo. The crude product was purified by chromatography (24 g reverse phase C18 cartridge, 15-65% (0.1% formic acid in MeCN)/0.1% formic acid(aq)) to afford the title compound (56 mg, 0.12 mmol, 51% yield, 95% purity) as a white solid. UPLC-MS (Method 2) m/z 439.4 (M+H)⁺ at 1.01 min. ¹H NMR (500 MHz, DMSO-d₆) δ 13.57-12.58 (m, 2H), 9.06 (d, J=5.0 Hz, 2H), 8.40-8.32 (m, 2H), 7.94 (dd, J=8.2, 1.9 Hz, 1H), 7.87 (d, J=5.7 Hz, 1H), 7.67 (t, J=5.0 Hz, 1H), 7.01 (d, J=8.2 Hz, 1H), 2.67-2.56 (m, 1H), 0.91-0.80 (m, 2H), 0.75-0.62 (m, 2H).

Example 183: 3-(N-(5-cyano-4-fluoro-2-(thiazol-2-yl)phenyl)sulfamoyl)-4-cyclopropylbenzoic acid

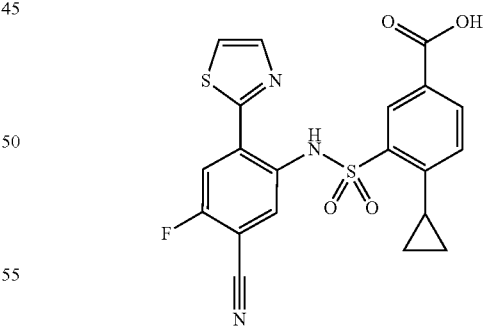

Step 1: 5-amino-2-fluoro-4-(thiazol-2-yl)benzonitrile: A mixture of the product from Example 181 Step 1 (165 mg, 607 μmol, 96% purity), 2-bromothiazole (55 μl, 610 μmol), 1 M K₃PO₄(aq) (1.00 ml, 1.00 mmol) and dioxane (5 ml) was treated with Pd(dppf)Cl₂·DCM complex (25 mg, 30.6 μmol). The resultant solution was degassed with N₂ for 10 min, then heated at 80° C. for 1 h. The reaction mixture was concentrated onto silica and purified by chromatography on silica gel (12 g cartridge, 0-40% EtOAc/isohexane) to afford the title compound (106 mg, 461 µmol, 76% yield, 95% purity) as a bright yellow solid. UPLC-MS (Method 1) m/z 220.2 (M+H)⁺ at 1.38 min.

Step 2: Methyl 3-(N-(5-cyano-4-fluoro-2-(thiazol-2-yl)phenyl)sulfamoyl)-4-cyclopropylbenzoate: The product from Step 1 above (106 mg, 461 µmol, 95% purity) was added to a solution of the product from Example 132 Step 5 (140 mg, 484 µmol, 95% purity) and pyridine (110 µl, 1.36 mmol) in DCM (2 ml). The resultant solution was stirred at RT for 4 days. The reaction mixture was diluted using 1 M HCl(aq) (12 ml) and extracted with DCM (2×10 ml). The combined organic phases were passed through a phase separator and concentrated in vacuo to afford the title compound (195 mg, 398 µmol, 86% yield, 93% purity) as a yellow solid. UPLC-MS (Method 1) m/z 458.6 (M+H)⁺ at 1.72 min.

Step 3: 3-(N-(5-cyano-4-fluoro-2-(thiazol-2-yl)phenyl)sulfamoyl)-4-cyclopropylbenzoic acid: To a solution of the product from Step 2 above (195 mg, 398 µmol, 93% purity) in THF (2.4 ml) was added 1 M LiOH(aq) (1.20 ml, 1.20 mmol). The reaction mixture stirred at RT overnight, concentrated in vacuo and the residue was dissolved in water (12 ml), washing with EtOAc (12 ml). The aqueous phase was acidified using 1 M HCl(aq) until pH 4-5 and extracted with EtOAc (2×12 ml). The combined organic phases were passed through a phase separator and concentrated in vacuo. The crude product was purified by chromatography (24 g reverse phase C18 cartridge, 15-65% (0.1% formic acid in MeCN)/0.1% formic acid(aq)) to afford the title compound (102 mg, 219 µmol, 55% yield, 95% purity) as a white solid. UPLC-MS (Method 2) m/z 444.3 (M+H)⁺ at 0.84 min. ¹H NMR (500 MHz, DMSO-d₆) δ 13.33 (br s, 1H), 12.03 (br s, 1H), 8.39 (d, J=1.8 Hz, 1H), 8.18-8.12 (m, 2H), 8.09 (d, J=3.3 Hz, 1H), 7.99 (dd, J=8.2, 1.9 Hz, 1H), 7.61 (d, J=5.8 Hz, 1H), 7.09 (d, J=8.3 Hz, 1H), 2.64-2.56 (m, 1H), 0.95-0.85 (m, 2H), 0.80-0.71 (m, 2H).

Example 184: 4-cyclopropyl-3-(N-(4-fluoro-5-(isothiazol-5-yl)-2-(pyridin-2-yl)phenyl) sulfamoyl) benzoic acid

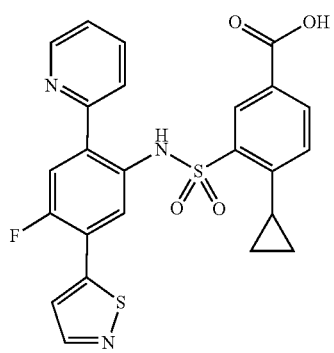 [SMILES: O=C(O)c1ccc(C2CC2)c(S(=O)(=O)Nc2cc(-c3ccns3)c(F)cc2-c2ccccn2)c1]

Step 1: 2-(4-bromo-5-fluoro-2-nitrophenyl)pyridine: A solution of 1-bromo-2-fluoro-4-iodo-5-nitrobenzene (1 g, 29 mmol) and 2-tributylstannyl pyridine (1.28 g, 35 mmol) in dioxane (15 ml) was purged with N₂ for 30 min, then Pd(PPh₃)₄ (0.167 g, 0.14 mmol) was added. The resultant reaction mixture was stirred with microwave heating at 120° C. for 90 min. The reaction mixture was diluted with water (100 ml) and extracted with EtOAc (3×50 ml). The organic phases were combined, dried over Na₂SO₄, and concentrated in vacuo. The residue was purified by manual chromatography on 60-120 mm silica (15% EtOAc in hexane) to afford the title compound (4.8 g, 16 mmol, 56% yield) as a yellow solid. UPLC-MS (Method 5) m/z 297.2 (M+H)⁺, at 2.26 min.

Step 2: 5-(tributylstannyl)isothiazole: A stirred solution of 5-bromo-1,2-thiazole (0.6 g, 3.6 mmol) in THF (30 ml) was cooled to −78° C. and treated dropwise with n-butyllithium (1.6 M in THF) (3.4 ml, 5.5 mmol). The reaction mixture was stirred at −78° C. for 30 min. The resultant mixture was then slowly treated with tributyltin chloride (1.79 g, 5.5 mmol) at −78° C. The reaction mixture was stirred at −78° C. for an additional 4 h. The mixture was poured into saturated NH₄Cl(aq) (30 ml) and extracted with EtOAc (2×30 ml). The organic phases were combined, dried over Na₂SO₄, and concentrated in vacuo to afford the title compound (1.5 g) as brown liquid, which was used directly in subsequent reactions without purification.

Step 3: 5-(2-fluoro-5-nitro-4-(pyridin-2-yl)phenyl)isothiazole: Two reactions were carried out on the same scale according to the following procedure and combined. A solution of the product from Step 1 (0.4 g, 1.3 mmol) in dioxane (10 ml) was treated with the product from Step 2 (0.51 g) and Na₂CO₃(s) (0.43 g, 4.1 mmol). The reaction mixture was purged with N₂ for 15 min, then Pd(OAc)₂ (0.02 g, 0.94 mmol) and X-Phos (0.09 g, 0.18 mmol) were added. The resultant mixture was heated at 90° C. for 16 h. The mixture was poured into water (50 ml) and extracted with EtOAc (3×30 ml). The organic phases were combined, dried over Na₂SO₄(s) and concentrated in vacuo. The residue was purified by chromatography (20% EtOAc/hexane) to afford the title compound (0.65 g, 2.16 mmol, 83% yield) as a yellow solid. UPLC-MS (Method 5) m/z 302.0 (M+H)⁺ at 1.91 min.

Step 4: 4-fluoro-5-(isothiazol-5-yl)-2-(pyridin-2-yl)aniline: A solution of the product from Step 3 above (0.65 g, 2.15 mmol) in MeOH (7 ml) and water (1 ml) was treated with iron powder (0.6 g, 10.8 mmol) and NH₄Cl(s) (0.6 g, 10.8 mmol). The reaction mixture was stirred at 80° C. for 4 h. The mixture was poured into water (50 ml) and extracted with EtOAc (3×30 ml). The organic phases were combined, dried over Na₂SO₄(s) and concentrated in vacuo. The residue was partially purified by chromatography on neutral alumina (15% EtOAc/hexane), then triturated in a mixture of Et₂O (5 ml) and pentane (5 ml) to afford the title compound as a yellow solid (0.27 g, 1.00 mmol, 47% yield). UPLC-MS (Method 5) m/z 272.3 (M+H)⁺ at 2.06 min.

Step 5: methyl 4-cyclopropyl-3-(N-(4-fluoro-5-(isothiazol-5-yl)-2-(pyridin-2-yl)phenyl)sulfamoyl)benzoate: A mixture of the product from Step 4 above (100 mg, 369 µmol), the product from Example 132 Step 5 (152 mg, 553 µmol) and pyridine (90 µL, 1.1 mmol) in DCM (2 ml) was stirred at RT overnight. The mixture was concentrated onto silica and purified by chromatography on silica gel (12 g cartridge, 0-100% EtOAc/isohexane) to afford the title compound (158 mg, 310 µmol) as a yellow solid. UPLC-MS (Method 1): m/z 510.3 (M+H)⁺, 508.2 (M−H)⁻, at 1.85 min.

Step 6: 4-cyclopropyl-3-(N-(4-fluoro-5-(isothiazol-5-yl)-2-(pyridin-2-yl)phenyl)sulfamoyl)benzoic acid: A mixture of the product from Step 5 above (158 mg, 310 µmol) and LiOH·H₂O (54 mg, 1.29 mmol) in THF/MeOH/H₂O (4:1:1, 1.5 ml) was stirred at 40° C. overnight. The mixture was diluted with water (10 ml), acidified to ~pH 4 using 1 M HCl(aq) and extracted with EtOAc (3×20 ml). The organic extracts were combined and washed with brine (10 ml), passed through a phase separator and the solvent was removed in vacuo. The residue was loaded onto silica and purified by chromatography on silica gel (4 g cartridge, 0-100% EtOAc/isohexane) to afford the title compound (72.4 mg, 145 μmol, 47% yield, 99% purity) as a pale-yellow solid. UPLC-MS (Method 1): m/z 496.3 (M+H)+, 494.1 (M−H)− at 1.72 min. $^1$H NMR (500 MHz, DMSO-$d_6$) δ 13.30 (s, 1H), 13.04 (s, 1H), 8.74-8.68 (m, 1H), 8.68-8.64 (m, 1H), 8.40 (d, J=1.9 Hz, 1H), 8.06-8.01 (m, 2H), 8.01-7.95 (m, 1H), 7.90 (dd, J=8.2, 1.9 Hz, 1H), 7.84 (d, J=6.9 Hz, 1H), 7.77 (d, J=1.8 Hz, 1H), 7.52-7.46 (m, 1H), 6.97 (d, J=8.2 Hz, 1H), 2.60-2.52 (m, 1H), 0.78-0.69 (m, 2H), 0.67-0.60 (m, 2H).

Example 185: 4-cyclopropyl-3-(N-(4-fluoro-5-(1-methylpyrazol-5-yl)-2-(pyridin-2-yl)phenyl)sulfamoyl)benzoic acid

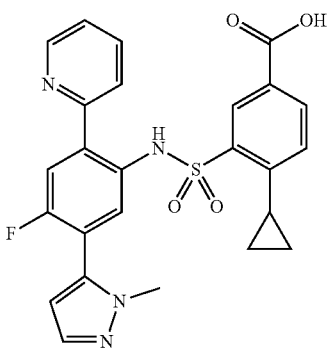 [SMILES: Cn1nccc1-c1cc(NS(=O)(=O)c2cc(C(=O)O)ccc2C2CC2)c(-c2ccccn2)cc1F]

Step 1: 2-(5-fluoro-4-(1-methylpyrazol-5-yl)-2-nitrophenyl)pyridine: Four reactions were carried out on the same scale according to the following procedure and combined. The product from Example 184 Step 1 (0.3 g, 1.01 mmol) and 1-methyl-5-(4,4,5,5-tetramethyl-1,3,2-dioxaborolan-2-yl)pyrazole (1.05 g, 5.08 mmol) were combined in dioxane (6 ml) and water (1 ml). K$_2$CO$_3$(s) (0.418 g, 3.03 mmol) was added and the resultant mixture stirred at RT for 15 min. The reaction mixture was purged with N$_2$ for 15 min, then Pd(PPh$_3$)$_4$ (0.116 g, 0.101 mmol) was added. The resultant reaction mixture was stirred at 100° C. for 3 h. The reaction mixture was poured into water (55 ml) and extracted with EtOAc (3×50 ml). The extracts were combined and washed with brine (10 ml), then dried over Na$_2$SO$_4$(s). The solvent was removed in vacuo and the resultant crude material was purified by chromatography on silica gel (15% EtOAc/hexane) to afford the title compound as a yellow solid (0.85 g, 2.85 mmol, 71% yield). UPLC-MS (Method 5): m/z 299.3 (M+H)+ at 1.97 min.

Step 2: 4-fluoro-5-(1-methylpyrazol-5-yl)-2-(pyridin-2-yl)aniline: A solution of the product from Step 1 above (0.85 g, 2.85 mmol) in MeOH (9 ml) and water (1 ml) was treated with iron powder (0.79 g, 14.2 mmol) and NH$_4$Cl(s) (0.748 g, 14.2 mmol). The reaction mixture was stirred at 100° C. for 2 h. The reaction mixture was poured into water (25 ml) and filtered through Celite®. The filtrate was extracted with EtOAc (3×25 ml). The organic phases were combined and dried over Na$_2$SO$_4$(s), then concentrated in vacuo. The residue was purified by chromatography on neutral alumina (20% EtOAc/hexane) to afford the title compound (0.27 g, 1.01 mmol, 35% yield) as an off-white solid. UPLC-MS (Method 5) m/z 269.3 (M+H)+ at 1.72 min.

Step 3: methyl 4-cyclopropyl-3-(N-(4-fluoro-5-(1-methylpyrazol-5-yl)-2-(pyridin-2-yl)phenyl)sulfamoyl)benzoate: A mixture of the product from Step 2 above (100 mg, 373 μmol), the product from Example 132 Step 5 (154 mg, 559 μmol) and pyridine (90 μL, 1.1 mmol) in DCM (2 ml) was stirred at RT overnight. The mixture was concentrated onto silica and purified by chromatography on silica gel (12 g cartridge, 0-100% EtOAc/isohexane) to afford the title compound (120 mg, 237 μmol, 64% yield) as a pale tan solid. UPLC-MS (Method 1): m/z 507.4 (M+H)+, 505.2 (M−H)− at 1.65 min.

Step 4: 4-cyclopropyl-3-(N-(4-fluoro-5-(1-methylpyrazol-5-yl)-2-(pyridin-2-yl)phenyl)sulfamoyl)benzoic acid: A mixture of the product from Step 3 above (120 mg, 237 μmol) and LiOH·H$_2$O (40 mg, 953 μmol) in THF/MeOH/H$_2$O (4:1:1, 1.2 ml) was stirred at 40° C. overnight. The mixture was diluted with water (10 ml), acidified to ~pH 4 using 1 M HCl(aq) and extracted with EtOAc (3×20 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to afford the title compound (86.7 mg, 174 μmol, 74% yield, 99% purity) as a grey solid. UPLC-MS (Method 1): m/z 493.3 (M+H)+, 491.2 (M−H)− at 1.52 min. $^1$H NMR (500 MHz, DMSO-$d_6$) δ 13.32 (s, 1H), 12.95 (s, 1H), 8.71 (dt, J=4.9, 1.4 Hz, 1H), 8.29 (d, J=1.8 Hz, 1H), 8.05-7.96 (m, 2H), 7.95 (d, J=11.2 Hz, 1H), 7.90 (dd, J=8.2, 1.9 Hz, 1H), 7.54 (d, J=1.9 Hz, 1H), 7.54-7.47 (m, 2H), 6.95 (d, J=8.2 Hz, 1H), 6.35 (d, J=1.9 Hz, 1H), 3.70 (s, 3H), 2.56-2.50 (m, 1H), 0.78-0.70 (m, 2H), 0.66-0.59 (m, 2H).

Example 186: 4-cyclopropyl-3-(N-(4-fluoro-5-(1-methyl-1,2,4-triazol-5-yl)-2-(pyridin-2-yl)phenyl)sulfamoyl)benzoic acid

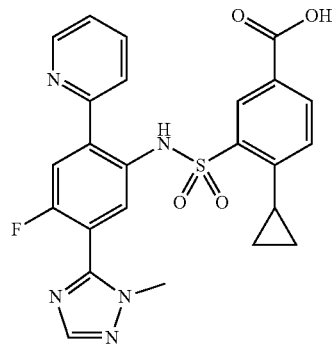

Step 1: 5-bromo-4-flouro-2-(pyridin-2-yl)aniline: A stirred solution of the product from Example 184 Step 1 (4.0 g, 13.5 mmol) in EtOH (18 ml) and water (2 ml) was treated with iron powder (3.76 g, 67.5 mmol) and NH$_4$Cl(s) (5.05 g, 94.5 mmol) at RT. The resultant mixture was stirred at 90° C. for 4 h. The reaction mixture was filtered through Celite®. The filtrate was poured into water (80 ml) and extracted with EtOAc (3×60 ml). The extracts were combined and dried over Na$_2$SO$_4$(s), then concentrated in vacuo. The residue was purified by chromatography (15% EtOAc/hexane) to afford the title compound (3.0 g, 11.3 mmol, 84% yield) as a yellow solid. UPLC-MS (Method 5) m/z 267.2 (M+H)+ at 2.10 min.

Step 2: 4-flouro-2-(pyridin-2-yl)-5-(4,4,5,5-tetramethyl-1,3,2-dioxaborolan-2-yl)aniline: A mixture of the product from Step 1 above (1.8 g, 6.7 mmol), KOAc (3.31 g, 33.5 mmol) and dioxane (15 ml) was treated with bis(pinacolato)diboron (5.15 g, 2.03 mmol) at RT and stirred for 15 min. The reaction mixture was purged with $N_2$ for 30 min, then $PdCl_2$(dppf)·DCM (0.55 g, 0.67 mmol) was added. The resultant reaction mixture was stirred at 120° C. for 3 h. The reaction mixture was filtered through Celite® washing with EtOAc (30 ml). The filtrate was washed with water (80 ml) and aqueous phase was extracted with EtOAc (3×60 ml). The organic phases were combined and dried over $Na_2SO_4$(s) and concentrated in vacuo. The residue was purified by chromatography (reverse phase, 60% acetonitrile in water) to afford the title compound (0.8 g, 2.6 mmol, 38% yield) as a yellow solid. UPLC-MS (Method 5) m/z 233.0 $(M+H+2H_2O\text{-pinacol})$ at 0.80 min.

Step 3: 5-iodo-1-methyl-1,2,4-triazole: A stirred solution of 1-methyl-1,2,4-triazole (1.0 g, 12 mmol) in THF was treated with n-butyllithium (1.6 M in hexane) (9.1 ml, 14.4 mmol) at −78° C. and stirred for 1 h. A solution of iodine (3.15 g, 12.3 mmol) in THF was added dropwise at −78° C. The reaction was stirred at RT for 1 h. The reaction mixture was poured into saturated $Na_2S_2O_3$(aq) (100 ml) and extracted with EtOAc (2×60 ml, then 2×80 ml). The extracts were combined and dried over $Na_2SO_4$(s), then concentrated in vacuo to afford the title compound (1.8 g, 8.61 mmol, 72% yield) as a yellow solid. UPLC-MS (Method 5) m/z 210.1 $(M+H)^+$ at 0.88 min Step 4: 4-flouro-5-(1-methyl-1,2,4-triazol-5-yl)-2-(pyridin-2-yl)aniline: A stirred solution of the product from Step 2 above (0.8 g, 2.5 mmol) in dioxane (15 ml) and water (3 ml) was treated with the product from Step 3 above (0.96 g, 4.6 mmol) and $Na_2CO_3$(s) (0.94 g, 8.9 mmol). The reaction mixture was purged with $N_2$ for 30 min. $PdCl_2$(dppf)·DCM (0.21 g, 0.25 mmol) was added and the mixture stirred at 140° C. for 2 h. The reaction mixture was filtered through Celite®. The filtrate was poured into water (120 ml) and extracted with EtOAc (3×100 ml). The organic phases were combined and dried over $Na_2SO_4$(s), then concentrated in vacuo. The residue was purified by chromatography (reverse phase, 45% acetonitrile in water) to afford the title compound (0.059 g, 0.219 mmol, 89%) as a light-yellow solid. UPLC-MS (Method 5) m/z 270.4 $(M+H)^+$ at 1.41 min.

Step 5: methyl 4-cyclopropyl-3-(N-(4-fluoro-5-(1-methyl-1,2,4-triazol-5-yl)-2-(pyridin-2-yl)phenyl)sulfamoyl)benzoate: A mixture of the product from Step 4 above (111 mg, 412 µmol), the product from Example 132 Step 5 (170 mg, 618 µmol) and pyridine (100 µl, 1.24 mmol) in DCM (2 ml) was stirred at RT overnight. The mixture was concentrated onto silica and purified by chromatography on silica gel (12 g cartridge, 0-100% EtOAc/isohexane) to afford the title compound (134 mg, 264 µmol, 64% yield) as a pale tan solid. UPLC-MS (Method 1): m/z 508.4 $(M+H)^+$, 506.2 $(M-H)^-$ at 1.48 min.

Step 6: 4-cyclopropyl-3-(N-(4-fluoro-5-(1-methyl-1,2,4-triazol-5-yl)-2-(pyridin-2-yl)phenyl)sulfamoyl)benzoic acid: A mixture of the product from Step 5 (134 mg, 264 µmol) and LiOH·H$_2$O (45 mg, 1.07 mmol) in THF/MeOH/H$_2$O (4:1:1, 1.2 ml) was stirred at 40° C. overnight. The mixture was diluted with water (10 ml), acidified to ~pH 4 using 1 M HCl(aq), and extracted with EtOAc (3×20 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to afford the title compound (79.7 mg, 157 µmol, 59% yield, 97% purity) as a pale-yellow solid. UPLC-MS (Method 1): m/z 494.3 $(M+H)^+$, 492.2 $(M-H)^-$ at 1.31 min. $^1$H NMR (500 MHz, DMSO-d$_6$) δ 13.22 (s, 1H), 12.74 (s, 1H), 8.71 (d, J=4.8 Hz, 1H), 8.20 (s, 1H), 8.10 (s, 1H), 7.98 (s, 3H), 7.88 (d, J=8.3 Hz, 1H), 7.67 (d, J=6.5 Hz, 1H), 7.49 (d, J=4.8 Hz, 1H), 6.93 (d, J=8.3 Hz, 1H), 3.77 (s, 3H), 2.55-2.52 (m, 1H), 0.82-0.75 (m, 2H), 0.67-0.60 (m, 2H).

Example 187: 3-(N-(4-chloro-2-(pyridin-2-yl)-5-(tetrazol-1-yl)phenyl)sulfamoyl)-4-cyclopropylbenzoic acid

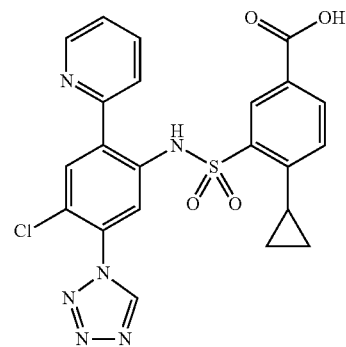 [SMILES: O=C(O)c1ccc(C2CC2)c(S(=O)(=O)Nc2cc(-n3cnnn3)c(Cl)cc2-c2ccccn2)c1]

Step 1: 1-(4-bromo-2-chloro-5-nitrophenyl)tetrazole: A solution of 4-bromo-2-chloro-5-nitroaniline (5.0 g, 20.0 mmol) in AcOH (100 ml) was stirred for 5 min. Triethylorthoformate (16.7 ml, 100 mmol) and trimethylsilylazide (13.2 ml, 100 mmol) were added at 0° C. The reaction mixture was stirred at 70° C. for 8 h. The reaction mixture was poured into ice cold water (300 ml). The resultant precipitate was collected by filtration and washed with water (100 ml), then dried in vacuo to afford the title compound (5.2 g, 17.1 mmol, 86% yield) as a yellow solid. UPLC-MS (Method 5) m/z no ionisation at 1.96 min.

Step 2: 2-bromo-4-chloro-5-(tetrazol-1-yl)aniline: A stirred solution of the product from Step 1 above (1.5 g, 4.95 mmol) in EtOAc (30 ml) was treated with SnCl$_2$·2H$_2$O (4.7 g, 24.7 mmol). The reaction mixture was stirred at 70° C. for 1 h. The reaction mixture was poured into water (200 ml) and extracted with EtOAc (2×75 ml). The extracts were combined and washed with brine (100 ml), dried over Na$_2$SO$_4$(s), then concentrated in vacuo to afford the title compound (1.1 g, 4.03 mmol, 81% yield). UPLC-MS (Method 5) m/z 274.1 $(M+H)^+$ at 1.90 min.

Step 3: 4-chloro-2-(pyridin-2-yl)-5-(tetrazol-1-yl)aniline hydrochloride: A stirred solution of the product from Step 2 above (1.1 g, 4.03 mmol) in dioxane (20 ml) was treated with 2-(tributylstannyl)pyridine (2.2 g, 6.04 mmol). The reaction mixture was purged with N$_2$ for 20 min and then Pd(PPh$_3$)$_4$ (0.698 g, 0.60 mmol) was added. The reaction mixture was stirred with microwave heating at 140° C. for 1.5 h. The reaction mixture was poured into water (250 ml) and extracted with EtOAc (2×50 ml). The extracts were combined and dried over anhydrous Na$_2$SO$_4$(s). The solvent was evaporated in vacuo. The residue was purified by chromatography on neutral alumina (20% EtOAc/hexane). The obtained material dissolved in DCM (2 ml) and treated with 4 M HCl in dioxane (1 ml). The residue was triturated using n-pentane (20 ml). The solvent was decanted and dried in vacuo to afford the title compound (0.195 g, 0.631 mmol, 16% yield). UPLC-MS (Method 5) m/z 273.3 $(M+H)^+$ at 1.86 min.

Step 4: methyl 3-(N-(4-chloro-2-(pyridin-2-yl)-5-(tetrazol-1-yl)phenyl)sulfamoyl)-4-cyclopropylbenzoate: A mixture of the product from Step 3 above (100 mg, 323 µmol), the product from Example 132 Step 5 (151 mg, 550 µmol) and pyridine (90 µL, 1.1 mmol) in DCM (2 ml) was stirred at RT overnight. The mixture was concentrated onto silica and purified by chromatography on silica gel (12 g cartridge, 0-100% EtOAc/isohexane) to afford the title compound (103 mg, 198 µmol, 54% yield, 98% purity) as a yellow solid. UPLC-MS (Method 1): m/z 533.3 (M+Na)$^+$, 509.1 (M−H)$^−$, at 1.62 min.

Step 5: 3-(N-(4-chloro-2-(pyridin-2-yl)-5-(tetrazol-1-yl)phenyl)sulfamoyl)-4-cyclopropylbenzoic acid: A mixture of the product from Step 4 above (103 mg, 198 µmol, 98% purity) and LiOH·H$_2$O (34 mg, 0.81 mmol) in THF/MeOH/H$_2$O (4:1:1, 0.75 ml) was stirred at 40° C. overnight. The mixture was diluted with water (10 ml), acidified to ~pH 4 using 1 M HCl(aq) and extracted with EtOAc (3×20 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to afford the title compound (54.5 mg, 107 µmol, 54% yield, 98% purity) as a yellow solid. UPLC-MS (Method 1): m/z 519.3 (M+Na)$^+$, 495.2 (M−H)$^−$, at 1.47 min. $^1$H NMR (500 MHz, DMSO-d$_6$) δ 13.41 (s, 1H), 13.25 (s, 1H), 9.91 (s, 1H), 8.74 (d, J=4.9 Hz, 1H), 8.36 (s, 1H), 8.33-8.29 (m, 1H), 8.14 (d, J=8.2 Hz, 1H), 8.07-8.01 (m, 1H), 7.93 (d, J=8.2 Hz, 1H), 7.79 (s, 1H), 7.58-7.52 (m, 1H), 7.00 (d, J=8.3 Hz, 1H), 2.57-2.52 (m, 1H), 0.79-0.72 (m, 2H), 0.69-0.62 (m, 2H).

Example 188: 3-(N-(4-chloro-5-(1-methylpyrazol-5-yl)-2-(pyridin-2-yl)phenyl)sulfamoyl)-4-cyclopropylbenzoic acid

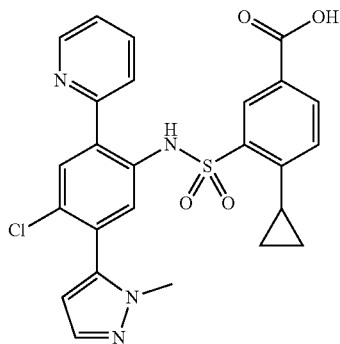 [SMILES: Cn1nccc1-c1cc(NS(=O)(=O)c2cc(C(=O)O)ccc2C2CC2)c(-c2ccccn2)cc1Cl]

Step 1: 2-(4-bromo-5-chloro-2-nitrophenyl)pyridine: Eight reactions were carried out on the same scale according to the following procedure and combined. A solution of 1-bromo-2-chloro-4-iodo-5-nitrobenzene (1 g, 2.7 mmol) and 2-(tributylstannyl)pyridine (1.22 g, 3.2 mmol) in dioxane (10 ml) was purged with N$_2$ for 30 min, then Pd(PPh$_3$)$_4$ (0.155 g, 0.13 mmol) was added. The resultant reaction mixture was stirred with microwave heating at 100° C. for 1.5 h. The reactions were combined, diluted with water (2×100 ml) and extracted with EtOAc (2×100 ml). The extracts were combined, washed with brine (50 ml), and then dried over Na$_2$SO$_4$(s). The solvent was evaporated in vacuo. The resultant crude material was purified by chromatography on 60-120 mm silica (12-15% EtOAc/hexane) to afford the title compound (5.5 g, 17.6 mmol, 82% yield) as a light-yellow solid. UPLC-MS (Method 5) m/z 312.9 (M+H)$^+$ at 2.12 min.

Step 2: 2-(5-chloro-4-(1-methylpyrazol-5-yl)-2-nitrophenyl)pyridine: Two reactions were carried out on the same scale according to the following procedure and combined. A solution of the product from Step 1 above (0.5 g, 1.61 mmol) and 1-methyl-5-(4,4,5,5-tetramethyl-1,3,2-dioxaborolan-2-yl)pyrazole (0.66 g, 3.21 mmol) in dioxane (5 ml) and water (1 ml) was treated with K$_2$CO$_3$(s) (0.66 g, 4.82 mmol) at RT. The reaction mixture was purged with N$_2$ for 30 min and then Pd(PPh$_3$)$_4$ (0.092 g 0.080 mmol) was added. The resultant mixture was stirred at 90° C. for 24 h. The reaction mixture was diluted with water (500 ml) and extracted with EtOAc (3×250 ml). The extracts were combined and dried over Na$_2$SO$_4$(s), then concentrated in vacuo. The resultant crude material was purified by chromatography on silica gel (20% EtOAc/hexane) to afford the title compound (0.56 g, 1.78 mmol, 55% yield) as a yellow solid. UPLC-MS (Method 5) m/z 315.3 (M+H)$^+$ at 2.09 min.

Step 3: 4-chloro-5-(1-methylpyrazol-5-yl)-2-(pyridin-2-yl)aniline: A solution of the product from Step 2 above (0.56 g, 1.78 mmol) in MeOH was treated with iron powder (0.50 g, 8.9 mmol), and NH$_4$Cl(s) (0.47 g, 8.9 mmol) in water (2 ml). The reaction mixture was stirred at 80° C. for 2 h. The reaction mixture was diluted with water (500 ml) and extracted with EtOAc (2×100 ml). The extracts were combined and dried over anhydrous Na$_2$SO$_4$(s), then concentrated in vacuo. The crude material was purified by chromatography on neutral alumina (10% EtOAc/hexane) to afford the title compound as a yellow solid (0.395 g, 1.39 mmol, 78% yield). UPLC-MS (Method 5) m/z 285.3 (M+H)$^+$ at 1.95 min.

Step 4: methyl 3-(N-(4-chloro-5-(1-methylpyrazol-5-yl)-2-(pyridin-2-yl)phenyl)sulfamoyl)-4-cyclopropylbenzoate: A mixture of the product from Step 3 above (100 mg, 351 µmol), the product from Example 132 Step 5 (145 mg, 527 µmol) and pyridine (90 µL, 1.1 mmol) in DCM (2 ml) was stirred at RT overnight. The mixture was concentrated onto silica and purified by chromatography on silica gel (12 g cartridge, 0-100% EtOAc/isohexane) to afford the title compound (80.2 mg, 153 µmol, 44% yield) as a pale tan solid. UPLC-MS (Method 1): m/z 523.3 (M+H)$^+$, 521.2 (M−H)$^−$ at 1.72 min.

Step 5: 3-(N-(4-chloro-5-(1-methylpyrazol-5-yl)-2-(pyridin-2-yl)phenyl)sulfamoyl)-4-cyclopropylbenzoic acid: A mixture of the product from Step 4 above (80.2 mg, 153 µmol) and LiOH·H$_2$O (26 mg, 620 µmol) in THF/MeOH/H$_2$O (4:1:1, 1.2 ml) was stirred at 40° C. overnight. The mixture was diluted with water (10 ml), acidified to ~pH 4 using 1 M HCl(aq) and extracted with EtOAc (3×20 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to afford the title compound (54.1 mg, 105 µmol, 69% yield, 99% purity) as a pale-yellow solid. UPLC-MS (Method 1): m/z 509.3 (M+H)$^+$, 507.1 (M−H)$^−$, at 1.58 min. $^1$H NMR (500 MHz, DMSO-d$_6$) δ 13.34 (s, 1H), 13.30 (s, 1H), 8.73 (d, J=4.9 Hz, 1H), 8.31 (d, J=1.9 Hz, 1H), 8.17-8.11 (m, 2H), 8.06-8.00 (m, 1H), 7.95-7.90 (m, 1H), 7.56-7.50 (m, 2H), 7.48 (s, 1H), 6.98 (d, J=8.3 Hz, 1H), 6.26 (d, J=1.9 Hz, 1H), 3.56 (s, 3H), 2.54-2.52 (m, 1H), 0.75-0.67 (m, 2H), 0.67-0.60 (m, 2H).

Example 189: 3-(N-(4-chloro-5-(1-methyl-1,2,4-triazol-5-yl)-2-(pyridin-2-yl)phenyl)sulfamoyl)-4-cyclopropylbenzoic acid

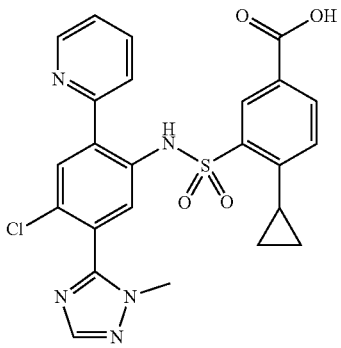

Step 1: 5-bromo-4-chloro-2-(pyridin-2-yl)aniline: A solution of the product from Example 188 Step 1 (1.6 g, 5.1 mmol) in MeOH (18 ml) and water (2 ml) was treated with iron powder (2.28 g, 40.8 mmol) and $NH_4Cl(s)$ (2.18 g, 40.8 mmol) at RT. The resultant reaction mixture was stirred at 90° C. for 4 h. The reaction mixture was filtered through Celite®. The filtrate was poured into water (120 ml) and extracted with EtoAc (3×100 ml). The extracts were combined, dried over $Na_2SO_4(s)$ and concentrated in vacuo. The residue was purified by chromatography (15% EtOAc/hexane) to afford the title compound (1.1 g, 3.9 mmol, 76% yield). UPLC-MS (Method 5) m/z 283.2 at 2.37 min.

Step 2: 4-chloro-5-(1-methyl-1,2,4-triazol-5-yl)-2-(pyridin-2-yl)aniline: A mixture of the product from Step 1 above (1.1 g, 3.9 mmol) and KOAc (1.15 g, 11.6 mmol) in dioxane (15 ml) was treated with bis(pinacolato)diboron (1.5 g, 5.8 mmol) at RT and stirred for 15 min. The reaction mixture was purged with $N_2$ for 30 min, then $PdCl_2$(dppf)-DCM (0.32 g, 0.389 mmol) was added. The resultant reaction mixture was stirred at 100° C. for 16 h. The reaction mixture was filtered through Celite® and the filtrate poured into water (100 ml). The mixture was extracted with EtOAc (2×60 ml, then 2×80 ml). The extracts were combined and dried over $Na_2SO_4$ and concentrated in vacuo to afford a brown liquid (2.6 g). This material was dissolved in dioxane (15 ml) and water (3 ml), then treated with the product from Example 186 Step 3 (1.35 g, 6.4 mmol) and $Na_2CO_3(s)$ (2.07 g, 19.3 mmol). The reaction mixture was purged with $N_2$ for 30 min. $PdCl_2$(dppf)-DCM (0.54 g, 0.64 mmol) was added and the reaction mixture stirred with microwave heating at 130° C. for 1 h. The reaction mixture was filtered through Celite®. The filtrate was poured into water (120 ml) and extracted with EtOAc (150 ml, then 2×100 ml). The extracts were combined and dried over $Na_2SO_4(s)$ and concentrated in vacuo. The residue was purified by reverse phase chromatography (37% MeCN/water) to afford the title compound (0.09 g, 0.32 mmol, 8% yield, 98% purity) as a light-yellow solid. UPLC-MS (Method 5) m/z 286.3 at 1.59 min.

Step 3: methyl 3-(N-(4-chloro-5-(1-methyl-1,2,4-triazol-5-yl)-2-(pyridin-2-yl)phenyl)sulfamoyl)-4-cyclopropylbenzoate: A mixture of the product from Step 2 above (100 mg, 350 µmol), the product from Example 132 Step 5 (144 mg, 525 µmol) and pyridine (90 µl, 1.1 mmol) in DCM (2 ml) was stirred at RT overnight. The mixture was concentrated onto silica and purified by chromatography on silica gel (12 g cartridge, 0-100% EtOAc/isohexane) to afford the title compound (118 mg, 225 µmol, 64% yield) as a pale tan solid. UPLC-MS (Method 1): m/z 524.3 (M+H)⁺, 522.2 (M–H)⁻, at 1.54 min.

Step 4: 3-(N-(4-chloro-5-(1-methyl-1,2,4-triazol-5-yl)-2-(pyridin-2-yl)phenyl)sulfamoyl)-4-cyclopropylbenzoic acid: A mixture of the product from Step 3 above (118 mg, 225 µmol) and LiOH·$H_2O$ (38 mg, 906 µmol) in THF/MeOH/$H_2O$ (4:1:1, 1.2 ml) was stirred at 40° C. overnight. The mixture was diluted with water (10 ml), acidified to ~pH 4 using 1 M HCl(aq) and extracted with EtOAc (3×20 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to afford (94.6 mg, 182 µmol, 81% yield, 98% purity) as a pale-yellow solid. UPLC-MS (Method 1): m/z 510.3 (M+H)⁺, 508.2 (M–H)⁻, at 1.38 min. ¹H NMR (500 MHz, DMSO-$d_6$) δ 13.27 (s, 1H), 13.17 (s, 1H), 8.73 (d, J=4.9 Hz, 1H), 8.25 (d, J=1.9 Hz, 1H), 8.21-8.17 (m, 1H), 8.13-8.07 (m, 2H), 8.03-8.00 (m, 1H), 7.91 (d, J=8.2 Hz, 1H), 7.57 (s, 1H), 7.54-7.51 (m, 1H), 6.97 (d, J=8.2 Hz, 1H), 3.63 (s, 3H), 2.53-2.52 (m, 1H), 0.79-0.72 (m, 2H), 0.67-0.60 (m, 2H).

Example 190: 4-cyclopropyl-3-(N-(4-fluoro-2-(pyridin-2-yl)-5-(tetrazol-1-yl)phenyl)sulfamoyl)benzoic acid

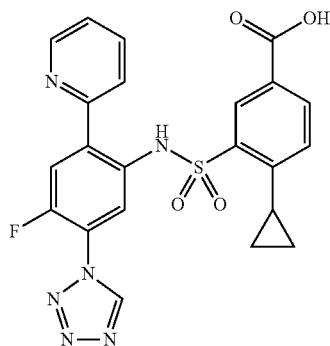 [SMILES: O=C(O)c1ccc(C2CC2)c(S(=O)(=O)Nc2cc(-n3cnnn3)c(F)cc2-c2ccccn2)c1]

Step 1: 1-(4-bromo-2-fluoro-5-nitrophenyl)tetrazole: A solution of 4-bromo-2-fluoro-5-nitroaniline (2.0 g, 8.5 mmol) in AcOH (40 ml) was treated with triethyl orthoformate (6.33 g, 43 mmol) and the resultant mixture stirred at RT for 5 min. The reaction mixture was then cooled to 0° C. and trimethylsilylazide (4.92 g, 43 mmol) was added. The resultant reaction mixture was heated at 70° C. for 7 h. The reaction mixture was diluted with ice cold water (100 ml) and the resultant precipitate was collected by filtration. The solid was purified by chromatography on silica gel (20% EtOAc/hexane) to afford the title compound (1.9 g, 6.6 mmol, 78% yield) as a brown solid. UPLC-MS (Method 5) m/z no ionisation at 1.84 min.

Step 2: 2-bromo-4-fluoro-5-(tetrazol-1-yl)aniline: A solution of the product from Step 1 above (1.6 g, 5.6 mmol) in EtOAc was treated with $SnCl_2(s)$ (5.29 g, 28 mmol) and the resultant mixture stirred at 80° C. for 2 h. The reaction mixture was diluted with water (80 ml) and extracted with EtOAc (3×60 ml). The extracts were combined and washed with brine (10 ml), then dried over $Na_2SO_4(s)$. The solvent was evaporated in vacuo. The residue was purified by chromatography on neutral alumina (23% EtOAc/hexane) to afford the title compound (0.7 g, 2.7 mmol, 48% yield) as a white solid. UPLC-MS (Method 5) m/z 258.1 (M+H)⁺ at 1.72 min.

Step 3: 4-fluoro-2-(pyridin-2-yl)-5-(tetrazol-1-yl)aniline hydrochloride: Two reactions were carried out on the same scale according to the following procedure and combined. A solution of the product from Step 2 above (0.350 g, 1.4 mmol) and 2-(tributylstannyl)pyridine (0.752 g, 2.0 mmol) in dioxane (7 ml) was purged with N₂ for 30 min, then Pd(PPh₃)₄ (0.162 g, 0.14 mmol) was added. The resultant reaction mixture was stirred with microwave heating at 140° C. for 1 h. The reaction mixture was diluted with water (80 ml) and extracted with EtOAc (3×50 ml). The extracts were combined and dried over Na₂SO₄(s). The filtrate was concentrated in vacuo and the residue partially purified chromatography on neutral alumina (99.4% EtOAc/hexane), then dissolved in DCM (10 ml). 4 M HCl in dioxane (3 ml) was added. The solution was stirred for 30 min, then concentrated in vacuo. The residue was triturated using Et₂O (10 ml) to afford the title compound (0.450 g, 1.53 mmol, 55% yield) as a yellow solid. UPLC-MS (Method 5) m/z 257.3 (M+H)⁺ at 1.65 min.

Step 4: methyl 4-cyclopropyl-3-(N-(4-fluoro-2-(pyridin-2-yl)-5-(tetrazol-1-yl)phenyl)sulfamoyl)benzoate: A mixture of the product from Step 3 above (100 mg, 342 µmol), the product from Example 132 Step 5 (161 mg, 585 µmol) and pyridine (90 µl, 1.1 mmol) in DCM (2 ml) was stirred at RT overnight. The mixture was concentrated onto silica and purified by chromatography on silica gel (12 g cartridge, 0-100% EtOAc/isohexane) to afford the title compound (96.8 mg, 176 µmol, 51% yield, 90% purity) as a pale-yellow solid. UPLC-MS (Method 1): m/z 517.3 (M+Na)⁺, 493.2 (M−H)⁻ at 1.56 min.

Step 5: 4-cyclopropyl-3-(N-(4-fluoro-2-(pyridin-2-yl)-5-(tetrazol-1-yl)phenyl)sulfamoyl)benzoic acid: A mixture of the product from Step 4 above (96.8 mg, 176 µmol, 90% purity) and LiOH·H₂O (30 mg, 715 µmol) in THF/MeOH/H₂O (4:1:1, 1.2 ml) was stirred at 40° C. overnight. The mixture was diluted with water (10 ml), acidified to ~pH 4 using 1 M HCl(aq), then extracted with EtOAc (3×20 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to afford the title compound (15.6 mg, 31.5 µmol, 18% yield, 97% purity) as a yellow solid. UPLC-MS (Method 1): m/z 503.3 (M+Na)⁺, 479.3 (M−H)⁻ at 1.41 min. ¹H NMR (500 MHz, DMSO-d₆) δ 13.22 (s, 1H), 13.13 (s, 1H), 9.93 (d, J=1.8 Hz, 1H), 8.72 (d, J=4.9 Hz, 1H), 8.32 (s, 1H), 8.22 (d, J=11.7 Hz, 1H), 8.08-7.95 (m, 3H), 7.93-7.87 (m, 1H), 7.53-7.50 (m, 1H), 6.97 (d, J=8.3 Hz, 1H), 2.56-2.53 (m, 1H), 0.81-0.73 (m, 2H), 0.68-0.61 (m, 2H).

Example 191: 3-(N-(4-chloro-5-(isothiazol-5-yl)-2-(pyridin-2-yl)phenyl)sulfamoyl)-4-cyclopropylbenzoic acid

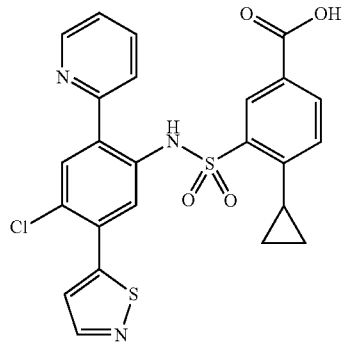

Step 1: 5-(2-chloro-5-nitro-4-(pyridin-2-yl)phenyl)isothiazole: A solution of the product from Example 188 Step 1 (1 g, 3.2 mmol) in dioxane (15 ml) was treated with the product from Example 184 Step 2 (2.40 g, 6.4 mmol) and Na₂CO₃(s) (1.01 g, 9.6 mmol). The reaction mixture was purged with N₂ for 30 min. PdCl₂(dppf) (0.114 g, 0.16 mmol) was added and the resultant mixture stirred at 100° C. for 4 h. The reaction mixture was poured into water (50 ml) and extracted with EtOAc (2×70 ml). The extracts were combined and dried over Na₂SO₄(s) and concentrated in vacuo. The residue was purified by chromatography on silica gel (20% EtOAc/hexane) to afford the title compound (0.36 g, 1.1 mmol, 36%) as a light-yellow solid. UPLC-MS (Method 5) m/z 318.1 (M+H)⁺ at 2.02 min.

Step 2: 4-chloro-5-(isothiazol-5-yl)-2-(pyridin-2-yl)aniline: A solution of the product from Step 1 above (0.36 g, 1.1 mmol) in MeOH (9 ml) and water (1 ml) was treated with iron powder (0.317 g, 5.5 mmol) and NH₄Cl(s) (0.299 g, 5.5 mmol). The reaction mixture was stirred at 80° C. for 4 h. The reaction mixture was poured into water (50 ml) and filtered through Celite®. The filtrate was extracted with EtOAc (3×30 ml). The extracts were combined and dried over Na₂SO₄(s) and concentrated in vacuo. The residue was purified by chromatography on neutral alumina (20% EtOAc/hexane) to afford the title compound (0.1 g, 0.35 mmol, 32% yield). UPLC-MS (Method 5) m/z 288.3 (M+H)⁺ at 2.31 min.

Step 3: methyl 3-(N-(4-chloro-5-(isothiazol-5-yl)-2-(pyridin-2-yl)phenyl)sulfamoyl)-4-cyclopropylbenzoate: A mixture of the product from Step 2 above (100 mg, 347 µmol), the product from Example 132 Step 5 (143 mg, 521 µmol) and pyridine (90 µl, 1.1 mmol) in DCM (2 ml) was stirred at RT overnight. The mixture was concentrated onto silica and purified by chromatography on silica gel (12 g cartridge, 0-100% EtOAc/isohexane) to afford the title compound (163 mg, 307 µmol, 88% yield, 99% purity) as a yellow solid. UPLC-MS (Method 1): m/z 526.3 (M+H)⁺, 524.2 (M−H)⁻ at 1.95 min.

Step 4: 3-(N-(4-chloro-5-(isothiazol-5-yl)-2-(pyridin-2-yl)phenyl)sulfamoyl)-4-cyclopropylbenzoic acid: A mixture of the product from Step 3 above (163 mg, 307 µmol, 88% yield, 99% purity) and LiOH·H₂O (52 mg, 1.24 mmol) in THF/MeOH/H₂O (4:1:1, 1.5 ml) was stirred at 40° C. overnight. The mixture was diluted with water (10 ml), acidified to ~pH 4 using 1 M HCl(aq) and extracted with EtOAc (3×20 ml). The combined organic extracts were washed with brine (10 ml), passed through a phase separator and the solvent was removed in vacuo. The residue was loaded onto silica and purified by chromatography on silica gel (4 g cartridge, 0-10% MeOH/DCM) to afford (21.6 mg, 40.9 μmol, 13% yield, 97% purity) as a pale-yellow solid. UPLC-MS (Method 1): m/z 512.2 (M+H)$^+$, 510.2 (M−H)$^−$, at 1.82 min. $^1$H NMR (500 MHz, DMSO-d$_6$) δ 13.44 (s, 1H), 13.37 (s, 1H), 8.73 (d, J=4.9 Hz, 1H), 8.65 (d, J=1.9 Hz, 1H), 8.48 (s, 1H), 8.22 (s, 1H), 8.19-8.14 (m, 1H), 8.06-8.01 (m, 1H), 7.94 (d, J=8.2 Hz, 1H), 7.77 (s, 1H), 7.71-7.67 (m, 1H), 7.55-7.51 (m, 1H), 7.02 (d, J=8.2 Hz, 1H), 2.58-2.54 (m, 1H), 0.75-0.70 (m, 2H), 0.68-0.62 (m, 2H).

Example 192: 3-(N-(4-chloro-5-cyano-2-(thiazol-2-yl)phenyl)sulfamoyl)-4-cyclopropylbenzoic acid

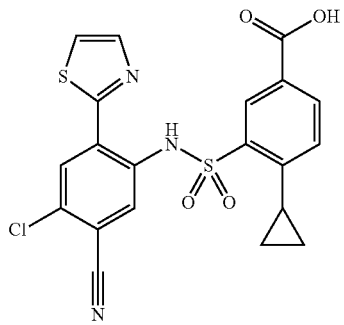 [SMILES: N#Cc1cc(NS(=O)(=O)c2cc(C(=O)O)ccc2C2CC2)c(-c2nccs2)cc1Cl]

Step 1: 5-amino-2-chloro-4-(thiazol-2-yl)benzonitrile: A mixture of the product from Example 178 Step 1 (250 mg, 784 μmol, 87% purity), 2-bromothiazole (72 μl, 799 μmol), 1 M K$_3$PO$_4$(aq) (1.30 ml, 1.30 mmol) and dioxane (5 ml) was treated with Pd(dppf)Cl$_2$·DCM complex (64 mg, 78 μmol). The resultant solution was degassed with N$_2$ for 10 min, then heated at 80° C. for 1 h. The reaction mixture was concentrated onto silica and purified by chromatography on silica gel (24 g cartridge, 0-40% EtOAc/isohexane) to afford the title compound (136 mg, 531 μmol, 68% yield, 92% purity) as a bright yellow solid. UPLC-MS (Method 1) m/z 236.2 (M+H)$^+$ at 1.50 min.

Step 2: Methyl 3-(N-(4-chloro-5-cyano-2-(thiazol-2-yl)phenyl)sulfamoyl)-4-cyclopropylbenzoate: To a solution of the product from Example 132 Step 5 (160 mg, 584 μmol, 95% purity) in pyridine (1.71 ml, 21.2 mmol) was added the product from Step 1 above (136 mg, 531 μmol, 92% purity). The resultant solution was stirred at RT for 4 days. The reaction mixture was concentrated in vacuo, azeotroping with toluene (50 ml), then dissolved in DCM (20 ml) and washed with saturated NaHCO$_3$(aq) (10 ml). The organic phase was passed through a phase separator and concentrated in vacuo. The crude product was purified by chromatography on silica gel (24 g cartridge, 0-100% EtOAc/isohexane) to afford the title compound (184 mg, 379 μmol, 71% yield, 98% purity) as a pale-yellow solid. UPLC-MS (Method 1) m/z 474.7 (M+H)$^+$ at 1.81 min.

Step 3: 3-(N-(4-chloro-5-cyano-2-(thiazol-2-yl)phenyl)sulfamoyl)-4-cyclopropylbenzoic acid: To a solution of the product from Step 2 above (184 mg, 379 μmol, 98% purity) in THF (2.4 ml) was added 1 M LiOH(aq) (1.20 ml, 1.20 mmol). The reaction mixture stirred at RT overnight, then concentrated in vacuo and the residue partitioned between water (12 ml) and EtOAc (12 ml). The aqueous phase was separated and acidified using 1 M HCl(aq) until pH 4-5, then the extracted with EtOAc (2×12 ml). The combined extracts were passed through a phase separator and concentrated in vacuo to afford the title compound (140 mg, 289 μmol, 76% yield, 95% purity) as a white solid. UPLC-MS (Method 1) m/z 460.2 (M+H)$^+$ at 1.67 min. $^1$H NMR (500 MHz, DMSO-d$_6$) δ 13.33 (br s, 1H), 8.46 (d, J=1.9 Hz, 1H), 8.28 (s, 1H), 8.15 (d, J=3.3 Hz, 1H), 8.10-8.06 (m, 1H), 7.99 (dd, J=8.2, 1.9 Hz, 1H), 7.70 (s, 1H), 7.09 (d, J=8.3 Hz, 1H), 2.70-2.58 (m, 1H), 0.91-0.81 (m, 2H), 0.78-0.70 (m, 2H). One exchangeable proton not observed.

Example 193: 3-(N-(4-chloro-5-(5-methylisoxazol-4-yl)-2-(pyridin-2-yl)phenyl)sulfamoyl)-4-cyclopropylbenzoic acid

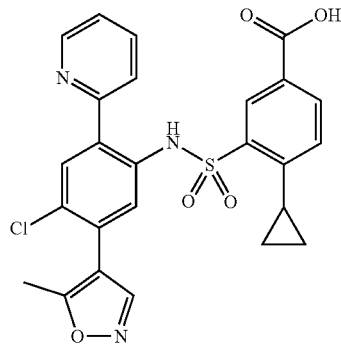 [SMILES: Cc1oncc1-c1cc(NS(=O)(=O)c2cc(C(=O)O)ccc2C2CC2)c(-c2ccccn2)cc1Cl]

Step 1: 4-chloro-5-(5-methylisoxazol-4-yl)-2-(pyridin-2-yl)aniline: A solution of the product from Example 189 Step 1 (0.6 g, 2.13 mmol) and KOAc (0.62 g, 6.29 mmol) in dioxane (6 ml) was treated with bis(pinacolato)diboron (1.35 g, 5.32 mmol) at RT. The reaction mixture was purged with N$_2$ for 20 min, then PdCl$_2$(dppf)-DCM (0.17 g, 0.21 mmol) was added. The resultant mixture was stirred at 110° C. for 3 h. The reaction mixture was diluted with water (100 ml) and filtered through Celite®. The filtrate was extracted with EtOAc (3×30 ml). The extracts were combined and dried over Na$_2$SO$_4$(s) and concentrated in vacuo to obtain a brown solid (1.5 g). A portion of this solid (0.475 g) in dioxane (8 ml) and water (2 ml) was treated with 4-iodo-5-methylisoxazole (0.25 g, 1.19 mmol) and K$_3$PO$_4$ (0.507 g, 2.39 mmol). The reaction mixture was purged with N$_2$ for 30 min, then XPhos Pd G2 (0.094 g, 0.12 mmol) was added and the resultant mixture stirred with microwave heating at 100° C. for 1 h. The reaction mixture was poured into water (100 ml) and extracted with Ethyl acetate (2×100 ml). The extracts were combined, dried over Na$_2$SO$_4$(s), and concentrated in vacuo. The residue was purified by chromatography on neutral alumina (10% EtOAc/hexane) to afford the title compound (0.158 g, 0.554 mmol, 82% yield) as brown solid. UPLC-MS (Method 5) m/z 286.3 (M+H)$^+$ at 2.15 min.

Step 2: methyl 3-(N-(4-chloro-5-(5-methylisoxazol-4-yl)-2-(pyridin-2-yl)phenyl)sulfamoyl)-4-cyclopropylbenzoate: A mixture of the product from Step 1 above (55 mg, 192 μmol), the product from Example 132 Step 5 (80 mg, 291 μmol) and pyridine (47 μl, 583 μmol) in DCM (1 ml) was stirred at RT overnight. The mixture was concentrated onto silica and purified by chromatography on silica gel (12 g cartridge, 0-100% EtOAc/isohexane) to afford the title compound (96.3 mg, 178 μmol, 93% yield, 97% purity) as a pale tan solid. UPLC-MS (Method 1): m/z 524.3 (M+H)$^+$, 522.2 (M−H)$^−$, at 1.85 min.

Step 3: 3-(N-(4-chloro-5-(5-methylisoxazol-4-yl)-2-(pyridin-2-yl)phenyl)sulfamoyl)-4-cyclopropylbenzoic acid: A mixture of the product from Step 2 above (96.3 mg, 178 μmol, 97% purity) and 4 M HCl in dioxane (250 μL, 1.00 mmol) in dioxane (0.5 ml) and water (0.25 ml) was heated at 50° C. and stirred overnight. Concentrated HCl(aq) (250 μL) was added and the mixture was heated at 70° C. and stirred for 5 h. The mixture was diluted with water (10 ml) and extracted with EtOAc (3×20 ml). The combined organic extracts were washed with brine (10 ml), passed through a phase separator and the solvent was removed in vacuo. The crude product was purified by preparative HPLC (Waters, Acidic (0.1% Formic acid), Acidic, Waters X-Select Prep-C18, 5 μm, 19×50 mm column, 50-80% (0.1% formic acid in MeCN)/0.1% formic acid(aq)) to afford the title compound (28.7 mg, 55.7 μmol, 31% yield, 99% purity) as a pale yellow solid. UPLC-MS (Method 1): m/z 510.2 (M+H)$^+$, 508.2 (M−H)$^-$, at 1.72 min. $^1$H NMR (500 MHz, DMSO-d$_6$) δ 13.28 (s, 2H), 8.72 (dd, J=4.8, 1.6 Hz, 1H), 8.68 (s, 1H), 8.35 (d, J=1.9 Hz, 1H), 8.15-8.08 (m, 2H), 8.04-7.98 (m, 1H), 7.93 (dd, J=8.2, 1.9 Hz, 1H), 7.54-7.48 (m, 1H), 7.45 (s, 1H), 7.01 (d, J=8.2 Hz, 1H), 2.56-2.52 (m, 1H), 2.32 (s, 3H), 0.78-0.71 (m, 2H), 0.71-0.63 (m, 2H).

Example 194: 4-cyclopropyl-3-(N-(5-(5-methylisoxazol-4-yl)-2-(pyrrol-1-yl)phenyl)sulfamoyl)benzoic acid

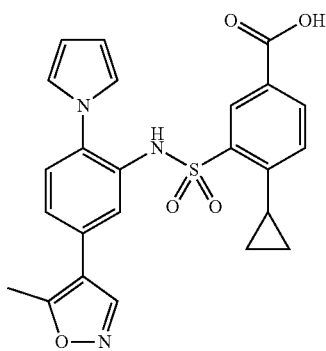 [SMILES: Cc1oncc1-c1ccc(-n2cccc2)c(NS(=O)(=O)c2cc(C(=O)O)ccc2C2CC2)c1]

Step 1: tert-butyl (4-bromo-2-nitrophenyl)carbamate: To a solution of 4-bromo-2-nitroaniline (5.02 g, 23.1 mmol) and di-tert-butyl dicarbonate (10.2 g, 46.7 mmol) in THF (50 ml) at 0° C. was added DMAP (286 mg, 2.34 mmol). The resultant mixture was allowed to warm to RT and was stirred for 90 min before concentration in vacuo to afford a yellow oil. The oil was dissolved in THF (23 ml) and then 2 N NaOH(aq) (23 ml, 46.0 mmol) was added. The resultant mixture was heated at 65° C. for 19 h. NaOH (2.63 g, 65.8 mmol) was added and the mixture was stirred at 65° C. for 4 h and then at 70° C. for 22 h. The reaction mixture was allowed to cool to RT and then the THF was removed in vacuo. The precipitate was isolated by filtration, washed with water (20 ml) and dried in vacuo to afford the title compound (7.74 g, 21.7 mmol, 94% yield, 89% purity) as an orange solid. UPLC-MS (Method 1) m/z 316.1 (M−H)$^-$ at 1.85 min. $^1$H NMR (500 MHz, DMSO-d$_6$) δ 9.67 (br s, 1H), 8.10 (d, J=2.4 Hz, 1H), 7.83 (dd, J=8.8, 2.3 Hz, 1H), 7.60 (d, J=8.8 Hz, 1H), 1.43 (s, 9H).

Step 2: tert-butyl (2-amino-4-bromophenyl)carbamate: Zinc (3.30 g, 50.5 mmol) and NH$_4$Cl (2.70 g, 50.5 mmol) were added to a solution of the product from Step 1 above (3.00 g, 8.42 mmol, 89% purity) in THF (21 ml) and water (7 ml). The suspension was stirred vigorously at RT for 17 h. The resultant mixture was filtered through Celite®, washed with EtOAc (60 ml) and concentrated onto silica gel. The crude product was purified by chromatography on silica gel (80 g cartridge, 0-35% EtOAc/isohexane) to afford the title compound (2.12 g, 6.79 mmol, 81% yield, 92% purity) as a yellow solid. UPLC-MS (Method 1) m/z 188.2 (M−Boc+H)$^+$ at 1.38 min. $^1$H NMR (500 MHz, DMSO-d$_6$) δ 8.30 (br s, 1H), 7.15 (br d, J=8.4 Hz, 1H), 6.85 (d, J=2.3 Hz, 1H), 6.64 (dd, J=8.5, 2.3 Hz, 1H), 5.14 (br s, 2H), 1.45 (s, 9H).

Step 3: methyl 3-(N-(2-amino-5-bromophenyl)sulfamoyl)-4-cyclopropylbenzoate: The product from Example 132, Step 5 (2.06 g, 7.13 mmol, 95% purity) was dissolved in pyridine (7.5 ml) and stirred for 5 min. A solution of the product from Step 2 above (2.12 g, 6.79 mmol, 92% purity) in pyridine (7.5 ml) was added and then the resultant mixture was stirred vigorously at RT for 23 h. The resultant mixture was concentrated in vacuo, diluted with DCM (15 ml) and washed with water (3×10 ml). The organic phase was dried by passage through a phase separator and concentrated in vacuo. The orange oil was azeotroped with PhMe (10 ml), concentrated in vacuo and then dissolved in DCM (20 ml). TFA (10.5 ml, 136 mmol) was added and then the resultant solution was stirred at RT for 45 min. The reaction was quenched by the careful, portion-wise addition of saturated NaHCO$_3$(aq) (100 ml) and then NaHCO$_3$(s) (~5 g). The phases were separated and then the aqueous phase was extracted with EtOAc (3×25 ml). The organic phases were combined, washed with brine (25 ml), dried by passage through a phase separator, and concentrated in vacuo to afford the title compound (3.21 g, 6.04 mmol, 89% yield, 80% purity) as a red sticky oil. UPLC-MS (Method 1) m/z 424.1 (M−H)$^-$ at 1.47 min. $^1$H NMR (500 MHz, DMSO-d$_6$) δ 9.72 (br s, 1H), 8.30 (d, J=1.9 Hz, 1H), 8.01 (dd, J=8.3, 1.9 Hz, 1H), 7.14 (d, J=8.3 Hz, 1H), 7.02 (dd, J=8.6, 2.4 Hz, 1H), 6.81 (d, J=2.4 Hz, 1H), 6.58 (d, J=8.6 Hz, 1H), 5.15 (br s, 2H), 3.84 (s, 3H), 2.84-2.76 (m, 1H), 1.17-1.12 (m, 2H), 0.94-0.86 (m, 2H).

Step 4: methyl 3-(N-(5-bromo-2-(pyrrol-1-yl)phenyl)sulfamoyl)-4-cyclopropylbenzoate: 2,5-dimethoxytetrahydrofuran (878 μl, 6.64 mmol) was added to a solution of the product from Step 3 above (3.21 g, 6.04 mmol, 80% purity) in AcOH (20 ml). The resultant solution was heated to 80° C. and stirred for 2 h. The reaction mixture was allowed to cool to RT and then quenched by the careful addition of saturated NaHCO$_3$(aq) (50 ml). EtOAc (30 ml) was added and then the phases were separated. The aqueous phase was extracted with EtOAc (3×30 ml) and then the organic phases were combined, washed with brine (30 ml), dried by passage through a phase separator, and then concentrated in vacuo. The slurry was dissolved in EtOAc (30 ml) and neutralised with saturated NaHCO$_3$(aq) (50 ml) and NaHCO$_3$ (3.50 g). The phases were separated and then the aqueous phase was extracted with EtOAc (2×30 ml). The organic phases were combined, washed with brine (30 ml), dried by passage through a phase separator, and concentrated in vacuo to afford the title compound (3.16 g, 5.65 mmol, 94% yield, 85% purity) as a light brown solid. UPLC-MS (Method 1) m/z 476.2 (M+H)$^+$, 474.2 (M−H)$^-$ at 1.78 min. $^1$H NMR (500 MHz, DMSO-d$_6$) δ 10.20 (br s, 1H), 8.20 (d, J=1.9 Hz, 1H), 8.07-7.98 (m, 1H), 7.53 (br d, J=8.5 Hz, 1H), 7.26 (d, J=8.5 Hz, 1H), 7.15 (d, J=8.3 Hz, 1H), 7.08 (d, J=2.3 Hz, 1H), 6.91-6.86 (m, 2H), 6.12-6.07 (m, 2H), 3.85 (d, J=1.0 Hz, 3H), 2.71-2.56 (m, 1H), 1.12-1.04 (m, 2H), 0.91-0.84 (m, 2H).

Step 5: methyl 3-(N-(2-(pyrrol-1-yl)-5-(4,4,5,5-tetramethyl-1,3,2-dioxaborolan-2-yl)phenyl)sulfamoyl)-4-cyclopropylbenzoate: A mixture of the product from Step 4 above (1.50 g, 2.68 mmol, 85% purity), bis(pinacolato)diboron (749 mg, 2.95 mmol), [Pd(dppf)Cl$_2$]-DCM complex (219 mg, 268 μmol) and potassium acetate (790 mg, 8.05 mmol) in dioxane (10 ml) was sparged with N$_2$ for 10 min. The reaction was heated at 80° C. for 1.5 h. The reaction mixture was allowed to cool to RT, filtered through Celite®, washed with EtOAc (20 ml) and concentrated in vacuo. The crude product was purified by chromatography on silica gel (40 g cartridge, 0-50% EtOAc/isohexane) to afford the title compound (1.20 g, 2.02 mmol, 75% yield, 88% purity) as a yellow oil. UPLC-MS (Method 1) m/z 523.6 (M+H)$^+$, 521.3 (M−H)$^−$ at 1.90 min. $^1$H NMR (500 MHz, DMSO-d$_6$) δ 9.98 (s, 1H), 8.20 (d, J=1.9 Hz, 1H), 8.03 (dd, J=8.2, 1.9 Hz, 1H), 7.55 (br d, J=7.8 Hz, 1H), 7.32 (d, J=7.9 Hz, 1H), 7.17 (d, J=8.3 Hz, 1H), 7.11 (s, 1H), 7.03 (t, J=2.2 Hz, 2H), 6.16 (t, J=2.1 Hz, 2H), 3.83 (s, 3H), 2.74-2.64 (m, 1H), 1.21 (s, 12H), 1.13-1.08 (m, 2H), 0.92-0.85 (m, 2H).

Step 6: methyl 4-cyclopropyl-3-(N-(5-(5-methylisoxazol-4-yl)-2-(pyrrol-1-yl)phenyl)sulfamoyl)benzoate: A mixture of the product from Step 5 above (400 mg, 674 μmol, 88% purity), 4-iodo-5-methylisoxazole (169 mg, 809 μmol), K$_3$PO$_4$ (286 mg, 1.35 mmol), XPhos Pd G3 (28 mg, 33.1 μmol) in dioxane (4 ml) and water (0.8 ml) was sparged with N$_2$ for 10 min before being heated at 80° C. for 2 h. The reaction mixture was allowed to cool to RT, filtered through Celite®, washed with EtOAc (10 ml) and concentrated in vacuo. The crude product was purified by chromatography on silica gel (12 g cartridge, 0-60% EtOAc/isohexane) to afford the title compound (233 mg, 464 μmol, 69% yield, 95% purity) as a yellow foam. UPLC-MS (Method 1) m/z 478.3 (M+H)$^+$, 476.2 (M−H)$^−$ at 1.64 min.

Step 7: 4-cyclopropyl-3-(N-(5-(5-methylisoxazol-4-yl)-2-(pyrrol-1-yl)phenyl)sulfamoyl)benzoic acid: Concentrated HCl(aq) (1 ml, 12.0 mmol) was added to a solution of the product from Step 6 above (233 mg, 464 μmol, 95% purity) in dioxane (2 ml) and water (200 μl) at RT. The resultant solution was heated to 70° C. and stirred for 20 h. Additional concentrated HCl(aq) (500 μl, 6.00 mmol) and water (200 μl) were added and the reaction mixture was heated at 70° C. and stirred for 4 h. The reaction was allowed to cool to RT and then concentrated in vacuo. The residue was dissolved in EtOAc (5 ml) and then saturated NaHCO$_3$(aq) (5 ml) was added. The phases were separated and then the aqueous phase was extracted with EtOAc (2×5 ml). The organic phases were combined, washed with brine (10 ml), dried by passage through a phase separator, and concentrated in vacuo. The crude product was purified by chromatography (24 g reverse phase C18 cartridge, 15-50% MeCN/10 mM ammonium bicarbonate(aq)) to afford the title compound (46 mg, 94 μmol, 20% yield, 95% purity) as a light tan solid. UPLC-MS (Method 1) m/z 464.3 (M+H)$^+$, 462.3 (M−H)$^−$ at 1.55 min. $^1$H NMR (500 MHz, DMSO-d$_6$) δ 13.22 (br s, 1H), 10.10 (br s, 1H), 8.69 (s, 1H), 8.28 (s, 1H), 8.01 (d, J=8.2 Hz, 1H), 7.61-7.45 (m, 1H), 7.41 (d, J=8.2 Hz, 1H), 7.16 (d, J=8.2 Hz, 1H), 7.01 (t, J=2.1 Hz, 2H), 6.97 (s, 1H), 6.18 (t, J=2.1 Hz, 2H), 2.78-2.65 (m, 1H), 2.26 (s, 3H), 1.12-1.02 (m, 2H), 0.96-0.81 (m, 2H).

Example 195: 4-cyclopropyl-3-(N-(5-(1-methyl-1,2,4-triazol-5-yl)-2-(pyrrol-1-yl)phenyl)sulfamoyl)benzoic acid

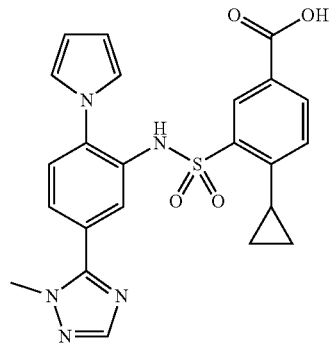 [SMILES: Cn1ncnc1-c1ccc(-n2cccc2)c(NS(=O)(=O)c2cc(C(=O)O)ccc2C2CC2)c1]

Step 1: methyl 4-cyclopropyl-3-(N-(5-(1-methyl-1,2,4-triazol-5-yl)-2-(pyrrol-1-yl)phenyl)sulfamoyl)benzoate: A mixture of Example 194 Step 5 (400 mg, 674 pNmol, 88% purity), 5-bromo-1-methyl-1,2,4-triazole (135 mg, 809 μmol), K$_3$PO$_4$ (286 mg, 1.35 mmol), XPhos Pd G3 (28 mg, 33.1 μmol) in dioxane (4 ml) and water (0.8 ml) was sparged with N$_2$ for 10 min before being heated at 80° C. for 1.5 h. Additional 5-bromo-1-methyl-1,2,4-triazole (135 mg, 809 μmol), K$_3$PO$_4$ (286 mg, 1.35 mmol) and XPhos Pd G3 (28 mg, 33.1 μmol) were added and then the resultant mixture was sparged with N$_2$ for 10 min before being heated at 80° C. for 2 h. The reaction mixture was allowed to cool to RT, filtered through Celite®, washed with EtOAc (10 ml) and then concentrated in vacuo. The crude product was purified by chromatography on silica gel (12 g cartridge, 0-100% then 100% EtOAc/isohexane) to afford the title compound (208 mg, 431 μmol, 64% yield, 99% purity) as a light brown solid. UPLC-MS (Method 1) m/z 478.4 (M+H)$^+$, 476.3 (M−H)$^−$ at 1.42 min.

Step 2: 4-cyclopropyl-3-(N-(5-(1-methyl-1,2,4-triazol-5-yl)-2-(pyrrol-1-yl)phenyl)sulfamoyl)benzoic acid: 1 M LiOH(aq) (1.75 ml, 1.75 mmol) was added to a suspension of the product from Step 1 above (208 mg, 431 μmol, 99% purity) in THF (3.5 ml) at RT. The resultant cloudy solution was stirred at RT over the weekend. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) and THF (10 ml) were added. The phases were separated and then the aqueous phase was extracted with EtOAc (2×10 ml). The gel-like substance which remained in the combined organic phases was partially dissolved by the addition of THF (15 ml). The combined organic phases were washed with brine (15 ml), dried by passage through a phase separator, and concentrated in vacuo. The crude product was purified by chromatography (24 g reverse phase C18 cartridge, 5-40% MeCN/10 mM ammonium bicarbonate(aq)) to afford the title compound (130 mg, 272 μmol, 63% yield, 97% purity) as an off-white solid. UPLC-MS (Method 1) m/z 464.3 (M+H)$^+$, 462.3 (M−H)$^−$ at 1.29 min. $^1$H NMR (500 MHz, DMSO-d$_6$) δ 9.38 (br s, 2H), 8.38 (d, J=1.8 Hz, 1H), 7.89 (dd, J=8.2, 1.9 Hz, 1H), 7.87 (s, 1H), 7.55 (d, J=2.0 Hz, 1H), 7.43-7.36 (m, 1H), 7.32 (d, J=8.2 Hz, 1H), 7.08 (t, J=2.2 Hz, 2H), 7.00 (d, J=8.2 Hz, 1H), 6.13 (t, J=2.1 Hz, 2H), 3.80 (s, 3H), 2.96-2.89 (m, 1H), 1.02-0.96 (m, 2H), 0.80-0.74 (m, 2H).

Example 196: 3-(N-(5-cyano-4-fluoro-2-(thiazol-4-yl)phenyl)sulfamoyl)-4-cyclopropylbenzoic acid

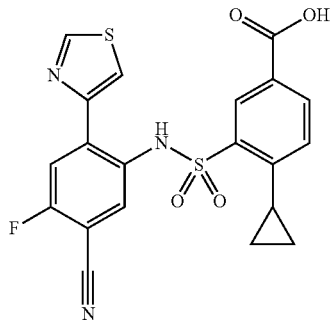 [SMILES: N#Cc1cc(NS(=O)(=O)c2cc(C(=O)O)ccc2C2CC2)c(-c2cscn2)cc1F]

Step 1: 5-amino-2-fluoro-4-(thiazol-4-yl)benzonitrile: A mixture of the product from Example 181 Step 1 (240 mg, 882 μmol, 96% purity), 4-bromothiazole (80 μl, 897 μmol), 1 M K$_3$PO$_4$(aq) (1.50 ml, 1.50 mmol) and dioxane (6 ml) was treated with Pd(dppf)Cl$_2$·DCM (36 mg, 44.1 μmol). The resultant solution was degassed with N$_2$ for 10 min, then heated at 80° C. for 1 h. The reaction mixture was concentrated onto silica and purified by chromatography on silica gel (40 g cartridge, 0-40% EtOAc/isohexane) to afford the title compound (134 mg, 590 μmol, 67% yield, 97% purity) as a pale-yellow solid. UPLC-MS (Method 1) m/z 220.2 (M+H)$^+$ at 1.21 min.

Step 2: Methyl 3-(N-(5-cyano-4-fluoro-2-(thiazol-4-yl)phenyl)sulfamoyl)-4-cyclopropylbenzoate: A solution of the product from Example 132 Step 5 (190 mg, 657 μmol, 95% purity) in pyridine (2 ml, 24.8 mmol) was treated with the product from Step 1 above (134 mg, 590 μmol, 97% purity). The resultant solution was stirred at RT for 3 days. The mixture was concentrated in vacuo, azeotroping with toluene (50 ml), then dissolved in DCM (20 ml) and washed with saturated NaHCO$_3$(aq) (10 ml). The phases were separated, and the organic phase was passed through a phase separator and dried in vacuo to afford the title compound (237 mg, 500 μmol, 82% yield, 97% purity) as a pale orange solid. UPLC-MS (Method 1) m/z 458.3 (M+H)$^+$ at 1.65 min.

Step 3: 3-(N-(5-cyano-4-fluoro-2-(thiazol-4-yl)phenyl)sulfamoyl)-4-cyclopropylbenzoic acid: To a solution of the product from Step 2 above (237 mg, 500 μmol, 97% purity) in THF (3 ml) was added 1 M LiOH(aq) (1.50 ml, 1.50 mmol). The reaction mixture was stirred at RT overnight, concentrated in vacuo and the residue dissolved in water (12 ml), washing with EtOAc (12 ml). The aqueous phase was acidified using 1 M HCl(aq) until pH 4-5, then extracted with EtOAc (2×12 ml). The combined organic phases were passed through a phase separator and concentrated in vacuo to afford the title compound (194 mg, 416 μmol, 83% yield, 95% purity) as a white solid. UPLC-MS (Method 1) m/z 444.3 (M+H)$^+$ at 0.87 min. $^1$H NMR (500 MHz, DMSO-d$_6$) δ 13.29 (s, 1H), 11.76 (s, 1H), 9.40 (d, J=1.9 Hz, 1H), 8.53 (s, 1H), 8.29 (d, J=1.9 Hz, 1H), 8.09 (d, J=10.5 Hz, 1H), 7.93 (dd, J=8.2, 1.9 Hz, 1H), 7.75 (d, J=5.9 Hz, 1H), 7.00 (d, J=8.3 Hz, 1H), 2.58-2.52 (m, 1H), 0.93-0.80 (m, 2H), 0.75-0.65 (m, 2H).

Example 197: 4-cyclopropyl-3-(N-(5-(1-methylpyrazol-5-yl)-2-(pyrrol-1-yl)phenyl) sulfamoyl) benzoic acid

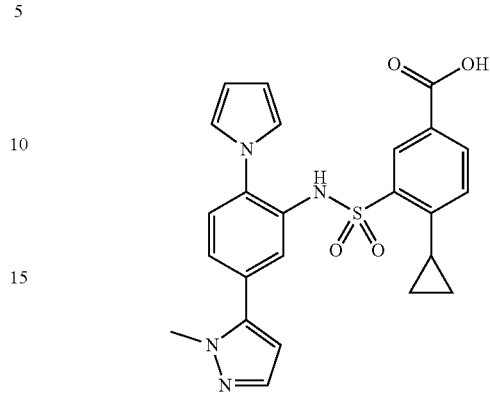

Step 1: methyl 4-cyclopropyl-3-(N-(5-(1-methylpyrazol-5-yl)-2-(pyrrol-1-yl)phenyl)sulfamoyl)benzoate: A mixture of Example 194, Step 5 (400 mg, 674 μmol, 88% purity), 5-bromo-1-methylpyrazole (114 mg, 708 μmol), K$_3$PO$_4$ (286 mg, 1.35 mmol), XPhos Pd G3 (28 mg, 33 μmol) in dioxane (4 ml) and water (0.8 ml) was sparged with N$_2$ for 10 min before being heated at 80° C. for 2 h. The reaction mixture was allowed to cool to RT, filtered through Celite®, washed with EtOAc (10 ml) and then concentrated in vacuo. The crude product was purified by chromatography on silica gel (12 g cartridge, 0-60% EtOAc/isohexane) to afford the title compound (191 mg, 397 μmol, 59% yield, 99% purity) as a pale-yellow solid. UPLC-MS (Method 1) m/z 477.3 (M+H)$^+$, 475.2 (M–H)$^-$ at 1.54 min.

Step 2: 4-cyclopropyl-3-(N-(5-(1-methylpyrazol-5-yl)-2-(pyrrol-1-yl)phenyl)sulfamoyl)benzoic acid: 1 M LiOH(aq) (1.60 ml, 1.60 mmol) was added to a suspension of the product from Step 1 above (191 mg, 397 μmol, 99% purity) in THF (3.2 ml) at RT. The resultant cloudy solution was stirred at RT for 17 h. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) and THF (15 ml) were added. The phases were separated and then the aqueous phase was extracted with EtOAc (2×10 ml). The fine suspension which remained in the combined organic phases was dissolved by the addition of THF (5 ml). The combined organic phases were dried by passage through a phase separator, then concentrated in vacuo. The crude product was purified by chromatography (24 g reverse phase C18 cartridge, 15-65% (0.1% formic acid in MeCN)/0.1% v/v formic acid(aq)) and by preparative HPLC (Waters, Acidic (0.1% Formic acid), Acidic, Waters X-Select Prep-C18, 5 μm, 19×50 mm column, 5-30% MeCN in water) to afford the title compound (35 mg, 75 μmol, 19% yield, 99% purity) as a white solid. UPLC-MS (Method 1) m/z 463.2 (M+H)$^+$, 461.2 (M–H)$^-$ at 1.40 min. $^1$H NMR (500 MHz, DMSO-d$_6$) δ 13.23 (br s, 1H), 10.14 (br s, 1H), 8.33-8.22 (m, 1H), 8.00 (br d, J=8.1 Hz, 1H), 7.58-7.32 (m, 3H), 7.14 (br d, J=8.3 Hz, 1H), 7.05 (t, J=2.2 Hz, 2H), 6.95 (br s, 1H), 6.19 (t, J=2.1 Hz, 2H), 6.15 (d, J=1.9 Hz, 1H), 3.64 (s, 3H), 2.79-2.65 (m, 1H), 1.12-1.00 (m, 2H), 0.92-0.81 (m, 2H).

Example 198: 4-cyclopropyl-3-(N-(4-fluoro-5-(isothiazol-5-yl)-2-(pyrrol-1-yl)phenyl) sulfamoyl)benzoic acid

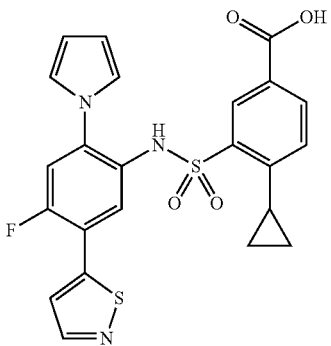 [SMILES: O=C(O)c1ccc(C2CC2)c(S(=O)(=O)Nc2cc(-c3ccns3)c(F)cc2-n2cccc2)c1]

Step 1: 1-(4-bromo-5-fluoro-2-nitrophenyl)pyrrole: A solution of 4-bromo-5-fluoro-2-nitroaniline (10.0 g, 39.8 mmol) and 2,5-dimethoxytetrahydrofuran (5.6 g, 42.4 mmol) in AcOH (112 ml) was stirred under reflux at 110° C. for 1.5 h. The reaction mixture was cooled to RT, poured into ice-water, and extracted with diethyl ether (2×100 ml). The combined organic extracts were washed with 10% w/v NaHCO$_3$(aq) (2×100 ml), followed by brine (50 ml), dried over Na$_2$SO$_4$, filtered, and concentrated in vacuo. The residue was triturated with n-pentane to afford the title compound (8.0 g, 28.1 mmol, 71% yield) as a grey solid. UPLC-MS (Method 5) m/z 285.2 (M+H)$^+$ at 2.50 min.

Step 2: 5-bromo-4-fluoro-2-(pyrrol-1-yl)aniline: A stirred solution of the product from Step 1 above (4.0 g, 14.0 mmol) in MeOH (90 ml and water (10 ml) was treated with iron powder (6.29 g, 113 mmol) and NH$_4$Cl(s) (27.5 g, 113 mmol) at RT. The resultant mixture was stirred at 90° C. for 2 h. The mixture was poured into ice-water (50 ml) and filtered through a Celite®. The filtrate was extracted with EtOAc (2×100 ml). The combined organic phases were dried over Na$_2$SO$_4$, filtered, and concentrated in vacuo. The residue was purified by column chromatography on silica gel (0-10% EtOAc/hexane) to afford the title compound (3.0 g, 11.8 mmol, 84% yield) as a yellow oil. UPLC-MS (Method 5) m/z 255.2 (M+H)$^+$ at 2.35 min.

Step 3: 4-fluoro-2-(pyrrol-1-yl)-5-(4,4,5,5-tetramethyl-1,3,2-dioxaborolan-2-yl)aniline: A stirred solution of the product from Step 2 above (0.500 g, 1.97 mmol) in dioxane (10 ml) was treated with KOAc (0.540 g, 2.77 mmol) and bis(pinacolato)diboron (0.750 g, 2.77 mmol) at RT under N$_2$ and the resultant mixture was purged with N$_2$ for 20 min. [Pd(dppf)Cl$_2$]-DCM (0.075 g, 0.09 mmol) was added into the reaction mixture and the resultant mixture was stirred at 110° C. for 4 h. The reaction mixture was diluted with EtOAc (100 ml) and filtered through Celite®. The filtrate was added to water and extracted with EtOAc (3×100 ml). The combined organic phases were dried over Na$_2$SO$_4$, filtered, and concentrated in vacuo to afford the title compound (2.0 g) as a dark brown solid, which was used in subsequent reactions without purification.

Step 4: 4-fluoro-5-(isothiazol-5-yl)-2-(pyrrol-1-yl)aniline: A stirred solution of 5-bromoisothiazole (0.500 g, 3.06 mmol) in dioxane (9 ml) and water (1 ml) was combined with the product from Step 3 above (1.85 g) and Na$_2$CO$_3$(s) (0.970 g, 9.19. mmol) at RT. The reaction mixture was purged with N$_2$ for 30 min, then [Pd(dppf)Cl$_2$]-DCM (0.125 g, 0.15 mmol) was added and the mixture stirred at 90° C. for 2 h. The reaction mixture was poured into water (100 ml) and extracted with EtOAc (3×50 ml). The organic phases were combined, dried over Na$_2$SO$_4$, filtered, and concentrated in vacuo. The residue was purified by chromatography on silica gel (0-10% EtOAc/hexane) to afford the title compound (0.254 g, 0.970 mmol, 53% yield over 2 steps, 99% purity) as a pale-yellow solid. UPLC-MS MS (Method 5) m/z 260.3 (M+H)$^+$ at 2.28 min.

Step 5: methyl 4-cyclopropyl-3-(N-(4-fluoro-5-(isothiazol-5-yl)-2-(pyrrol-1-yl)phenyl)sulfamoyl)benzoate: The product from Example 132, Step 5 (174 mg, 601 μmol, 95% purity) was dissolved in pyridine (1.50 ml) and stirred for 5 min. The product from Step 4 above (150 mg, 573 μmol, 99% purity) was added and then the resultant mixture was stirred vigorously at RT for 20 h. The reaction mixture was diluted with PhMe (3 ml) and concentrated in vacuo. The residue was dissolved in EtOAc (10 ml), washed with saturated NaHCO$_3$(aq) (5 ml) and then the aqueous phase was extracted with EtOAc (2×5 ml). The combined organic phases were washed with brine (5 ml), dried by passage through a phase separator and concentrated in vacuo. The crude product was purified by chromatography on silica gel (24 g cartridge, 0-40% EtOAc/isohexane) to afford the title compound (228 mg, 454 μmol, 79% yield, 99% purity) as a pale-yellow foam. UPLC-MS (Method 1) m/z 498.3 (M+H)$^+$, 496.2 (M−H)$^−$, at 1.73 min.

Step 6: 4-cyclopropyl-3-(N-(4-fluoro-5-(isothiazol-5-yl)-2-(pyrrol-1-yl)phenyl)sulfamoyl)benzoic acid: 1 M LiOH (aq) (1.80 ml, 1.80 mmol) was added to a suspension of the product from Step 1 above (228 mg, 454 μmol, 99% purity) in THF (3.6 ml) at RT. The resultant mixture was stirred at RT for 16 h. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) and THF (5 ml) were added. The phases were separated and then the aqueous phase extracted with EtOAc (2×10 ml). The combined organic phases were dried by passage through a phase separator and then concentrated in vacuo to afford the title compound (205 mg, 424 μmol, 93% yield, 98% purity) as a cream solid. UPLC-MS (Method 1): m/z 484.2 (M+H)$^+$, 482.2 (M−H)$^−$ at 1.61 min. $^1$H NMR (500 MHz, DMSO-d$_6$) δ 13.19 (br s, 1H), 10.20 (br s, 1H), 8.60 (t, J=1.8 Hz, 1H), 8.21 (d, J=1.9 Hz, 1H), 8.01 (dd, J=8.2, 1.9 Hz, 1H), 7.54 (d, J=11.5 Hz, 1H), 7.51 (d, J=1.9 Hz, 1H), 7.26 (d, J=7.6 Hz, 1H), 7.19-7.07 (m, 3H), 6.17 (t, J=2.2 Hz, 2H), 2.77-2.66 (m, 1H), 1.13-1.04 (m, 2H), 0.94-0.84 (m, 2H).

Example 199: 4-cyclopropyl-3-(N-(4-fluoro-5-(1-methylpyrazol-5-yl)-2-(pyrrol-1-yl)phenyl)sulfamoyl)benzoic acid

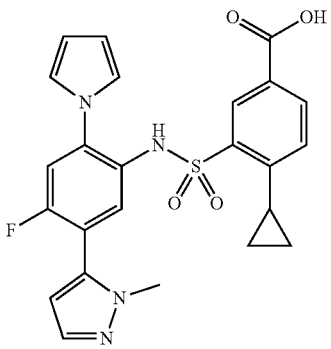 [SMILES: Cn1nccc1-c1cc(NS(=O)(=O)c2cc(C(=O)O)ccc2C2CC2)c(-n2cccc2)cc1F]

Step 1: 5-(2-fluoro-5-nitro-4-(pyrrol-1-yl)phenyl)-1-methylpyrazole: Four reactions were carried out on the same scale and combined. A stirred solution of the product from Example 198 Step 1 (0.600 g, 2.12 mmol) and 1-methyl-5-(4,4,5,5-tetramethyl-1,3,2-dioxaborolan-2-yl)pyrazole (2.2 g, 10.6 mmol) in dioxane (8 ml) and water (2 ml) was treated with $K_2CO_3$(s) (0.870 g, 6.30 mmol) at RT. The reaction mixture purged with $N_2$ for 15 min, then Pd(PPh$_3$)$_4$ (0.120 g, 0.16 mmol) was added and the resultant reaction mixture was stirred at 90° C. for 3 h, then cooled to RT. The four reaction mixtures were combined, diluted with water (250 ml), then extracted with EtOAc (3×100 ml). The combined organic extracts were dried over $Na_2SO_4$, filtered, and concentrated in vacuo. The resultant crude material was partially purified by chromatography on silica gel (4% EtOAc/hexane) to provide the title compound (3.50 g) as yellow solid. UPLC-MS (Method 5) m/z 287.3 (M+H)$^+$ at 2.18 min.

Step 2: 4-fluoro-5-(1-methylpyrazol-5-yl)-2-(pyrrol-1-yl) aniline: A stirred solution of the product from Step 1 above (3.50 g) in MeOH (35 ml) was treated with iron powder (3.41 g, 61.1 mmol), and a solution of $NH_4Cl$ (3.26 g, 61.11 mmol) in water (10 ml) at room temperature. The resultant mixture was stirred at 80° C. for 3 h. The reaction mixture was cooled to RT, filtered through Celite® washing with EtOAc (100 ml). The combined filtrate was concentrated in vacuo, diluted with water (200 ml) and extracted with EtOAc (2×60 ml). The organic phases were combined, dried over $Na_2SO_4$, filtered, and concentrated in vacuo. The residue was purified by chromatography on neutral alumina (1% EtOAc/hexane) to afford the title compound (0.39 g, 1.46 mmol, 17% yield over 2 steps, 96% purity) as an off-white solid. UPLC-MS (Method 5) m/z 257.3 (M+H)$^+$ at 2.02 min.

Step 3: methyl 4-cyclopropyl-3-(N-(4-fluoro-5-(1-methylpyrazol-5-yl)-2-(pyrrol-1-yl)phenyl)sulfamoyl)benzoate: The product from Example 132, Step 5 (162 mg, 562 μmol, 95% purity) was dissolved in pyridine (1.5 ml) and stirred for 5 min. The product from Step 2 above (150 mg, 562 μmol, 96% purity) was added and then the resultant mixture was stirred vigorously at RT for 20 h. Additional product from Example 132, Step 5 (41 mg, 0.14 mmol, 95% purity) added and the mixture stirred at RT for 16 h. The reaction mixture was diluted with PhMe (3 ml) and concentrated in vacuo. The residue was dissolved in EtOAc (10 ml), washed with saturated NaHCO$_3$(aq) (5 ml) and then the aqueous phase was extracted with EtOAc (2×5 ml). The combined organic phases were washed with brine (5 ml), dried by passage through a phase separator and then concentrated in vacuo. The crude product was purified by chromatography on silica gel (24 g cartridge, 0-50% EtOAc/isohexane) to afford the title compound (217 mg, 412 μmol, 73% yield, 94% purity) as a pale-yellow solid. UPLC-MS (Method 1): m/z 495.3 (M+H)$^+$, 493.3 (M−H)$^-$, at 1.58 min.

Step 4: 4-cyclopropyl-3-(N-(4-fluoro-5-(1-methylpyrazol-5-yl)-2-(pyrrol-1-yl)phenyl)sulfamoyl)benzoic acid: 1 M LiOH(aq) (1.65 ml, 1.65 mmol) was added to a suspension of the product from Step 3 above (217 mg, 412 μmol, 94% purity) in THF (3.3 ml) at RT. The resultant solution was stirred at RT for 17 h. The reaction mixture was concentrated in vacuo to remove the THF. The residue was diluted with water (10 ml) and then washed with TBME (6 ml). The aqueous phase was acidified using 1 M HCl(aq) until pH 4-5. The precipitate was isolated by filtration, washed with water (10 ml) and then dried in vacuo to afford the title compound (175 mg, 0.353 mmol, 86% yield, 97% purity) as an off-white solid. UPLC-MS (Method 1): m/z 481.3 (M+H)$^+$, 479.3 (M−H)$^-$, at 1.45 min. $^1$H NMR (500 MHz, DMSO-d$_6$) δ 13.24 (br s, 1H), 10.15 (br s, 1H), 8.20 (d, J=1.9 Hz, 1H), 7.99 (dd, J=8.2, 1.9 Hz, 1H), 7.52-7.45 (m, 2H), 7.16-7.08 (m, 3H), 6.88 (d, J=7.5 Hz, 1H), 6.21-6.14 (m, 3H), 3.57 (s, 3H), 2.71-2.62 (m, 1H), 1.11-1.06 (m, 2H), 0.90-0.83 (m, 2H).

Example 200: 3-(N-(4-chloro-5-(1-methylpyrazol-5-yl)-2-(pyrrol-1-yl)phenyl)sulfamoyl)-4-cyclopropylbenzoic acid

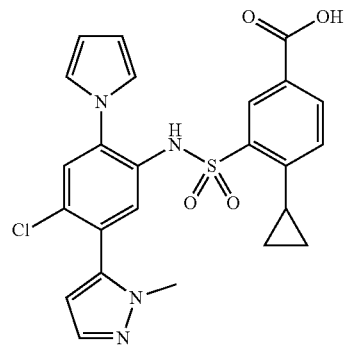 [SMILES: Cn1nccc1-c1cc(NS(=O)(=O)c2cc(C(=O)O)ccc2C2CC2)c(-n2cccc2)cc1Cl]

Step 1: 1-(4-bromo-5-chloro-2-nitrophenyl)pyrrole: A stirred solution of 4-bromo-5-chloro-2-nitroaniline (10.0 g, 39.8 mmol) and 2,5-dimethoxytetrahydrofuran (5.60 g, 42.4 mmol) in AcOH (112 ml) was heated under vigorous reflux at 110° C. for 1.5 h. The mixture was cooled to RT, then poured into water, and extracted with Et$_2$O (2×100 ml). The organic extracts were combined and washed with 10% w/v NaHCO$_3$ (2×100 ml) followed by brine (50 ml), dried over Na$_2$SO$_4$, filtered, and concentrated in vacuo. The residue was triturated with n-pentane to afford the title compound (8.0 g, 26.7 mmol, 67% yield) as a grey solid. UPLC-MS (Method 5) m/z 301.2 (M+H)$^+$ at 2.65 min.

Step 2: 5-(2-chloro-5-nitro-4-(pyrrol-1-yl)phenyl)-1-methylpyrazole: Five reactions were carried out on the same scale and combined. A stirred solution of the product from Step 1 above (0.6 g, 2.0 mmol) and 1-methyl-5-(4,4,5,5-tetramethyl-1,3,2-dioxaborolan-2-yl)pyrazole (2.07 g, 10.0 mmol) in dioxane (8 ml) and water (2 ml) was treated with K₂CO₃ (0.820 g, 4.82 mmol) at RT. The reaction mixture was purged with N₂ for 15 min, then Pd(PPh₃)₄ (0.110 g, 0.10 mmol) was added and the resultant mixture was stirred at 90° C. for 3 h, then cooled to RT. The five reaction mixtures were combined, diluted with water (250 ml) and extracted with EtOAc (3×100 ml). The combined organic extracts were dried over Na₂SO₄, filtered, and concentrated in vacuo. The residue was purified by chromatography on silica gel (6% EtOAc/hexane) to afford the title compound (0.52 g, 1.72 mmol, 17% yield) as a yellow solid. UPLC-MS (Method 5) m/z 303.3 (M+H)⁺ at 2.28 min.

Step 3: 4-fluoro-5-(1-methylpyrazol-5-yl)-2-(pyrrol-1-yl) aniline: A stirred solution of the product from Step 2 above (0.52 g, 1.72 mmol) in MeOH (10 ml) was treated with iron powder (0.48 g, 8.64 mmol), and a solution of NH₄Cl(s) (0.46 g, 8.64 mmol) in water (2 ml) at RT. The resultant reaction mixture was stirred at 80° C. for 3 h. The reaction mixture was cooled to RT, filtered through Celite®, washing with EtOAc (100 ml). The combined filtrate was concentrated in vacuo, diluted with water (200 ml) and was extracted with EtOAc (2×60 ml). The organic phases were combined, dried over Na₂SO₄, filtered, and concentrated in vacuo. The residue was purified by chromatography on neutral alumina (16% EtOAc/hexane) to afford the title compound (0.320 g, 1.14 mmol, 66% yield, 97% purity) as pale-yellow solid. UPLC-MS (Method 5) m/z 273.3 (M+H)⁺ at 2.16 min.

Step 4: methyl 3-(N-(4-chloro-5-(1-methylpyrazol-5-yl)-2-(pyrrol-1-yl)phenyl)sulfamoyl)-4-cyclopropylbenzoate: The product from Example 132, Step 5 (154 mg, 533 μmol, 95% purity) was dissolved in pyridine (1.5 ml) and stirred for 15 min. The product from Step 3 above (150 mg, 533 μmol, 97% purity) was added and then the resultant mixture was stirred vigorously at RT for 27 h. Additional product from Example 132, Step 5 (77 mg, 0.27 mmol, 97% purity) was added and the mixture stirred at RT for 16 h. The reaction mixture was diluted with PhMe (3 ml) and concentrated in vacuo. The residue was dissolved in EtOAc (10 ml), washed with saturated NaHCO₃(aq) (5 ml) and then the aqueous phase was extracted with EtOAc (2×5 ml). The combined organic phases were washed with brine (5 ml), dried by passage through a phase separator and concentrated in vacuo. The crude product was purified by chromatography on silica gel (24 g cartridge, 0-70% EtOAc/isohexane) to afford the title compound (210 mg, 395 μmol, 74% yield, 96% purity) as a yellow solid. UPLC-MS (Method 1): m/z 511.3 (M+H)⁺, 509.2 (M−H)⁻, at 1.66 min.

Step 5: 3-(N-(4-chloro-5-(1-methylpyrazol-5-yl)-2-(pyrrol-1-yl)phenyl)sulfamoyl)-4-cyclopropylbenzoic acid: 1 M LiOH(aq) (1.60 ml, 1.60 mmol) was added to a suspension of the product from Step 4 above (210 mg, 395 μmol, 96% purity) in THF (3.2 ml) at RT. The resultant solution was stirred at RT for 17 h. The reaction mixture was concentrated in vacuo to remove the THF. The residue was diluted with water (10 ml) and then washed with TBME (6 ml). The aqueous phase was acidified using 1 M HCl(aq) until pH 4-5. The precipitate was isolated by filtration, then dissolved in THF (30 ml) and dried by passage through a phase separator and concentrated in vacuo to afford the title compound (127 mg, 0.243 mmol, 62% yield, 95% purity) as a cream solid. UPLC-MS (Method 1): m/z 497.3 (M+H)⁺, 495.2 (M−H)⁻, at 1.54 min. ¹H NMR (500 MHz, DMSO-d₆) δ 13.25 (br s, 1H), 10.23 (br s, 1H), 8.20 (d, J=1.9 Hz, 1H), 7.98 (dd, J=8.2, 1.9 Hz, 1H), 7.64 (s, 1H), 7.47 (d, J=1.9 Hz, 1H), 7.11 (d, J=8.3 Hz, 1H), 7.08 (t, J=2.2 Hz, 2H), 6.88 (s, 1H), 6.21-6.13 (m, 3H), 3.52 (s, 3H), 2.70-2.59 (m, 1H), 1.10-1.04 (m, 2H), 0.88-0.78 (m, 2H).

Example 201: 4-cyclopropyl-3-(N-(4-fluoro-5-(1-methyl-1,2,4-triazol-5-yl)-2-(pyrrol-1-yl)phenyl) sulfamoyl)benzoic acid

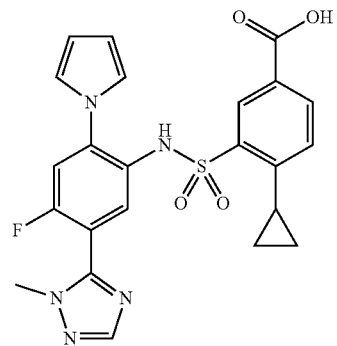

Step 1: 5-iodo-1-methyl-1,2,4-triazole: To a stirred solution of 1-methyl-1,2,4-triazole (3.00 g, 36.1 mmol) in THF (15 ml) was added n-BuLi (1.6 M in Hexane, 27.1 ml, 43.4 mmol) at −78° C. under N₂. After 1 h, a solution of iodine (9.44 g, 37.2 mmol) in THF (15 ml) was added dropwise and then stirred at −78° C. for 1 h. The reaction was allowed to warm to RT and poured into saturated Na₂S₂O₃(aq) solution (150 ml). The solution was extracted with EtOAc (3×80 ml). The organic phases were combined, dried over Na₂SO₄, filtered, and concentrated in vacuo to afford the title compound (6.00 g, 28.7 mmol, 79% yield, 99% purity) as a yellow solid, which was used without purification. ¹H NMR (500 MHz, DMSO-d₆) δ 7.99 (s, 1H), 3.85 (s, 3H).

Step 2: 4-fluoro-5-(1-methyl-1,2,4-triazol-5-yl)-2-(pyrrol-1-yl)aniline: To a stirred solution of the product from Step 1 above (3.30 g, 15.6 mmol, 99% purity) in 9:1 dioxane/water (10 ml) were added the product from Example 198, Step 3 (5.73 g) and Na₂CO₃ (5.04 g, 47.4 mmol) at RT under N₂. The reaction mixture was sparged with N₂ for 30 min and [Pd(dppf)Cl₂]-DCM (1.29 g, 1.57 mmol) was added. The resultant reaction mixture was stirred at 110° C. for 16 h. The reaction was allowed to cool to RT, poured into ice-water (150 ml) and extracted with EtOAc (3×80 ml). The organic phases were combined, dried over Na₂SO₄, filtered, and concentrated in vacuo. The crude product was purified by chromatography on silica gel (0-30% EtOAc/hexane) to afford the title product (0.29 g, 1.10 mmol, 7% yield, 98% purity) as a light brown solid. UPLC-MS (Method 5) m/z 258.3 (M+H)⁺ at 1.72 min.

Step 3: methyl 4-cyclopropyl-3-(N-(4-fluoro-5-(1-methyl1,2,4-triazol-5-yl)-2-(pyrrol-1-yl)phenyl)sulfamoyl) benzoate: The product from Example 132, Step 5 (207 mg, 714 μmol, 95% purity) was dissolved in pyridine (1.5 ml) and stirred for 10 min. The product from Step 2 above (150 mg, 571 μmol, 98% purity) was added and then the resultant mixture was stirred vigorously at RT for 21 h. Additional product from Example 132, Step 5 (42 mg, 153 μmol, 95% purity) was added and stirred at RT for 4 h. The reaction mixture was diluted with PhMe (3 ml) and concentrated in vacuo. The residue was dissolved in EtOAc (10 ml), washed with saturated NaHCO₃(aq) (5 ml) and then the aqueous phase was extracted with EtOAc (2×5 ml). The organic phases were combined, washed with brine (5 ml), dried by passage through a phase separator, and concentrated in vacuo. The crude product was purified by chromatography on silica gel (24 g cartridge, 0-70% EtOAc/isohexane) to afford the title compound (121 mg, 244 µmol, 43% yield) as a yellow solid. UPLC-MS (Method 1) m/z 496.3 (M+H)⁺, 494.2 (M−H)⁻ at 1.44 min.

Step 4: 4-cyclopropyl-3-(N-(4-fluoro-5-(1-methyl-1,2,4-triazol-5-yl)-2-(pyrrol-1-yl)phenyl)sulfamoyl)benzoic acid: 1 M LiOH(aq) (1.00 ml, 1.00 mmol) was added to a suspension of the product from Step 3 above (121 mg, 244 µmol) in THF (2 ml) at RT. The resultant solution was stirred at RT over the weekend. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) was added. The phases were separated and then the aqueous phase was extracted with EtOAc (2×10 ml). The organic phases were combined, dried by passage through a phase separator, and concentrated in vacuo to afford the title compound (109 mg, 222 µmol, 91% yield, 98% purity) as a pale-yellow solid. UPLC-MS (Method 1) m/z 482.3 (M+H)⁺, 480.2 (M−H)⁻ at 1.29 min. ¹H NMR (500 MHz, DMSO-d₆) δ 13.18 (s, 1H), 10.18 (s, 1H), 8.16 (d, J=1.9 Hz, 1H), 8.05 (s, 1H), 7.95 (dd, J=8.2, 1.9 Hz, 1H), 7.54 (d, J=10.6 Hz, 1H), 7.18 (d, J=7.2 Hz, 1H), 7.11-7.04 (m, 3H), 6.16 (t, J=2.2 Hz, 2H), 3.69 (d, J=1.7 Hz, 3H), 2.69-2.59 (m, 1H), 1.11-1.03 (m, 2H), 0.89-0.82 (m, 2H).

Example 202: 4-cyclopropyl-3-(N-(4-fluoro-5-(5-methylisoxazol-4-yl)-2-(pyrrol-1-yl)phenyl)sulfamoyl)benzoic acid

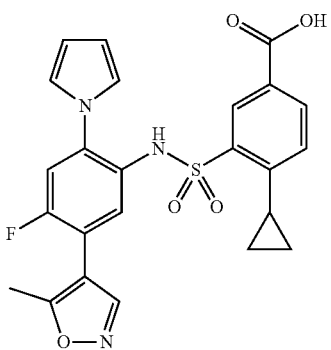 [SMILES: Cc1oncc1-c1cc(NS(=O)(=O)c2cc(C(=O)O)ccc2C2CC2)c(-n2cccc2)cc1F]

Step 1: 4-fluoro-5-(5-methylisoxazol-4-yl)-2-(pyrrol-1-yl)aniline: A stirred solution 4-iodo-5-methylisoxazole (0.85 g, 4.06 mmol) in dioxane (12 ml) and water (3 ml) was treated with the crude product from Example 198 Step 3 (1.47 g) and Na₂CO₃(s) (1.3 g, 12.2 mmol) at RT under N₂. The resultant mixture was purged with N₂ for 30 min, then Pd(dppf)Cl₂·DCM (0.34 g, 0.40 mmol) was added and the reaction mixture stirred with microwave heating at 130° C. for 1 h. The reaction mixture was diluted with water (80 ml), filtered through Celite® and the filtrate was extracted with EtOAc (2×50 ml). The combined organic phases were dried over Na₂SO₄(s) and concentrated in vacuo. The crude product was purified by chromatography on silica gel (0-100% EtOAc/hexane) to afford the title compound (0.31 g, 1.21 mmol, 99% purity) as a light-yellow solid. UPLC-MS (Method 1) m/z 258.4 (M+H)⁺ at 2.22 min.

Step 2: Methyl 4-cyclopropyl-3-(N-(4-fluoro-5-(5-methylisoxazol-4-yl)-2-(pyrrol-1-yl)phenyl)sulfamoyl)benzoate: A solution of the product from Example 132 Step 5 (120 mg, 415 µmol, 95% purity) in pyridine (1.5 ml) was treated with the product from Step 1 above (100 mg, 385 µmol, 99% purity). The resultant solution was stirred at RT overnight. Additional product from Example 132 Step 5 (55 mg, 0.19 mmol, 95% purity) was added and the reaction mixture was stirred at RT for 3 days. The reaction mixture was concentrated in vacuo, azeotroping with toluene (50 ml), dissolved in DCM (20 ml) and washed with saturated NaHCO₃(aq) (10 ml). The organic phase was passed through a phase separator and concentrated onto silica. The crude product was purified by chromatography on silica gel (12 g cartridge, 0-50% EtOAc/heptane) to afford the title compound (145 mg, 235 µmol, 61% yield, 80% purity) as a white foam. UPLC-MS (Method 1) m/z 496.1 (M+H)⁺ at 1.70 min.

Step 2: 4-cyclopropyl-3-(N-(4-fluoro-5-(5-methylisoxazol-4-yl)-2-(pyrrol-1-yl)phenyl)sulfamoyl)benzoic acid: 6 M HCl(aq) (200 µl, 1.20 mmol) was added to a solution of the product from Step 2 above (145 mg, 235 µmol, 80% purity) in dioxane (1 ml) at RT. The resultant solution was heated to 70° C. and stirred overnight. Additional 6 M HCl(aq) (97.8 µl, 587 µmol) was added and the reaction mixture was stirred at 70° C. for 4 days. The reaction mixture was allowed to cool to RT, concentrated in vacuo and the residue purified by preparative HPLC (Waters, Acidic (0.1% Formic acid), Acidic, Waters X-Select Prep-C18, 5 µm, 19×50 mm column, 35-65% MeCN in Water) to afford the title compound (40 mg, 79 µmol, 34% yield, 95% purity) as a white solid. UPLC-MS (Method 1) m/z 482.3 (M+H)⁺ at 1.58 min. ¹H NMR (500 MHz, DMSO-d₆) δ 13.21 (br s, 1H), 10.13 (br s, 1H), 8.59 (s, 1H), 8.26-8.18 (m, 1H), 8.01-7.94 (m, 1H), 7.43 (d, J=10.7 Hz, 1H), 7.12 (d, J=8.3 Hz, 1H), 7.07 (t, J=2.2 Hz, 2H), 6.95 (d, J=7.6 Hz, 1H), 6.17 (t, J=2.2 Hz, 2H), 2.69 (s, 1H), 2.21 (s, 3H), 1.13-1.05 (m, 2H), 0.92-0.83 (m, 2H).

Example 203: 3-(N-(4-chloro-5-(isothiazol-5-yl)-2-(pyrrol-1-yl)phenyl)sulfamoyl)-4-cyclopropylbenzoic acid

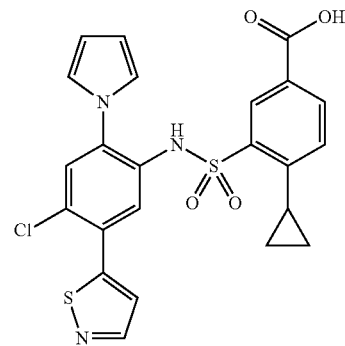 [SMILES: O=C(O)c1ccc(C2CC2)c(S(=O)(=O)Nc2cc(-c3ccns3)c(Cl)cc2-n2cccc2)c1]

Step 1: 1-(4-bromo-5-chloro-2-nitrophenyl)pyrrole: To a stirred solution of 4-bromo-5-chloro-2-nitroaniline (10.0 g, 39.8 mmol) and 2,5-dimethoxytetrahydrofuran (5.60 g, 42.4 mmol) in AcOH (112 ml). The reaction mixture was vigorous refluxed at 110° C. for 1.5 h. The reaction was allowed to cool to RT, poured into water and extracted with diethyl ether (2×100 ml). The organic phases were combined, washed with 10% w/v NaHCO₃(aq) (2×100 ml), brine (50 ml) and then dried over Na₂SO₄, filtered, and concentrated in vacuo. The crude material was triturated with n-pentane to afford the title compound (8.00 g, 25.7 mmol, 65% yield, 97% purity) as grey solid. UPLC-MS (Method 5) m/z 302.2 (M+H)⁺ at 2.65 min.

Step-2: 5-bromo-4-chloro-2-(pyrrol-1-yl)aniline: To a solution of the product from Step 1 above (4.00 g, 12.9 mmol, 97% purity) in 9:1 MeOH/water (100 ml) was added iron powder (5.95 g, 107 mmol) and NH$_4$Cl(s) (5.72 g, 107 mmol). The reaction mixture was stirred at 90° C. for 2 h. The reaction mixture was poured into water (50 ml), filtered through Celite® and then the filtrate was extracted with EtOAc (2×100 ml). The organic phases were combined, dried over Na$_2$SO$_4$, filtered, and concentrated in vacuo. The crude product was purified by chromatography on silica gel (0-10% EtOAc-hexane) to afford the title compound (3.00 g, 10.4 mmol, 81% yield, 94% purity) as a yellow oil. UPLC-MS (Method 5) m/z 272.2 (M+H)$^+$ at 2.53 min.

Step-3: 4-chloro-2-(pyrrol-1-yl)-5-(4,4,5,5-tetramethyl-1,3,2-dioxaborolan-2-yl)aniline: To a stirred solution the product from Step 2 above (500 mg, 1.73 mmol, 94% purity) and KOAc (540 mg, 5.50 mmol) in 1,4-dioxane (10 ml) was added bis(pinacolato)diboron (750 mg, 2.95 mmol) at RT. The resultant suspension was sparged with N$_2$ for 20 min. [Pd(dppf)Cl$_2$]-DCM (75 mg, 91.8 µmol) was added and the resultant mixture was heated at 110° C. for 4 h. The reaction mixture was allowed to cool to RT and diluted with water (2×100 ml) and filtered through Celite®. The filtrate was extracted with EtOAc (3×100 ml). The organic phases were combined, dried over Na$_2$SO$_4$, filtered, and concentrated in vacuo to afford the title compound (2.00 g) as a dark brown solid, which was used without purification.

Step-4: 4-chloro-5-(isothiazol-5-yl)-2-(pyrrol-1-yl)aniline: To a stirred solution of 5-bromoisothiazole (500 mg, 3.05 mmol) in dioxane (9 ml) and water (1 ml) were added the product from Step 3 above (1.95 g) and Na$_2$CO$_3$ (970 mg, 9.15 mmol) at RT. After sparging the reaction mixture with N$_2$ for 30 min, [Pd(dppf)Cl$_2$]-DCM (125 mg, 153 µmol) was added. The reaction mixture was heated at 90° C. for 2 h. The reaction mixture was allowed to cool to RT, poured into water (100 ml) and extracted with EtOAc (3×50 ml). The organic phases were combined, dried over Na$_2$SO$_4$, filtered, and concentrated in vacuo. The crude product was purified by chromatography on silica gel (0-10% EtOAc-hexane) to afford the title compound (256 mg, 901 µmol, 51% yield over 2 steps, 97% purity) as pale-yellow solid. UPLC-MS (Method 5) m/z 277.3 (M+H)$^+$ at 2.43 min.

Step 5: methyl 3-(N-(4-chloro-5-(isothiazol-5-yl)-2-(pyrrol-1-yl)phenyl)sulfamoyl)-4-cyclopropylbenzoate: The product from Example 132, Step 5 (153 mg, 528 µmol, 95% purity) was dissolved in pyridine (1.5 ml) and stirred for 10 min. The product from Step 4 above (150 mg, 528 µmol, 97% purity) was added and then the resultant mixture was stirred vigorously at RT for 27 h. Additional product from Example 132, Step 5 (76 mg, 263 µmol, 95% purity) was added and stirred at RT for 16 h. The reaction mixture was diluted with PhMe (3 ml) and concentrated in vacuo. The residue was dissolved in EtOAc (10 ml), washed with saturated NaHCO$_3$(aq) (5 ml) and then the aqueous phase was extracted with EtOAc (2×5 ml). The organic phases were combined, washed with brine (5 ml), dried by passage through a phase separator, and concentrated in vacuo. The crude product was purified by chromatography on silica gel (24 g cartridge, 0-50% EtOAc/isohexane) to afford the title compound (144 mg, 275 µmol, 52% yield, 98% purity) as a yellow solid. UPLC-MS (Method 1) m/z 515.3 (M+H)$^+$, 513.1 (M−H)$^-$ at 1.83 min.

Step 6: 3-(N-(4-chloro-5-(isothiazol-5-yl)-2-(pyrrol-1-yl)phenyl)sulfamoyl)-4-cyclopropylbenzoic acid: 1 M LiOH (aq) (1.10 ml, 1.10 mmol) was added to a solution of the product from Step 5 above (144 mg, 275 µmol, 98% purity) in THF (2.2 ml) at RT. The resultant solution was stirred at RT over the weekend. The reaction mixture was concentrated in vacuo to remove the THF. The residue was diluted with water (10 ml) and washed with TBME (6 ml). The aqueous phase was acidified using 1 M HCl(aq) until pH 4-5 and then EtOAc (10 ml) was added. The phases were separated and then the aqueous phase was extracted with EtOAc (2×10 ml). The organic phases were combined, dried by passage through a phase separator, and concentrated in vacuo. The resultant solid was dissolved in THF (4 ml), concentrated in vacuo, triturated with MeCN (3×5 ml) and then concentrated in vacuo to afford the title compound (132 mg, 259 µmol, 94% yield, 98% purity) as a pale yellow solid. UPLC-MS (Method 1) m/z 501.2 (M+H)$^+$, 499.1 (M−H)$^-$ at 1.71 min. $^1$H NMR (500 MHz, DMSO-d$_6$) δ 13.25 (br s, 1H), 10.30 (br s, 1H), 8.59 (d, J=1.8 Hz, 1H), 8.24 (d, J=1.9 Hz, 1H), 8.02 (dd, J=8.2, 1.9 Hz, 1H), 7.69 (s, 1H), 7.46 (d, J=1.8 Hz, 1H), 7.17 (s, 1H), 7.15 (d, J=8.3 Hz, 1H), 7.11 (t, J=2.2 Hz, 2H), 6.19 (t, J=2.2 Hz, 2H), 2.72-2.64 (m, 1H), 1.11-1.04 (m, 2H), 0.90-0.84 (m, 2H).

Example 204: 3-(N-(4-chloro-5-(1-methyl-1,2,4-triazol-5-yl)-2-(pyrrol-1-yl)phenyl)sulfamoyl)-4-cyclopropylbenzoic acid

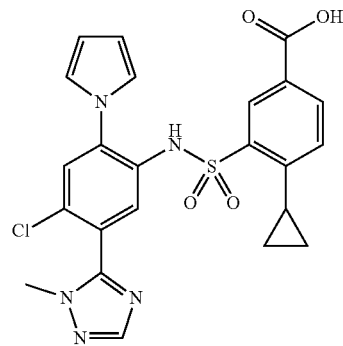 [SMILES: Cn1ncnc1-c1cc(NS(=O)(=O)c2cc(C(=O)O)ccc2C2CC2)c(-n2cccc2)cc1Cl]

Step 1: 5-bromo-4-chloro-2-(pyrrol-1-yl)aniline: To a stirred solution of the product from Example 203, Step 1 (2.00 g, 6.43 mmol, 97% purity) in MeOH (27 ml) and water (3 ml) were added iron powder (2.97 g, 53.3 mmol) and NH$_4$Cl(s) (2.85 g, 53.3 mmol) at RT. The reaction mixture was heated at 90° C. for 2 h. The reaction mixture was allowed to cool to RT and concentrated in vacuo. The residue was diluted with EtOAc (200 ml) and filtered through Celite®. The filtrate was washed with water (2×100 ml), dried over Na$_2$SO$_4$, filtered, and concentrated in vacuo. The crude product was purified by chromatography on silica gel (0-10% EtOAc-hexane) to afford the title compound (1.20 g, 4.29 mmol, 67% yield, 97% purity) as a yellow oil. UPLC-MS (Method 5) m/z 272.2 (M+H)$^+$ at 2.53 min.

Step 2: 4-chloro-2-(pyrrol-1-yl)-5-(4,4,5,5-tetramethyl-1,3,2-dioxaborolan-2-yl)aniline: To a stirred solution of the product from Step 1 above (1.00 g, 3.57 mmol, 97% purity) in dioxane (20 ml) were added KOAc (1.08 g, 11.0 mmol) and bis(pinacolato)diboron (1.40 g, 5.51 mmol) at RT under N$_2$. The resultant mixture was sparged with N$_2$ for 20 min before [Pd(dppf)Cl$_2$]-DCM (151 mg, 185 µmol) was added. The reaction mixture was heated at 110° C. for 18 h. The reaction mixture was allowed to cool to RT, diluted with EtOAc (100 ml), filtered through Celite® and concentrated in vacuo. The residue was diluted with water (50 ml) and extracted with EtOAc (3×200 ml). The organic phases were combined, dried over Na$_2$SO$_4$, filtered, and concentrated in vacuo to afford the title compound (2.52 g) as a dark brown solid, which was used without purification.

Step-3: 4-chloro-5-(1-methyl-1,2,4-triazol-5-yl)-2-(pyrrol-1-yl)aniline: To a stirred solution of the product from Example 201, Step 1 (2.15 g, 10.2 mmol, 99% purity) in 4:1 dioxane-water (32 ml) was added the product from Step 2 above (4.24 g) and Na$_2$CO$_3$ (3.27 g, 30.8 mmol) at RT. The reaction mixture was sparged with N$_2$ for 10 min before [Pd(dppf)Cl$_2$]-DCM (419 mg, 513 μmol) was added. The reaction mixture was heated at 90° C. for 2 h. The reaction mixture was allowed to cool to RT, poured into water (100 ml) and extracted with EtOAc (3×200 ml). The organic phases were combined, dried over Na$_2$SO$_4$, filtered, and concentrated in vacuo. The crude product was purified by chromatography on silica gel (0-30% EtOAc-hexane) to afford the title compound (150 mg, 5% yield, 98% purity) as an off-white solid. UPLC-MS (Method 5) m/z 274.3 (M+H)$^+$ at 1.85 min.

Step 4: methyl 3-(N-(4-chloro-5-(1-methyl-1,2,4-triazol-5-yl)-2-(pyrrol-1-yl)phenyl)sulfamoyl)-4-cyclopropylbenzoate: The product from Example 132, Step 5 102 mg, 354 μmol, 95% purity) was dissolved in pyridine (1 ml) and stirred for 15 min. The product from Step 3 above (100 mg, 354 μmol, 97% purity) was added and then the resultant mixture was stirred vigorously at RT for 27 h. Additional product from Example 132, Step 5 (51 mg, 176 μmol, 95% purity) was added and stirred at RT for 16 h. The reaction mixture was diluted with PhMe (3 ml) and concentrated in vacuo. The residue was dissolved in EtOAc (10 ml), washed with saturated NaHCO$_3$(aq) (5 ml) and then the aqueous phase was extracted with EtOAc (2×5 ml). The organic phases were combined, washed with brine (5 ml), dried by passage through a phase separator, and concentrated in vacuo. The crude product was purified by chromatography on silica gel (24 g cartridge, 0-70% EtOAc/isohexane) and by chromatography on silica gel (12 g cartridge, 0-40% EtOAc/DCM) to afford the title compound (95 mg, 184 μmol, 52% yield, 99% purity) as a cream solid. UPLC-MS (Method 1) m/z 513.3 (M+H)$^+$, 511.2 (M−H)$^-$ at 1.50 min.

Step 5: 3-(N-(4-chloro-5-(1-methyl-1,2,4-triazol-5-yl)-2-(pyrrol-1-yl)phenyl)sulfamoyl)-4-cyclopropylbenzoic acid: 1 M LiOH(aq) (0.75 ml, 0.75 mmol) was added to a suspension of the product from Step 4 above (95 mg, 184 μmol, 99% purity) in THF (1.5 ml) at RT. The resultant solution was stirred at RT for 17 h. The reaction mixture was concentrated in vacuo to remove the THF. The residue was diluted with water (10 ml) and washed with TBME (6 ml). The aqueous phase was acidified using 1 M HCl(aq) until pH 4-5 and then EtOAc (10 ml) was added. The phases were separated, and the aqueous phase was extracted with EtOAc (2×10 ml). The organic phases were combined, dried by passage through a phase separator, and concentrated in vacuo. The resultant solid was dissolved in THF (4 ml), concentrated in vacuo, triturated with MeCN (3×5 ml) and then concentrated in vacuo to afford the title product (83 mg, 162 μmol, 88% yield, 97% purity) as a cream solid. UPLC-MS (Method 1) m/z 499.3 (M+H)$^+$, 497.2 (M−H)$^-$ at 1.37 min. $^1$H NMR (500 MHz, DMSO-d$_6$) δ 13.20 (br s, 1H), 10.27 (br s, 1H), 8.17 (d, J=1.9 Hz, 1H), 8.05 (s, 1H), 7.95 (dd, J=8.2, 1.9 Hz, 1H), 7.68 (br s, 1H), 7.13 (s, 1H), 7.08 (d, J=8.3 Hz, 1H), 7.06 (t, J=2.2 Hz, 2H), 6.16 (t, J=2.2 Hz, 2H), 3.62 (s, 3H), 2.69-2.58 (m, 1H), 1.10-1.01 (m, 2H), 0.89-0.81 (m, 2H).

Example 205: 3-(N-(4-chloro-5-(5-methylisoxazol-4-yl)-2-(pyrrol-1-yl)phenyl)sulfamoyl)-4-cyclopropylbenzoic acid

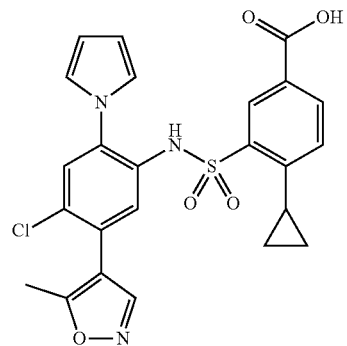 [SMILES: Cc1oncc1-c1cc(NS(=O)(=O)c2cc(C(=O)O)ccc2C2CC2)c(-n2cccc2)cc1Cl]

Step 1: 4-chloro-5-(5-methylisoxazol-4-yl)-2-(pyrrol-1-yl)aniline: A stirred solution 4-iodo-5-methylisoxazole (1.50 g, 7.17 mmol) in dioxane (25 ml) and water (5 ml) was treated with the crude product from Example 203 Step 3 (3.00 g) and Na$_2$CO$_3$(s) (2.28 g, 21.5 mmol). The reaction mixture was purged with N$_2$ for 10 min and Pd(dppf)Cl$_2$·DCM (0.292 g, 0.350 mmol) was added. The reaction mixture was stirred at 90° C. for 3 h, allowed to cool to RT, poured into water (50 ml) and extracted with EtOAc (3×100 ml). The combined organic phases were dried, Na$_2$SO$_4$ and concentrated under reduced pressure. The crude product was combined with the crude product from GLD8-A-460-GLD8-X-008-050 (300 mg) and was purified by chromatography on silica gel (0-100% EtOAc/hexane) to afford the title compound (0.235 g, 0.861 mmol, 95% purity) as an off-white solid. UPLC-MS (Method 1) m/z 274.3 (M+H)$^+$ at 2.37 min.

Step 2: Methyl 3-(N-(4-chloro-5-(5-methylisoxazol-4-yl)-2-(pyrrol-1-yl)phenyl)sulfamoyl)-4-cyclopropylbenzoate: To a solution of the product from Example 132 Step 5 (85 mg, 0.26 mmol, 95% purity) in pyridine (1.10 ml, 13.6 mmol) was the product from Step 1 above (76 mg, 0.28 mmol, 95% purity). The resultant solution was stirred at RT for 3 days. A solution of the product from Example 132 Step 5 (40 mg, 0.14 mmol, 95% purity) in pyridine (200 μl, 2.48 mmol) was added and the reaction mixture was stirred at RT overnight. Additional product from Example 132 Step 5 (40 mg, 0.14 mmol, 95% purity) was added and the reaction mixture was stirred at RT overnight. The reaction mixture was concentrated in vacuo, azeotroping with toluene (50 ml), then dissolved in DCM (20 ml) and washed with saturated NaHCO$_3$(aq) (10 ml). The organic phase was passed through a phase separator and concentrated onto silica. The crude product was purified by chromatography on silica gel (12 g cartridge, 0-50% EtOAc/isohexane) to afford the title compound (207 mg, 0.28 mmol, quantitative yield, 69% purity) as a pale-yellow foam. UPLC-MS (Method 1) m/z 512.0 (M+H)$^+$ at 1.77 min.

Step 3: 3-(N-(4-chloro-5-(5-methylisoxazol-4-yl)-2-(pyrrol-1-yl)phenyl)sulfamoyl)-4-cyclopropylbenzoic acid: 6 M HCl(aq) (330 μl, 1.98 mmol) was added to a solution of the product from Step 2 above (207 mg, 0.28 mmol, 69% purity) in dioxane (2 ml) at RT. The resultant solution was heated to 70° C. and stirred overnight. Additional 6 M HCl(aq) (160 μl, 960 μmol) was added and the reaction mixture was stirred at 70° C. for 3 days. Additional 6 M HCl(aq) (160 μl, 960

μmol) was added and the reaction mixture was stirred at 70° C. for 2 h. The reaction mixture was diluted using 1 M HCl(aq) (10 ml) and extracted with EtOAc (3×20 ml). The combined organic extracts were passed through a phase separator and the crude product was concentrated onto silica. The crude product was purified by chromatography on silica gel (24 g cartridge, 0-10% (1% AcOH in MeOH)/DCM) followed by purification by preparative HPLC (Waters, Acidic (0.1% Formic acid), Acidic, Waters X-Select Prep-C18, 5 μm, 19×50 mm column, 50-80% MeCN in Water) to afford the title compound (60 mg, 0.11 mmol, 29% yield, 95% purity) as a white solid. UPLC-MS (Method 1) m/z 498.3 (M+H)$^+$ at 1.05 min. $^1$H NMR (500 MHz, DMSO-d$_6$) δ13.23 (br s, 1H), 10.23 (br s, 1H), 8.62 (s, 1H), 8.27-8.21 (m, 1H), 7.98 (d, J=8.4 Hz, 1H), 7.61-7.54 (m, 1H), 7.11 (d, J=8.2 Hz, 1H), 7.06-7.02 (m, 2H), 6.97-6.90 (m, 1H), 6.21-6.14 (m, 2H), 2.74-2.60 (m, 1H), 2.18 (s, 3H), 1.12-1.03 (m, 2H), 0.92-0.82 (m, 2H).

Example 206: 3-(N-(4-chloro-2-(pyrrol-1-yl)-5-(tetrazol-1-yl)phenyl)sulfamoyl)-4-cyclopropylbenzoic acid

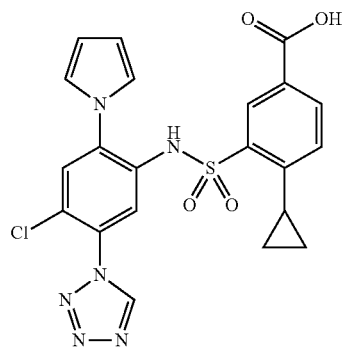 [SMILES: O=C(O)c1ccc(C2CC2)c(S(=O)(=O)Nc2cc(-n3cnnn3)c(Cl)cc2-n2cccc2)c1]

Step 1: 1-(2-chloro-4-nitrophenyl)tetrazole: A solution of 2-chloro-4-nitroaniline (10.0 g, 57.9 mmol) in AcOH (200 ml) was stirred for 5 min at RT before triethylorthoformate (43.1 g, 291 mmol) and then trimethylsilyl azide (16.8 g, 145 mmol) were added at 0° C. under N$_2$. The resultant reaction mixture was stirred at 70° C. for 7 h. The reaction was allowed to cool to RT, poured into water (500 ml) and extracted with EtOAc (3×250 ml). The organic phases were combined, washed with saturated NaHCO$_3$(aq) (100 ml), dried over Na$_2$SO$_4$, filtered, and concentrated in vacuo. The crude product was triturated with n-hexane (2×200 ml) and dried in vacuo to afford the title compound (10.0 g) as a yellow solid, which was used without purification.

Step-2: 3-chloro-4-(tetrazol-1-yl)aniline: To a stirred solution of the product from Step 1 above (10.0 g) in 7:3 MeOH/water (200 ml) was added iron powder (24.5 g, 439 mmol) and NH$_4$Cl (23.5 g, 439 mmol) at RT. The reaction mixture was stirred at 80° C. for 4 h. The reaction was allowed to cool to RT, filtered through Celite® and washed with MeOH (2×100 ml). The filtrate was concentrated in vacuo and the residue was dissolved in water (500 ml). The aqueous phase was extracted with EtOAc (3×200 ml). The organic phases were combined, dried over Na$_2$SO$_4$, filtered, and concentrated in vacuo to afford the title compound (7.70 g, 39.4 mmol, 68% yield over 2 steps) as a pale-yellow solid. UPLC-MS (Method 5) m/z 196.3 (M+H)$^+$ at 1.32 min.

Step-3: N-(3-chloro-4-(tetrazol-1-yl)phenyl)acetamide: To a stirred solution of the product from Step 2 above (7.50 g, 38.3 mmol) in DCM (150 ml) was added Et$_3$N (29.2 ml, 209 mmol) at RT. After 5 min, acetyl chloride (10.5 g, 133.8 mmol) was added dropwise at 0° C. and the resultant mixture was heated at reflux for 4 h. The reaction mixture was allowed to cool to RT and quenched with water (200 ml). The phases were separated, and the aqueous phase was extracted with DCM (2×200 ml). The organic phases were combined, washed with brine, dried over Na$_2$SO$_4$, filtered, and concentrated in vacuo to afford (8.50 g) as a pale-yellow solid, which was used without purification.

Step-4: N-(5-chloro-2-nitro-4-(tetrazol-1-yl)phenyl)acetamide: To a stirred solution of concentrated sulfuric acid (12.7 ml, 238 mmol) was added the product from Step 3 above (2.00 g) portionwise at 0° C. After 5 min, potassium nitrate (1.88 g, 18.6 mmol) was added and the reaction mixture was stirred at 0° C. for 4 h. The reaction mixture was quenched with ice-water (100 ml) and extracted with EtOAc (3×250 ml). The organic phases were combined, dried over Na$_2$SO$_4$, filtered, and concentrated in vacuo. The crude product was purified by chromatography on silica gel (0-40% EtOAc-hexane) to afford the title compound (450 mg, 1.39 mmol, 15% yield over 2 steps, 87% purity) as a yellow solid. UPLC-MS (Method 5) m/z 283.3 (M+H)$^+$ at 1.58 min.

Step-5: 5-chloro-2-nitro-4-(tetrazol-1-yl)aniline: A solution of the product from Step 4 above (700 mg, 2.15 mmol, 87% purity) in 4 M HCl(aq) (7 ml) was heated at reflux for 3 h. The reaction mixture was allowed to cool to RT and basified with 6 M NaOH(aq) (100 ml), which afforded a precipitate. The precipitate was isolated by filtration, washed with water, and dried in vacuo to afford the title compound (380 mg, 1.53 mmol, 71% yield, 97% purity) as a brown solid. UPLC-MS (Method 5) m/z 241.3 (M+H)$^+$ at 1.54 min.

Step-6: 1-(2-chloro-5-nitro-4-(pyrrol-1-yl)phenyl)tetrazole: Three reactions were carried out according to the following procedure and combined. A solution of the product from Step 5 above (400 mg, 1.61 mmol, 97% purity) and 2,5-dimethoxytetrahydrofuran (550 mg, 4.16 mmol) in AcOH (4 ml) was stirred at 80° C. for 4 h. The reaction mixture was allowed to cool to RT and concentrated in vacuo. The three reaction mixtures were combined and then water (20 ml) and EtOAc (25 ml) were added. The phases were separated and then the aqueous phase was extracted with EtOAc (25 ml). The organic phases were combined, washed with 10% w/v NaHCO$_3$(aq), dried over anhydrous Na$_2$SO$_4$, filtered, and concentrated in vacuo. The crude product was purified by chromatography on silica gel (0-20% EtOAc-hexane) to afford the title compound (400 mg, 1.31 mmol, 27% yield, 95% purity) as a yellow solid. UPLC-MS (Method 5) m/z 291.3 (M+H)$^+$ at 2.08 min.

Step-7: 4-chloro-2-(pyrrol-1-yl)-5-(tetrazol-1-yl)aniline: To a stirred solution of the product from Step 6 above (400 mg, 1.31 mmol, 95% purity) in MeOH (7 ml) and water (3 ml) were added iron powder (770 mg, 13.8 mmol) and NH$_4$Cl (3.36 g, 62.8 mmol) at RT. The reaction mixture was stirred at 80° C. for 1 h. The reaction mixture was allowed to cool to RT and then concentrated in vacuo. The crude product was purified by chromatography on silica gel (0-40% EtOAc-hexane) to afford the title compound (180 mg, 663 μmol, 51% yield, 96% purity) as an off-white solid.

Step 8: methyl 3-(N-(4-chloro-2-(pyrrol-1-yl)-5-(tetrazol-1-yl)phenyl)sulfamoyl)-4-cyclopropylbenzoate: The product from Example 132, Step 5 (112 mg, 387 μmol, 95% purity) was dissolved in pyridine (1 ml) and stirred for 5 min. The product from Step 7 above (100 mg, 368 μmol, 96% purity) was added and then the resultant mixture was stirred vigorously at RT for 23 h. Additional product from Example 132, Step 5 (54 mg, 187 μmol, 95% purity) in pyridine (0.5 ml) was premixed for 5 min, added and then the resultant mixture was stirred vigorously at RT for 17 h. The reaction mixture was diluted with PhMe (6 ml) and concentrated in vacuo. The residue was dissolved in EtOAc (10 ml), washed with saturated NaHCO$_3$(aq) (5 ml) and then the aqueous phase was extracted with EtOAc (2×5 ml). The organic phases were combined, washed with brine (5 ml), dried by passage through a phase separator, and concentrated in vacuo. The crude product was purified by chromatography on silica gel (24 g cartridge, 0-60% EtOAc/heptane) to afford an inseparable mixture of the title product (132 mg, 167 μmol, 45% yield, 63% purity) and dimethyl 3,3'-(((4-chloro-2-(pyrrol-1-yl)-5-(tetrazol-1-yl)phenyl)(hydrosulfonyl)amino)sulfonyl)bis(4-cyclopropylbenzoate) (132 mg, 63 μmol, 17% yield, 35% purity) as a cream foam. UPLC-MS (Method 1) m/z 500.3 (M+H)$^+$, 498.2 (M−H)$^-$ at 1.57 min.

Step 9: 3-(N-(4-chloro-2-(pyrrol-1-yl)-5-(tetrazol-1-yl)phenyl)sulfamoyl)-4-cyclopropylbenzoic acid: 1 M LiOH (aq) (0.70 ml, 0.70 mmol) was added to a solution of the inseparable mixture of the product from Step 8 above (132 mg, 167 μmol, 63% purity) and dimethyl 3,3'-(((4-chloro-2-(pyrrol-1-yl)-5-(tetrazol-1-yl)phenyl)(hydrosulfonyl) amino)sulfonyl)bis(4-cyclopropylbenzoate) (132 mg, 62.7 μmol, 35% purity) in THF (1.40 ml) at RT. The resultant solution was stirred at RT for 17 h. The reaction mixture was concentrated in vacuo to remove the THF. The residue was diluted with water (6 ml) and then washed with TBME (4 ml). The aqueous phase was acidified using 1 M HCl(aq) until pH 4-5 and then EtOAc (6 ml) and THF (6 ml) were added. The phases were separated and then the aqueous phase was extracted with EtOAc (2×6 ml). The organic phases were combined, dried by passage through a phase separator, and concentrated in vacuo to afford a yellow solid. The solid was triturated with MeCN (~15-20 ml), isolated by filtration, washed with MeCN (20 ml) and dried in vacuo to afford the title compound (64 mg, 131 μmol, 57% yield, 99% purity) as an off-white solid. UPLC-MS (Method 1) m/z 486.2 (M+H)$^+$, 484.2 (M−H)$^-$ at 1.38 min. $^1$H NMR (500 MHz, DMSO-d$_6$) δ 13.17 (br s, 1H), 10.43 (br s, 1H), 9.88 (s, 1H), 8.19 (d, J=1.8 Hz, 1H), 7.96 (dd, J=8.2, 1.9 Hz, 1H), 7.82 (br s, 1H), 7.45 (s, 1H), 7.07 (d, J=8.3 Hz, 1H), 7.03 (t, J=2.2 Hz, 2H), 6.13 (t, J=2.2 Hz, 2H), 2.69-2.57 (m, 1H), 1.09-1.01 (m, 2H), 0.89-0.80 (m, 2H).

Example 207: 4-cyclopropyl-3-(N-(4-fluoro-2-(pyrrol-1-yl)-5-(tetrazol-1-yl)phenyl)sulfamoyl)benzoic acid

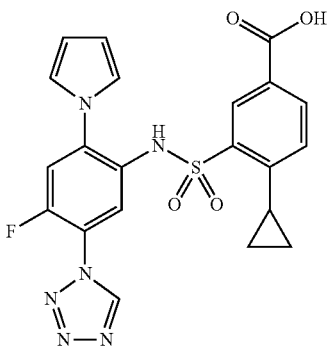 [SMILES: O=C(O)c1ccc(C2CC2)c(S(=O)(=O)Nc2cc(-n3cnnn3)c(F)cc2-n2cccc2)c1]

Step 1: 1-(2-fluoro-4-nitrophenyl)tetrazole: Two reactions were carried out on 10 g scale and an additional three reactions were carried out on 5 g scale according to the following procedure and combined. A solution of 2-fluoro-4-nitroaniline (10.0 g, 64.1 mmol) in AcOH (200 ml) was stirred for 5 min at RT before triethylorthoformate (47.5 g, 321 mmol) and then trimethylsilyl azide (18.4 g, 160 mmol) were added at 0° C. under N$_2$. The reaction mixture was heated at 70° C. for 4 h. The reaction mixtures were combined, poured into water (500 ml) and extracted with EtOAc (3×250 ml). The organic phases were combined, washed with saturated NaHCO$_3$(aq) (100 ml), dried over Na$_2$SO$_4$, filtered, and concentrated in vacuo. The crude product was purified by chromatography on silica gel (0-25% EtOAc-hexane) to afford the title compound) (27.8 g, 133 mmol, 59% yield) as a yellow solid. UPLC-MS (Method 5) m/z 210.5 (M+H)$^+$ at 1.86 min.

Step-2: 3-fluoro-4-(tetrazol-1-yl)aniline: To a stirred solution of the product from Step 1 above (27.4 g, 131 mmol) in 7:3 MeOH/water (274 ml) was added iron powder (73.2 g, 1.31 mmol) and NH$_4$Cl (70.1 g, 1.31 mmol) at RT. The reaction mixture was heated at 80° C. for 4 h. The reaction mixture was allowed to cool to RT, filtered through Celite® and washed with MeOH (2×100 ml). The organic phases were combined and concentrated in vacuo. The residue was dissolved in water (500 ml) and extracted with EtOAc (3×200 ml). The organic phases were combined, dried over Na$_2$SO$_4$, filtered, and concentrated in vacuo to afford the title compound (22.4 g, 121 mmol, 93% yield, 97% purity) as a yellow solid. LC-MS (Method 8) m/z 179.8 (M+H)$^+$ at 3.38 min.

Step-3: N-(3-fluoro-4-(tetrazol-1-yl) phenyl)acetamide: To a stirred solution of the product from Step 2 above (17.8 g, 96.4 mmol, 97% purity) in DCM (178 ml) was added Et$_3$N (34.6 ml, 248 mmol) at RT. After 5 min, acetyl chloride (11.7 g, 149 mmol) was added dropwise at 0° C. and the reaction mixture was stirred at 0° C. for 1 h and then at RT for 4 h. The reaction mixture was quenched with saturated NaHCO$_3$(aq) (500 ml) and the precipitate was isolated by filtration and dried in vacuo to afford the title compound (15.5 g, 67.3 mmol, 70% yield, 96% purity) as a grey solid. LC-MS (Method 8) m/z 221.8 (M+H)$^+$ at 3.45 min.

Step-4: N-(5-fluoro-2-nitro-4-(tetrazol-1-yl) phenyl)acetamide: Three reactions were carried out according to the following procedure and combined. To a stirred solution of concentrated sulfuric acid (20 ml) was added concentrated nitric acid (20 ml) dropwise at 0° C. After 30 min, the product from Step 3 above (2.00 g, 8.68 mmol, 96% purity) was added portionwise and the reaction mixture was stirred at 0° C. for 7 h. The three reaction mixtures were combined and quenched with ice-water (200 ml) and extracted with EtOAc (3×250 ml). The organic phases were combined, dried over Na$_2$SO$_4$, filtered, and concentrated in vacuo. The crude product was purified by chromatography on silica gel (0-40% EtOAc-hexane to afford the title compound (3.15 g, 11.5 mmol, 44% yield, 97% purity) as a yellow solid. LC-MS (Method 8) m/z 221.8 (M+H)$^+$ at 3.82 min.

Step-5: 5-fluoro-2-nitro-4-(tetrazol-1-yl)aniline: A solution of the product from Step 4 above (3.00 g, 10.9 mmol, 97% purity) in 4 M HCl(aq) (30 ml) was heated at reflux for 1 h. The reaction mixture was allowed to cool to RT and basified with 6 M NaOH(aq) (100 ml). The precipitate was isolated by filtration, washed with water, and dried in vacuo to afford the title compound (2.44 g, 10.9 mmol, 100% yield) as a yellow solid. LC-MS (Method 8) m/z 223.0 (M+H)$^+$ at 3.78 min.

Step-6: 1-(2-fluoro-5-nitro-4-(pyrrol-1-yl) phenyl)tetrazole: Three reactions were carried out on the same scale according to the following procedure and combined. A solution of the product from Step 5 above (1.10 g, 4.91 mmol) and 2,5-dimethoxytetrahydrofuran (1.62 g, 12.3 mmol) in AcOH (11 ml) was stirred at 80° C. for 3 h. The reaction mixture was allowed to cool to RT and concentrated in vacuo. The three reaction mixtures were combined and purified by chromatography on silica gel (0-20%) to afford the title compound (900 mg, 3.12 mmol, 21% yield, 95% purity) as a yellow solid. UPLC-MS (Method 5) m/z 275.2 (M+H)$^+$ at 1.98 min.

Step-7: 4-fluoro-2-(pyrrol-1-yl)-5-(tetrazol-1-yl)aniline: Three reactions were carried out on 500 mg scale and two reactions were carried out on 400 mg scale according to the following procedure and combined. To a stirred solution of the product from Step 6 above (500 mg, 1.73 mmol, 95% purity) in MeOH (3.5 ml) and water (1.5 ml) were added iron powder (1.33 g, 23.8 mmol) and NH$_4$Cl (1.27 g, 23.7 mmol) at RT. The reaction mixture was stirred at 80° C. for 4 h. The reaction mixtures were combined and concentrated in vacuo. The crude product was purified by chromatography on silica gel (100% EtOAc) and then the solid was suspended in MeOH (10 ml) and stirred for 30 min. The solid was isolated by filtration and dried in vacuo to afford the title compound (456 mg, 1.85 mmol, 23% yield, 99% purity) as a pale-yellow solid. UPLC-MS (Method 5) m/z 245.6 (M+H)$^+$ at 2.41 min.

Step 8: methyl 4-cyclopropyl-3-(N-(4-fluoro-2-(pyrrol-1-yl)-5-(tetrazol-1-yl)phenyl)sulfamoyl)benzoate: The product from Example 132, Step 5 (185 mg, 638 μmol, 95% purity) was dissolved in pyridine (1.5 ml) and stirred for 5 min. The product from Step 7 above (150 mg, 608 μmol, 99% purity) was added and then the resultant mixture was stirred vigorously at RT for 23 h. Additional product from Example 132, Step 5 (88 mg, 304 μmol, 95% purity) in pyridine (0.5 ml) was premixed for 5 min, added and then the resultant mixture was stirred vigorously at RT for 17 h. The reaction mixture was diluted with PhMe (8 ml) and concentrated in vacuo. The crude product was purified by chromatography on silica gel (24 g cartridge, 0-60% EtOAc/heptane) to afford an inseparable mixture of the title compound (259 mg, 370 μmol, 61% yield, 69% purity) and dimethyl 3,3'-(((4-fluoro-2-(pyrrol-1-yl)-5-(tetrazol-1-yl)phenyl)(hydrosulfonyl)amino)sulfonyl)bis(4-cyclopropylbenzoate) (259 mg, 108 μmol, 18% yield, 30% purity) as a cream solid. UPLC-MS (Method 1) m/z 483.4 (M+H)$^+$, 481.2 (M–H)$^-$ at 1.50 min.

Step 9: 4-cyclopropyl-3-(N-(4-fluoro-2-(pyrrol-1-yl)-5-(tetrazol-1-yl)phenyl)sulfamoyl)benzoic acid: 1 M LiOH (aq) (1.50 ml, 1.50 mmol) was added to a solution of the inseparable mixture of the product from Step 8 above (259 mg, 370 μmol, 69% purity) and dimethyl 3,3'-(((4-fluoro-2-(pyrrol-1-yl)-5-(tetrazol-1-yl)phenyl)(hydrosulfonyl)amino)sulfonyl)bis(4-cyclopropylbenzoate) (259 mg, 108 μmol, 30% purity) in THF (3 ml) at RT. The resultant solution was stirred at RT for 17 h. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) was added. The phases were separated and then the aqueous phase was extracted with EtOAc (2×10 ml). The organic phases contained a fine suspension which was dissolved with THF (10 ml). The organic phases were combined, dried by passage through a phase separator, and concentrated in vacuo to afford a light tan solid. The solid was triturated with MeCN (~15 ml), isolated by filtration, washed with MeCN (10 ml) and dried in vacuo. The crude product was purified by preparative HPLC (Waters, Acidic (0.1% Formic acid), Acidic, Waters X-Select Prep-C18, 5 μm, 19×50 mm column, 35-65% MeCN in Water) to afford the title compound (70 mg, 146 μmol, 31% yield, 98% purity) as a white solid and (22 mg, 45 μmol, 9% yield, 96% purity) as an off-white solid. UPLC-MS (Method 1) m/z 469.3 (M+H)$^+$, 467.2 (M–H)$^-$ at 0.83 min. $^1$H NMR (500 MHz, DMSO-d$_6$) δ 13.16 (br s, 1H), 10.33 (br s, 1H), 9.87 (d, J=1.7 Hz, 1H), 8.19 (d, J=1.8 Hz, 1H), 7.97 (dd, J=8.2, 1.9 Hz, 1H), 7.73 (d, J=11.1 Hz, 1H), 7.51 (d, J=7.4 Hz, 1H), 7.09 (d, J=8.3 Hz, 1H), 7.06 (t, J=2.2 Hz, 2H), 6.14 (t, J=2.2 Hz, 2H), 2.71-2.57 (m, 1H), 1.11-1.00 (m, 2H), 0.90-0.81 (m, 2H).

Example 208: 3-(N-(2-(pyrrol-1-yl)-5-(tetrazol-1-yl)phenyl)sulfamoyl)-4-cyclopropylbenzoic acid

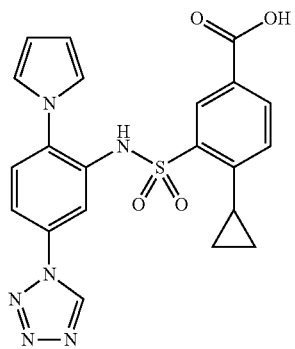 [SMILES: O=C(O)c1ccc(C2CC2)c(S(=O)(=O)Nc2cc(-n3cnnn3)ccc2-n2cccc2)c1]

Step 1: 1-(4-fluoro-3-nitrophenyl)tetrazole: 4-fluoro-3-nitroaniline (5.00 g, 32.0 mmol) and triethyl orthoformate (26.7 ml, 160 mmol) in AcOH (125 ml) were stirred at 80° C. for 1 h. Trimethylsilylazide (4.68 ml, 35.2 mmol) was added dropwise and the mixture was stirred at 80° C. for 2 h. Additional trimethylsilylazide (0.850 ml, 6.41 mmol) was added and the mixture was stirred at 80° C. for 2 h then allowed to cool to RT and stirred overnight. The solvent was removed in vacuo and the crude product was purified by chromatography on silica gel (12 g cartridge, 0-100% EtOAc/isohexane) to afford the title product (5.18 g, 24.8 mmol, 77% yield) as an off-white solid. $^1$H NMR (500 MHz, DMSO-d$_6$) δ 10.20 (s, 1H), 8.76 (dd, J=6.4, 2.7 Hz, 1H), 8.38 (ddd, J=9.1, 3.7, 2.7 Hz, 1H), 7.94 (dd, J=10.8, 9.1 Hz, 1H).

Step 2: 2-nitro-4-(tetrazol-1-yl)aniline: NH$_4$OH(aq) (2.30 ml, 16.2 mmol) was added to a suspension of the product from Step 1 above (300 mg, 1.43 mmol) in MeOH (9.2 ml). The resultant solution was stirred with microwave heating at 100° C. for 1.5 h. The precipitate was isolated by filtration, washed with water (10 ml) and dried in vacuo to afford the title compound (235 mg, 1.12 mmol, 78% yield, 98% purity) as an orange solid. UPLC-MS (Method 1) m/z no ionisation at 0.74 min. $^1$H NMR (500 MHz, DMSO-d$_6$) δ 10.02 (s, 1H), 8.48 (d, J=2.6 Hz, 1H), 7.90 (dd, J=9.2, 2.6 Hz, 1H), 7.82 (s, 2H), 7.23 (d, J=9.2 Hz, 1H).

Step 3: 1-(3-nitro-4-(pyrrol-1-yl)phenyl)tetrazole: 2,5-dimethoxytetrahydrofuran (185 μl, 1.40 mmol) was added to a solution of the product from Step 2 above (235 mg, 1.12 mmol, 98% purity) in AcOH (3.3 ml). The resultant solution was heated to 80° C. and stirred for 4 h. Additional 2,5-dimethoxytetrahydrofuran (36 μl, 274 μmol) was added and the reaction was heated to 80° C. and stirred for 2 h. The reaction mixture was allowed to cool to RT, concentrated in vacuo and then basified with saturated NaHCO$_3$(aq) (5 ml). EtOAc (5 ml) was added and then the phases were separated. The aqueous phase was extracted with EtOAc (3×5 ml) and then the organic phases were combined, washed with brine (5 ml), dried by passage through a phase separator, and concentrated in vacuo. The crude product was purified by chromatography on silica gel (12 g cartridge, 0-60% EtOAc/heptane) to afford the title compound (219 mg, 812 μmol, 73% yield, 95% purity) as an orange solid. UPLC-MS (Method 1) m/z 257.0 (M+H)$^+$ at 1.22 min.

Step 4: Methyl 3-(N-(2-(pyrrol-1-yl)-5-(tetrazol-1-yl)phenyl)sulfamoyl)-4-cyclopropylbenzoate: Zinc (531 mg, 8.12 mmol) and NH$_4$Cl (434 mg, 8.12 mmol) were added to a solution of the product from Step 3 above (219 mg, 812 μmol, 95% purity) in THF (3 ml) and water (1 ml). The suspension was stirred vigorously at RT for 16 h. The reaction mixture was combined with a similar reaction mixture performed on 112 μmol scale (total=924 μmol). The mixture was filtered through Celite®, washed with THF (10 ml) and then concentrated in vacuo. The solid was dissolved in THF (10 ml), dried by passage through a phase separator, and concentrated in vacuo. The residue was added to a solution of the product from Example 132, Step 5 (281 mg, 970 μmol, 95% purity) in pyridine (2 ml) which had been stirred for 5 min. The resultant mixture was stirred at RT for 20 h. Additional product from Example 132, Step 5 (281 mg, 970 μmol, 95% purity) in pyridine (0.5 ml) was premixed for 5 min, added and the resultant mixture was stirred at RT for 24 h. The reaction mixture was concentrated in vacuo. The residue was dissolved in EtOAc (8 ml) and washed with saturated NaHCO$_3$(aq) (8 ml). The aqueous phase was extracted with EtOAc (2×8 ml) and then the organic phases were combined, washed with brine (5 ml), dried by passage through a phase separator, and concentrated in vacuo. The crude product was purified by chromatography on silica gel (24 g cartridge, 0-70% EtOAc/heptane) to afford an inseparable mixture of the title product (360 mg, 543 μmol, 59% yield, 70% purity) and dimethyl 3,3'-(((2-(pyrrol-1-yl)-5-(tetrazol-1-yl)phenyl)(hydrosulfonyl)amino)sulfonyl)bis(4-cyclopropylbenzoate) (360 mg, 149 μmol, 16% yield, 29% purity) as a pale yellow foam. UPLC-MS (Method 1) m/z 465.3 (M+H)$^+$, 463.3 (M−H)$^-$ at 1.49 min.

Step 5: 3-(N-(2-(pyrrol-1-yl)-5-(tetrazol-1-yl)phenyl)sulfamoyl)-4-cyclopropylbenzoic acid: 1 M LiOH(aq) (4.00 ml, 4.00 mmol) was added to a solution of the inseparable mixture of the product from Step 4 above (360 mg, 543 μmol, 70% purity) and dimethyl 3,3'-(((2-(pyrrol-1-yl)-5-(tetrazol-1-yl)phenyl)(hydrosulfonyl)amino)sulfonyl)bis(4-cyclopropylbenzoate) (360 mg, 149 μmol, 29% purity) in THF (4 ml) at RT. The resultant solution was stirred at RT for 17 h. Additional 1 M LiOH(aq) (1.43 ml, 1.43 mmol) was added and the solution was stirred at RT and stirred over the weekend. The reaction mixture was concentrated in vacuo to remove the THF. The residue was diluted with water (10 ml) and then washed with TBME (6 ml). The aqueous phase was acidified using 1 M HCl(aq) until pH 4-5 and then EtOAc (10 ml) was added. The phases were separated and then the aqueous phase was extracted with EtOAc (2×10 ml). The organic phases were combined, dried by passage through a phase separator, and concentrated in vacuo. The crude product was purified by preparative HPLC (Waters X-Bridge Prep-C18, 5 μm, 19×50 mm column, 10-40% MeCN in 10 mM ammonium bicarbonate(aq)) to afford the title compound (133 mg, 289 μmol, 42% yield, 98% purity) as an off-white solid. UPLC-MS (Method 1) m/z 451.3 (M+H)$^+$, 449.2 (M−H)$^-$ at 0.83 min. $^1$H NMR (500 MHz, DMSO-d$_6$) δ 9.82 (s, 1H), 8.34 (d, J=1.9 Hz, 1H), 7.95 (dd, J=8.2, 1.9 Hz, 1H), 7.70 (d, J=2.4 Hz, 1H), 7.69-7.60 (m, 1H), 7.47 (d, J=8.5 Hz, 1H), 7.06 (d, J=8.2 Hz, 1H), 7.02-6.94 (m, 2H), 6.18-6.08 (m, 2H), 2.83-2.74 (m, 1H), 1.05-0.98 (m, 2H), 0.84-0.78 (m, 2H).

Biological Investigations

The following assays can be used to illustrate the commercial utilities of the compounds according to the present invention.

Biological Assay 1: ERAP1 Mediated Hydrolysis of an Amide Substrate Measured in a Biochemical System Materials and Solutions 1× Assay buffer (AB): 25 mM Bis-tris propane, 0.05% w/v Hydroxypropylmethylcellulose pH 7.75 made with Optima grade water Decapeptide WRVYEKC(Dnp)ALK-acid (where Dnp is Dinitrophenyl maleimide) (10-mer) L-Leucine 7-amido-4-methylcoumarin (L-AMC)

Purified ERAP1(37-941)-10His (ERAP1)

Assay Procedure:

12.5 μL ERAP1 enzyme in 1×AB was combined with 250 nL test compound in DMSO. 12.5 μL of either 240 μM L-AMC in 1×AB or 200 μM 10-mer in 1×AB was added to the reaction and incubated at 23° C. for 1 h. For detection, plates were read at excitation 365 nm and emission 442 nm (L-AMC) or excitation 279 nm and emission 355 nm (10-mer). Compound IC$_{50}$ was determined using a 4 parameter equation. The results for selected compounds according to the invention are shown in Table 1.

OVA Antigen Presentation Assay

The cellular effect of representative compounds according to the invention on antigen presentation can be measured by assessing their effect on the presentation of an ovalbumin-specific peptide (SIINFEKL) to T-cells, as previously described [Reeves et al, (2014) Proc. Natl. Acad. Sci. USA 111; 17594-17599]. Briefly, SiHa cells are transiently transfected with plasmids encoding mouse H2Kb and an ER-targeted N-terminally extended precursor peptide derived from ovalbumin (MRYMILGLLALAAVCSAAIVMKSIINFEHL) using Lipofectamine 3000. The cells are harvested 6 h post-transfection and transfected SiHa cells are plated compounds across a 12-point concentration response curve to quantify ERAP1 inhibitor IC$_{50}$. SiHa cells are cultured in the presence of compound for 48 h. Subsequently, B3Z cells [Karttunen et al, (1992) Proc. Natl. Acad. Sci. USA 89; 6020-6024] are added to the cell culture for 4 h; the B3Z T-cell hybridoma encodes a TCR recognizing specifically the SIINFEHL/H2Kb complex at the cell surface, which upon activation, triggers a signalling cascade leading to the transcription of the LacZ gene that is under the control of the IL-2 promoter. Intracellular β-galactosidase activity as a readout of T-cell activation is measured by quantifying the conversion of chlorophenored-β-D-galacto-pyrannoside (CPRG) to chlorophenol red by measuring absorbance at 570 nm.

Immunopeptidomics

The effect of representative compounds according to the invention on global antigen processing can be determined using an unbiased proteomics pipeline as described by Purcell and colleagues [Purcell et al, (2019) Nat Protoc. 14; 1687-1707]. Briefly, 500 million SiHa cells are treated with compound for 24 h or siRNA for 72 hours and then harvested, lysed and MHC-bound peptides isolated by immunoaffinity capture. The peptides are eluted using 10% (v/v) acetic acid and separated from the MHC-1 and p32-microglobulin proteins by HPLC before analysis by LC-MS/MS.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

| | Activity of selected compounds according to the invention |
|---|---|
| 1 | High |
| 2 | High |
| 3 | High |
| 4 | Medium |
| 5 | Medium |
| 6 | High |
| 7 | High |
| 8 | High |
| 9 | High |
| 10 | Medium |
| 11 | Medium |
| 12 | High |
| 13 | Medium |
| 14 | Low |
| 15 | High |
| 16 | Medium |
| 17 | Medium |
| 18 | High |
| 19 | High |
| 20 | High |
| 21 | High |
| 22 | High |
| 23 | High |
| 24 | High |
| 25 | Medium |
| 26 | High |
| 27 | High |
| 28 | Low |
| 29 | Medium |
| 30 | Medium |
| 31 | High |
| 32 | High |
| 33 | High |
| 34 | High |
| 35 | High |
| 36 | High |
| 37 | High |
| 38 | High |
| 39 | High |
| 40 | High |
| 41 | High |
| 42 | High |
| 43 | High |
| 44 | High |
| 45 | High |
| 46 | High |
| 47 | Low |
| 48 | Low |
| 49 | High |
| 50 | High |
| 51 | Medium |
| 52 | High |
| 53 | High |
| 54 | High |
| 55 | High |
| 56 | High |
| 57 | High |
| 58 | High |
| 59 | High |
| 60 | High |
| 61 | High |
| 62 | High |
| 63 | High |
| 64 | High |
| 65 | High |
| 66 | High |
| 67 | High |
| 68 | High |
| 69 | High |
| 70 | High |
| 71 | High |
| 72 | High |
| 73 | High |
| 74 | High |
| 75 | High |
| 76 | High |
| 77 | High |
| 78 | High |
| 79 | High |
| 80 | High |
| 81 | High |
| 82 | High |
| 83 | High |
| 84 | High |
| 85 | High |
| 86 | High |
| 87 | High |
| 88 | High |
| 89 | High |
| 90 | High |
| 91 | High |
| 92 | High |
| 93 | High |
| 94 | High |
| 95 | High |
| 96 | High |
| 97 | High |
| 98 | High |
| 99 | High |
| 100 | High |
| 101 | High |
| 102 | High |
| 103 | High |
| 104 | High |
| 105 | High |
| 106 | High |
| 107 | High |
| 108 | High |
| 109 | High |
| 110 | High |
| 111 | High |
| 112 | High |
| 113 | High |
| 114 | High |
| 115 | High |
| 116 | High |
| 117 | High |
| 118 | High |
| 119 | High |
| 120 | High |
| 121 | High |
| 122 | High |
| 123 | High |
| 124 | High |
| 125 | High |
| 126 | High |
| 127 | High |
| 128 | High |
| 129 | High |
| 130 | High |
| 131 | High |
| 132 | High |
| 133 | High |
| 134 | High |
| 135 | High |
| 136 | High |
| 137 | High |

TABLE 1-continued

Activity of selected compounds according to the invention

| | |
|---|---|
| 138 | High |
| 139 | High |
| 140 | High |
| 141 | High |
| 142 | High |
| 143 | High |
| 144 | High |
| 145 | High |
| 146 | High |
| 147 | High |
| 148 | High |
| 149 | High |
| 150 | High |
| 151 | High |
| 152 | High |
| 153 | High |
| 154 | High |
| 155 | High |
| 156 | High |
| 157 | High |
| 158 | High |
| 159 | High |
| 160 | High |
| 161 | High |
| 162 | High |
| 163 | High |
| 164 | High |
| 165 | High |
| 166 | High |
| 167 | High |
| 168 | High |
| 169 | High |
| 170 | High |
| 171 | High |
| 172 | High |
| 173 | Medium |
| 175 | Low |
| 176 | High |
| 177 | High |
| 178 | High |
| 179 | High |
| 180 | High |
| 181 | High |
| 182 | High |
| 183 | High |
| 184 | High |
| 185 | High |
| 186 | High |
| 187 | High |
| 188 | High |
| 189 | High |
| 190 | High |
| 191 | High |
| 192 | High |
| 193 | High |
| 194 | High |
| 196 | High |
| 196 | High |
| 197 | High |
| 198 | High |
| 199 | High |
| 200 | High |
| 201 | High |
| 202 | High |
| 203 | High |
| 204 | High |
| 205 | High |
| 206 | High |
| 207 | High |
| 208 | High |

$IC_{50}$ vs Decapeptide WRVYEKC(Dnp)ALK-acid (where Dnp is Dinitrophenyl maleimide) (10-mer); High (<500 nM), Medium (<5 μM), Low (>5 μM).

REFERENCES

1. Serwold et al, (2002), ERAAP customizes peptides for MHC class I molecules in the endoplasmic reticulum; Nature: 419, p480.
2. Snyder et al, (2014), Genetic Basis for Clinical Response to CTLA-4 Blockade in Melanoma; NEJM: 371, p2189.
3. Van Allen et al, (2015), Genomic correlates of response to CTLA-4 blockade in metastatic melanoma; Science: 348, p124.
4. James et al, (2013), Induction of Protective Antitumor Immunity through Attenuation of ERAAP Function; J Immunol: 190, p5839.
5. Niranjana et al, (2016), ERAAP Shapes the Peptidome Associated with Classical and Nonclassical MHC Class I Molecules; J Immunol: 197, p1035.
6. Pepelyayeva et al, (2018), ERAP1 deficient mice have reduced Type 1 regulatory T cells and develop skeletal and intestinal features of Ankylosing Spondylitis; Sci. Reports: 8: p12464.
7. Cifaldi et al, (2015), ERAP1 Regulates Natural Killer Cell Function by Controlling the Engagement of Inhibitory Receptors, Cancer Res.: 75, p824.
8. Steinbach et al, (2017), ERAP1 overexpression in HPV-induced malignancies: A possible novel immune evasion mechanism, Oncoimmunol: 6, e1336594.
9. Kim et al, (2011), Human cytomegalovirus microRNA miR-US4-1 inhibits CD8+ T cell responses by targeting the aminopeptidase ERAP1, Nat. Immunol.: 12, p984.
10. Tenzer et al, (2009), Antigen processing influences HIV-specific cytotoxic T lymphocyte immunodominance, Nat. Immunol.: 10, p636.
11. Reeves et al, (2018), The role of polymorphic ERAP1 in autoinflammatory disease, Biosci. Rep.: 29, p38.
12. Chen et al, (2014), Silencing or inhibition of endoplasmic reticulum aminopeptidase 1 (ERAP1) suppresses free heavy chain expression and Th17 responses in ankylosing spondylitis, Ann Rheum Dis: 75, p916.
13. Sheehan, NJ (January 2004). "The ramifications of HLA-B27". *Journal of the Royal Society of Medicine.* 97 (1): 10-4.
14. Smith, JA (January 2015). "Update on ankylosing spondylitis: current concepts in pathogenesis". Current allergy and asthma reports. 15 (1): 489.
15. Kuiper J J W, Mutis T, de Jager W, de Groot-Mijnes J D, Rothova A (2011). "Intraocular interleukin-17 and proinflammatory cytokines in HLA-A29-associated birdshot chorioretinopathy". *Am J Ophthalmol.* 152 (2): 177-182
16. Kuiper J J W, Emmelot M E, Rothova A, Mutis T (2013). "Interleukin-17 production and T helper 17 cells in peripheral blood mononuclear cells in response to ocular lysate in patients with birdshot chorioretinopathy". *Mol Vis.* 19: 2606-14
17. Kuiper J J W, van Setten J, Ripke S, Van't Slot R, Mulder F, Missotten T, Baarsma G S, Francioli L C, Pulit S L, de Kovel C G, Ten Dam-van Loon N, den Hollander AI, Huis In Het Veld P, Hoyng C B, Cordero-Coma M, Martin J, Lloreng V, Arya B, Thomas D, Bakker S C, Ophoff R A, Rothova A, de Bakker P I, Mutis T, Koeleman B P (2014). "A genome-wide association study identifies a functional ERAP2 haplotype associated with birdshot chorioretinopathy". *Hum Mol Genet.* 23 (22): 6081-6087
18. Evans et al (2011), Interaction between ERAP1 and HLA-B27 in ankylosing spondylitis implicates peptide handling in the mechanism for HLA-B27 in disease susceptibility. Nat Genet. 10; 43(8):761-7

19. Conde-Jaldon et al (2014), Epistatic interaction of ERAP1 and HLA-B in Behçet disease: a replication study in the Spanish population. PLoS One. 14; 9(7)
20. Kuiper et al (2018), Functionally distinct ERAP1 and ERAP2 are a hallmark of HLA-A29-(Birdshot) Uveitis. Hum Mol Genet. doi: 10.1093/hmg/ddy319
21. Strange et al (2010), A genome-wide association study identifies new psoriasis susceptibility loci and an interaction between HLA-C and ERAP1. Nat Genet.; 42(11): 985-90.

What is claimed is:

1. A compound of formula (Ia), or a pharmaceutically acceptable salt or hydrate thereof,

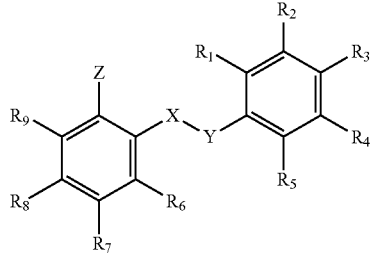

wherein:
the group X—Y is —NHSO$_2$— or —SO$_2$NH—;
Z is:
a monocyclic aryl group, or
a monocyclic heteroaryl group selected from pyridinyl, thienyl, tetrazoyl, imidazolyl, pyrimidinyl, thiazolyl, pyradizinyl, isothiazolyl, 1H-pyrazol-5-yl, 1H-pyrazol-3-yl, 1H-pyrazol-4-yl, triazinyl, 1H-pyrrol-2-yl, 1H-pyrrol-3-yl, 1H-pyrrol-4-yl, furanyl, oxazolyl, 1H-1,2,4-triazol-3-yl, 1H-1,2,4-triazol-5-yl, 1H-1,2,3-triazol-4-yl, 1H-1,2,3-triazol-5-yl and 1H-1,2,3-triazol-1-yl;
each of which is optionally substituted by one or more substituents selected from alkyl, cycloalkyl, halo, alkoxy, CN, haloalkyl and OH;
$R_1$ is H, CN or alkyl;
$R_2$ is selected from COOH and a tetrazolyl group;
$R_3$ is selected from H, Cl and alkyl;
$R_4$ is selected from H and halo;
$R_5$ is selected from H, alkyl, haloalkyl, SO$_2$-alkyl, Cl, alkoxy, OH, CN, hydroxyalkyl, alkylthio, heteroaryl, cycloalkyl, heterocycloalkyl and haloalkoxy;
$R_6$ is H;
$R_7$ is selected from CN, haloalkyl, halo, SO$_2$-alkyl, SO$_2$NR$_{12}$R$_{13}$, heteroaryl, CONR$_{10}$R$_{11}$ and alkyl, wherein said heteroaryl group is optionally substituted by one or more substituents selected from alkyl, halo, alkoxy, CN, haloalkyl and OH;
$R_8$ is selected from H, alkyl, haloalkyl and halo;
$R_9$ is H, alkyl or halo;
$R_{10}$ and $R_{11}$ are each independently H or alkyl; and
$R_{12}$ and $R_{13}$ are each independently H or alkyl.

2. The compound of formula (Ia) according to claim 1 wherein Z is selected from pyridin-2-yl, pyrimidin-2-yl, thiazol-4-yl and isothiazol-3-yl, each of which is optionally substituted by one or more substituents selected from alkyl, cycloalkyl, halo, alkoxy, CN, haloalkyl and OH.

3. The compound of formula (Ia) according to claim 1, wherein:
$R_2$ is COOH;
X—Y is NH—SO$_2$;
$R_5$ is selected from cyclopropyl, OMe and Et;
$R_1$, $R_3$, $R_4$, $R_6$, and $R_9$ are all H;
$R_7$ is selected from CN, haloalkyl, heteroaryl and SO$_2$-alkyl;
$R_8$ is H, Cl or F; and
Z is selected from the group consisting of:

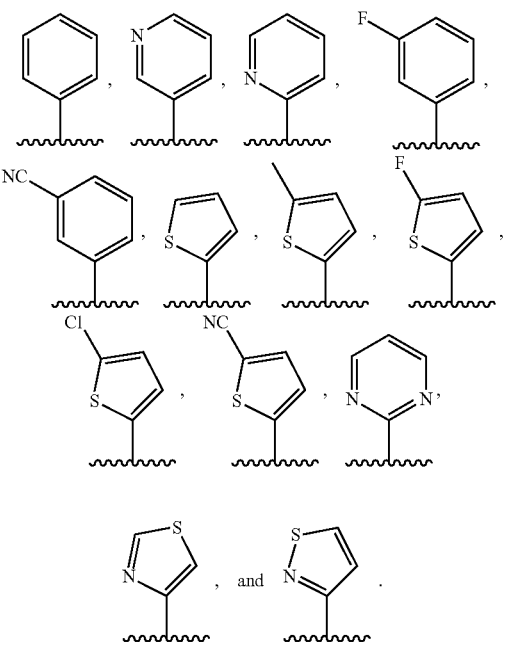

4. The compound of formula (Ia) according to claim 1 wherein Z is selected from phenyl, pyridinyl, thienyl, tetrazolyl, imidazolyl, furanyl and oxazolyl, each of which is optionally substituted by one or more substituents selected from alkyl, cycloalkyl, halo, alkoxy, CN, haloalkyl and OH.

5. The compound of formula (Ia) according to claim 1 wherein $R_2$ is COOH.

6. The compound of formula (Ia) according to claim 1 wherein X—Y is NH—SO$_2$.

7. The compound of formula (Ia) according to claim 1 wherein $R_5$ is selected from alkyl, haloalkyl, SO$_2$-alkyl, Cl, alkoxy, OH, CN, hydroxyalkyl, alkylthio, heteroaryl, cycloalkyl, heterocycloalkyl and haloalkoxy.

8. The compound of formula (Ia) according to claim 1 wherein $R_7$ is selected from CN, haloalkyl, Cl, F, SO$_2$-alkyl, CONR$_{10}$R$_{11}$, heteroaryl and alkyl, wherein the heteroaryl group is selected from pyrazol-3-yl, pyrazol-4-yl, pyrazol-5-yl, isothiazol-3-yl, isothiazol-4-yl, isothiazol-5-yl, 1,2,4-triazol-5-yl, tetrazol-1-yl, tetrazol-5-yl, isoxazol-3-yl, isoxazol-4-yl and isoxazol-5-yl, each of which is optionally substituted by one or more substituents selected from alkyl, halo, alkoxy, CN, haloalkyl and OH.

9. The compound according to claim 1, which is selected from the group consisting of:

(1) 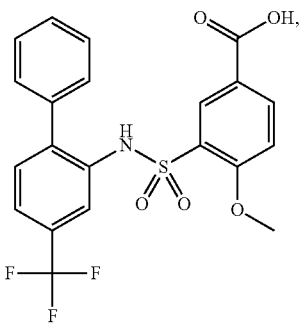
(2) 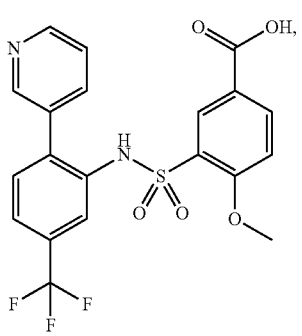
(3) 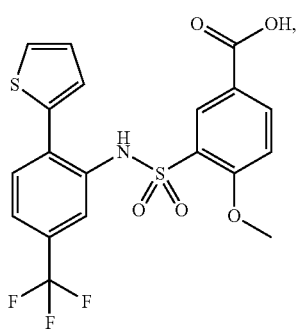
(4) 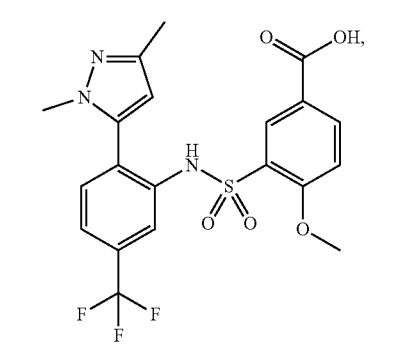
(5) 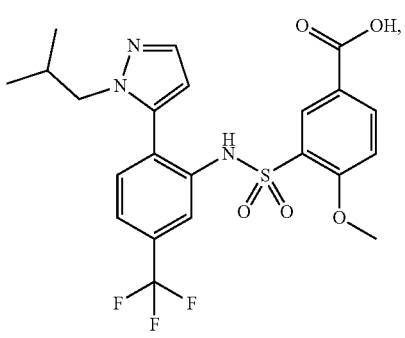
-continued
(6) 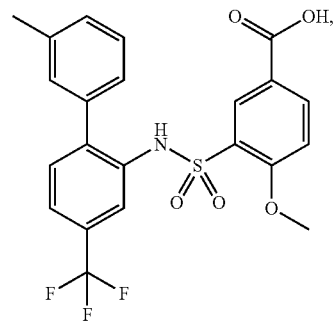
(7) 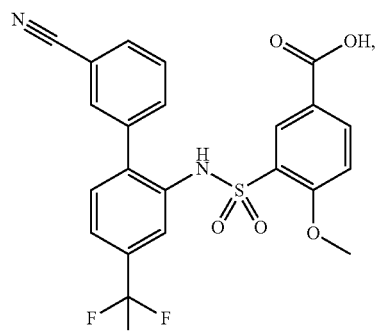
(8) 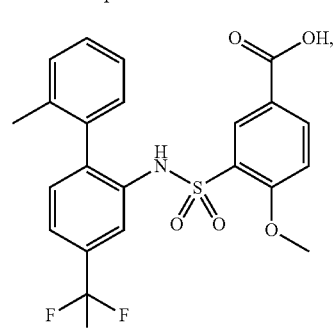
(9) 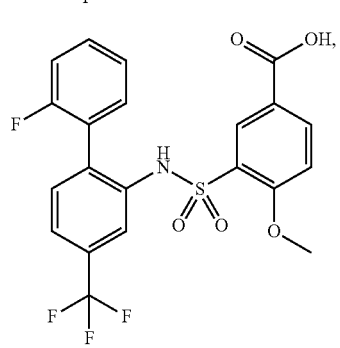
(10) 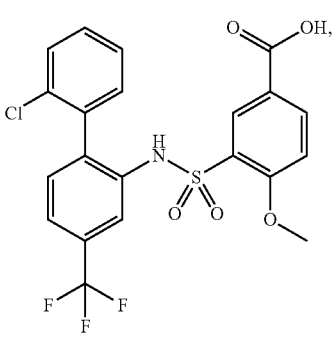

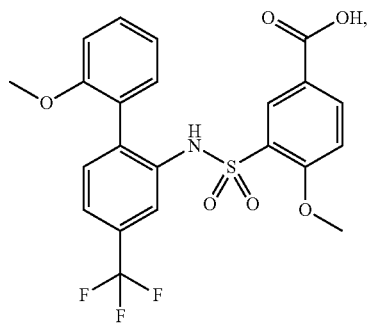
(11)
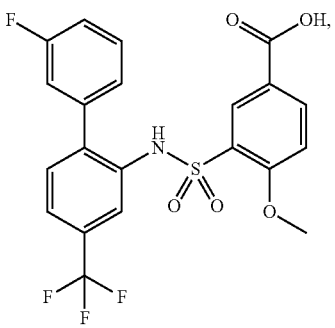
(15)
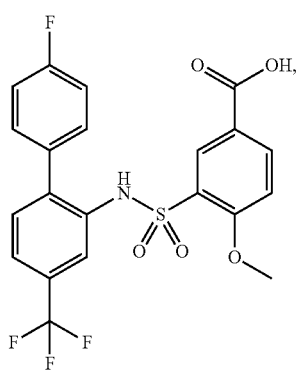
(12)
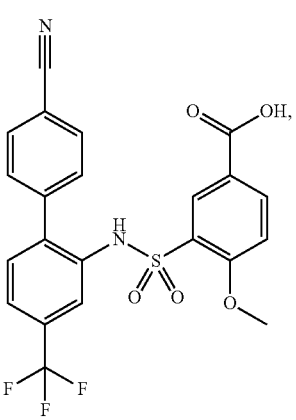
(16)
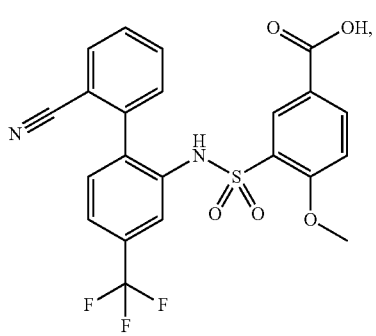
(13)
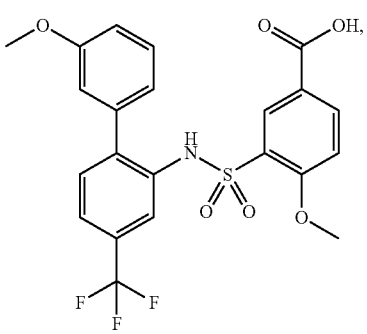
(17)
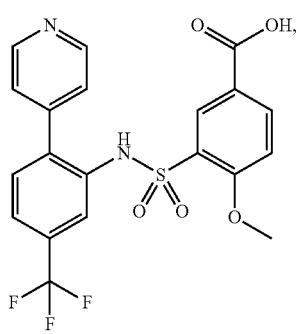
(14)
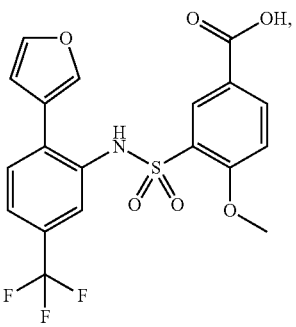
(18)

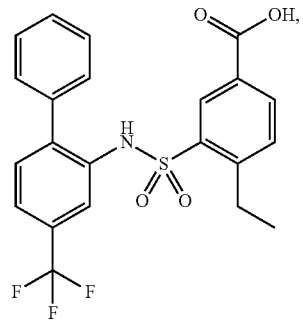
(19)
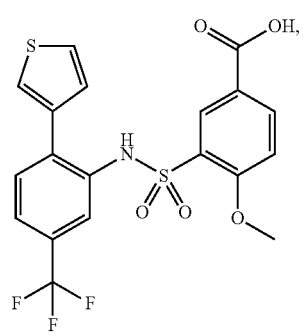
(20)
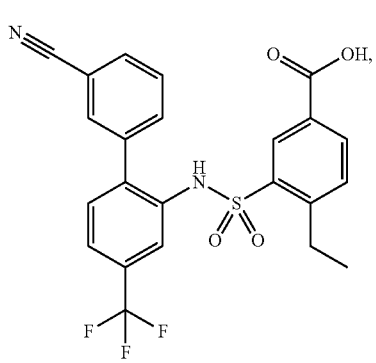
(21)
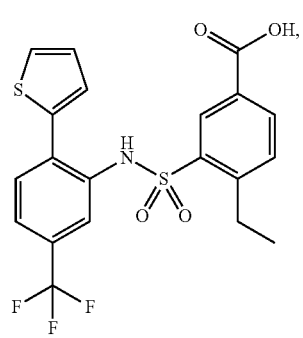
(22)
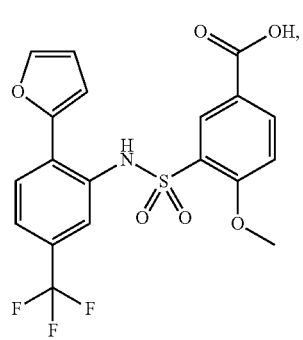
(23)
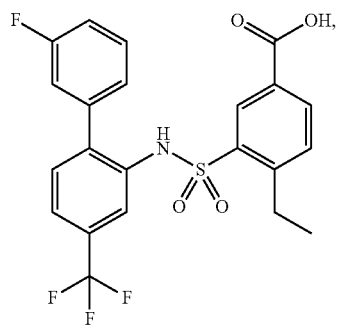
(24)
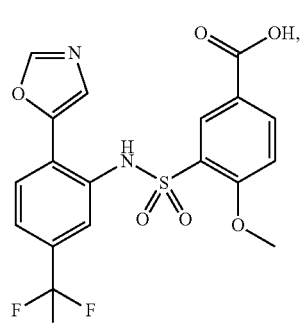
(25)
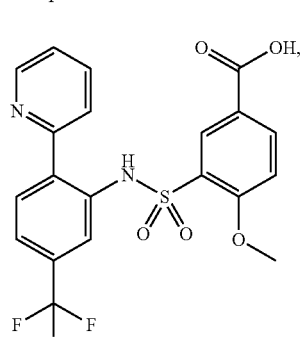
(26)
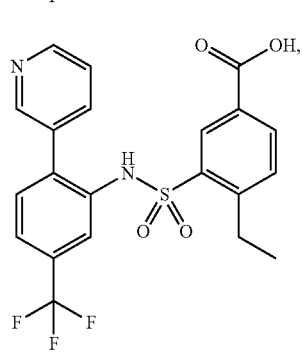
(27)
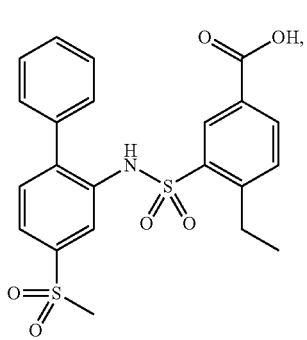
(32)

-continued
(33) 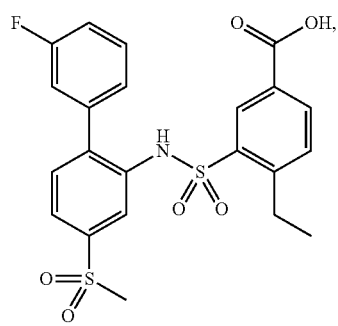
(34) 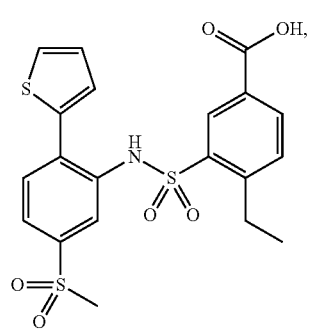
(37) 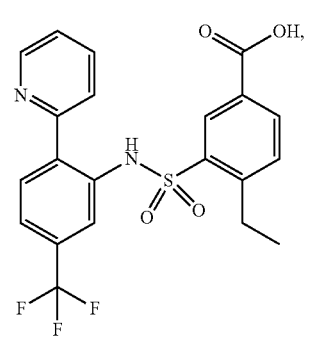
(38) 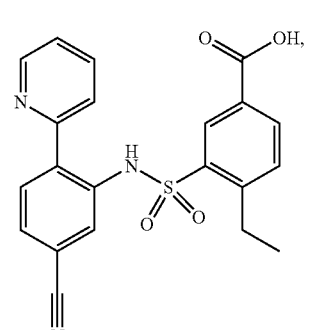
(39) 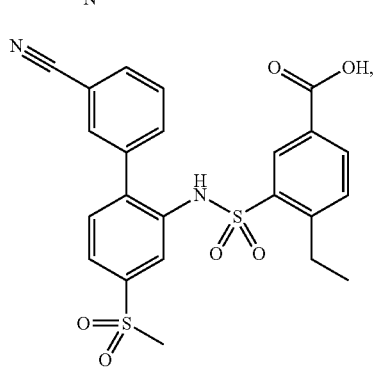
-continued
(40) 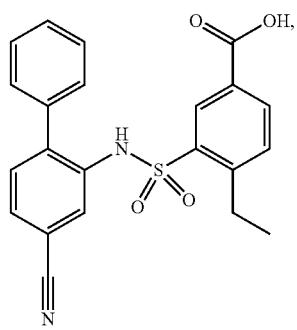
(41) 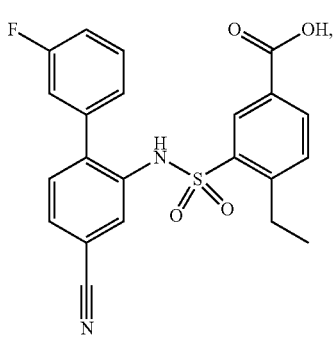
(42) 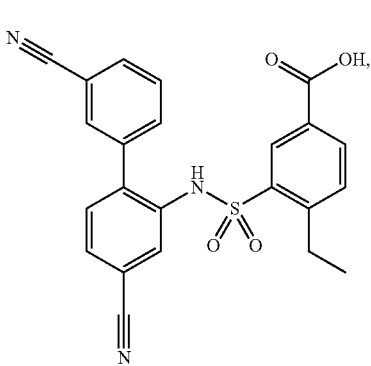
(43) 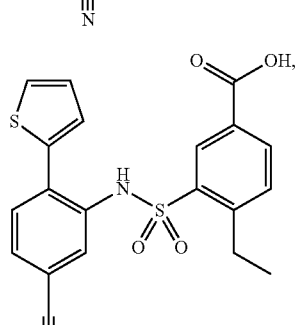
(44) 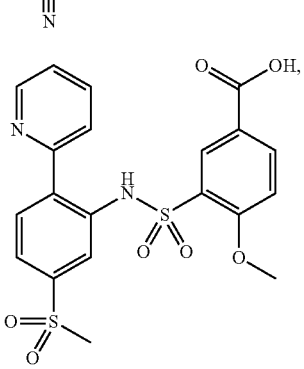

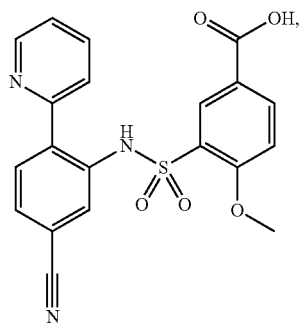 (45)
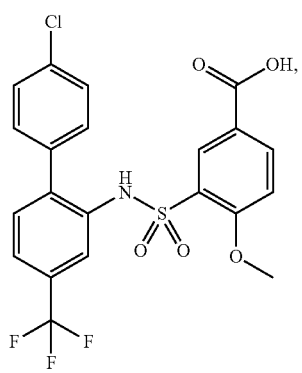 (49)
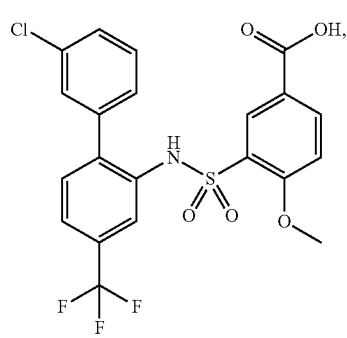 (46)
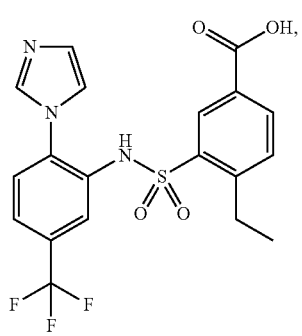 (50)
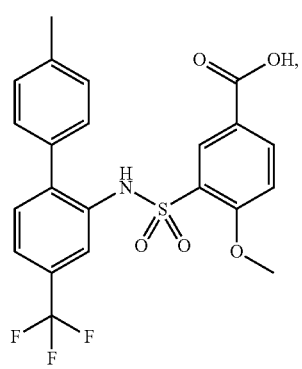 (47)
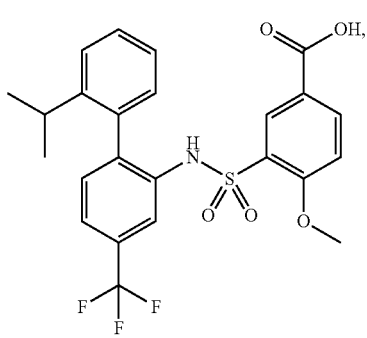 (51)
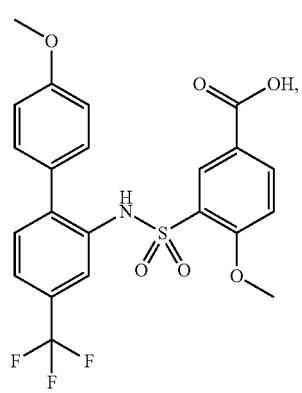 (48)
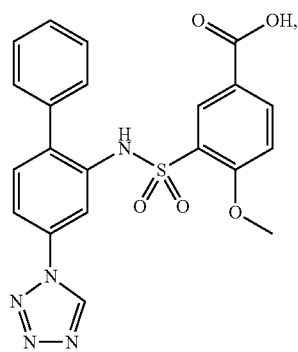 (52)

(53) 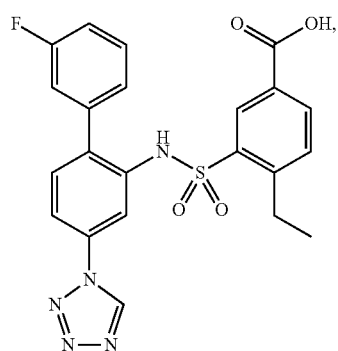
(54) 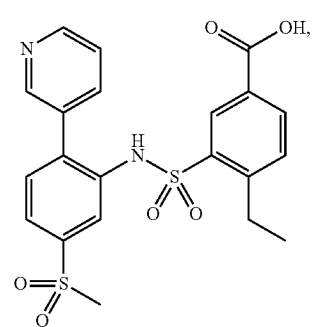
(55) 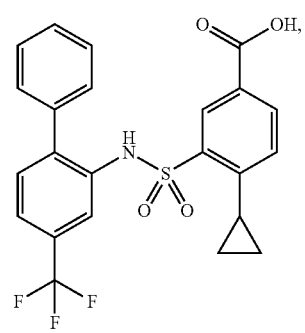
(56) 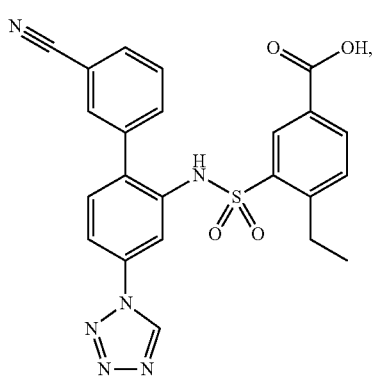
(57) 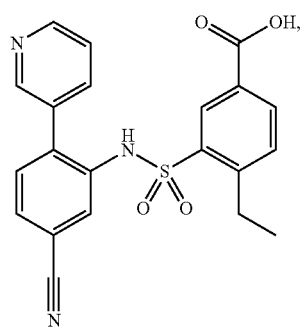
(58) 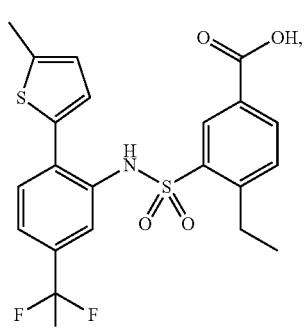
(59) 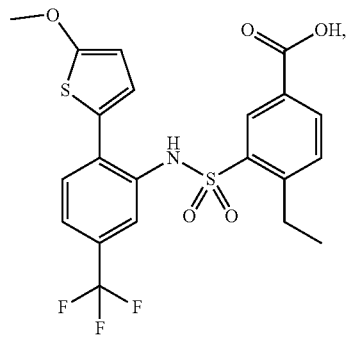
(60) 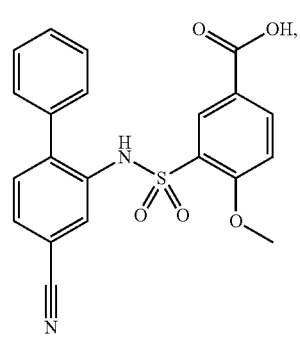
(61) 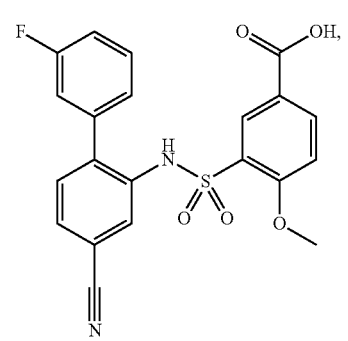

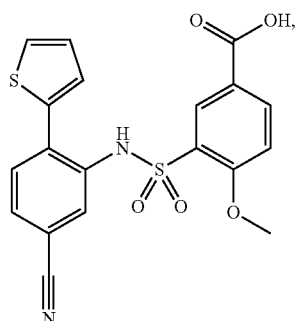
(62)
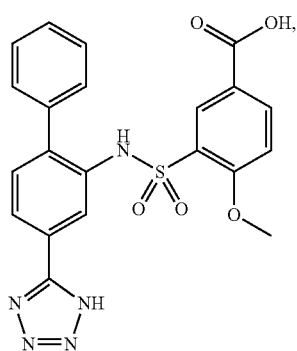
(63)
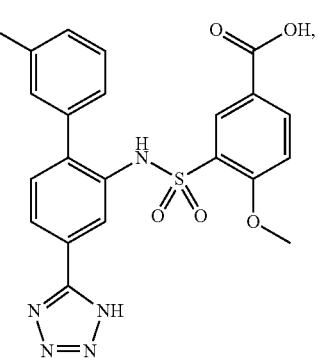
(64)
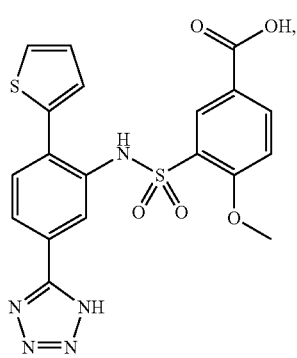
(65)
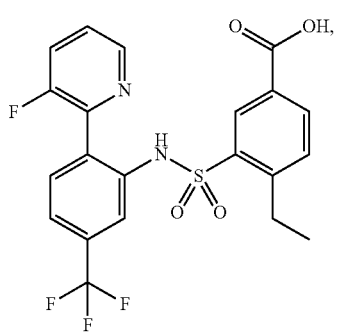
(66)
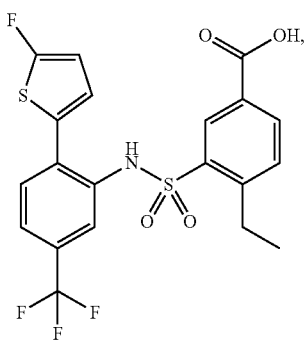
(67)
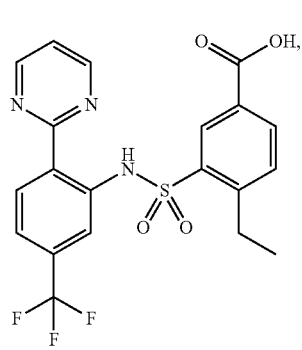
(68)
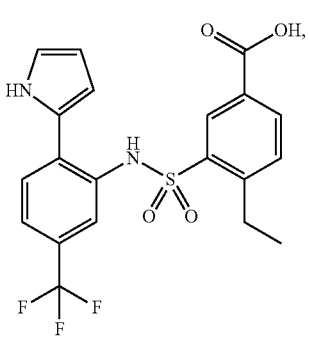
(69)

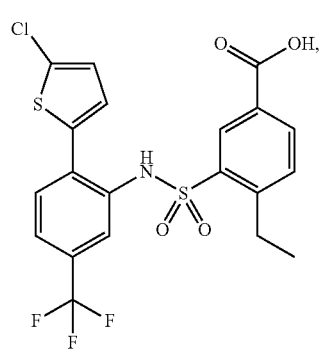
(70)
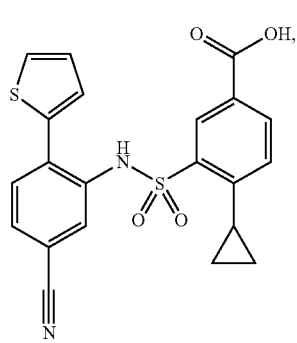
(75)
(71)
(72)
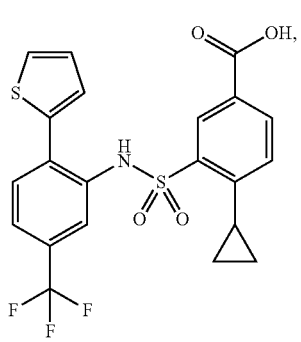
(76)
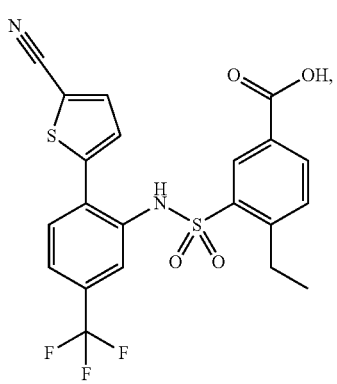
(77)
(73)
(74)
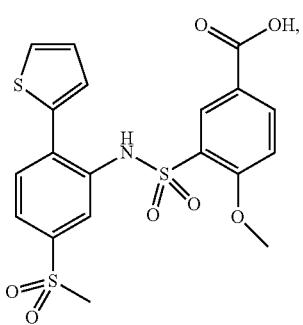
(78)

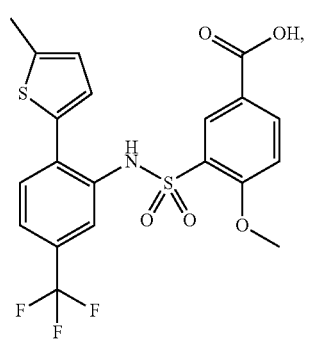
(79)
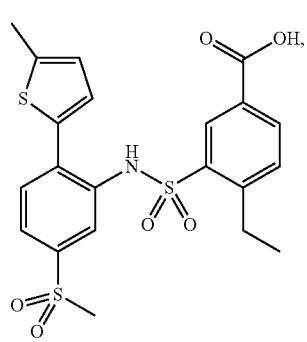
(84)
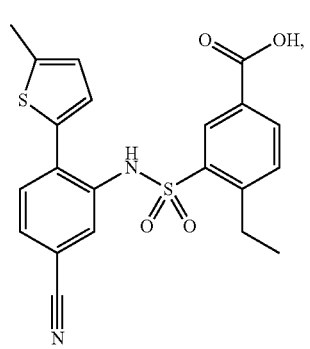
(80)
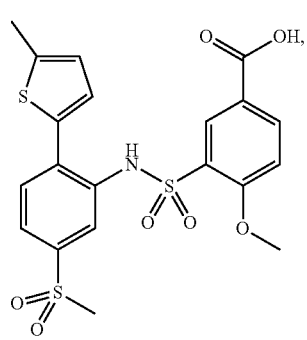
(85)
(81)
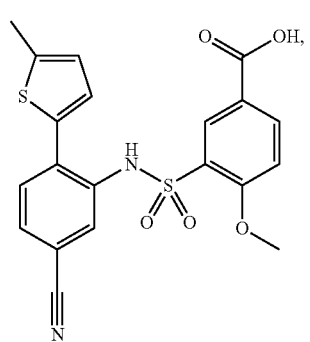
(82)
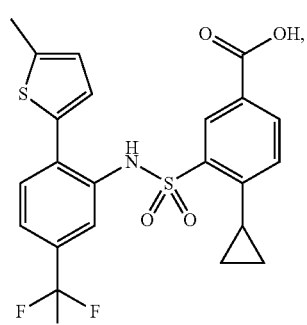
(86)
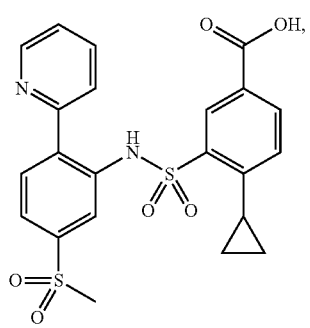
(83)
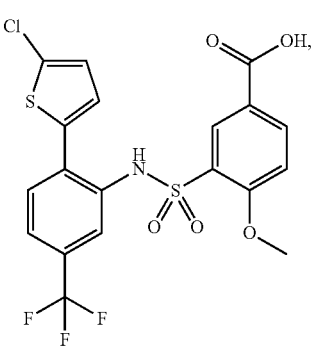
(87)

-continued
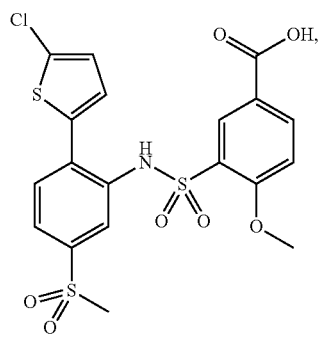
(88)
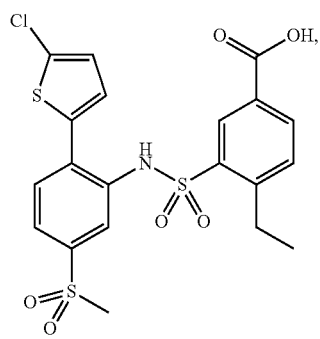
(89)
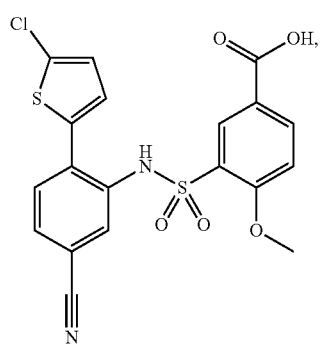
(90)
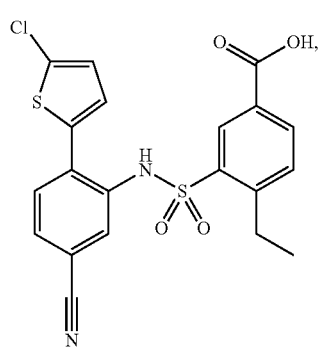
(91)
-continued
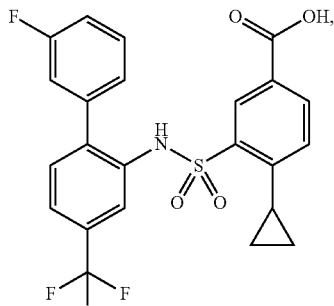
(92)
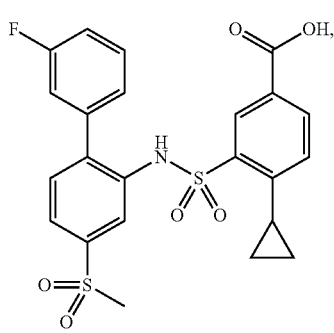
(93)
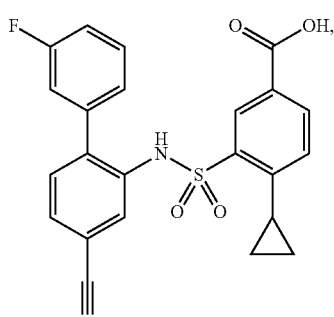
(94)
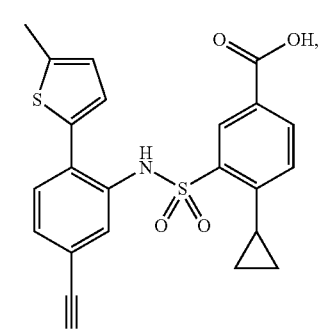
(95)
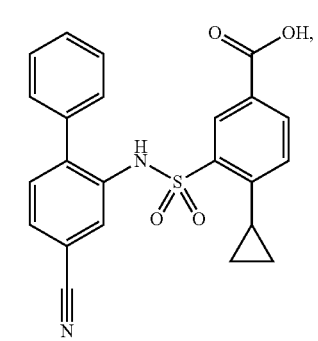
(96)

-continued
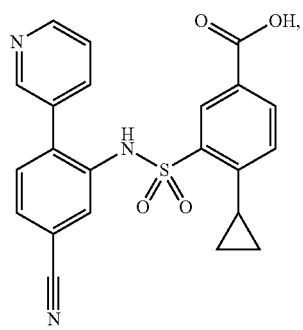
(97)
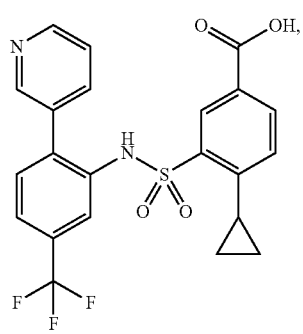
(98)
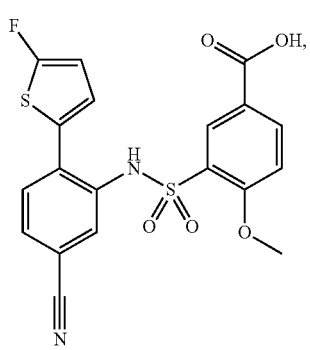
(100)
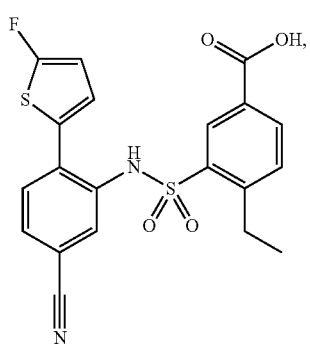
(101)
-continued
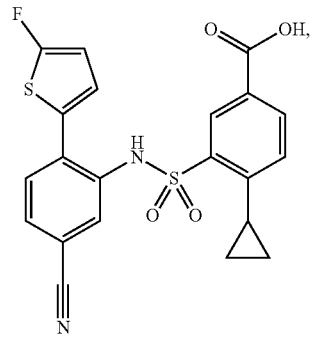
(102)
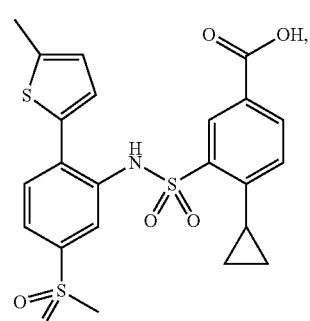
(103)
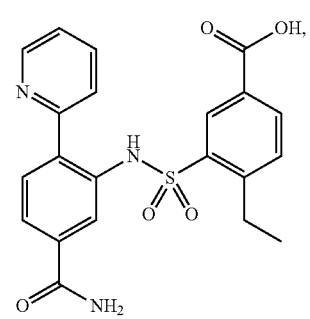
(104)
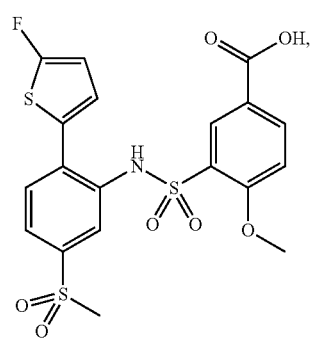
(105)
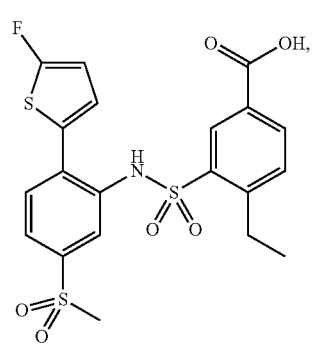
(106)

-continued
(111) 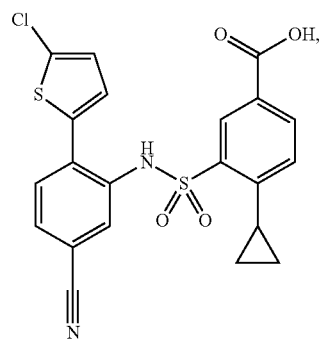
(112) 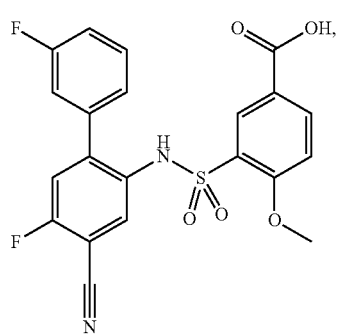
(113) 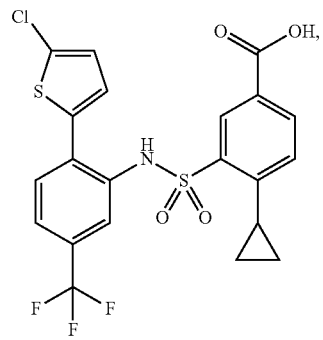
(114) 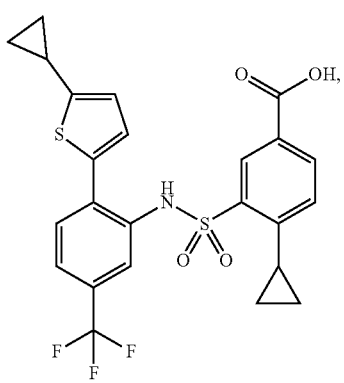
-continued
(115) 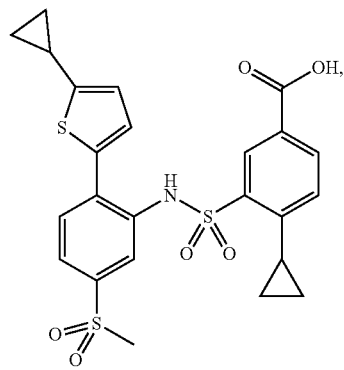
(116) 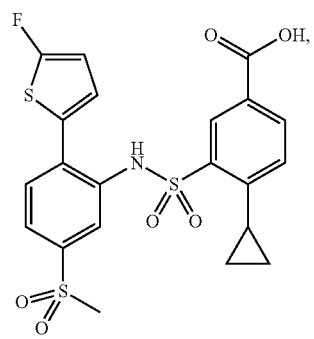
(117) 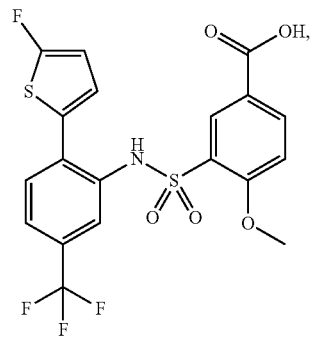
(118) 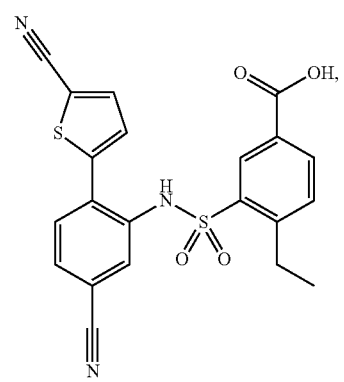

(119) 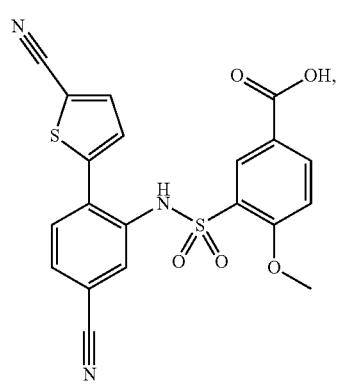
(120) 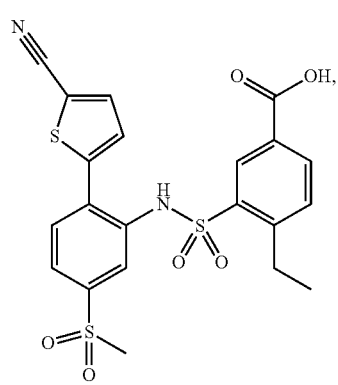
(122) 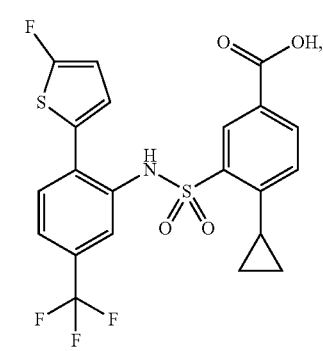
(123) 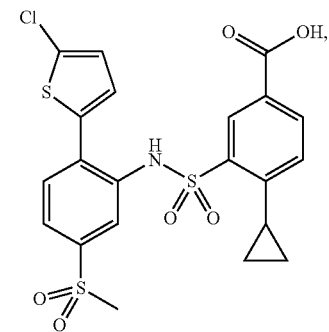
(124) 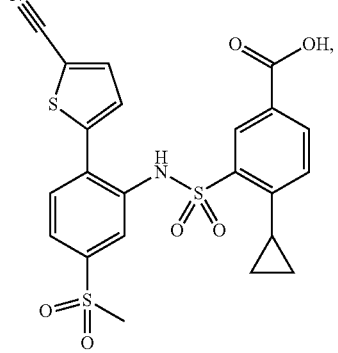
(125) 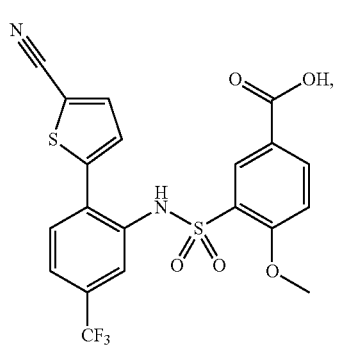
(126) 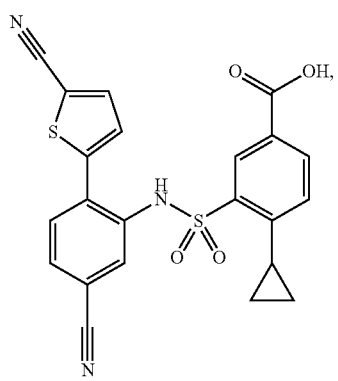
(127) 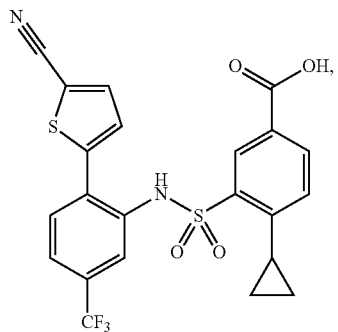

439
-continued
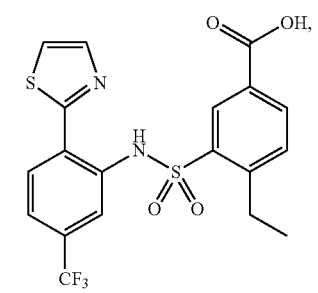
(128)
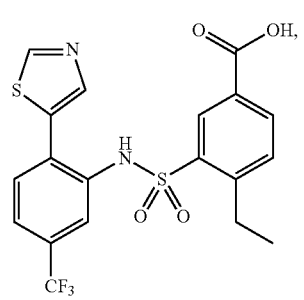
(129)
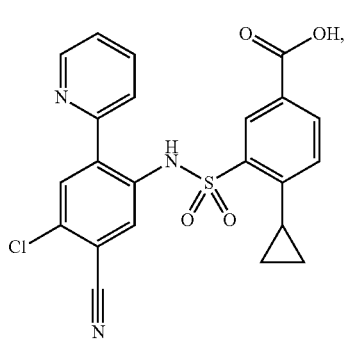
(132)
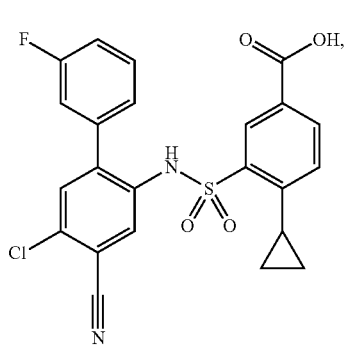
(133)
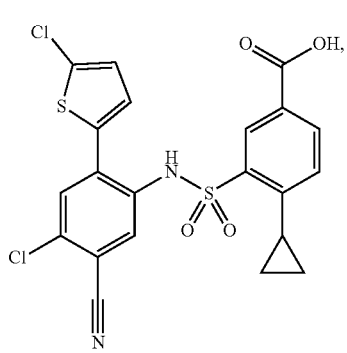
(134)
440
-continued
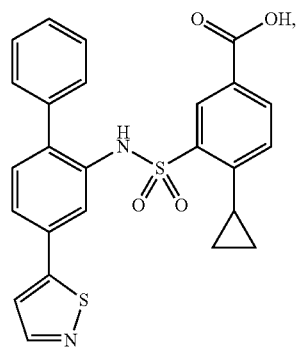
(135)
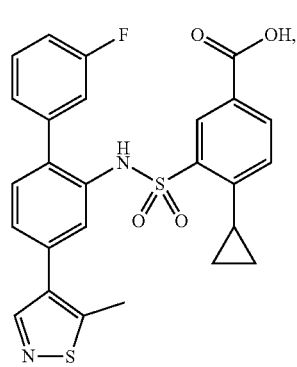
(136)
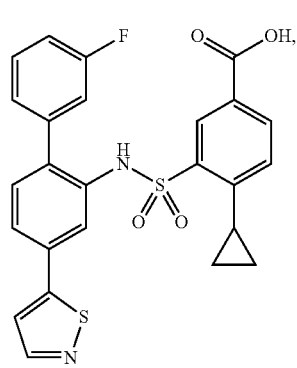
(137)
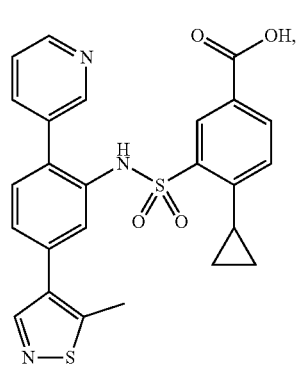
(138)

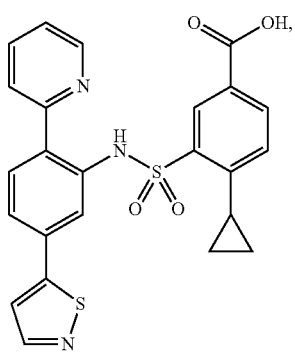
(139)
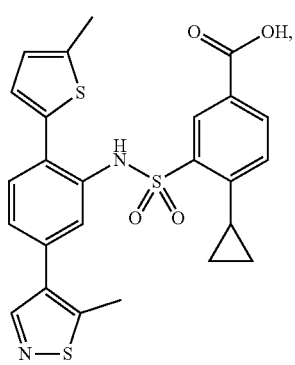
(140)
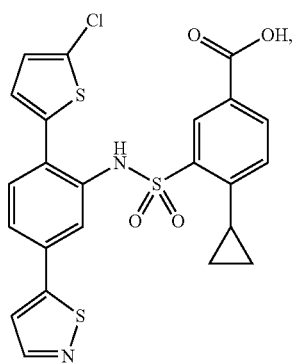
(141)
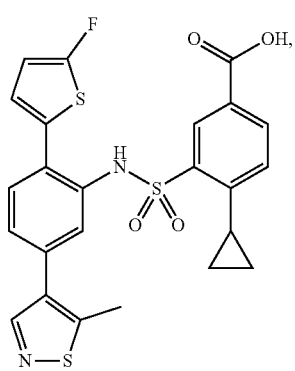
(142)
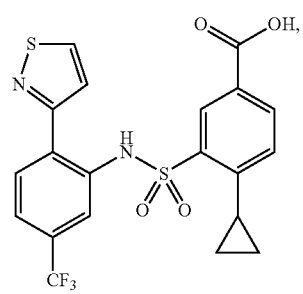
(151)
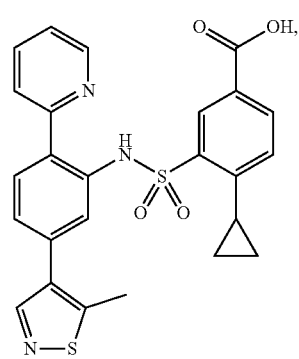
(144)
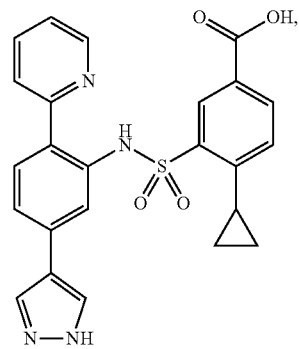
(145)
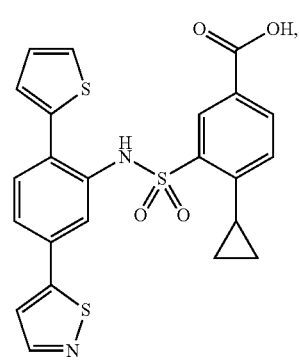
(146)

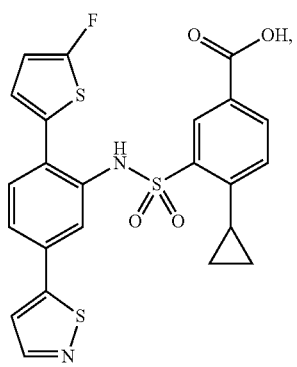
(147)
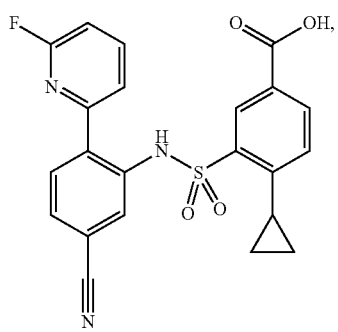
(153)
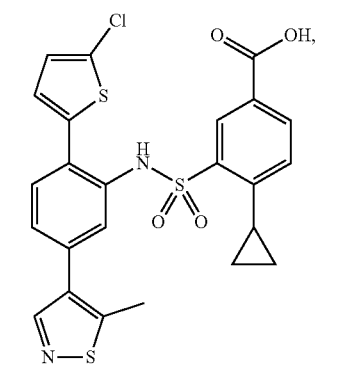
(148)
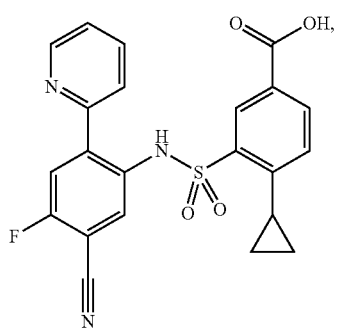
(154)
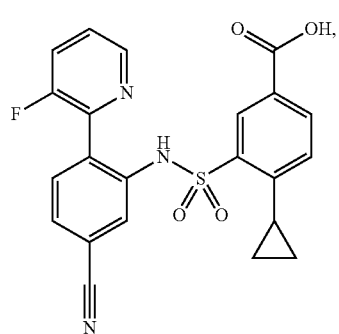
(149)
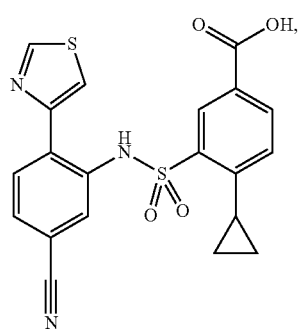
(159)
(152)
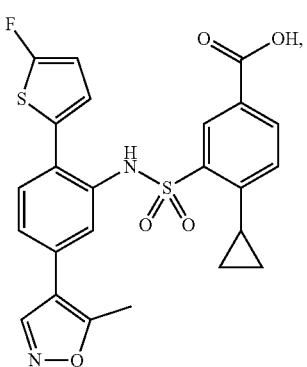
(160)

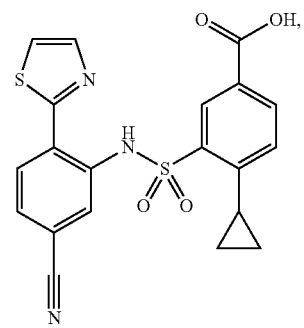 (163)
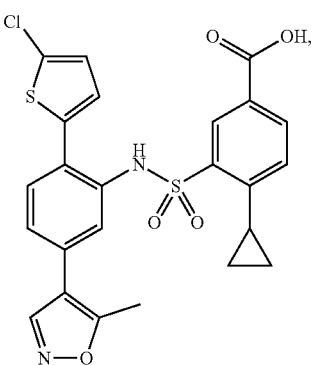 (164)
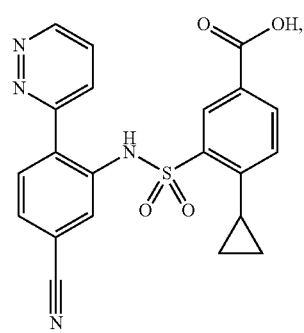 (165)
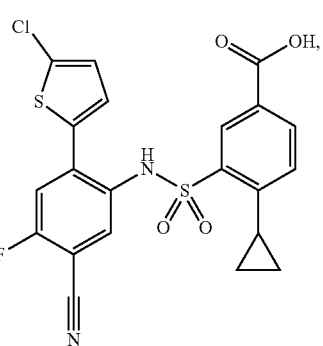 (166)
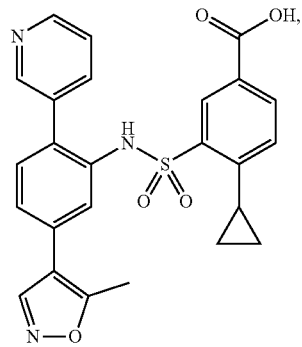 (167)
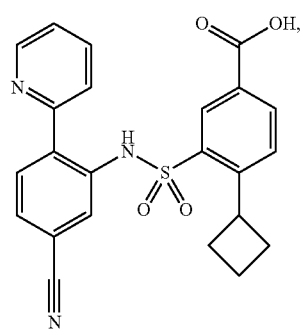 (168)
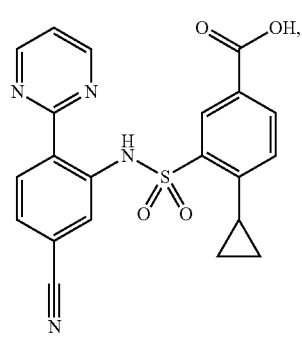 (169)
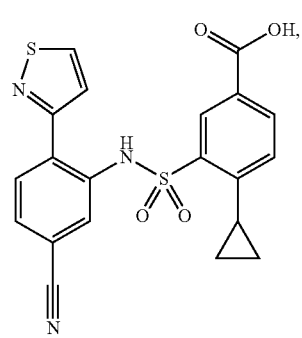 (170)
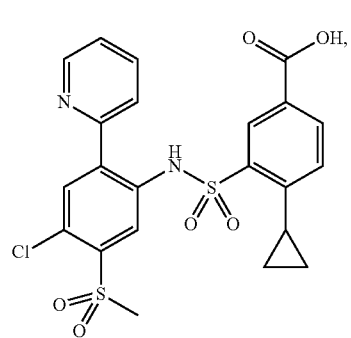 (171)

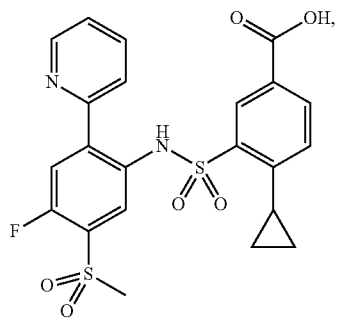
(172)
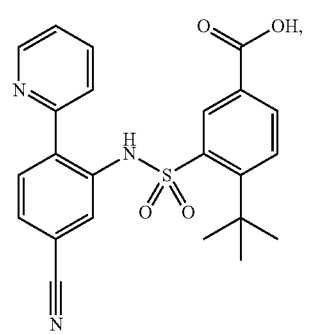
(173)
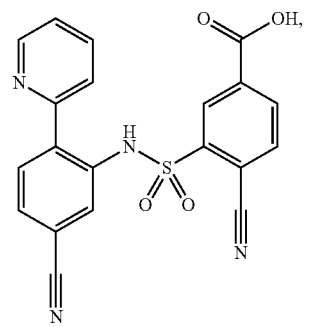
(175)
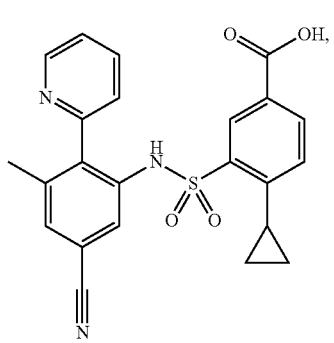
(176)
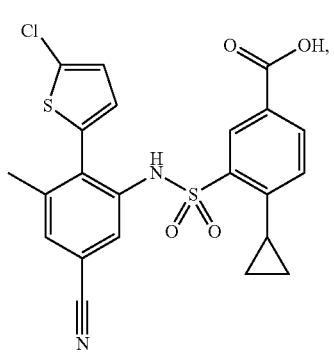
(177)
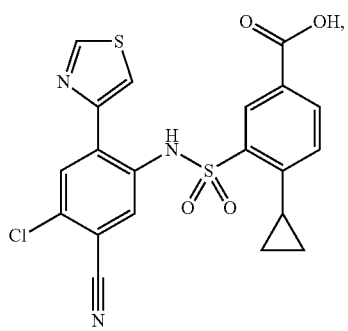
(178)
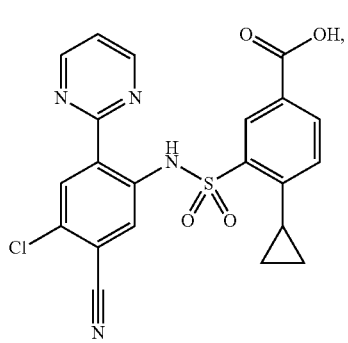
(179)
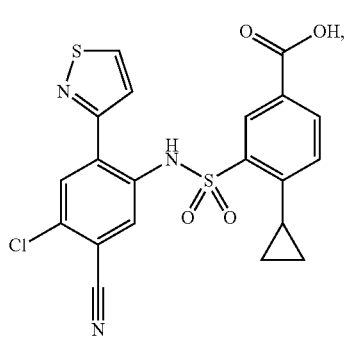
(180)
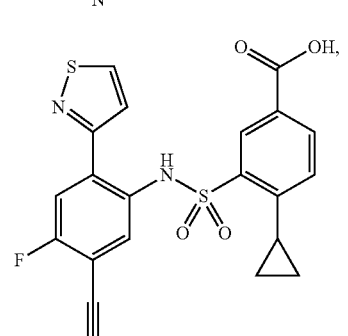
(181)
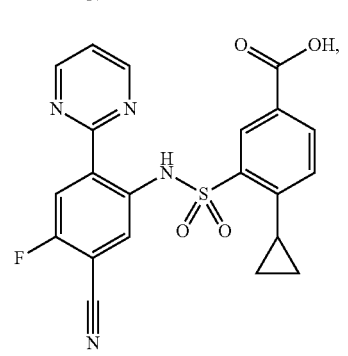
(182)

449
-continued
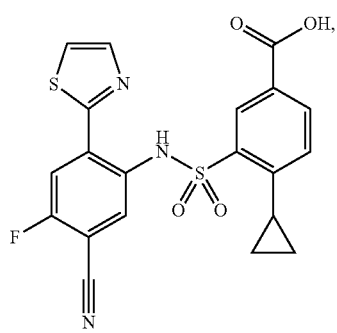
(183)
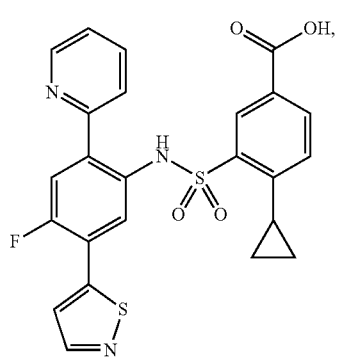
(184)
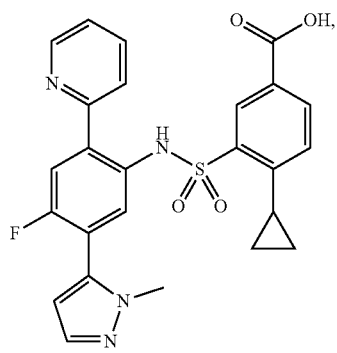
(185)
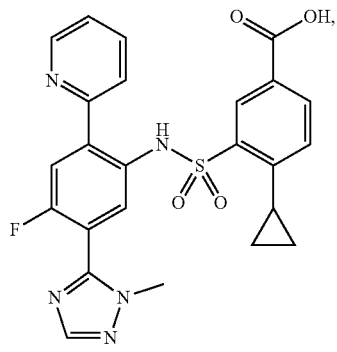
(186)
450
-continued
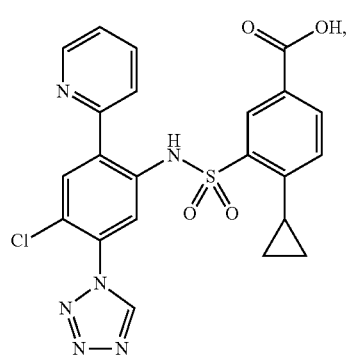
(187)
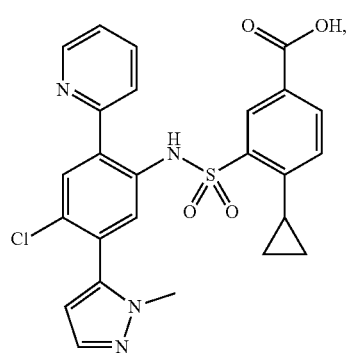
(188)
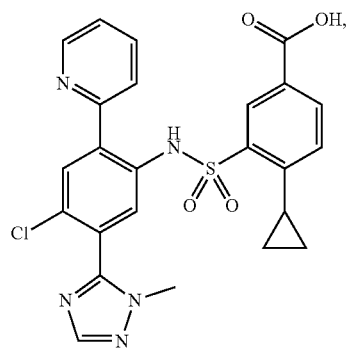
(189)
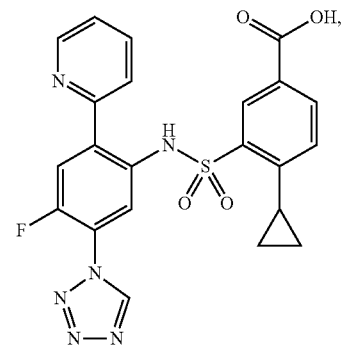
(190)

(191) 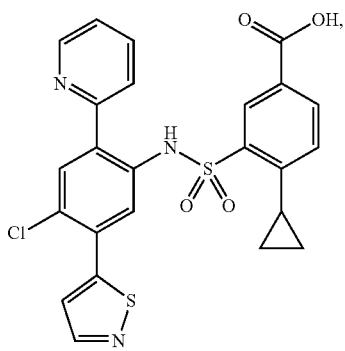
(193) 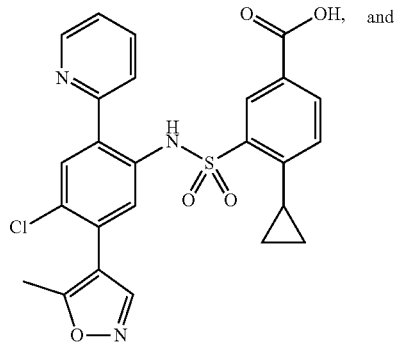
(192) 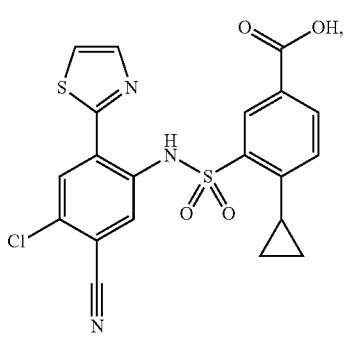
(196) 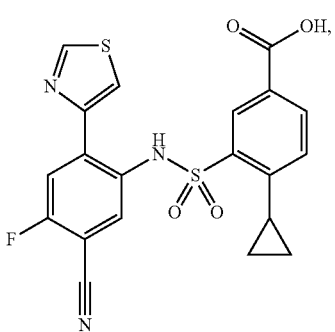
and pharmaceutically acceptable salts and hydrates thereof.
10. A pharmaceutical composition comprising a compound as defined in claim 1 admixed with a pharmaceutically acceptable carrier, diluent or excipient.
11. A combination comprising a compound as defined in claim 1 and a further active agent.
* * * * *